(12) United States Patent
Choi et al.

(10) Patent No.: US 9,034,921 B2
(45) Date of Patent: May 19, 2015

(54) DIPHENYLMETHANE DERIVATIVES AS SGLT2 INHIBITORS

(75) Inventors: Soongyu Choi, Yongin-si (KR); Kwang Seop Song, Yongin-si (KR); Suk Ho Lee, Yongin-si (KR); Min Ju Kim, Yongin-si (KR); Hee Jeong Seo, Yongin-si (KR); Eun-Jung Park, Yongin-si (KR); Younggyu Kong, Yongin-si (KR); So Ok Park, Yongin-si (KR); Hyunku Kang, Yongin-si (KR); Myung Eun Jung, Yongin-si (KR); Kinam Lee, Yongin-si (KR); Hyun Jung Kim, Yongin-si (KR); Jun Sung Lee, Yongin-si (KR); Min Woo Lee, Yongin-si (KR); Mi-Soon Kim, Yongin-si (KR); Dong Ho Hong, Yongin-si (KR); Misuk Kang, Yongin-si (KR)

(73) Assignee: GREEN CROSS CORPORATION, Yongin-Si (KR)

(*) Notice: Subject to any disclaimer, the term of this patent is extended or adjusted under 35 U.S.C. 154(b) by 0 days.

(21) Appl. No.: 14/122,836

(22) PCT Filed: Jun. 1, 2012

(86) PCT No.: PCT/KR2012/004366
§ 371 (c)(1),
(2), (4) Date: Nov. 27, 2013

(87) PCT Pub. No.: WO2012/165914
PCT Pub. Date: Dec. 6, 2012

(65) Prior Publication Data
US 2014/0088079 A1     Mar. 27, 2014

Related U.S. Application Data

(60) Provisional application No. 61/492,143, filed on Jun. 1, 2011.

(51) Int. Cl.
*A61K 31/351* (2006.01)
*C07D 407/04* (2006.01)
*C07D 309/10* (2006.01)
*C07D 405/10* (2006.01)
*C07D 407/10* (2006.01)
*C07D 407/14* (2006.01)
*C07D 409/04* (2006.01)
*C07D 409/10* (2006.01)
*C07D 411/10* (2006.01)
*C07D 413/04* (2006.01)
*C07D 405/14* (2006.01)
*C07D 413/10* (2006.01)

(52) U.S. Cl.
CPC ............ *C07D 309/10* (2013.01); *C07D 405/10* (2013.01); *C07D 407/04* (2013.01); *C07D 407/10* (2013.01); *C07D 407/14* (2013.01); *C07D 409/04* (2013.01); *C07D 409/10* (2013.01); *C07D 411/10* (2013.01); *C07D 413/04* (2013.01); *C07D 405/14* (2013.01); *C07D 413/10* (2013.01)

(58) Field of Classification Search
CPC .......................... A61K 31/351; C07D 407/04
USPC ..................... 549/356, 414; 514/451, 460
See application file for complete search history.

(56) References Cited

U.S. PATENT DOCUMENTS

| | | | |
|---|---|---|---|
| 8,039,441 B2 * | 10/2011 | Himmelsbach et al. | 514/23 |
| 8,476,413 B2 * | 7/2013 | Harrison et al. | 536/4.1 |
| 8,541,380 B2 * | 9/2013 | Lee et al. | 514/23 |
| 8,586,550 B2 * | 11/2013 | Lee et al. | 514/23 |
| 8,828,951 B2 * | 9/2014 | Bebernitz et al. | 514/23 |
| 2003/0114390 A1 | 6/2003 | Washburn et al. | |

FOREIGN PATENT DOCUMENTS

| | | |
|---|---|---|
| WO | 2011/048112 A1 | 4/2011 |
| WO | 2012140596 A1 | 10/2012 |
| WO | 2012140597 A1 | 10/2012 |

OTHER PUBLICATIONS

Suk Youn Kang et al., "Glucosides with cyclic diarylpolynoid as novel C-aryl glucoside SGLT2 inhibitors," Bioorganic & Medicinal Chemistry Letters, 2011, pp. 3759-3763, vol. 21.

Irene M Stratton et al., "Association of glycaemia with macrovascular and microvascular complications of type 2 diabetes (UKPDS 35): prospective observational study," Br. Med. J., 2000, pp. 405-412, vol. 321.

Sharon H. Saydah et al., "Poor Control of Risk Factors for Vascular Disease Among Adults With Previously Diagnosed Diabetes," J. Am. Med. Assoc., 2004, pp. 335-342, vol. 291, No. 3.

Junwon Lee et al., "Novel C-aryl glucoside SGLT2 inhibitors as potential antidiabetic agents: 1,3,4-Thiadiazolylmethylphenyl glucoside congeners," Bioorganic & Medicinal Chemistry, 2010, pp. 2178-2194, vol. 18.

L. P. Van Den Heuvel et al., "Autosomal recessive renal glucosuria attributable to a mutation in the sodium glucose cotransporter (SGLT2)," Hum. Genet., 2002, pp. 544-547, vol. 111.

(Continued)

*Primary Examiner* — Golam M M Shameem
(74) *Attorney, Agent, or Firm* — Sughrue Mion, PLLC

(57) ABSTRACT

A compound with a diphenylmethane moiety having an inhibitory activity against sodium-dependent glucose cotransporter 2 (SGLT2) being present in the intestine and kidney is disclosed. A pharmaceutical composition including the compound as an active ingredient, which is useful for preventing or treating metabolic disorders, particularly diabetes is disclosed. A method for preparing the compound, and a method for preventing or treating metabolic disorders, particularly diabetes, by using the compound is provided.

12 Claims, 2 Drawing Sheets

(56) References Cited

OTHER PUBLICATIONS

Wei Meng et al., "Discovery of Dapagliflozin: A Potent, Selective Renal Sodium-Dependent Glucose Cotransporter 2 (SGLT2) Inhibitor for the Treatment of Type 2 Diabetes," J. Med. Chem., 2008, pp. 1145-1149, vol. 51.

William N. Washburn, "Evolution of sodium glucose co-transporter 2 inhibitors as anti-diabetic agents," Expert Opin. Ther. Patents, 2009, pp. 1485-1499, vol. 19.

William N. Washburn, "Development of the Renal Glucose Reabsorption Inhibitors: A New Mechanism for the Pharmacotherapy of Diabetes Mellitus Type 2," J. Med. Chem., 2009, pp. 1785-1794, vol. 52, No. 7.

International Searching Authority, International Search Report of PCT/KR2012/004366 dated Dec. 5, 2012.

Database, PubChem Compound [Online] NCBI; May 23 2011, XP002729947, Database accession No. CID 52914757.

European Patent Office, Communication dated Dec. 1, 2014, issued in corresponding European Application No. 12793162.4.

\* cited by examiner

I

DIPHENYLMETHANE DERIVATIVES AS SGLT2 INHIBITORS

CROSS REFERENCE TO RELATED APPLICATIONS

This is a National Stage of International Application No. PCT/KR2012/004366 filed Jun. 1, 2012, claiming priority based on U.S. Patent Application No. 61/492,143 filed Jun. 1, 2011, the contents of all of which are incorporated herein by reference in their entirety.

FIELD OF THE INVENTION

The present invention relates to a novel compound with a diphenylmethane moiety having an inhibitory activity against sodium-dependent glucose cotransporter 2 (SGLT2) being present in the intestine and kidney, and a pharmaceutical composition comprising the same as an active ingredient, which is useful for preventing or treating diabetes.

BACKGROUND OF THE INVENTION

The prevalence of diabetes has become an increasing concern to the world's population. An estimated 285 million people, corresponding to 6.4% of the world's adult population, will live with diabetes in 2010. The number is expected to grow to 438 million by 2030, corresponding to 7.8% of the adult population. Diabetes is characterized by a chronic metabolic disorder that is caused by failure of the body to produce insulin and/or an inability of the body to respond adequately to circulating insulin. Secreted by the pancreas, insulin increases the ability of tissue to absorb blood glucose. Accordingly, disruption of insulin function results in the high level of blood glucose that is commonly associated with diabetic patients. There are two generally recognized form of diabetes: Type 1 diabetes, or insulin-dependent diabetes mellitus (IDDM), is characterized as an autoimmune disease involving pancreatic β-cells, while type 2 diabetes, or noninsulin-dependent diabetes mellitus (NIDDM), is characterized by β-cell dysfunction and insulin resistance. Type 2 diabetes is the most prevalent abnormality of glucose homeostasis, accounting for approximately 90-95% of all cases of diabetes. The diabetes has been widespread throughout the whole world due to ageing populations and rapid cultural changes such as increasing urbanization, dietary change, decreased physical activity and other unhealthy behavioral patterns.

The burden of diabetes is driven by vascular complications such as cardiovascular disease, stroke, nephropathy, retinopathy, renal failure, and lower limb infection and gangrene. Although these complications result from multiple metabolic disorders, hyperglycemia is considered as the main cause of both the vascular consequences of the disease and the progressive nature of diabetes itself. Most harmful of all is that high glucose levels aggravate insulin resistance, impair β-cell function and finally contribute to β-cell apoptosis. The loss of β-cell function deteriorates hyperglycemia, resulting in a vicious cycle that culminates in the abject destruction of the β-cells. The United Kingdom Prevention of Diabetes Study (UKPDS) showed that incremental reductions in glycosylated hemoglobin (HbAlC) lowered the risk of diabetes-related events [Stratton, I. M. et al. *Br. Med. J.* 2000, 321, 405-412]. Thus, it is recommended that patients with type 2 diabetes should reduce HbAlC values to 7% and less.

The most important strategy for treatment of type 2 diabetes involves lifestyle interventions that promote body weight loss, leading to an improvement in glycemic control. In case lifestyle interventions are not enough for the management of diabetes, an extensive range of antidiabetic drugs might be considered for the treatment of the condition (monotherapies and combination therapies). These therapies target the liver to reduce glucose output, small intestine to decrease glucose absorption, adipose deposits or muscle to elevate glucose cellular uptake or to promote glucose metabolism, serum proteases to prolong incretin action, and the pancreas to enhance insulin release. Despite the wide range of antihyperglycemic agent, it is difficult for many patients to achieve HbAlC target level. In a study reviewing diabetic patients for control of vascular risk factors, only 37.0% of participants achieved the target goal of HbAlC level of less than 7.0% [Saydah, S. H. et al. *J. Am. Med. Assoc.* 2004, 291, 335-342]. In addition, current therapies have limited durability and/or are associated with significant side effects such as gastrointestinal intolerance, hypoglycemia, weight gain, lactic acidosis and edema. Thus, significant unmet medical needs still remain for the treatment of diabetes. In particular, safer, better tolerated medications which provide increased efficacy and long-term durability are desired.

The obvious need for new approaches to treat patients with uncontrolled type 2 diabetes has promoted continuous exploration of alternative targets in organs involved in maintenance of glucose homeostasis. In the context of type 2 diabetes, renal glucose reabsorption contributes to plasma glucose levels and the concomitant microvascular complications. Evaluation of molecular targets available in the kidney (a major unexploited contributor to glucose homeostasis) stimulated interest in the development of a new class of antihyperglycemic agents that promote urinary glucose excretion. Inhibitors of the SGLT2 prevent renal glucose reabsorption from the glomerular filtrate and provide an insulin-independent way of controlling hyperglycemia.

Sodium-dependent glucose cotransporters (SGLTs) couple the transport of glucose against a concentration gradient with the simultaneous transport of $Na^+$ down a concentration gradient. Two important SGLT isoforms have been cloned and identified as SGLT1 and SGLT2. SGLT1 is located in the gut, kidney, and heart where its expression regulates cardiac glucose transport. SGLT1 is a high-affinity, low-capacity transporter and therefore accounts for only a small fraction of renal glucose reabsorption. In contrast, SGLT2 is a low-affinity, high-capacity transporter located exclusively at the apical domain of the epithelial cells in the early proximal convoluted tubule. In healthy individuals, greater than 99% of the plasma glucose that filtered in the kidney glomerulus is reabsorbed, resulting in less than 1% of the total filtered glucose being excreted in urine. It is estimated that 90% of renal glucose reabsorption is facilitated by SGLT2; the remaining 10% is likely mediated by SGLT1 in the late proximal straight tubule. Genetic mutations in SGLT2 lead to increased renal glucose excretion of as much as 140 g/day depending on the mutation with no apparent adverse effects on carbohydrate metabolism. Since SGLT2 appears to be responsible for the majority of renal glucose reabsorption based on human mutation studies, it has become a target of therapeutic interest [Lee, J. et al. *Bioorg. Med. Chem.* 2010, 18, 2178-2194; van den Heuvel, L. P. et al. *Hum. Genet.* 2020, 111, 544-547].

Phlorizin was isolated from the root bark of the apple tree and evaluated as the first SGLT inhibitor. Despite antidiabetic potency of phlorizin, its metabolic instability due to β-glucosidase cleavage in the intestinal tract has prevented its development as a drug for the treatment of diabetes. Subsequently, T-1095, by Tanabe Seiyaku, was reported as the first orally absorbable SGLT2 inhibitor, overcoming the disadvantage of phlorizin. T-1095 was absorbed in the intestine and converted to an active form, T-1095A. Following the discovery of T-1095, O-aryl glucosides such as sergliflozin and remogliflozin advanced furthest in clinical trials. Again, concern regarding gut β-glucosidase-mediated degradation, resulted in developing sergliflozin A and remogliflozin A being administered as the ethyl carbonate prodrugs sergliflozin and remogliflozin, respectively. Subsequent endeavors to identify SGLT2 inhibitors suitable for oral administration without the need for a prodrug led to the discovery of C-aryl glucoside-derived SGLT2 inhibitors. C-aryl glucoside appears to have drug-like properties with enhanced chemical stability of the glucosidic bond. Extensive SAR studies by Bristol-Myers Squibb identified dapagliflozin, a potent, selective SGLT2 inhibitor for the treatment of type 2 diabetes. At present, dapagliflozin is the most advanced SGLT2 inhibitor in clinical trials and is believed to be the first SGLT2 inhibitor to go to market [Meng, W. et al. *J. Med. Chem.* 2008, 51, 1145-1149]. On the other hand, Mitsubishi Tanabe Pharma, in collaboration with Johnson & Johnson, is developing canagliflozin, another novel C-aryl glucoside-derived SGLT2 inhibitor [Tanabe Seiyaku, WO2008013321].

Considering the important impact of diabetes on public health and unmet medical needs of current therapy, it is no surprise that SGLT2 inhibitors are currently interesting topics of studies, which were published in the following review articles [Washburn, W. N. *Expert Opin. Ther. Patents*, 2009, 19, 1485-1499; Washburn, W. N. *J. Med. Chem.* 2009, 52, 1785-1794].

SUMMARY OF THE INVENTION

It is an object of the present invention to provide a novel compound bearing a diphenylmethane moiety of formula I, or a pharmaceutically acceptable salt thereof, or a prodrug thereof, which is effective as SGLT2 inhibitor, useful for the prevention and/or treatment of metabolic disorders, particularly diabetes.

It is another object of the present invention to provide a method for preparing the inventive compound.

It is another object of the present invention to provide a pharmaceutical composition for preventing or treating metabolic disorders, particularly diabetes.

It is yet another object of the present invention to provide a method for preventing or treating a metabolic disorder, particularly diabetes, in a mammal.

It is still another object of the present invention to provide a method for inhibiting sodium-dependent glucose cotransporter 2 (SGLT2) in a mammal.

It is a further object of the present invention to provide a use of the inventive compound.

In accordance with one aspect of the present invention, there is provided a compound of formula I, or a pharmaceutically acceptable salt thereof, or a prodrug thereof, wherein formula I is as defined herein.

In accordance with another aspect of the present invention, there is provided a method for preparing the compound of formula I-a of claim 1, comprising:

(a) reacting a compound of formula II with a compound of formula III to obtain a compound of formula IV; and (b) deprotecting and reducing the compound of formula IV to obtain a compound of formula I-a, wherein formulae II, III, IV and I-a are as defined herein.

In accordance with another aspect of the present invention, there is provided a pharmaceutical composition for preventing or treating a metabolic disorder, comprising as an active ingredient the compound of formula I, or a pharmaceutically acceptable salt or a prodrug thereof, and a pharmaceutically acceptable carrier.

In accordance with yet another aspect of the present invention, there is provided a method for preventing or treating a metabolic disorder in a mammal, which comprises administering the compound of formula I or a pharmaceutically acceptable salt or a prodrug thereof to the mammal.

In accordance with still another aspect of the present invention, there is provided a method for inhibiting sodium-dependent glucose cotransporter 2 (SGLT2) in a mammal, which comprises administering the compound of formula I or a pharmaceutically acceptable salt or a prodrug thereof to the mammal.

In accordance with a further aspect of the present invention, there is provided a use of the compound of formula I or a pharmaceutically acceptable salt or a prodrug thereof for the manufacture of a medicament for preventing or treating a metabolic disorder.

DETAILED DESCRIPTION OF THE INVENTION

Figure 1:
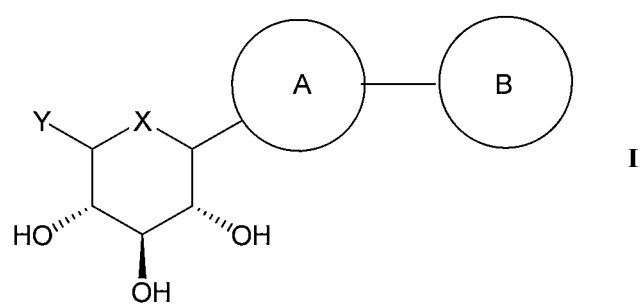
FIG. 1 is the chemical formula of Compound I.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted by one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of $C_{1-3}$ alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of $C_{1-3}$ alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" refers to a non-aromatic cyclic hydrocarbon radical composed of three to seven carbon atoms. Five-to seven-membered rings may contain a double bond in the ring structure. Exemplary "carbocycle" groups include, but are not limited to, cyclopropyl, cyclobutyl, cyclopentyl, cyclopentenyl, cyclohexyl and cycloheptyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, $SO_2$, O, N, or N-oxide, or refers to such an aromatic ring fused to one or more rings such as heteroaryl rings, aryl rings, heterocyclic rings, or carbocycle rings (e.g., a bicyclic or tricyclic ring system), each having optional substituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" refers to a three to seven-membered ring containing one or more heteroatomic moieties selected from S, SO, $SO_2$, O, N, or N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, amino sulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents.

Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein the term "aralkoxy" refers to the group —$OR_aR_b$, wherein $R_a$ is alkyl and $R_b$ is aryl as defined above.

As used herein the term "aryloxy" refers to the group —$OR_b$, wherein $R_b$ is aryl as defined above.

As used herein, the term "mercapto" refers to the group —SH.

As used herein, the term "sulfanyl" refers to the group —$SR_c$, wherein $R_c$ is substituted alkyl, substituted carbocycle, aryl, heteroaryl or heterocyclic, as defined above.

As used herein, the term "sulfinyl" refers to the group —S—(O)$R_c$, wherein $R_c$ is substituted alkyl, substituted carbocycle, aryl, heteroaryl or heterocyclic, as defined above.

As used herein, the term "sulfonyl" refers to the group —$S(O)_2R_c$, wherein $R_c$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —$NH_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted by substituted alkyl, substituted carbocycle, aryl, heteroaryl or heterocyclic, as defined above.

As used herein, the term "sulfonylamino" refers to the group —NHS(O)$_2$R$_c$ wherein R$_c$ is substituted alkyl, substituted carbocycle, aryl, heteroaryl or heterocyclic, as defined above.

As used herein, the term "carboxyamide" refers to the group —NHC(O)R$_c$ wherein R$_c$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" refers to the group —C(O)NH$_2$. The aminocarbonyl group is optionally substituted by substituted alkyl, substituted carbocycle, aryl, heteroaryl or heterocyclic, as defined above.

As used herein, the term "ureido" refers to the group —NHC(O)NHR$_d$ wherein R$_d$ is hydrogen, alkyl, carbocycle or aryl as defined above.

As used herein, the term "guanidino" refers to the group —NHC(=NH)NH$_2$.

As used herein, the term "acyl" refers to the group —C(O)R$_e$, wherein R$_e$ is alkyl, carbocycle, or heterocyclic as defined herein.

As used herein, the term "aroyl" refers to the group —C(O)R$_b$, wherein R$_b$ is aryl as defined herein.

As used herein, the term "heteroaroyl" refers to the group —C(O)R$_f$, wherein R$_f$ is heteroaryl as defined herein.

As used herein, the term "acyloxy" refers to the group —OC(O)R$_e$, wherein R$_e$ is alkyl, carbocycle, or heterocyclic as defined herein.

As used herein, the term "aroyloxy" refers to the group —OC(O)R$_b$, wherein R$_b$ is aryl as defined herein.

As used herein, the term "heteroaroyloxy" refers to the group —OC(O)R$_f$, wherein R$_f$ is heteroaryl as defined herein.

It is to be understood that the present invention also includes a pharmaceutically acceptable salt and an addition salt of the inventive compound, such as a hydrochloride, hydrobromide or trifluoroacetate addition salt and a sodium, potassium and magnesium salt.

Further, it should be construed that the present invention also includes prodrugs of the inventive compound. The term "prodrug" refers to a pharmacologically inactive compound that is converted to an active drug by a metabolic biotransformation. Examples of the prodrug include carrier-linked prodrugs (e.g., ester analogs), and bioprecursor prodrugs. Those skilled in the art can easily design and prepare suitable prodrugs based on the inventive compound.

The compounds of the present invention may contain one or more asymmetric carbon atoms and may exist in racemic and optically active forms. All of these compounds and diastereomers are incorporated within the scope of the present invention.

In one aspect of the present invention, the compound of the present invention has the following structure:

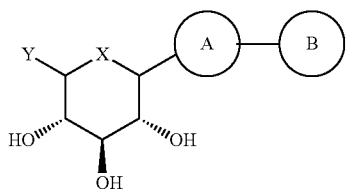

I wherein,

X is oxygen or sulfur;

Y is C$_{1-7}$ alkyl, C$_{2-7}$ alkenyl, C$_{2-7}$ alkynyl, C$_{1-7}$ alkoxy, C$_{1-7}$ alkoxy-C$_{1-7}$ alkyl, C$_{1-7}$ alkylsulfinyl, C$_{1-7}$ alkylsulfonyl, or C$_{1-7}$ alkylthio;

ring A is

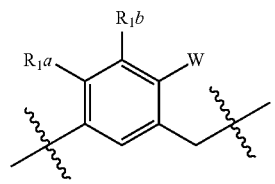

A-1

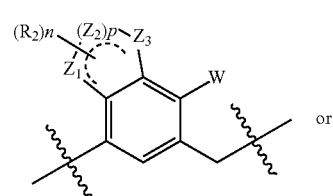

A-2 or

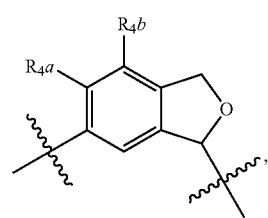

A-3 said R$_{1a}$, R$_{1b}$, R$_{4a}$, R$_{4b}$ and W being each independently selected from the group consisting of hydrogen, halogen, hydroxy, mercapto, cyano, nitro, amino, carboxy, C$_{1-7}$ alkyl, C$_{2-7}$ alkenyl, C$_{2-7}$ alkynyl, C$_{1-7}$ alkoxy, C$_{1-7}$ alkoxy-C$_{1-7}$ alkyl, C$_{2-7}$ alkenyl-C$_{1-7}$ alkyloxy, C$_{2-7}$ alkynyl-C$_{1-7}$ alkyloxy, C$_{3-10}$ cycloalkyl, C$_{5-10}$ cycloalkenyl, C$_{3-10}$ cycloalkyloxy, phenyl-C$_{1-7}$ alkoxy, mono- or di-C$_{1-7}$ alkylamino, C$_{1-7}$ alkanoyl, C$_{1-7}$ alkanoylamino, C$_{1-7}$ alkoxycarbonyl, carbamoyl, mono- or di-C$_{1-7}$ alkylcarbamoyl, C$_{1-7}$ alkylsulfonylamino, phenylsulfonylamino, C$_{1-7}$ alkylsulfanyl, C$_{1-7}$ alkylsulfinyl, C$_{1-7}$ alkylsulfonyl, C$_{6-14}$ arylsulfanyl, C$_{6-14}$ arylsulfonyl, C$_{6-14}$ aryl, 5 to 13-membered heteroaryl, or 5 to 10-membered heterocycloalkyl, said R$_2$ being each independently hydroxy, C$_{1-7}$ alkyl, or C$_{1-7}$ alkoxy, said n being an integer of 0 to 3, said Z$_1$, Z$_2$, and Z$_3$ being each independently —CH$_2$—, —CH=, —(CO)—, —O—, —S—, —NH—, or —N=, and said p being an integer of 1 to 3;

ring B is

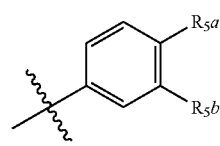

B-1

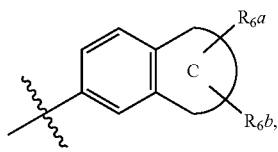

with the proviso that when ring A is A-1, then ring B is B-2, wherein, said $R_{5a}$, $R_{5b}$, $R_{6a}$, and $R_{6b}$ being each independently selected from the group consisting of hydrogen, halogen, hydroxy, mercapto, cyano, nitro, amino, carboxy, oxo, $C_{1-7}$ alkyl, $C_{1-7}$ alkylthio, $C_{2-7}$ alkenyl, $C_{2-7}$ alkynyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{3-7}$ cycloalkylthio, $C_{5-10}$ cycloalkenyl, $C_{3-10}$ cycloalkyloxy, $C_{3-10}$ cycloalkyloxy-$C_{1-7}$ alkoxy, phenyl-$C_{1-7}$ alkyl, $C_{1-7}$ alkylthio-phenyl, phenyl-$C_{1-7}$ alkoxy, mono- or di-$C_{1-7}$ alkylamino, mono- or di-$C_{1-7}$ alkylamino-$C_{1-7}$ alkyl, $C_{1-7}$ alkanoyl, $C_{1-7}$ alkanoylamino, $C_{1-7}$ alkylcarbonyl, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfinyl, $C_{6-14}$ arylsulfanyl, $C_{6-14}$ arylsulfonyl, $C_{6-14}$ aryl, 5 to 13-membered heteroaryl, 5 to 10-membered heterocycloalkyl, 5 to 10-membered heterocycloalkyl-$C_{1-7}$ alkyl, or 5 to 10-membered heterocycloalkyl-$C_{1-7}$ alkoxy, and said ring C being $C_{3-10}$ cycloalkyl, $C_{5-10}$ cycloalkenyl, $C_{6-14}$ aryl, 5 to 13-membered heteroaryl, or 5 to 10-membered heterocycloalkyl;

said alkyl, alkenyl, alkynyl, or alkoxy is optionally substituted with at least one substituent selected from the group consisting of halogen, hydroxy, cyano, nitro, amino, mercapto, $C_{1-7}$ alkyl, and $C_{2-7}$ alkynyl; and said cycloalkyl, cycloalkenyl, aryl, heteroaryl, or heterocycloalkyl is optionally substituted with at least one substituent selected from the group consisting of halogen, hydroxy, cyano, nitro, amino, mercapto, $C_{1-4}$ alkyl, and $C_{1-4}$ alkoxy.

In one embodiment of the present invention, ring A-2 may be selected from the group consisting of:

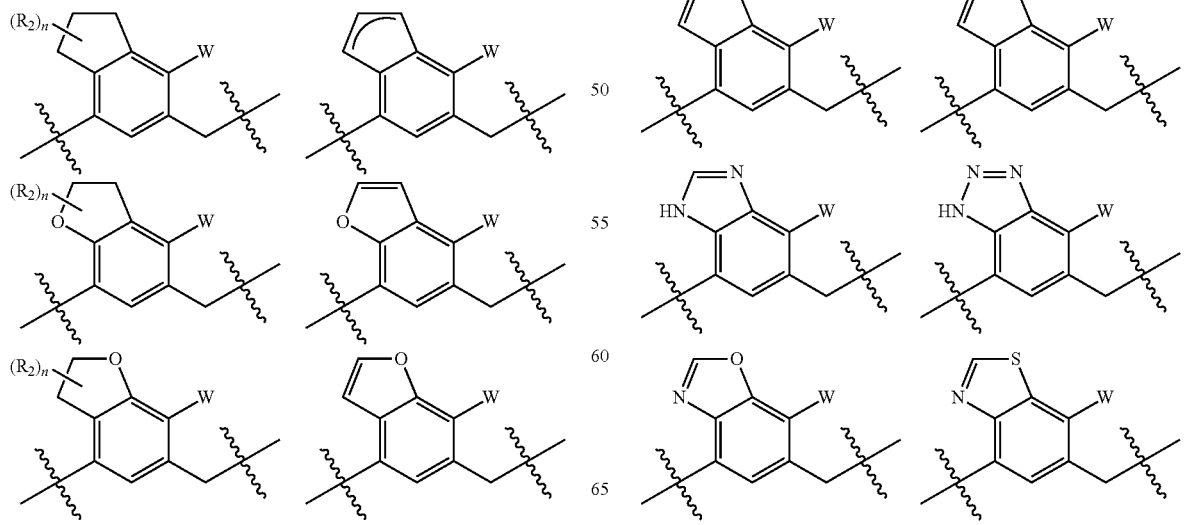
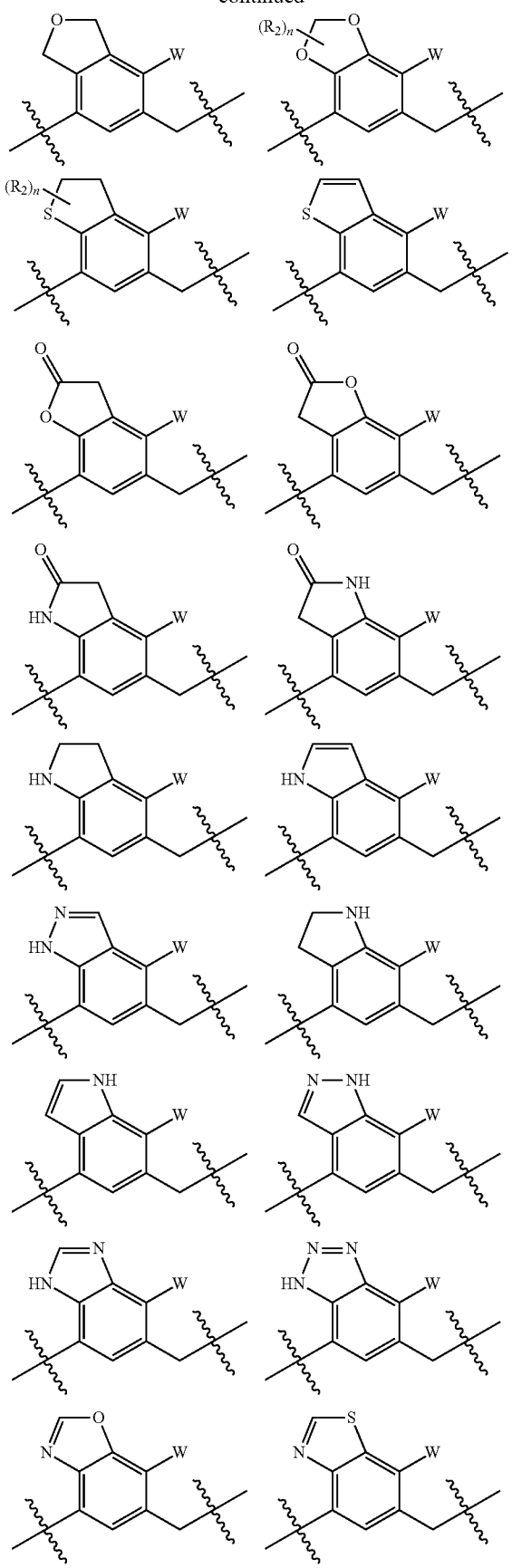

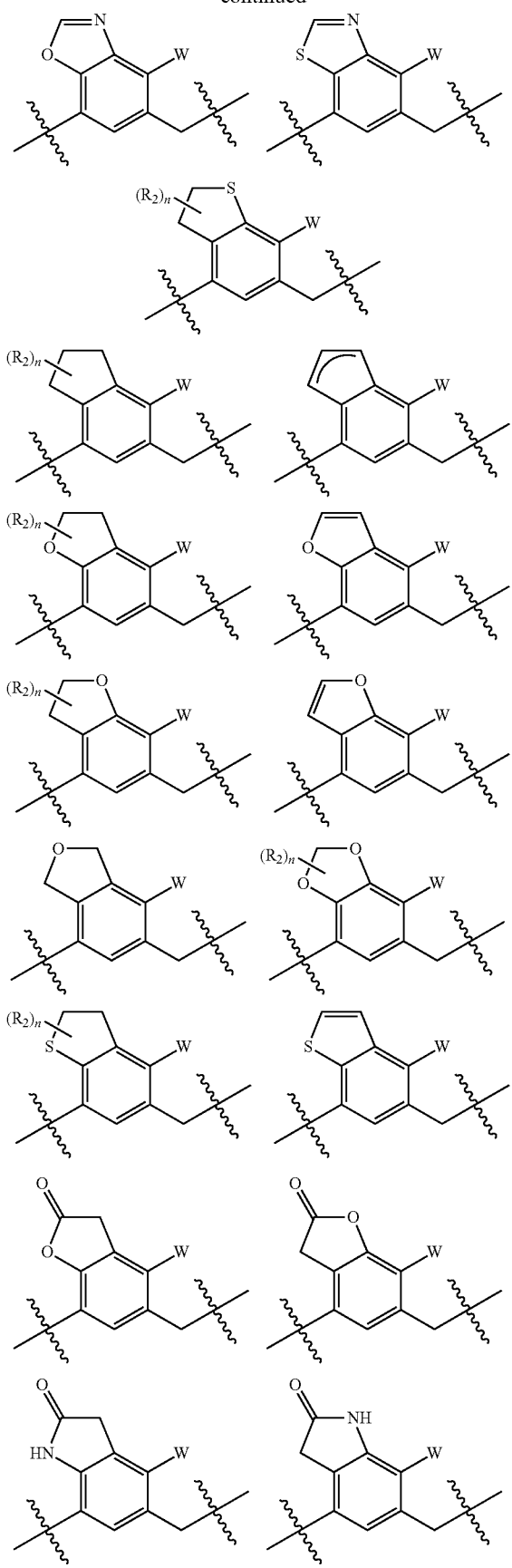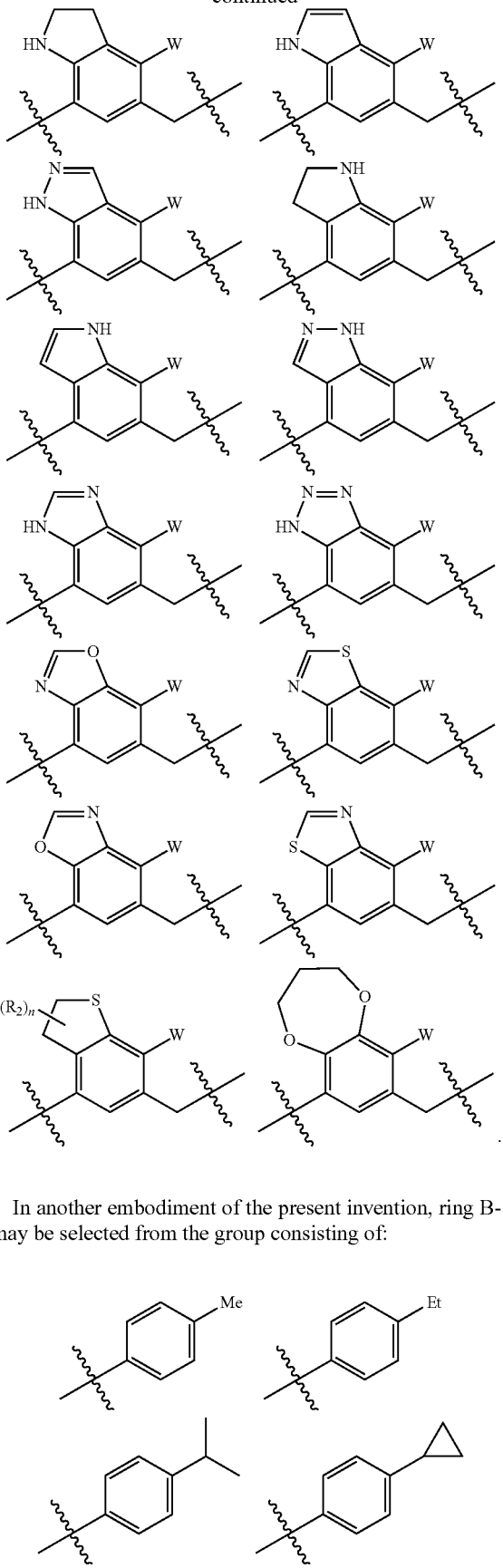
In another embodiment of the present invention, ring B-1 may be selected from the group consisting of:
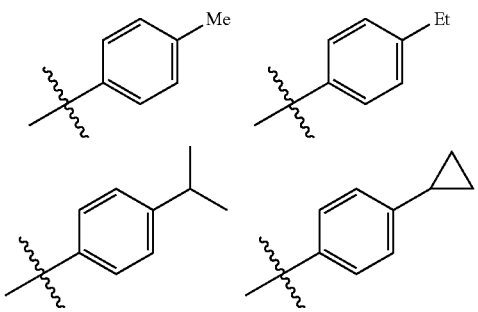

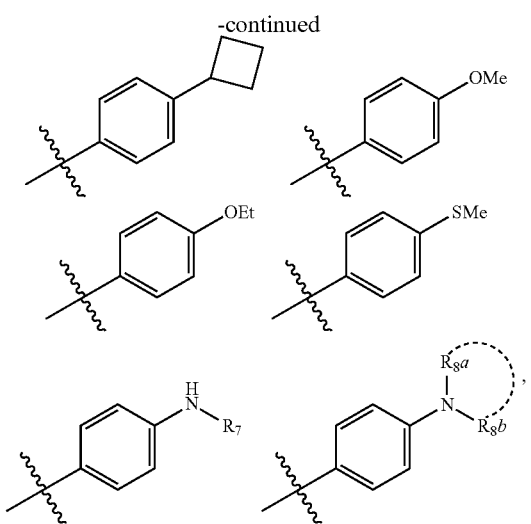

in which $R_7$ is hydrogen, or $C_{1-7}$ alkyl, and $R_{8a}$ and $R_{8b}$ are each independently $C_{1-7}$ alkyl, or $R_{8a}$ and $R_{8b}$ are connected to form a 5 to 10-membered heterocycloalkyl.

In yet another embodiment of the present invention, ring B-2 may be selected from the group consisting of:

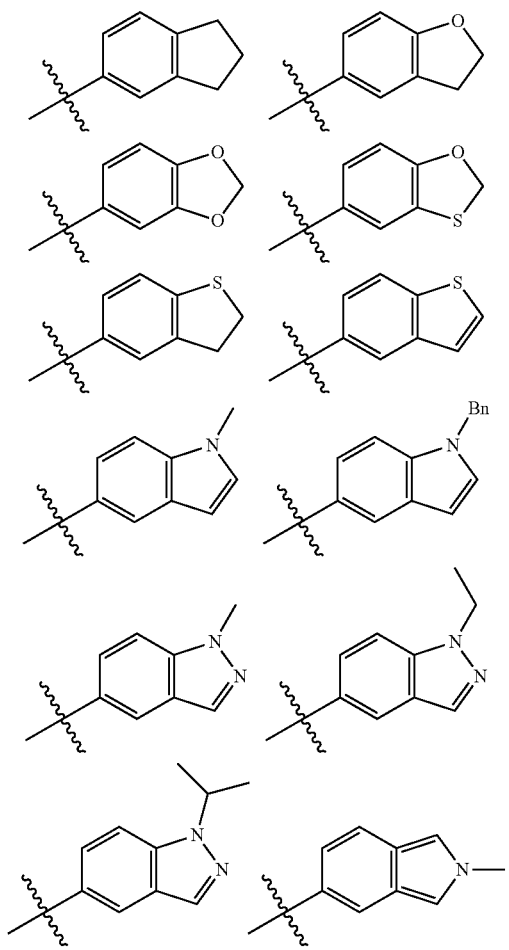

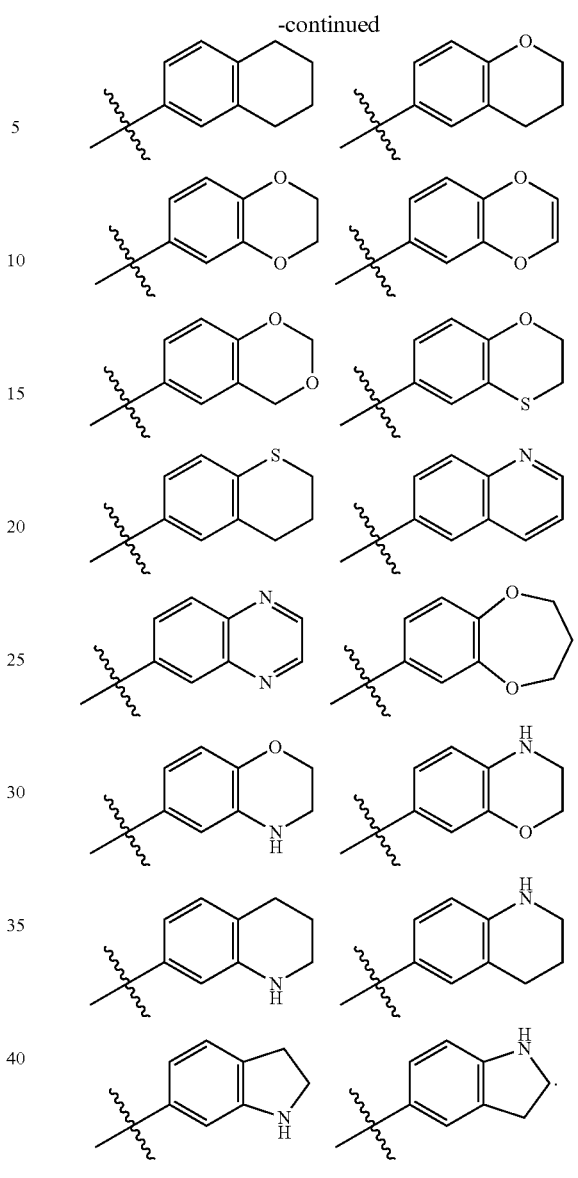

In a preferred embodiment of the present invention, ring A is a benzene, indane, indene, dihydrobenzofuran, dihydroisobenzofuran, benzofuran, dihydrobenzothiophene, benzothiophene, tetrahydronaphthalene, dihydronaphthalene, chroman, chromene, isochroman, isochromene, benzodioxole, benzodioxane, benzooxazine, tetrahydroquinoline, tetrahydroquinoxaline, tetrahydroisoquinoline, indazole, indole, indoline, benzoimidazole, benzooxazole, benzothiazole, benzotriazole, quinazoline, quinoxaline, cinnoline, phthalazine, or benzotriazine ring, which is optionally substituted with a substituent as defined herein.

In a preferred embodiment of the present invention, ring B is a quinoline, quinoxaline, 3,4-dihydro-2H-benzo[b][1,4]dioxepine, 2,3-dihydrobenzo[b]thiophene, indazole, indole, 2,3-dihydrobenzo[b][1,4]dioxine, benzodioxole, indane, tetrahydronaphthalene, 3,4-dihydro-2H-thiochromene, dihydrobenzofuran, benzo[d][1,3]oxathiole, tetrahydroquinoline, or 3,4-dihydro-2H-benzo[b][1,4]oxazine ring, which is optionally substituted with a substituent as defined herein.

Compounds especially useful in the present invention are selected from the group consisting of:

(1) (2S,3R,4R,5S,6R)-2-(7-bromo-6-(4-methoxybenzyl)-2,3-dihydro-1H-inden-4-yl)-6-(hydroxymethyl)tetrahydro-2H-pyran-3,4,5-triol;
(2) (2S,3R,4R,5S,6R)-2-(7-bromo-6-(4-ethoxybenzyl)-2,3-dihydro-1H-inden-4-yl)-6-(hydroxymethyl)tetrahydro-2H-pyran-3,4,5-triol;
(3) (2S,3R,4R,5S,6R)-2-(7-bromo-6-(4-ethylbenzyl)-2,3-dihydro-1H-inden-4-yl)-6-(hydroxymethyl)tetrahydro-2H-pyran-3,4,5-triol;
(4) (2S,3R,4R,5S,6R)-2-(7-chloro-6-(4-methoxybenzyl)-2,3-dihydro-1H-inden-4-yl)-6-(hydroxymethyl)tetrahydro-2H-pyran-3,4,5-triol;
(5) (2S,3R,4R,5S,6R)-2-(7-fluoro-6-(4-methoxybenzyl)-2,3-dihydro-1H-inden-4-yl)-6-(hydroxymethyl)tetrahydro-2H-pyran-3,4,5-triol;
(6) (2R,3S,4R,5R,6S)-2-(hydroxymethyl)-6-(6-(4-methoxybenzyl)-7-methyl-2,3-dihydro-1H-inden-4-yl)tetrahydro-2H-pyran-3,4,5-triol;
(7) (2S,3R,4R,5S,6R)-2-(7-chloro-6-(4-ethoxybenzyl)-2,3-dihydro-1H-inden-4-yl)-6-(hydroxymethyl)tetrahydro-2H-pyran-3,4,5-triol
(8) (2S,3R,4R,5S,6R)-2-(6-(4-ethoxybenzyl)-7-methyl-2,3-dihydro-1H-inden-4-yl)-6-(hydroxymethyl)tetrahydro-2H-pyran-3,4,5-triol;
(9) (2S,3R,4R,5S,6R)-2-(4-chloro-5-(4-ethylbenzyl)-2,3-dihydrobenzofuran-7-yl)-6-(hydroxymethyl)tetrahydro-2H-pyran-3,4,5-triol;
(10) (2S,3R,4R,5S,6R)-2-(4-chloro-5-(4-ethoxybenzyl)-2-methyl-2,3-dihydrobenzofuran-7-yl)-6-(hydroxymethyl)tetrahydro-2H-pyran-3,4,5-triol;
(11) (2S,3R,4R,5S,6R)-2-(5-chloro-6-(4-ethoxybenzyl)chroman-8-yl)-6-(hydroxymethyl)tetrahydro-2H-pyran-3,4,5-triol;
(12) (2S,3R,4R,5S,6R)-2-(8-chloro-7-(4-ethoxybenzyl)-2,3-dihydrobenzo[b][1,4]dioxin-5-yl)-6-(hydroxymethyl)tetrahydro-2H-pyran-3,4,5-triol;
(13) (2S,3R,4R,5S,6R)-2-(5-chloro-6-(4-methoxybenzyl)chroman-8-yl)-6-(hydroxymethyl)tetrahydro-2H-pyran-3,4,5-triol;
(14) (2S,3R,4R,5S,6R)-2-(5-chloro-6-(4-ethylbenzyl)chroman-8-yl)-6-(hydroxymethyl)tetrahydro-2H-pyran-3,4,5-triol;
(15) (2S,3R,4R,5S,6R)-2-(7-chloro-6-(4-methoxybenzyl)-2,3-dihydrobenzofuran-4-yl)-6-(hydroxymethyl)tetrahydro-2H-pyran-3,4,5-triol;
(16) (2S,3R,4R,5S,6R)-2-(6-(4-ethylbenzyl)-7-chloro-2,3-dihydrobenzofuran-4-yl)-6-(hydroxymethyl)-tetrahydro-2H-pyran-3,4,5-triol;
(17) (2S,3R,4R,5S,6R)-2-(4-chloro-5-(4-methoxybenzyl)-2,3-dihydrobenzofuran-7-yl)-6-(hydroxymethyl)tetrahydro-2H-pyran-3,4,5-triol;
(18) (2S,3R,4R,5S,6R)-2-(4-chloro-5-(4-ethoxybenzyl)-2,3-dihydrobenzofuran-7-yl)-6-(hydroxymethyl)tetrahydro-2H-pyran-3,4,5-triol;
(19) (2S,3R,4R,5S,6R)-2-(8-chloro-7-(4-ethylbenzyl)chroman-5-yl)-6-(hydroxymethyl)tetrahydro-2H-pyran-3,4,5-triol;
(20) (2S,3R,4R,5S,6R)-2-(7-chloro-6-(4-ethoxybenzyl)-2,3-dihydrobenzofuran-4-yl)-6-(hydroxymethyl)tetrahydro-2H-pyran-3,4,5-triol;
(21) (2S,3R,4R,5S,6R)-2-(5-chloro-6-((2,3-dihydrobenzo[b][1,4]dioxin-6-yl)methyl)chroman-8-yl)-6-(hydroxymethyl)tetrahydro-2H-pyran-3,4,5-triol;
(22) (2S,3R,4R,5S,6R)-2-(7-chloro-6-((2,3-dihydrobenzo[b][1,4]dioxin-6-yl)methyl)-2,3-dihydrobenzofuran-4-yl)-6-(hydroxymethyl)tetrahydro-2H-pyran-3,4,5-triol;
(23) (2S,3R,4R,5S,6R)-2-(5-(4-(ethoxybenzyl)-6-methylbiphenyl-3-yl)-6-(hydroxymethyl)-tetrahydro-2H-pyran-3,4,5-triol;
(24) (2S,3R,4R,5S,6R)-2-(5-((2,3-dihydrobenzo[b][1,4]dioxin-6-yl)methyl)-6-methylbiphenyl-3-yl)-6-(hydroxymethyl)-tetrahydro-2H-pyran-3,4,5-triol;
(25) (2S,3R,4R,5S,6R)-2-(3-(4-ethoxybenzyl)-4-methyl-5-(thiophen-3-yl)phenyl)-6-(hydroxymethyl)-tetrahydro-2H-pyran-3,4,5-triol;
(26) (2S,3R,4R,5S,6R)-2-(3-(4-ethoxybenzyl)-4-methyl-5-(thiophen-2-yl)phenyl)-6-(hydroxymethyl)-tetrahydro-2H-pyran-3,4,5-triol;
(27) (2S,3R,4R,5S,6S)-2-(7-bromo-6-(4-methoxybenzyl)-2,3-dihydro-1H-inden-4-yl)-6-methoxy-tetrahydro-2H-pyran-3,4,5-triol;
(28) (2S,3R,4R,5S,6R)-2-(8-chloro-7-((2,3-dihydrobenzo[b][1,4]dioxin-6-yl)methyl)-2,3-dihydrobenzo[b][1,4]dioxin-5-yl)-6-(hydroxymethyl)tetrahydro-2H-pyran-3,4,5-triol;
(29) (2S,3R,4R,5S,6R)-2-(8-chloro-7-(4-methoxybenzyl)-2,3-dihydrobenzo[b][1,4]dioxin-5-yl)-6-(hydroxymethyl)tetrahydro-2H-pyran-3,4,5-triol;
(30) (2S,3R,4R,5S,6R)-2-(8-chloro-7-(4-ethylbenzyl)-2,3-dihydrobenzo[b][1,4]dioxin-5-yl)-6-(hydroxymethyl)tetrahydro-2H-pyran-3,4,5-triol;
(31) (2S,3R,4R,5S,6R)-2-(7-chloro-6-((2,3-dihydrobenzo[b][1,4]dioxin-6-yl)methyl)-2,3-dihydro-1H-inden-4-yl)-6-(hydroxymethyl)tetrahydro-2H-pyran-3,4,5-triol;
(32) (2S,3R,4R,5S,6R)-2-(6-((2,3-dihydrobenzo[b][1,4]dioxin-6-yl)methyl)-7-methyl-2,3-dihydro-1H-inden-4-yl)-6-(hydroxymethyl)tetrahydro-2H-pyran-3,4,5-triol;
(33) (2S,3R,4R,5S,6R)-2-(7-(difluoromethyl)-6-((2,3-dihydrobenzo[b][1,4]dioxin-6-yl)methyl)-2,3-dihydro-1H-inden-4-yl)-6-(hydroxymethyl)tetrahydro-2H-pyran-3,4,5-triol;
(34) (2S,3R,4R,5S,6R)-2-(2-(allyloxy)-4-chloro-5-(4-methoxybenzyl)phenyl)-6-(methylthio)tetrahydro-2H-pyran-3,4,5-triol;
(35) (2S,3R,4R,5S,6R)-2-(4-chloro-5-(4-ethoxybenzyl)-2-methoxyphenyl)-6-(methylthio)tetrahydro-2H-pyran-3,4,5-triol;
(36) (2S,3R,4R,5S,6R)-2-(4-chloro-5-(4-ethoxybenzyl)-2-methoxyphenyl)-6-(methylsulfonyl)tetrahydro-2H-pyran-3,4,5-triol;
(37) (2S,3R,4R,5S,6R)-2-(4-chloro-3-((2,3-dihydrobenzo[b][1,4]dioxin-6-yl)methyl)-5-methoxyphenyl)-6-(methylthio)tetrahydro-2H-pyran-3,4,5-triol;
(38) (2S,3R,4R,5S,6R)-2-(4-chloro-3-(4-ethoxybenzyl)-5-methoxyphenyl)-6-(methylthio)tetrahydro-2H-pyran-3,4,5-triol;
(39) (2S,3R,4R,5S,6S)-2-(2-(allyloxy)-4-chloro-5-(4-methoxybenzyl)phenyl)-6-methoxytetrahydro-2H-pyran-3,4,5-triol;
(40) (2S,3R,4R,5S,6R)-2-(7-chloro-6-(4-(dimethylamino)benzyl)-2,3-dihydro-1H-inden-4-yl)-6-(hydroxymethyl)tetrahydro-2H-pyran-3,4,5-triol;
(41) (2S,3R,4R,5S,6R)-2-(7-chloro-6-(4-vinylbenzyl)-2,3-dihydro-1H-inden-4-yl)-6-(hydroxymethyl)tetrahydro-2H-pyran-3,4,5-triol;
(42) (2S,3R,4R,5S,6R)-2-(7-chloro-6-(4-cyclopropylbenzyl)-2,3-dihydro-1H-inden-4-yl)-6-(hydroxymethyl)tetrahydro-2H-pyran-3,4,5-triol;
(43) (2S,3R,4R,5S,6R)-2-(4-chloro-5-(4-vinylbenzyl)-2,3-dihydrobenzofuran-7-yl)-6-(hydroxymethyl)tetrahydro-2H-pyran-3,4,5-triol;

(44) (2S,3R,4R,5S,6R)-2-(4-chloro-5-(4-cyclopropylbenzyl)-2,3-dihydrobenzofuran-7-yl)-6-(hydroxymethyl)tetrahydro-2H-pyran-3,4,5-triol;

(45) ((2S,3R,4R,5S,6R)-2-(5-chloro-6-(4-cyclopropylbenzyl)chroman-8-yl)-6-(hydroxymethyl)tetrahydro-2H-pyran-3,4,5-triol;

(46) (2S,3R,4R,5S,6R)-2-(4-chloro-5-(4-(trifluoromethyl)benzyl)-2,3-dihydrobenzofuran-7-yl)-6-(hydroxymethyl)tetrahydro-2H-pyran-3,4,5-triol;

(47) (2S,3R,4R,5S,6R)-2-(4-chloro-5-(4-chlorobenzyl)-2,3-dihydrobenzofuran-7-yl)-6-(hydroxymethyl)tetrahydro-2H-pyran-3,4,5-triol;

(48) (2S,3R,4R,5S,6R)-2-(7-chloro-6-(4-(trifluoromethyl)benzyl)-2,3-dihydrobenzofuran-4-yl)-6-(hydroxymethyl)tetrahydro-2H-pyran-3,4,5-triol;

(49) (2S,3R,4S,5S,6R)-2-(7-chloro-6-(4-ethoxybenzyl)-2,3-dihydrobenzofuran-4-yl)-6-methyltetrahydro-2H-pyran-3,4,5-triol;

(50) (2S,3R,4R,5S,6S)-2-(7-chloro-6-(4-ethoxybenzyl)-2,3-dihydrobenzofuran-4-yl)-6-(fluoromethyl)tetrahydro-2H-pyran-3,4,5-triol;

(51) (2S,3R,4R,5S,6R)-2-(7-chloro-6-(4-ethoxybenzyl)-2,3-dihydrobenzofuran-4-yl)-6-(1-hydroxyethyl)tetrahydro-2H-pyran-3,4,5-triol;

(52) (2S,3R,4R,5S,6S)-2-(7-chloro-6-(4-ethoxybenzyl)-2,3-dihydrobenzofuran-4-yl)-6-(difluoromethyl)tetrahydro-2H-pyran-3,4,5-triol;

(53) (2S,3R,4R,5S,6R)-2-(6-(4-ethoxybenzyl)-7-methyl-2,3-dihydrobenzofuran-4-yl)-6-(hydroxymethyl)tetrahydro-2H-pyran-3,4,5-triol;

(54) (2S,3R,4R,5S,6R)-2-(7-chloro-6-(4-methoxybenzyl)-2-methyl-2,3-dihydrobenzofuran-4-yl)-6-(hydroxymethyl)tetrahydro-2H-pyran-3,4,5-triol;

(55) (2S,3R,4R,5S,6R)-2-(4-chloro-5-(4-methoxybenzyl)-2-methyl-2,3-dihydrobenzofuran-7-yl)-6-(hydroxymethyl)tetrahydro-2H-pyran-3,4,5-triol;

(56) (2S,3R,4R,5S,6R)-2-(4-chloro-5-(4-ethylbenzyl)-2-methyl-2,3-dihydrobenzofuran-7-yl)-6-(hydroxymethyl)tetrahydro-2H-pyran-3,4,5-triol;

(57) (2S,3R,4R,5S,6R)-2-(4-chloro-5-(4-cyclopropylbenzyl)-2-methyl-2,3-dihydrobenzofuran-7-yl)-6-(hydroxymethyl)tetrahydro-2H-pyran-3,4,5-triol;

(58) (2S,3R,4R,5S,6R)-2-(4-chloro-2-methyl-5-(4-propylbenzyl)-2,3-dihydrobenzofuran-7-yl)-6-(hydroxymethyl)tetrahydro-2H-pyran-3,4,5-triol;

(59) (2S,3R,4R,5S,6R)-2-(7-chloro-6-(4-ethoxybenzyl)-2-methyl-2,3-dihydrobenzofuran-4-yl)-6-(hydroxymethyl)tetrahydro-2H-pyran-3,4,5-triol;

(60) (2S,3R,4R,5S,6R)-2-(7-chloro-6-(4-ethylbenzyl)-2-methyl-2,3-dihydrobenzofuran-4-yl)-6-(hydroxymethyl)tetrahydro-2H-pyran-3,4,5-triol;

(61) (2S,3R,4R,5S,6R)-2-(7-chloro-2-methyl-6-(4-vinylbenzyl)-2,3-dihydrobenzofuran-4-yl)-6-(hydroxymethyl)tetrahydro-2H-pyran-3,4,5-triol;

(62) ((2S,3R,4R,5S,6R)-2-(7-chloro-6-(4-cyclopropylbenzyl)-2-methyl-2,3-dihydrobenzofuran-4-yl)-6-(hydroxymethyl)tetrahydro-2H-pyran-3,4,5-triol;

(63) (2S,3R,4R,5S,6R)-2-(7-chloro-6-(4-methylbenzyl)-2,3-dihydro-1H-inden-4-yl)-6-(hydroxymethyl)tetrahydro-2H-pyran-3,4,5-triol;

(64) (2S,3R,4R,5S,6R)-2-(7-chloro-6-(4-(methylamino)benzyl)-2,3-dihydro-1H-inden-4-yl)-6-(hydroxymethyl)tetrahydro-2H-pyran-3,4,5-triol 2,2,2-trifluoroacetate

(65) (2S,3R,4R,5S,6R)-2-(7-chloro-6-(4-(methylamino)benzyl)-2,3-dihydrobenzofuran-4-yl)-6-(hydroxymethyl)tetrahydro-2H-pyran-3,4,5-triol 2,2,2-trifluoroacetate

(66) (2S,3R,4R,5S,6R)-2-(4-chloro-5-(4-methoxybenzyl)-2-methyl-2,3-dihydrobenzo[b]thiophen-7-yl)-6-(hydroxymethyl)tetrahydro-2H-pyran-3,4,5-triol;

(67) (2S,3R,4R,5S,6R)-2-(4-chloro-5-(4-ethoxybenzyl)-2-methyl-2,3-dihydrobenzo[b]thiophen-7-yl)-6-(hydroxymethyl)tetrahydro-2H-pyran-3,4,5-triol;

(68) (2S,3R,4R,5S,6R)-2-(4-chloro-5-(4-ethylbenzyl)-2-methyl-2,3-dihydrobenzo[b]thiophen-7-yl)-6-(hydroxymethyl)tetrahydro-2H-pyran-3,4,5-triol;

(69) (2S,3R,4R,5S,6R)-2-(4-chloro-5-(4-ethoxybenzyl)-2-methyl-2,3-dihydrobenzofuran-7-yl)-6-(methylthio)tetrahydro-2H-pyran-3,4,5-triol;

(70) (2S,3R,4R,5S,6R)-2-(4-chloro-5-(4-ethoxybenzyl)-2-methyl-2,3-dihydrobenzofuran-7-yl)-6-(methylsulfonyl)tetrahydro-2H-pyran-3,4,5-triol;

(71) (2S,3R,4R,5S,6R)-2-(4-chloro-5-(4-ethoxybenzyl)-2-methyl-2,3-dihydrobenzofuran-7-yl)-6-((S)-methylsulfinyl)tetrahydro-2H-pyran-3,4,5-triol;

(72) (2S,3R,4R,5S,6R)-2-(8-chloro-7-(4-ethoxybenzyl)-2,3-dihydrobenzo[b][1,4]dioxin-5-yl)-6-(methylthio)tetrahydro-2H-pyran-3,4,5-triol;

(73) (2S,3R,4R,5S,6R)-2-(4-chloro-5-(4-isopropylbenzyl)-2-methyl-2,3-dihydrobenzofuran-7-yl)-6-(hydroxymethyl)tetrahydro-2H-pyran-3,4,5-triol;

(74) (2S,3R,4R,5S,6R)-2-(4-chloro-5-(4-isopropylbenzyl)-2-methyl-2,3-dihydrobenzofuran-7-yl)-6-(hydroxymethyl)tetrahydro-2H-pyran-3,4,5-triol;

(75) (2S,3R,4R,5S,6R)-2-(4-chloro-5-(4-ethoxybenzyl)-2,3-dimethoxyphenyl)-6-(hydroxymethyl)tetrahydro-2H-pyran-3,4,5-triol;

(76) (2S,3R,4R,5S,6R)-2-(4-chloro-5-(4-ethoxybenzyl)-3-hydroxy-2-methoxyphenyl)-6-(hydroxymethyl)tetrahydro-2H-pyran-3,4,5-triol;

(77) (2S,3R,4R,5S,6R)-2-(7-chloro-6-(4-ethylbenzyl)-3-methyl-2,3-dihydrobenzofuran-4-yl)-6-(hydroxymethyl)tetrahydro-2H-pyran-3,4,5-triol;

(78) (2S,3R,4R,5S,6R)-2-(5-chloro-6-(4-(methylthio)benzyl)chroman-8-yl)-6-(hydroxymethyl)tetrahydro-2H-pyran-3,4,5-triol;

(79) (2S,3R,4R,5S,6R)-2-(8-chloro-7-(4-cyclopropylbenzyl)chroman-5-yl)-6-(hydroxymethyl)tetrahydro-2H-pyran-3,4,5-triol;

(80) (2S,3R,4R,5S,6R)-2-(8-chloro-7-(4-methoxybenzyl)chroman-5-yl)-6-(hydroxymethyl)tetrahydro-2H-pyran-3,4,5-triol;

(81) (2S,3R,4R,5S,6R)-2-(8-chloro-7-(4-ethoxybenzyl)chroman-5-yl)-6-(hydroxymethyl)tetrahydro-2H-pyran-3,4,5-triol;

(82) (2S,3R,4R,5S,6R)-2-(7-chloro-6-(4-cyclopropylbenzyl)benzo[d][1,3]dioxol-4-yl)-6-(hydroxymethyl)tetrahydro-2H-pyran-3,4,5-triol;

(83) (2S,3R,4R,5S,6R)-2-(7-chloro-6-(4-isopropylbenzyl)benzo[d][1,3]dioxol-4-yl)-6-(hydroxymethyl)tetrahydro-2H-pyran-3,4,5-triol;

(84) (2S,3R,4R,5S,6R)-2-(7-chloro-6-(4-ethoxybenzyl)benzo[d][1,3]dioxol-4-yl)-6-(hydroxymethyl)tetrahydro-2H-pyran-3,4,5-triol;

(85) (2S,3R,4R,5S,6R)-2-(7-chloro-6-(4-methoxybenzyl)benzo[d][1,3]dioxol-4-yl)-6-(hydroxymethyl)tetrahydro-2H-pyran-3,4,5-triol;

(86) (2S,3R,4R,5S,6R)-2-(7-chloro-6-(4-ethylbenzyl)benzo[d][1,3]dioxol-4-yl)-6-(hydroxymethyl)tetrahydro-2H-pyran-3,4,5-triol;

(87) (2S,3R,4R,5S,6R)-2-(8-chloro-7-(4-cyclopropylbenzyl)-2,3-dihydrobenzo[b][1,4]dioxin-5-yl)-6-(hydroxymethyl)tetrahydro-2H-pyran-3,4,5-triol;

(88) (2S,3R,4R,5S,6R)-2-(9-chloro-8-(4-ethoxybenzyl)-3,4-dihydro-2H-benzo[b][1,4]dioxepin-6-yl)-6-(hydroxymethyl)tetrahydro-2H-pyran-3,4,5-triol;

(89) (2S,3R,4R,5S,6R)-2-(9-chloro-8-(4-ethylbenzyl)-3,4-dihydro-2H-benzo[b][1,4]dioxepin-6-yl)-6-(hydroxymethyl)tetrahydro-2H-pyran-3,4,5-triol;

(90) (2S,3R,4R,5S,6R)-2-(6-benzyl-7-chloro-2,3-dihydrobenzofuran-4-yl)-6-(hydroxymethyl)tetrahydro-2H-pyran-3,4,5-triol;

(91) 1-(4-((7-chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)phenyl)ethanone;

(92) (2S,3R,4R,5S,6R)-2-(7-chloro-6-(4-(1-hydroxyethyl)benzyl)-2,3-dihydrobenzofuran-4-yl)-6-(hydroxymethyl)tetrahydro-2H-pyran-3,4,5-triol;

(93) (2S,3R,4R,5S,6R)-2-(7-chloro-6-(4-(1-fluoroethyl)benzyl)-2,3-dihydrobenzofuran-4-yl)-6-(hydroxymethyl)tetrahydro-2H-pyran-3,4,5-triol;

(94) (2S,3R,4R,5S,6R)-2-(7-chloro-6-(4-vinylbenzyl)-2,3-dihydrobenzofuran-4-yl)-6-(hydroxymethyl)tetrahydro-2H-pyran-3,4,5-triol;

(95) (2S,3R,4R,5S,6R)-2-(7-chloro-6-(4-cyclopropylbenzyl)-2,3-dihydrobenzofuran-4-yl)-6-(hydroxymethyl)tetrahydro-2H-pyran-3,4,5-triol;

(96) (2S,3R,4R,5S,6R)-2-(4-chloro-5-(4-cyclopropylbenzyl)benzofuran-7-yl)-6-(hydroxymethyl)tetrahydro-2H-pyran-3,4,5-triol;

(97) (2S,3R,4R,5S,6R)-2-(7-chloro-6-(4-(2-hydroxypropan-2-yl)benzyl)-2,3-dihydrobenzofuran-4-yl)-6-(hydroxymethyl)tetrahydro-2H-pyran-3,4,5-triol;

(98) (2S,3R,4R,5S,6R)-2-(7-chloro-6-(4-(difluoromethyl)benzyl)-2,3-dihydrobenzofuran-4-yl)-6-(hydroxymethyl)tetrahydro-2H-pyran-3,4,5-triol;

(99) (2S,3R,4R,5S,6R)-2-(7-chloro-6-(4-(1,1-difluoroethyl)benzyl)-2,3-dihydrobenzofuran-4-yl)-6-(hydroxymethyl)tetrahydro-2H-pyran-3,4,5-triol;

(100) (2S,3R,4R,5S,6R)-2-(6-(4-cyclopropylbenzyl)-7-methyl-2,3-dihydrobenzofuran-4-yl)-6-(hydroxymethyl)tetrahydro-2H-pyran-3,4,5-triol;

(101) (2S,3R,4R,5S,6R)-2-(7-chloro-6-(4-(2-hydroxybut-3-yn-2-yl)benzyl)-2,3-dihydrobenzofuran-4-yl)-6-(hydroxymethyl)tetrahydro-2H-pyran-3,4,5-triol;

(102) (2S,3R,4R,5S,6R)-2-(7-chloro-6-(4-(prop-1-en-2-yl)benzyl)-2,3-dihydrobenzofuran-4-yl)-6-(hydroxymethyl)tetrahydro-2H-pyran-3,4,5-triol;

(103) (2S,3R,4R,5S,6R)-2-(7-chloro-6-(4-isopropylbenzyl)-2,3-dihydrobenzofuran-4-yl)-6-(hydroxymethyl)tetrahydro-2H-pyran-3,4,5-triol;

(104) (2S,3R,4R,5S,6R)-2-(7-chloro-6-(4-ethynylbenzyl)-2,3-dihydrobenzofuran-4-yl)-6-(hydroxymethyl)tetrahydro-2H-pyran-3,4,5-triol;

(105) 4-((7-chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)benzonitrile;

(106) (2S,3R,4R,5S,6R)-2-(7-chloro-6-(4-propylbenzyl)-2,3-dihydrobenzofuran-4-yl)-6-(hydroxymethyl)tetrahydro-2H-pyran-3,4,5-triol;

(107) (2S,3R,4R,5S,6R)-2-(7-chloro-6-(4-methoxybenzyl)-2,3-dihydrobenzofuran-4-yl)-6-(hydroxymethyl)tetrahydro-2H-thiopyran-3,4,5-triol;

(108) (2S,3R,4R,5S,6R)-2-(7-chloro-6-(4-(methylthio)benzyl)-2,3-dihydrobenzofuran-4-yl)-6-(hydroxymethyl)tetrahydro-2H-pyran-3,4,5-triol;

(109) (2S,3R,4R,5S,6R)-2-(7-chloro-6-(4-(dimethylamino)benzyl)-2,3-dihydrobenzofuran-4-yl)-6-(hydroxymethyl)tetrahydro-2H-pyran-3,4,5-triol;

(110) (2S,3R,4R,5S,6R)-2-(4-chloro-5-((2,3-dihydrobenzo[b][1,4]dioxin-6-yl)methyl)-2,3-dihydrobenzofuran-7-yl)-6-(hydroxymethyl)tetrahydro-2H-pyran-3,4,5-triol;

(111) (2S,3R,4R,5S,6R)-2-(7-chloro-6-(4-hydroxybenzyl)-2,3-dihydrobenzofuran-4-yl)-6-(hydroxymethyl)tetrahydro-2H-pyran-3,4,5-triol;

(112) (2S,3R,4R,5S,6R)-2-(7-chloro-6-(4-(3-hydroxypropoxy)benzyl)-2,3-dihydrobenzofuran-4-yl)-6-(hydroxymethyl)tetrahydro-2H-pyran-3,4,5-triol;

(113) (2S,3R,4R,5S,6R)-2-(7-chloro-6-(4-propoxybenzyl)-2,3-dihydrobenzofuran-4-yl)-6-(hydroxymethyl)tetrahydro-2H-pyran-3,4,5-triol;

(114) 4-chloro-5-(4-methoxybenzyl)-7-((2S,3R,4R,5S,6R)-3,4,5-trihydroxy-6-(hydroxymethyl)tetrahydro-2H-pyran-2-yl)benzofuran-3(2H)-one;

(115) (2S,3R,4R,5S,6R)-2-(4-chloro-3-hydroxy-5-(4-methoxybenzyl)-2,3-dihydrobenzofuran-7-yl)-6-(hydroxymethyl)tetrahydro-2H-pyran-3,4,5-triol;

(116) (2S,3R,4R,5S,6R)-2-(4-chloro-5-(4-(dimethylamino)benzyl)-2,3-dihydrobenzofuran-7-yl)-6-(hydroxymethyl)tetrahydro-2H-pyran-3,4,5-triol;

(117) (2S,3R,4R,5S,6R)-2-(7-chloro-6-(4-(2-cyclopropoxyethoxy)benzyl)-2,3-dihydrobenzofuran-4-yl)-6-(hydroxymethyl)tetrahydro-2H-pyran-3,4,5-triol;

(118) (2S,3R,4R,5S,6R)-2-(6-(4-(azetidin-1-yl)benzyl)-7-chloro-2,3-dihydrobenzofuran-4-yl)-6-(hydroxymethyl)tetrahydro-2H-pyran-3,4,5-triol;

(119) (2S,3R,4R,5S,6R)-2-(7-chloro-6-(4-(trifluoromethoxy)benzyl)-2,3-dihydrobenzofuran-4-yl)-6-(hydroxymethyl)tetrahydro-2H-pyran-3,4,5-triol;

(120) 2-(4-((7-chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)phenyl)acetonitrile;

(121) (2S,3R,4R,5S,6R)-2-(7-chloro-6-(4-(oxetan-3-yloxy)benzyl)-2,3-dihydrobenzofuran-4-yl)-6-(hydroxymethyl)tetrahydro-2H-pyran-3,4,5-triol;

(122) (2S,3R,4R,5S,6R)-2-(7-chloro-6-(4-isopropoxybenzyl)-2,3-dihydrobenzofuran-4-yl)-6-(hydroxymethyl)tetrahydro-2H-pyran-3,4,5-triol;

(123) (2S,3R,4R,5S,6R)-2-(7-chloro-6-(4-(cyclopropylthio)benzyl)-2,3-dihydrobenzofuran-4-yl)-6-(hydroxymethyl)tetrahydro-2H-pyran-3,4,5-triol;

(124) (2S,3R,4R,5S,6R)-2-(7-chloro-6-((5-methoxythiophen-2-yl)methyl)-2,3-dihydrobenzofuran-4-yl)-6-(hydroxymethyl)tetrahydro-2H-pyran-3,4,5-triol;

(125) (2S,3R,4R,5S,6R)-2-(5-chloro-6-(4-methoxybenzyl)chroman-8-yl)-6-(methylthio)tetrahydro-2H-pyran-3,4,5-triol;

(126) (2S,3R,4R,5S,6R)-2-(4-chloro-5-(4-methoxybenzyl)-2,3-dihydrobenzo[b]thiophen-7-yl)-6-(hydroxymethyl)tetrahydro-2H-pyran-3,4,5-triol;

(127) (2S,3R,4R,5S,6R)-2-(5-chloro-6-(4-ethoxybenzyl)-3,4-dihydro-2H-benzo[b][1,4]oxazin-8-yl)-6-(hydroxymethyl)tetrahydro-2H-pyran-3,4,5-triol;

(128) (2S,3R,4R,5S,6R)-2-(5-chloro-6-(4-ethoxybenzyl)-4-methyl-3,4-dihydro-2H-benzo[b][1,4]oxazin-8-yl)-6-(hydroxymethyl)tetrahydro-2H-pyran-3,4,5-triol;

(129) (2S,3R,4R,5S,6R)-2-(5-chloro-6-(4-ethylbenzyl)-3,4-dihydro-2H-benzo[b][1,4]oxazin-8-yl)-6-(hydroxymethyl)tetrahydro-2H-pyran-3,4,5-triol;

(130) (2S,3R,4R,5S,6R)-2-(4-chloro-5-(4-ethylbenzyl)-3-methyl-2,3-dihydrobenzofuran-7-yl)-6-(hydroxymethyl)tetrahydro-2H-pyran-3,4,5-triol;

(131) (2S,3R,4R,5S,6R)-2-(4-chloro-5-(4-methoxybenzyl)-3-methyl-2,3-dihydrobenzofuran-7-yl)-6-(hydroxymethyl)tetrahydro-2H-pyran-3,4,5-triol;

(132) (2S,3R,4R,5S,6R)-2-(4-chloro-5-(4-ethylbenzyl)-3,3-dimethyl-2,3-dihydrobenzofuran-7-yl)-6-(hydroxymethyl)tetrahydro-2H-pyran-3,4,5-triol;

(133) (2S,3R,4R,5S,6R)-2-(4-chloro-5-(4-methoxybenzyl)-3,3-dimethyl-2,3-dihydrobenzofuran-7-yl)-6-(hydroxymethyl)tetrahydro-2H-pyran-3,4,5-triol;

(134) (2S,3R,4R,5S,6R)-2-(4-chloro-5-(4-methoxybenzyl)-2,2-dimethyl-2,3-dihydrobenzofuran-7-yl)-6-(hydroxymethyl)tetrahydro-2H-pyran-3,4,5-triol;

(135) (2S,3R,4R,5S,6R)-2-(4-chloro-5-(4-ethoxybenzyl)-2,2-dimethyl-2,3-dihydrobenzofuran-7-yl)-6-(hydroxymethyl)tetrahydro-2H-pyran-3,4,5-triol;

(136) (2S,3R,4R,5S,6R)-2-(4-chloro-3-(4-(pyrrolidin-1-yl)benzyl)-6-(hydroxymethyl)-tetrahydro-2H-pyran-3,4,5-triol;

(137) (2S,3R,4R,5S,6R)-2-(4-chloro-5-(4-ethoxybenzyl)-3-methyl-2,3-dihydrobenzofuran-7-yl)-6-(hydroxymethyl)-tetrahydro-2H-pyran-3,4,5-triol;

(138) (2S,3R,4R,5S,6R)-2-(4-chloro-5-(4-ethoxybenzyl)-3,3-dimethyl-2,3-dihydrobenzofuran-7-yl)-6-(hydroxymethyl)-tetrahydro-2H-pyran-3,4,5-triol;

(139) (2S,3R,4R,5S,6R)-2-(7-chloro-6-(4-ethoxybenzyl)-3-methyl-2,3-dihydrobenzofuran-4-yl)-6-(hydroxymethyl)-tetrahydro-2H-pyran-3,4,5-triol;

(140) (2S,3R,4R,5S,6R)-2-(7-chloro-6-(4-ethoxybenzyl)-3,3-dimethyl-2,3-dihydrobenzofuran-4-yl)-6-(hydroxymethyl)-tetrahydro-2H-pyran-3,4,5-triol;

(141) 7-chloro-6-(4-ethoxybenzyl)-4-(2S,3R,4R,5S,6R)-3,4,5-trihydroxy-6-(hydroxymethyl)-tetrahydro-2H-pyran-2-yl)benzofuran-3(2H)-one (142) (2S,3R,4R,5S,6R)-2-(7-chloro-6-(4-ethoxybenzyl)-3-methoxy-2,3-dihydrobenzofuran-4-yl)-6-(hydroxymethyl)-tetrahydro-2H-pyran-3,4,5-triol;

(143) (2S,3R,4R,5S,6R)-2-(7-cyclopropyl-6-(4-ethoxybenzyl)-2,3-dihydrobenzofuran-4-yl)-6-(hydroxymethyl)-tetrahydro-2H-pyran-3,4,5-triol;

(144) (2S,3R,4R,5S,6R)-2-(6-(4-ethoxybenzyl)-7-propyl-2,3-dihydrobenzofuran-4-yl)-6-(hydroxymethyl)-tetrahydro-2H-pyran-3,4,5-triol;

(145) (2S,3R,4R,5S,6R)-2-(7-chloro-6-((1,2,3,4-tetrahydroquinolin-7-yl)methyl)-2,3-dihydrobenzofuran-4-yl)-6-(hydroxymethyl)-tetrahydro-2H-pyran-3,4,5-triol;

(146) (2S,3R,4R,5S,6R)-2-(7-chloro-6-((3,4-dihydro-2H-benzo[b][1,4]oxazin-6-yl)methyl)-2,3-dihydrobenzofuran-4-yl)-6-(hydroxymethyl)-tetrahydro-2H-pyran-3,4,5-triol;

(147) (2S,3R,4R,5S,6R)-2-(7-chloro-6-(4-(cyclopentyloxy)benzyl)-2,3-dihydrobenzofuran-4-yl)-6-(hydroxymethyl)-tetrahydro-2H-pyran-3,4,5-triol;

(148) (2S,3R,4R,5S,6R)-2-(7-chloro-6-(4-cyclopentylbenzyl)-2,3-dihydrobenzofuran-4-yl)-6-(hydroxymethyl)-tetrahydro-2H-pyran-3,4,5-triol;

(149) (2S,3R,4R,5S,6R)-2-(7-chloro-6-(4-cyclobutoxybenzyl)-2,3-dihydrobenzofuran-4-yl)-6-(hydroxymethyl)-tetrahydro-2H-pyran-3,4,5-triol;

(150) (2S,3R,4R,5S,6R)-2-(6-(4-tert-butylbenzyl)-7-chloro-2,3-dihydrobenzofuran-4-yl)-6-(hydroxymethyl)-tetrahydro-2H-pyran-3,4,5-triol;

(151) (2S,3R,4R,5S,6R)-2-(7-chloro-6-(4-cyclobutylbenzyl)-2,3-dihydrobenzofuran-4-yl)-6-(hydroxymethyl)-tetrahydro-2H-pyran-3,4,5-triol;

(152) (2S,3R,4R,5S,6R)-2-(7-(difluoromethyl)-6-(4-methoxybenzyl)-2,3-dihydro-1H-inden-4-yl)-6-(hydroxymethyl)tetrahydro-2H-pyran-3,4,5-triol;

(153) (2S,3R,4R,5S,6R)-2-(7-chloro-6-(4-ethylbenzyl)-2,3-dihydro-1H-inden-4-yl)-6-(hydroxymethyl)tetrahydro-2H-pyran-3,4,5-triol;

(154) (2S,3R,4R,5S,6R)-2-(7-(difluoromethyl)-6-(4-ethylbenzyl)-2,3-dihydro-1H-inden-4-yl)-6-(hydroxymethyl)tetrahydro-2H-pyran-3,4,5-triol;

(155) (2S,3R,4R,5S,6R)-2-(6-(4-(azetidin-1-yl)benzyl)-7-chloro-2,3-dihydro-1H-inden-4-yl)-6-(hydroxymethyl)tetrahydro-2H-pyran-3,4,5-triol;

(156) (2S,3R,4R,5S,6R)-2-(7-chloro-6-(4-methoxybenzyl)-2,3-dihydrobenzo[b]thiophen-4-yl)-6-(hydroxymethyl)tetrahydro-2H-pyran-3,4,5-triol;

(157) (2S,3R,4R,5S,6R)-2-(8-chloro-7-(4-methoxybenzyl)thiochroman-5-yl)-6-(hydroxymethyl)tetrahydro-2H-pyran-3,4,5-triol;

(158) (2R,3S,4R,5R,6S)-2-(hydroxymethyl)-6-(3-(4-methoxybenzyl)-4-methyl-5,6,7,8-tetrahydronaphthalen-1-yl)tetrahydro-2H-pyran-3,4,5-triol;

(159) (2S,3R,4R,5S,6R)-2-(4-chloro-5-((2,3-dihydrobenzo[b][1,4]dioxin-6-yl)methyl)-2-methoxyphenyl)-6-(hydroxymethyl)tetrahydro-2H-thiopyran-3,4,5-triol; and (160) (2S,3R,4R,5S,6R)-2-(7-chloro-6-(4-isopropylbenzyl)-2-methyl-2,3-dihydrobenzofuran-4-yl)-6-(hydroxymethyl)tetrahydro-2H-pyran-3,4,5-triol.

The inventive compound of formula I is effective as an inhibitor against sodium-dependent glucose cotransporter (SGLT2), thereby preventing or treating a metabolic disease.

Accordingly, the present invention provides a pharmaceutical composition for preventing or treating a metabolic disorder, which comprises the compound of formula I, or a pharmaceutically acceptable salt or a prodrug thereof as an active ingredient, and a pharmaceutically acceptable carrier.

The metabolic disorder may be diabetes, cardiovascular disease, or hypertension, preferably diabetes.

Further, the present invention provides a method for preventing or treating a metabolic disorder in a mammal, which comprises administering the compound of formula I or a pharmaceutically acceptable salt or a prodrug thereof to the mammal.

Also, the present invention provides a method for inhibiting SGLT2 in a mammal, which comprises administering the compound of formula I or a pharmaceutically acceptable salt or a prodrug thereof to the mammal.

The pharmaceutical composition may be administered orally or parenterally, e.g., intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerine or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg, and preferably from 1 mg to 100 mg of the compound of formula I or its pharmaceutically acceptable salt or prodrug.

The suitable daily dosage for oral administration is about 0.01 mg/kg body weight to 40 mg/kg body weight of the compound of formula I or its pharmaceutically acceptable salt or prodrug, and may be administered 1 to 6 times a day, depending on the patient's condition.

The present invention further provides a use of the compound of formula I or a pharmaceutically acceptable salt or a prodrug thereof for the manufacture of a medicament for preventing or treating a metabolic disorder, particularly diabetes.

The compounds of present invention may be prepared by several synthetic procedures. The compounds of the present invention and the preparation thereof will be better understood in connection with the following synthetic schemes, which are merely illustrative of the methods by which the compounds of the invention may be prepared and are not intended to limit the scope of the invention as defined in the appended claims.

General Synthetic Sequence

Some particular compounds of the present invention such as compounds of formula I-a can be prepared by a) reacting a compound of formula II with a compound of formula III to obtain a compound of formula IV; and (b) deprotecting and reducing the compound of formula IV to obtain a compound of formula I-a,

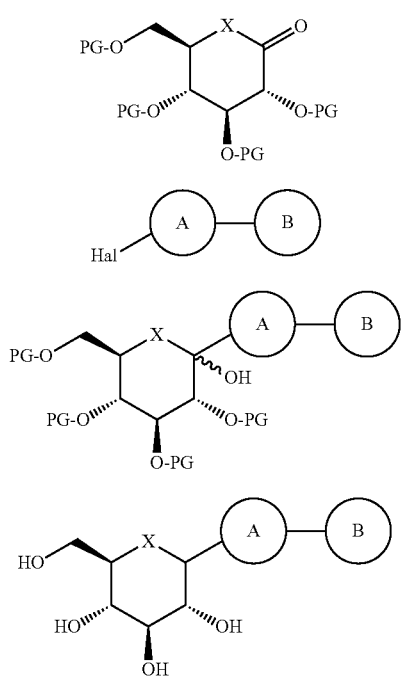

wherein, X, ring A and ring B are same as defined herein, Hal is halogen, and PG is trimethylsilyl or benzyl.

In one embodiment of the present invention, step (b) is carried out by deprotecting the compound of formula IV to obtain a compound of formula V, and reducing the compound of formula V to obtain the compound of formula I-a, when PG is trimethylsilyl:

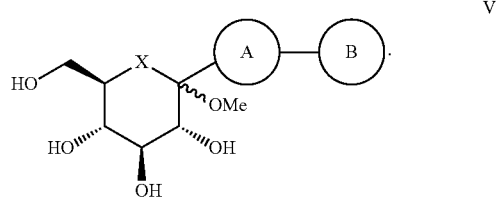

In another embodiment of the present invention, step (b) is carried out by reducing the compound of formula IV to obtain a compound of formula VI, and deprotecting the compound of formula VI to obtain the compound of formula I-a, when PG is benzyl:

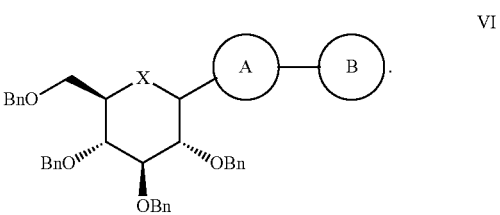

Hereinafter, the particular examples of the procedure are described in detail.

Scheme 1

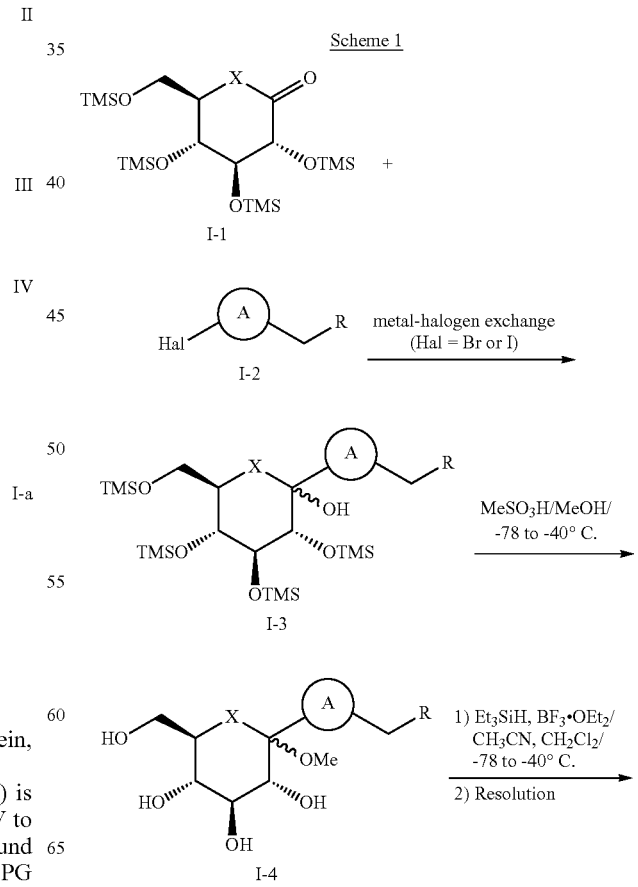

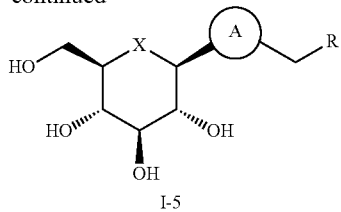

X: O or S
R: Aryl

A general synthetic route to desired compound I-5 is illustrated in Scheme 1. Metal-halogen exchange of halogenated compound I-2, followed by addition of the nascent organo metallic compound to persilylated gluconolactone or thiogluconolactone (*Tetrahedron Lett.* 1981, 22, 5061-5062; *J. Med. Chem.* 2010, 53, 3247-3261) I-1, produces a mixture of the corresponding lactol I-3, which is converted in situ to the desilylated O-methyl lactol by treatment with methansulfonic acid in methanol at cold conditions (−78~−40° C.). The reduction of the anomeric methoxy group of lactol I-4 using triethylsilane and boron trifluoride diethyl etherate is performed to generate the corresponding mixture of α,β-isomers. The required β-isomers I-5 are resolved by selective crystallization of peracetylated mixtures or prep. HPLC (reverse phase) of final compounds.

Scheme 2

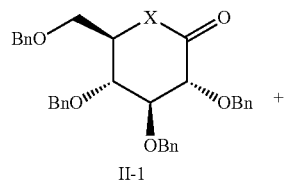

II-1

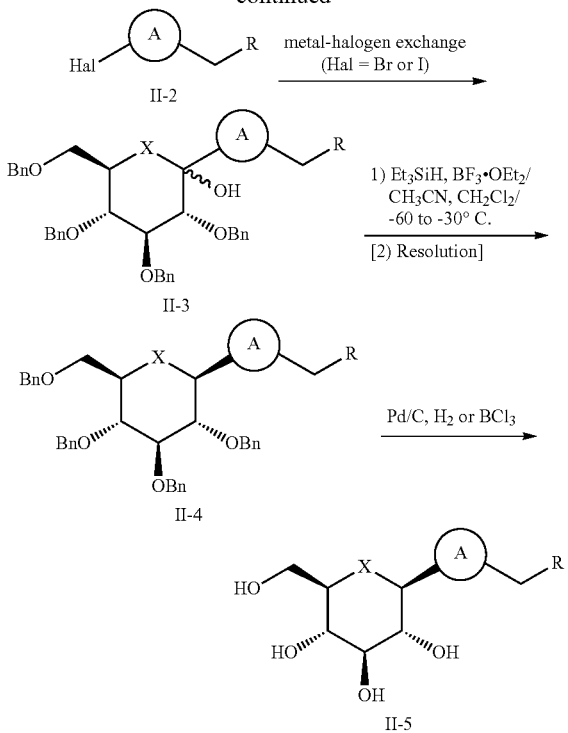

X: O or S
R: Aryl or O-Protective group

Perbenzylated gluconolactone or thiogluconolactone (*Tetrahedron Lett.* 1981, 22, 5061-5062; *J. Med. Chem.* 2010, 53, 3247-3261) II-1, instead of persilylated gluconolactone or thiogluconolactone I-1, is also used to prepare the corresponding lactols II-3, which are reduced using triethylsilane and boron trifluoride diethyl etherate. Deprotection of benzyl groups is performed using Pd/C under hydrogen atmosphere or BCl₃ at low temperature (<0° C.).

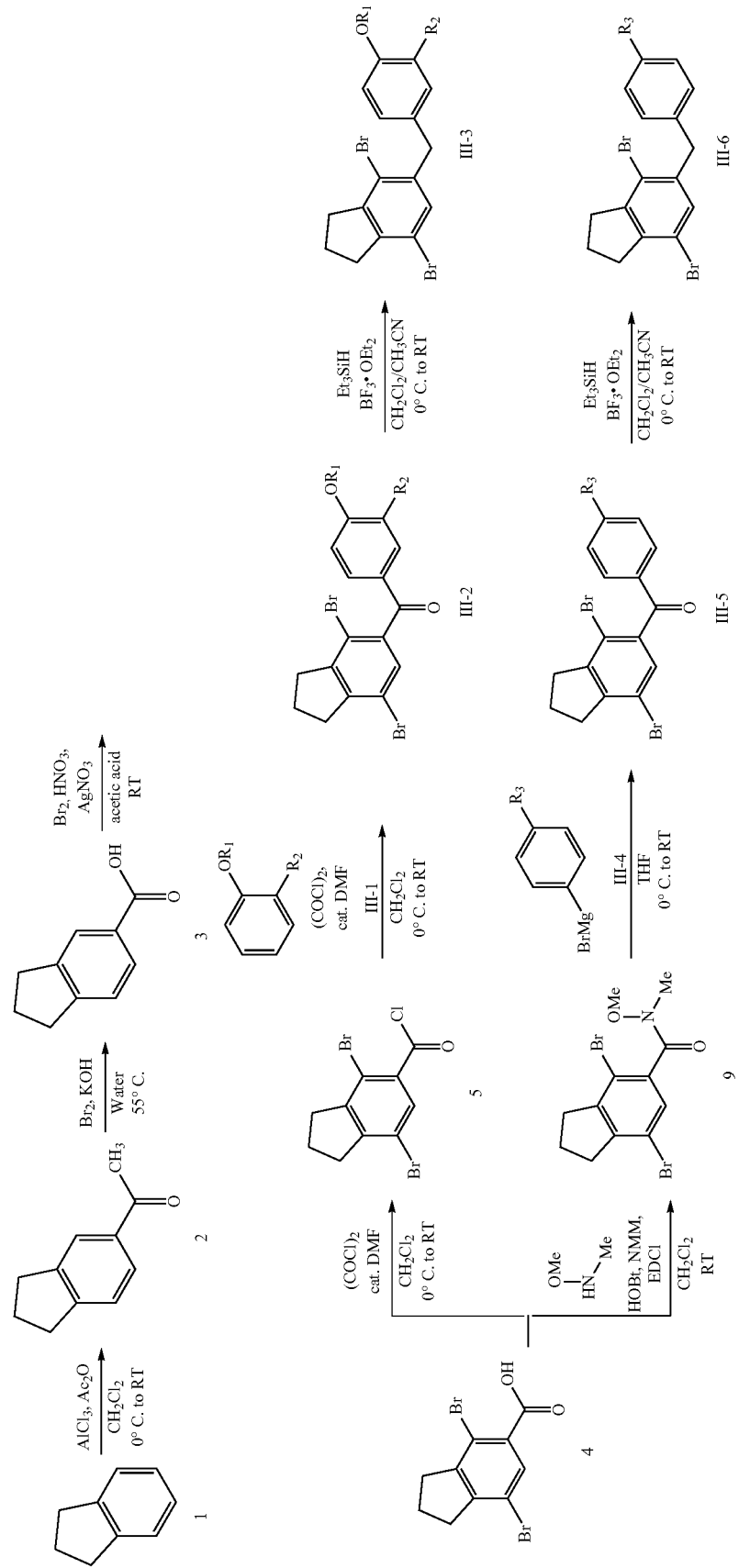

A key intermediate 4 is prepared from compound 1 through three steps. The starting material 1 is converted into the corresponding 5-acetylated intermediate 2 by the Friedel-Crafts reaction with acetyl anhydride in quantitative yield. The methyl ketone compound 2 is brought into haloform reaction to obtain benzoic acid 3 at heating conditions (55° C.). Bromination of the benzoic acid 3 with bromine and AgNO₃ gives the 2,5-dibromide intermediate 4 in acidic conditions.

The dibominated benzoic acid 4 is converted to the corresponding acyl chloride 5, which is used for the Friedel-Crafts acylation of compound III-1 to provide the desired diarylketone III-2. Reduction of diarylketone III-2 by triethylsilane in the presence of boron trifluoride etherate provides aglycon III-3. Alternatively, another desired aglycons III-6 are also synthesized through Weinreb amide 9, which is prepared from the acid 4 by treatment of N,O-dimethylhydroxylamine hydrochloride, HOBt, EDCI and NMM under mild conditions in good yield. Reaction of Weinreb amide 9 with proper organometallic nucleophiles, such as Grignard reagents III-4, produces the desired ketones III-5. Finally, the diarylketones III-5 are reduced by triethylsilane in the presence of boron trifluoride etherate to yield aglycon III-6.

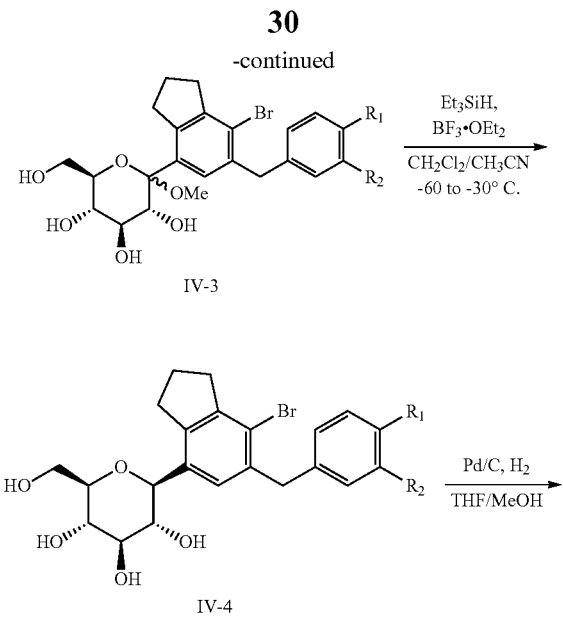

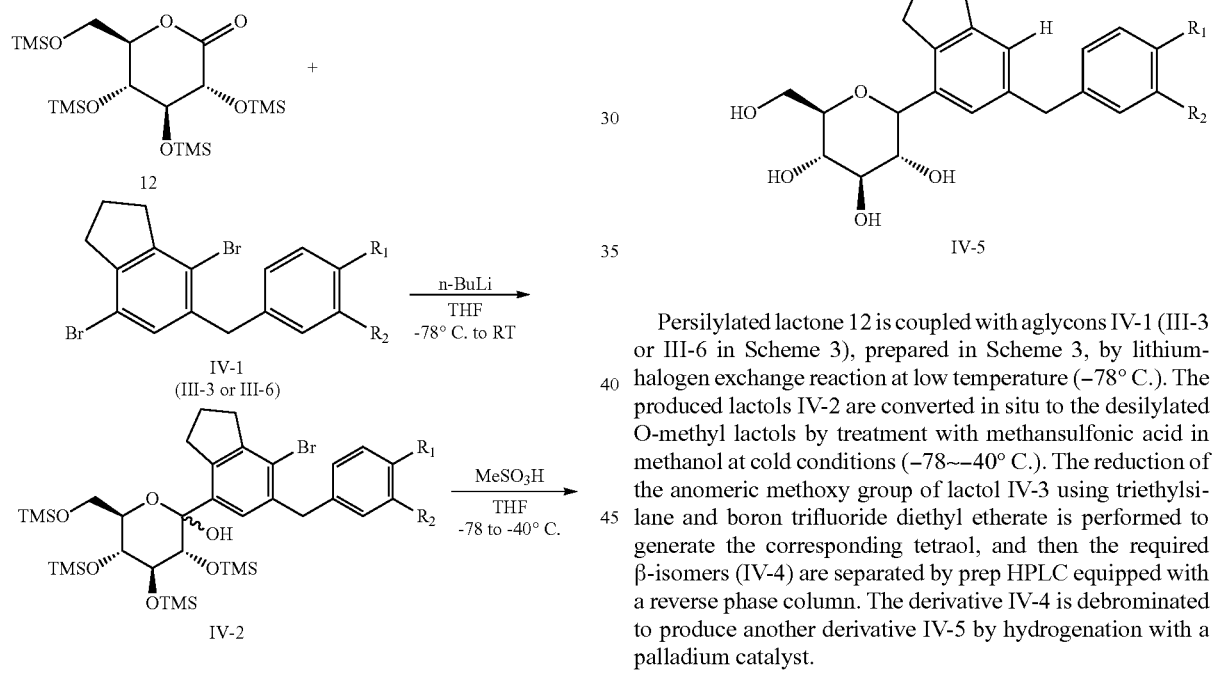

Persilylated lactone 12 is coupled with aglycons IV-1 (III-3 or III-6 in Scheme 3), prepared in Scheme 3, by lithium-halogen exchange reaction at low temperature (−78° C.). The produced lactols IV-2 are converted in situ to the desilylated O-methyl lactols by treatment with methansulfonic acid in methanol at cold conditions (−78~−40° C.). The reduction of the anomeric methoxy group of lactol IV-3 using triethylsilane and boron trifluoride diethyl etherate is performed to generate the corresponding tetraol, and then the required β-isomers (IV-4) are separated by prep HPLC equipped with a reverse phase column. The derivative IV-4 is debrominated to produce another derivative IV-5 by hydrogenation with a palladium catalyst.

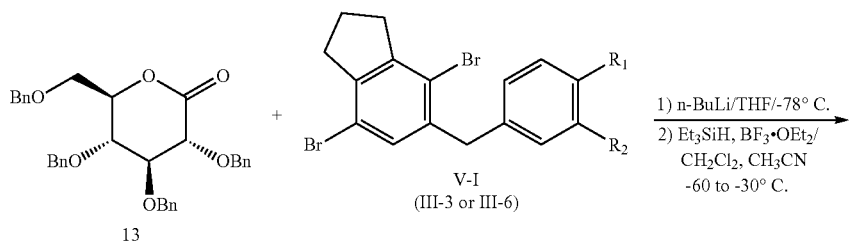

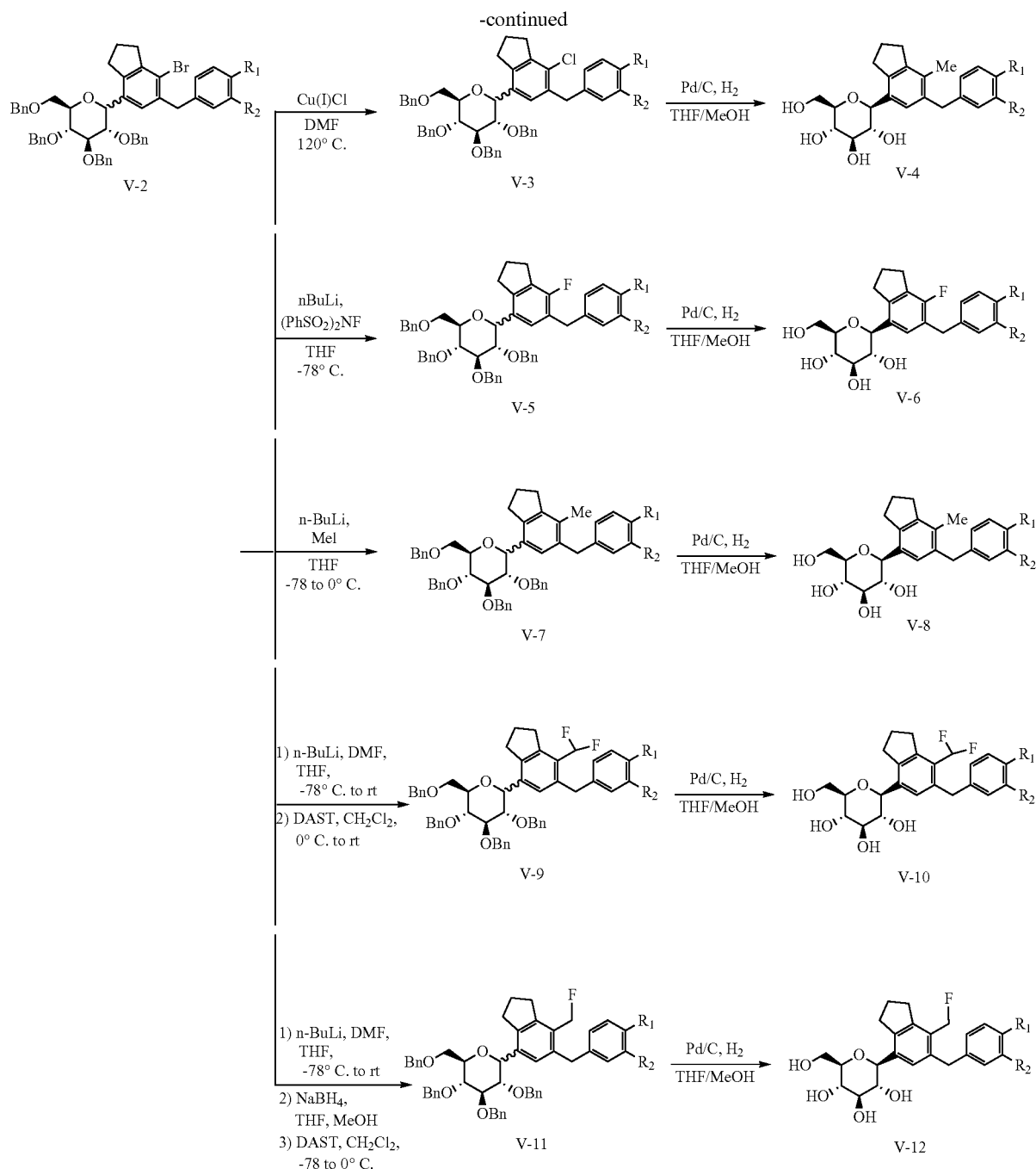

Aglycons V-1 (III-3 or III-6 in Scheme 3), prepared in Scheme 3, are incorporated into perbenzylated lactone 13 by lithium-halogen exchange reaction at low temperature (−78° C.). The produced lactols are reduced using triethylsilane and boron trifluoride diethyl etherate to provide bromide intermediates V-2, which are used as starting materials for further derivatizations, as illustrated in Scheme 5. The bromo substituent of intermediate V-2 is converted into a chloro substituent V-3 by the treatment of Cu(I)Cl at heating conditions (120° C.) in quantitative yield. The bromide intermediate V-2 is lithiated with n-BuLi and subsequently reacted with N-fluorobenzenesulfonimide at low temperature (−78° C.) to afford the corresponding fluoride compound V-5. The lithiation of the bromide V-2 followed by the treatment of iodomethane is also applied to prepare a methyl substituted derivative V-7. The bromide V-2 is lithiated and treated with DMF to give a corresponding benzaldehyde, which is reacted with DAST ((diethylamino)sulfur trifluoride) to produce a difluoromethyl substituted compound V-9. The benzaldehyde is converted to a benzyl alcohol with $NaBH_4$, and the benzyl alcohol is treated with DAST to give a monofluoromethyl substituted compound V-11. Benzyl groups are deprotected by hydrogenation using Pd/C under hydrogen atmosphere and then the required β-isomers (V-4, V-6, V-8, V-10, V-12) are separated by prep HPLC equipped with a reverse phase column.

Scheme 6
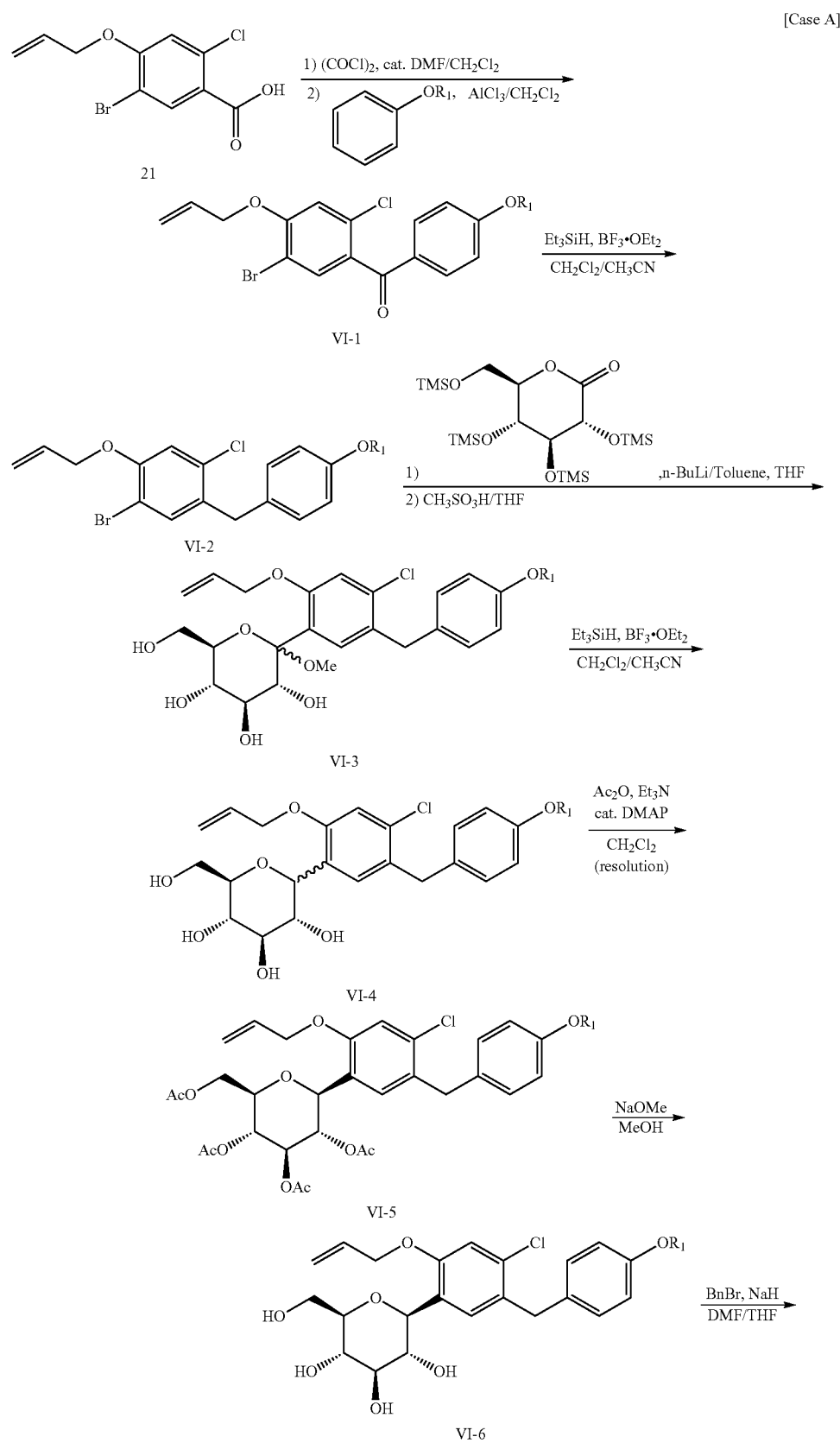
[Case A]

-continued

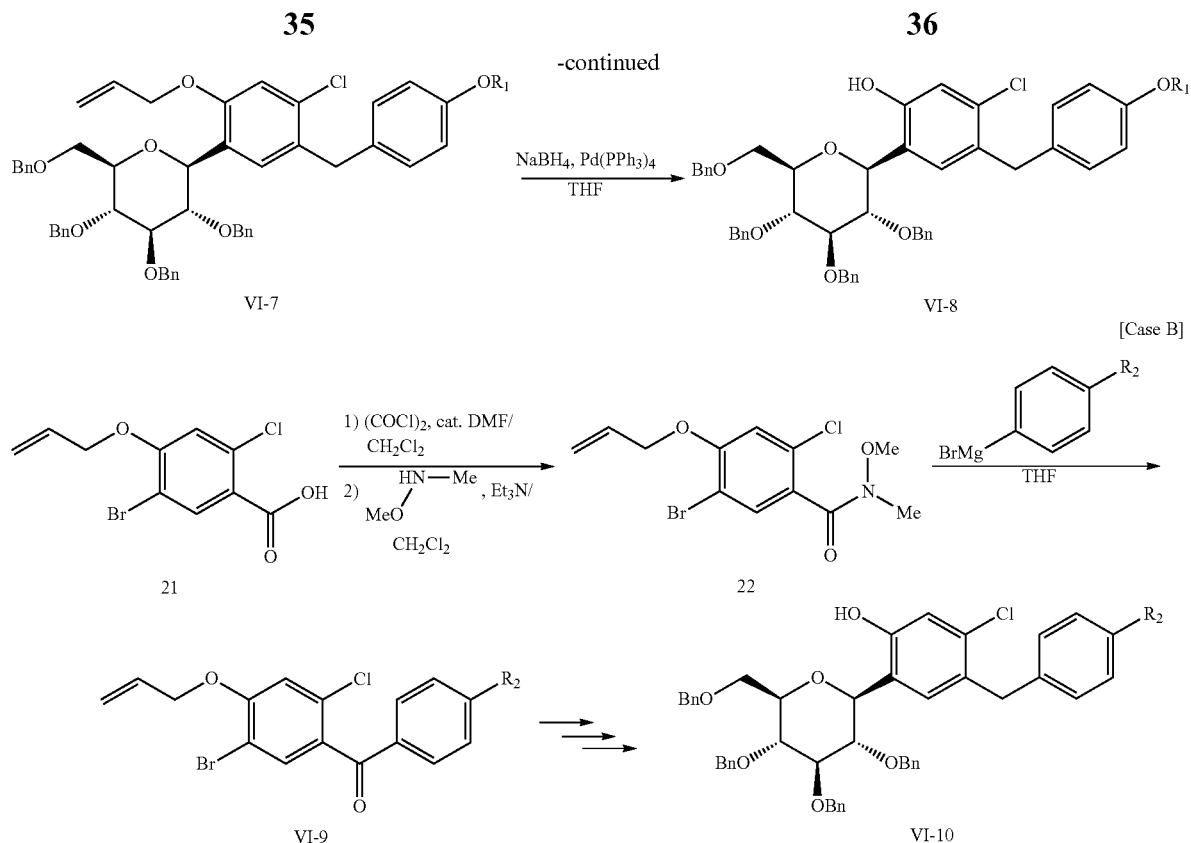

Aglycon moieties VI-2, containing an allyloxy group, are prepared from an acid 21 (refer to Scheme 8). The acid 21 is changed into the corresponding acyl chloride with oxalyl chloride, and subsequently coupled with substituted benzenes through the Friedel-Crafts acylation. The produced ketones VI-1 are reduced by triethylsilane in the presence of boron trifluoride etherate to yield aglycons VI-2. The aglycon VI-2 is lithiated by treatment of n-BuLi and coupled with persilylated lactone to produce an α,β-mixture of lactol, which is converted into a desilylated O-methyl lactol VI-3 by methanesulfonic acid. The anomeric methoxy group of compound VI-3 is reduced using triethylsilane and boron trifluoride etherate. After peracetylation, the resulting tetraacetate is recrystallized from ethanol to a pure β-anomer VI-5. Hydrolysis of compound VI-5 with NaOMe generates a tetraol VI-6 in quantitative yield. The tetraols VI-6 are protected by treatment with benzyl bromide and NaH for next reactions. Finally, an allyl group of the perbenzylated intermediate VI-7 is reductively deprotected with NaBH$_4$ and a catalytic amount of Pd(PPh$_3$)$_4$ to yield the key intermediate VI-8, containing phenol moiety.

Case B, in Scheme 6, represents another route to a key intermediate VI-10, which also includes phenol moiety. The same starting material 21 is used to prepare desired ketones VI-9 through Weinreb-amide, and then the similar reactions (from VI-1 to VI-8, in Case A) are applied to produce VI-10 from VI-9.

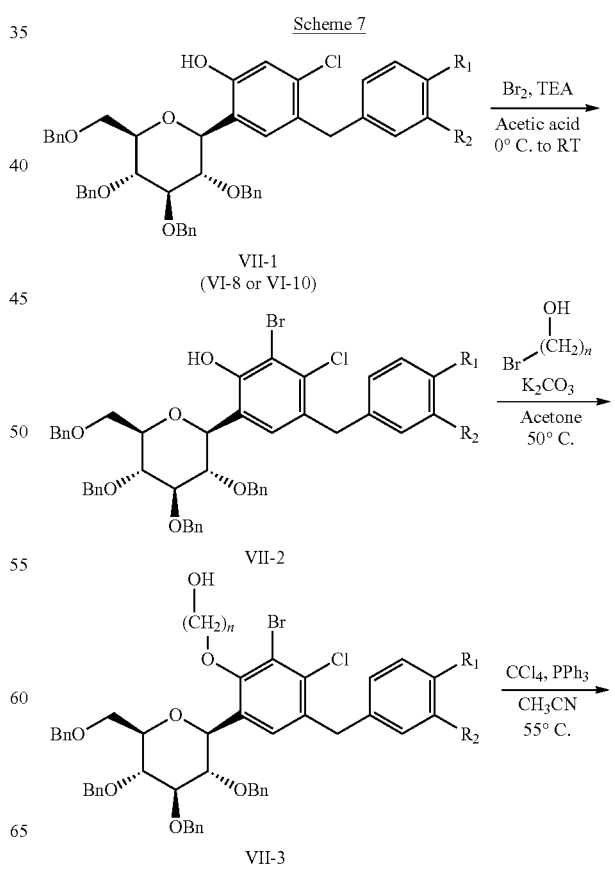

Scheme 7

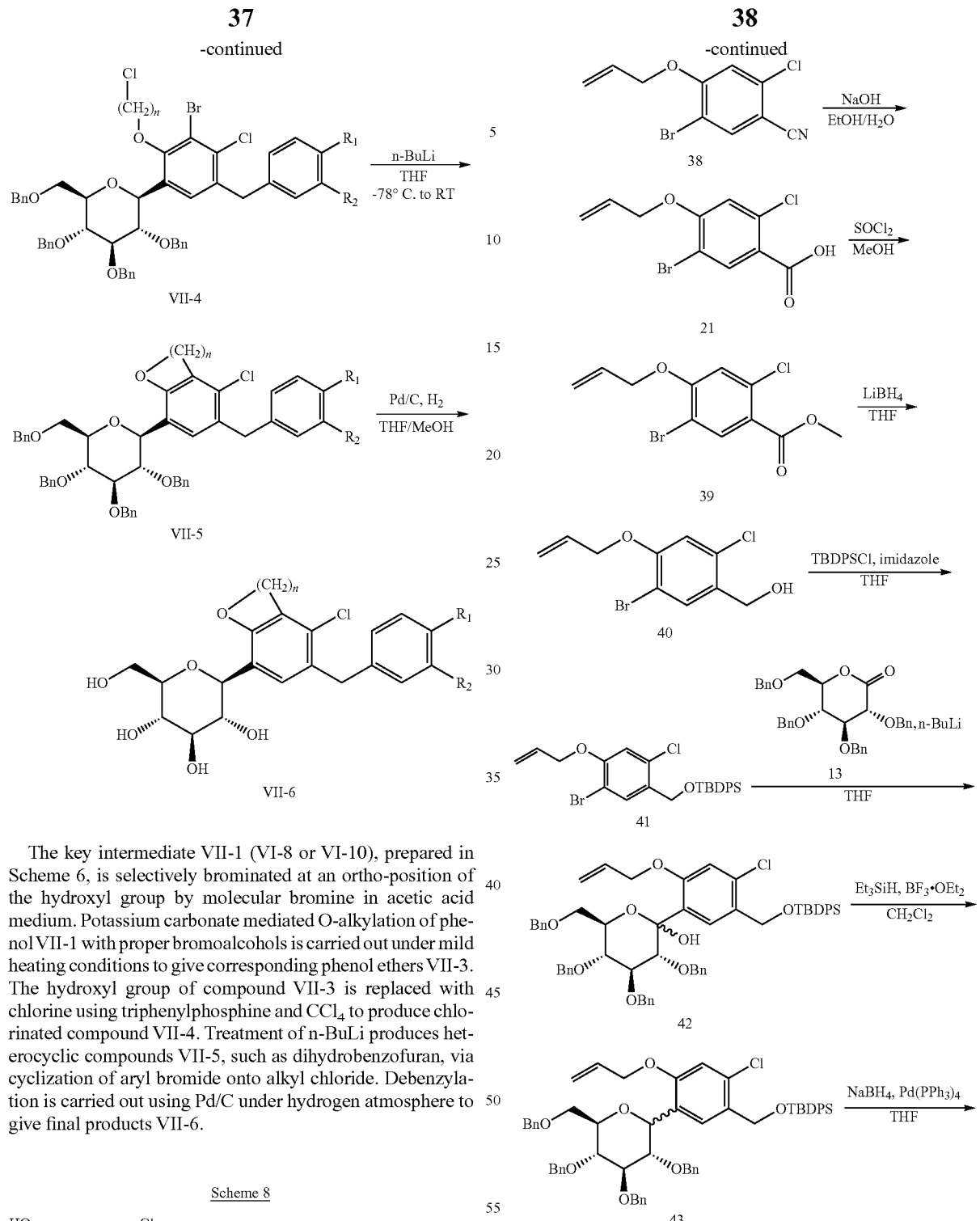

The key intermediate VII-1 (VI-8 or VI-10), prepared in Scheme 6, is selectively brominated at an ortho-position of the hydroxyl group by molecular bromine in acetic acid medium. Potassium carbonate mediated O-alkylation of phenol VII-1 with proper bromoalcohols is carried out under mild heating conditions to give corresponding phenol ethers VII-3. The hydroxyl group of compound VII-3 is replaced with chlorine using triphenylphosphine and CCl₄ to produce chlorinated compound VII-4. Treatment of n-BuLi produces heterocyclic compounds VII-5, such as dihydrobenzofuran, via cyclization of aryl bromide onto alkyl chloride. Debenzylation is carried out using Pd/C under hydrogen atmosphere to give final products VII-6.

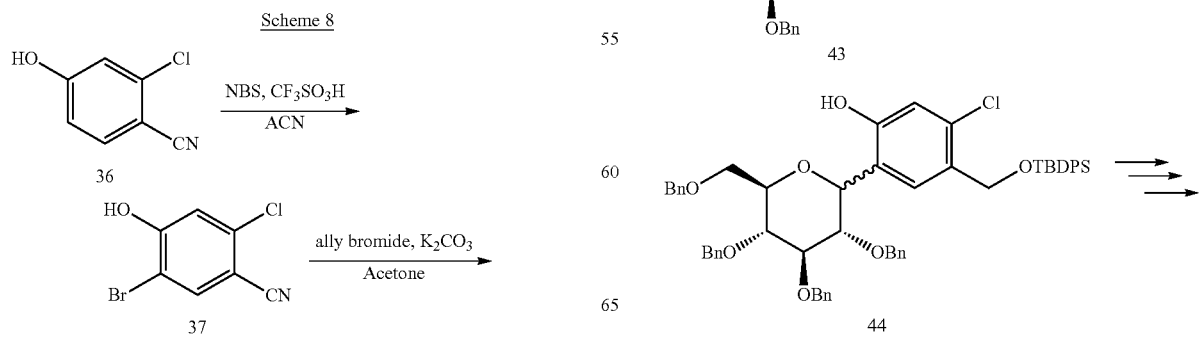

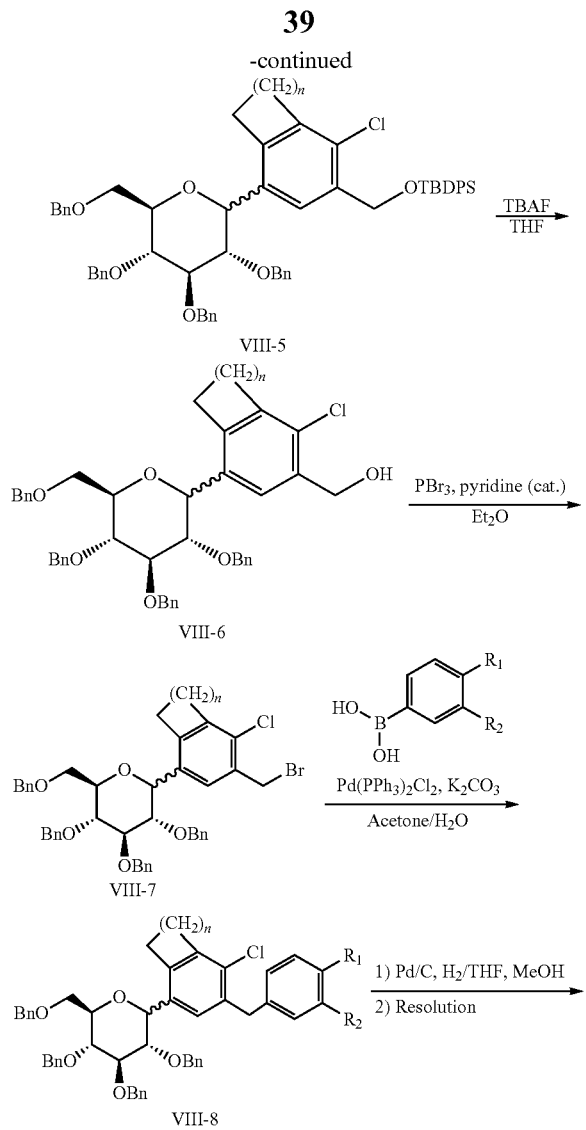

Commercially available cyanide 36 is used as a starting material. The selective monobromination of compound 36 with NBS in acetonitrile is promoted by $CF_3SO_3H$. Phenol protection of compound 37 is carried out efficiently with allyl bromide in the presence of $K_2CO_3$. The resulting compound 38 is hydrolyzed with sodium hydroxide in aqueous ethanol, and subsequently converted to the corresponding methylester 39 using $SOCl_2$ and methanol. The silyl-protected alcohol 41 is prepared by reduction of the ester 39 with $LiBH_4$, and subsequent silylation of the resulting alcohol 40 with tert-butyldiphenylchlorosilane (TBDPSCl) in the presence of imidazole.

After lithiation of bromide 41 using n-BuLi, the lithiated aromatic compound is added to perbenzylated gluconolactone to generate a α,β-isomer mixture of the lactols 42. The anomeric alcohol is reduced using triethylsilane and boron trifluoride diethyl etherate, and subsequently the selective deprotection of allyl group is performed by treatment of $NaBH_4$ and $Pd(PPh_3)_4$ to yield the key intermediate 44. A heterocyclic intermediate VIII-5 is prepared by the general procedure, described in Scheme 7 (from VIM to VII-5). The cleavage of silyl ether VIII-5 to alcohol VIII-6 using TBAF is followed by replacement of a hydroxyl group with a bromine atom by treatment of $PBr_3$ in the presence of a catalytic amount of pyridine to produce the corresponding benzylbromide VIII-7. Proper phenylboronic acids are coupled with the benzylbromide VIII-7, through palladium-catalyzed reaction, Suzuki coupling, to provide compounds VIII-8, which are debenzylated using Pd/C under hydrogen atmosphere to yield final products VIII-9.

Scheme 9

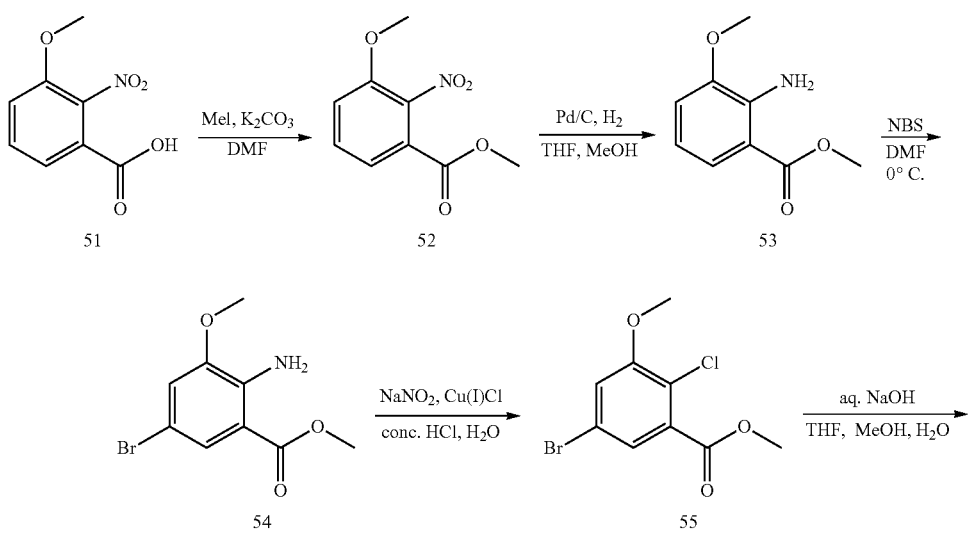

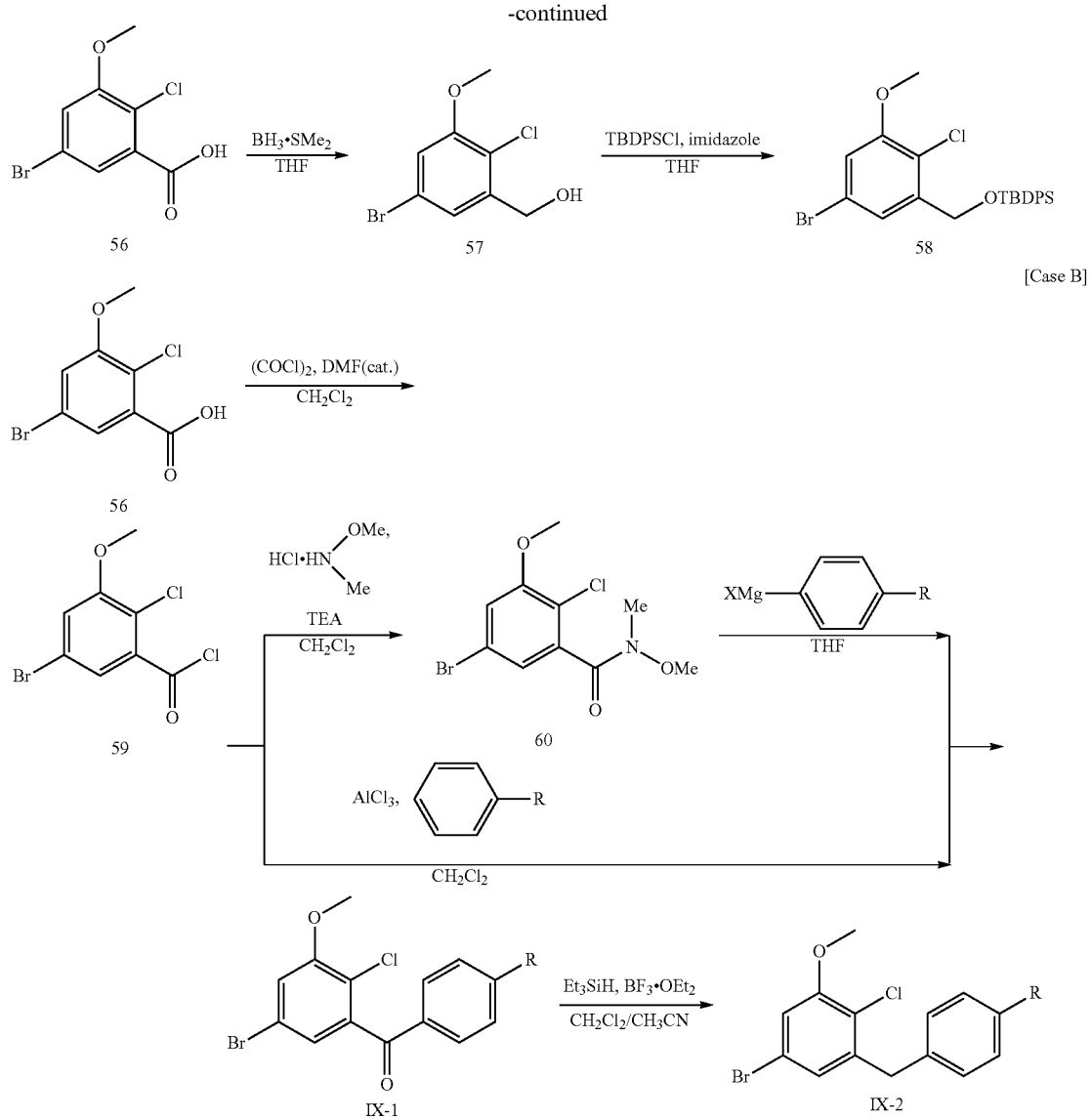

[Case B]

A commercially available acid 51 is converted to the corresponding methyl ester 52 using MeI and $K_2CO_3$. The nitro group of 52 is changed to an amine group 53 by catalytic reduction under hydrogen atmosphere. Bromination of 53 is performed using a brominating agent such as NBS to obtain compound 54. The amine compound 54 is diazotized with $NaNO_2$ in acidic conditions, and then chlorinated with Cu(I)Cl to give compound 55. Hydrolysis of compound 55 in basic conditions produces the benzoic acid 56, which is reduced to the benzyl alcohol 57 with borane dimethylsulfide complex. Silyl protection of the benzyl alcohol 57 is carried out using tert-butyldiphenylchlorosilane (TBDPSCl) in the presence of imidazole to provide a key intermediate 58.

As shown in Case B (Scheme 9), another key intermediate IX-2 is prepared from the acid 56, which is already mentioned in Case A (Scheme 9). The acid 56 is converted to the corresponding acyl chloride 59 using oxalyl chloride and DMF as a catalyst, and subsequently coupled with N,O-dimethylhydroxylamine hydrochloride to give Weinreb-amide 60. Reaction of Weinreb amide 60 with proper organometallic nucleophiles, such as Grignard reagents, produces the diarylketones IX-1. On the other hand, the acyl chloride 59 is directly converted into the diarylketone IX-1 through the Friedel-Crafts reaction. The treatment of triethylsilane and boron trifluoride etherate reduces the ketone IX-1 to provide the desired aglycon IX-2.

Scheme 10

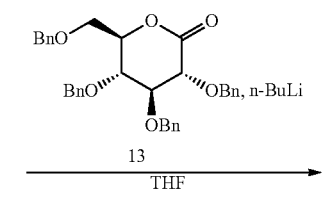

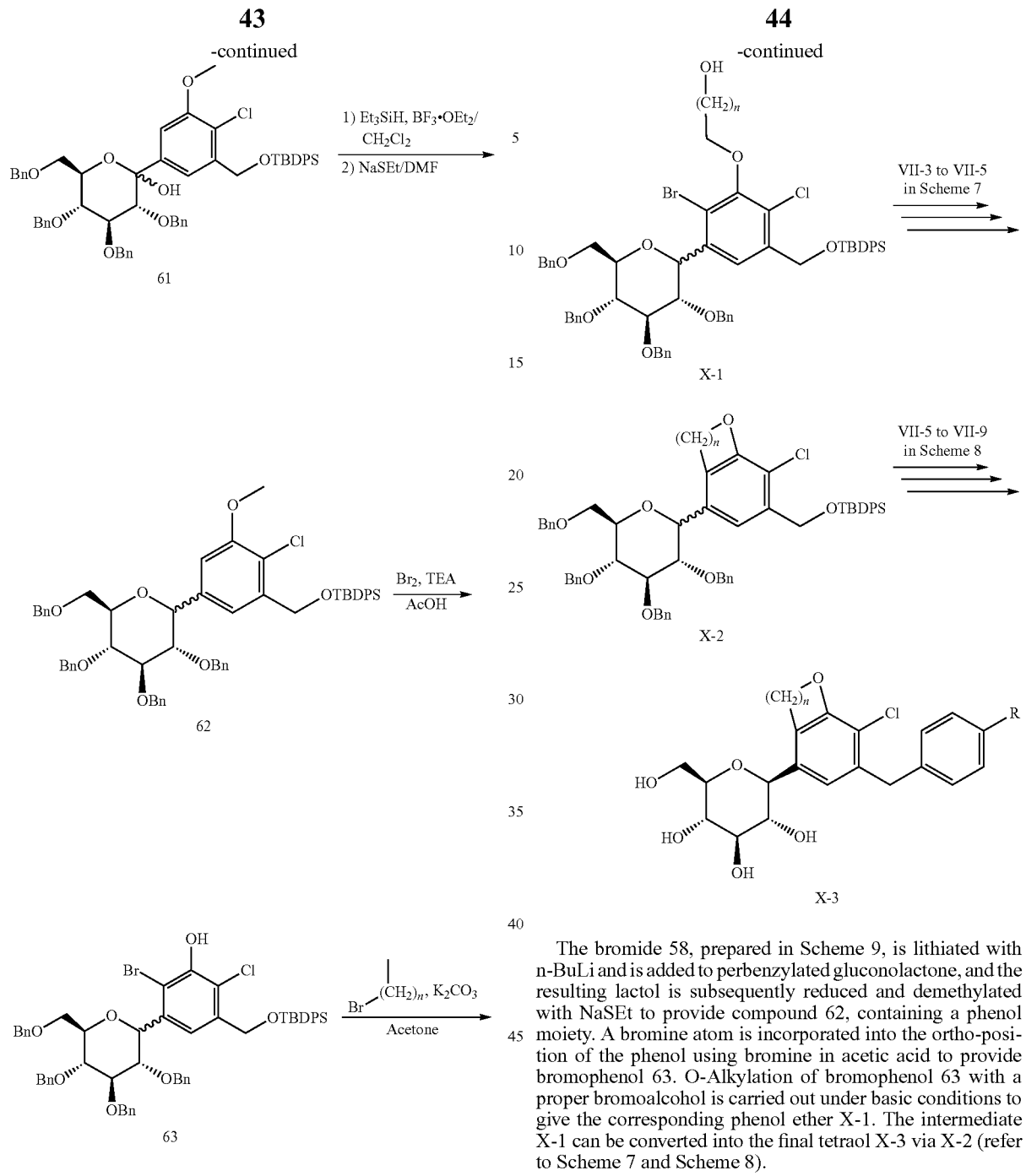

The bromide 58, prepared in Scheme 9, is lithiated with n-BuLi and is added to perbenzylated gluconolactone, and the resulting lactol is subsequently reduced and demethylated with NaSEt to provide compound 62, containing a phenol moiety. A bromine atom is incorporated into the ortho-position of the phenol using bromine in acetic acid to provide bromophenol 63. O-Alkylation of bromophenol 63 with a proper bromoalcohol is carried out under basic conditions to give the corresponding phenol ether X-1. The intermediate X-1 can be converted into the final tetraol X-3 via X-2 (refer to Scheme 7 and Scheme 8).

Scheme 11

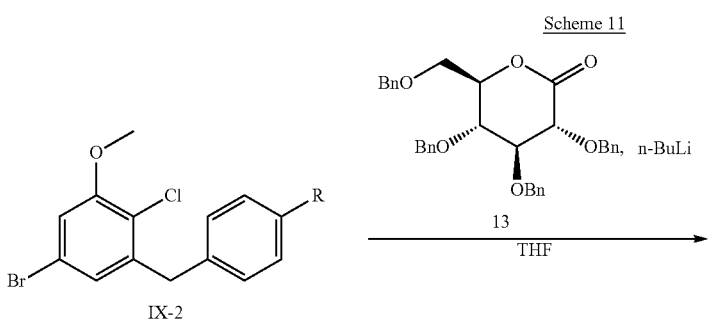

-continued

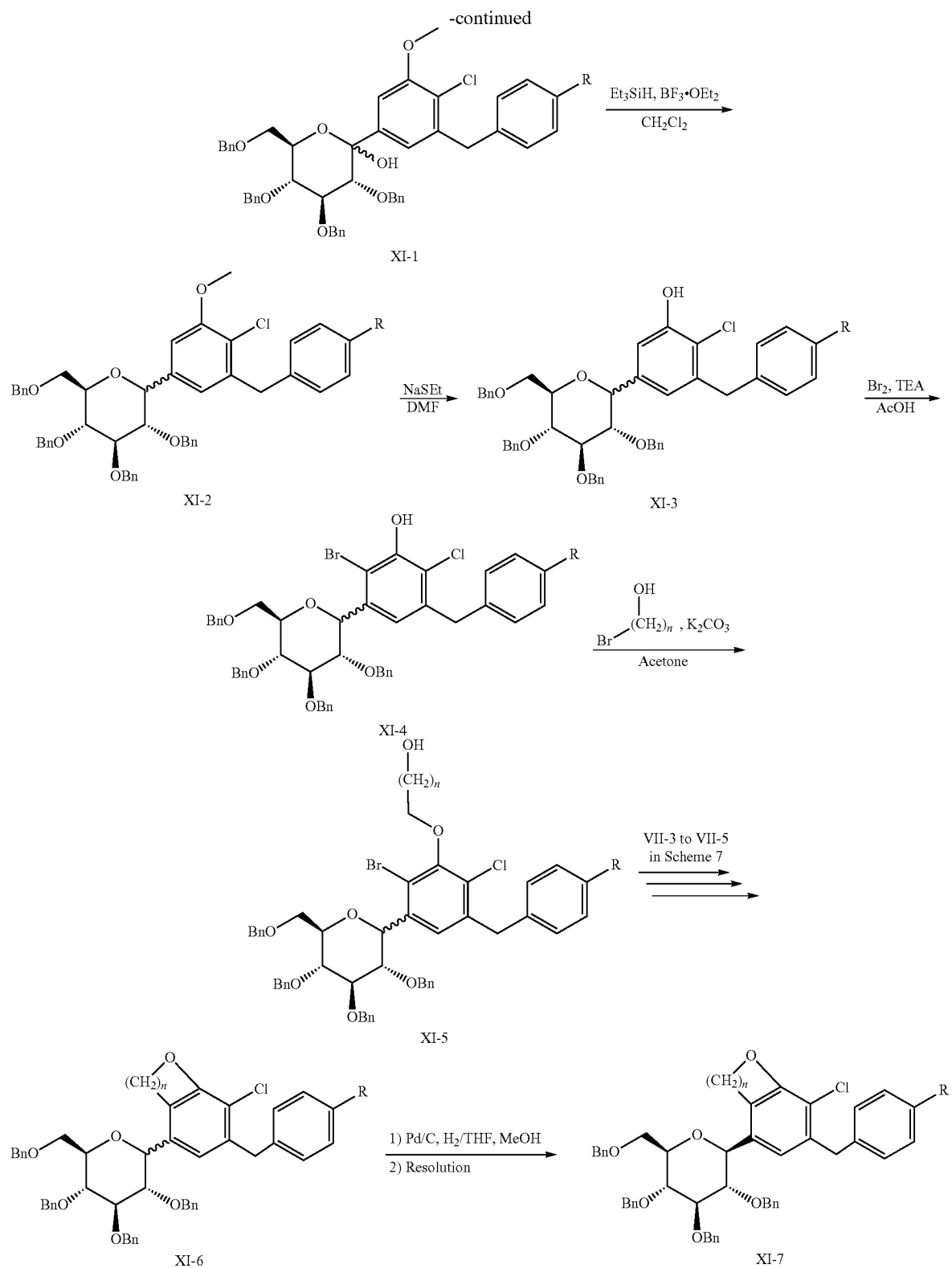

Lithiation of the bromide IX-2, prepared in Scheme 9 [Case B], is followed by the coupling reaction with perbenzylated gluconolactone to generate a mixture of lactol XI-1. Reduction of an anomeric hydroxyl group with Et$_3$SiH in the presence of BF$_3$.OEt$_2$, and subsequent demethylation of XI-2 using NaSEt produces the intermediate XI-3, containing a phenol group. Monobromination with bromine in an acidic medium provides an ortho-bromophenol compound XI-4. The treatment of a proper bromophenol and a base produces O-alkylated intermediate XI-5, which is cyclized by the same procedures used in Scheme 7 to generate compound XI-6. Deprotection of XI-6 is performed using Pd/C under hydrogen atmosphere, and followed by chromatographical purification (reverse phase) to yield final compound XI-7.

followed by RCM using Grubb's 2$^{nd}$ generation catalyst to give a cyclized alkenyl compound 84. Hydrogenation using Pd/C under hydrogen atmosphere is performed for debenzylation and alkene reduction to yield a final compound E023.

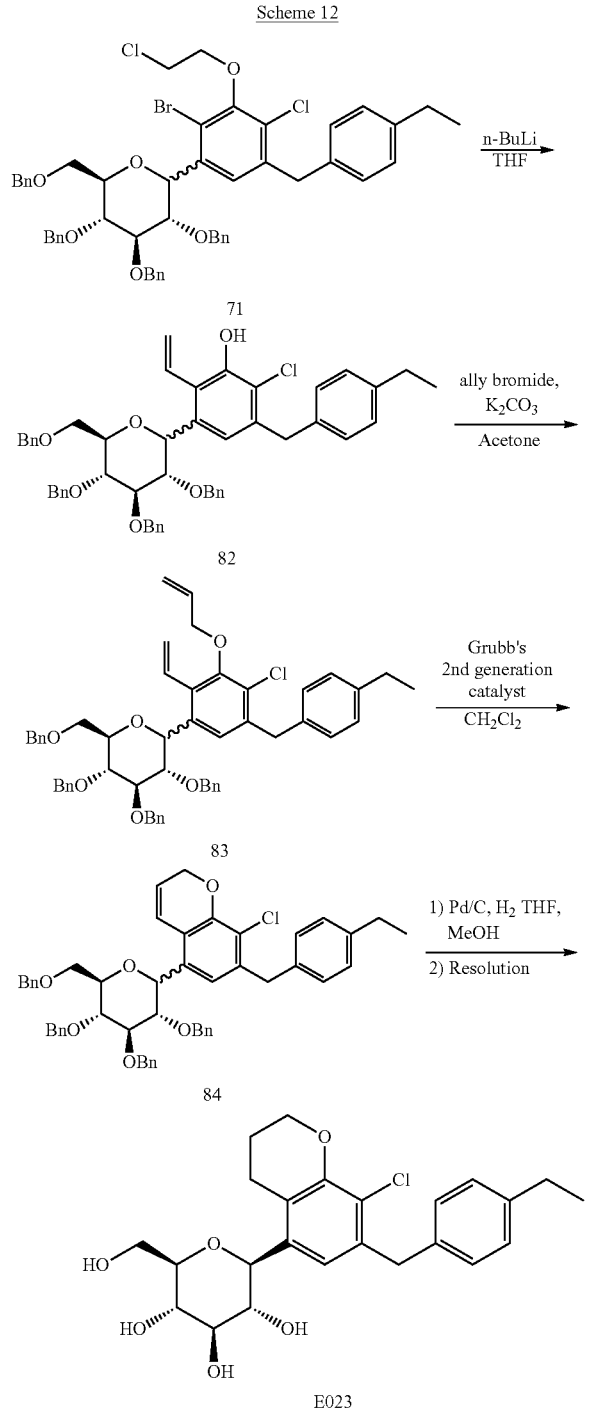

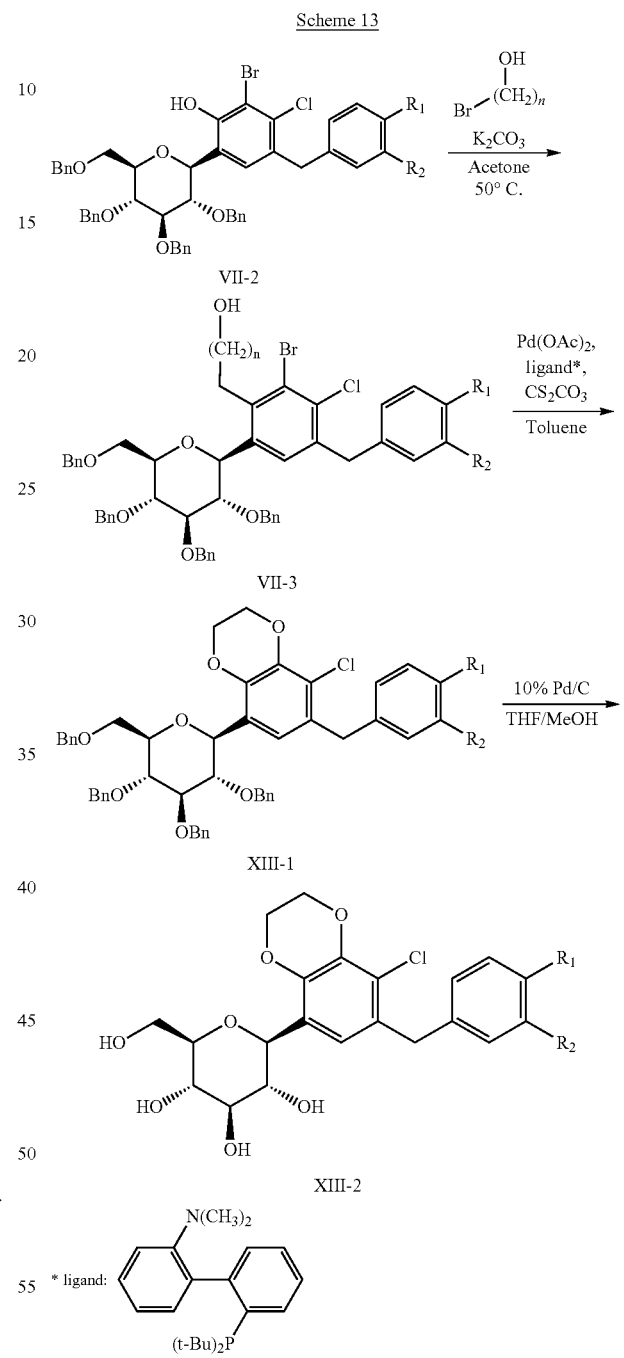

Another synthetic route through the ring-closing metathesis (RCM) is also developed to generate various heterobicyclic moieties, as shown in Scheme 12. Compound 71 is treated with excess n-BuLi to produce an intermediate 82 containing an o-hydroxystyrene moiety. The phenol group of 82 is alkylated with allyl bromide under basic conditions, and The key intermediate VII-3, referred to in Scheme 7, is used for preparing other heterobicyclic moieties, as shown in Scheme 13. Palladium-catalyzed intramolecular etherification using a dialkylphosphinobiaryl ligand is applied to cyclization of VII-3. The produced heterobicycles XIII-1 are subsequently debenzylated by hydrogenation to give final products XIII-2.

Scheme 14
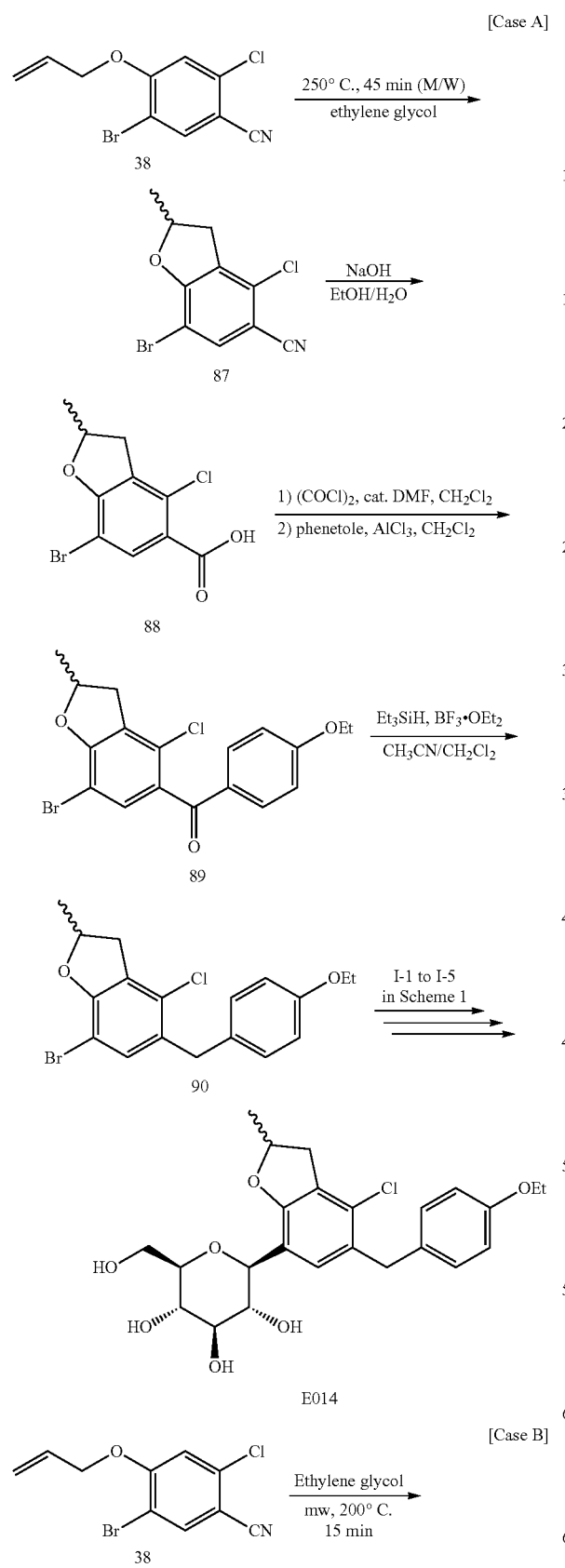
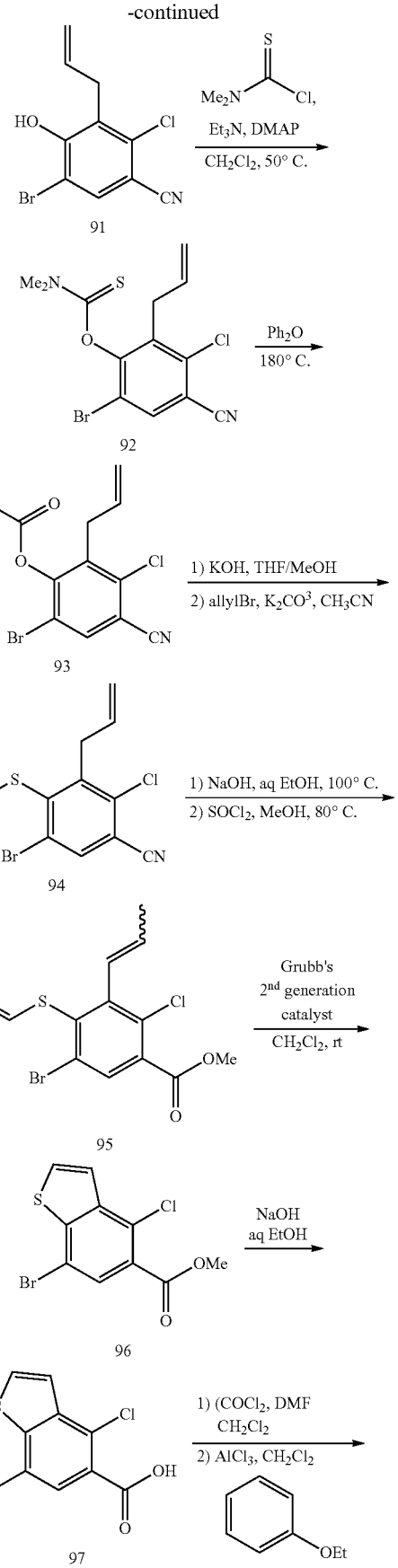

-continued

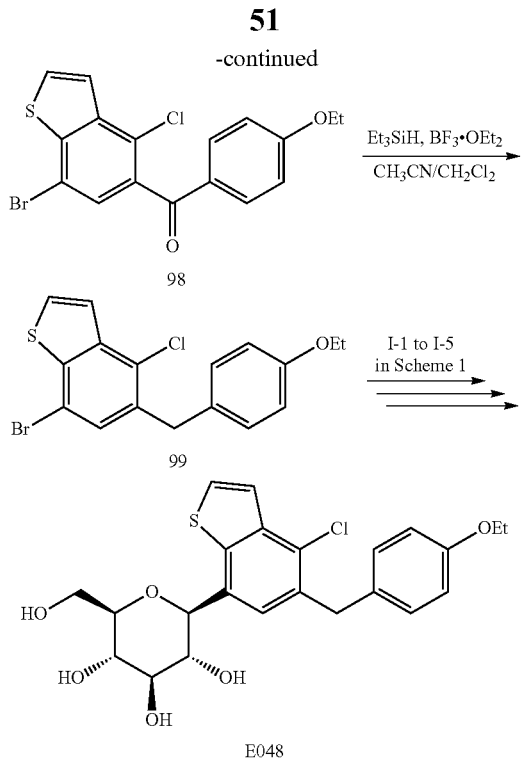

Synthetic routes of other aglycons, containing various heterobicyclic moieties, are illustrated in Scheme 14. In Case A (Scheme 14), a branched heterobicyclic moiety is prepared from compound 38 (refer to Scheme 8). Intramolecular cyclization of an allyl group generates a methyl-branched dihydrobenzofuran moiety of compound 87. Subsequent hydrolysis with NaOH in aqueous ethanol produces the corresponding acid 88. Treatment of oxalyl chloride in the presence of a catalytic amount of DMF yields the acyl chloride, which is coupled with an aryl compound through the Friedel-Crafts reaction to generate the diarylketone 89. Reduction of the ketone 89 with Et$_3$SiH and BF$_3$.OEt$_2$ gives the desired aglycon 90. This aglycon 90 is coupled with the gluconolactone, deprotected, reduced, and purified to the final compound E014 (refer to Scheme 1).

In Case B (Scheme 14), a benzothiophene moiety is prepared from compound 38 (refer to Scheme 8). Intramolecular migration of an allyl group by microwave radiation is performed to produce the key intermediate 91. Compound 91 is coupled with dimethylthiocarbamoyl chloride in basic conditions to generate a thionoester 92, which is converted into the corresponding thiocarbamate 93 through the Newman-Kwart rearrangement in heating conditions. Hydrolysis of 93 is followed by allylation in the presence of K$_2$CO$_3$ to give compound 94. The cyano group of compound 94 is efficiently converted to the corresponding methyl ester 95 by conventional procedures. Intramolecular cyclization of compound 95 by Grubb's 2$^{nd}$ generation catalyst generates a benzothiophene moiety 96, which is treated with NaOH in aqueous ethanol and oxalyl chloride to produce the corresponding acyl chloride. Friedel-Crafts acylation of the acyl chloride with an aryl compound generates the diarylketone 98. Reduction of the ketone 98 with Et$_3$SiH and BF$_3$.OEt$_2$ gives the desired aglycon 99. This aglycon 99 is coupled with the gluconolactone, deprotected, reduced, and purified to the final compound E048 (refer to Scheme 1).

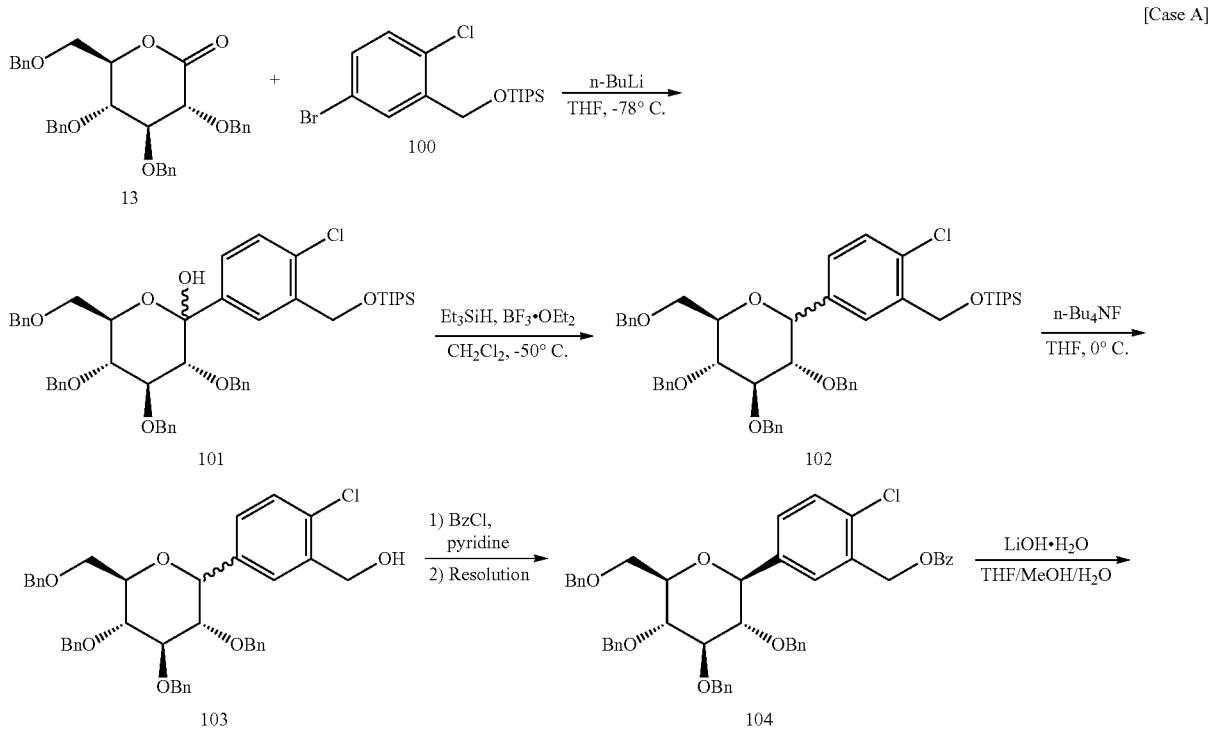

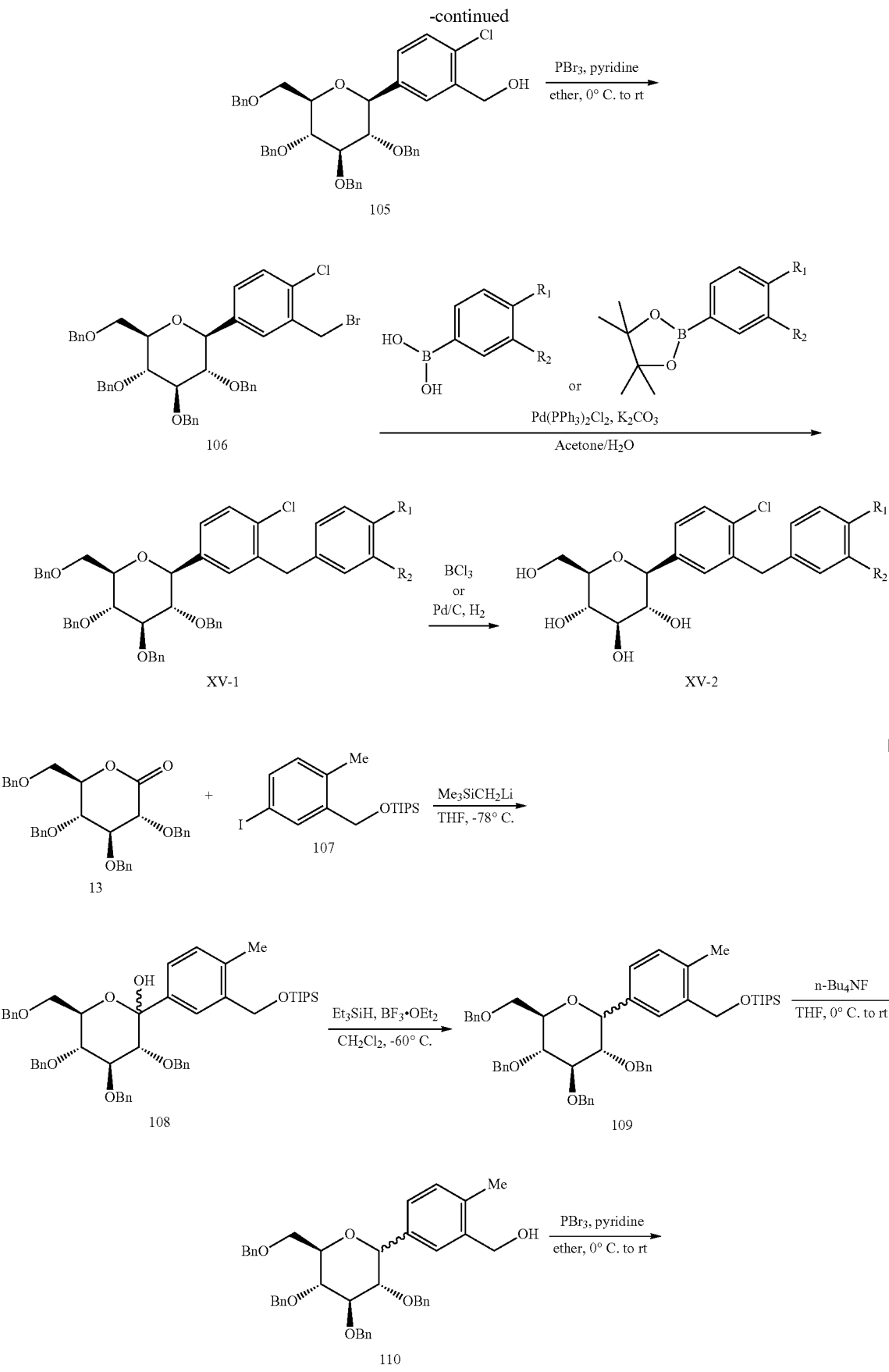

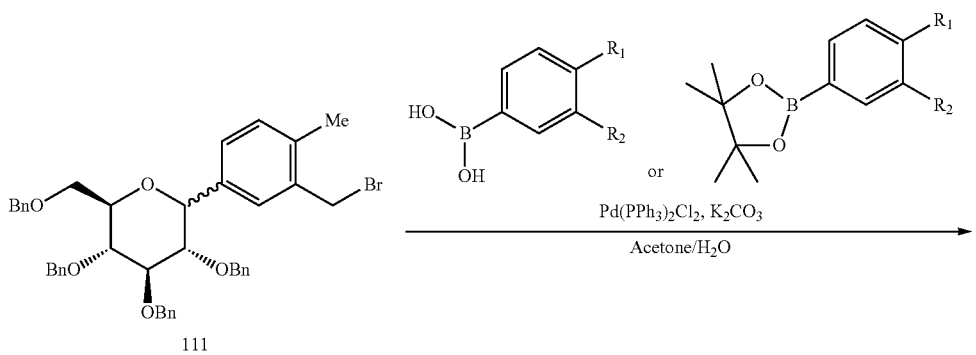

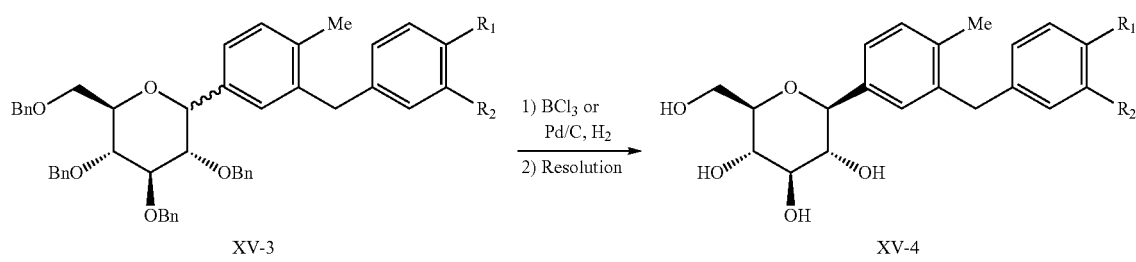

As shown in Scheme 15, various phenyl moieties can be incorporated into the benzyl bromide intermediates (106 in Case A; 111 in Case B). Halogenated compounds (100 or 107) are lithiated with n-BuLi and followed by coupling with perbenzylated lactone 13. The resulting lactols (101 or 108) are reduced by $Et_3SiH$ and $BF_3.OEt_2$. Deprotection of compound 102 and 109 is accomplished by TBAF-mediated desilylation to produce benzyl alcohols 103 and 110. After esterification of compound 103 by benzyl chloride in the presence of pyridine, the required β-isomer 104 is resolved by selective crystallization from isopropanol. The β-isomer 104 is hydrolyzed by LiOH to give benzyl alcohol 105. The benzyl alcohols (105 and 110) are brominated by treatment of $PBr_3$ with pyridine to generate the corresponding benzyl bromides (106 and 111). The Suzuki cross-coupling reaction between the benzyl bromides (106 and 111) and proper phenylboron compounds (Commercially unavailable phenylboron compounds are prepared in Scheme 16) produces the diphenylmethyl intermediates (XV-1 or XV-3). Debenzylation of compound XV-1 and XV-3 is achieved by hydrogenation with Pd/C under hydrogen atmosphere or the treatment of $BCl_3$ at low temperature. Crude products are purified by prep HPLC equipped with a reverse phase column to provide pure β-isomers (XV-2 or XV-4).

Scheme 16

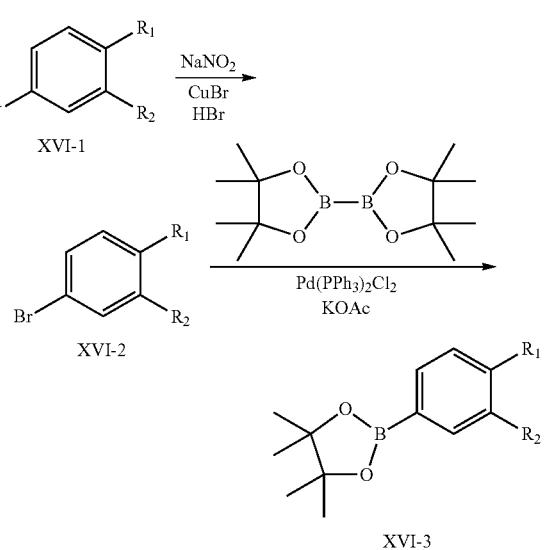

Commercially available anilines XVI-1 can be converted into the corresponding bromides XVI-2 through the Sandmeyer reaction with $NaNO_2$ and CuBr. Palladium catalyzed borylation of XVI-2 with bis(pinacolato)diboron is performed to generate the desired phenylboronic ester XVI-3. The boronic esters XVI-3 are used for the Suzuki cross-coupling reaction mentioned in Scheme 8, 10 and 15.

Scheme 17
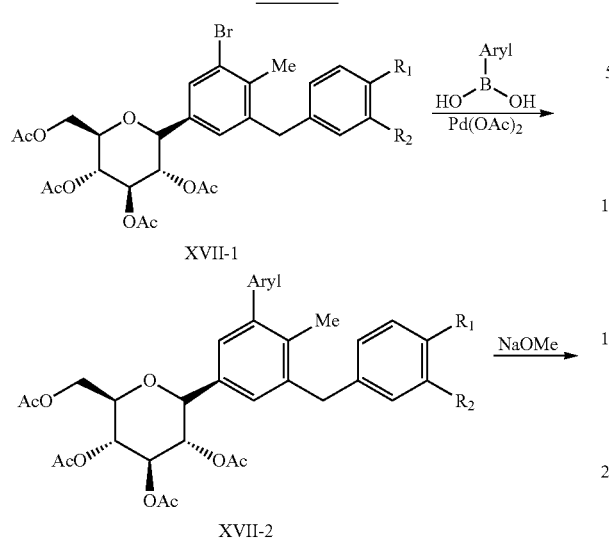
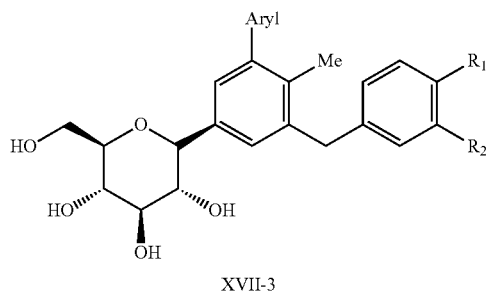
The starting bromides XVII-1, prepared by the known procedure (WO2008/101939, Example V), are used to provide arylphenyl linked compounds XVII-2 through the Suzuki cross-coupling reaction with proper boronic acids. Deacetylation of compounds XVII-2 with NaOMe produces final products XVII-3.
Scheme 18
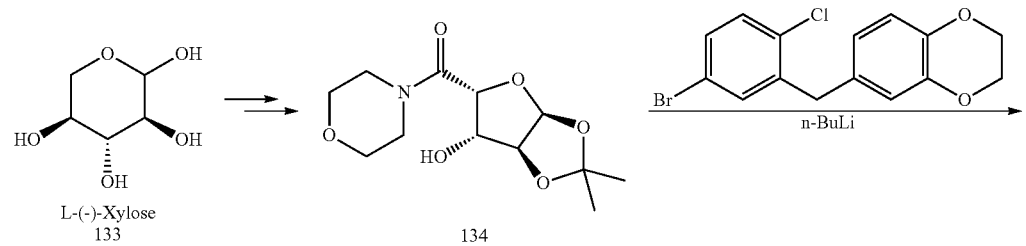
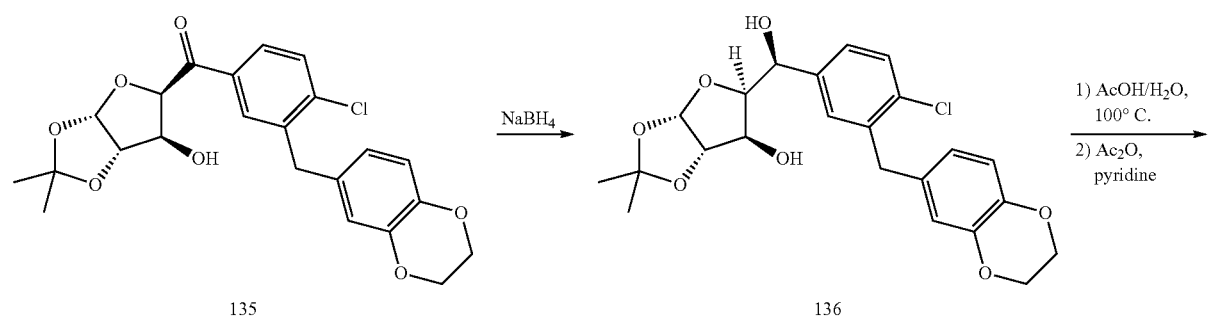
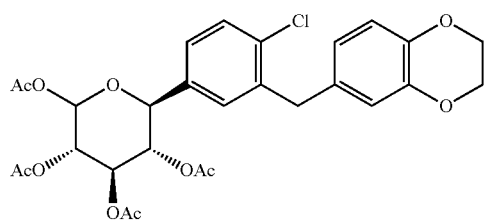

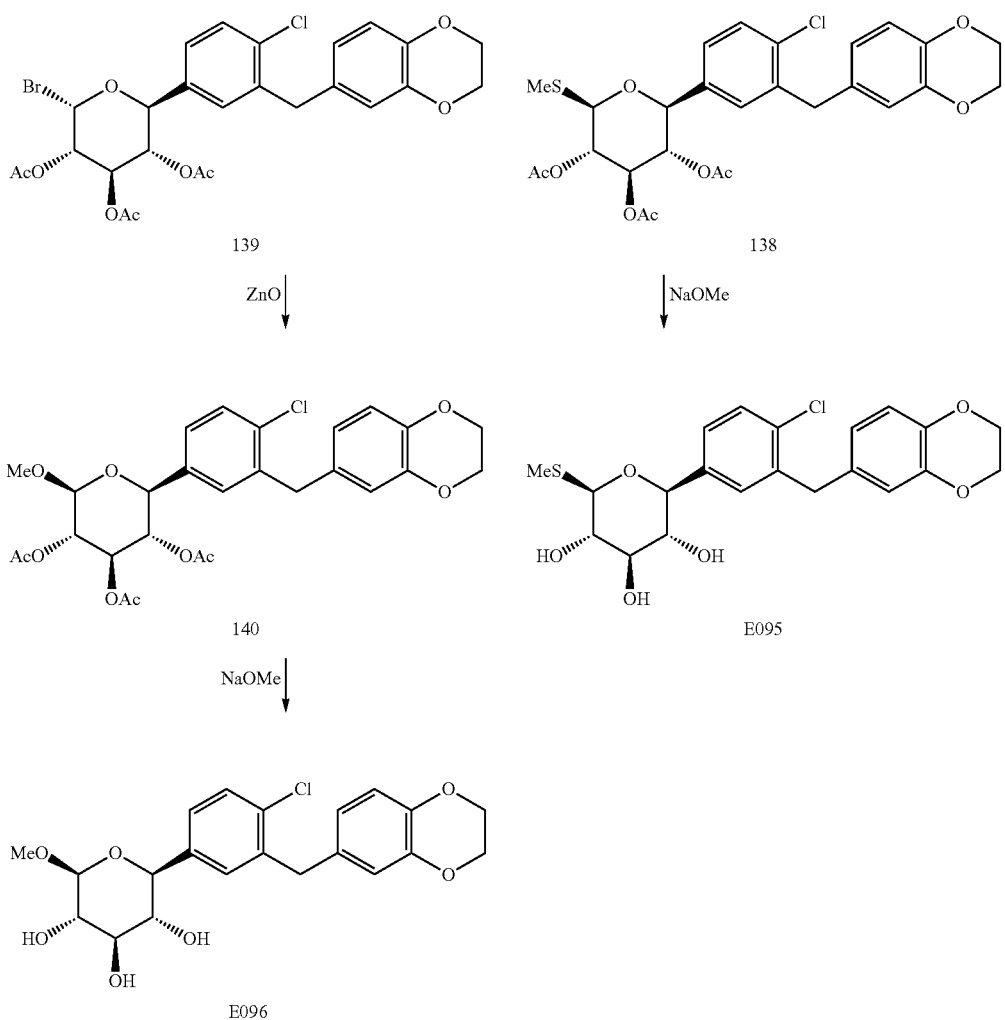

As shown in Scheme 18 and 19, the main sugar core is changed from D-glucose to L-xylose. A morpholino amide 134 is provided from L-xylose 133 through the known procedures (WO 2009/014970 A1). A halogenated aglycon is coupled by the treatment of n-BuLi with the morpholino amide 134 to generate a ketone 135, which is subsequently reduced to the corresponding alcohol, key intermediate 136, by NaBH$_4$. In acidic conditions, the furanose 136 is changed to a pyranose, and then acetylated by a conventional procedure to give a peracetylated compound 137. A thiomethyl group is directly incorporated into the intermediate 137 by the treatment of thiourea and TMSOTf, followed by addition of MeI and DIPEA. The resulting methanthiopyranose 138 is deacetylated using NaOMe to give the final product E095. On the other hand, a methoxypyranose 140 is prepared via a bromide 139. The treatment of intermediate 137 with HBr in acetic acid provides the xylopyranosyl bromide 139, which is converted into the corresponding methoxypyranose 140 with ZnO in methanol. Deacetylation with NaOMe is achieved to yield the final product E096. The synthetic route for a compound E097, an isomer of methoxypyranose E096, is illustrated in Scheme 19. Peracetylated isomeric intermediate 143 is separated from 140 by prep HPLC equipped with a reverse column.

Scheme 19

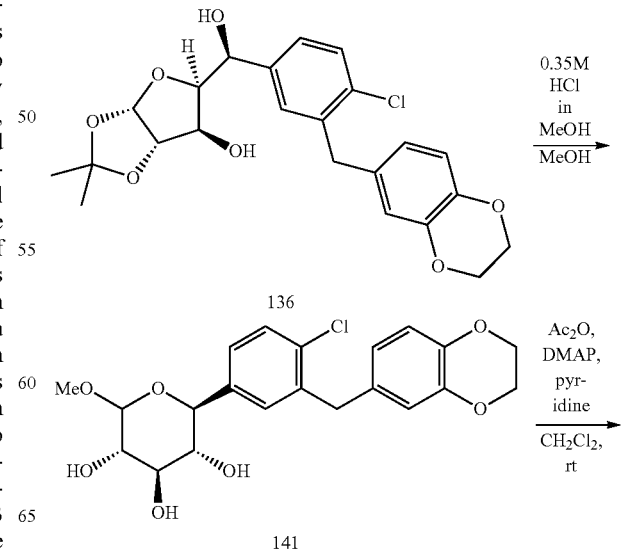

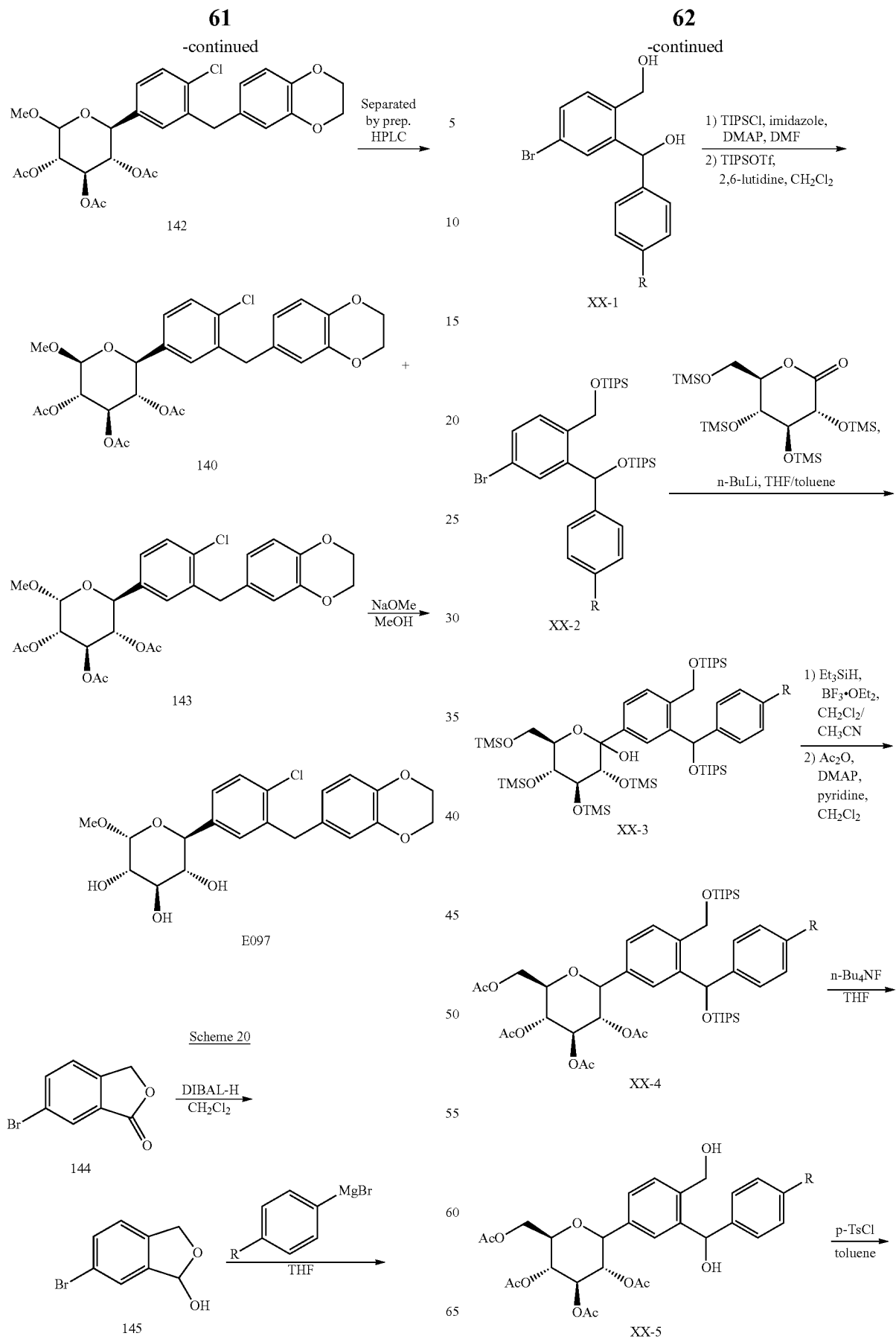

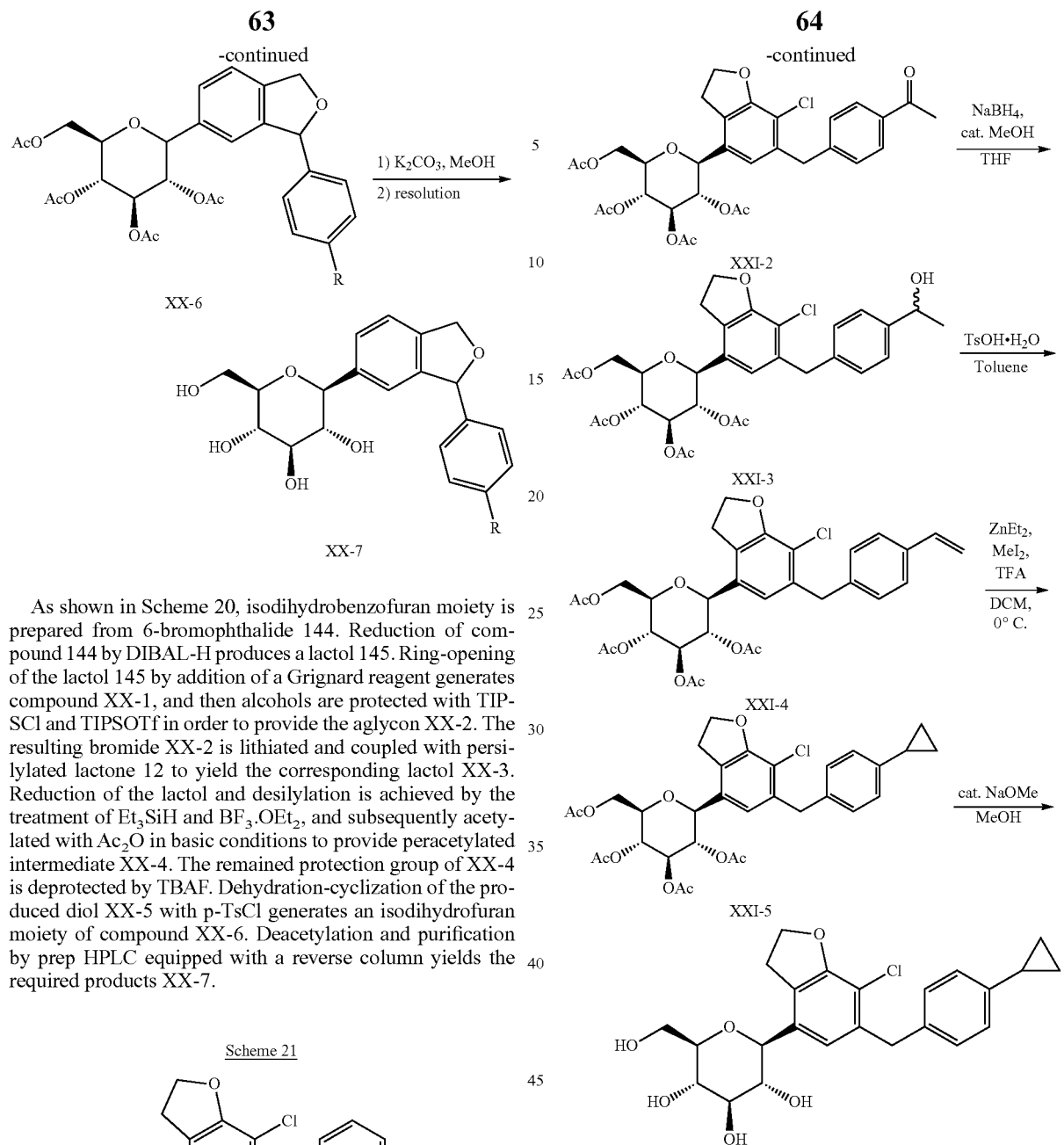

As shown in Scheme 20, isodihydrobenzofuran moiety is prepared from 6-bromophthalide 144. Reduction of compound 144 by DIBAL-H produces a lactol 145. Ring-opening of the lactol 145 by addition of a Grignard reagent generates compound XX-1, and then alcohols are protected with TIPSCl and TIPSOTf in order to provide the aglycon XX-2. The resulting bromide XX-2 is lithiated and coupled with persilylated lactone 12 to yield the corresponding lactol XX-3. Reduction of the lactol and desilylation is achieved by the treatment of $Et_3SiH$ and $BF_3 \cdot OEt_2$, and subsequently acetylated with $Ac_2O$ in basic conditions to provide peracetylated intermediate XX-4. The remained protection group of XX-4 is deprotected by TBAF. Dehydration-cyclization of the produced diol XX-5 with p-TsCl generates an isodihydrofuran moiety of compound XX-6. Deacetylation and purification by prep HPLC equipped with a reverse column yields the required products XX-7.

As shown in Scheme 21, various substituents, such as acetyl, hydroxyethyl, vinyl and cyclopropyl, are incorporated into para-position of the non-substituted phenyl ring (*Bioorg. Med. Chem. Lett.* 2011, 21, 4465-4470).

EXPERIMENTAL SECTION

As used herein the symbols and conventions used describing the processes, schemes and examples of the present invention are consistent with those used in the contemporary scientific literature, for example, the *Journal of the American Chemical Society* or the *Journal of Biological Chemistry*.

Hz (Hertz)
TLC (thin layer chromatography)
$T_r$ (retention time)
RP (reverse phase)
MeOH (methanol)

i-PrOH (isopropanol)
TFA (trifluoroacetic acid)
TEA (triethylamine)
EtOH (ethanol)
THF (tetrahydrofuran)
DMSO (dimethylsulfoxide)
EtOAc (ethyl acetate)
DCM (dichloromethane)
HOAc (acetic acid)
DMF (N,N-dimethylformamide)
Ac (acetyl)
CDI (1,1-carbonyldiimidazole)
Bn (benzyl)
TES (Triethylsilyl)
NBS (N-Bromosuccinimide)
HOBt (1-hydroxybenzotriazole)
Boc (tert-butyloxycarbonyl)
mCPBA (meta-chloroperbenzoic acid)
NMM (N-methyl morpholine)
TBAF (tetra-n-butylammonium fluoride)
DMAP (4-dimethylaminopyridine)
HPLC (high performance liquid chromatography)
EDCI (1-ethyl-3-[3-dimethylaminopropyl]carbodiimide hydrochloride)
DME (1,2-dimethoxyethane)
AIBN (2,2'-azobis(2-methylpropionitrile))
DIEA (N,N'-diisopropylethylamine)
TIPSCl (triisopropylsilyl chloride)
TIPSOTf (triisopropylsilyl trifluoromethanesulfonate)
TMSI (iodotrimethylsilane)
TMSOTf (trimethylsilyl trifluoromethanesulfonate)
DDQ (2,3-dichloro-5,6-dicyano-p-benzoquinone)
DAST (diethylaminosulfur trifluoride)
NMP (1-methyl-2-pyrrolidinone)
MW (microwave irradiation)

All reactions are conducted under an inert atmosphere at room temperature (rt or r.t.), unless otherwise noted. n-Butyllithium (Aldrich) was titrated with N-benzylbenzamide as indicator. All reagents were purchased at the highest commercial quality and used without further purification, unless otherwise indicated. All experiment involving moisture- and/or air-sensitive compounds were performed in oven- and/or flame-dried glassware with rubber septa under a positive pressure of nitrogen using standard Schlenck technique. Microwave reaction was conducted with a Biotage Initiator microwave reactor. NMR spectra were obtained on a Varian 400-MR (400 MHz $^1$H, 100 MHz $^{13}$C) spectrometer or a Bruker Ultrashield 400 plus (400 MHz $^1$H, 100 MHz $^{13}$C) spectrometer. NMR spectra were recorded in ppm (δ) relative to tetramethylsilane (δ=0.00) as an internal standard unless otherwise stated and are reported as follows: chemical shift, multiplicity (s=singlet, d=doublet, t=triplet, q=quartet, quint=quintet, sext=sextet, m=multiplet, and br=broad), coupling constant, and integration. $^{13}$C NMR spectra were referenced to the residual chloroform-$d_1$ (δ=77.0) or DMSO-$d_6$ (δ=39.7). Mass spectra were obtained with an Agilent 6110 quadruple LC-MSD (ESI+). High resolution mass spectra were obtained on a Jeol JMS-700 Mstation (10 kV, HFAB). Optical rotations were obtained on a Rudolph Autopol III digital polarimeter. Preparative HPLC purifications were performed on a Gilson purification system. For preparative HPLC, ca. 100 mg of a product was injected in 1 mL of methanol onto a SunFire Prep C18 OBD 5 µm 30×100 mm Column with a 30 min gradient from 5 to 90% acetonitrile in water and a 45 mL/min flow rate. Biotage SP1 and Isolera purification systems were used for normal phase column chromatography with ethyl acetate and hexane. Flash chromatography was performed using E. Merck 230-400 mesh silica gel according to the procedure of Still et al (*J. Org. Chem.* 43, 2923, 1978). Reactions were monitored by either thin-layer chromatography (TLC) on 0.25 mm E. Merck silica gel plates (60F-254) using UV light and p-anisaldehyde solution as visualizing agents or HPLC analysis on an Agilent 1200 series system.

The following synthetic schemes are merely illustrative of the methods by which the compounds of the invention may be prepared and are not intended to limit the scope of the invention as defined in the appended claims.

PREPARATION OF THE INTERMEDIATES

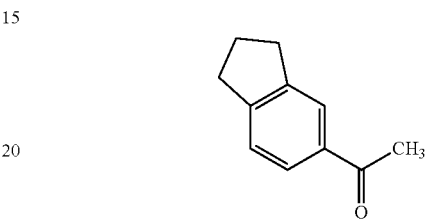

1-(2,3-Dihydro-1H-inden-5-yl)ethanone (2)

A mixture of indane (1, 12.25 mL, 0.10 mol) and Ac$_2$O (11.34 mL, 0.12 mol) was added dropwise for 1 h to a slurry of AlCl$_3$ (26.7 g, 0.2 mol) in DCM (100 mL) at 0° C. The reaction mixture was warmed up to room temperature and stirred for 15 h. The mixture was cooled to 0° C. and quenched by slow addition of water (20~30 mL) and 1M HCl (50 mL). The organic layer was separated, washed with brine and saturated NaHCO$_3$ solution, dried over anhydrous MgSO$_4$, filtered and concentrated in vacuo. The crude product 2 was dried under high vacuum and used without further purification (16.1 g, 0.10 mol, 100%).

$^1$H NMR (400 MHz, CDCl$_3$) δ 7.82 (s, 1H), 7.76 (d, J=7.6 Hz, 1H), 7.29 (d, J=7.6 Hz, 1H), 2.95 (t, J=7.6 Hz, 4H), 2.58 (s, 3H), 2.12 (m, 2H); [M+H]$^+$ 161.

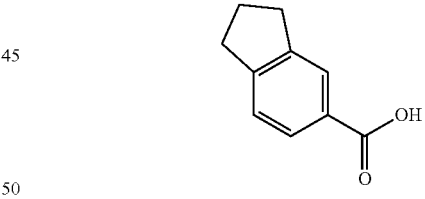

2,3-Dihydro-1H-indene-5-carboxylic acid (3)

Bromine (20.5 mL, 0.4 mol) was added to a solution of KOH (72.9 g, 1.3 mol) in water (250 mL) at 0° C. To the resulting solution was slowly added compound 2 (16.0 g, 0.1 mol) at 0° C. The reaction mixture was heated at 55° C. overnight and quenched with Na$_2$S$_2$O$_3$ (14.8 g, 0.094 mol). The mixture was acidified to pH 2-3 with conc. HCl (40~50 mL). The precipitate was collected by filtration, and washed with water. The crude product 3 was dried under high vacuum and used without further purification (15.4 g, 0.095 mol, 95%).

$^1$H NMR (400 MHz, CDCl$_3$) δ 10.89 (br s, —COOH, 1H), 7.95 (s, 1H), 7.90 (d, J=8.0 Hz, 1H), 7.30 (d, J=8.0 Hz, 1H), 2.97 (t, J=7.6 Hz, 4H), 2.13 (m, 2H); [M+H]$^+$ 163.

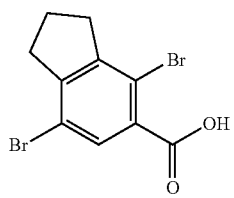 [SMILES: O=C(O)c1cc(Br)c2c(c1Br)CCC2]

4,7-Dibromo-2,3-dihydro-1H-indene-5-carboxylic acid (4)

To a mixture of compound 3 (5.0 g, 30.8 mmol) and conc. HNO$_3$ (20.0 mL) in acetic acid (92 mL) was added dropwise bromine (4.6 mL, 62.1 mmol) and AgNO$_3$ (12.3 g, 72.6 mmol) in water (31 mL). After stirring at rt overnight, the reaction was quenched with brine (250 mL), and the mixture was extracted with ethyl acetate (450 mL). The organic layer was washed with brine, dried over anhydrous MgSO$_4$, filtered and concentrated in vacuo. The crude product 4 was dried under high vacuum and used without further purification (8.5 g, 26.7 mmol, 87%).

$^1$H NMR (400 MHz, CDCl$_3$) δ 7.96 (s, 1H), 3.16-3.09 (m, 4H), 2.16 (m, 2H); [M+H]$^+$ 321.

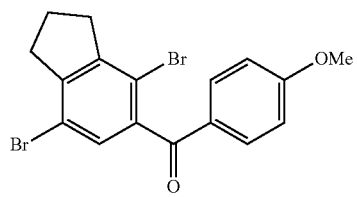 [SMILES: COc1ccc(C(=O)c2cc(Br)c3c(c2Br)CCC3)cc1]

(4,7-Dibromo-2,3-dihydro-1H-inden-5-yl)(4-methoxyphenyl)methanone (5-1)

To a mixture of the crude acid 4 (12.1 g, 37.9 mmol) and catalytic amounts of DMF (0.45 mL) in DCM (63 mL) was added dropwise oxalyl chloride (4.95 mL, 56.8 mmol) at 0° C. under nitrogen atmosphere. The reaction mixture was stirred at rt for 3 h and evaporated in vacuo to provide a crude acyl chloride (compound 5). To a solution of compound 5 in DCM (67 mL) was added anisole (4.23 mL, 38.8 mmol) at 0° C. After stirring for 5 min, AlCl$_3$ (5.2 g, 38.8 mmol) was added portionwise. The reaction mixture was warmed up to rt and stirred at rt overnight. After cooling to 0° C., the reaction mixture was quenched with saturated NH$_4$Cl solution (50 mL) and extracted with DCM (100 mL). The organic layer was washed with brine, dried over anhydrous MgSO$_4$, filtered and concentrated in vacuo. The residue was purified by silica gel column chromatography to provide the compound 5-1 (3.9 g, 9.5 mmol, 25%).

$^1$H NMR (400 MHz, CDCl$_3$) δ 7.80 (d, J=11.6 Hz, 2H), 7.26 (s, 1H), 6.94 (d, J=12.0 Hz, 2H), 3.88 (s, 3H), 3.14-3.08 (m, 4H), 2.19 (m, 2H); [M+H]$^+$ 411.

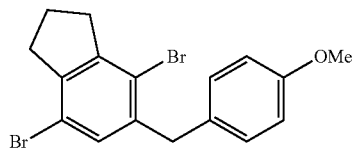 [SMILES: COc1ccc(Cc2cc(Br)c3c(c2Br)CCC3)cc1]

4,7-Dibromo-5-(4-methoxybenzyl)-2,3-dihydro-1H-indene (6)

To a solution of ketone 5-1 (3.9 g, 9.5 mmol) in CH$_2$Cl$_2$/CH$_3$CN (31 mL/31 mL) were added triethylsilane (4.8 mL, 28.5 mmol) and boron trifluoride diethyl etherate (3.7 mL, 28.5 mmol) at 0° C. under nitrogen atmosphere. The mixture was warmed up to room temperature slowly and stirred at room temperature for 15 h. To the mixture was added saturated K$_2$CO$_3$ solution (50 mL) slowly and the mixture was extracted with EtOAc (100 mL). The organic layer was dried over MgSO$_4$, filtered, and concentrated in vacuo. The residue was purified by silica gel column chromatography to provide the desired product 6 (3.2 g, 8.1 mmol, 85%).

$^1$H NMR (400 MHz, CDCl$_3$) δ 7.11 (d, J=8.8 Hz, 2H), 7.07 (s, 1H), 6.84 (d, J=8.8 Hz, 2H), 3.99 (s, 2H), 3.79 (s, 3H), 3.06 (t, J=7.8 Hz, 2H), 3.02 (t, J=7.6 Hz, 2H), 2.11 (m, 2H).

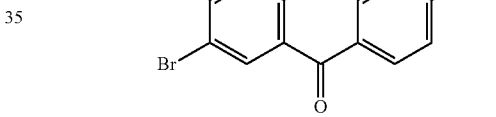

(4,7-Dibromo-2,3-dihydro-1H-inden-5-yl)(4-ethoxyphenyl)methanone (7)

$^1$H NMR (400 MHz, CDCl$_3$) δ 7.78 (d, J=8.8 Hz, 2H), 7.26 (s, 1H), 6.92 (d, J=9.2 Hz, 2H), 4.11 (q, J=7.2 Hz, 2H), 3.14-3.06 (m, 4H), 2.21-2.14 (m, 2H), 1.45 (t, J=6.8 Hz, 3H); [M+H]$^+$ 425.

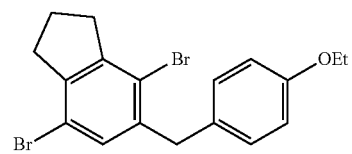 [SMILES: CCOc1ccc(Cc2cc(Br)c3c(c2Br)CCC3)cc1]

4,7-Dibromo-5-(4-ethoxybenzyl)-2,3-dihydro-1H-indene (8)

$^1$H NMR (400 MHz, CDCl$_3$) δ 7.09 (d, J=8.8 Hz, 2H), 7.07 (s, 1H), 6.82 (d, J=8.8 Hz, 2H), 4.01 (q, J=7.2 Hz, 2H), 3.98 (s, 2H), 3.08-2.98 (m, 4H), 2.12 (m, 2H), 1.40 (t, J=7.2 Hz, 3H).

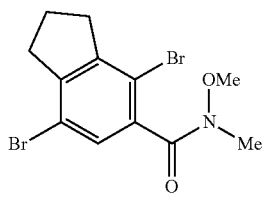 [SMILES: CON(C)C(=O)c1cc(Br)c2c(c1Br)CCC2]

4,7-Dibromo-N-methoxy-N-methyl-2,3-dihydro-1H-inden-5-carboxamide (9)

To a solution of acid 4 (4.8 g, 15.0 mmol) in CH$_2$Cl$_2$ (80 mL) were added EDCI (3.83 g, 20 mmol), HOBT (2.70 g, 20 mmol), NMM (8.8 mL, 80 mmol) and N,O-dimethylhydroxylamine-HCl (1.95 g, 20 mmol) at rt. The mixture was stirred at rt overnight. The reaction mixture was quenched with water (50 mL) and extracted with DCM (100 mL). The organic layer was washed with brine, dried over anhydrous MgSO$_4$, filtered and concentrated in vacuo. The residue was purified by silica gel column chromatography to provide the compound 9 (0.27 g, 0.73 mmol, 7%).

$^1$H NMR (400 MHz, CDCl$_3$) δ 7.26 (s, 1H), 3.51 (s, 3H), 3.36 (s, 3H), 3.10-3.04 (m, 4H), 2.14 (m, 2H); [M+H]$^+$ 364.

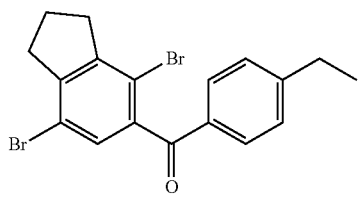 [SMILES: CCc1ccc(C(=O)c2cc(Br)c3c(c2Br)CCC3)cc1]

(4,7-Dibromo-2,3-dihydro-1H-inden-5-yl)(4-ethylphenyl)methanone (10)

To a solution of amide 9 (0.27 g, 0.73 mmol) in anhydrous THF (2.7 mL) was added dropwise 4-ethylphenylmagnesium bromide (3.65 mL of 0.5M in THF, 1.83 mol) at 0° C. under nitrogen atmosphere. The mixture was warmed up to room temperature slowly and stirred at room temperature for 15 h. The reaction mixture was quenched with 1M HCl solution (10 mL) and extracted with EtOAc (20 mL). The organic layer was dried over MgSO$_4$, filtered, and concentrated in vacuo. The residue was purified by silica gel column chromatography to provide the compound 10 (0.25 g, 0.62 mmol, 85%). [M+H]$^+$ 409.

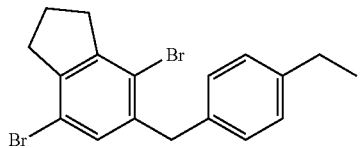 [SMILES: CCc1ccc(Cc2cc(Br)c3c(c2Br)CCC3)cc1]

4,7-Dibromo-5-(4-ethylbenzyl)-2,3-dihydro-1H-indene (11)

$^1$H NMR (400 MHz, CDCl$_3$) δ 7.11 (d, J=3.2 Hz, 4H), 7.09 (s, 1H), 4.02 (s, 2H), 3.08-2.99 (m, 4H), 2.62 (q, J=7.6 Hz, 2H), 2.14 (m, 2H), 1.22 (t, J=7.2 Hz, 3H).

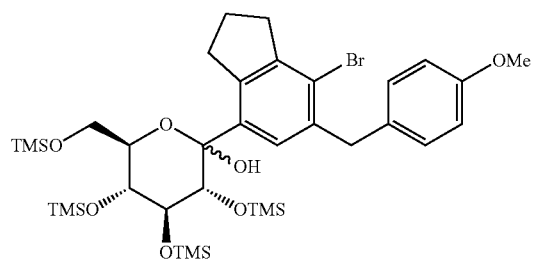

(3R,4S,5R,6R)-2-(7-Bromo-6-(4-methoxybenzyl)-2,3-dihydro-1H-inden-4-yl)-3,4,5-tris(trimethylsilyloxy)-6-((trimethylsilyloxy)methyl)tetrahydro-2H-pyran-2-ol (14)

To a solution of bromide 6 (0.92 g, 2.32 mmol) in anhydrous THF (12.3 mL) was added dropwise n-BuLi (2.5M in hexane, 1.21 mL, 3.02 mmol) at −78° C. under nitrogen atmosphere, and the mixture was stirred for 0.5-1 h at the same temperature. Then a solution of TMS-protected gluconolactone (1.41 g, 3.02 mmol) in THF (6 mL) was added dropwise, and the mixture was stirred for 3 h at the same temperature. The reaction mixture was quenched with saturated NH$_4$Cl solution (15 mL) and extracted with EtOAc (50 mL). The organic layer was washed with brine, dried over anhydrous MgSO$_4$, filtered and concentrated in vacuo to provide the crude intermediate 14, which was used without further purification (2.03 g, 2.59 mmol, 111%). TLC (10% EtOAc/hexane) R$_f$=0.33.

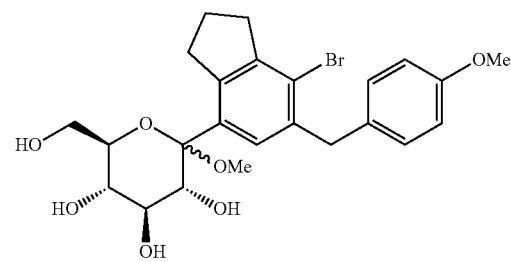 [SMILES: COc1ccc(Cc2cc(C3(OC)O[C@H](CO)[C@@H](O)[C@H](O)[C@H]3O)c3c(c2Br)CCC3)cc1]

(3R,4S,5S,6R)-2-(7-Bromo-6-(4-methoxybenzyl)-2,3-dihydro-1H-inden-4-yl)-6-(hydroxymethyl)-2-methoxytetrahydro-2H-pyran-3,4,5-triol (15)

To a solution of crude alcohol 14 (2.03 g) in anhydrous THF (11.9 mL) were added CH$_3$SO$_3$H (0.6 N in MeOH, 7.0 mL, 4.18 mmol) at −78° C. under nitrogen atmosphere. The mixture was slowly warmed up to −40° C. for 2 h. The reaction mixture was quenched with saturated NaHCO$_3$ solution (15 mL) and extracted with EtOAc (50 mL). The organic layer was washed with brine, dried over anhydrous MgSO$_4$, filtered and concentrated in vacuo to provide the crude intermediate 15, which was used without further purification (0.94 g, 1.85 mmol, 80%). [M−OMe]$^+$ 477.

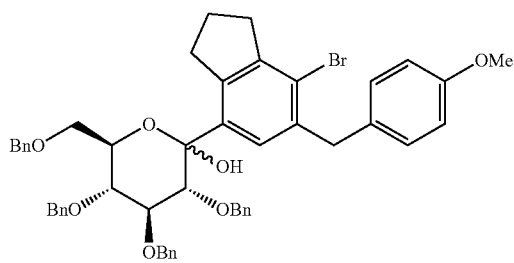 [SMILES: COc1ccc(Cc2cc(C3(O)O[C@H](COCc4ccccc4)[C@@H](OCc4ccccc4)[C@H](OCc4ccccc4)[C@H]3OCc3ccccc3)c3c(c2Br)CCC3)cc1]

(3R,4S,5R,6R)-3,4,5-Tris(benzyloxy)-6-(benzyloxymethyl)-2-(7-bromo-6-(4-methoxybenzyl)-2,3-dihydro-1H-inden-4-yl)tetrahydro-2H-pyran-2-ol (16)

To a solution of bromide 6 (3.21 g, 8.10 mmol) in anhydrous THF (28.3 mL) was added dropwise n-BuLi (2.5M in hexane, 3.40 mL, 8.51 mmol) at −78° C. under nitrogen atmosphere, and the mixture was stirred for 0.5-1 h at the same temperature. Then a solution of perbenzylated gluconolactone 13 (4.37 g, 8.10 mmol) in THF (9.6 mL) was added dropwise, and the mixture was stirred for 3 h at the same temperature. The reaction mixture was quenched with saturated NH$_4$Cl solution (30 mL) and extracted with EtOAc (100 mL). The organic layer was washed with brine, dried over anhydrous MgSO$_4$, filtered and concentrated in vacuo to provide the crude intermediate 16, which was used without further purification (6.96 g, 8.13 mmol, 100%).

TLC (25% EtOAc/hexane) R$_f$=0.24; [M+H]$^+$ 877.

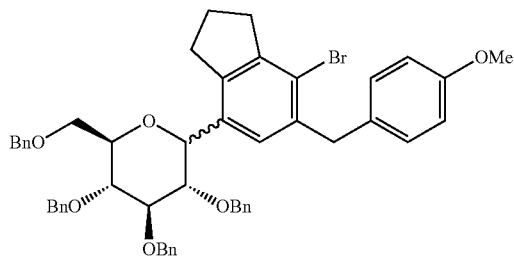 [SMILES: COc1ccc(Cc2cc(C3O[C@H](COCc4ccccc4)[C@@H](OCc4ccccc4)[C@H](OCc4ccccc4)[C@H]3OCc3ccccc3)c3c(c2Br)CCC3)cc1]

(2R,3R,4R,5S)-3,4,5-Tris(benzyloxy)-2-(benzyloxymethyl)-6-(7-bromo-6-(4-methoxybenzyl)-2,3-dihydro-1H-inden-4-yl)tetrahydro-2H-pyran (17)

To a solution of the intermediate 16 (6.96 g, 8.13 mmol) in CH$_2$Cl$_2$ (40.1 mL) were added triethylsilane (3.24 mL, 16.2 mmol) and boron trifluoride diethyl etherate (2.55 mL, 16.2 mmol) at −60° C. under nitrogen atmosphere. The mixture was warmed up to −30° C. for 3 h. To the mixture was added saturated K$_2$CO$_3$ solution (50 mL) slowly and the mixture was extracted with EtOAc (100 mL). The organic layer was dried over MgSO$_4$, filtered, and concentrated in vacuo. The residue was purified by silica gel column chromatography to provide the desired intermediate 17 (2.87 g, 3.42 mmol, 42%).

TLC (25% EtOAc/hexane) R$_f$=0.53; [M+Na]$^+$ 863.

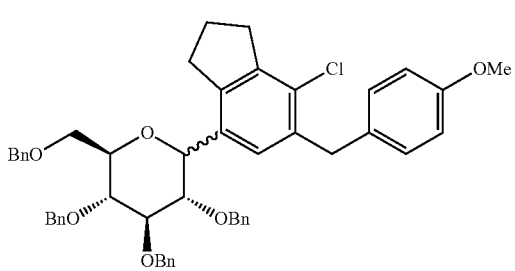 [SMILES: COc1ccc(Cc2cc(C3O[C@H](COCc4ccccc4)[C@@H](OCc4ccccc4)[C@H](OCc4ccccc4)[C@H]3OCc3ccccc3)c3c(c2Cl)CCC3)cc1]

(2R,3R,4R,5S)-3,4,5-Tris(benzyloxy)-2-(benzyloxymethyl)-6-(7-chloro-6-(4-methoxybenzyl)-2,3-dihydro-1H-inden-4-yl)tetrahydro-2H-pyran (18)

To a solution of the intermediate 17 (0.76 g, 0.91 mmol) in DMF (3.8 mL) were added Cu(I)Cl (2.24 g, 22.6 mmol). The mixture was stirred at 120° C. for 4 h. The reaction mixture was quenched with brine (50 mL) and extracted with EtOAc (50 mL). The organic layer was dried over MgSO$_4$, filtered, and concentrated in vacuo to provide the crude intermediate 18, which was used without further purification (0.77 g, 0.97 mmol, 106%).

[M+Na]$^+$ 817.

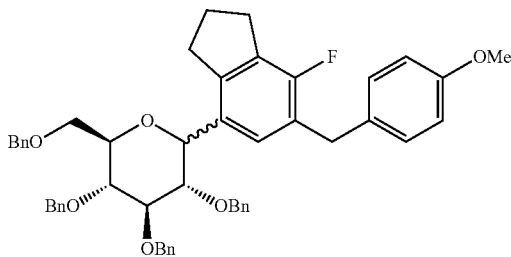 [SMILES: COc1ccc(Cc2cc(C3O[C@H](COCc4ccccc4)[C@@H](OCc4ccccc4)[C@H](OCc4ccccc4)[C@H]3OCc3ccccc3)c3c(c2F)CCC3)cc1]

(2R,3R,4R,5S)-3,4,5-Tris(benzyloxy)-2-(benzyloxymethyl)-6-(7-fluoro-6-(4-methoxybenzyl)-2,3-dihydro-1H-inden-4-yl)tetrahydro-2H-pyran (19)

To a solution of the intermediate 17 (1.01 g, 1.2 mmol) in anhydrous THF (12.0 mL) were added dropwise n-BuLi (2.5M in hexane, 0.77 mL, 1.92 mmol) at −78° C. under nitrogen atmosphere, and the mixture was stirred for 20 min at the same temperature. Then a solution of N-fluorobenzenesulfonimide (0.68 g, 2.16 mmol) in THF (3.0 mL) was added dropwise, and the mixture was stirred for 1 h at the same temperature. The reaction mixture was quenched with saturated NaCl solution (10 mL) and extracted with EtOAc (50 mL). The organic layer was washed with brine, dried over anhydrous MgSO$_4$, filtered and concentrated in vacuo to provide the crude intermediate 19, which was used without further purification (0.95 g, 1.21 mmol, 101%).

[M+Na]$^+$ 801.

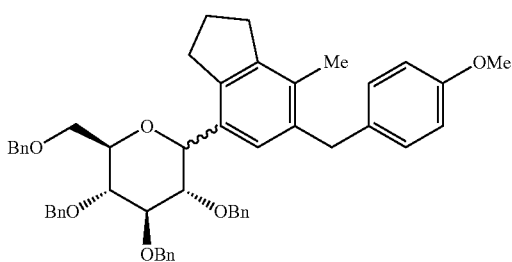 [SMILES: COc1ccc(Cc2cc(C3O[C@H](COCc4ccccc4)[C@@H](OCc4ccccc4)[C@H](OCc4ccccc4)[C@H]3OCc3ccccc3)c3c(c2C)CCC3)cc1]

(2R,3R,4R,5S)-3,4,5-Tris(benzyloxy)-2-(benzyloxymethyl)-6-(6-(4-methoxybenzyl)-7-methyl-2,3-dihydro-1H-inden-4-yl)tetrahydro-2H-pyran (20)

To a solution of the intermediate 17 (0.95 g, 1.13 mmol) in anhydrous THF (12.0 mL) were added dropwise n-BuLi (2.5M in hexane, 0.72 mL, 1.81 mmol) at −78° C. under nitrogen atmosphere, and the mixture was stirred for 0.5 h at the same temperature. Then a solution of iodomethane (0.13 mL, 2.03 mmol) in THF (1.0 mL) was added dropwise, and the mixture was slowly warmed up to 0° C. for 3 h. The reaction mixture was quenched with 1M HCl solution (30 mL) and extracted with EtOAc (50 mL). The organic layer was washed with brine, dried over anhydrous MgSO$_4$, filtered and concentrated in vacuo to provide the crude intermediate 20, which was used without further purification (0.88 g, 1.13 mmol, 100%).

[M+Na]$^+$ 797.

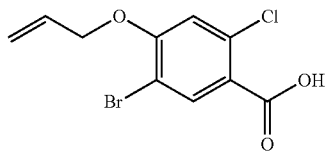

4-(Allyloxy)-5-bromo-2-chlorobenzoic acid (21)

A mixture of compound 38 (15.6 g, 57.4 mmol) and NaOH (80.0 g, 2.11 mol) in EtOH (220 mL) and water (110 mL) was stirred for 6 hours under reflux. The cooled mixture was concentrated in vacuo and diluted with water (400 mL). The mixture was cooled down to 5° C. and acidified with conc. HCl. The precipitated solid was collected by filtration. The solid was dissolved with EtOAc and washed with brine, dried over MgSO$_4$, filtered and concentrated in vacuo to provide a crude product 21 (17.0 g, 100%) as a white solid.

$^1$H NMR (400 MHz, CDCl$_3$) δ 8.30 (s, 1H), 6.96 (s, 1H), 6.10-6.01 (m, 1H), 5.52 (dq, J=8.6, 0.8 Hz, 1H), 5.39 (dq, J=8.6, 0.8 Hz, 1H), 4.68 (dt, J=4.6, 1.6 Hz, 2H).

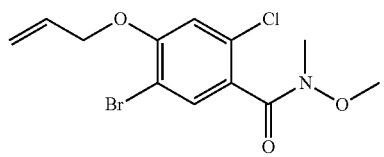 [SMILES: C=CCOc1cc(Cl)c(C(=O)N(C)OC)cc1Br]

4-(Allyloxy)-5-bromo-2-chloro-N-methoxy-N-methylbenzamide (22)

To a suspension of 4-(allyloxy)-5-bromo-2-chlorobenzoic acid 21 (5.0 g, 17.2 mmol) in CH$_2$Cl$_2$ (50 mL) were added N,O-dimethylhydroxylamine HCl (2.1 g, 20.6 mmol), EDCI (4.9 g, 25.8 mmol), HOBT (4.7 g, 34.4 mmol) and NMM (9.5 mL, 86.0 mmol). The reaction mixture was stirred at rt for 15 hours and evaporated in vacuo to remove volatiles. The mixture was extracted with EtOAc/H$_2$O (100 mL/100 mL). The organic layer was dried over MgSO$_4$, filtered and concentrated in vacuo. The residue was triturated with hexane (100 mL) and stirred at r.t. for 30 min. The solid was precipitated, filtered, washed with hexane (50 mL) and dried under high vacuum to obtain the desired product (5.5 g, 95%).

$^1$H NMR (400 MHz, CDCl$_3$) δ 7.57 (s, 1H), 6.93 (s, 1H), 6.15-6.01 (m, 1H), 5.53 (ddd, J=17.3 Hz, 3.0 Hz, 1.7 Hz, 1H), 5.39 (ddd, J=10.6 Hz, 2.8 Hz, 1.4 Hz, 1H), 4.70 (dt, J=4.2 Hz, 1.6 Hz, 2H), 3.57 (br s, 3H), 3.35 (br s, 3H); [M+Na]$^+$ 334.

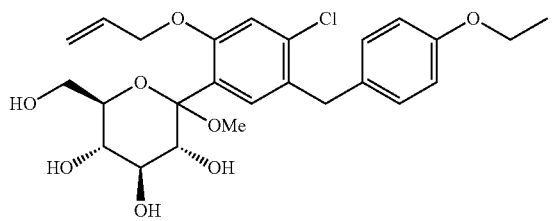 [SMILES: C=CCOc1cc(Cl)c(Cc2ccc(OCC)cc2)cc1C1(OC)O[C@H](CO)[C@@H](O)[C@H](O)[C@H]1O]

(3R,4S,5S,6R)-2-(2-(Allyloxy)-4-chloro-5-(4-ethoxybenzyl)phenyl)-6-(hydroxymethyl)-2-methoxytetrahydro-2H-pyran-3,4,5-triol (23)

Compound 23 was prepared in Scheme 14 from 4-(allyloxy)-5-bromo-2-chlorobenzoic acid (21).

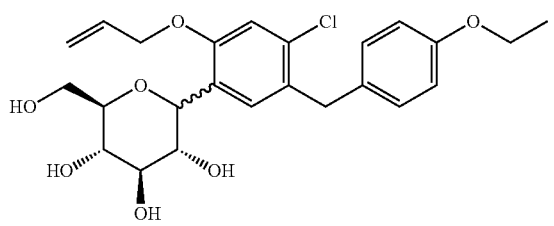 [SMILES: C=CCOc1cc(Cl)c(Cc2ccc(OCC)cc2)cc1C1O[C@H](CO)[C@@H](O)[C@H](O)[C@H]1O]

(3R,4R,5S,6R)-2-(2-(Allyloxy)-4-chloro-5-(4-ethoxybenzyl)phenyl)-6-(hydroxymethyl)tetrahydro-2H-pyran-3,4,5-triol (24)

To a solution of crude compound 23 (7.14 g 14.4 mmol) in CH$_2$Cl$_2$/CH$_3$CN (75 mL/75 mL) were added triethylsilane (4.6 mL, 28.9 mmol) and boron trifluoride diethyl etherate (3.6 mL, 28.9 mmol) at −55° C. The mixture was allowed to slowly warm to 0° C. To a mixture was added aq. saturated NaHCO$_3$ solution (75 mL) to quench the reaction and the mixture was evaporated in vacuo to remove CH$_2$Cl$_2$ and CH$_3$CN. The mixture was extracted with EtOAc (100 mL×2). The combined organic layer was dried over MgSO$_4$, filtered, and concentrated in vacuo. The crude (3R,4R,5S,6R)-2-(2-(allyloxy)-4-chloro-5-(4-ethoxybenzyl)phenyl)-6-(hydroxymethyl)tetrahydro-2H-pyran-3,4,5-triol (24, 6.36 g) was carried on to the next step without further purification.

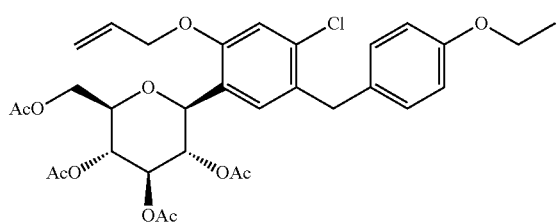 [SMILES: C=CCOc1cc(Cl)c(Cc2ccc(OCC)cc2)cc1[C@@H]1O[C@H](COC(C)=O)[C@@H](OC(C)=O)[C@H](OC(C)=O)[C@H]1OC(C)=O]

(2R,3R,4R,5S,6S)-2-(Acetoxymethyl)-6-(2-(allyloxy)-4-chloro-5-(4-ethoxybenzyl)phenyl)tetrahydro-2H-pyran-3,4,5-triyl triacetate (25)

To a solution of crude compound 24 (6.36 g) in CH$_2$Cl$_2$ (100 mL) were added Ac$_2$O (13.0 mL, 137.0 mmol), Et$_3$N (20.0 mL, 137.0 mmol) and catalytic amount of DMAP at 0° C. The mixture was stirred at 0° C. for 15 min and at room temperature for 3 hours. The mixture was concentrated under reduced pressure to remove volatiles. The residue was diluted with EtOAc (50 mL), washed with H$_2$O (100 mL), aq. 1N HCl solution (100 mL) and brine (100 mL) successively. The organic layer was dried over MgSO$_4$, filtered, and concentrated in vacuo. The residue was recrystallized with EtOH (50 mL). The desired product was precipitated and the precipitate was collected by filtration and washed with cold EtOH (50 mL) and dried under high vacuum to obtain the title compound 25 (1.37 g).
[M+Na]$^+$ 655.

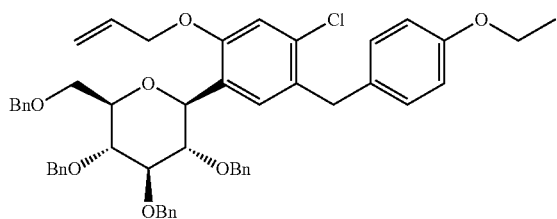 [SMILES: C=CCOc1cc(Cl)c(Cc2ccc(OCC)cc2)cc1[C@@H]1O[C@H](COCc2ccccc2)[C@@H](OCc2ccccc2)[C@H](OCc2ccccc2)[C@H]1OCc1ccccc1]

(2S,3S,4R,5R,6R)-2-(2-(Allyloxy)-4-chloro-5-(4-ethoxybenzyl)phenyl)-3,4,5-tris(benzyloxy)-6-(benzyloxymethyl)tetrahydro-2H-pyran (26)

To a suspension of acetate 25 (1.37 g, 2.16 mmol) in MeOH (50 mL) was added NaOMe (25 wt % in MeOH, 0.5 mL) at room temperature. The mixture was stirred at room temperature for 1 hour. Glacial AcOH was added to the mixture to acidify the mixture. The mixture was concentrated under a reduced pressure. The crude ((2S,3R,4R,5S,6R)-2-(2-(allyloxy)-4-chloro-5-(4-ethoxybenzyl)phenyl)-6-(hydroxymethyl)tetrahydro-2H-pyran-3,4,5-triol (25-1) was carried on to the next step without further purification.

To a solution of the crude compound 25-1 and benzyl bromide (2.6 mL, 21.6 mmol) in THF/DMF (30 mL/10 mL) was added NaH (60% dispersion in mineral oil, 1.3 g, 32.4 mmol) portionwise at 0° C. The reaction mixture was gradually raised to room temperature and stirred at r.t. for 15 hour. The mixture was cooled to 0° C. and aqueous saturated NH$_4$Cl solution (150 mL) was added to the mixture. The organic layer was washed with brine, dried over anhydrous MgSO$_4$, filtered and concentrated in vacuo. The residue was purified using normal phase column chromatography to provide the desired product 26 (1.50 g, 85% (2-steps)).

$^1$H NMR (400 MHz, CDCl$_3$) δ 7.49-7.23 (m, 14H), 7.21-7.11 (m, 5H), 7.08-7.03 (m, 3H), 6.83 (d, J=6.4 Hz, 2H), 6.71 (d, J=8.8 Hz, 2H), 6.02-5.91 (m, 1H), 5.38 (d, J=17.2 Hz, 1H), 5.18 (d, J=10.4 Hz, 1H), 4.80 (s, 2H), 4.76 (d, J=11.2 Hz, 1H), 4.61-4.48 (m, 7H), 3.95-3.86 (m, 5H), 3.79-3.72 (m, 2H), 3.64-3.56 (m, 4H), 1.25 (t, J=7.2 Hz, 3H); [M+Na]$^+$ 847.

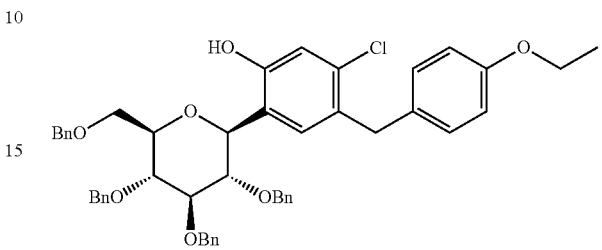

5-Chloro-4-(4-ethoxybenzyl)-2-((2S,3S,4R,5R,6R)-3,4,5-tris(benzyloxy)-6-(benzyloxymethyl)tetrahydro-2H-pyran-2-yl)phenol (27)

To a suspension of compound 26 (1.50 g, 1.82 mmol) and tetrakis(triphenylphosphine)palladium(0) (0.22 g, 0.18 mmol) in THF (20 mL) was added NaBH$_4$ (0.56 g, 14.6 mmol) at 0° C. The mixture was warmed up to r.t. slowly and stirred at r.t. for 12 hours. The reaction mixture was cooled to 0° C. and aqueous saturated NH$_4$Cl solution (50 mL) was added to the mixture. The mixture was extracted with EtOAc (100 mL). The organic layer was washed with brine, dried over anhydrous MgSO$_4$, filtered and concentrated in vacuo. The residue was purified using normal phase column chromatography to provide the title product 27 (0.98 g, 68%).

$^1$H NMR (400 MHz, CDCl$_3$) δ 7.75 (s, 1H), 7.38-7.18 (m, 16H), 7.17-7.11 (m, 2H), 7.03-6.91 (m, 5H), 6.88 (s, 1H), 6.75-6.68 (m, 2H), 4.94-4.79 (m, 3H), 4.59-4.42 (m, 4H), 4.31 (d, J=9.2 Hz, 1H), 4.02-3.82 (m, 5H), 3.79-3.63 (m, 5H), 3.57-3.49 (m, 1H), 1.38 (t, J=7.0 Hz, 3H); [M+Na]$^+$ 807.

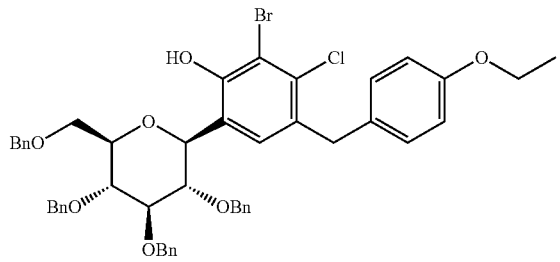 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)c(O)c(Br)c2Cl)cc1]

2-Bromo-3-chloro-4-(4-ethoxybenzyl)-6-((2S,3S,4R,5R,6R)-3,4,5-tris(benzyloxy)-6-(benzyloxymethyl)tetrahydro-2H-pyran-2-yl)phenol (28)

To a solution of phenol 27 (0.98 g, 1.24 mmol) in AcOH (12 mL) were added Et$_3$N (0.37 mL, 1.86 mmol) and bromine (77 µL, 1.50 mmol) at 0° C. The mixture was stirred at 0° C. for 5 min and at room temperature for 12 hours. The reaction mixture was cooled to 0° C. and aqueous saturated NH$_4$Cl solution (30 mL) was added to the mixture. The mixture was extracted with EtOAc (100 mL). The organic layer was washed with H$_2$O (50 mL×2), aqueous saturated NaHCO$_3$ solution (100 mL), dried over anhydrous MgSO₄, filtered and concentrated in vacuo. The crude 2-bromo-3-chloro-4-(4-ethoxybenzyl)-6-((2S,3S,4R,5R,6R)-3,4,5-tris(benzyloxy)-6-(benzyloxymethyl)tetrahydro-2H-pyran-2-yl)phenol (28, 1.08 g) was carried on to the next step without further purification.

[M+Na]⁺ 885.

¹H NMR (400 MHz, CDCl₃) δ 7.33-7.22 (m, 13H), 7.21-7.10 (m, 6H), 7.02 (d, J=8.6 Hz, 2H), 6.80 (d, J=6.7 Hz, 2H), 6.71 (d, J=8.6 Hz, 2H), 4.89 (s, 2H), 4.87 (d, J=11.0 Hz, 1H), 4.63 (d, J=10.8 Hz, 1H), 4.55-4.43 (m, 4H), 4.10-4.03 (m, 4H), 3.99-3.91 (m, 4H), 3.88-3.65 (m, 7H), 2.21-2.04 (m, 2H), 1.38 (t, J=7.0 Hz, 3H); [M+Na]⁺ 961.

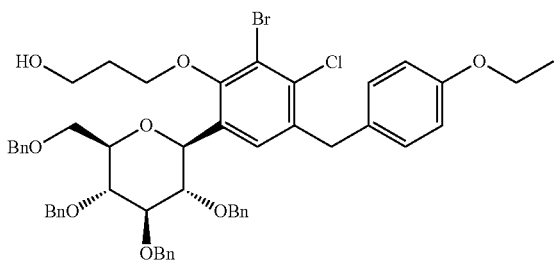 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)c(OCCCO)c(Br)c2Cl)cc1]

3-(2-Bromo-3-chloro-4-(4-ethoxybenzyl)-6-((2S,3S,4R,5R,6R)-3,4,5-tris(benzyloxy)-6-(benzyloxymethyl)tetrahydro-2H-pyran-2-yl)phenoxy)propan-1-ol (29)

To a suspension of crude compound 28 (1.33 g, 1.54 mmol) and K₂CO₃ (0.322 g, 2.31 mmol) in acetone (20 mL) was added 3-bromopropanol (0.30 mL, 2.31 mmol) at r.t. The mixture was stirred at 55° C. for 15 hours. The reaction mixture was cooled to r.t and filtered off to remove inorganic salts. The filtrate was concentrated in vacuo. The residue was purified using normal phase column chromatography to provide the title product 29 (1.47 g, 100%).

¹H NMR (400 MHz, CDCl₃) δ 7.38-7.22 (m, 13H), 7.21-7.11 (m, 6H), 7.03 (d, J=8.6 Hz, 2H), 6.80 (d, J=6.7 Hz, 2H), 6.73 (d, J=8.6 Hz, 2H), 4.90 (s, 2H), 4.87 (d, J=10.8 Hz, 1H), 4.61 (d, J=10.8 Hz, 1H), 4.59-4.42 (m, 3H), 4.10-3.94 (m, 6H), 3.93-3.75 (m, 5H), 3.55-3.49 (m, 3H), 2.33 (dd, J=6.9 Hz, 5.3 Hz, 1H), 2.11 (quint, J=6.0 Hz, 2H), 1.97-1.93 (m, 2H), 1.38 (t, J=7.0 Hz, 3H); [M+Na]⁺ 943.

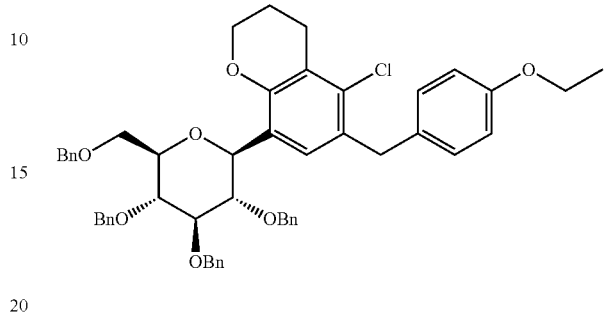

5-Chloro-6-(4-ethoxybenzyl)-8-((2S,3S,4R,5R,6R)-3,4,5-tris(benzyloxy)-6-(benzyloxymethyl)tetrahydro-2H-pyran-2-yl)chroman (30)

To a solution of chloride 29-1 (1.03 g, 1.09 mmol) in THF (30 mL) was added n-BuLi (2.5M in hexane, 0.87 mL, 2.18 mmol) at −78° C. The mixture was allowed to slowly warm to r.t. and stirred at r.t. for 12 hours. To the mixtures was added aqueous saturated NH₄Cl solution (50 mL). The mixture was extracted with EtOAc (100 mL). The organic layer was washed with brine, dried over anhydrous MgSO₄, filtered and concentrated in vacuo. The residue was purified using normal phase column chromatography to provide the title product 30 (255 mg, 28%).

¹H NMR (400 MHz, CDCl₃) δ 7.35-7.23 (m, 13H), 7.21-7.07 (m, 6H), 7.02 (d, J=8.6 Hz, 2H), 6.80 (d, J=6.7 Hz, 2H), 6.71 (d, J=8.6 Hz, 2H), 4.96-4.83 (m, 3H), 4.68-4.61 (m, 2H), 4.49 (dd, J=12.6 Hz, 11.6 Hz, 2H), 4.09-3.91 (m, 8H), 3.83-3.69 (m, 4H), 3.61-3.54 (m, 2H), 2.76 (t, J=6.7 Hz, 2H), 1.98-1.83 (m, 2H), 1.34 (t, J=7.0 Hz, 3H); [M+Na]⁺ 847.

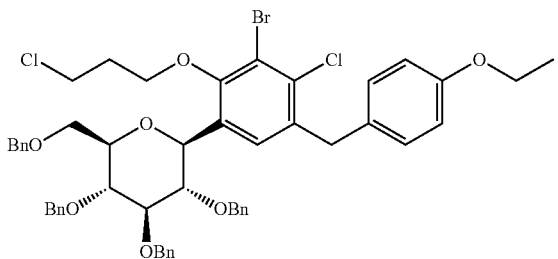 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)c(OCCCCl)c(Br)c2Cl)cc1]

(2R,3R,4R,5S,6S)-3,4,5-Tris(benzyloxy)-2-(benzyloxymethyl)-6-(3-bromo-4-chloro-2-(3-chloropropoxy)-5-(4-ethoxybenzyl)phenyl)tetrahydro-2H-pyran (29-1)

To a suspension of bromide 29 (1.47 g, 1.59 mmol) in CH₃CN (25 mL) were added triphenylphosphine (1.1 g, 3.98 mmol) and CCl₄ (2.5 mL) at r.t. The mixture was stirred at 55° C. for 3 hours. The reaction mixture was cooled to r.t and concentrated in vacuo. The residue was purified using normal phase column chromatography to provide the desired product 29-1 (1.03 g, 70%).

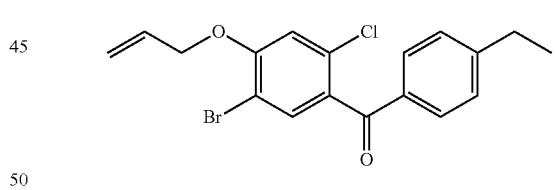

(4-(Allyloxy)-5-bromo-2-chlorophenyl)(4-ethylphenyl)methanone (31)

To solution of Weinreb amide 22 (4.5 g, 13.4 mmol) in THF (100 mL) was added 4-ethylphenylmagnesium bromide (0.5M in THF, 50.8 mL, 26.9 mmol) at 0° C. The reaction mixture was warmed up to r.t. slowly and stirred at r.t. for 15 hours. To the reaction mixture was added aqueous saturated NH₄Cl solution (100 mL). The mixture was extracted with EtOAc (100 mL). The organic layer was dried over MgSO₄, filtered and concentrated in vacuo. The residue was triturated with hexane (100 mL) and stirred at r.t. for 30 min. The solid was precipitated, filtered, washed with hexane (50 mL) and dried under high vacuum to obtain the title product (4.30 g, 73%).

¹H NMR (400 MHz, CDCl₃) δ 7.67 (d, J=6.5 Hz, 2H), 7.62 (s, 1H), 7.25 (d, J=8.0 Hz, 2H), 6.98 (s, 1H), 6.18-6.03 (m, 1H), 5.55 (ddd, J=17.3 Hz, 3.0 Hz, 1.7 Hz, 1H), 5.41 (ddd, J=10.6 Hz, 2.8 Hz, 1.4 Hz, 1H), 4.71 (dt, J=4.2 Hz, 1.6 Hz, 2H), 2.77 (q, J=7.6 Hz, 2H), 1.30 (t, J=7.6 Hz, 3H); [M+Na]⁺ 379.

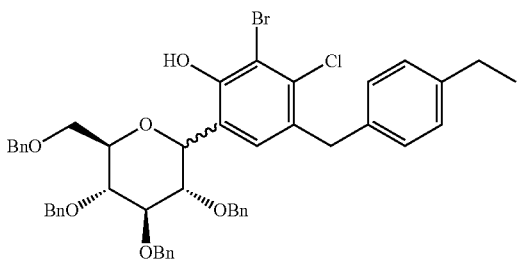 [SMILES: CCc1ccc(Cc2cc(C3O[C@H](COCc4ccccc4)[C@@H](OCc4ccccc4)[C@H](OCc4ccccc4)[C@H]3OCc3ccccc3)c(O)c(Br)c2Cl)cc1]

2-Bromo-3-chloro-4-(4-ethylbenzyl)-6-((3S,4R,5R,6R)-3,4,5-tris(benzyloxy)-6-(benzyloxymethyl)tetrahydro-2H-pyran-2-yl)phenol (32)

To a mixture of 5-chloro-4-(4-ethylbenzyl)-2-((3S,4R,5R,6R)-3,4,5-tris(benzyloxy)-6-(benzyloxymethyl)tetrahydro-2H-pyran-2-yl)phenol (3.0 g, 3.90 mmol) and TEA (1.63 mL) in acetic acid (20.1 mL) was added dropwise bromine (0.30 mL, 5.85 mmol) at 0° C. under nitrogen atmosphere. After stirring for 2 h at rt, the reaction mixture was quenched with saturated NH₄Cl solution (50 mL) and extracted with EtOAc (100 mL). The organic layer was washed with brine, dried over anhydrous MgSO₄, filtered and concentrated in vacuo. The residue was purified by silica gel column chromatography to provide the compound 32 (2.99 g, 3.53 mmol, 90%).
[M+Na]⁺ 871.

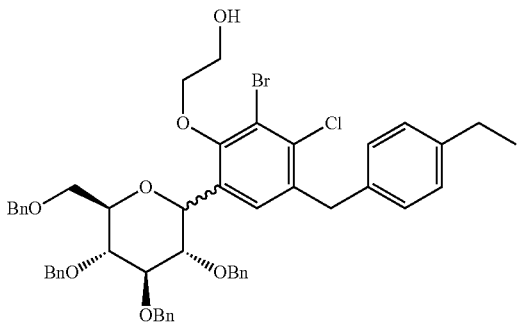 [SMILES: CCc1ccc(Cc2cc(C3O[C@H](COCc4ccccc4)[C@@H](OCc4ccccc4)[C@H](OCc4ccccc4)[C@H]3OCc3ccccc3)c(OCCO)c(Br)c2Cl)cc1]

2-(2-Bromo-3-chloro-4-(4-ethylbenzyl)-6-((3S,4R,5R,6R)-3,4,5-tris(benzyloxy)-6-(benzyloxymethyl)tetrahydro-2H-pyran-2-yl)phenoxy)ethanol (33)

To a mixture of the intermediate 32 (2.99 g, 3.53 mmol) and K₂CO₃ (0.73 g, 5.29 mmol) in acetone (35 mL) was added 2-bromoethanol (0.38 mL, 5.29 mmol) at rt. After stirring for 15 h at 50° C., the reaction mixture was cooled to rt. The precipitate was removed by filtration and the filtrate was concentrated in vacuo. The residue was dissolved in EtOAc (100 mL), washed with brine, dried over anhydrous MgSO₄, filtered and concentrated in vacuo to provide the crude intermediate 33, which was used without further purification (3.04 g, 3.41 mmol, 97%).
[M+Na]⁺ 915.

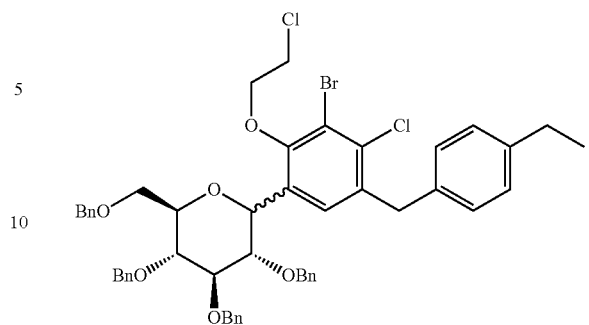

(2R,3R,4R,5S)-3,4,5-Tris(benzyloxy)-2-(benzyloxymethyl)-6-(3-bromo-4-chloro-2-(2-chloroethoxy)-5-(4-ethylbenzyl)phenyl)tetrahydro-2H-pyran (34)

To a solution of the intermediate 33 (3.04 g, 3.41 mmol) were added triphenylphosphine (2.23 g, 8.52 mmol) and CCl₄ (3.7 mL). After stirring for 2 h at 55° C., the solvent was evaporated off. The residue was dissolved in EtOAc (100 mL), washed with saturated NaHCO₃ solution, dried over anhydrous MgSO₄, filtered and concentrated in vacuo. The residue was purified by silica gel column chromatography to provide the compound 34 (1.62 g, 1.78 mmol, 52%).
[M+Na]⁺ 933.

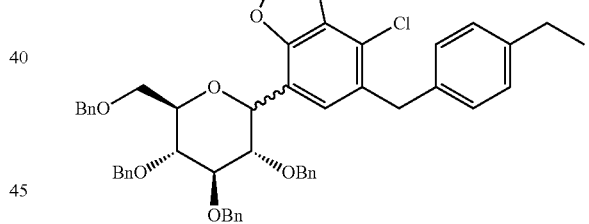

4-Chloro-5-(4-ethylbenzyl)-7-((3S,4R,5R,6R)-3,4,5-tris(benzyloxy)-6-(benzyloxymethyl)tetrahydro-2H-pyran-2-yl)-2,3-dihydrobenzofuran (35)

To a solution of the intermediate 34 (1.18 g, 1.30 mmol) in anhydrous THF (15 mL) was added dropwise n-BuLi (2.5M in hexane, 0.78 mL, 1.94 mmol) at −78° C. under nitrogen atmosphere. The mixture was slowly warmed up to rt and stirred overnight. The reaction mixture was quenched with 1M HCl solution (10 mL) and extracted with EtOAc (50 mL). The organic layer was washed with brine, dried over anhydrous MgSO₄, filtered and concentrated in vacuo to provide the crude intermediate 35, which was used without further purification (1.03 g, 1.30 mmol, 100%).
[M+Na]⁺ 817.

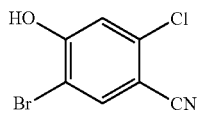

5-Bromo-2-chloro-4-hydroxybenzonitrile (37)

To a solution of 2-chloro-4-hydroxybenzonitrile (10 g, 65.1 mmol) in CH$_3$CN (200 mL) was added CF$_3$SO$_3$H (6.33 g, 71.6 mmol) and NBS (16.2 g, 94.1 mmol) at −30° C. After being stirred for 18 hours at room temperature, the mixture was quenched with aq. saturated NaHSO$_4$ solution and extracted with EtOAc. The organic layer was washed with brine, dried over MgSO$_4$, filtered and concentrated in vacuo. The residue was purified by silica gel column chromatography to afford the product 37 (10.5 g, 66%) as a white solid.
$^1$H NMR (400 MHz, CDCl$_3$) δ 7.79 (s, 1H), 7.17 (s, 1H); [M+H]$^+$ 232.

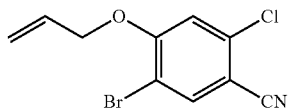

4-(Allyloxy)-5-bromo-2-chlorobenzonitrile (38)

A mixture of compound 37 (20.5 g, 88.1 mmol), allyl bromide (11.2 mL, 132 mmol) and K$_2$CO$_3$ (24.4 g, 176 mmol) in acetone (440 mL) was stirred for 3 hours under reflux. The mixture was filtrated and concentrated in vacuo. The resultant was partitioned between EtOAc and water. The organic layer was washed with brine, dried over MgSO$_4$, filtered and concentrated in vacuo. The residue was purified by silica gel column chromatography to afford the product 38 (15.6 g, 65%) as a white solid.
$^1$H NMR (400 MHz, CDCl$_3$) δ 7.82 (s, 1H), 7.00 (s, 1H), 6.09-5.99 (m, 1H), 5.51 (dq, J=8.6, 0.8 Hz, 1H), 5.30 (dq, J=8.6, 0.8 Hz, 1H), 4.68 (dt, J=4.6, 1.6 Hz, 2H); [M+H]$^+$ 272.

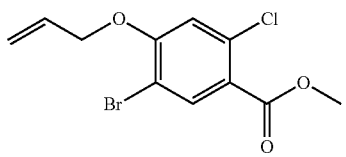 [SMILES: C=CCOc1cc(Cl)c(C(=O)OC)cc1Br]

Methyl 4-(allyloxy)-5-bromo-2-chlorobenzoate (39)

To a solution of compound 21 (17.0 g, 58.0 mmol) in MeOH (380 mL) was added dropwise SOCl$_2$ (21.1 mL, 291 mmol) at 0° C. under an atmosphere of nitrogen. The mixture was stirred at 0° C. for 30 min and then, stirred at 0° C. for 14 hours. The mixture was concentrated in vacuo and poured into aq. saturated NaHCO$_3$ solution and extracted with EtOAc. The organic layer was washed with brine, dried over MgSO$_4$, filtered and concentrated in vacuo to provide the crude product 39 (17.7 g, 99%) as a white solid.
$^1$H NMR (400 MHz, CDCl$_3$) δ 8.14 (s, 1H), 6.93 (s, 1H), 6.10-6.00 (m, 1H), 5.50 (dq, J=8.6, 0.8 Hz, 1H), 5.37 (dq, J=8.6, 0.8 Hz, 1H), 4.66 (dt, J=4.6, 1.6 Hz, 2H), 3.91 (s, 3H); [M+H]$^+$ 305.

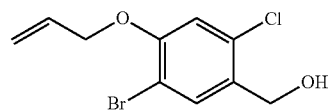

(4-(Allyloxy)-5-bromo-2-chlorophenyl)methanol (40)

To a solution of compound 40 (17.7 g, 58.0 mmol) in THF (230 mL) was added dropwise LiBH$_4$ (2.0M in THF, 72.5 mL, 145 mmol) at 0° C. under an atmosphere of nitrogen. The mixture was stirred for 30 min at 0° C. and then, stirred for 5 hours under reflux. To a cooled mixture was added MeOH (50 mL) at 0° C. and extracted with EtOAc. The organic layer was washed with brine, dried over MgSO$_4$, filtered and concentrated in vacuo to provide the crude product 40 (16.2 g, 100%) as colorless oil.
$^1$H NMR (400 MHz, CDCl$_3$) δ 7.66 (s, 1H), 6.89 (s, 1H), 6.10-6.03 (m, 1H), 5.49 (dq, J=8.6, 0.8 Hz, 1H), 5.34 (dq, J=8.6, 0.8 Hz, 1H), 4.69 (d, J=3.6 Hz, 2H), 4.60 (dt, J=4.6, 1.6 Hz, 2H).

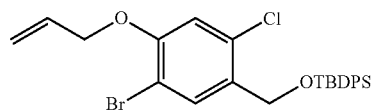

(4-(Allyloxy)-5-bromo-2-chlorobenzyloxy)(tert-butyl)diphenylsilane (41)

To a mixture of compound 40 (16.2 g, 58.0 mmol) and imidazole (5.17 g, 75.8 mmol) in THF (116 mL) was added tert-butyldiphenylchlorosilane (TBDPSCl) (19.4 mL, 75.8 mmol) dropwise at 0° C. under an atmosphere of nitrogen. The mixture was stirred at room temperature for 4 hours. To the mixture was added water (100 mL) and extracted with EtOAc (100 mL). The organic layer was dried over MgSO$_4$, filtered, and concentrated in vacuo. The residue was purified by silica gel column chromatography to provide the desired TBDPS-protected product 41 (26.6 g, 88%) as colorless oil.
$^1$H NMR (400 MHz, CDCl$_3$) δ 7.80 (s, 1H), 7.69-7.67 (m, 4H), 7.44-7.37 (m, 6H), 6.83 (s, 1H), 6.10-6.00 (m, 1H), 5.49 (dq, J=8.6, 0.8 Hz, 1H), 5.33 (dq, J=8.6, 0.8 Hz, 1H), 4.72 (s, 2H), 4.59 (dt, J=4.6, 1.6 Hz, 2H), 1.11 (s, 9H); [M+Na]$^+$ 515.

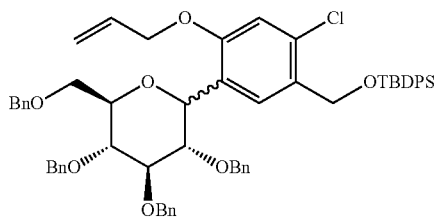

((2R,3R,4R,5S)-5-((3S,4R,5R,6R)-3,4,5-Tris(benzyloxy)-6-(benzyloxymethyl)-tetrahydro-2H-pyran-2-yl)-4-(allyloxy)-2-chlorobenzyloxy)(tert-butyl)diphenylsilane (43)

Step 1) To a solution of bromide compound 41 (5.53 g, 10.7 mmol) in THF (60 mL) at −78° C. under an atmosphere of nitrogen was added dropwise n-butyllithium (2.5 M in hexane, 4.66 mL, 11.67 mmol), and the mixture was stirred for 40 min at the same temperature. Then a solution of benzyl-protected gluconolactone (5.24 g, 9.73 mmol) in THF (10 mL) was added dropwise, and the mixture was stirred for 2 hours at the same temperature. The reaction mixture was quenched by addition of saturated ammonium chloride. After completing the addition, the solution was gradually raised to room temperature. The organic layer was separated and the aqueous layer was extracted with EtOAc. The organic layers were washed with brine, dried over anhydrous MgSO$_4$, filtered and concentrated in vacuo to afford the compound 42 (9.57 g), which was carried on to the next step without further purification.

[M+Na]$^+$ 997.

Step 2) To a solution of crude compound 42 (6.57 g, 6.73 mmol) in CH$_2$Cl$_2$ (42 mL) were added triethylsilane (1.61 mL, 10.0 mmol) and boron trifluoride diethyl etherate (1.26 mL, 10.0 mmol) at −60° C. The mixture was allowed to slowly warm to −20° C. To a mixture was added aq. saturated K$_2$CO$_3$ solution (20 mL) to quench the reaction and extracted with EtOAc (100 mL). The organic layer was dried over MgSO$_4$, filtered, and concentrated in vacuo. The residue was purified by silica gel column chromatography to provide the product 43 (1.81 g, 27%) as colorless oil.

[M+Na]$^+$ 981.

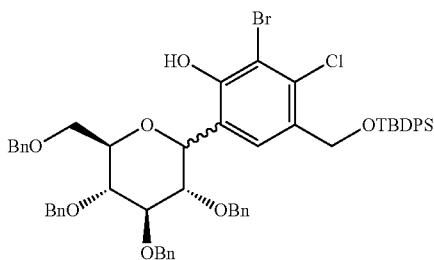

6-((3S,4R,5R,6R)-3,4,5-Tris(benzyloxy)-6-(benzyloxymethyl)-tetrahydro-2H-pyran-2-yl)-2-bromo-4-((tert-butyldiphenylsilyloxy)methyl)-3-chlorophenol (45)

Step 1) To a mixture of compound 43 (1.81 g, 1.88 mmol) and Pd(PPh)$_3$ (427 mg, 0.37 mmol) in THF (25 mL) was added NaBH$_4$ (569 mg, 15.0 mmol) at 0° C. under an atmosphere of nitrogen. The mixture was stirred for 20 hours at room temperature. To the mixture was quenched with aq. saturated NH$_4$Cl solution. The mixture was extracted with EtOAc. The organic layers were washed with brine, dried over anhydrous MgSO$_4$, filtered and concentrated in vacuo to provide the compound 44 (1.5 g, 86%), which was carried on to the next step without further purification.

[M+Na]$^+$ 941.

Step 2) To a solution of compound 44 (2.19 g, 2.38 mmol) in AcOH (12 mL) were added TEA (0.497 mL, 3.57 mmol) and Br$_2$ (0.146 mL, 2.85 mmol) dropwise at 0° C. The mixture was stirred at 0° C. for 15 min and at room temperature for 3 hours. To a mixture was added saturated ammonium chloride and extracted with EtOAc (100 mL). The organic layer was washed with brine, dried over MgSO$_4$, filtered, and concentrated in vacuo. The residue was purified by silica gel column chromatography to provide the product 45 (2.05 g, 79%) as colorless oil.

[M+Na]$^+$ 1019.

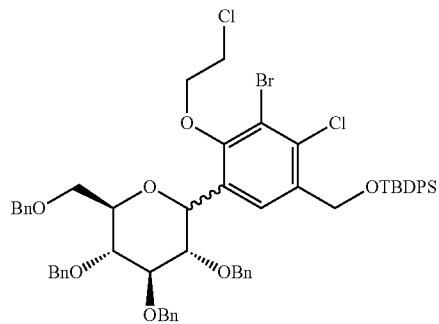

((2R,3R,4R,5S)-5-((3S,4R,5R,6R)-3,4,5-Tris(benzyloxy)-6-(benzyloxymethyl)-tetrahydro-2H-pyran-2-yl)-3-bromo-2-chloro-4-(2-chloroethoxy)benzyloxy)(tert-butyl)diphenylsilane (46)

Step 1) A mixture of compound 45 (2.0 g, 1.85 mmol), 2-bromoalcohol (0.196 mL, 2.77 mmol) and K$_2$CO$_3$ (511 mg, 3.70 mmol) in acetone (10 mL) was stirred for 18 hours under reflux. The mixture was filtrated and concentrated in vacuo. The resultant was partitioned between EtOAc and water. The organic layer was washed with brine, dried over MgSO$_4$, filtered and concentrated in vacuo to afford the crude product 45-1 (1.9 g, 100%) as brown oil.

[M+Na]$^+$ 1063.

Step 2) A mixture of compound 45-1 (2.4 g, 2.3 mmol), triphenylphosphine (1.50 g, 5.76 mmol) and CCl$_4$ (2.40 mL, 27.6 mmol) in CH$_3$CN (23 mL) was stirred for 2 hours under reflux. The mixture was concentrated in vacuo. The resultant was partitioned between EtOAc and water. The organic layer was washed with brine, dried over MgSO$_4$, filtered and concentrated in vacuo. The residue purified by silica gel column chromatography to provide the product 46 (1.3 g, 53%) as colorless oil.

[M+Na]$^+$ 1081.

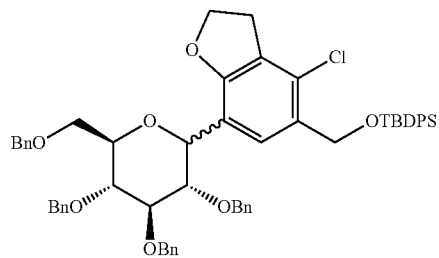

((7-((3S,4R,5R,6R)-3,4,5-Tris(benzyloxy)-6-(benzyloxymethyl)-tetrahydro-2H-pyran-2-yl)-4-chloro-2,3-dihydrobenzofuran-5-yl)methoxy)(tert-butyl)diphenylsilane (47)

To a solution of compound 46 (1.3 g, 1.22 mmol) in THF (12 mL) was added dropwise n-butyllithium (2.5M in hexane, 0.73 mL, 1.83 mmol) at −78° C. under an atmosphere of nitrogen. The mixture was stirred for 18 hours at −78° C. to 5° C. The mixture was quenched with 1N HCl and extracted with EtOAc. The organic layer was washed with brine, dried over MgSO$_4$, filtered and concentrated in vacuo. The residue was purified by silica gel column chromatography to provide the product 47 (827 mg, 71%) as colorless oil, which was contained a major β-isomer as a α:β=1:3 ratio.

¹H NMR (400 MHz, CDCl₃) δ 7.72-7.69 (m, 4H), 7.50 (s, 1H), 7.40-7.27 (m, 18H), 7.22-7.15 (m, 6H), 6.92-6.99 (m, 2H), 4.98-4.87 (m, 3H), 4.82-4.72 (m, 2H), 4.66-4.41 (m, 7H), 4.032 (d, J=11.2 Hz, 1H), 3.86-3.59 (m, 6H), 3.14-3.09 (m, 2H), 1.10 (s, 9H); [M+Na]⁺ 967.

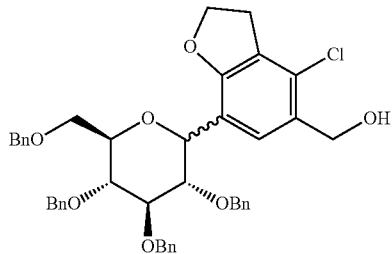 [SMILES: OCc1cc(C2O[C@H](COCc3ccccc3)[C@@H](OCc3ccccc3)[C@H](OCc3ccccc3)[C@H]2OCc2ccccc2)c2c(c1Cl)CCO2]

(7-((3S,4R,5R,6R)-3,4,5-Tris(benzyloxy)-6-(benzyloxymethyl)-tetrahydro-2H-pyran-2-yl)-4-chloro-2,3-dihydrobenzofuran-5-yl)methanol (48)

To a solution of compound 47 (827 mg, 0.87 mmol) in THF (4.0 mL) was added dropwise tetra-n-butylammonium fluoride (1.0M in THF, 2.17 mL, 2.17 mmol) at 0° C. After being stirred for 2 hours at room temperature, the mixture was partitioned between EtOAc and water. The organic layer was washed with brine, dried over MgSO₄, filtered and concentrated in vacuo. The residue was purified by silica gel column chromatography to provide the product 48 (578 mg, 93%) as a white solid.

[M+Na]⁺ 729.

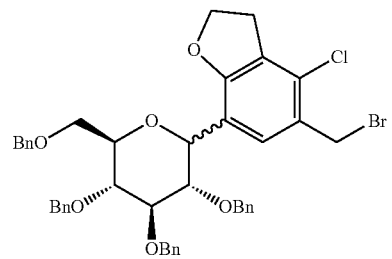 [SMILES: Clc1c(CBr)cc(C2O[C@H](COCc3ccccc3)[C@@H](OCc3ccccc3)[C@H](OCc3ccccc3)[C@H]2OCc2ccccc2)c2c1CCO2]

7-((3S,4R,5R,6R)-3,4,5-Tris(benzyloxy)-6-(benzyloxymethyl)-tetrahydro-2H-pyran-2-yl)-5-(bromomethyl)-4-chloro-2,3-dihydrobenzofuran (49)

To a solution of compound 48 (578 mg, 0.81 mmol) in Et₂O (14 mL) was added pyridine (0.007 mL, cat.) and phosphorus tribromide (0.038 mL, 0.40 mmol) at 0° C. under an atmosphere of nitrogen. After being stirred for 20 hours at room temperature, the mixture was partitioned between EtOAc and water. The organic layer was washed with brine, dried over MgSO₄, filtered and concentrated in vacuo to provide the crude product 49 (654 mg) as yellow oil.

[M+Na]⁺ 791.

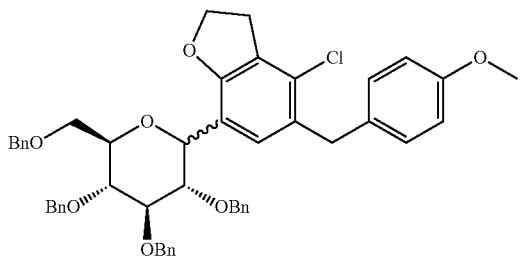 [SMILES: COc1ccc(Cc2cc(C3O[C@H](COCc4ccccc4)[C@@H](OCc4ccccc4)[C@H](OCc4ccccc4)[C@H]3OCc3ccccc3)c3c(c2Cl)CCO3)cc1]

4-Chloro-5-(4-methoxybenzyl)-7-((3S,4R,5R,6R)-3,4,5-tris(benzyloxy)-6-(benzyloxymethyl)tetrahydro-2H-pyran-2-yl)-2,3-dihydrobenzofuran (50)

To a mixture of compound 49 (623 mg, 0.81 mmol), K₂CO₃ (447 mg, 3.24 mmol) and 4-methoxyphenyl boronic acid (306 mg, 2.02 mmol) in acetone (7.5 mL) and H₂O (2.5 mL) was added bis(triphenylphosphine)palladium chloride (56 mg, 0.08 mmol) at 0° C. under atmosphere of nitrogen. The mixture was stirred at 0° C. for 30 min and then, stirred at room temperature for 16 hours. The mixture was partitioned between EtOAc and water. The organic layer was washed with brine, dried over MgSO₄, filtered and concentrated in vacuo. The residue was purified by silica gel column chromatography to provide the product 50 (407 mg, 62%) as colorless oil.

[M+Na]⁺ 819.

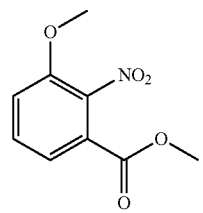

Methyl 3-methoxy-2-nitrobenzoate (52)

To a mixture of 3-methoxy-2-nitrobenzoic acid (25.0 g, 126 mmol) and K₂CO₃ (35.0 g, 253 mmol) in DMF (126 mL) was added MeI (15.8 mL, 253 mmol) at room temperature. The mixture was stirred at room temperature for 2 hours. To the mixture was poured the water (200 mL) and then stirred at 5° C. for 30 min. The precipitated solid was collected by filtration, washed with water and hexane. The solid was dried under reduced pressure to afford the compound 52 in a crude form (26.2 g, 98%) as a white solid.

¹H NMR (400 MHz, CDCl₃) δ 7.60 (dd, J=8.2, 1.2 Hz, 1H), 7.50 (t, J=8.2 Hz, 1H), 7.26 (dd, J=8.2, 1.2 Hz, 1H), 3.39 (s, 3H), 3.99 (s, 3H); [M+Na]⁺ 235.

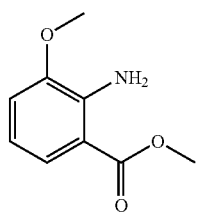

Methyl 2-amino-3-methoxybenzoate (53)

A suspension of compound 52 (26.2 g, 124 mmol) and Pd/C (10 wt. %, 6.0 g) in THF (400 mL) and MeOH (200 mL) was stirred under an atmosphere of H$_2$ at room temperature for 18 hours. EtOAc (300 mL) was added to the mixture and filtered through a Celite pad. The filtrate was concentrated in vacuo to provide the crude product 53 (22.4 g, 99%) as colorless oil.

$^1$H NMR (400 MHz, CDCl$_3$) δ 7.47 (dd, J=8.2, 1.2 Hz, 1H), 6.85 (dd, J=8.2, 1.2 Hz, 1H), 6.58 (t, J=8.2 Hz, 1H), 6.00 (brs, 2H), 3.87 (s, 3H); [M+H]$^+$ 182.

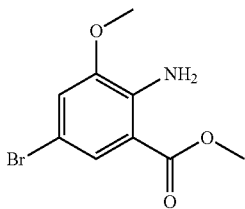

Methyl 2-amino-5-bromo-3-methoxybenzoate (54)

To a solution of compound 53 (22.4 g, 123 mmol) in DMF (250 mL) was added N-bromosuccinimide (21.9 g, 123 mmol) portionwise at 0° C. The mixture was stirred at 0° C. for 0.5 h. To the mixture was added water and extracted with EtOAc (500 mL×2). The combined organic layer was dried over MgSO$_4$, filtered, and concentrated in vacuo. The residue was purified by silica gel column chromatography to provide the desired compound 54 (27.5 g, 86%) as a white solid.

$^1$H NMR (400 MHz, CDCl$_3$) δ 7.60 (d, J=2.2 Hz, 1H), 6.90 (d, J=2.2 Hz, 1H), 6.03 (brs, 1H), 3.87 (s, 3H); [M+H]$^+$ 260.

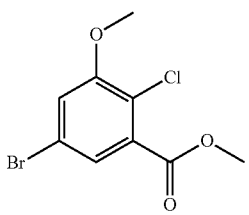

Methyl 5-bromo-2-chloro-3-methoxybenzoate (55)

To a solution of compound 54 (27.0 g, 103 mmol) in H$_2$O (70 mL) and conc.HCl (70 mL) was added dropwise a solution of NaNO$_2$ (21.5 g, 311 mmol) in H$_2$O (50 mL) at 0° C. After being stirred for 1 hour, a solution of Cu(I)Cl in conc.HCl (80 mL) was added to the reaction mixture dropwise at 0° C. The mixture was stirred at room temperature for 18 hours. To the mixture was added water (300 mL) and extracted with EtOAc (500 mL). The organic layer was dried over MgSO$_4$, filtered, and concentrated in vacuo. The crude product 55 was dried under high vacuum and used without further purification (29.0 g, 100%) as a white solid.

$^1$H NMR (400 MHz, CDCl$_3$) δ 7.49 (d, J=2.4 Hz, 1H), 7.16 (d, J=2.4 Hz, 1H), 3.93 (s, 36H), 3.92 (s, 3H); [M+H]$^+$ 278.

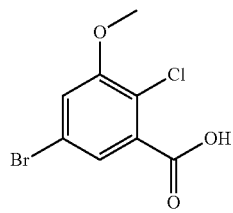

5-Bromo-2-chloro-3-methoxybenzoic acid (56)

To a solution of compound 55 (25.0 g, 89.4 mmol) in THF (100 mL), H$_2$O (100 mL) and MeOH (100 mL) was added aq. 5 N NaOH dropwise at 0° C. The mixture was stirred at room temperature for 1 hour. Conc. HCl was added to the mixture to acidify and the mixture was extracted with EtOAc (500 mL×2). The combined organic layers were dried over MgSO$_4$, filtered and concentrated in vacuo to afford the crude acid 56 (22.6 g, 96%) as an orange solid.

$^1$H NMR (400 MHz, CDCl$_3$) δ 7.55 (s, 1H), 7.13 (s, 1H), 3.89 (s, 3H); [M+H]$^+$ 265.

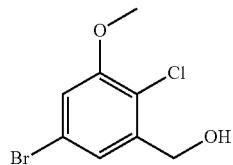

(5-Bromo-2-chloro-3-methoxyphenyl)methanol (57)

To a solution of acid 56 (10.1 g, 38.0 mmol) in THF (100 mL) was added borontrifluoride-dimethylsulfide (14.4 mL, 152 mmol) dropwise at 0° C. under an atmosphere of nitrogen. The mixture was stirred at room temperature for 18 hours. MeOH was added to the reaction mixture dropwise at 0° C. The mixture was extracted with EtOAc/H$_2$O (150 mL/150 mL), dried over MgSO$_4$, filtered, and concentrated in vacuo to provide the crude alcohol 57 (9.50 g, 100%) as yellow oil.

$^1$H NMR (400 MHz, CDCl$_3$) δ 7.30 (d, J=2.2 Hz, 1H), 7.01 (d, J=2.2 Hz, 1H), 4.77 (s, 2H), 3.91 (s, 3H); [M+Na]$^+$ 273.

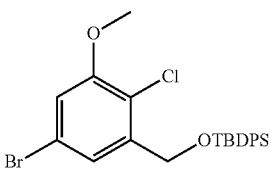

(5-Bromo-2-chloro-3-methoxybenzyloxy)(tert-butyl)diphenylsilane (58)

To a mixture of alcohol 57 (6.49 g, 25.8 mmol) and imidazole (2.30 g, 33.5 mmol) in THF (50 mL) was added TBDPSCl (8.59 mL, 33.5 mmol) dropwise at 0° C. under an atmosphere of nitrogen. The mixture was stirred at room temperature for 5 hours. To the mixture was added water (100 mL) and extracted with EtOAc (100 mL). The organic layer was dried over $MgSO_4$, filtered, and concentrated in vacuo. The residue was purified by silica gel column chromatography to provide the desired TBDPS-protected product 58 (9.60 g, 75%) as colorless oil.

$^1$H NMR (400 MHz, $CDCl_3$) δ 7.70-7.67 (m, 4H), 7.52-7.51 (m, 1H), 7.46-7.37 (m, 6H), 6.99 (d, J=2.4 Hz, 1H), 4.78 (s, 2H), 3.88 (s, 3H), 1.21 (s, 9H).

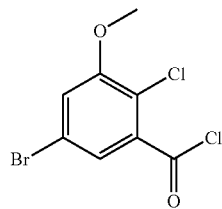

5-Bromo-2-chloro-3-methoxybenzoyl chloride (59)

To a solution of compound 56 (3.82 g, 14.3 mmol) in $CH_2Cl_2$ (63 mL) was added dropwise DMF (0.20 mL) and $(COCl)_2$ (1.63 mL, 18.7 mmol) at 0° C. under an atmosphere of nitrogen. After being stirred for 20 hours at room temperature, the mixture was concentrated in vacuo to provide the crude acid chloride 59, which was used for the next reaction without further purification.

$^1$H NMR (400 MHz, $CDCl_3$) δ 7.49 (d, J=2.4 Hz, 1H), 7.16 (d, J=2.4 Hz, 1H), 3.93 (s, 3H), 3.92 (s, 3H).

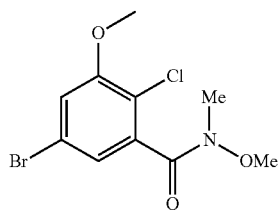 [SMILES: COc1cc(Br)cc(C(=O)N(C)OC)c1Cl]

5-Bromo-2-chloro-N,3-dimethoxy-N-methylbenzamide (60)

To a solution of acid chloride 59 (3.41 g, 14.3 mmol) in $CH_2Cl_2$ (70 mL) was added dropwise N,O-dimethylhydroxylamine hydrochloride (4.18 g, 42.9 mmol) at 0° C. under an atmosphere of nitrogen. Then, TEA (12.0 mL, 85.8 mmol) was added to the mixture at 0° C. After being stirred for 18 hours, the mixture was partitioned between EtOAc (150 mL) and water (100 mL). The organic layer was washed with brine, dried over $MgSO_4$, filtered and concentrated in vacuo. The residue was purified by silica gel column chromatography to afford the product 60 (3.45 g, 80%) as a white solid.

$^1$H NMR (400 MHz, $CDCl_3$) δ 7.08 (s, 2H), 3.92 (s, 3H), 3.51 (s, 3H), 3.37 (s, 3H); [M+H]$^+$ 308.

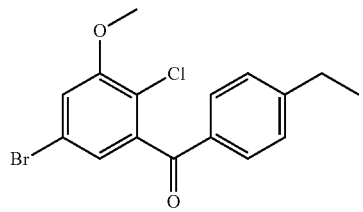 [SMILES: CCc1ccc(C(=O)c2cc(Br)cc(OC)c2Cl)cc1]

(5-Bromo-2-chloro-3-methoxyphenyl)(4-ethylphenyl)methanone (61)

To a solution of compound 60 (3.45 g, 11.2 mmol) in THF (44 mL) was added dropwise 4-ethoxyphenyl magnesium bromide (0.5M in THF, 44.8 mL, 22.4 mmol) at 0° C. under an atmosphere of nitrogen. After being stirred for 15 hours at room temperature, the mixture was quenched with 1N HCl (10 mL). The mixture was extracted with EtOAc (100 mL). The organic layer was dried over $MgSO_4$, filtered, and concentrated in vacuo. The residue was purified by silica gel column chromatography to afford the product 61 (3.92 g, 99%) as a white solid.

$^1$H NMR (400 MHz, $CDCl_3$) δ 7.73 (d, J=8.4 Hz, 2H), 7.29 (d, J=8.4 Hz, 2H), 7.16 (d, J=2.2 Hz, 1H), 7.08 (d, J=2.2 Hz, 1H), 3.95 (s, 3H), 2.72 (q, J=7.6 Hz, 2H), 1.27 (t, J=7.6 Hz, 3H); [M+H]$^+$ 353.

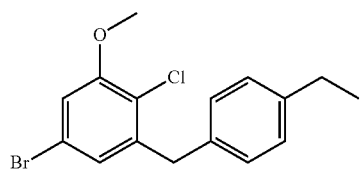 [SMILES: CCc1ccc(Cc2cc(Br)cc(OC)c2Cl)cc1]

1-(4-Ethylbenzyl)-5-bromo-2-chloro-3-methoxybenzene (62)

To a solution of compound 61 (4.45 g, 12.6 mmol) in $CH_2Cl_2$ (80 mL) was added dropwise triethylsilane (6.00 mL, 37.8 mmol) and boron trifluoride diethyl etherate (4.67 mL, 37.8 mmol) at 0° C. under an atmosphere of nitrogen. After being stirred for 5 hours at room temperature, the mixture was quenched with aq. saturated $K_2CO_3$ solution (30 mL) and extracted with EtOAc. The organic layer was washed with brine, dried over $MgSO_4$, filtered and concentrated in vacuo. The residue was purified by silica gel column chromatography to afford the product 62 (2.40 g, 56%) as colorless oil.

$^1$H NMR (400 MHz, $CDCl_3$) δ 7.14-7.08 (m, 4H), 6.93 (q, J=2.4 Hz, 2H), 4.04 (s, 2H), 3.88 (s, 3H), 2.62 (q, J=7.6 Hz, 2H), 1.22 (t, J=7.6 Hz, 3H); [M+H]$^+$ 339.

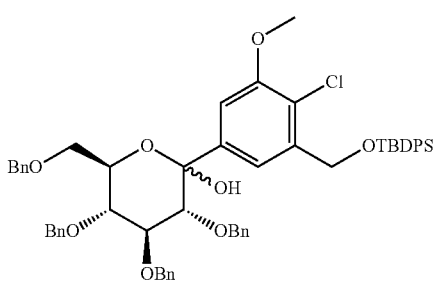

(3R,4S,5R,6R)-3,4,5-Tris(benzyloxy)-6-(benzyloxymethyl)-2-(3-((tert-butyldiphenylsilyloxy)methyl)-4-chloro-5-methoxyphenyl)tetrahydro-2H-pyran-2-ol (61-1)

To a solution of bromide compound 58 (8.69 g, 17.7 mmol) in THF (80 mL) at −78° C. under an atmosphere of nitrogen was added dropwise n-butyllithium (2.5M in hexane, 7.73 mL, 19.3 mmol), and the mixture was stirred for 40 min at the same temperature. Then a solution of benzyl-protected gluconolactone (8.67 g, 16.1 mmol) in THF (20 mL) was added dropwise, and the mixture was stirred for 2 hours at the same temperature. The reaction mixture was quenched by addition of saturated ammonium chloride. After complete addition, the solution was gradually raised to room temperature. The organic layer was separated and the aqueous layer was extracted with EtOAc. The combined organic layers were washed with brine, dried over anhydrous MgSO₄, filtered and concentrated in vacuo to yield the title compound 61-1 (15.0 g), which was carried on to the next step without further purification.

[M+Na]⁺ 971.

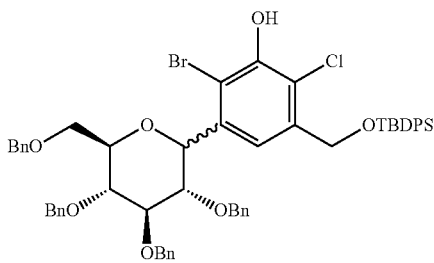

2-Bromo-5-((tert-butyldiphenylsilyloxy)methyl)-6-chloro-3-((3S,4R,5R,6R)-3,4,5-tris(benzyloxy)-6-(benzyloxymethyl)tetrahydro-2H-pyran-2-yl)phenol (63)

Step 1) To a solution of crude compound 61-1 (15.0 g, 16.1 mmol) in CH₂Cl₂ (100 mL) were added triethylsilane (5.14 mL, 32.2 mmol) and boron trifluoride diethyl etherate (4.04 mL, 32.2 mmol) at −60° C. The mixture was allowed to slowly warm to −20° C. for 5 hours. To a mixture was added aq. saturated K₂CO₃ solution (30 mL) to quench the reaction and extracted with EtOAc (150 mL). The organic layer was dried over MgSO₄, filtered, and concentrated in vacuo. The crude product 61-2 (6.83 g) was carried on to the next step without further purification.

[M+Na]⁺ 955.

Step 2) A mixture of crude compound 61-2 (6.83 g, 7.31 mmol) and sodium ethanethiolate (1.84 g, 21.9 mmol) in DMF (36 mL) was stirred for 6 hours at 90° C. To a mixture was added 1N HCl (50 mL) and extracted EtOAc (100 mL). The organic layer was washed with brine, dried over MgSO₄, filtered, and concentrated in vacuo. The crude product 62 (5.32 g) was carried on to the next step without further purification.

[M+Na]⁺ 941.

Step 3) To a solution of compound 62 (5.32 g, 5.76 mmol) in AcOH (28 mL) were added TEA (1.2 mL, 8.64 mmol) and Br₂ (0.295 mL, 5.76 mmol) dropwise at 0° C. The mixture was stirred at 0° C. for 15 min and at room temperature for 3 hours. To a mixture was added saturated ammonium chloride and extracted with EtOAc (100 mL). The organic layer was washed with brine, dried over MgSO₄, filtered, and concentrated in vacuo. The residue was purified by silica gel column chromatography to provide the product 63 (5.08 g, 31%) as colorless oil.

[M+Na]⁺ 1014.

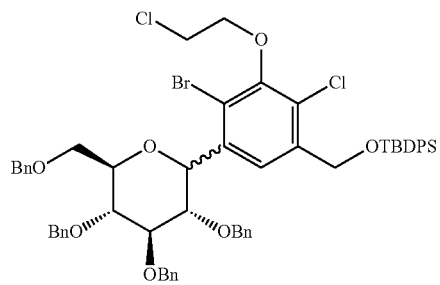

((2R,3R,4R,5S)-5-((3S,4R,5R,6R)-3,4,5-Tris(benzyloxy)-6-(benzyloxymethyl)-tetrahydro-2H-pyran-2-yl)-4-bromo-2-chloro-3-(2-chloroethoxy)benzyloxy)(tert-butyl)diphenylsilane (64)

Step 1) A mixture of compound 63 (2.90 g, 2.9 mmol), 2-bromoalcohol (0.308 mL, 4.35 mmol) and K₂CO₃ (801 mg, 5.80 mmol) in acetone (15 mL) was stirred for 17 hours under reflux. The mixture was filtrated and concentrated in vacuo. The resultant was partitioned between EtOAc and water. The organic layer was washed with brine, dried over MgSO₄, filtered and concentrated in vacuo to afford the crude product 63-1 (2.92 g, 96%) as colorless oil.

[M+Na]⁺ 1063.

Step 2) A mixture of compound 63-1 (2.90 g, 2.78 mmol), triphenylphosphine (1.83 g, 6.95 mmol) and CCl₄ (2.90 mL, 3.36 mmol) in CH₃CN (27 mL) was stirred for 2 hours under reflux. The mixture was concentrated in vacuo. The resultant was partitioned between EtOAc and water. The organic layer was washed with brine, dried over MgSO₄, filtered and concentrated in vacuo. The residue was purified by silica gel column chromatography to provide the product 64 (2.76 g, 93%) as colorless oil.

[M+Na]⁺ 1081.

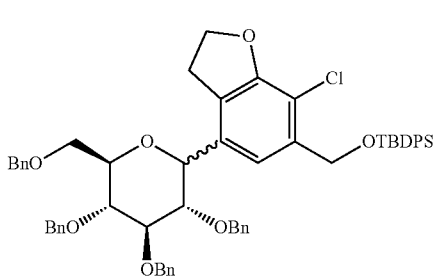

((4-((3S,4R,5R,6R)-3,4,5-Tris(benzyloxy)-6-(benzyloxymethyl)-tetrahydro-2H-pyran-2-yl)-7-chloro-2,3-dihydrobenzofuran-6-yl)methoxy)(tert-butyl)diphenylsilane (65)

To a solution of compound 64 (2.70 g, 2.54 mmol) in THF (25 mL) was added dropwise n-butyllithium (2.5M in hexane, 2.03 mL, 5.08 mmol) at −78° C. under an atmosphere of nitrogen. The mixture was stirred for 18 hours at −78° C. to 5° C. The mixture was quenched with 1N HCl and extracted with EtOAc. The organic layer was washed with brine, dried over MgSO$_4$, filtered and concentrated in vacuo. The residue was purified by silica gel column chromatography to provide the product 65 (1.87 g, 77%) as colorless oil, which contained a major β-isomer as a α:β=1:3 ratio.

$^1$H NMR (400 MHz, CDCl$_3$) δ 7.72-7.69 (m, 4H), 7.41-7.28 (m, 22H), 7.22-7.16 (m, 4H), 6.90 (dd, J=7.4, 1.4 Hz, 1H), 5.00-4.90 (m, 3H), 4.84-4.77 (m, 2H), 4.71-4.60 (m, 2H), 4.54-4.51 (m, 4H), 4.44-4.37 (m, 1H), 4.22 (d, J=9.6 Hz, 1H), 3.93 (d, J=10.4 Hz, 1H), 3.81-3.68 (m, 5H), 3.27-3.06 (m, 2H), 1.10 (s, 9H); [M+Na]$^+$ 967.

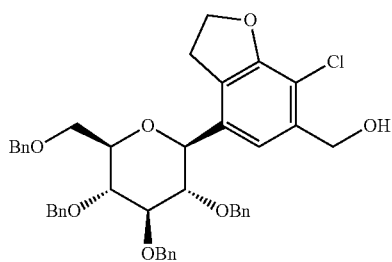 [SMILES: OCc1cc([C@@H]2O[C@H](COCc3ccccc3)[C@@H](OCc3ccccc3)[C@H](OCc3ccccc3)[C@H]2OCc2ccccc2)c2c(c1Cl)OCC2]

(7-Chloro-4-((2S,3S,4R,5R,6R)-3,4,5-tris(benzyloxy)-6-(benzyloxymethyl)tetrahydro-2H-pyran-2-yl)-2,3-dihydrobenzofuran-6-yl)methanol (66)

To a solution of compound 65 (1.80 g, 1.9 mmol) in THF (9.5 mL) was added dropwise tetra-n-butylammonium fluoride ((1.0M in THF, 4.75 mL, 4.75 mmol) at 0° C. After being stirred for 2 hours at room temperature, the mixture was partitioned between EtOAc and water. The organic layer was washed with brine, dried over MgSO$_4$, filtered and concentrated in vacuo. The residue was purified by silica gel column chromatography to provide the product 66 (1.28 g, 94%) as colorless oil.

$^1$H NMR (400 MHz, CDCl$_3$) δ 7.36-7.27 (m, 12H), 7.24-7.17 (m, 6H), 7.01 (s, 1H), 6.90 (dd, J=7.6, 1.6 Hz, 2H), 4.95 (ABq, Δν$_{AB}$=12.5 Hz, J$_{AB}$=11.2 Hz, 2H), 4.86 (d, J=10.8 Hz, 1H), 4.72 (d, J=6.8 Hz, 2H), 4.63 (d, J=10.8 Hz, 1H), 4.57-4.53 (m, 3H), 4.49-4.42 (m, 1H), 4.20 (d, J=9.6 Hz, 1H), 3.95 (d, J=10.8 Hz, 1H), 3.81-3.72 (m, 4H), 3.57-3.50 (m, 2H), 3.32-3.24 (m, 1H), 3.17-3.08 (m, 1H), 1.7 (t, J=6.6 Hz, 1H); [M+Na]$^+$ 729.

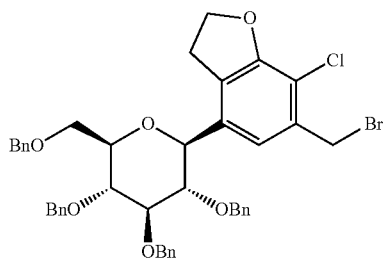 [SMILES: Clc1c(CBr)cc([C@@H]2O[C@H](COCc3ccccc3)[C@@H](OCc3ccccc3)[C@H](OCc3ccccc3)[C@H]2OCc2ccccc2)c2c1OCC2]

6-(Bromomethyl)-7-chloro-4-((2S,3S,4R,5R,6R)-3,4,5-tris(benzyloxy)-6-(benzyloxymethyl)tetrahydro-2H-pyran-2-yl)-2,3-dihydrobenzofuran (67)

To a solution of compound 66 (1.28 g, 1.80 mmol) in Et$_2$O (30 mL) was added pyridine (0.015 mL, cat.) and phosphorus tribromide (0.085 mL, 0.9 mmol) at 0° C. under an atmosphere of nitrogen. After being stirred for 20 hours at room temperature, the mixture was partitioned between EtOAc and water. The organic layer was washed with brine, dried over MgSO$_4$, filtered and concentrated in vacuo. The residue was purified by silica gel column chromatography to provide the product 67 (1.42 g) as brown oil.

$^1$H NMR (400 MHz, CDCl$_3$) δ 7.35-7.29 (m, 12H), 7.22-7.16 (m, 6H), 7.00 (s, 1H), 6.90 (dd, J=6.4, 1.2 Hz, 2H), 4.95 (ABq, Δν$_{AB}$=10.9 Hz, J$_{AB}$=11.2 Hz, 2H), 4.87 (d, J=10.8 Hz, 1H), 4.63 (d, J=10.8 Hz, 1H), 4.60-4.48 (m, 5H), 4.34-4.37 (m, 1H), 4.16 (d, J=9.2 Hz, 1H), 4.00 (d, J=10.8 Hz, 1H), 3.80-3.70 (m, 4H), 3.56-3.49 (m, 2H), 3.29-3.20 (m, 1H), 3.10-3.02 (m, 1H); [M+Na]$^+$ 791.

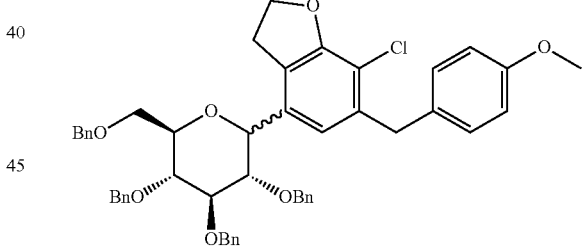

7-Chloro-6-(4-methoxybenzyl)-4-((3S,4R,5R,6R)-3,4,5-tris(benzyloxy)-6-(benzyloxymethyl)tetrahydro-2H-pyran-2-yl)-2,3-dihydrobenzofuran (68)

To a mixture of compound 67 (700 mg, 0.9 mmol), K$_2$CO$_3$ (497 mg, 3.6 mmol) and 4-methoxyphenyl boronic acid (341 mg, 2.25 mmol) in acetone (9.0 mL) and H$_2$O (3.0 mL) was added bis(triphenylphosphine)palladiumchloride (63 mg, 0.09 mmol) at 0° C. under atmosphere of nitrogen. The mixture was stirred at 0° C. for 30 min and then, stirred at room temperature for 16 hours. The mixture was partitioned between EtOAc and water. The organic layer was washed with brine, dried over MgSO$_4$, filtered and concentrated in vacuo. The residue was purified by silica gel column chromatography to provide the product 68 (340 mg, 46%) as colorless oil.

[M+Na]$^+$ 819.

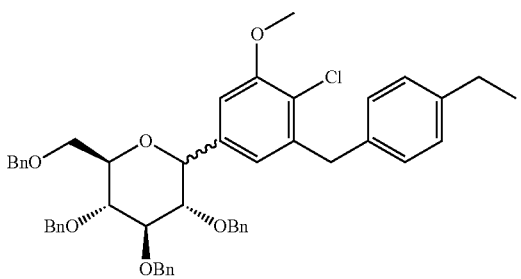 [SMILES: CCc1ccc(Cc2cc(C3O[C@H](COCc4ccccc4)[C@@H](OCc4ccccc4)[C@H](OCc4ccccc4)[C@H]3OCc3ccccc3)cc(OC)c2Cl)cc1]

(3S,4R,5R,6R)-2-(3-(4-Ethylbenzyl)-4-chloro-5-methoxyphenyl)-3,4,5-tris(benzyloxy)-6-(benzyloxymethyl)-tetrahydro-2H-pyran (69)

Step 1) To a solution of bromide compound 62 (2.40 g, 7.00 mmol) in THF (26.0 mL) at −78° C. under an atmosphere of nitrogen was added dropwise n-butyllithium (2.5M in hexane, 2.94 mL, 7.35 mmol), and the mixture was stirred for 40 min at the same temperature. Then a solution of benzyl-protected gluconolactone (3.60 g, 6.70 mmol) in THF (8.8 mL) was added dropwise, and the mixture was stirred for 2 hours at the same temperature. The reaction mixture was quenched by addition of saturated ammonium chloride. After complete addition, the solution was gradually raised to room temperature. The organic layer was separated and the aqueous layer was extracted with EtOAc. The combined organic layers were washed with brine, dried over anhydrous MgSO$_4$, filtered and concentrated in vacuo to provide a mixture of lactol compounds (5.4 g), which was carried on to the next step without further purification.

[M+Na]$^+$ 821.

Step 2) To a solution of the crude lactol compound (5.4 g, 6.70 mmol) in CH$_2$Cl$_2$ (27 mL) was added triethylsilane (2.14 mL, 13.4 mmol) and boron trifluoride diethyl etherate (1.65 mL, 13.4 mmol) at −60° C. The mixture was allowed to slowly warm to −20° C. To a mixture was added aq. saturated K$_2$CO$_3$ solution (20 mL) to quench the reaction and extracted with EtOAc (100 mL). The organic layer was dried over MgSO$_4$, filtered, and concentrated in vacuo. The residue was purified by silica gel column chromatography to provide the product 69 (3.96 g, 75%) as colorless oil.

For β anomer $^1$H NMR (400 MHz, CDCl$_3$) δ 7.32-7.270 (m, 12H), 7.23-7.15 (m, 8H), 7.10-7.07 (m, 4H), 6.90 (d, J=1.4 Hz, 1H), 6.84 (d, J=1.4 Hz, 1H), 6.39 (ABq, Δv$_{AB}$=10.8 Hz, J$_{AB}$=11.0 Hz, 2H), 4.86 (d, J=10.8 Hz, 1H), 4.77 (t, J=10.8 Hz, 1H), 4.67-4.53 (m, 4H), 4.49-4.41 (m, 2H), 4.14 (t, J=9.2 Hz, 1H), 3.97-3.86 (m, 1H), 3.79-3.74 (m, 6H), 3.65-3.56 (m, 1H), 3.52-3.43 (m, 1H), 2.57 (q, J=7.6 Hz, 2H), 1.18 (t, J=7.6 Hz, 3H);

For α anomer $^1$H NMR (400 MHz, CDCl$_3$) δ 7.32-7.270 (m, 12H), 7.23-7.15 (m, 8H), 7.10-7.07 (m, 4H), 6.92 (d, J=1.4 Hz, 1H), 6.88 (d, J=1.4 Hz, 1H), 5.13 (d, J=4.8 Hz, 1H), 4.86 (d, J=10.8 Hz, 1H), 4.77 (t, J=10.8 Hz, 1H), 4.67-4.53 (m, 4H), 4.49-4.41 (m, 2H), 4.14 (t, J=9.2 Hz, 1H), 3.97-3.86 (1H, m), 3.77-3.74 (m, 4H), 3.71 (s, 3H), 3.65-3.56 (m, 1H), 3.52-3.43 (m, 1H), 2.52 (q, J=7.6 Hz, 2H), 1.14 (t, J=7.6 Hz, 3H); [M+Na]$^+$ 805.

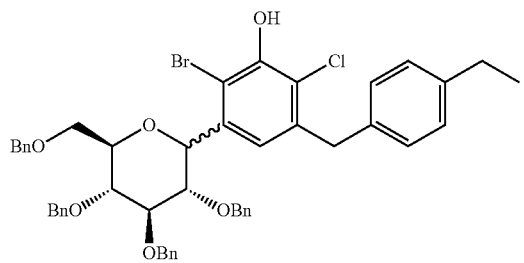

3-((3S,4R,5R,6R)-3,4,5-Tris(benzyloxy)-6-(benzyloxymethyl)-tetrahydro-2H-pyran-2-yl)-5-(4-ethylbenzyl)-2-bromo-6-chlorophenol (70)

Step 1) A mixture of crude compound 69 (1.50 g, 1.91 mmol) and sodium sodium ethanethiolate (482 mg, 5.73 mmol) in DMF (9.5 mL) was stirred for 6 hours at 90° C. To a mixture was added 1N HCl (50 mL) and extracted EtOAc (100 mL). The organic layer was washed with brine, dried over MgSO$_4$, filtered, and concentrated in vacuo. The crude phenol compound (1.50 g) was carried on to the next step without further purification.

[M+Na]$^+$ 791.

Step 2) To a solution of the crude phenol compound (1.49 g, 1.94 mmol) in AcOH (9.70 mL) were added TEA (0.405 mL, 2.91 mmol) and Br$_2$ (0.119 mL, 2.32 mmol) dropwise at 0° C. The mixture was stirred at 0° C. for 15 min and at room temperature for 3 hours. To a mixture was added saturated ammonium chloride and extracted with EtOAc (100 mL). The organic layer was washed with brine, dried over MgSO$_4$, filtered, and concentrated in vacuo. The residue was purified by silica gel column chromatography to provide the product 70 (1.42 g, 86%) as colorless oil.

[M+Na]$^+$ 869.

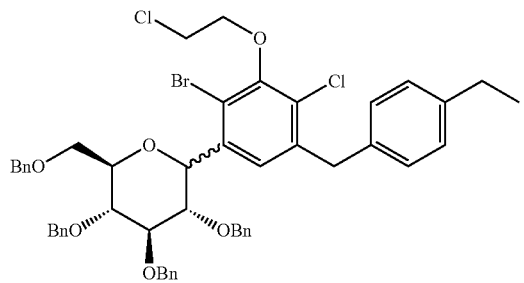 [SMILES: CCc1ccc(Cc2cc(C3O[C@H](COCc4ccccc4)[C@@H](OCc4ccccc4)[C@H](OCc4ccccc4)[C@H]3OCc3ccccc3)c(Br)c(OCCCl)c2Cl)cc1]

(3S,4R,5R,6R)-2-(5-(4-Ethylbenzyl)-2-bromo-4-chloro-3-(2-chloroethoxy)phenyl)-3,4,5-tris(benzyloxy)-6-(benzyloxymethyl)-tetrahydro-2H-pyran (71)

Step 1) A mixture of compound 70 (1.42 g, 1.67 mmol), 2-bromoalcohol (0.178 mL, 2.51 mmol) and K$_2$CO$_3$ (348 mg, 2.51 mmol) in acetone (20 mL) was stirred for 17 hours under reflux. The mixture was filtrated and concentrated in vacuo. The resultant was partitioned between EtOAc and water. The organic layer was washed with brine, dried over MgSO$_4$, filtered and concentrated in vacuo to afford the crude product 70-1 (1.29 g, 86%) as colorless oil.

[M+Na]$^+$ 913.

Step 2) A mixture of compound 70-1 (1.29 g, 1.44 mmol), triphenylphosphine (945 mg, 3.61 mmol) and CCl₄ (1.5 mL, 17.5 mmol) in CH₃CN (14 mL) was stirred for 2 hours under reflux. The mixture was concentrated in vacuo. The resultant was partitioned between EtOAc and water. The organic layer was washed with brine, dried over MgSO₄, filtered and concentrated in vacuo. The residue purified by silica gel column chromatography to provide the product 71 (1.16 g, 88%) as colorless oil.

[M+Na]⁺ 931.

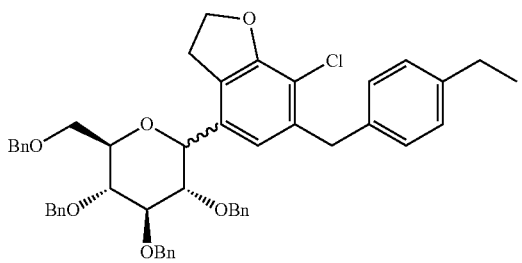 [SMILES: CCc1ccc(Cc2cc(C3O[C@H](COCc4ccccc4)[C@@H](OCc4ccccc4)[C@H](OCc4ccccc4)[C@H]3OCc3ccccc3)c3c(c2Cl)OCC3)cc1]

4-((3S,4R,5R,6R)-3,4,5-Tris(benzyloxy)-6-(benzyloxymethyl)-tetrahydro-2H-pyran-2-yl)-6-(4-ethylbenzyl)-7-chloro-2,3-dihydrobenzofuran (72)

To a solution of compound 71 (1.16 g, 1.27 mmol) in THF (12.7 mL) was added dropwise n-butyllithium (2.5M in hexane, 1.27 mL, 3.17 mmol) at −78° C. under an atmosphere of nitrogen. The mixture was stirred for 18 hours at −78° C. to 5° C. The mixture was quenched with 1N HCl and extracted with EtOAc. The organic layer was washed with brine, dried over MgSO₄, filtered and concentrated in vacuo. The residue was purified by silica gel column chromatography to provide the product 72 (493 mg, 48%) as brown oil.

[M+Na]⁺ 817.

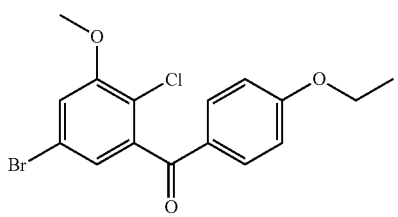 [SMILES: CCOc1ccc(C(=O)c2cc(Br)cc(OC)c2Cl)cc1]

(5-Bromo-2-chloro-3-methoxyphenyl)(4-ethoxyphenyl)methanone (73)

To a solution of acid 56 (4.9 g, 18.57 mmol) in CH₂Cl₂ (62 mL) were added oxalyl chloride (2.1 mL, 24.14 mmol) and catalytic amounts of DMF at room temperature. The mixture was stirred at room temperature for 3 hours. The mixture was evaporated in vacuo and dried under high vacuum. The crude acid chloride was dissolved with CH₂Cl₂ (93 mL) and cooled to 0° C. To the mixture was added phenetole (2.4 mL, 18.57 mmol) at 0° C. and stirred at 0° C. for 5 min. To the reaction mixture was added AlCl₃ (2.7 g, 20.43 mmol) portionwise at 0° C. The mixture was stirred at 0° C. for 30 min, warmed up to room temperature and stirred at room temperature for 15 hours. The mixture was poured into ice-water and extracted with CH₂Cl₂ (100 mL×2). The combined organic layer was dried over MgSO₄, filtered, and concentrated in vacuo. The crude product 73 was dried under high vacuum and used without further purification (7.0 g).

[M−H]⁺ 368.

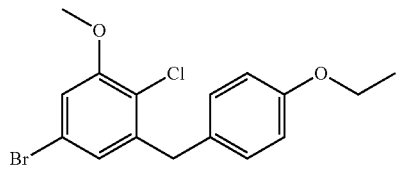 [SMILES: CCOc1ccc(Cc2cc(Br)cc(OC)c2Cl)cc1]

5-Bromo-2-chloro-1-(4-ethoxybenzyl)-3-methoxybenzene (74)

To a solution of methanone 73 (7.0 g, 18.94 mmol) in CH₂Cl₂/CH₃CN (60 mL/60 mL) were added triethylsilane (9.1 mL, 56.81 mmol) and boron trifluoride diethyl etherate (7.0 mL, 56.81 mmol) at 0° C. The mixture was warmed up to room temperature slowly and stirred at room temperature for 15 hours. To the mixture was added aq. saturated K₂CO₃ solution (80 mL) slowly and extracted with EtOAc (100 mL×2). The combined organic layer was dried over MgSO₄, filtered, and concentrated in vacuo. The residue was purified by silica gel column chromatography to provide the desired product 74 (5.7 g, 87%).

¹H NMR (400 MHz, CDCl₃) δ 7.09-7.07 (m, 2H), 6.92 (d, J=2.0 Hz, 1H), 6.88 (d, J=2.0 Hz, 1H), 6.83-6.81 (m, 2H), 4.03-3.98 (m, 4H), 3.88 (s, 3H), 1.40 (t, J=7.2 Hz, 3H).

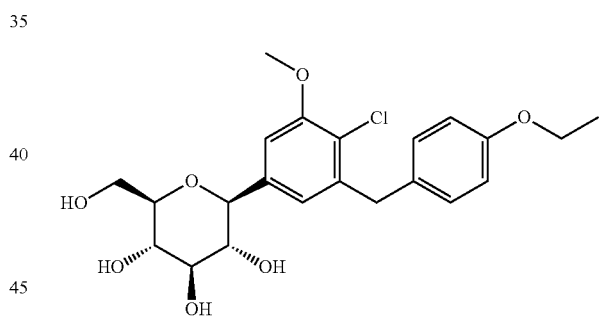

(2S,3R,4R,5S,6R)-2-(4-Chloro-3-(4-ethoxybenzyl)-5-methoxyphenyl)-6-(hydroxymethyl)tetrahydro-2H-pyran-3,4,5-triol (75)

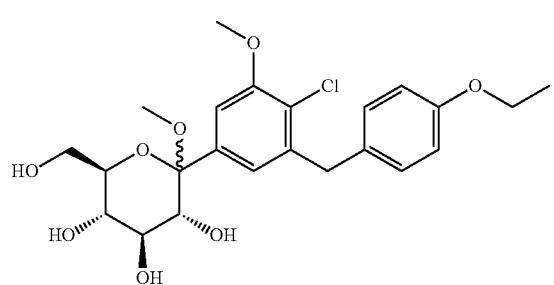 [SMILES: CCOc1ccc(Cc2cc(C3(OC)O[C@H](CO)[C@@H](O)[C@H](O)[C@H]3O)cc(OC)c2Cl)cc1]

Step 1)

(3R,4S,5S,6R)-2-(4-Chloro-3-(4-ethoxybenzyl)-5-methoxyphenyl)-6-(hydroxymethyl)-2-methoxytetrahydro-2H-pyran-3,4,5-triol (74-3)

To a solution of bromide 74 (5.74 g, 16.14 mmol) in toluene/THF (72 mL/36 mL) at −78° C. under an atmosphere of nitrogen was added dropwise n-butyllithium (2.5M in hexane, 7.8 mL, 19.36 mmol), and the mixture was stirred for 40 min at the same temperature. Then a solution of TMS-protected gluconolactone 74-1 (9.04 g, 19.36 mmol) in toluene (30 mL) was added dropwise, and the mixture was stirred for 1 hour at the same temperature. To a solution of crude alcohol 74-2 were added $CH_3SO_3H$ (0.6 N in MeOH, 53.8 mL, 32.28 mmol) at −78° C. The mixture was allowed to slowly warm to −40° C. To a mixture was added aq. saturated $NaHCO_3$ solution (50 mL) to quench the reaction. After dilution with water, the mixture was stirred at room temperature for 30 min and extracted with EtOAc (100 mL). The organic layer was dried over anhydrous $MgSO_4$, filtered and concentrated in vacuo. The (3R,4S,5S,6R)-2-(4-chloro-3-(4-ethoxybenzyl)-5-methoxyphenyl)-6-(hydroxymethyl)-2-methoxytetrahydro-2H-pyran-3,4,5-triol 74-3 (6.6 g) was carried on to the next step without further purification.

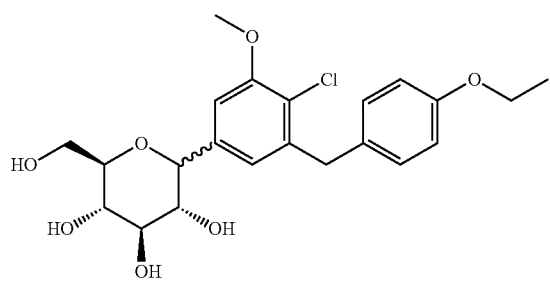 [SMILES: CCOc1ccc(Cc2cc(C3O[C@H](CO)[C@@H](O)[C@H](O)[C@H]3O)cc(OC)c2Cl)cc1]

Step 2)

(3R,4R,5S,6R)-2-(4-Chloro-3-(4-ethoxybenzyl)-5-methoxyphenyl)-6-(hydroxymethyl)tetrahydro-2H-pyran-3,4,5-triol (74-4)

To a solution of triol 74-3 (6.6 g, 14.14 mmol) in $CH_2Cl_2$/$CH_3CN$ (70 mL/70 mL) were added triethylsilane (4.5 mL, 28.28 mmol) and boron trifluoride diethyl etherate (3.6 mL, 28.28 mmol) at −50° C. The mixture was warmed up to 0° C. slowly and stirred at 0° C. for 2 hours. To the mixture was added aq. saturated $NaHCO_3$ solution (50 mL) slowly and extracted with EtOAc (100 mL×2). The combined organic layer was dried over $MgSO_4$, filtered, and concentrated in vacuo. The residue was carried on to the next step without purification.

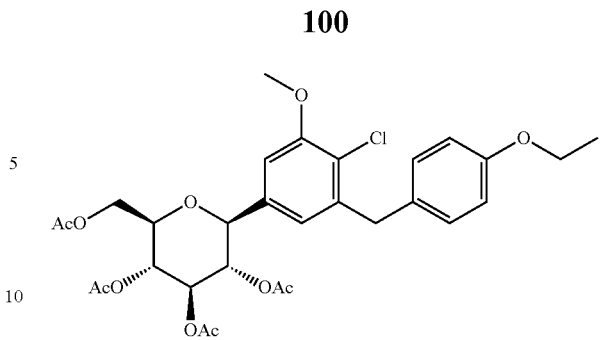

Step 3)

(2S,3S,4S,5R,6R)-6-(Acetoxymethyl)-2-(4-chloro-3-(4-ethoxybenzyl)-5-methoxyphenyl)-5-hydroxytetrahydro-2H-pyran-3,4-diyl diacetate (74-5)

To a solution of compound 74-4 (6.2 g) in $CH_2Cl_2$ (95 mL) were added $Ac_2O$ (13.4 mL, 141.4 mmol), $Et_3N$ (19.7 mL, 141.4 mmol) and catalytic amount of DMAP at 0° C. The mixture was stirred at 0° C. for 15 min and at room temperature for 15 hours. The mixture was concentrated under reduced pressure to remove volatiles. The residue was diluted with EtOAc (200 mL), washed with $H_2O$ (100 mL), aq. 1N HCl solution (100 mL) and brine (100 mL) successively. The organic layer was dried over $MgSO_4$, filtered, and concentrated in vacuo. The residue was purified by silica gel column chromatography to provide the α,β-isomer mixture of the title compound 74-4 (1.9 g). The anomeric mixture of 74-4 was recrystallized with EtOH (100 mL). The precipitate was collected by filtration and washed with cold EtOH (50 mL) and dried under high vacuum to obtain the title compound 74-5 (2.5 g, 26% (5-steps)).
$^1$H NMR (400 MHz, $CDCl_3$) δ 7.06-7.04 (m, 2H), 6.84 (d, J=1.6 Hz, 1H), 6.81-6.79 (m, 2H), 6.67 (d, J=2.0 Hz, 1H), 5.30-5.19 (m, 2H), 5.09 (t, J=9.6 Hz, 1H), 4.31-4.25 (m, 2H), 4.15 (dd, J=12.4, 2.4 Hz, 1H), 4.08-3.95 (m, 4H), 3.91 (s, 3H), 3.82-3.77 (m, 1H), 2.07 (s, 3H), 2.05 (s, 3H), 1.99 (s, 3H), 1.69 (s, 3H), 1.39 (t, J=7.2 Hz, 3H);
$[M+Na]^+$ 629.

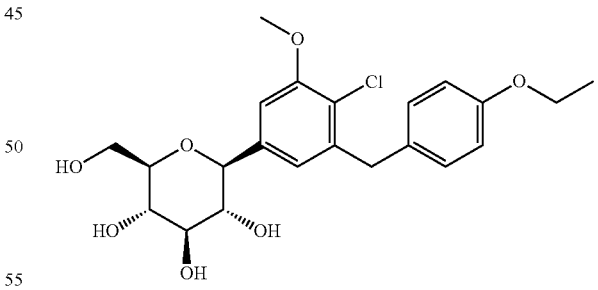

Step 4)

(2S,3R,4R,5S,6R)-2-(4-Chloro-3-(4-ethoxybenzyl)-5-methoxyphenyl)-6-(hydroxymethyl)tetrahydro-2H-pyran-3,4,5-triol (75)

To a suspension of acetate 74-5 (2.5 g, 4.12 mmol) in MeOH (40 mL) was added NaOMe (25 wt % in MeOH, 0.75 mL) at room temperature. The mixture was stirred at room temperature for 1 hour. Glacial AcOH was added to the mix-

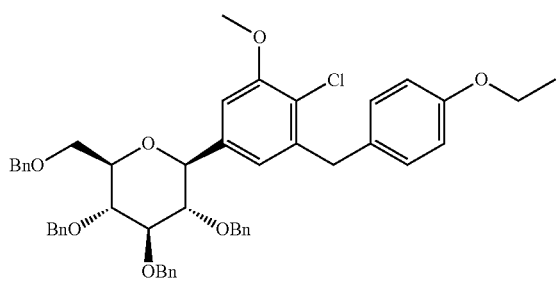 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)cc(OC)c2Cl)cc1]

(2R,3R,4R,5S,6S)-3,4,5-Tris(benzyloxy)-2-(benzyloxymethyl)-6-(4-chloro-3-(4-ethoxybenzyl)-5-methoxyphenyl)tetrahydro-2H-pyran (76)

To a solution of compound 75 (4.12 mmol) in DMF/THF (20 mL/60 mL) at 0° C. under an atmosphere of nitrogen were added NaH (60% oil, 825 mg, 20.6 mmol) and benzyl bromide (4.9 mL, 41.2 mmol) dropwise, and the mixture was stirred for 16 hours at the room temperature. To the mixture was added water (20 mL) to quench the reaction. After dilution with water, the mixture was stirred at room temperature for 30 min and extracted with EtOAc (200 mL). The organic layer was dried over anhydrous MgSO$_4$, filtered and concentrated in vacuo. The residue was purified by silica gel column chromatography to provide the product 76 (3.0 g, 93%) as colorless oil.

[M+Na]$^+$ 821.

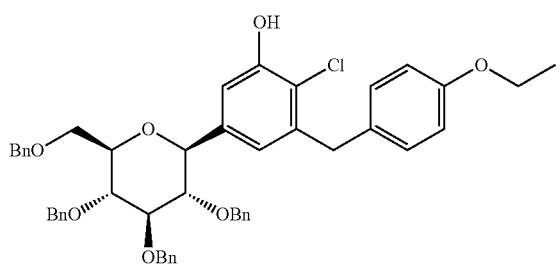 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)cc(O)c2Cl)cc1]

2-Chloro-3-(4-ethoxybenzyl)-5-((2S,3S,4R,5R,6R)-3,4,5-tris(benzyloxy)-6-(benzyloxymethyl)tetrahydro-2H-pyran-2-yl)phenol (77)

A mixture of compound 76 (3.0 g, 3.82 mmol) in DMF (38 mL) was added NaSEt (1.1 g, 13.35 mmol) at 90° C. The mixture was stirred at 90° C. for 6 hours. To a mixture was added 1N HCl (50 mL) and extracted EtOAc (200 mL). The organic layer was washed with brine, dried over MgSO$_4$, filtered, and concentrated in vacuo. The residue was purified by silica gel column chromatography to provide the product 77 (3.0 g).

[M+Na]$^+$ 807.

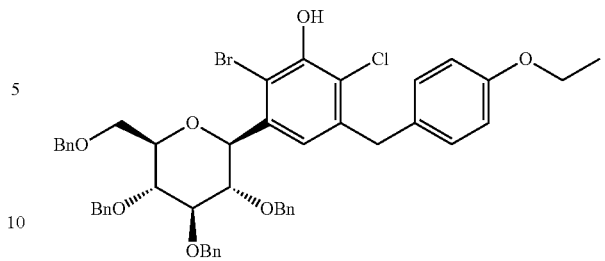

2-Bromo-6-chloro-5-(4-ethoxybenzyl)-3-((2S,3S,4R,5R,6R)-3,4,5-tris(benzyloxy)-6-(benzyloxymethyl)tetrahydro-2H-pyran-2-yl)phenol (78)

To a solution of compound 77 (2.36 g, 3.0 mmol) in AcOH (30 mL) were added TEA (0.6 mL, 4.51 mmol) and Br$_2$ (0.18 mL, 3.61 mmol) dropwise at 0° C. The mixture was stirred at 0° C. for 15 min and at room temperature for 15 hours. To a mixture was added saturated ammonium chloride and extracted with EtOAc (100 mL). The organic layer was washed with brine, dried over MgSO$_4$, filtered, and concentrated in vacuo. The residue was carried on to the next step without purification.

[M+Na]$^+$ 885.

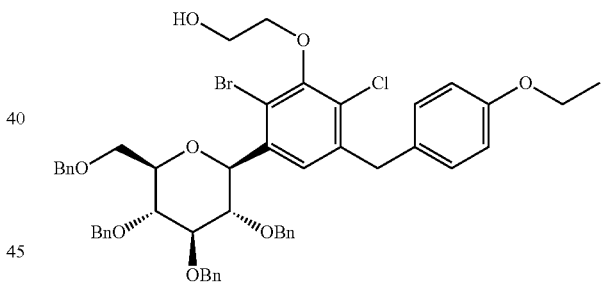

2-(2-Bromo-6-chloro-5-(4-ethoxybenzyl)-3-((2S,3S,4R,5R,6R)-3,4,5-tris(benzyloxy)-6-(benzyloxymethyl)tetrahydro-2H-pyran-2-yl)phenoxy)ethanol (79)

To a solution of crude compound 78 (2.67 g, 3.1 mmol) in acetone (30 mL) were added 2-bromoethanol (0.33 mL, 4.63 mmol) and K$_2$CO$_3$ (640 mg, 4.63 mmol) at 0° C. The mixture was stirred at 50° C. for 15 hours. The mixture was filtrated and concentrated in vacuo. The resultant was partitioned between EtOAc and water. The organic layer was washed with brine, dried over MgSO$_4$, filtered and concentrated in vacuo. The residue was purified by silica gel column chromatography to provide the product 79 (2.68 g, 95%).

[M+Na]$^+$ 929.

103

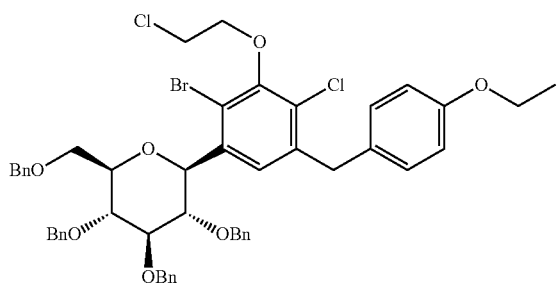 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)c(Br)c(OCCCl)c2Cl)cc1]

(2R,3R,4R,5S,6S)-3,4,5-Tris(benzyloxy)-2-(benzyloxymethyl)-6-(2-bromo-4-chloro-3-(2-chloroethoxy)-5-(4-ethoxybenzyl)phenyl)tetrahydro-2H-pyran (80)

To a solution of alcohol 79 (2.68 g, 2.95 mmol) in acetonitrile (30 mL) were added CCl$_4$ (3.4 mL, 35.41 mmol) and PPh$_3$ (1.9 g, 7.38 mmol) at 0° C. The mixture was stirred at 55° C. for 3 hours. The mixture was filtrated and concentrated in vacuo. The resultant was partitioned between EtOAc and water. The organic layer was washed with brine, dried over MgSO$_4$, filtered and concentrated in vacuo. The residue was purified by silica gel column chromatography to provide the product 80 (2.59 g, 95%).

[M+Na]$^+$ 947.

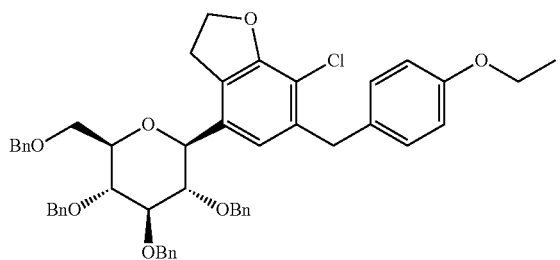 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)c3c(c2Cl)OCC3)cc1]

7-Chloro-6-(4-ethoxybenzyl)-4-((2S,3S,4R,5R,6R)-3,4,5-tris(benzyloxy)-6-(benzyloxymethyl)tetrahydro-2H-pyran-2-yl)-2,3-dihydrobenzofuran (81)

To a solution of compound 80 (2.59 g, 2.79 mmol) in THF (28 mL) was added dropwise n-butyllithium (2.5M in hexane, 2.2 mL, 5.59 mmol) at −78° C. under an atmosphere of nitrogen. The mixture was stirred for 18 hours at −78° C. to 10° C. The mixture was quenched with 1N HCl and extracted with EtOAc. The organic layer was washed with brine, dried over MgSO$_4$, filtered and concentrated in vacuo. The residue was purified by silica gel column chromatography to provide the product 81 (2.0 g, 88%) as brown oil.

[M+Na]$^+$ 833.

104

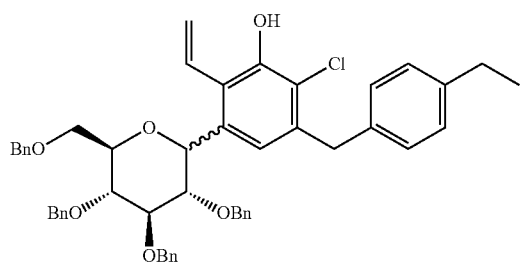 [SMILES: C=Cc1c(C2O[C@H](COCc3ccccc3)[C@@H](OCc3ccccc3)[C@H](OCc3ccccc3)[C@H]2OCc2ccccc2)cc(Cc2ccc(CC)cc2)c(Cl)c1O]

2-Chloro-3-(4-ethylbenzyl)-5-((3S,4R,5R,6R)-3,4,5-tris(benzyloxy)-6-(benzyloxymethyl)tetrahydro-2H-pyran-2-yl)-6-vinylphenol (82)

To a solution of compound 71 (1.16 g, 1.27 mmol) in THF (12.7 mL) was added dropwise n-butyllithium (2.5M in hexane, 1.27 mL, 3.17 mmol) at −78° C. under an atmosphere of nitrogen. The mixture was stirred for 18 hours at −78° C. to 5° C. The mixture was quenched with 1N HCl and extracted with EtOAc. The organic layer was washed with brine, dried over MgSO$_4$, filtered and concentrated in vacuo. The residue was purified by silica gel column chromatography to provide the product 82 (404 mg, 40%) as brown oil.

$^1$H NMR (400 MHz, CDCl$_3$) δ 7.32-7.28 (m, 16H), 7.22-7.16 (m, 4H), 7.10-7.01 (m, 4H), 6.88 (d, J=8.0 Hz, 1H), 5.68-5.59 (m, 1H), 4.95-4.84 (m, 2H), 4.64-4.38 (m, 7H), 4.17-3.91 (m, 3H), 3.80-3.54 (m, 4H), 3.53-3.51 (m, 1H), 3.31-3.22 (m, 1H), 2.57 (q, J=7.6 Hz, 2H), 1.18 (t, J=7.6 Hz, 3H); [M+Na]$^+$ 817.

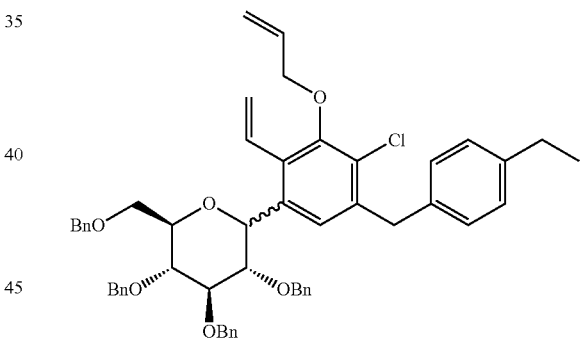

(3S,4R,5R,6R)-2-(3-(Allyloxy)-4-chloro-5-(4-ethylbenzyl)-2-vinylphenyl)-3,4,5-tris(benzyloxy)-6-(benzyloxymethyl)tetrahydro-2H-pyran (83)

A mixture of compound 82 (320 mg, 0.4 mmol) and allyl bromide (0.05 mL, 0.6 mmol) and K$_2$CO$_3$ (110 mg, 0.8 mmol) in acetone (2.0 mL) was stirred for 18 hours under reflux. The mixture was partitioned between EtOAc and water. The organic layer was washed with brine, dried over MgSO$_4$, filtered and concentrated in vacuo. The residue was purified by silica gel column chromatography to provide the product 83 (130 mg, 37%) as colorless oil.

$^1$H NMR (400 MHz, CDCl$_3$) δ 7.30-7.28 (m, 16H), 7.20-7.15 (m, 5H), 7.06-6.99 (m, 4H), 6.86-6.84 (d, J=8.0 Hz, 2H), 6.13-6.03 (m, 1H), 5.71 (d, J=17.5 Hz, 1H), 5.54 (d, J=10.8 Hz, 1H), 5.37 (d, J=17.5 Hz, 1H), 5.22 (d, J=10.8 Hz, 1H), 4.88-4.84 (m, 3H), 4.63-4.56 (m, 3H), 4.48 (d, J=12.0 Hz, 1H), 4.39-4.33 (m, 3H), 4.06 (q, J=18.1 Hz, 2H), 3.90 (d,

J=10.8 Hz, 1H), 3.76-3.64 (m, 4H), 3.532 (s, 1H), 2.55 (q, J=7.6 Hz, 2H), 1.16 (t, J=7.6 Hz, 3H); [M+Na]+ 857.

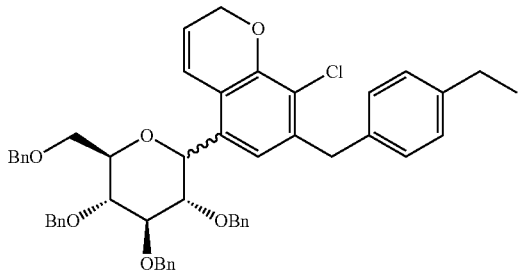 [SMILES: CCc1ccc(Cc2cc(C3O[C@H](COCc4ccccc4)[C@@H](OCc4ccccc4)[C@H](OCc4ccccc4)[C@H]3OCc3ccccc3)c3c(c2Cl)OCC=C3)cc1]

8-Chloro-7-(4-ethylbenzyl)-5-((3S,4R,5R,6R)-3,4,5-tris(benzyloxy)-6-(benzyloxymethyl)tetrahydro-2H-pyran-2-yl)-2H-chromene (84)

A mixture of compound 83 (145 mg, 0.17 mmol) and Grubb's 2nd generation cat. (25 mg, 0.03 mmol) in CH₂Cl₂ (34 mL) was stirred at room temperature for 3 hours. The mixture was concentrated in vacuo. The residue was purified by silica gel column chromatography to provide the product 84 (120 mg, 82%) as colorless oil.

¹H NMR (400 MHz, CDCl₃) δ 7.31-7.29 (m, 12H), 7.23-7.15 (m, 6H), 7.06 (q, J=8.4 Hz, 4H), 6.94-6.91 (m, 3H), 6.87 (s, 1H), 5.76-5.72 (m, 1H), 4.92-4.85 (m, 3H), 4.81-4.79 (m, 2H), 4.66-4.49 (m, 3H), 4.40-4.34 (m, 2H), 4.02 (q, J=16.4 Hz, 2H), 3.93 (d, J=10.8 Hz, 1H), 3.82-3.70 (m, 4H), 3.60-3.54 (m, 2H), 2.57 (q, J=7.6 Hz, 2H), 1.19 (t, J=7.6 Hz, 3H); [M+Na]+ 829.

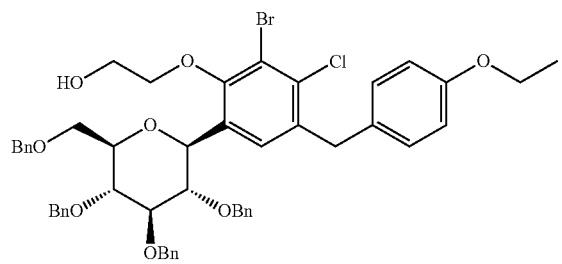 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)c(OCCO)c(Br)c2Cl)cc1]

2-(2-Bromo-3-chloro-4-(4-ethoxybenzyl)-6-((2S,3S,4R,5R,6R)-3,4,5-tris(benzyloxy)-6-(benzyloxymethyl)tetrahydro-2H-pyran-2-yl)phenoxy)ethanol (85)

¹H NMR (400 MHz, CDCl₃) δ 7.41-7.31 (m, 13H), 7.27-7.18 (m, 6H), 7.09 (d, J=8.7 Hz, 2H), 6.87 (d, J=6.5 Hz, 2H), 6.79 (d, J=8.7 Hz, 2H), 4.95 (s, 2H), 4.93 (d, J=10.8 Hz, 1H), 4.65 (d, J=10.9 Hz, 1H), 4.60-4.49 (m, 4H), 4.18-4.12 (m, 3H), 4.07-4.00 (m, 5H), 3.93 (q, J=6.0 Hz, 1H), 3.87-3.79 (m, 4H), 3.67-3.63 (m, 1H), 3.56 (t, J=5.5 Hz, 1H), 2.83-2.77 (m, 1H), 1.38 (t, J=7.0 Hz, 3H); [M+Na]+ 929.

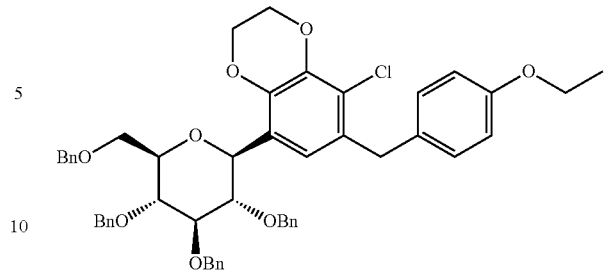

5-Chloro-6-(4-ethoxybenzyl)-8-((2S,3S,4R,5R,6R)-3,4,5-tris(benzyloxy)-6-(benzyloxymethyl)tetrahydro-2H-pyran-2-yl)-2,3-dihydrobenzo[b][1,4]dioxine (86)

To a solution of alcohol 85 (1.02 g, 1.12 mmol) in toluene (20 mL) were added Pd(OAc)₂ (5 mg, 0.023 mmol), 2'-(di-tert-butylphosphino)-N,N-dimethylbiphenyl-2-amine (10 mg, 0.028 mmol) and Cs₂CO₃ (0.55 g, 1.68 mmol) at r.t. The mixture was evacuated and back-filled with nitrogen. The mixture was stirred at 100° C. for 20 hours. The mixture was cooled to r.t. and filtered off to remove inorganic salts. The filtrate was concentrated in vacuo and the residue was purified using normal phase column chromatography to provide the crude product 86 (509 mg, 55%).

¹H NMR (400 MHz, CDCl₃) δ 7.35-7.23 (m, 13H), 7.21-7.08 (m, 6H), 7.05-6.98 (m, 2H), 6.92-6.85 (m, 1H), 6.83-6.77 (m, 1H), 6.75-6.68 (m, 2H), 4.97-4.84 (m, 3H), 4.69-4.57 (m, 2H), 4.53-4.44 (m, 3H), 4.17-4.05 (m, 3H), 3.99-3.84 (m, 6H), 3.82-3.71 (m, 6H), 1.39-1.31 (m, 3H); [M+Na]+ 849.

7-Bromo-4-chloro-2-methyl-2,3-dihydrobenzofuran-5-carbonitrile (87)

The compound 38 (2.03 g, 7.45 mmol) in ethylene glycol (5 mL) was subjected to microwave conditions (Biotage®) at 250° C. for 90 min. The reaction mixture was cooled to r.t. and extracted with EtOAc/H₂O (50 mL/100 mL). The organic layer was dried over MgSO₄, filtered off, and evaporated in vacuo. The residue was purified using normal phase column chromatography to obtain the title product (1.05 g, 52%).

¹H NMR (400 MHz, CDCl₃) δ 7.62 (s, 1H), 5.26-5.14 (m, 1H), 3.50 (dd, J=16.6 Hz, 9.0 Hz, 1H), 2.97 (dd, J=16.4 Hz, 7.6 Hz, 1H), 1.57 (d, J=6.0 Hz, 3H); [M+H]+ 272.

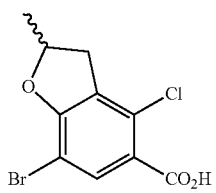

7-Bromo-4-chloro-2-methyl-2,3-dihydrobenzofuran-5-carboxylic acid (88)

To a suspension of compound 87 (2.1 g, 7.71 mmol) in EtOH (40 mL) and H$_2$O (20 mL) was added NaOH (11 g, 270 mmoL). The mixture was stirred at 100° C. for 15 hours. The mixture was cooled to r.t. and evaporated in vacuo to remove EtOH. The mixture was diluted with H$_2$O (100 mL) and cooled to 0° C. To the mixture was added conc. HCl to acidify the reaction mixture with stirring. The product was precipitated, filtered and washed with H$_2$O (150 mL). The desired product was dried under high vacuum at 45° C. for 12 hours (2.4 g, 100%).

$^1$H NMR (400 MHz, CDCl$_3$) δ 13.05 (br s, 1H), 8.13 (s, 1H), 5.25-5.13 (m, 1H), 3.52 (dd, J=16.2 Hz, 9.0 Hz, 1H), 2.99 (dd, J=16.2 Hz, 7.4 Hz, 1H), 1.57 (d, J=6.4 Hz, 3H); [M+H]$^+$ 291.

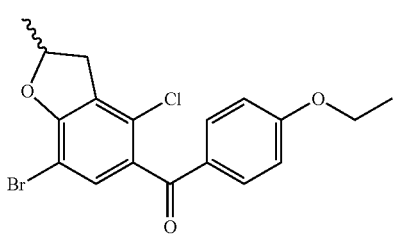 [SMILES: CCOc1ccc(C(=O)c2cc(Br)c3c(c2Cl)CC(C)O3)cc1]

(7-Bromo-4-chloro-2-methyl-2,3-dihydrobenzofuran-5-yl)(4-ethoxyphenyl)methanone (89)

To a suspension of compound 88 (2.4 g, 8.23 mmol) in CH$_2$Cl$_2$ (50 mL) were added oxalyl chloride (0.87 mL, 9.88 mmol) and catalytic amounts of DMF at room temperature. The mixture was stirred at room temperature for 2 hours. The mixture was evaporated in vacuo and dried under high vacuum. The crude acid chloride was dissolved with CH$_2$Cl$_2$ (45 mL) and cooled to 0° C. To the mixture was added phenetole (1.1 mL, 8.28 mmol) at 0° C. and stirred at 0° C. for 5 min. To the reaction mixture was added AlCl$_3$ (1.1 g, 8.28 mmol) portionwise at 0° C. The mixture was stirred at 0° C. for 30 min, warmed up to room temperature and stirred at the temperature for 15 hours. The mixture was poured into ice-water and extracted with CH$_2$Cl$_2$ (50 mL×2). The combined organic layer was dried over MgSO$_4$, filtered, and concentrated in vacuo. The crude product 89 was carried on to the next step without further purification (3.15 g).

$^1$H NMR (400 MHz, CDCl$_3$) δ 7.77 (d, J=2.4 Hz, 2H), 6.95-6.85 (m, 3H), 5.11-5.01 (m, 1H), 4.11 (q, J=7.0 Hz, 2H), 3.50 (dd, J=16.1 Hz, 9.0 Hz, 1H), 2.99 (dd, J=16.0 Hz, 7.6 Hz, 1H), 1.51 (d, J=6.4 Hz, 3H), 1.42 (t, J=7.0 Hz, 3H); [M+H]$^+$ 395.

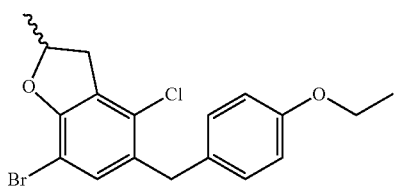 [SMILES: CCOc1ccc(Cc2cc(Br)c3c(c2Cl)CC(C)O3)cc1]

7-Bromo-4-chloro-5-(4-ethoxybenzyl)-2-methyl-2,3-dihydrobenzofuran (90)

To a solution of crude methanone 89 (3.15 g, 7.96 mmol) in CH$_2$Cl$_2$/CH$_3$CN (25 mL/25 mL) were added triethylsilane (3.8 mL, 23.9 mmol) and boron trifluoride diethyl etherate (3.0 mL, 23.9 mmol) at 0° C. The mixture was warmed up to room temperature slowly and stirred at room temperature for 15 hours. To the mixture was added aq. saturated K$_2$CO$_3$ solution (70 mL) slowly and extracted with EtOAc (50 mL×2). The combined organic layer was dried over MgSO$_4$, filtered, and concentrated in vacuo. The residue was purified by normal phase column chromatography to provide the desired product 90 (2.68 g, 85% (2-steps)).

$^1$H NMR (400 MHz, CDCl$_3$) δ 7.08 (s, 1H), 7.06 (d, J=2.4 Hz, 2H), 6.82 (d, J=6.2 Hz, 2H), 5.11-5.01 (m, 1H), 4.00 (q, J=7.0 Hz, 2H), 3.90 (s, 2H), 3.42 (dd, J=16.1 Hz, 8.9 Hz, 1H), 2.91 (dd, J=16.1 Hz, 7.6 Hz, 1H), 1.51 (d, J=6.3 Hz, 3H), 1.39 (t, J=7.0 Hz, 3H); [M+H]$^+$ 381.

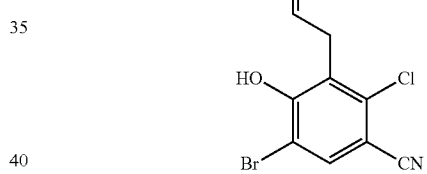

3-Allyl-5-bromo-2-chloro-4-hydroxybenzonitrile (91)

4-(allyloxy)-5-bromo-2-chlorobenzonitrile 38 (2.5 g, 9.17 mmol) was dissolved in ethyleneglycol (10 mL). And the solution was irradiated under microwave for 15 min under control of internal temperature as 200° C. After cooling down to room temperature, the resulting solution was purified by silica gel chromatography to afford title compound 91 (1.7 g, 68%) as a white solid.

$^1$H NMR (CDCl$_3$) δ 7.74 (s, 1H), 5.96-5.86 (m, 1H), 5.14-5.09 (m, 2H), 3.68 (dt, J=1.6, 6.4 Hz, 2H); [M+H]$^+$ 272.

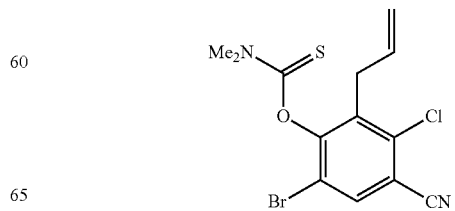

O-2-Allyl-6-bromo-3-chloro-4-cyanophenyl dimethylcarbamothioate (92)

To a solution of 3-allyl-5-bromo-2-chloro-4-hydroxybenzonitrile 91 (1.7 g, 6.24 mmol), Et₃N (2.6 mL, 18.7 mmol) in CH₂Cl₂ (50 mL) was added dimethylthicarbamoyl chloride (925 mg, 7.5 mmol). After adding DMAP (762 mg, 6.24 mmol) to reaction mixture, the resulting solution was stirred overnight at 50° C. Water (50 mL) and EtOAc (50 mL) were poured into the flask, and normal work-up was performed. The organic phase was collected, and then purified by silica gel chromatography to give the desired product (1.7 g, 75.8%) as a white solid.

¹H NMR (CDCl₃) δ 7.84 (s, 1H), 5.92-5.82 (m, 1H), 5.16-5.05 (m, 2H), 3.68-3.63 (m, 1H), 3.51 (s, 3H), 3.50-3.44 (m, 1H), 3.43 (s, 3H); [M+H]⁺ 359.

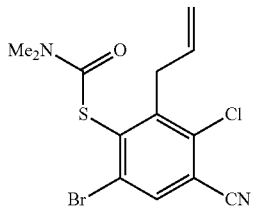 [SMILES: C=CCc1c(Cl)c(C#N)cc(Br)c1SC(=O)N(C)C]

S-2-Allyl-6-bromo-3-chloro-4-cyanophenyl dimethylcarbamothioate (93)

After dissolving O-2-allyl-6-bromo-3-chloro-4-cyanophenyl dimethylcarbamothioate 92 (1.7 g, 4.73 mmol) in diphenylether (20 mL), reaction mixture was heated to 180° C. overnight. The reaction progress was monitored by HPLC. After the reaction was completed, the resulting solution was purified by silica gel chromatography (at first, diphenylether was washed with n-hexane) to afford the title compound 93 (1.55 g, 91.2%) as a light yellow solid.

¹H NMR (CDCl₃) δ 7.86 (s, 1H), 5.94-5.80 (m, 1H), 5.19-5.09 (m, 2H), 3.77-3.69 (m, 1H), 3.59 (s, 3H), 3.52-3.48 (m, 1H), 3.37 (s, 3H); [M+H]⁺ 359.

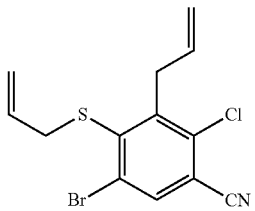 [SMILES: C=CCSc1c(Br)cc(C#N)c(Cl)c1CC=C]

3-Allyl-4-(allylthio)-5-bromo-2-chlorobenzonitrile (94)

To a solution of S-2-allyl-6-bromo-3-chloro-4-cyanophenyl dimethylcarbamothioate 93 (1.55 g, 4.31 mmol) in a mixture of THF (60 mL) and MeOH (30 mL) was added KOH (440 mg, 8.62 mmol) at 0° C. The reaction solution was stirred for 4 hours at room temperature. After the reaction was completed, the volatile solvent was evaporated under reduced pressure. Normal work-up with EtOAc was preceded by acidification with 1N HCl. The resulting solution was dried with MgSO₄ and then solvent was removed by evaporation. After further purification, the crude compound was used for the next step.

In a mixture of crude 3-allyl-5-bromo-2-chloro-4-mercaptobenzonitrile and K₂CO₃ (1.79 g, 12.9 mmol) in CH₃CN (80 mL), allylbromide (1.12 mL, 12.9 mmol) was added dropwise. The reaction mixture was stirred overnight at room temperature, and then filtered off. The resulting solution was evaporated and purified by silica gel chromatography to give the desired product 94 (1.1 g, 77.7% overall yield) as a white solid.

¹H NMR (CDCl₃) δ 7.81 (s, 1H), 5.92-5.82 (m, 1H), 5.79-5.71 (m, 1H), 5.56-5.49 (m, 2H), 5.28-5.09 (m, 2H), 4.79-4.70 (m, 2H), 3.51-3.48 (m, 2H); [M+H]⁺ 328.

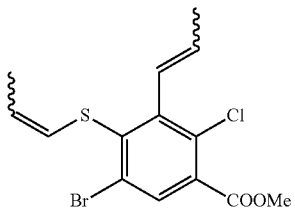

Methyl 5-bromo-2-chloro-3-(prop-1-enyl)-4-(prop-1-enylthio)benzoate (95)

To a solution of 3-allyl-4-(allylthio)-5-bromo-2-chlorobenzonitrile 94 (1.1 g, 3.35 mmol) in a mixture of EtOH (90 mL) and H₂O (10 mL) was added NaOH (545 mg, 13.4 mmol). The reaction mixture was warmed up to 100° C., and stirred overnight. After reaction complete, the resulting solution was cooled down to room temperature. 1N HCl solution was used for acidify reaction solution, and normal work-up with EtOAc was proceeded. Removal of volatile solvent was preceded by drying with MgSO₄. Without further purification, crude acid was used for next step. The crude acid was dissolved in MeOH (50 mL), treated with SOCl₂ (1 mL) provisionally. The reaction mixture was refluxed overnight and resulting solution was cooled down to room temperature and evaporated in vacuo. The residue was purified by silica gel chromatography to afford the desired product (710 mg, 63% overall yield) as a white solid.

[M+H]⁺ 362.

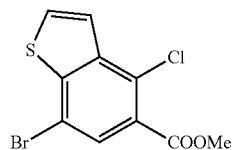

Methyl 7-bromo-4-chlorobenzo[b]thiophene-5-carboxylate (96)

To a solution of starting diene compound (710 mg, 1.96 mmol) in CH₂Cl₂ (40 mL) was added 2$^{nd}$ generation Grubb's catalyst (170 mg, 0.20 mmol) at room temperature. The resulting solution was stirred overnight at room temperature, filtered with Celite, and evaporated volatile solvent. The residue was purified by silica gel chromatography to afford the title compound (567 mg, 88%) as a light yellow solid.

¹H NMR (CDCl₃) δ 8.10 (s, 1H), 7.81-7.74 (m, 2H), 4.15 (s, 3H); [M+H]⁺ 305.

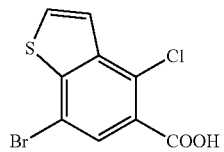 [SMILES: O=C(O)c1cc(Br)c2sccc2c1Cl]

7-Bromo-4-chlorobenzo[b]thiophene-5-carboxylic acid (97)

To a solution of methyl 7-bromo-4-chlorobenzo[b]thiophene-5-carboxylate 96 (1.06 g, 3.3 mmol) in aqueous EtOH (40 mL) was added NaOH (400 mg, 10 mmol). The reaction mixture was stirred for 3 hours at room temperature. After the reaction was completed, the volatile solvent was removed under reduced pressure, acidification with 1N HCl was accomplished. Drying with MgSO₄ was followed by normal work-up with EtOAc. After evaporating volatile solvent, the residue was used without further purification in ~88% yield.

[M+H]⁺ 292.

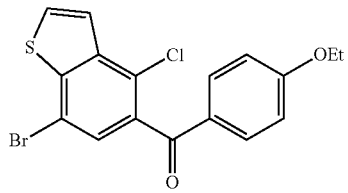 [SMILES: CCOc1ccc(C(=O)c2cc(Br)c3sccc3c2Cl)cc1]

(7-Bromo-4-chlorobenzo[b]thiophen-5-yl)(4-ethoxyphenyl)methanone (98)

After dissolving crude 7-bromo-4-chlorobenzo[b]thiophene-5-carboxylic acid 97 (847 mg, 2.91 mmol) in CH₂Cl₂, (COCl)₂ (0.49 mL, 5.82 mmol) and catalytic amount DMF was added carefully at 0° C. The resulting solution was stirred overnight at room temperature. The volatiles were evaporated under reduced pressure and dried in vacuo. The crude compound was used for the next step without further purification. To a solution of crude 7-bromo-4-chlorobenzo[b]thiophene-5-carbonyl chloride in CH₂Cl₂ (50 mL) was added ethoxybenzene (462 mg, 3.78 mmol) and AlCl₃ (464 mg, 3.49 mmol) at 0° C. After warming the reaction mixture up to room temperature, it was stirred for 4 hours. The resulting compound was quenched with aq. NH₄Cl solution and the normal work-up with EtOAc was conducted. Purification by silica gel chromatography gave the title compound (917 mg, 79.8%) as an off-white solid.

¹H NMR (CDCl₃) δ 8.20 (s, 1H), 7.64-7.58 (m, 2H), 7.54-7.48 (m, 2H), 7.20-7.16 (m, 2H), 4.19 (q, J=8.4 Hz, 2H), 1.34 (t, J=8.4 Hz, 3H); [M+H]⁺ 395.

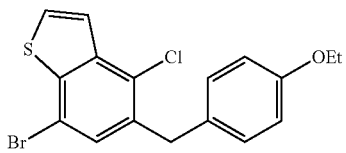 [SMILES: CCOc1ccc(Cc2cc(Br)c3sccc3c2Cl)cc1]

7-Bromo-4-chloro-5-(4-ethoxybenzyl)benzo[b]thiophene (99)

To a solution of (7-bromo-4-chlorobenzo[b]thiophen-5-yl)(4-ethoxyphenyl)methanone 98 (917 mg, 2.32 mmol) in a mixture of CH₂Cl₂ (9 mL) and CH₃CN (30 mL) at 0° C. was added Et₃SiH (1.6 mL, 9.27 mmol) and BF₃.Et₂O (0.47 mL, 3.48 mmol). The reaction mixture was warmed to room temperature, and then stirred overnight. The resulting solution was quenched with aqueous sat. NH₄Cl solution (40 mL) and normal work-up with EtOAc was accomplished. After evaporating volatile solvents, the residue was purified by silica gel chromatography to afford the title compound (761 mg, 84%) as an off-white solid.

¹H NMR (CDCl₃) δ 8.19 (s, 1H), 7.65-7.58 (m, 2H), 7.52-7.47 (m, 2H), 7.22-7.18 (m, 2H), 4.18 (q, J=8.4 Hz, 2H), 3.88 (s, 2H), 1.35 (t, J=8.4 Hz, 3H); [M+H]⁺ 381.

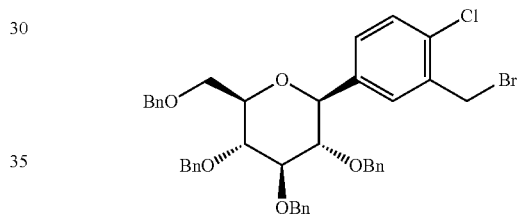

(2R,3R,4R,5S,6S)-3,4,5-Tris(benzyloxy)-2-(benzyloxymethyl)-6-(3-(bromomethyl)-4-chlorophenyl) tetrahydro-2H-pyran (106)

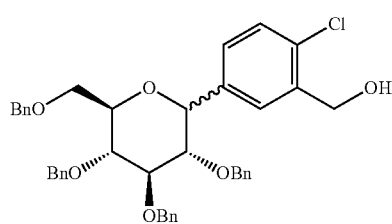

Step 1)

(2-Chloro-5-((3S,4R,5R,6R)-3,4,5-tris(benzyloxy)-6-(benzyloxymethyl)tetrahydro-2H-pyran-2-yl)phenyl)methanol (103)

The title compound 103 was prepared from commercially available 5-bromo-2-chlorobenzoic acid according to the known procedure. (*Bioorg. Med. Chem.* 2010, 18, 2178-2194)

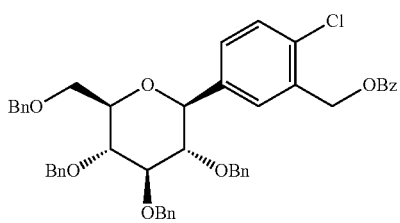

Step 2)

2-Chloro-5-((2S,3S,4R,5R,6R)-3,4,5-tris(benzyloxy)-6-(benzyloxymethyl)tetrahydro-2H-pyran-2-yl)benzyl benzoate (104)

To a solution of alcohol 103 (9.9 g, 14.88 mmol) in pyridine (36 mL) was added benzoyl chloride (1.9 mL, 16.37 mmol) at room temperature. The mixture was stirred at room temperature for 6 hours. The mixture was washed with aq. saturated $NaHCO_3$ solution. The organic layer was dried over $MgSO_4$, filtered, and concentrated in vacuo. The residue was purified by silica gel column chromatography to provide the mixture of anomers of the title compound (10.5 g). The anomeric mixture of 104 was recrystallized with IPA (150 mL). The precipitate was collected by filtration and washed with cold IPA (50 mL) and dried under high vacuum to obtain β-anomer of the title compound 104 (6.13 g, 54%).

$^1$H NMR (400 MHz, $CDCl_3$) δ 8.04 (dd, J=1.2, 1.6 Hz, 2H), 7.56-7.52 (m, 2H), 7.42-7.37 (m, 4H), 7.33-7.27 (m, 13H), 7.20-7.11 (m, 5H), 6.90 (dd, J=1.6, 2.0 Hz, 2H), 5.42 (s, 2H), 4.91 (q, J=11.2 Hz, 2H), 4.86 (d, J=10.8 Hz, 1H), 4.64-4.44 (m, 4H), 4.23 (d, J=9.6 Hz, 1H), 3.90 (d, J=10.4 Hz, 1H), 3.82-3.72 (m, 4H), 3.61-3.57 (m, 1H), 3.46 (t, J=9.2 Hz, 1H); $[M+Na]^+$ 791.

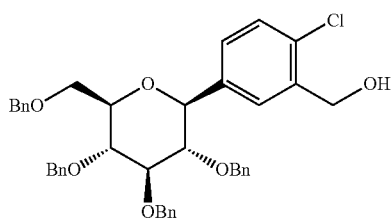 [SMILES: OCc1cc([C@@H]2O[C@H](COCc3ccccc3)[C@@H](OCc3ccccc3)[C@H](OCc3ccccc3)[C@H]2OCc2ccccc2)ccc1Cl]

Step 3)

(2-Chloro-5-((2S,3S,4R,5R,6R)-3,4,5-tris(benzyloxy)-6-(benzyloxymethyl)tetrahydro-2H-pyran-2-yl)phenyl)methanol (105)

To a solution of benzoate 104 (6.13 g, 7.97 mmol) in $THF/MeOH/H_2O$ (150 mL/5 mL/5 mL) was added LiOH monohydrate (1.0 g, 23.9 mmol) at room temperature. The mixture was stirred at room temperature for 15 hours. The mixture was extracted with EtOAc/aq. saturated $NH_4Cl$ solution (100 mL/100 mL). The organic layer was dried over anhydrous $MgSO_4$, filtered and concentrated in vacuo to yield the title compound 105 (5.33 g, 10%), which was carried on to the next step without further purification.

$^1$H NMR (400 MHz, $CDCl_3$) δ 7.50 (s, 1H), 7.38-7.17 (m, 20H), 6.94-6.92 (m, 2H), 4.96-4.46 (m, 9H), 4.23 (d, J=9.2 Hz, 1H), 3.86 (d, J=10.4 Hz, 1H), 3.81-3.67 (m, 4H), 3.61-3.59 (m, 1H), 3.44 (t, J=9.2 Hz, 1H); $[M+Na]^+$ 687.

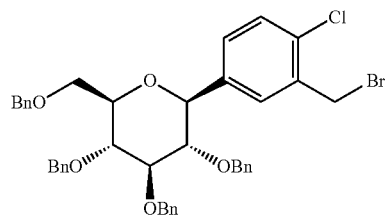 [SMILES: Clc1ccc([C@@H]2O[C@H](COCc3ccccc3)[C@@H](OCc3ccccc3)[C@H](OCc3ccccc3)[C@H]2OCc2ccccc2)cc1CBr]

Step 4)

(2R,3R,4R,5S,6S)-3,4,5-Tris(benzyloxy)-2-(benzyloxymethyl)-6-(3-(bromomethyl)-4-chlorophenyl)tetrahydro-2H-pyran (106)

To a solution of alcohol 105 (5.33 g, 8.01 mmol) in ether (50 mL) were added phosphorus tribromide (0.26 mL, 2.80 mmol) and catalytic amount of pyridine at 0° C. The mixture was allowed to warm to room temperature and stirred at room temperature for 15 hours. The mixture was extracted with $EtOAc/H_2O$ (100 mL/150 mL). The combined organic layer was dried over $MgSO_4$, filtered, and concentrated in vacuo. The residue was purified by silica gel column chromatography to provide the title bromide 106 (4.15 g, 71%).

$^1$H NMR (400 MHz, $CDCl_3$) δ 7.47 (d, J=1.6 Hz, 1H), 7.34-7.25 (m, 15H), 7.22-7.11 (m, 5H), 6.94-6.92 (m, 2H), 4.96-4.85 (m, 3H), 4.69-4.46 (6H), 4.19 (d, J=9.2 Hz, 1H), 3.91 (d, J=10.8 Hz, 1H), 3.82-3.71 (m, 4H), 3.59-3.56 (m, 1H), 3.45 (t, J=9.2 Hz, 1H); $[M+Na]^+$ 749.

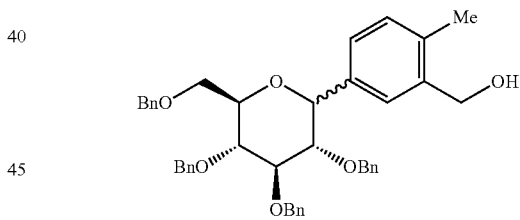

(2-Methyl-5-((3S,4R,5R,6R)-3,4,5-tris(benzyloxy)-6-(benzyloxymethyl)tetrahydro-2H-pyran-2-yl)phenyl)methanol (110)

The title compound 110 was prepared from commercially available 5-bromo-2-methylbenzoic acid according to the known procedure. (*ACS Med. Chem. Lett.* 2011, 2, 182-187)

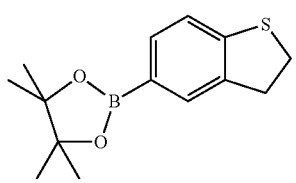 [SMILES: CC1(C)OB(c2ccc3c(c2)CCS3)OC1(C)C]

2-(2,3-Dihydrobenzo[b]thiophen-5-yl)-4,4,5,5-tetramethyl-1,3,2-dioxaborolane (114)

Step 1)

2,3-Dihydrobenzo[b]thiophene (112)

Trifluoroacetic acid (5.2 mL) was slowly added to the mixture of benzothiophene (1 g, 7.45 mmol) and triethylsilane (3.6 mL, 22.35 mmol) with heating under reflux at 50° C. for 125 hours. After cooling to 0° C., the reaction was quenched by addition of aq. saturated NH$_4$Cl solution. The mixture was diluted with water and extracted with EtOAc. The organic layer was washed with brine, dried over anhydrous MgSO$_4$, filtered and evaporated in vacuo. The residue was purified by silica gel column chromatography to provide the intermediate 112 (415 mg, 41%).

$^1$H NMR (400 MHz, CDCl$_3$) δ 7.22-7.16 (m, 2H), 7.12-7.08 (m, 1H), 7.00 (td, J=7.4, 1.2 Hz, 1H), 3.36-3.32 (m, 2H), 3.29-3.25 (m, 2H).

Step 2)

5-Bromo-2,3-dihydrobenzo[b]thiophene (113)

Iron powder (10.4 mg, 1.47 mmol) was added to a solution of 2,3-dihydrobenzo[b]thiophene 112 (400 mg, 2.94 mmol) in dichloromethane (5.9 mL). Bromine (0.15 mL, 2.94 mmol) was added dropwise to the mixture with stirring under ice-cooling. This mixture was stirred at the same temperature for 30 minutes. Saturated aqueous sodium hydrogen carbonate solution was added to the mixture and this was extracted with dichloromethane. The organic layer was washed with water, dried over magnesium sulfate and then concentrated under reduced pressure. The residue was purified by silica gel column chromatography to provide the desired product 113 (396 mg, 63%).

$^1$H NMR (400 MHz, CDCl$_3$) δ 7.30-7.29 (m, 1H), 7.23-7.20 (m, 1H), 7.05 (d, J=8.0 Hz, 1H), 3.38-3.34 (m, 2H), 3.28-3.24 (m, 2H); [M+H]$^+$ 215.

Step 3)

2-(2,3-Dihydrobenzo[b]thiophen-5-yl)-4,4,5,5-tetramethyl-1,3,2-dioxaborolane (114)

To a solution of 5-bromo-2,3-dihydrobenzo[b]thiophene (113) (390 mg, 1.81 mmol) in DMF (7.5 mL) were added bis(pinacolato)diboron (1.38 g, 5.44 mmol), Pd(dppf)$_2$Cl$_2$ (30 mg, 0.036 mmol) and CH$_3$CO$_2$K (890 mg, 9.07 mmol) at room temperature. The mixture was stirred at 100° C. for 15 hours. The reaction mixture was cooled to room temperature and filtered off through Celite. The filtrate was concentrated in vacuo. The residue was purified by silica gel column chromatography to provide the title compound 114 (260 mg, 55%).

$^1$H NMR (400 MHz, CDCl$_3$) δ 7.61 (s, 1H), 7.55 (dd, J=8.4, 0.8 Hz, 1H), 7.22 (d, J=7.6 Hz, 1H), 3.37-3.32 (m, 2H), 3.29-3.25 (m, 2H), 1.33 (s, 12H); [M+H]$^+$ 263.

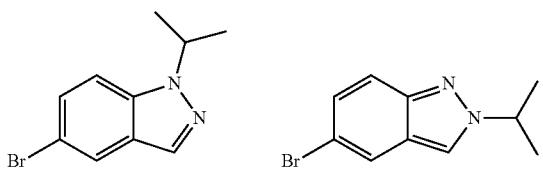

5-Bromo-1-isopropyl-1H-indazole (115) and 5-bromo-2-isopropyl-2H-indazole (116)

To a solution of 5-bromo-1H-indazole (1 g, 5.07 mmol) in DMF (17 mL) were added 2-bromopropane (0.7 mL, 7.61 mmol) and sodium hydride (60% oil) (223 mg, 5.58 mmol) at 0° C. The mixture was stirred at room temperature for 12 hours. The mixture was poured into water and extracted with EtOAc (50 mL×2). The combined organic layer was dried over MgSO$_4$, filtered, and concentrated in vacuo. The residue was purified by silica gel column chromatography to provide the title compounds 115 (680 mg, 47%) and 116 (500 mg, 35%).

$^1$H NMR (400 MHz, CDCl$_3$) δ 7.94 (s, 1H), 7.86 (dd, J=1.8, 0.8 Hz, 1H), 7.43 (dd, J=8.8, 2.0 Hz, 1H), 7.33 (d, J=9.2 Hz, 1H), 4.86-4.76 (m, 1H), 1.59 (s, 3H), 1.57 (s, 3H); δ 7.90 (d, J=0.8 Hz, 1H), 7.80 (dd, J=1.8, 0.8 Hz, 1H), 7.43 (dt, J=9.2, 0.8 Hz, 1H), 7.32 (dd, J=9.0, 2.0 Hz, 1H), 4.83-4.73 (m, 1H), 1.66 (s, 3H), 1.64 (s, 3H); [M+H]$^+$ 239.

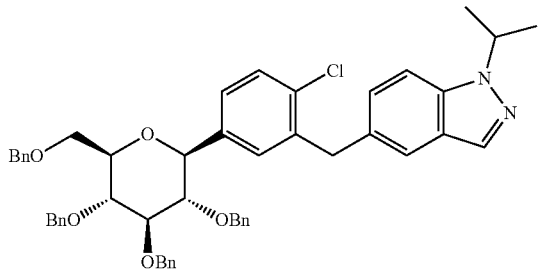 [SMILES: CC(C)n1ncc2cc(Cc3cc([C@@H]4O[C@H](COCc5ccccc5)[C@@H](OCc5ccccc5)[C@H](OCc5ccccc5)[C@H]4OCc4ccccc4)ccc3Cl)ccc21]

5-(2-Chloro-5-((2S,3S,4R,5R,6R)-3,4,5-tris(benzyloxy)-6-(benzyloxymethyl)tetrahydro-2H-pyran-2-yl)benzyl)-1-isopropyl-1H-indazole (117)

To a solution of benzyl bromide (1.1 g, 1.52 mmol) in toluene/EtOH (1.35 mL/1.5 mL) were added a pinacol ester of the compound 115 (870 mg, 3.04 mmol), Pd(PPh$_3$)$_4$ (90 mg, 0.076 mmol) and Cs$_2$CO$_3$ (990 mg, 3.04 mmol) at 0° C. The mixture was stirred at 100° C. for 15 hours. The reaction mixture was cooled to room temperature and filtered off through celite. The filtrate was concentrated in vacuo. The residue was purified by silica gel column chromatography to provide the title compound 117 (780 mg, 63%).

[M+Na]$^+$ 829.

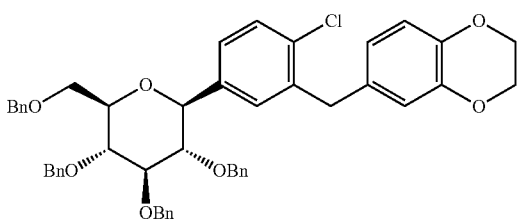

6-(2-Chloro-5-(2S,3S,4R,5R,6R)-3,4,5-tris(benzyloxy)-6-(benzyloxymethyl)-tetrahydro-2H-pyran-2-yl)benzyl-2,3-dihydrobenzo[b][1,4]dioxine (119)

To a solution of (2R,3R,4R,5S,6S)-3,4,5-tris(benzyloxy)-2-(benzyloxymethyl)-6-(3-(bromomethyl)-4-chlorophenyl)-tetrahydro-2H-pyran (106) (500 mg, 0.687 mmole) in acetone (6 mL) and water (2 mL) was added 2,3-dihydrobenzo[b][1,4]dioxin-6-ylboronic acid (247 mg, 1.37 mmole) and K$_2$CO$_3$ (380 mg, 2.75 mmole). The reaction mixture was cooled in an ice-bath, and then bis(triphenylphosphine) palladium(II) dichloride (24.1 mg, 0.0344 mmole) was added. The reaction mixture was stirred at ambient temperature overnight. Then brine was added and the resulting mixture was extracted with ethyl acetate. The organic layer was dried over MgSO$_4$, and the solvent was concentrated in vacuo. The residue was purified by silica gel chromatography to yield the title compound (501 mg, 0.640 mmole, 93%) as a colorless gum.

[M+Na]$^+$ 805.

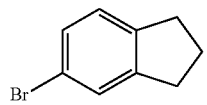

5-Bromo-2,3-dihydro-1H-indene (120)

5-Aminoindane was treated with concentrated hydrobromic acid. The suspension was cooled to −5° C., and 5M sodium nitrite solution was added at a temperature between 0° C. to 5° C. in period of 30 minutes through an addition funnel. Stirring was continued for 20 minutes at 0° C. to 5° C. The reaction mixture was now very dark fluid slurry. In a second reaction vessel, a solution of copper (I) bromide in concentrated hydrobromic acid had been prepared and preheated to 40° C. When the diazonium salt slurry was added in portions, a very slow gas evolution was observed which became vehement when heating to 60° C. After stirring at 60° C. for 40 min, the gas evolution ceased. The mixture was poured onto water. The product was extracted twice with ethyl acetate. Some of the precipitated copper bromide was removed by filtration to facilitate phase separation. The organic extracts were washed twice with water and one time with brine. The combined organic extracts were dried over anhydrous magnesium sulfate, filtered, and evaporated to dryness. After flash chromatography, the title compound was obtained as pale yellow oil.

$^1$H NMR (400 MHz, CDCl$_3$) δ 7.29 (s, 1H), 7.18-7.20 (m, 1H), 7.02 (d, J=8.0 Hz, 1H), 2.78-2.86 (m, 4H), 1.99-2.06 (m, 2H).

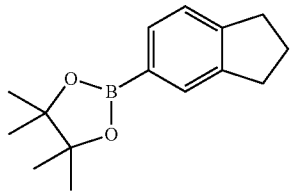 [SMILES: CC1(C)OB(c2ccc3c(c2)CCC3)OC1(C)C]

2-(2,3-Dihydro-1H-inden-5-yl)-4,4,5,5-tetramethyl-1,3,2-dioxaborolane (121)

To a stirred solution of 5-bromo-2,3-dihydro-1H-indene (120) (800 mg, 4.1 mmol) in N,N-dimethylformamide (10 mL), bis(pinacolato)diboron (2.1 g, 8.2 mmol) was added and deoxygenated twice. Potassium acetate (2.0 g, 20.5 mmol) and Pd(PPh$_3$)$_2$Cl$_2$ (84 mg, 0.12 mmol) were added thereto and again deoxygenated. The reaction mixture was heated to 100° C. for 12 h. The reaction mixture was filtered through Celite bed and evaporated to dryness. The crude compound was purified through column chromatography on silica gel to afford the title compound (820 mg, 83%).

$^1$H NMR (400 MHz, CDCl$_3$) δ 7.69 (s, 1H), 7.57 (d, J=7.6 Hz, 1H), 7.24-7.26 (m, 1H), 2.91 (q, J=7.2, 6.0 Hz, 4H), 2.05 (m, 2H), 1.34 (s, 12H).

[M+H]$^+$ 245.

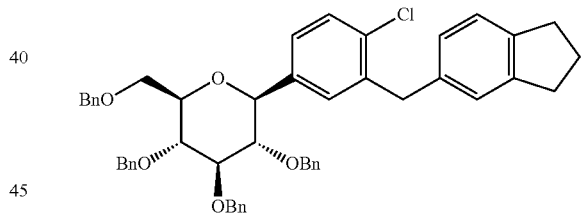

(2R,3R,4R,5S,6S)-3,4,5-Tris(benzyloxy)-2-(benzyloxymethyl)-6-(4-chloro-3-((2,3-dihydro-1H-inden-5-yl)methyl)phenyl)-tetrahydro-2H-pyran (122)

To a solution of (2R,3R,4R,5S,6S)-3,4,5-tris(benzyloxy)-2-(benzyloxymethyl)-6-(3-(bromomethyl)-4-chlorophenyl)-tetrahydro-2H-pyran (106) (580 mg, 0.8 mmole) in toluene/EtOH (9 mL/8 mL) were added 2-(2,3-dihydro-1H-inden-5-yl)-4,4,5,5-tetramethyl-1,3,2-dioxaborolane (121) (400 mg, 1.6 mmol), tetrakis(triphenylphosphin)palladium (180 mg, 0.16 mmol), and Cs$_2$CO$_3$ (2.1 g, 2.32 mmole) at room temperature. The mixture was stirred at 100° C. The mixture was cooled to room temperature and concentrated in vacuo. The residue was purified by silica gel column chromatography to provide the title compound (425 mg, 70%).

[M+Na]$^+$ 787.

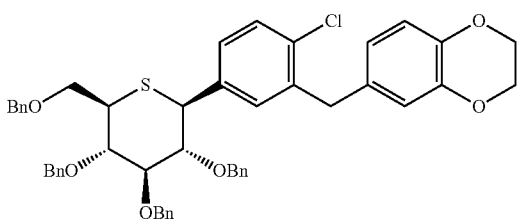 [SMILES: Clc1ccc([C@@H]2S[C@H](COCc3ccccc3)[C@@H](OCc3ccccc3)[C@H](OCc3ccccc3)[C@H]2OCc2ccccc2)cc1Cc1ccc2c(c1)OCCO2]

6-(2-Chloro-5-((2S,3R,4R,5S,6R)-3,4,5-tris(benzyloxy)-6-((benzyloxy)methyl)tetrahydro-2H-thiopyran-2-yl)benzyl)-2,3-dihydrobenzo[b][1,4]dioxine (126)

To a solution of 6-(5-bromo-2-chlorobenzyl)-2,3-dihydrobenzo[b][1,4]dioxine (124, 384 mg, 1.1 mmol) in tetrahydrofuran (5 mL) at −78° C. under an atmosphere of nitrogen was added dropwise n-butyllithium (2.5M in hexane, 0.45 mL, 1.1 mmol), and the mixture was stirred for 0.5 h at the same temperature. Then a solution of (3R,4S,5S,6R)-3,4,5-tris(benzyloxy)-6-((benzyloxy)methyl)tetrahydro-2H-thiopyran-2-one (123, 300 mg, 0.54 mmol, This compound was synthesized by reference to H. Driguez and B. Henrissat, *Tetrahedron Lett.* 1981, 22, 5061-5062, Kakinuma, H., et al., *J. Med. Chem.* 2010, 53, 3247-3261) in tetrahydrofuran (5 mL) was added dropwise, and the mixture was stirred for 15 min at the same temperature. The reaction mixture was quenched by addition of saturated ammonium chloride solution. After complete addition, the solution was gradually raised to room temperature. The organic layer was separated and the aqueous layer was extracted with ethyl acetate. The combined organic layers were washed with brine, dried over magnesium sulfate, filtered and concentrated in vacuo. The crude residue was purified by silica gel chromatography (silica gel, 3 to 30% tetrahydrofuran in hexane) to yield (3R,4S,5S,6R)-3,4,5-tris(benzyloxy)-6-(benzyloxymethyl)-2-(4-chloro-3-((2,3-dihydrobenzo[b][1,4]dioxin-6-yl)methyl)phenyl)tetrahydro-2H-thiopyran-2-ol (125, 416 mg, 0.51 mmol, 95%) as a white solid.

To a stirred −15° C. solution of lactol (125, 410 mg, 0.50 mmol) in dichloromethane/acetonitrile (4 mL/4 mL) was added triethylsilane (0.49 mL, 3.02 mmol) followed by boron trifluoride diethyl etherate (0.26 mL, 2.01 mmol) at a rate such that the reaction temperature was maintained between −15 and 0° C. The solution was allowed to warm to 0° C. over 0.5 h prior to quenching with saturated sodium bicarbonate solution. After removal of organic volatiles under a reduced pressure, the residue was partitioned between ethyl acetate and water. Following extraction of the aqueous layer with ethyl acetate, the combined organic layers were washed with brine, dried over magnesium sulfate, filtered and concentrated in vacuo. The crude residue was purified by silica gel chromatography (silica gel, 3 to 25% ethyl acetate in hexane) to yield the title compound (126, 215 mg, 0.27 mmol, 53%) as a white solid.

$^1$H NMR (400 MHz, CDCl$_3$) δ 7.41 (d, J=4.4 Hz, 1H), 7.36-7.25 (m, 15H), 7.21-7.14 (m, 5H), 6.76-6.72 (m, 4H), 6.64 (dd, J=2.0, 8.4 Hz, 1H), 4.93 (d, J=10.8 Hz, 1H), 4.90 (s, 2H), 4.63 (d, J=10.4 Hz, 1H), 4.55-4.53 (m, 3H), 4.22 (s, 4H), 4.06 (d, J=15.2 Hz, 3H), 3.96-3.88 (m, 4H), 3.85-3.81 (m, 2H), 3.73 (dd, J=2.8, 9.6 Hz, 1H), 3.55 (t, J=8.8 Hz, 1H), 3.15-3.10 (m, 1H); [M+Na]$^+$ 821.

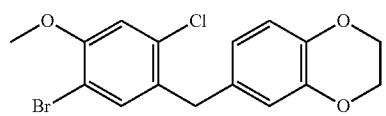 [SMILES: COc1cc(Cl)c(Cc2ccc3c(c2)OCCO3)cc1Br]

6-(5-Bromo-2-chlorobenzyl)-2,3-dihydrobenzo[b][1,4]dioxine (130)

To a stirred suspension of 5-bromo-4-methoxy-2-chlorobenzoic acid (128, 4 g, 15.2 mmol) in dichloromethane (100 mL) was added oxalyl chloride (1.6 mL, 18.3 mmol) and DMF (2 drops) at 0° C. and stirred for 2 h. The mixture was concentrated, and the residual colorless solid was dissolved in dichloromethane (100 mL). To this solution were added 1,4-benzodioxane (2 mL, 16.7 mmol) and then AlCl$_3$ (2.23 g, 16.7 mmol) portionwise. After being stirred at room temperature overnight, the mixture was poured into ice water and extracted with dichloromethane two times. The combined organic layers were washed with 1M HCl, water, and brine, then dried over magnesium sulfate, filtered and concentrated in vacuo. The crude residue was diluted with dichloromethane/acetonitrile (35 mL/35 mL) and added triethylsilane (7.4 mL, 45.6 mmol) followed by boron trifluoride diethyl etherate (5.8 mL, 45.6 mmol) at −10° C. The solution was allowed to warm to room temperature over 5 h prior to quenching with saturated sodium bicarbonate solution. After removal of organic volatiles under a reduced pressure, the crude residue was purified by silica gel chromatography (3 to 10% tetrahydrofuran in hexane) to yield the title compound (130, 3.6 g, 9.74 mmol, 64%; 3 steps) as a white solid.

$^1$H NMR (400 MHz, CDCl$_3$) δ 7.35 (s, 1H), 6.94 (s, 1H), 6.83 (dd, J=1.6, 6.8 Hz, 1H), 6.69 (s, 1H), 6.69-6.67 (m, 1H), 4.27 (s, 4H), 3.93 (s, 2H), 3.90 (s, 3H).

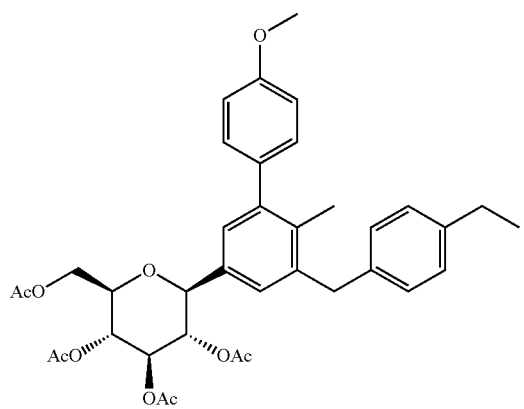 [SMILES: CCc1ccc(Cc2cc([C@@H]3O[C@H](COC(C)=O)[C@@H](OC(C)=O)[C@H](OC(C)=O)[C@H]3OC(C)=O)cc(-c3ccc(OC)cc3)c2C)cc1]

(2R,3R,4R,5S,6S)-2-(Acetoxymethyl)-6-(5-(4-ethylbenzyl)-4'-methoxy-6-methylbiphenyl-3-yl)-tetrahydro-2H-pyran-3,4,5-triyl triacetate (132)

To a solution of (2R,3R,4R,5S,6S)-2-(acetoxymethyl)-6-(3-bromo-5-(4-ethylbenzyl)-4-methylphenyl)-tetrahydro-2H-pyran-3,4,5-triyl triacetate (131) (WO2008/101939, Example V) (500 mg, 0.807 mmole) in toluene (6 mL) and water (3 mL) were added 4-methoxyphenylboronic acid (147 mg, 0.969 mmole), Pd(OAc)$_2$ (18.1 mg, 0.0807 mmole), tricyclohexylphosphonium tetrafluoroborate (59.4 mg, 0.161 mmole), and K$_3$PO$_4$ (685 mg, 3.23 mmole). The mixture was stirred at 100° C. overnight. After cooling to ambient temperature, the mixture was diluted with water and extracted with ethyl acetate. The organic layer was washed with brine, dried over MgSO$_4$, filtered, and concentrated in vacuo. The crude residue was purified by silica gel chromatography to yield the title compound (484 mg, 0.748 mmole, 93%) as a yellow solid.

[M+Na]$^+$ 669.

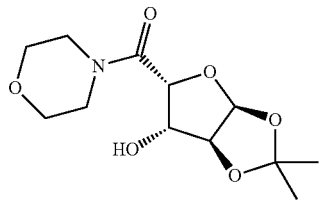 [SMILES: CC1(C)O[C@@H]2O[C@@H](C(=O)N3CCOCC3)[C@@H](O)[C@@H]2O1]

(3aS,5R,6S,6aS)-6-Hydroxy-2,2-dimethyltetrahydrofuro[3,2-d][1,3]dioxol-5-yl)(morpholino)methanone (134

Step 1)

(3aS,5S,6R,6aS)-5-(Hydroxymethyl)-2,2-dimethyltetrahydrofuro[3,2-d][1,3]dioxol-6-ol To a suspension of L-(−)-xylose (133, 19.15 g, 127.5 mmol) and MgSO$_4$ (30.72 g, 255.0 mmol) in acetone (190 mL) was added conc. H$_2$SO$_4$ (1.9 mL) at room temperature. After 12 h, the reaction mixture (all L-(−)-xylose had been consumed) was filtered and the collected solids were washed with acetone (twice, 20 mL per wash). The stirring yellow filtrate was neutralized with NH$_4$OH solution to pH≈9. The suspended solids were removed by filtration. The filtrate was concentrated to afford crude bis-acetonide intermediate as yellow oil. The yellow oil was suspended in water (5 mL), and then the pH was adjusted from 9 to 2 with 1N HCl in water solution. The reaction mixture was stirred for 12 h at room temperature. The resulting mixture was neutralized by the addition of 25% (w/w) K$_3$PO$_4$ in water until pH≈7. The mixture was extracted with EtOAc. The organic layer was dried over MgSO$_4$, filtered, and concentrated in vacuo. The crude product was purified by silica gel column chromatography to provide the title compound (12.63 g, 52%) as yellow oil.

$^1$H NMR (400 MHz, CD$_3$OD) δ 5.88 (d, J=4.0 Hz, 1H), 4.47 (d, J=4.0 Hz, 1H), 4.18-4.14 (m, 1H), 4.11 (d, J=2.8 Hz, 1H), 3.83-3.71 (m, 2H), 1.45 (s, 3H), 1.29 (s, 3H).

Step 2)

(3aS,5R,6S,6aS)-6-Hydroxy-2,2-dimethyltetrahydrofuro[3,2-d][1,3]dioxole-5-carboxylic acid To a solution of (3aS,5S,6R,6aS)-5-(Hydroxymethyl)-2,2-dimethyltetrahydrofuro[3,2-d][1,3]dioxol-6-ol (14.6 g, 76.7 mmol), NaHCO$_3$ (19.3 g, 230.3 mmol) and NaBr (1.6 g, 15.4 mmol) in acetone/water (120/40 mL) was added TEMPO (2,2,6,6-Tetramethyl-1-piperidinyloxy free radical) (0.24 g, 1.5 mmol) at room temperature. The mixture was cooled to 0° C., and trichloroisocyanuric acid (17.8 g, 76.7 mmol) was then added in portions. The suspension was stirred for 12 h at room temperature. Methanol (2.0 mL) was added and the mixture was stirred for 2 h at room temperature. The mixture was filtered, washed with acetone (twice, 20 mL per wash).

The organic solvent was removed under vacuum and the aqueous layer was extracted with EtOAc and the organic layer was concentrated in vacuo. Acetone was added and the mixture was filtered. The filtrate was concentrated to afford the desired acid (9.0 g, 58%) as a pale yellow solid.

$^1$H NMR (400 MHz, CD$_3$OD) δ 5.98 (d, J=3.6 Hz, 1H), 4.71 (d, J=3.2 Hz, 1H), 4.51 (d, J=3.6 Hz, 1H), 4.36 (d, J=3.6 Hz, 1H), 1.45 (s, 3H), 1.31 (s, 3H).

Step 3)

(3aS,5R,6S,6aS)-6-Hydroxy-2,2-dimethyltetrahydrofuro[3,2-d][1,3]dioxol-5-yl)(morpholino)methanone (134

To a suspension of (3aS,5R,6S,6aS)-6-Hydroxy-2,2-dimethyltetrahydrofuro[3,2-d][1,3]dioxole-5-carboxylic acid (9.0 g, 44.2 mmol) and HBTU (25.1 g, 66.3 mmol, N,N,N',N'-tetramethyl-O-(1H-benzotriazol-1-yl)uronium hexafluorophosphate) in tetrahydrofuran was added 4-methylmorpholine (7.3 mL, 66.3 mmol) at room temperature. After 1 h, morpholine (5.8 mL, 66.3 mmol) was added to the mixture at room temperature. After 12 h, the resulting mixture was filtered and the filter cake was washed with tetrahydrofuran. The filtrate was concentrated in vacuo, and the crude was purified by silica gel column chromatography to provide the title compound (5.8 g, 48%) as a yellow solid.

$^1$H NMR (400 MHz, CD$_3$OD) δ 6.01 (d, J=3.6 Hz, 1H), 5.10 (s, 1H), 4.59 (d, J=2.4 Hz, 1H), 4.57 (d, J=3.6 Hz, 1H), 4.47 (d, J=2.4 Hz, 1H), 3.85-3.62 (m, 6H), 3.53-3.49 (m, 2H), 1.49 (s, 3H), 1.33 (s, 3H); [M+H]$^+$ 274.

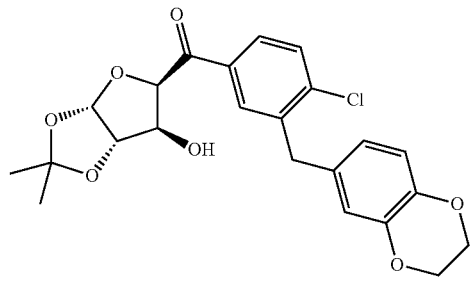 [SMILES: CC1(C)O[C@@H]2O[C@@H](C(=O)c3ccc(Cl)c(Cc4ccc5c(c4)OCCO5)c3)[C@@H](O)[C@@H]2O1]

(4-Chloro-3-((2,3-dihydrobenzo[b][1,4]dioxin-6-yl)methyl)phenyl)((3aS,5R,6S,6aS)-6-hydroxy-2,2-dimethyltetrahydrofuro[3,2-d][1,3]dioxol-5-yl)methanone (135)

To a solution of bromide (2.5 g, 7.4 mmol) in toluene/tetrahydrofuran (10/5 mL) was added n-BuLi (2.5M solution in hexane) at −78° C. After 1 h, 134 (0.67 g, 2.5 mmol) in toluene (5 mL) was added to the mixture (using cannula) at −78° C. After 1 h, the resulting mixture was quenched with CH$_3$OH, diluted with EtOAc and washed with saturated NaCl solution. The organic layer was dried over MgSO$_4$, filtered, and concentrated in vacuo. The crude product was purified by silica gel column chromatography to provide the title compound (0.77 g, 70%) as a white solid.

$^1$H NMR (400 MHz, CDCl$_3$) δ 7.87 (dd, J=8.4, 2.4 Hz, 1H), 7.81 (d, J=2.0 Hz, 1H), 7.48 (d, J=8.4 Hz, 1H), 6.80 (dd, J=7.2, 1.6 Hz, 1H), 6.68-6.65 (m, 2H), 6.06 (d, J=3.6 Hz, 1H), 5.21 (d, J=2.4 Hz, 1H), 4.57 (d, J=4.0 Hz, 1H), 4.55 (br s, 1H), 4.23 (s, 4H), 4.04-4.02 (m, 2H), 1.54 (s, 3H), 1.35 (s, 3H); [M+H]$^+$ 447.

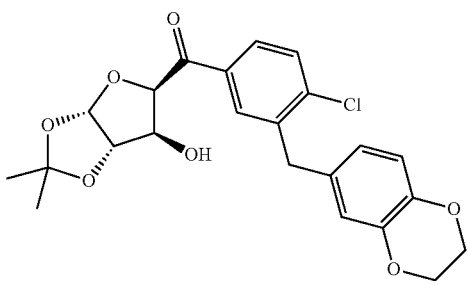 [SMILES: CC1(C)O[C@@H]2O[C@@H](C(=O)c3ccc(Cl)c(Cc4ccc5c(c4)OCCO5)c3)[C@@H](O)[C@@H]2O1]

(3aS,5S,6R,6aS)-5-((S)-(4-Chloro-3-((2,3-dihydrobenzo[b][1,4]dioxin-6-yl)methyl)phenyl)(hydroxy)methyl)-2,2-dimethyltetrahydrofuro[3,2-d][1,3]dioxol-6-ol (136)

To a solution of compound 135 (0.77 g, 1.7 mmol) in CH$_3$OH was added CeCl$_3$.7H$_2$O and the mixture was stirred at room temperature until all solids were dissolved. The mixture was then cooled to −78° C. and NaBH$_4$ was added in portions. The mixture was stirred for 1 h at −78° C., slowly warmed to 0° C. and quenched with saturated NH$_4$Cl solution. The mixture was concentrated under reduced pressure to remove CH$_3$OH and then extracted with EtOAc and washed with saturated NaCl solution. The organic layer was dried over MgSO$_4$, filtered, and concentrated in vacuo to afford the desired alcohol (0.67 g, 87%) as a white solid. The obtained product was used for the next step without purification.

$^1$H NMR (400 MHz, CDCl$_3$) δ 7.39 (d, J=8.4 Hz, 1H), 7.28 (d, J=2.0 Hz, 1H), 7.21 (d, J=2.4 Hz, 1H), 6.78 (d, J=8.4 Hz, 1H), 6.68 (d, J=1.6 Hz, 1H), 6.66 (dd, J=8.0, 2.0 Hz, 1H), 6.02 (d, J=3.6 Hz, 1H), 5.18 (t, J=2.8 Hz, 1H), 4.50 (d, J=4.0 Hz, 1H), 4.23 (s, 4H), 4.13-4.12 (m, 2H), 4.01-3.99 (m, 2H), 3.81 (d, J=2.8 Hz, 1H), 1.55 (s, 3H), 1.30 (s, 3H); [M+Na]$^+$ 471.

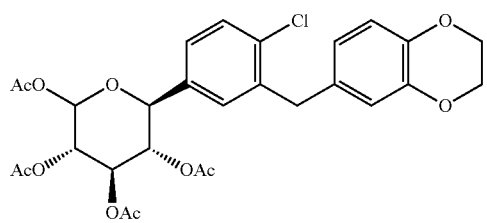 [SMILES: CC(=O)OC1O[C@@H](c2ccc(Cl)c(Cc3ccc4c(c3)OCCO4)c2)[C@H](OC(C)=O)[C@@H](OC(C)=O)[C@@H]1OC(C)=O]

(3S,4R,5S,6S)-6-(4-Chloro-3-((2,3-dihydrobenzo[b][1,4]dioxin-6-yl)methyl)phenyl)tetrahydro-2H-pyran-2,3,4,5-tetrayl tetraacetate (137)

A solution of compound 136 (0.67 g, 1.5 mmol) in AcOH/water (4.0/2.5 mL) was stirred for 12 h at 100° C. The resulting mixture was cooled to room temperature and concentrated under reduced pressure. The crude oil was treated with acetic anhydride (1.2 mL, 12.0 mmol) in pyridine (4.0 mL) at 0° C. The mixture was stirred for 8 h at room temperature. The resulting mixture was quenched with water, extracted with EtOAc and washed with brine. The organic layer was dried over dried over MgSO$_4$, filtered, and concentrated in vacuo. The residue was purified by silica gel column chromatography to provide the title compound (0.65 g, 75%) as a white solid.

$^1$H NMR (400 MHz, CDCl$_3$) δ 7.35 (dd, J=8.4, 2.0 Hz, 1H), 7.19 (dd, J=8.4, 1.6 Hz, 1H), 7.09-7.07 (m, 1H), 6.78 (d, J=7.6 Hz, 1H), 6.64-6.60 (m, 2H), 6.44 (d, J=3.6 Hz, 1H α), 5.84 (d, J=8.4 Hz, 1H β), 5.56 (t, J=10.0 Hz, 1H α), 5.34 (t, J=9.2 Hz, 1H β), 5.27-5.19 (m, 1H), 5.12-5.06 (m, 1H β), 5.06-5.01 (m, 1H α), 4.79 (d, J=10.4 Hz, 1H α), 4.47 (d, J=9.6 Hz, 1H β), 4.23 (s, 4H), 4.04-3.88 (m, 2H), 2.19 (s, 3H α), 2.10 (s, 3H β), 2.06 (s, 3H β), 2.04 (s, 3H α), 2.01 (s, 3H α), 2.00 (s, 3H β), 1.76 (s, 3H α), 1.74 (s, 3H β); [M+Na]$^+$ 599.

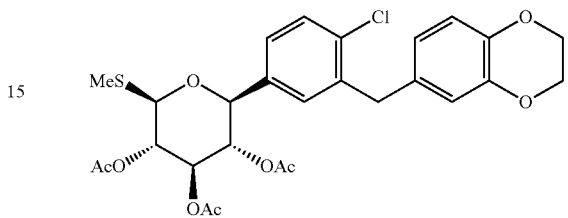

(2S,3S,4R,5S,6R)-2-(4-Chloro-3-((2,3-dihydrobenzo[b][1,4]dioxin-6-yl)methyl)phenyl)-6-(methylthio)tetrahydro-2H-pyran-3,4,5-triyl triacetate (138)

To a solution of compound 137 (200 mg, 0.35 mmol) and thiourea (53 mg, 0.70 mmol) in 1,4-dioxane (5.0 mL) was added TMSOTf (96 μL, 0.53 mmol) and the reaction mixture was heated to 80° C. for 3 h. The mixture was cooled to room temperature, and MeI (55 μL, 0.87 mmol) and DIPEA (0.30 mL, 1.75 mmol) were added thereto and the mixture was stirred for 3 h. The resulting mixture was diluted with EtOAc and washed with water. The organic layer was dried over dried over MgSO$_4$, filtered, and concentrated in vacuo. The crude was purified by preparative HPLC (reverse phase) to provide the title compound (60 mg, 30%) as a white solid.

$^1$H NMR (400 MHz, CDCl$_3$) δ 7.35 (d, J=8.0 Hz, 1H), 7.19 (dd, J=8.4, 2.0 Hz, 1H), 7.05 (d, J=2.4 Hz, 1H), 6.78 (d, J=8.0 Hz, 1H), 6.65-6.61 (m, 2H), 5.31 (d, J=9.2 Hz, 1H), 5.19 (d, J=9.6 Hz, 1H), 5.04 (d, J=9.6 Hz, 1H), 4.50 (d, J=10.0 Hz, 1H), 4.37 (d, J=10.0 Hz, 1H), 4.23 (s, 4H), 4.03-3.89 (m, 2H), 2.17 (s, 3H), 2.09 (s, 3H), 2.00 (s, 3H), 1.74 (s, 3H); [M+Na]$^+$ 587.

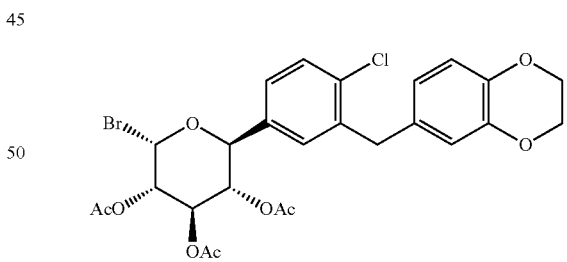

(2S,3S,4R,5S,6S)-2-Bromo-6-(4-chloro-3-((2,3-dihydrobenzo[b][1,4]dioxin-6-yl)methyl)phenyl)tetrahydro-2H-pyran-3,4,5-triyl triacetate (139)

Compound 137 (100 mg, 0.17 mmol) was treated with 33% HBr in AcOH (350 μL) for 30 min at room temperature. The reaction mixture was diluted with CH$_2$Cl$_2$ (1 mL), stirred for 30 min, diluted with more CH$_2$Cl$_2$ (50 mL), and washed with cold water (10 mL×2), and saturated NaHCO$_3$ solution (40 mL). The organic layer was dried over MgSO$_4$, filtered, and concentrated in vacuo to provide the title compound (100 mg, 99%) as an off-white solid. The obtained product was used for the next step without purification.

$^1$H NMR (400 MHz, CDCl$_3$) δ 7.36 (d, J=8.4 Hz, 1H), 7.17 (d, J=8.0 Hz, 1H), 7.12 (d, J=1.6 Hz, 1H), 6.78 (d, J=8.0 Hz, 1H), 6.71 (d, J=4.0 Hz, 1H), 6.64-6.61 (m, 2H), 5.64 (t, J=9.6 Hz, 1H), 5.11 (t, J=10.0 Hz, 1H), 4.95 (dd, J=10.0, 2.8 Hz, 2H), 4.23 (s, 4H), 4.05-3.88 (m, 2H), 2.12 (s, 3H), 2.02 (s, 3H), 1.77 (s, 3H); [M+Na]$^+$ 619.

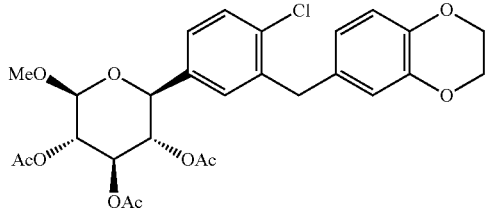 [SMILES: CS[C@H]1O[C@@H](c2ccc(Cl)c(Cc3ccc4c(c3)OCCO4)c2)[C@H](OC(C)=O)[C@@H](OC(C)=O)[C@@H]1OC(C)=O]

(2S,3S,4R,5S,6S)-2-(4-Chloro-3-((2,3-dihydrobenzo [b][1,4]dioxin-6-yl)methyl)phenyl)-6-methoxytetrahydro-2H-pyran-3,4,5-triyl triacetate (140)

A mixture of compound 139 (100 mg, 0.17 mmol) and ZnO (14 mg, 0.17 mmol) in CH$_3$OH (2.0 mL) was stirred for 1 h at 70° C. The resulting mixture was filtered through Celite® with EtOAc, and concentrated in vacuo. The crude was purified by preparative HPLC (reverse phase) to provide the title compound (40 mg, 43%) as a white solid.

$^1$H NMR (400 MHz, CDCl$_3$) δ 7.36 (d, J=8.4 Hz, 1H), 7.23 (dd, J=8.4, 2.0 Hz, 1H), 7.09 (d, J=2.0 Hz, 1H), 6.78 (d, J=8.0 Hz, 1H), 6.65-6.61 (m, 2H), 5.28 (t, J=9.6 Hz, 1H), 5.10 (dd, J=9.6, 8.0 Hz, 1H), 5.02 (t, J=9.6 Hz, 1H), 4.54 (d, J=8.0 Hz, 1H), 4.34 (d, J=10.0 Hz, 1H), 4.23 (s, 4H), 4.04-3.90 (m, 2H), 3.48 (s, 3H), 2.07 (s, 3H), 1.99 (s, 3H), 1.74 (s, 3H); [M+Na]$^+$ 571.

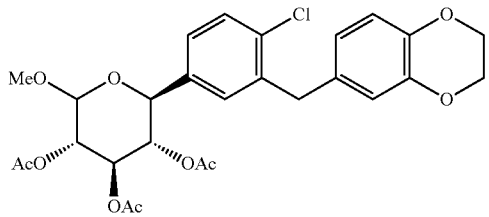 [SMILES: COC1O[C@@H](c2ccc(Cl)c(Cc3ccc4c(c3)OCCO4)c2)[C@H](OC(C)=O)[C@@H](OC(C)=O)[C@@H]1OC(C)=O]

(2S,3S,4R,5S)-2-(4-Chloro-3-((2,3-dihydrobenzo[b] [1,4]dioxin-6-yl)methyl)phenyl)-6-methoxytetrahydro-2H-pyran-3,4,5-triyl triacetate (142)

To a suspension of E093 (210 mg, 0.5 mmol) in CH$_2$Cl$_2$ (5.0 mL) was added pyridine (350 μL, 4.4 mmol), Ac$_2$O (410 μL, 4.4 mmol) and DMAP (3.0 mg, 0.03 mmol) at room temperature. After 12 h, the resulting mixture was diluted with EtOAc and washed with brine. The organic layer was dried over MgSO$_4$, filtered, and concentrated in vacuo. The residue was purified by silica gel column chromatography to provide the title compound (240 mg, 87%) as a white solid.

$^1$H NMR (400 MHz, CDCl$_3$) δ 7.36 (dd, J=8.0, 2.4 Hz, 1H), 7.24-7.21 (m, 1H), 7.13-7.08 (m, 1H), 5.56 (t, J=9.6 Hz, 1H α), 5.28 (t, J=9.6 Hz, 1H β), 5.10 (dd, J=9.6, 8.0 Hz, 1H β), 5.04-4.99 (m, 4H), 4.64 (d, J=10.0 Hz, 1H α), 4.54 (d, J=8.4 Hz, 1H β), 4.34 (d, J=10.0 Hz, 1H β), 4.23 (s, 4H), 4.01-3.92 (m, 2H), 3.48 (s, 3H β), 3.41 (s, 3H α), 2.10 (s, 3H α), 2.07 (s, 3H β), 1.99 (s, 3H α), 1.98 (s, 3H β), 1.74 (s, 3H α), 1.73 (s, 3H β); [M+Na]$^+$ 571.

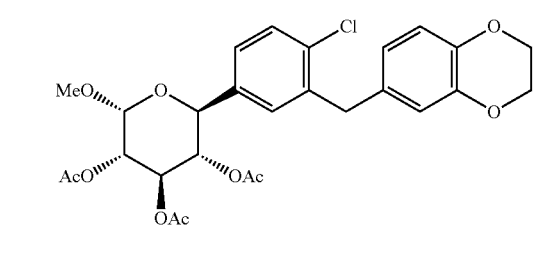 [SMILES: CO[C@@H]1O[C@@H](c2ccc(Cl)c(Cc3ccc4c(c3)OCCO4)c2)[C@H](OC(C)=O)[C@@H](OC(C)=O)[C@@H]1OC(C)=O]

(2S,3S,4R,5S,6R)-2-(4-Chloro-3-((2,3-dihydrobenzo [b][1,4]dioxin-6-yl)methyl)phenyl)-6-methoxytetrahydro-2H-pyran-3,4,5-triyl triacetate (143)

A sample of anomeric mixture 142 was separated into the two isomers by preparative HPLC (reverse phase). The first isomer was identified as the β-isomer (140, 30 mg, white solid) and the second isomer was identified as the α-isomer (143, 40 mg, white solid).

α isomer: $^1$H NMR (400 MHz, CDCl$_3$) δ 7.36 (d, J=8.0 Hz, 1H), 7.24-7.20 (m, 1H), 7.13 (d, J=2.0 Hz, 1H), 6.79-6.76 (m, 1H), 6.66-6.62 (m, 2H), 5.56 (t, J=9.6 Hz, 1H), 5.04-4.98 (m, 3H), 4.64 (d, J=10.0 Hz, 1H), 4.23 (s, 4H), 4.05-3.89 (m, 2H), 3.41 (s, 3H), 2.10 (s, 3H), 1.99 (s, 3H), 1.74 (s, 3H); [M+Na]$^+$ 571.

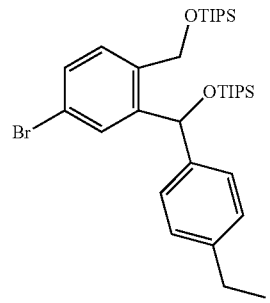

(4-Bromo-2-((4-ethylphenyl)(triisopropylsilyloxy) methyl)benzyloxy)triisopropyl silane (147)

Step 1) To a solution of 6-bromophthalide (144, 550 mg, 2.58 mmol) in dichloromethane (20.0 mL) was slowly added DIBAL-H (2.7 mL, 1.0M solution in hexane) at −78° C., and the reaction mixture was stirred for 1.5 h at −78° C. The resulting mixture was quenched with sat. Na$_2$SO$_4$ and allowed to warm to room temperature. To the mixture was added anhydrous Na$_2$SO$_4$, and the mixture was stirred for 12 h, then filtered and concentrated in vacuo. The crude was purified by silica gel column chromatography to provide 6-bromo-1,3-dihydroisobenzofuran-1-ol (145, 530 mg, 96%) as yellow oil.

Step 2) To a solution of compound 145 (2.1 g, 9.77 mmol) in tetrahydrofuran (40.0 mL) was slowly added 4-ethylphenylmagnesium bromide (39 mL, 0.5M solution in THF) at 0° C., and the reaction mixture was stirred for 12 h at room temperature. The resulting mixture was quenched with sat. NH$_4$Cl, diluted with EtOAc and washed with brine. The organic layer was dried over MgSO$_4$, filtered, and concentrated in vacuo. The crude was purified by silica gel column chromatography to provide (5-bromo-2-(hydroxymethyl)phenyl)(4-ethylphenyl)methanol (146, 1.53 g, 49%) as yellow oil. $^1$H NMR (400 MHz, CDCl$_3$) δ 7.50 (d, J=2.0 Hz, 1H), 7.42 (dd, J=8.0, 2.0 Hz, 1H), 7.26-7.17 (m, 5H), 5.97 (s, 1H), 4.58 (d, J=12.8 Hz, 1H), 4.43 (d, J=12.4 Hz, 1H), 2.65 (q, J=7.6 Hz, 2H), 1.23 (t, J=7.6 Hz, 3H).

Step 3) To a solution of compound 146 (1.53 g, 4.76 mmol), imidazole (1.1 g, 16.66 mmol) and DMAP (57 mg, 0.47 mmol) in DMF (20.0 mL) was slowly added TIPSCl (2.0 mL, 9.52 mmol) at 0° C., and the reaction mixture was stirred for 8 h at room temperature. The resulting mixture was diluted with EtOAc and washed with brine. The organic layer was dried over MgSO$_4$, filtered, and concentrated in vacuo to afford the desired title compound as yellow oil. The obtained product was used for the next step without purification.

Step 4) To a solution of (5-bromo-2-((triisopropylsilyloxy)methyl)phenyl)(4-ethylphenyl)methanol (4.76 mmol) and 2,6-lutidine (1.6 mL, 13.51 mmol) in dichloromethane (30.0 mL) was slowly added TIPSOTf (1.8 mL, 6.75 mmol) at 0° C., and the reaction mixture was stirred for 12 h at room temperature. The resulting mixture was quenched with CH$_3$OH, diluted with EtOAc and washed with brine. The organic layer was dried over MgSO$_4$, filtered, and concentrated in vacuo. The crude was purified by silica gel column chromatography to provide the title compound (2.94 g, 97% 2-step) as yellow oil.

$^1$H NMR (400 MHz, CDCl$_3$) δ 7.78 (d, J=2.4 Hz, 1H), 7.45 (d, J=8.0 Hz, 1H), 7.39 (dd, J=8.0, 2.0 Hz, 1H), 7.21 (d, J=8.4 Hz, 2H), 7.08 (d, J=8.0 Hz, 2H), 5.81 (s, 1H), 4.63-4.61 (m, 2H), 2.59 (q, J=7.6 Hz, 2H), 1.18 (t, J=7.6 Hz, 3H), 1.11-0.94 (m, 42H).

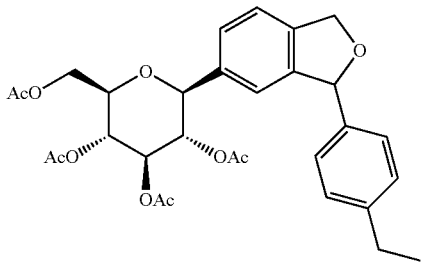 [SMILES: CCc1ccc(C2OCc3ccc([C@@H]4O[C@H](COC(C)=O)[C@@H](OC(C)=O)[C@H](OC(C)=O)[C@H]4OC(C)=O)cc32)cc1]

(2R,3R,4R,5S,6S)-2-(Acetoxymethyl)-6-(3-(4-ethylphenyl)-1,3-dihydroisobenzofuran-5-yl)tetrahydro-2H-pyran-3,4,5-triyl triacetate (151)

Step 1) To a solution of bromide (147, 2.94 g, 4.64 mmol) in tetrahydrofuran/toluene (5.0/10.0 mL) was slowly added n-butyllithium solution (2.0 mL, 2.5M in hexane) at −78° C. and the reaction mixture was stirred for 1 h. Then a solution of TMS-protected gluconolactone 12 (2.4 g, 5.10 mmol) in toluene (5 mL) was added dropwise, and the mixture was stirred for 1 hour at −78° C. After 1 h, the resulting mixture was quenched with sat. NH$_4$Cl solution, and then the solution was gradually raised to room temperature. The mixture was diluted with EtOAc and washed with brine. The organic layer was dried over MgSO$_4$, filtered and concentrated in vacuo to afford the desired (3R,4S,5R,6R)-2-(3-((4-ethylphenyl)(triisopropylsilyloxy)methyl)-4-((triisopropylsilyl oxy)methyl)phenyl)-3,4,5-tris(trimethylsilyloxy)-6-((trimethylsilyloxy)methyl)-tetrahydro-2H-pyran-2-ol 148 as a yellow oil. The obtained product was used for the next step without purification.

Step 2) To a solution of compound 148 (4.88 g, 4.77 mmol) in dichloromethane/acetonitrile (15.0/15.0 mL) was slowly added triethylsilane (1.5 mL, 9.54 mmol) and boron trifluoride diethyl etherate (0.9 mL, 7.15 mmol) at −30° C. and the reaction mixture was stirred for 0.5 h. The mixture was quenched with CH$_3$OH, diluted with EtOAc and washed with brine. The organic layer was dried over MgSO$_4$, filtered, and concentrated in vacuo.

Step 3) To a solution of (2S,3R,4R,5S,6R)-2-(3-((4-ethylphenyl)(triisopropylsilyloxy)methyl)-4-((triisopropylsilyloxy)methyl)phenyl)-6-(hydroxymethyl)tetrahydro-2H-pyran-3,4,5-triol in dichloromethane (30.0 mL) was added Ac$_2$O (3.9 mL, 41.5 mmol), DMAP (30 mg, 0.24 mmol) and pyridine (3.3 mL, 41.5 mL) at room temperature and the mixture was stirred for 12 h. The resulting mixture was diluted with EtOAc and washed with brine. The organic layer was dried over MgSO$_4$, filtered, and concentrated in vacuo. The crude was purified by silica gel column chromatography to provide (2R,3R,4R,5S,6S)-2-(acetoxymethyl)-6-(3-((4-ethylphenyl)(triisopropyl silyloxy)methyl)-4-((triisopropylsilyloxy)methyl)phenyl)tetrahydro-2H-pyran-3,4,5-triyl triacetate (149, 870 mg, 20%) as a white solid.

$^1$H NMR (400 MHz, CDCl$_3$) δ 7.70-7.69 (m, 2H), 7.25-7.15 (m, 3H), 7.07-7.04 (m, 2H), 5.89-5.84 (m, 1H), 5.38-5.15 (m, 3H), 4.76-4.60 (m, 2H), 4.45-4.41 (m, 1H), 4.33-4.28 (m, 1H), 4.20-4.13 (m, 1H), 3.89-3.83 (m, 1H), 2.60-2.54 (m, 2H), 2.09-2.08 (m, 3H), 2.06 (s, 3H), 2.02-2.00 (m, 3H), 1.78 (s, 3H), 1.19-1.10 (m, 3H), 1.09-0.95 (m, 42H).

Step 4) To a solution of compound 149 (870 mg, 0.98 mmol) in tetrahydrofuran (10.0 mL) was slowly added tetrabutylammonium fluoride solution (5.0 mL, 1.0M in tetrahydrofuran) at 0° C. and the reaction mixture was stirred for 2 h. The resulting mixture was quenched with sat. NH$_4$Cl solution, diluted with EtOAc and washed with brine. The organic layer was dried over MgSO$_4$, filtered, and concentrated in vacuo. The crude was purified by silica gel column chromatography to provide (2R,3R,4R,5S,6S)-2-(acetoxymethyl)-6-(3-((4-ethylphenyl)(hydroxy)methyl)-4-(hydroxymethyl)phenyl)tetrahydro-2H-pyran-3,4,5-triyl triacetate (150, 500 mg, 89%) as a pale yellow solid.

$^1$H NMR (400 MHz, CDCl$_3$) δ 7.35-7.32 (m, 2H), 7.26-7.21 (m, 3H), 7.19-6.98 (m, 2H), 6.06-6.04 (m, 1H), 5.33-5.28 (m, 1H), 5.25-5.19 (m, 1H), 5.13-5.02 (m, 1H), 4.66-4.63 (m, 1H), 4.52-4.48 (m, 1H), 4.40-4.37 (m, 1H), 4.30-4.25 (m, 1H), 4.18-4.13 (m, 1H), 3.84-3.80 (m, 1H), 2.68-2.61 (m, 2H), 2.08 (s, 3H), 2.05 (s, 3H), 2.00-1.99 (m, 3H), 1.84-1.83 (m, 3H), 1.25-1.20 (m, 3H).

Step 5) To a solution of compound 150 (500 mg, 0.87 mmol) in toluene (10.0 mL) was added p-TsCl (183 mg, 0.96 mmol) and the reaction mixture was heated to 90° C. for 12 h. The resulting mixture was diluted with EtOAc and washed with brine. The organic layer was dried over MgSO$_4$, filtered, and concentrated in vacuo. The crude was purified by silica gel column chromatography to provide (2R,3R,4R,5S,6S)-2-(Acetoxymethyl)-6-(3-(4-ethylphenyl)-1,3-dihydroisobenzofuran-5-yl)tetrahydro-2H-pyran-3,4,5-triyl triacetate (151, 380 mg, 79%) as a yellow solid.

$^1$H NMR (400 MHz, CDCl$_3$) δ 7.38-7.25 (m, 3H), 7.22-6.87 (m, 4H), 6.11-6.10 (m, 1H), 5.34-5.07 (m, 5H), 4.35-4.32 (m, 1H), 4.28-4.22 (m, 1H), 4.17-4.10 (m, 1H), 3.81-3.74 (m, 1H), 2.68-2.57 (m, 2H), 2.07-2.06 (m, 3H), 2.04 (s, 3H), 1.99-1.97 (m, 3H), 1.81 (s, 3H), 1.25-1.16 (m, 3H).

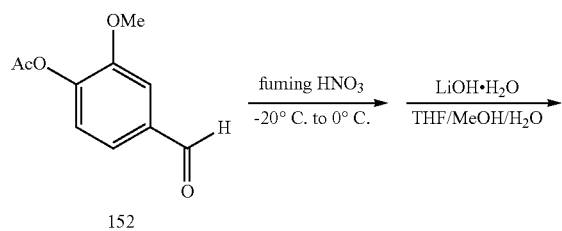

152

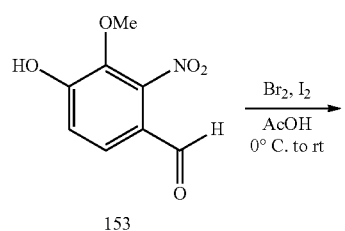

153

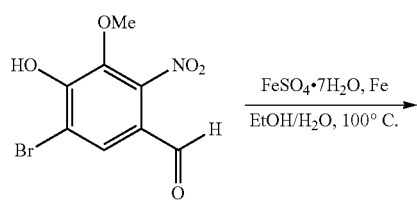

154

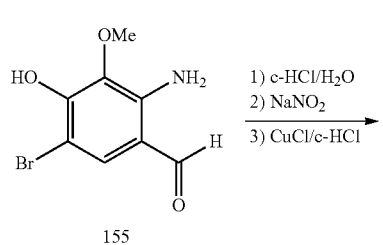

155

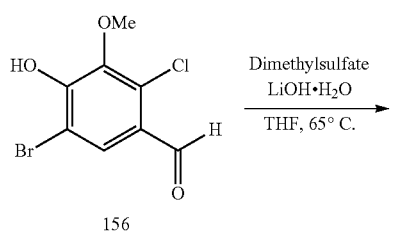

156

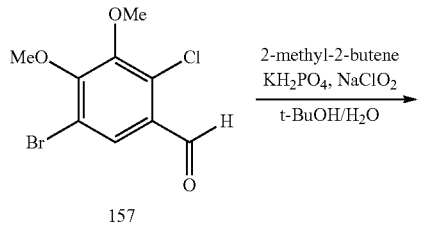

157

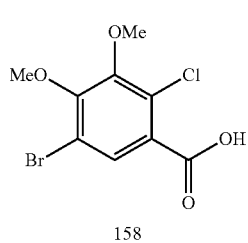

158

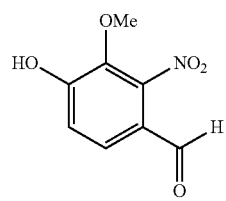 [SMILES: COc1c(O)ccc(C=O)c1[N+](=O)[O-]]

4-Hydroxy-3-methoxy-2-nitrobenzaldehyde (153)

Step 1) To the fuming $HNO_3$ (230 mL), acetate 152 (56 g, 288 mmol) was added portionwise while the temperature should be maintained from −20° C. to 0° C. The mixture was stirred at 0° C. for 30 min after the completion of addition. The mixture was poured into water (1.3 L) with stirring. The mixture was stirred at r.t. for 1 hr and the crude product was precipitated. The crude product was filtered and washed with $H_2O$ (1 L) and dried under high vacuum.

Step 2) To the mixture of crude nitro compound in THF/MeOH/H2O (450 mL/150 mL/150 mL) was added LiOH monohydrate (25 g, 576 mmol). The mixture was stirred at r.t for 15 hours. The mixture was acidified with aq. 10% HCl solution (pH~5). The mixture was extracted with EtOAc (500 mL×2). The organic layer was dried over $MgSO_4$, filtered, and concentrated in vacuo. The residue was purified by silica gel column chromatography to provide the compound 153 (38 g, 67% (2-steps)).

$^1$H NMR (400 MHz, DMSO-$d_6$) δ 11.83 (s, 1H), 9.75 (s, 1H), 7.65 (d, J=8.57 Hz, 1H), 7.21 (d, J=8.5 Hz, 1H), 3.85 (s, 3H).

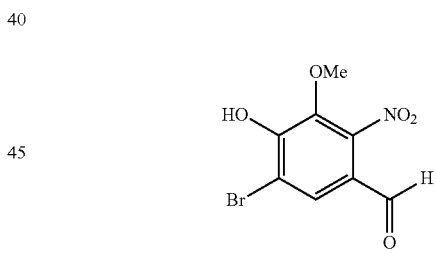

5-Bromo-4-hydroxy-3-methoxy-2-nitrobenzaldehyde (154)

To the mixture of aldehyde 153 (28.0 g, 142 mmol) and $I_2$ (1.5 g) in AcOH (160 mL) was added $Br_2$ (8.0 mL, 157 mmol) at 0° C. The mixture was warmed up to r.t. and stirred at r.t. for 15 hours. The mixture was poured into water (2.0 L) with stirring. The mixture was stirred at r.t. for 30 min. The mixture was extracted with EtOAc (1 L×2). The combined organic layer was dried over $MgSO_4$, filtered, and concentrated in vacuo to provide the compound 154 (38 g, 98%).

$^1$H NMR (400 MHz, DMSO-$d_6$) δ 11.53 (s, 1H), 10.12 (s, 1H), 7.80 (s, 1H), 3.81 (s, 3H).

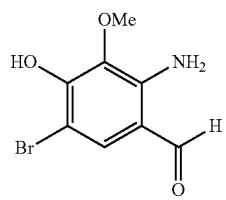 [SMILES: COc1c(N)c(C=O)cc(Br)c1O]

2-Amino-5-bromo-4-hydroxy-3-methoxybenzaldehyde (155)

To the mixture of phenol 154 (25.4 g, 92 mmol) in EtOH/H$_2$O (350 mL/100 mL) were added FeSO$_4$7H$_2$O (4.7 g) and Fe powder (47 g). The mixture was stirred at 100° C. for 1 hr. The mixture was cooled down to 50° C. and filtered to remove inorganic materials through celite. The filtrate was concentrated in vacuo to provide the title compound 155 (19.0 g, 84%).

$^1$H NMR (400 MHz, DMSO-d$_6$) δ 10.57 (s, 1H), 9.63 (s, 1H), 7.56 (s, 1H), 6.94 (br s, 2H), 3.65 (s, 3H).

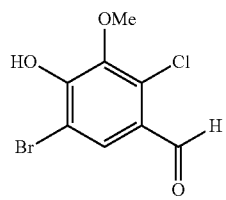 [SMILES: COc1c(O)c(Br)cc(C=O)c1Cl]

5-Bromo-2-chloro-4-hydroxy-3-methoxybenzaldehyde (156)

A mixture of phenol 155 (13.0 g, 52.8 mmol) in c-HCl (40 mL) was added H$_2$O (20 mL). The mixture was cooled to 0° C. NaNO$_2$ (5 g) was added portionwise slowly to the mixture at 0° C., and CuCl (8.0 g, dissolved in c-HCl (80 mL) was added thereto very slowly at 0° C. The mixture was stirred at 100° C. for 1 hr and cooled to r.t. The product was precipitated, filtered, washed with H$_2$O (500 mL and dried under high vacuum to provide the title compound 156 (12.9 g, 92%).

$^1$H NMR (400 MHz, DMSO-d$_6$) δ 11.51 (s, 1H), 10.11 (s, 1H), 7.80 (s, 1H), 3.12 (s, 3H).

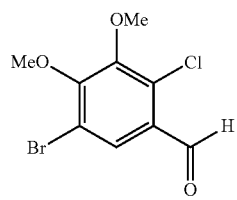 [SMILES: COc1c(Br)cc(C=O)c(Cl)c1OC]

5-Bromo-2-chloro-3,4-dimethoxybenzaldehyde (157)

To the mixture of aldehyde 156 (15.0 g, 56.5 mmol) in THF (300 mL) were added dimethylsulfate (7.0 mL, 73.5 mmol) and LiOH monohydrate (3.1 g, 73.5 mmol). The mixture was stirred for 3 hours at 65° C. The mixture was cooled to r.t. and filtered to remove insoluble materials through celite. The filtrate was extracted with EtOAc/aq. 50% NaCl solution (200 mL/500 mL). The organic layer was dried over MgSO$_4$, filtered, and concentrated in vacuo. The residue was purified by silica gel column chromatography to provide the compound 157 (11.1 g, 70%).

$^1$H NMR (400 MHz, CDCl$_3$) δ 10.37 (s, 1H), 7.96 (s, 1H), 3.97 (s, 3H), 3.94 (s, 3H).

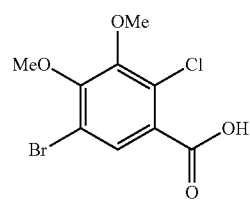 [SMILES: COc1c(Br)cc(C(=O)O)c(Cl)c1OC]

5-Bromo-2-chloro-3,4-dimethoxybenzoic acid (158)

To the mixture of aldehyde 157 (11.1 g, 39.4 mmol), 2-methyl-2-butene (105 mL, 985 mmol) in t-BuOH (300 mL) was added KH$_2$PO$_4$ (38 g, 276 mmol). NaClO$_2$ (32 g, 355 mmol, dissolved in H$_2$O (160 mL)) was added to the reaction mixture. The mixture was stirred at r.t. for 15 hours. The mixture was evaporated in vacuo to remove the solvent. The residue was extracted with EtOAc/aq. 5% HCl solution (500 mL/300 mL). The organic layer was dried over MgSO$_4$, filtered, and concentrated in vacuo to provide the title compound 158 (11.6 g, 99%).

$^1$H NMR (400 MHz, DMSO-d$_6$) δ 13.51 (s, 1H), 7.80 (s, 1H), 3.91 (s, 3H), 3.87 (s, 3H).

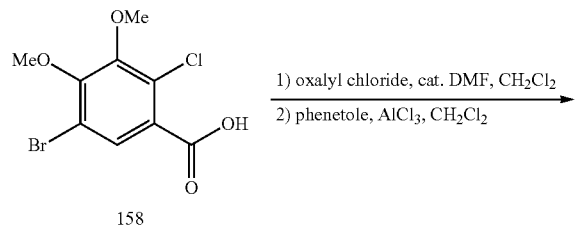
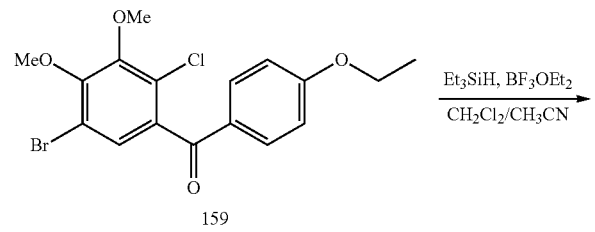

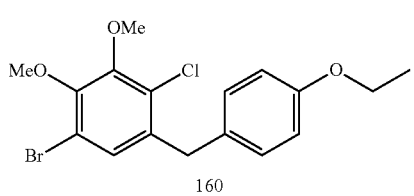
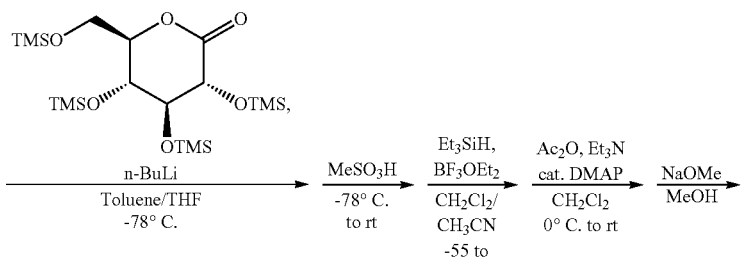

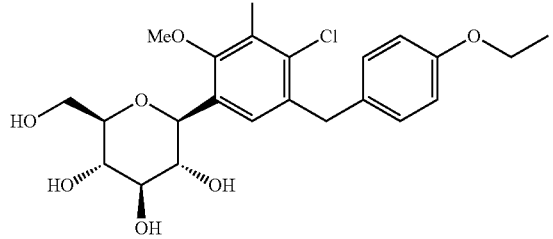

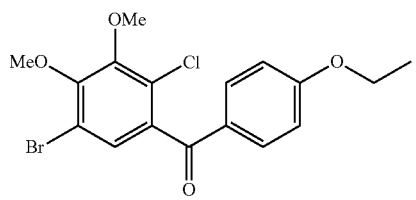 [SMILES: CCOc1ccc(C(=O)c2cc(Br)c(OC)c(OC)c2Cl)cc1]

(5-Bromo-2-chloro-3,4-dimethoxyphenyl)(4-ethoxyphenyl)methanonemethylbenzamide (159)

Similar procedure with preparation of 73 proceeded except for using compound 158 to obtain the compound 159.

¹H NMR (400 MHz, CDCl₃) δ 7.81 (d, J=8.6 Hz, 2H), 7.29 (s, 1H), 6.96 (d, J=8.6 Hz, 2H), 4.05 (q, J=6.99 Hz, 2H), 4.00 (s, 3H), 3.98 (s, 3H), 1.48 (t, J=7.0 Hz, 3H).

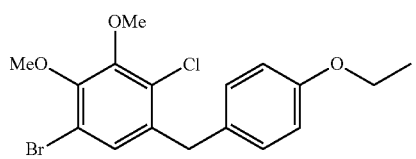 [SMILES: CCOc1ccc(Cc2cc(Br)c(OC)c(OC)c2Cl)cc1]

1-Bromo-4-chloro-5-(4-ethoxybenzyl)-2,3-dimethoxybenzene (160)

Similar procedure with preparation of 74 proceeded except for using compound 159 to obtain the compound 160.

¹H NMR (400 MHz, CDCl₃) δ 7.121 (d, J=8.6 Hz, 2H), 7.09 (s, 1H), 6.87 (d, J=8.6 Hz, 2H), 4.05 (q, J=6.99 Hz, 2H), 3.99 (s, 2H), 3.94 (s, 3H), 1.44 (t, J=7.0 Hz, 3H).

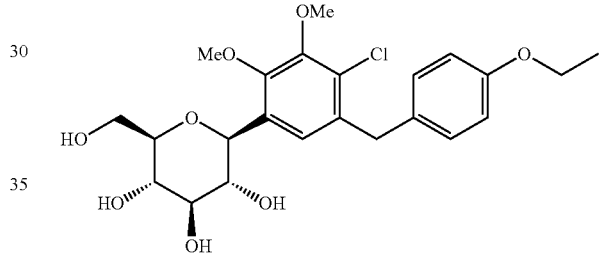

(2S,3R,4R,5S,6R)-2-(4-Chloro-5-(4-ethoxybenzyl)-2,3-dimethoxyphenyl)-6-(hydroxymethyl)tetrahydro-2H-pyran-3,4,5-triol (E151)

Similar procedure with preparation of 75 proceeded except for using compound 160 to obtain the compound E151.

¹H NMR (400 MHz, CD₃OD) δ 7.14 (s, 1H), 7.12 (d, J=8.8 Hz, 2H), 7.82 (d, J=8.7 Hz, 2H), 4.87 (s, 4H), 4.56 (d, J=9.2 Hz, 1H), 4.13-3.94 (m, 4H), 3.93-3.84 (m, 7H), 3.67 (dd, J=11.9 Hz, 5.7 Hz, 1H), 3.59-3.45 (m, 2H), 3.42-3.34 (m, 2H), 1.38 (t, J=7.0 Hz, 3H); [M+Na]⁺ 491.

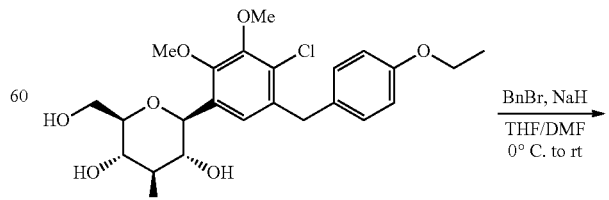

-continued

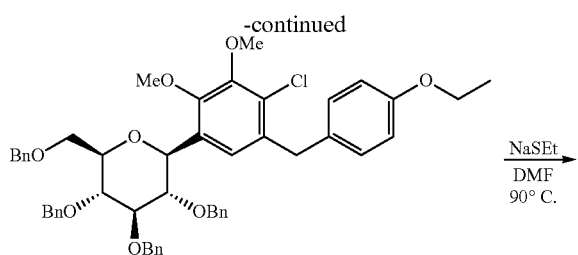
162

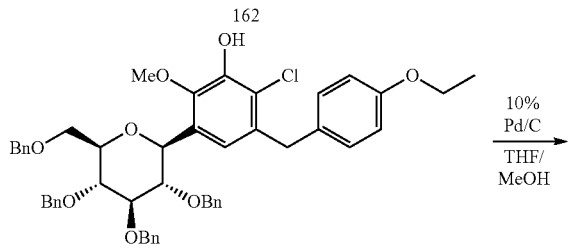
163

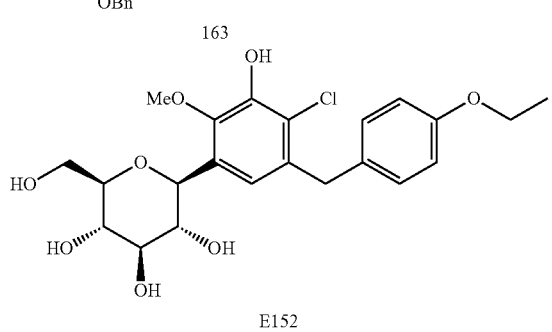
E152

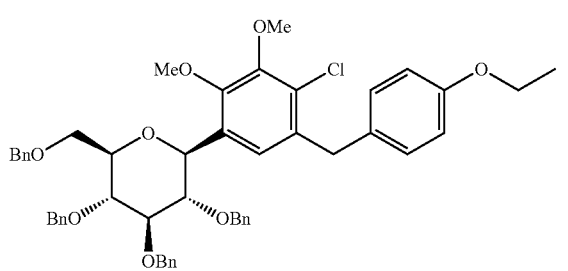 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)c(OC)c(OC)c2Cl)cc1]

(2R,3R,4R,5S,6S)-3,4,5-Tris(benzyloxy)-2-((benzyloxy)methyl)-6-(4-chloro-5-(4-ethoxybenzyl)-2,3-dimethoxyphenyl)tetrahydro-2H-pyran (162)

Similar procedure with preparation of 76 proceeded except for using compound E151 to obtain the compound 162. [M+Na]+ 851.

2-Chloro-3-(4-ethoxybenzyl)-6-methoxy-5-((2S,3S,4R,5R,6R)-3,4,5-tris(benzyloxy)-6-((benzyloxy)methyl)tetrahydro-2H-pyran-2-yl)phenol (163)

Similar procedure with preparation of 77 proceeded except for using compound 162 to obtain the compound 163. [M+Na]+ 837.

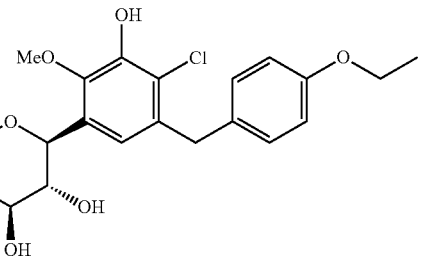

(2S,3R,4R,5S,6R)-2-(4-Chloro-5-(4-ethoxybenzyl)-3-hydroxy-2-methoxyphenyl)-6-(hydroxymethyl)tetrahydro-2H-pyran-3,4,5-triol (E152)

Similar procedure with preparation of E005 proceeded except for using compound 163 to obtain the compound E152.
$^1$H NMR (400 MHz, CD$_3$OD) δ 7.11 (d, J=8.6 Hz, 2H), 6.86 (s, 1H), 6.82 (d, J=8.7 Hz, 2H), 4.87 (s, 4H), 4.52 (d, J=9.6 Hz, 1H), 4.06-3.97 (m, 4H), 3.91-3.83 (m, 4H), 3.66 (dd, J=12.0 Hz, 5.6 Hz, 1H), 3.59 (t, J=9.2 Hz, 1H), 3.50 (t, J=8.4 Hz, 1H), 3.46-3.34 (m, 2H), 1.38 (t, J=7.0 Hz, 3H); [M+Na]+ 477.

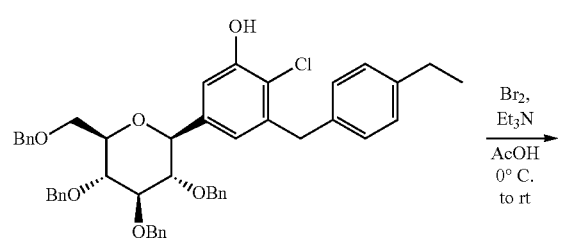

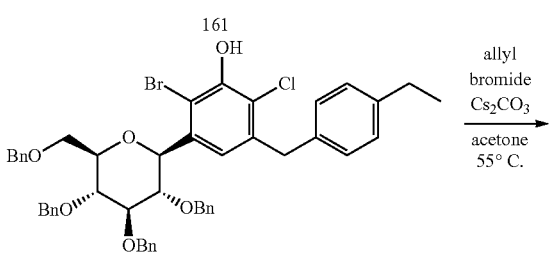
161

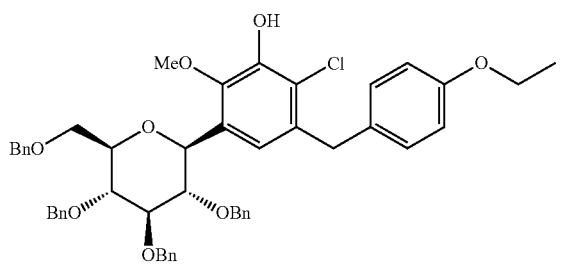 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)c(OC)c(O)c2Cl)cc1]

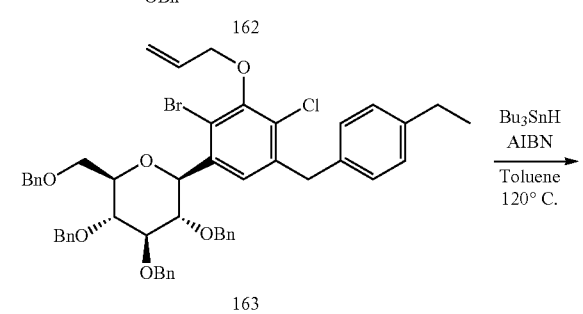
163

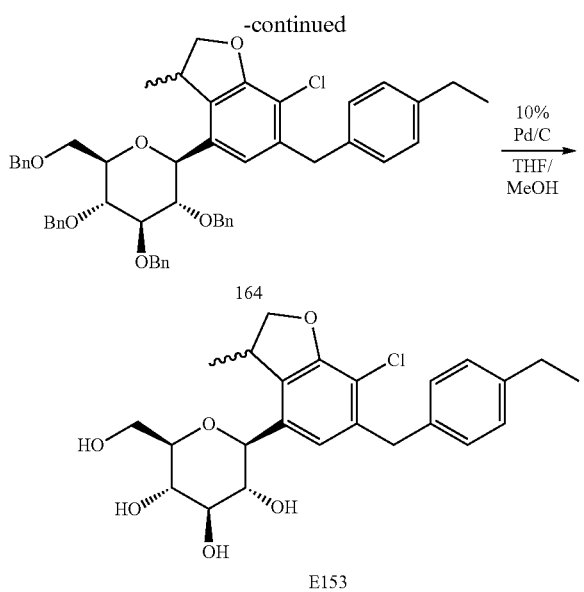

E153

2-Chloro-3-(4-ethylbenzyl)-5-((2S,3S,4R,5R,6R)-3,4,5-tris(benzyloxy)-6-((benzyloxy)methyl)tetrahydro-2H-pyran-2-yl)phenol (161)

Similar procedure with preparation of 27 proceeded to obtain the compound 161.

[M+Na]+ 791.

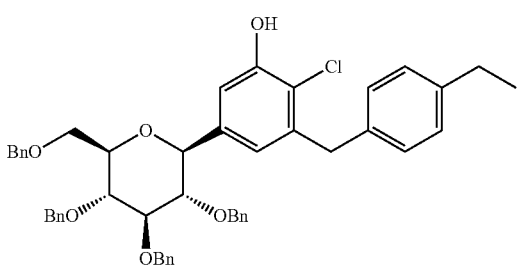 [SMILES: CCc1ccc(Cc2cc([C@@H]3O[C@H](COCc4ccccc4)[C@@H](OCc4ccccc4)[C@H](OCc4ccccc4)[C@H]3OCc3ccccc3)cc(O)c2Cl)cc1]

2-Bromo-6-chloro-5-(4-ethylbenzyl)-3-((2S,3S,4R,5R,6R)-3,4,5-tris(benzyloxy)-6-((benzyloxy)methyl)tetrahydro-2H-pyran-2-yl)phenol (162)

Similar procedure with preparation of 28 proceeded to obtain the compound 162.

[M+Na]+ 869.

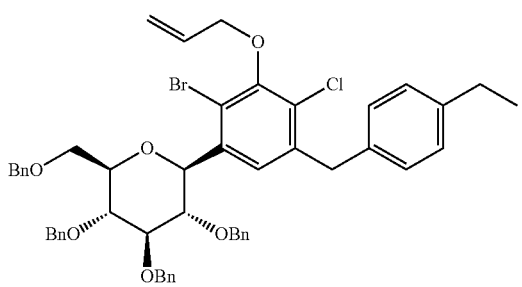 [SMILES: C=CCOc1c(Cl)c(Cc2ccc(CC)cc2)cc([C@@H]2O[C@H](COCc3ccccc3)[C@@H](OCc3ccccc3)[C@H](OCc3ccccc3)[C@H]2OCc2ccccc2)c1Br]

(2S,3S,4R,5R,6R)-2-(3-(Allyloxy)-2-bromo-4-chloro-5-(4-ethylbenzyl)phenyl)-3,4,5-tris(benzyloxy)-6-((benzyloxy)methyl)tetrahydro-2H-pyran (163)

Similar procedure with preparation of 29 proceeded except for using allyl bromide and Cs₂CO₃ to obtain the compound 163.

[M+Na]+ 909.

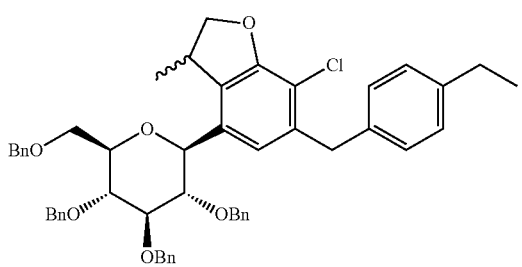 [SMILES: CCc1ccc(Cc2cc([C@@H]3O[C@H](COCc4ccccc4)[C@@H](OCc4ccccc4)[C@H](OCc4ccccc4)[C@H]3OCc3ccccc3)c3c(c2Cl)OCC3C)cc1]

7-Chloro-6-(4-ethylbenzyl)-3-methyl-4-((2S,3S,4R,5R,6R)-3,4,5-tris(benzyloxy)-6-((benzyloxy)methyl)tetrahydro-2H-pyran-2-yl)-2,3-dihydrobenzofuran (164)

To a solution of the 163 (1.52 g, 1.71 mmol) were added Bu₃SnH (3.7 ml, 13.7 mmol) and AIBN (112 mg, 0.68 mmol). After stirring for 20 h at 120° C., aq. 10% KF solution was added to quench the reaction. The residue was dissolved in EtOAc (100 mL), washed with saturated NaHCO₃ solution, dried over anhydrous MgSO₄, filtered and concentrated in vacuo. The residue was purified by silica gel column chromatography to provide the compound 164 (538 mg, 40%).

[M+Na]+ 831.

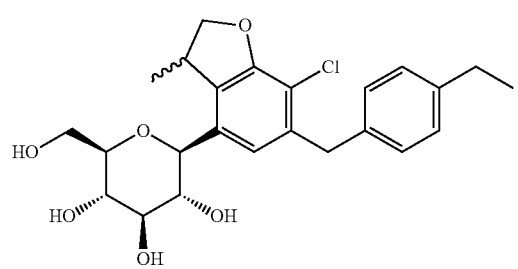 [SMILES: CCc1ccc(Cc2cc([C@@H]3O[C@H](CO)[C@@H](O)[C@H](O)[C@H]3O)c3c(c2Cl)OCC3C)cc1]

(2S,3R,4R,5S,6R)-2-(7-Chloro-6-(4-ethylbenzyl)-3-methyl-2,3-dihydrobenzofuran-4-yl)-6-(hydroxymethyl)tetrahydro-2H-pyran-3,4,5-triol (E153)
Similar procedure with preparation of 73 proceeded to obtain the compound E152.
$^1$H NMR (400 MHz, CD$_3$OD) δ 7.13-7.07 (m, 4H), 6.98 (s, 0.7H), 6.92 (s, 0.3H), 4.87 (s, 4H), 4.68-4.55 (m, 1H), 4.33-4.24 (m, 2H), 4.08-3.98 (m, 2H), 3.90 (dd, J=12.7 Hz, 0.9 Hz, 1H), 3.81-3.60 (m, 2H), 3.51-3.33 (m, 4H), 2.61 (q, J=7.6 Hz, 2H), 1.39 (d, J=6.9 Hz, 0.9H), 1.33 (d, J=7.0 Hz, 2.1H), 1.22 (t, J=7.6 Hz, 3H); [M+Na]$^+$ 471.
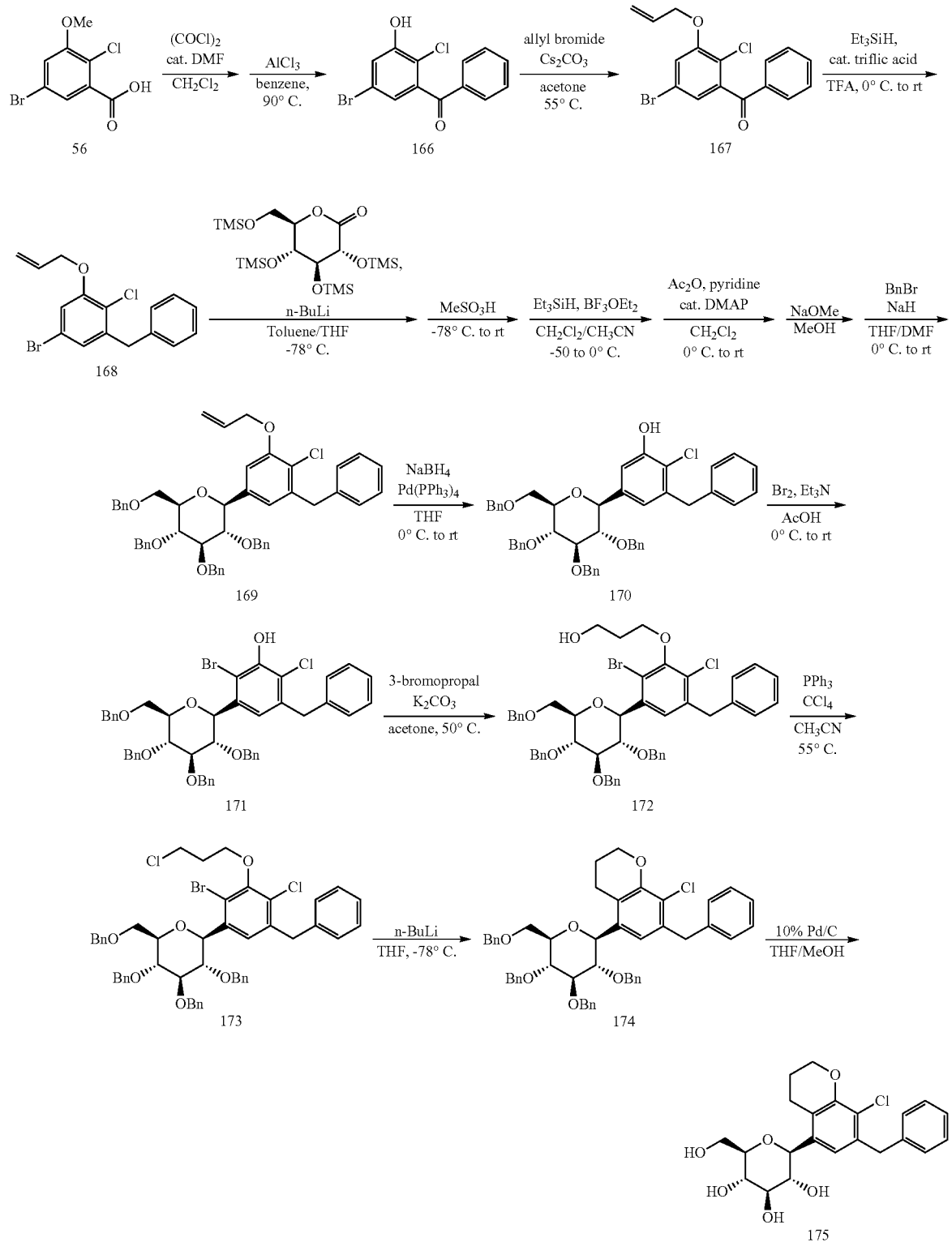

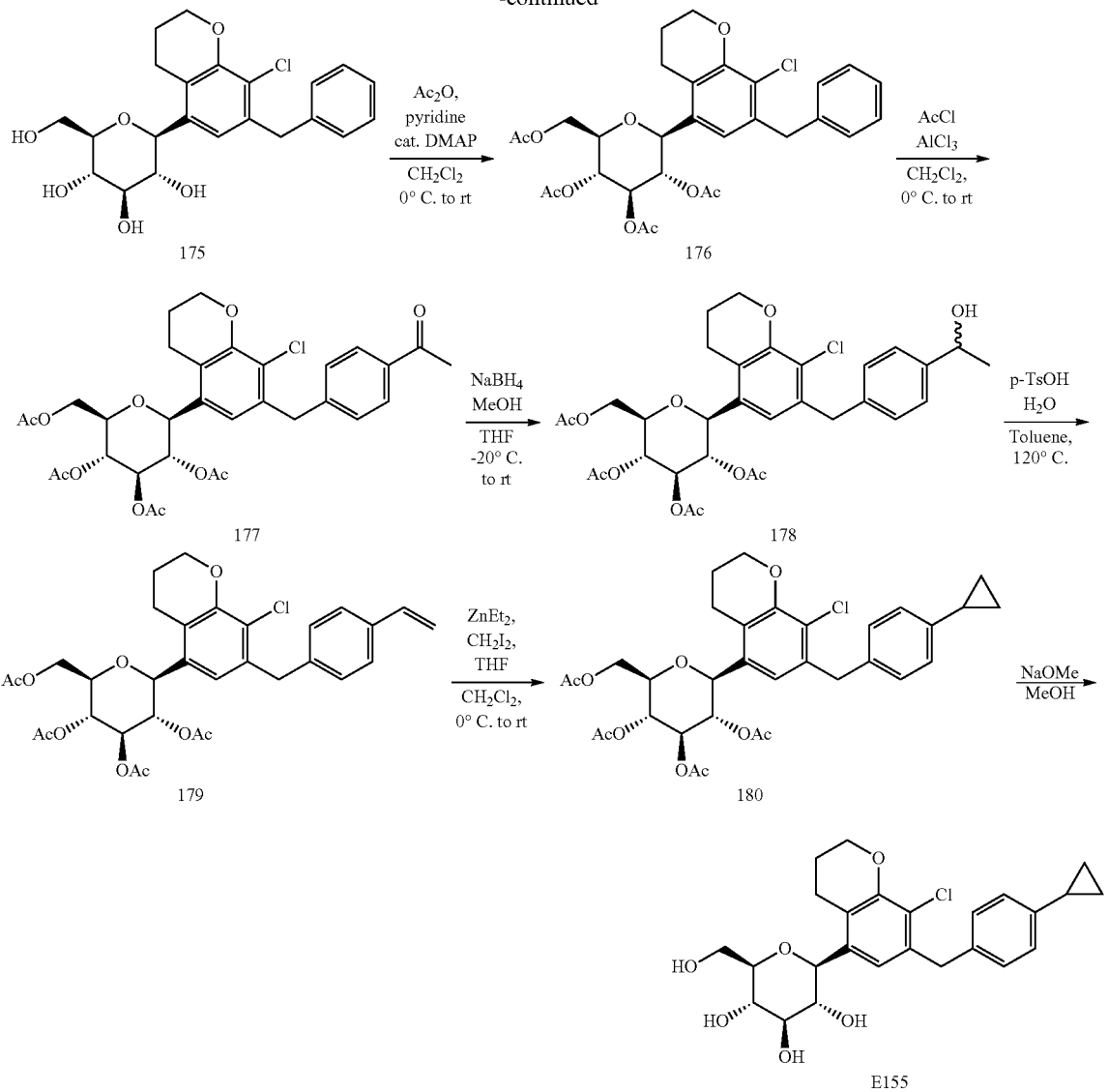

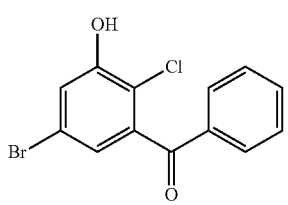 [SMILES: O=C(c1ccccc1)c1cc(Br)cc(O)c1Cl]

(5-Bromo-2-chloro-3-hydroxyphenyl)(phenyl)
methanone (166)

To a suspension of compound 56 (6.0 g, 22.6 mmol) in CH$_2$Cl$_2$ (100 mL) were added oxalyl chloride (2.4 mL, 27.1 mmol) and catalytic amounts of DMF at room temperature. The mixture was stirred at room temperature for 2 hours. The mixture was evaporated in vacuo and dried under high vacuum. The crude acid chloride was dissolved with benzene (100 mL) and cooled to 0° C. To the reaction mixture was added AlCl$_3$ (6.9 g, 52.0 mmol) portionwise at 0° C. The mixture was stirred at 90° C. for 15 hours. The mixture was cooled to rt and evaporated in vacuo. The residue was cooled to 0° C. and aq. 1N HCl solution was added. The mixture was extracted with EtOAc (150 mL×1). The organic layer was dried over MgSO$_4$, filtered, and concentrated in vacuo. The residue was purified by silica gel column chromatography to provide the compound 166 (7.33 g, quantitative yield).

$^1$H NMR (400 MHz, CDCl$_3$) δ 7.85-7.82 (m, 2H), 7.70-7.64 (m, 1H), 7.55-7.49 (m, 2H), 7.37 (d, J=2.2 Hz, 1H), 7.13 (d, J=2.2 Hz, 1H), 5.94 (s, 1H).

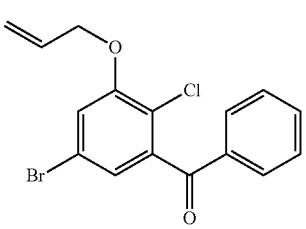 [SMILES: C=CCOc1cc(Br)cc(C(=O)c2ccccc2)c1Cl]

(3-(Allyloxy)-5-bromo-2-chlorophenyl)(phenyl)methanone (167)

Similar procedure with preparation of 163 proceeded to obtain the compound 167.

[M+H]$^+$ 351.

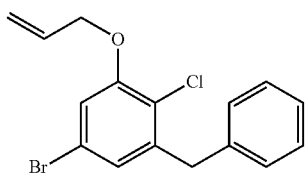 [SMILES: C=CCOc1cc(Br)cc(Cc2ccccc2)c1Cl]

1-(Allyloxy)-3-benzyl-5-bromo-2-chlorobenzene (168)

To a solution of methanone 167 (7.9 g, 22.6 mmol) in TFA (90 mL) were added triethylsilane (18.5 mL, 113 mmol) and catalytic triflic acid at 0° C. The mixture was warmed up to room temperature slowly and stirred at room temperature for 15 hours. The mixture was evaporated in vacuo. The residue was diluted with EtOAc (150 mL) and neutralized with aq. Saturated NaHCO$_3$ solution. The mixture was extracted with EtOAc (150 mL×1). The organic layer was dried over MgSO$_4$, filtered, and concentrated in vacuo. The residue was purified by silica gel column chromatography to provide the compound 168 (6.1 g, 80.1%).

$^1$H NMR (400 MHz, CDCl$_3$) δ 7.34-7.19 (m, 5H), 6.96 (dd, J=9.4 Hz, 2.1 Hz, 2H), 6.13-6.03 (m, 1H), 5.51 (dd, J=17.2 Hz, 1.4 Hz, 1H), 5.37 (dd, J=10.5 Hz, 1.2 Hz, 1H), 4.62 (dd, J=3.6 Hz, 1.4 Hz, 1H), 4.11 (s, 2H).

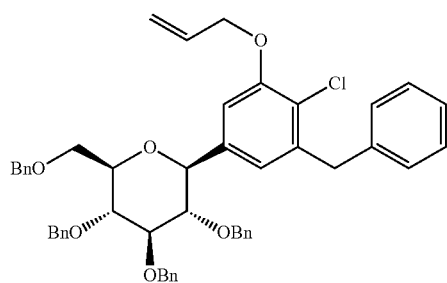 [SMILES: C=CCOc1cc([C@@H]2O[C@H](COCc3ccccc3)[C@@H](OCc3ccccc3)[C@H](OCc3ccccc3)[C@H]2OCc2ccccc2)cc(Cc2ccccc2)c1Cl]

(2S,3S,4R,5R,6R)-2-(3-(Allyloxy)-5-benzyl-4-chlorophenyl)-3,4,5-tris(benzyloxy)-6-((benzyloxy)methyl)tetrahydro-2H-pyran (169)

Similar procedure with preparation of 76 proceeded except for using compound 168 to obtain the compound 169.

[M+Na]$^+$ 803.

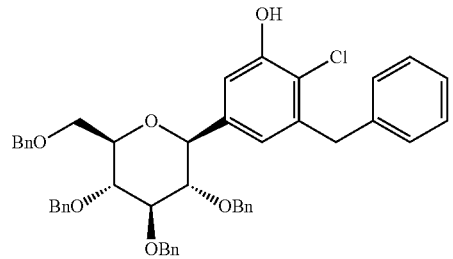 [SMILES: Oc1cc([C@@H]2O[C@H](COCc3ccccc3)[C@@H](OCc3ccccc3)[C@H](OCc3ccccc3)[C@H]2OCc2ccccc2)cc(Cc2ccccc2)c1Cl]

3-Benzyl-2-chloro-5-((2S,3S,4R,5R,6R)-3,4,5-tris(benzyloxy)-6-((benzyloxy)methyl)tetrahydro-2H-pyran-2-yl)phenol (170)

Similar procedure with preparation of 27 proceeded except for using compound 169 to obtain the compound 170.

[M+Na]$^+$ 763.

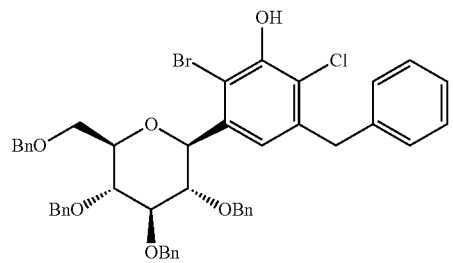 [SMILES: Oc1c(Cl)c(Cc2ccccc2)cc([C@@H]2O[C@H](COCc3ccccc3)[C@@H](OCc3ccccc3)[C@H](OCc3ccccc3)[C@H]2OCc2ccccc2)c1Br]

3-Benzyl-6-bromo-2-chloro-5-((2S,3S,4R,5R,6R)-3,4,5-tris(benzyloxy)-6-((benzyloxy)methyl)tetrahydro-2H-pyran-2-yl)phenol (171)

Similar procedure with preparation of 28 proceeded except for using compound 170 to obtain the compound 171.

[M+Na]$^+$ 841.

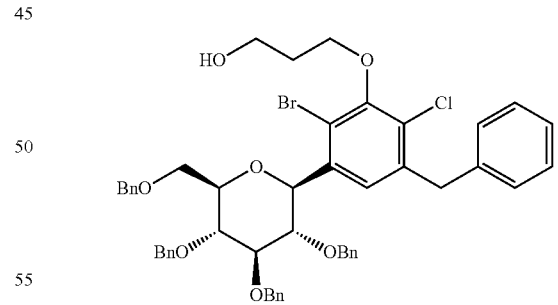

3-(3-Benzyl-6-bromo-2-chloro-5-((2S,3S,4R,5R,6R)-3,4,5-tris(benzyloxy)-6-((benzyloxy)methyl)tetrahydro-2H-pyran-2-yl)phenoxy)propan-1-ol (172)

Similar procedure with preparation of 29 proceeded except for using compound 171 to obtain the compound 172.

[M+Na]$^+$ 899.

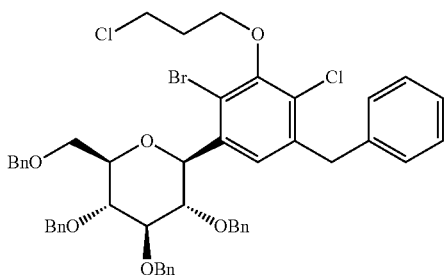 [SMILES: ClCCCOc1c(Cl)c(Cc2ccccc2)cc([C@@H]2O[C@H](COCc3ccccc3)[C@@H](OCc3ccccc3)[C@H](OCc3ccccc3)[C@H]2OCc2ccccc2)c1Br]

(2S,3S,4R,5R,6R)-2-(5-Benzyl-2-bromo-4-chloro-3-(3-chloropropoxy)phenyl)-3,4,5-tris(benzyloxy)-6-((benzyloxy)methyl)tetrahydro-2H-pyran (173)

Similar procedure with preparation of 29-1 proceeded except for using compound 172 to obtain the compound 173.
[M+Na]⁺ 917.

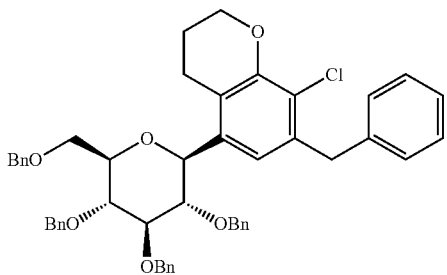

7-Benzyl-8-chloro-5-((2S,3S,4R,5R,6R)-3,4,5-tris(benzyloxy)-6-((benzyloxy)methyl)tetrahydro-2H-pyran-2-yl)chroman (174)

Similar procedure with preparation of 30 proceeded except for using compound 173 to obtain the compound 174.
[M+Na]⁺ 803.

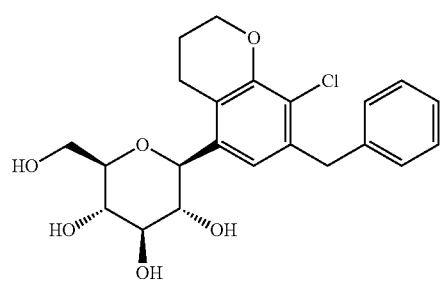 [SMILES: OC[C@H]1O[C@@H](c2cc(Cc3ccccc3)c(Cl)c3c2CCCO3)[C@H](O)[C@@H](O)[C@@H]1O]

(2S,3R,4R,5S,6R)-2-(7-Benzyl-8-chlorochroman-5-yl)-6-(hydroxymethyl)tetrahydro-2H-pyran-3,4,5-triol (175)

Similar procedure with preparation of E005 proceeded except for using compound 174 to obtain the compound 175.
[M+Na]⁺ 443.

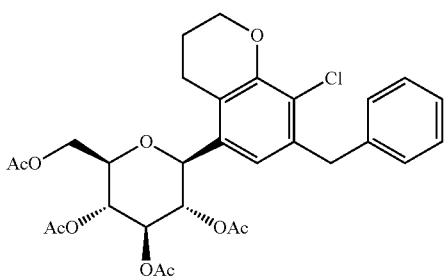 [SMILES: CC(=O)OC[C@H]1O[C@@H](c2cc(Cc3ccccc3)c(Cl)c3c2CCCO3)[C@H](OC(C)=O)[C@@H](OC(C)=O)[C@@H]1OC(C)=O]

(2R,3R,4R,5S,6S)-2-(Acetoxymethyl)-6-(7-benzyl-8-chlorochroman-5-yl)tetrahydro-2H-pyran-3,4,5-triyl triacetate (176)

Similar procedure with preparation of 25 proceeded except for using compound 175 to obtain the compound 176.
[M+Na]⁺ 611.

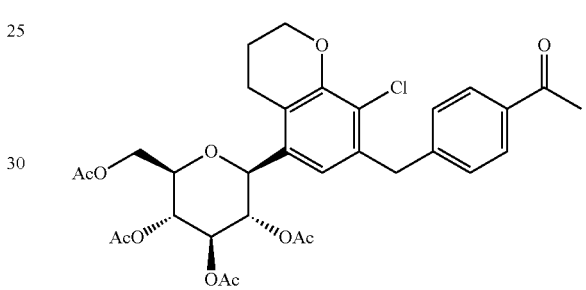

(2R,3R,4R,5S,6S)-2-(Acetoxymethyl)-6-(7-(4-acetylbenzyl)-8-chlorochroman-5-yl)tetrahydro-2H-pyran-3,4,5-triyl triacetate (177)

To a solution of the acetate 176 (500 mg, 0.85 mmol) in CH₂Cl₂ (20 mL) were added AlCl₃ (691 mg, 5.18 mmol) and acetyl chloride (0.37 mL, 5.18 mmol) at 0° C. The mixture was warmed up to rt slowly and left at rt for 3 hours. The mixture was cooled to 0° C. and added aq. 1N HCl solution to quench the reaction. The mixture was extracted with EtOAc (100 mL). The organic layer was washed with brine, dried over MgSO₄, filtered, and concentrated in vacuo. The residue was purified by silica gel column chromatography to provide the product 177 (540 mg, quantitative yield).
[M+Na]⁺ 653.

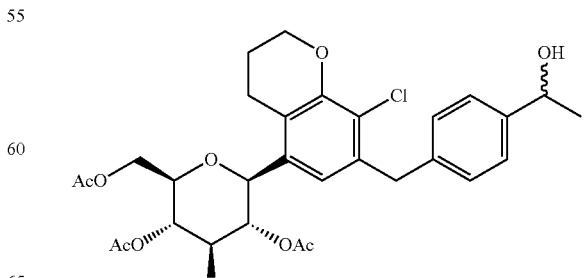

(2R,3R,4R,5S,6S)-2-(Acetoxymethyl)-6-(7-(4-acetylbenzyl)-8-chlorochroman-5-yl)tetrahydro-2H-pyran-3,4,5-triyl triacetate (178)

To a solution of the acetate 177 (540 mg, 0.86 mmol) in THF (20 mL) were added NaBH$_4$ (65 mg, 1.71 mmol) and MeOH (0.23 mL, 5.56 mmol) at −20° C. The mixture was warmed up to rt slowly and at room temperature for 3 hours. To the mixture, aq. saturated NaHCO$_3$ solution was added to quench the reaction. The mixture was extracted with EtOAc (100 mL). The organic layer was washed with brine, dried over MgSO$_4$, filtered, and concentrated in vacuo. The residue was purified by silica gel column chromatography to provide the product 178 (480 mg, 89%).

[M+Na]$^+$ 655.

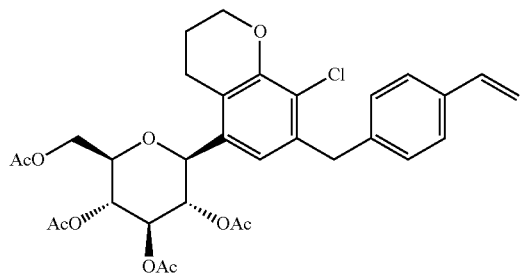 [SMILES: C=Cc1ccc(Cc2cc([C@@H]3O[C@H](COC(C)=O)[C@@H](OC(C)=O)[C@H](OC(C)=O)[C@H]3OC(C)=O)c3c(c2Cl)OCCC3)cc1]

(2R,3R,4R,5S,6S)-2-(Acetoxymethyl)-6-(8-chloro-7-(4-vinylbenzyl)chroman-5-yl)tetrahydro-2H-pyran-3,4,5-triyl triacetate (179)

To a solution of acetate 178 (480 mg, 0.76 mmol) in Toluene (10 mL) was added p-TsOH monohydrate. The mixture was stirred for 90 min at 120° C. The mixture was cooled to rt and evaporated in vacuo. The residue was purified by silica gel column chromatography to provide the product 179 (270 mg, 58%).

[M+Na]$^+$ 637.

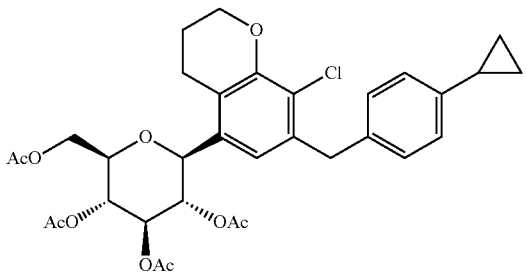 [SMILES: CC(=O)OC[C@H]1O[C@@H](c2cc(Cc3ccc(C4CC4)cc3)c(Cl)c3c2CCCO3)[C@H](OC(C)=O)[C@@H](OC(C)=O)[C@@H]1OC(C)=O]

(2R,3R,4R,5S,6S)-2-(Acetoxymethyl)-6-(8-chloro-7-(4-cyclopropylbenzyl)chroman-5-yl)tetrahydro-2H-pyran-3,4,5-triyl triacetate (180)

The mixture of Et$_2$Zn (1.1M in toluene, 4 mL, 4.39 mmol) and CH$_2$Cl$_2$ (8 mL) was cooled to 0° C. TFA ((0.34 mL, 4.39 mmol) in CH$_2$Cl$_2$ (4 mL)) was added to the mixture at 0° C. The mixture was stirred at 0° C. for 1 hr. CH$_2$I$_2$ ((0.36 mL, 4.39 mmol) in CH$_2$Cl$_2$ (4 mL)) was added to the mixture at 0° C. The mixture was stirred at 0° C. for 1 hr. The acetate 179 ((270 mg, 0.44 mmol) in CH$_2$Cl$_2$ (4 mL)) was added to the mixture at 0° C. The mixture was warmed up to rt slowly and stirred at room temperature for 15 hours. The mixture was extracted with EtOAc/aq. sat'd NH$_4$Cl (50 mL/50 mL). The organic layer was dried over MgSO$_4$, filtered, and concentrated in vacuo. The residue was purified using normal phase column chromatography to provide the title product 180 (152 mg, 55%).

[M+Na]$^+$ 651.

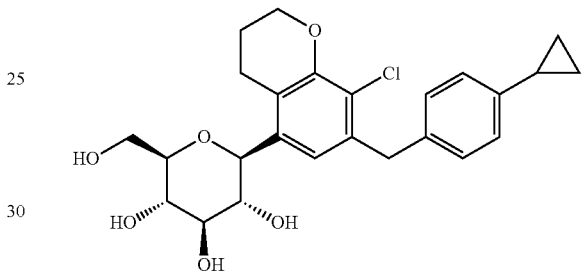

(2S,3R,4R,5S,6R)-2-(8-Chloro-7-(4-cyclopropylbenzyl)chroman-5-yl)-6-(hydroxymethyl)tetrahydro-2H-pyran-3,4,5-triol (E155)

To a suspension of acetate 180 (152 mg, 0.24 mmol) in MeOH (5 mL) was added NaOMe (25 wt % in MeOH, 0.05 mL) at room temperature. The mixture was stirred at room temperature for 1 hour. Glacial AcOH was added to the mixture to acidify the mixture. The mixture was concentrated under reduced pressure. The residue was purified by prep HPLC (reverse phase) to provide the compound E155 (37 mg, 34%).

$^1$H NMR (400 MHz, CD$_3$OD) δ 7.08 (d, J=8.2 Hz, 2H), 7.00 (s, 1H), 6.97 (d, J=8.2 Hz, 2H), 4.90 (s, 4H), 4.43-4.37 (m, 1H), 4.38-4.16 (m, 2H), 4.03 (ABq, Δv$_{AB}$=10.0 Hz, J$_{AB}$=15.0 Hz, 2H), 3.92-3.85 (m, 1H), 3.71-3.64 (m, 1H), 3.55-3.44 (m, 2H), 3.37-3.32 (m, 2H), 3.05-2.92 (m, 1H), 2.91-2.83 (m, 1H), 2.07-1.99 (m, 2H), 1.91-1.82 (m, 1H), 0.97-0.90 (m, 2H), 0.66-0.61 (m, 2H); [M+Na]$^+$ 483.

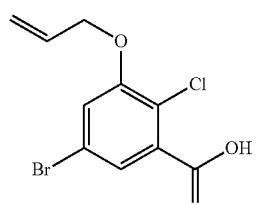

181

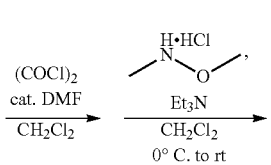

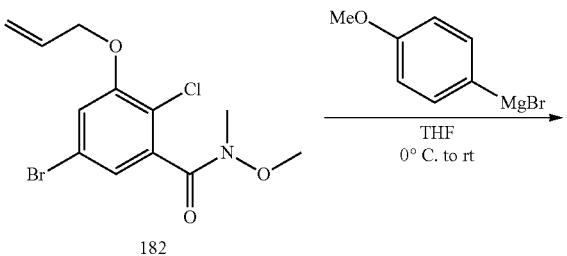

182

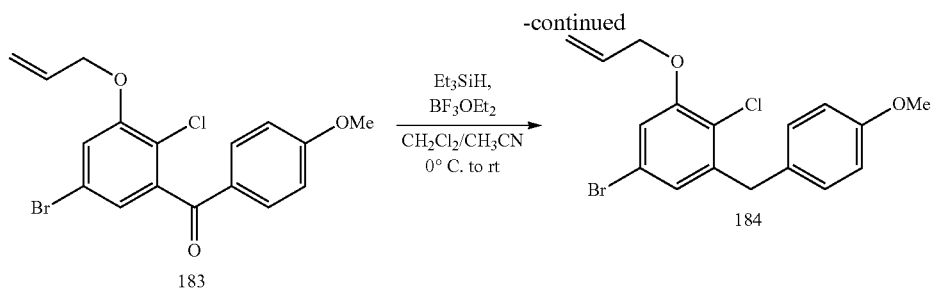
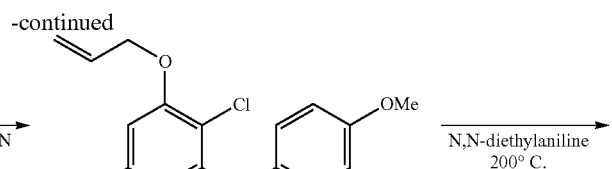
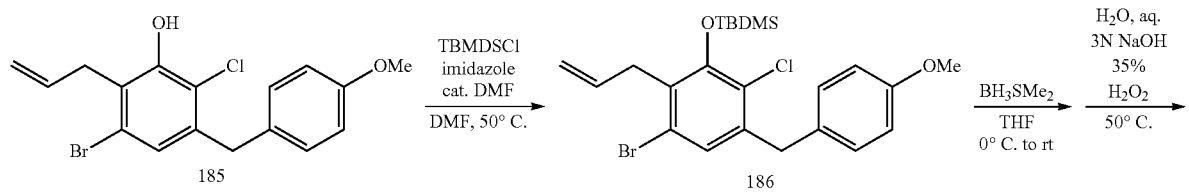
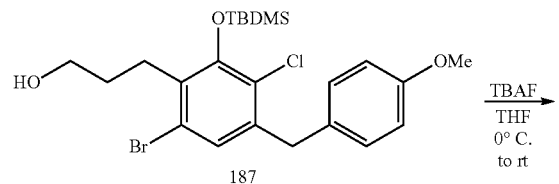
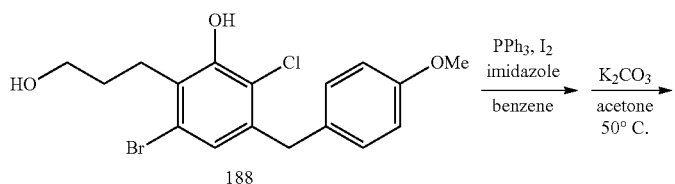
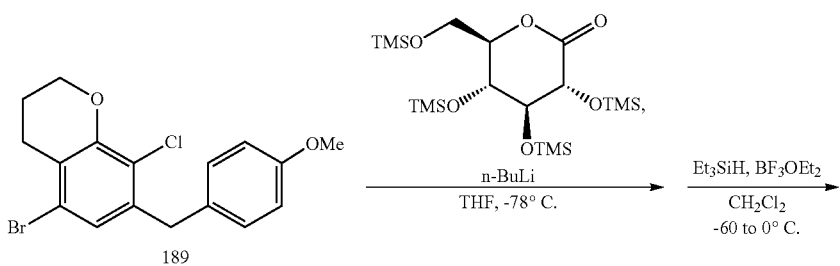
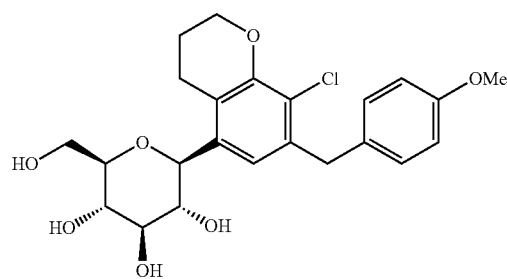

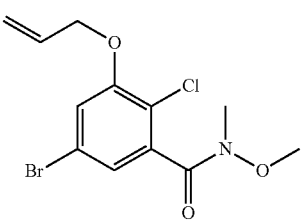 [SMILES: C=CCOc1cc(Br)cc(C(=O)N(C)OC)c1Cl]

3-(Allyloxy)-5-bromo-2-chloro-N-methoxy-N-methylbenzamide (182)

Similar procedure with preparation of 22 proceeded to obtain the compound 182.
[M+H]+ 334.

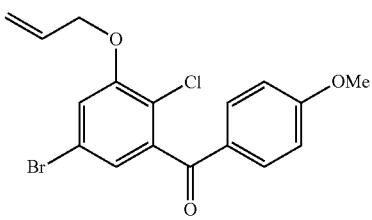 [SMILES: C=CCOc1cc(Br)cc(C(=O)c2ccc(OC)cc2)c1Cl]

(3-(Allyloxy)-5-bromo-2-chlorophenyl)(4-methoxyphenyl)methanone (183)

Similar procedure with preparation of 31 proceeded except for using compound 182 to obtain the compound 183.
[M+H]+ 381.

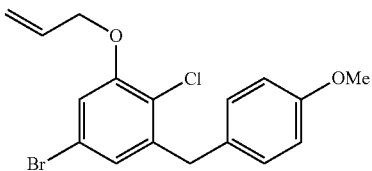 [SMILES: C=CCOc1cc(Br)cc(Cc2ccc(OC)cc2)c1Cl]

1-(Allyloxy)-5-bromo-2-chloro-3-(4-methoxybenzyl)benzene (184)

Similar procedure with preparation of 74 proceeded except for using compound 183 to obtain the compound 184.
¹H NMR (400 MHz, CDCl₃) δ 7.12 (d, J=8.7 Hz, 2H), 6.94 (dd, J=14.3 Hz, 2.1 Hz, 2H), 6.88 (d, J=8.7 Hz, 2H), 6.14-6.03 (m, 1H), 5.51 (qd, J=8.6 Hz, 0.76 Hz, 1H), 5.51 (qd, J=5.3 Hz, 0.66 Hz, 1H), 4.63-4.59 (m, 2H), 4.04 (s, 2H), 3.82 (s, 3H).

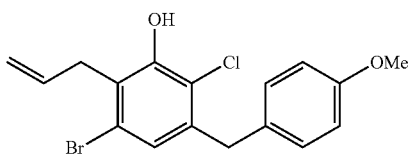 [SMILES: C=CCc1c(Br)cc(Cc2ccc(OC)cc2)c(Cl)c1O]

2-Allyl-3-bromo-6-chloro-5-(4-methoxybenzyl)phenol (185)

The mixture of bromide 184 (2.52 g, 6.85 mmol) in N,N-diethylaniline (8 mL) was stirred at 200° C. for 45 hours. The mixture was cooled to rt and extracted with EtOAc/aq. 1N HCl solution (100 mL/100 mL). The organic layer was washed with brine, dried over MgSO₄, filtered, and concentrated in vacuo. The residue was purified by silica gel column chromatography to provide the desired product 185 (2.3 g, 91%).
¹H NMR (400 MHz, CDCl₃) δ 7.12 (d, J=8.7 Hz, 2H), 6.99 (s, 1H), 6.87 (d, J=8.7 Hz, 2H), 6.00-5.95 (m, 1H), 5.87 (s, 1H), 5.15-5.05 (m, 2H), 3.98 (s, 2H), 3.82 (s, 3H), 3.62 (dt, J=5.4 Hz, 1.5 Hz, 2H).

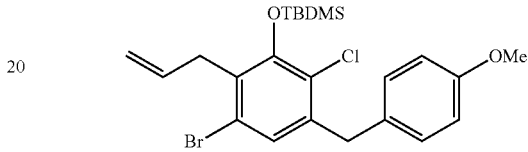

(2-Allyl-3-bromo-6-chloro-5-(4-methoxybenzyl)phenoxy)(tert-butyl)dimethylsilane (186)

To a solution of phenol 185 (2.29 g, 6.23 mmol) in DMF (30 mL) were added tert-butyldimethylsilyl chloride (1M in THF, 9.35 mL, 9.35 mmol), imidazole (1.3 g, 18.7 mmol) and catalytic DMAP. The mixture was stirred at 50° C. for 15 hours. The mixture was extracted with EtOAc/aq. 50% NaCl solution (100 mL/500 mL). The organic layer was washed with brine, dried over MgSO₄, filtered and concentrated in vacuo. The residue was purified by silica gel column chromatography to provide the product 186 (2.57 g, 86%).
¹H NMR (400 MHz, CDCl₃) δ 7.12 (d, J=8.7 Hz, 2H), 7.01 (s, 1H), 6.87 (d, J=8.7 Hz, 2H), 5.93-5.81 (m, 1H), 5.08-4.96 (m, 2H), 3.99 (s, 2H), 3.83 (s, 3H), 3.58 (dt, J=5.1 Hz, 1.6 Hz, 2H), 1.05 (s, 9H), 0.30 (s, 6H).

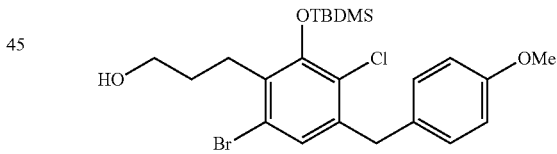

3-(6-Bromo-2-((tert-butyldimethylsilyl)oxy)-3-chloro-4-(4-methoxybenzyl)phenyl)propan-1-ol (187)

To a solution of bromide 186 (2.57 g, 5.33 mmol) in THF (35 mL) was added borane dimethylsulfide complex (10M in THF, 0.18 mL, 1.76 mmol) at 0° C. The mixture was stirred at rt for 1 hr. The mixture was cooled to 0° C. and H₂O (0.5 mL), aq. 3N NaOH solution (1.1 mL), 35% H₂O₂ (0.65 mL) were added to the mixture.) The mixture was stirred at 50° C. for 30 min and cooled to rt. The mixture was extracted with EtOAc/aq. 50% NaCl solution (100 mL/100 mL). The organic layer was washed with brine, dried over MgSO₄, filtered and concentrated in vacuo. The residue was purified by silica gel column chromatography to provide the product 187 (1.73 g, 65%).

$^1$H NMR (400 MHz, CDCl$_3$) δ 7.12 (d, J=8.7 Hz, 2H), 7.01 (s, 1H), 6.87 (d, J=8.7 Hz, 2H), 3.99 (s, 2H), 3.83 (s, 3H), 3.63 (q, J=5.9 Hz, 2H), 2.91 (t, J=7.5 Hz, 2H), 1.86-1.77 (m, 2H), 1.47-1.44 (m, 1H), 1.05 (s, 9H), 0.30 (s, 3H).

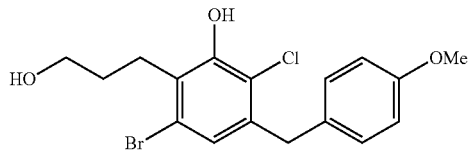 [SMILES: COc1ccc(Cc2cc(Br)c(CCCO)c(O)c2Cl)cc1]

3-Bromo-6-chloro-2-(3-hydroxypropyl)-5-(4-methoxybenzyl)phenol (188)

To a solution of alcohol 187 (1.73 g, 3.46 mmol) in THF (28 mL) was added TBAF (1M in THF, 7.0 mL, 6.92 mmol) at 0° C. The mixture was stirred for 1 hr at rt. The mixture was extracted with EtOAc/aq. sat'd NH$_4$Cl solution (500 mL/50 mL). The organic layer was washed with brine, dried over MgSO$_4$, filtered and concentrated in vacuo. The residue was purified by silica gel column chromatography to provide the product 188 (1.19 g, 89%).
$^1$H NMR (400 MHz, CDCl$_3$) δ 7.14 (d, J=8.7 Hz, 2H), 6.98 (s, 1H), 6.88 (d, J=8.7 Hz, 2H), 6.79 (br s, 1H), 3.99 (s, 2H), 3.83 (s, 3H), 3.68 (t, J=6.0 Hz, 2H), 2.98 (t, J=7.0 Hz, 2H), 1.97-1.87 (m, 3H).

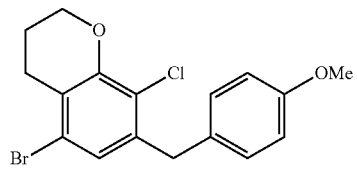 [SMILES: COc1ccc(Cc2cc(Br)c3c(c2Cl)OCCC3)cc1]

5-Bromo-8-chloro-7-(4-methoxybenzyl)chroman (189)

(step 1) To a solution of alcohol 188 (1.19 g, 3.09 mmol) in benzene (30 mL) were added PPh$_3$ (1.21 g, 4.63 mmol) and imidazole (1.18 g, 4.63 mmol) at rt. I$_2$ (in benzene (3 mL), 0.42 g, 6.18 mmol) was added to the reaction mixture. The mixture was stirred at room temperature for 15 hours. The mixture was extracted with ether/aq. sat'd NaHCO$_3$ solution (100 mL/100 mL). The organic layer was dried over MgSO$_4$, filtered, and concentrated in vacuo. The crude iodide was carried on to the next step without further purification.

(step 2) To a solution of crude iodide (1.60 g) in acetone (35 mL) was added K$_2$CO$_3$ (0.64 g, 4.64 mmol). The mixture was stirred at 50° C. for 15 hours. The mixture was cooled to r.t. and concentrated in vacuo. The residue was purified by silica gel column chromatography to provide the desired product 189 (0.97 g, 85% (2-steps)).
$^1$H NMR (400 MHz, CDCl$_3$) δ 7.14 (d, J=8.7 Hz, 2H), 6.96 (s, 1H), 6.86 (d, J=8.7 Hz, 2H), 4.28 (t, J=5.2 Hz, 2H), 4.01 (s, 2H), 3.82 (s, 3H), 2.77 (t, J=6.6 Hz, 2H), 2.10-2.02 (m, 2H).

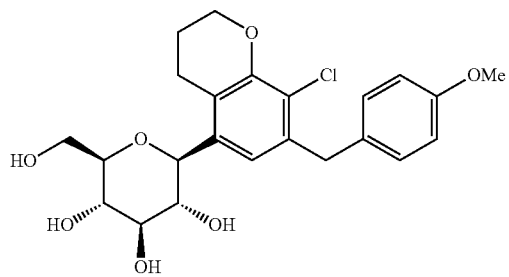 [SMILES: COc1ccc(Cc2cc([C@@H]3O[C@H](CO)[C@@H](O)[C@H](O)[C@H]3O)c3c(c2Cl)OCCC3)cc1]

(2S,3R,4R,5S,6R)-2-(8-Chloro-7-(4-methoxybenzyl)chroman-5-yl)-6-(hydroxymethyl)tetrahydro-2H-pyran-3,4,5-triol (E156)

Similar procedure with preparation of E011 proceeded except for using compound 189 to obtain the compound E156.
$^1$H NMR (400 MHz, CD$_3$OD) δ 7.12 (d, J=8.7 Hz, 2H), 7.00 (s, 1H), 6.81 (d, J=8.7 Hz, 2H), 4.91 (s, 4H), 4.42-4.36 (m, 1H), 4.25-4.19 (m, 2H), 4.01 (ABq, Δv$_{AB}$=10.0 Hz, J$_{AB}$=15.1 Hz, 2H), 3.91-3.85 (m, 1H), 3.77 (s, 3H), 3.71-3.63 (m, 1H), 3.55-3.33 (m, 4H), 3.05-2.97 (m, 1H), 2.93-2.84 (m, 1H), 2.05-1.99 (m, 2H); [M+Na]$^+$ 473.

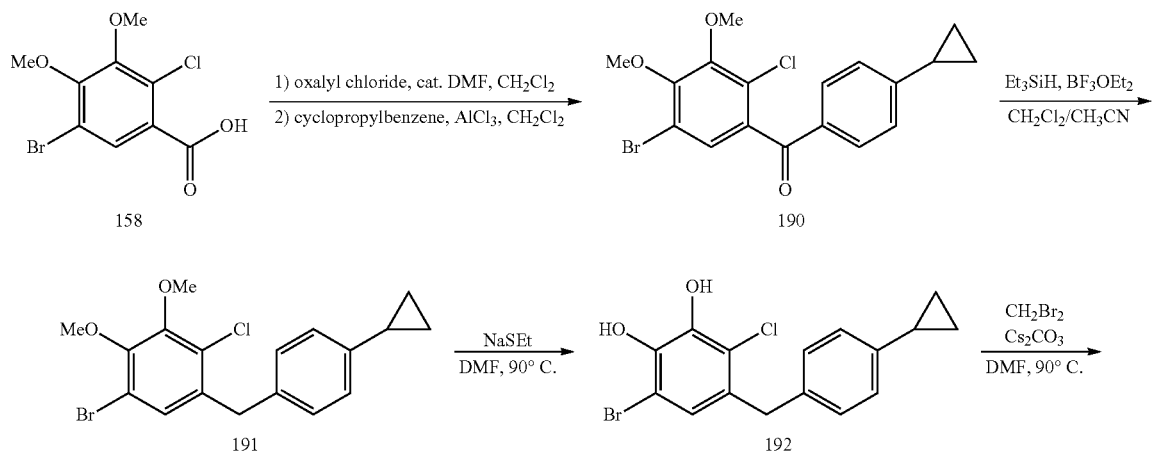

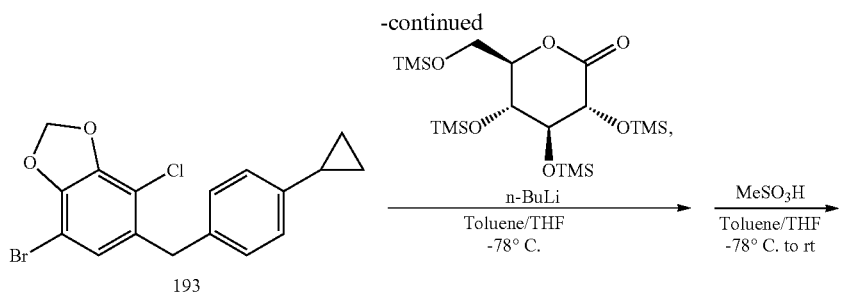

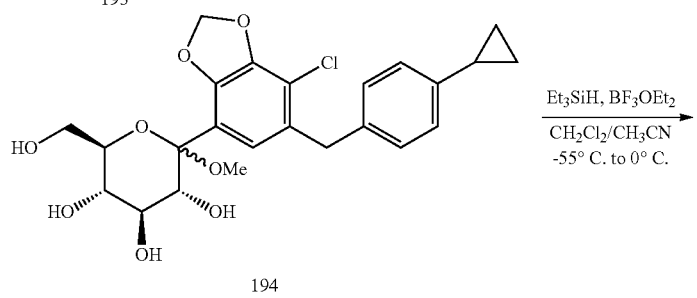

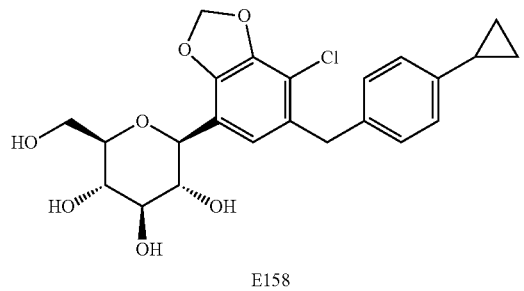

E158

¹H NMR (400 MHz, CDCl₃) δ 7.13-7.09 (m, 3H), 7.05 (d, J=8.2 Hz, 2H), 4.01 (s, 2H), 3.94 (s, 3H), 3.92 (s, 3H), 1.95-1.85 (m, 1H), 1.01-0.94 (m, 2H), 0.75-0.67 (m, 2H).

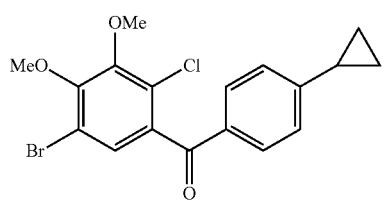 [SMILES: COc1c(Br)cc(C(=O)c2ccc(C3CC3)cc2)c(Cl)c1OC]

(5-Bromo-2-chloro-3,4-dimethoxyphenyl)(4-cyclopropylphenyl)methanone (190)

Similar procedure with preparation of 159 proceeded to obtain the compound 190.
[M+H]⁺ 395.

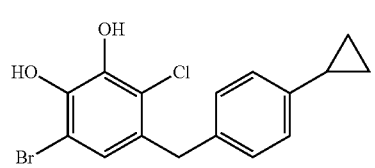

6-Bromo-3-chloro-4-(4-cyclopropylbenzyl)benzene-1,2-diol (192)

Similar procedure with preparation of 77 proceeded to obtain the compound 192.

¹H NMR (400 MHz, CDCl₃) δ 7.09 (d, J=8.2 Hz, 2H), 7.03 (d, J=8.2 Hz, 2H), 6.90 (s, 1H), 5.74 (s, 1H), 5.59 (s, 1H), 3.98 (s, 2H), 1.95-1.84 (m, 1H), 1.00-0.94 (m, 2H), 0.73-0.67 (m, 2H).

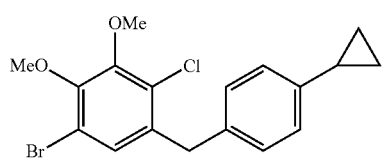 [SMILES: COc1c(Br)cc(Cc2ccc(C3CC3)cc2)c(Cl)c1OC]

1-Bromo-4-chloro-5-(4-cyclopropylbenzyl)-2,3-dimethoxybenzene (191)

Similar procedure with preparation of 160 proceeded to obtain the compound 191.

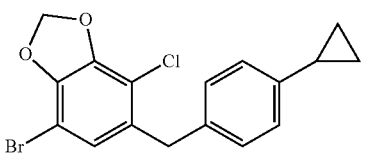 [SMILES: Clc1c(Cc2ccc(C3CC3)cc2)cc(Br)c2c1OCO2]

7-Bromo-4-chloro-5-(4-cyclopropylbenzyl)benzo[d][1,3]dioxole (193)

To a solution of phenol 192 (1.75 g, 4.95 mmol) in DMF (25 mL) were added dibromomethane (0.42 mL, 5.94 mmol) and Cs$_2$CO$_3$ (5.7 g, 17.3 mmol) at r.t. The mixture was stirred at 90° C. for 12 hours. The mixture was cooled to r.t. and filtered off to remove inorganic salts. The filtrate was extracted with EtOAc/aq. 50% NaCl solution (100 mL/500 mL). The organic layer was washed with brine, dried over MgSO$_4$, filtered and concentrated in vacuo. The residue was purified by silica gel column chromatography to provide the product 193 (1.17 g, 65%).

$^1$H NMR (400 MHz, CDCl$_3$) δ 7.05 (d, J=8.2 Hz, 2H), 7.00 (d, J=8.2 Hz, 2H), 6.77 (s, 1H), 6.10 (s, 2H), 3.93 (s, 2H), 1.91-1.83 (m, 1H), 0.99-0.90 (m, 2H), 0.69-0.63 (m, 2H).

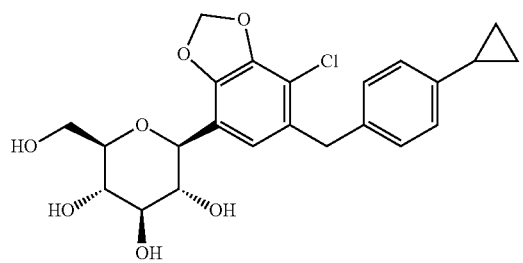

(2S,3R,4R,5S,6R)-2-(7-Chloro-6-(4-cyclopropylbenzyl)benzo[d][1,3]dioxol-4-yl)-6-(hydroxymethyl)tetrahydro-2H-pyran-3,4,5-triol (E158)

Similar procedure with preparation of E011 proceeded except for using compound 193 to obtain the compound E158.

$^1$H NMR (400 MHz, CD$_3$OD) δ 7.07 (d, J=8.2 Hz, 2H), 6.98 (d, J=8.2 Hz, 2H), 6.88 (s, 1H), 6.06 (dd, J=7.0 Hz, 1.0 Hz, 2H), 4.85 (s, 4H), 4.28 (d, J=9.6 Hz, 1H), 3.98 (ABq, Δν$_{AB}$=10.9 Hz, J$_{AB}$=15.2 Hz, 2H), 3.88 (d, J=10.5 Hz, 1H), 3.72-3.63 (m, 1H), 3.60 (t, J=9.2 Hz, 1H), 3.49-3.33 (m, 3H), 1.93-1.81 (m, 1H), 0.97-0.89 (m, 2H), 0.68-0.60 (m, 2H); [M+Na]$^+$ 471.

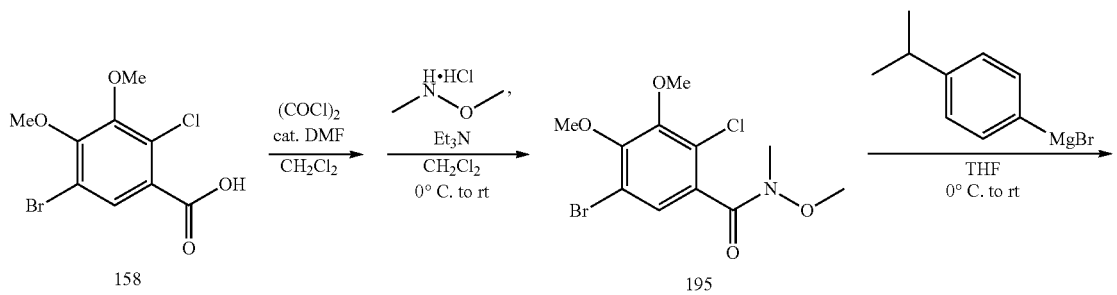

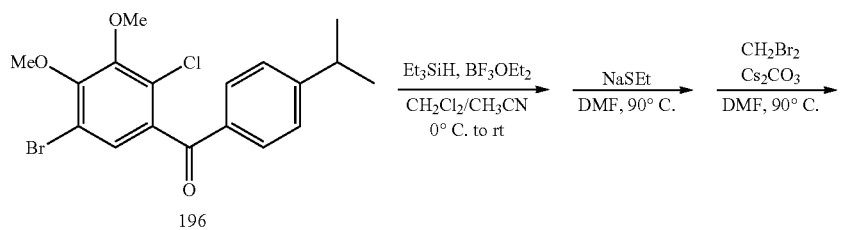

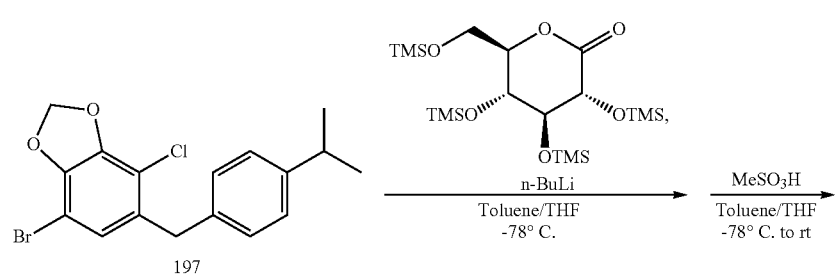

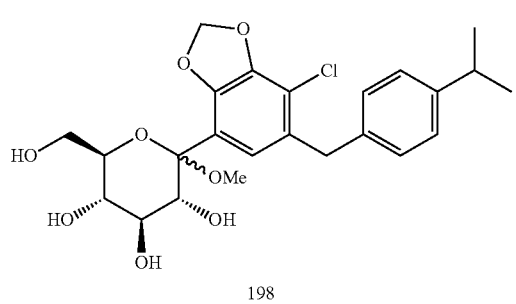

198

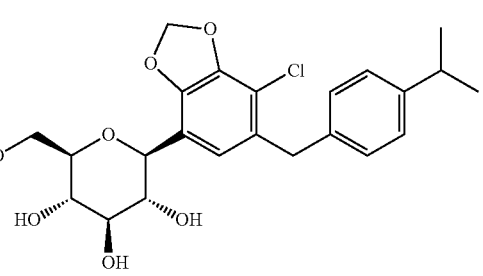

E159

7-Bromo-4-chloro-5-(4-isopropylbenzyl)benzo[d][1,3]dioxole (197)

Similar procedure with preparation of 193 proceeded to obtain the compound 197.

$^1$H NMR (400 MHz, CDCl$_3$) δ 7.19 (d, J=8.1 Hz, 2H), 7.13 (d, J=8.2 Hz, 2H), 6.84 (s, 1H), 6.13 (s, 2H), 3.99 (s, 2H), 2.98-2.85 (m, 1H), 1.27 (d, J=6.9 Hz, 6H).

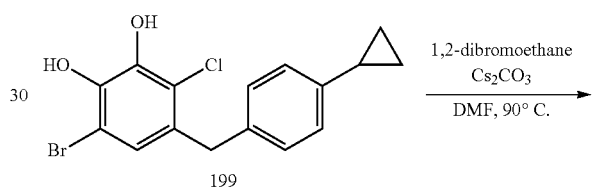

199

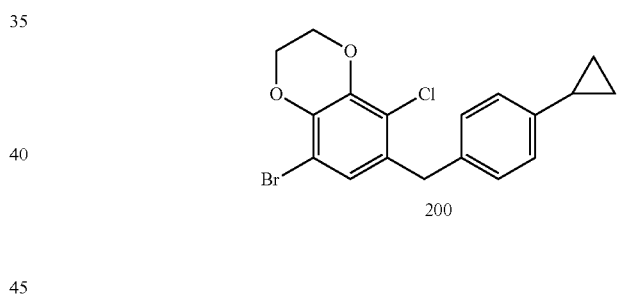

200

8-Bromo-5-chloro-6-(4-cyclopropylbenzyl)-2,3-dihydrobenzo[b][1,4]dioxine (200)

Similar procedure with preparation of 193 proceeded except for using 1,2-dibromoethane to obtain the compound 200.

$^1$H NMR (400 MHz, CDCl$_3$) δ 7.09 (d, J=8.2 Hz, 2H), 7.03 (d, J=8.2 Hz, 2H), 6.96 (s, 1H), 4.41-4.36 (m, 4H), 3.99 (s, 2H), 2.09-1.83 (m, 1H), 0.99-0.91 (m, 2H), 0.71-0.66 (m, 2H).

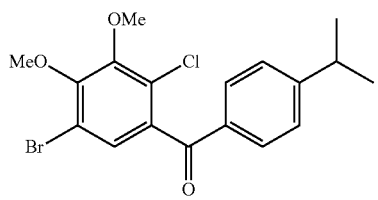 [SMILES: COc1c(Br)cc(C(=O)c2ccc(C(C)C)cc2)c(Cl)c1OC]

5-Bromo-2-chloro-N,3,4-trimethoxy-N-methylbenzamide (195)

Similar procedure with preparation of 182 proceeded except for using compound 158 to obtain the compound 195.

$^1$H NMR (400 MHz, CDCl$_3$) δ 7.33 (s, 1H), 3.96 (s, 3H), 3.95 (s, 3H), 3.55 (br s, 3H), 3.39 (br s, 3H).

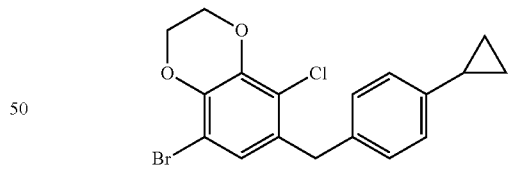

(5-Bromo-2-chloro-3,4-dimethoxyphenyl)(4-isopropylphenyl)methanone (196)

Similar procedure with preparation of 183 proceeded except for using compound 195 to obtain the compound 196.

$^1$H NMR (400 MHz, CDCl$_3$) δ 7.78 (d, J=8.4 Hz, 2H), 7.35 (d, J=8.4 Hz, 2H), 7.30 (s, 1H), 4.01 (s, 3H), 3.99 (s, 3H), 3.08-2.95 (m, 1H), 1.31 (d, J=6.9 Hz, 6H).

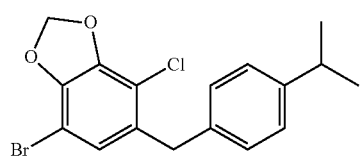 [SMILES: CC(C)c1ccc(Cc2cc(Br)c3c(c2Cl)OCO3)cc1]

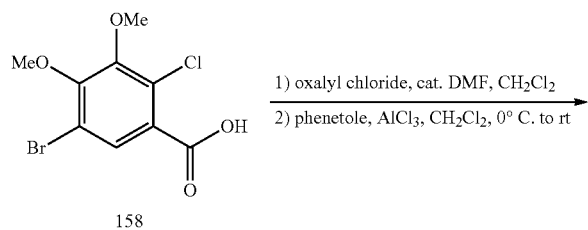
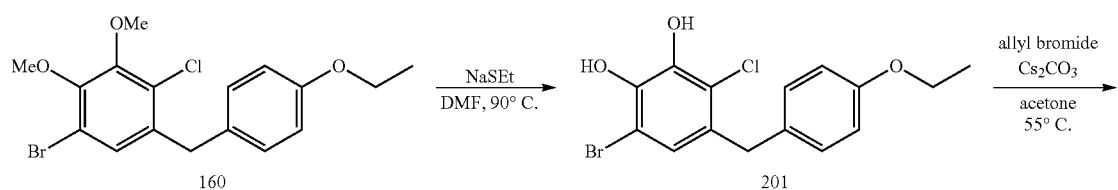
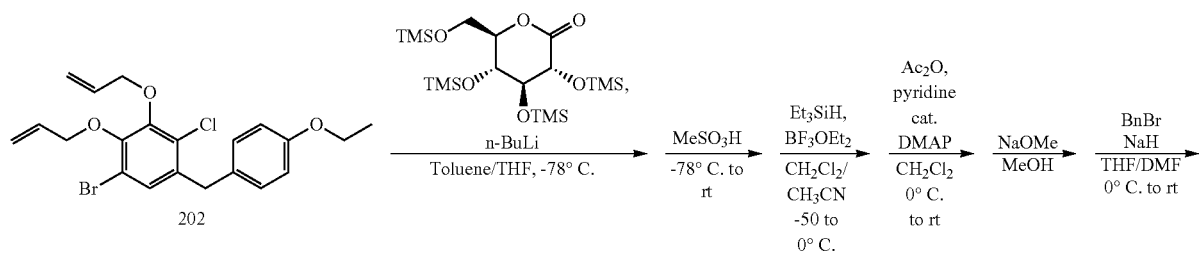
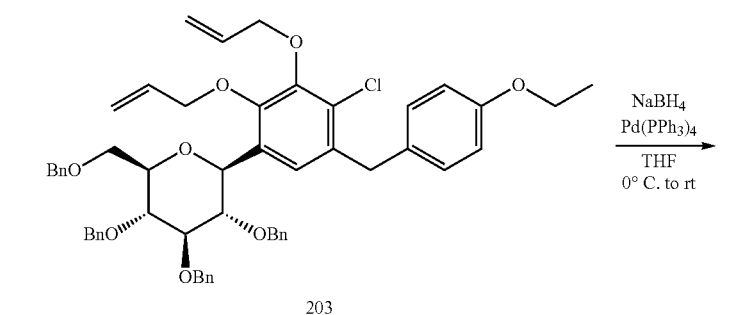
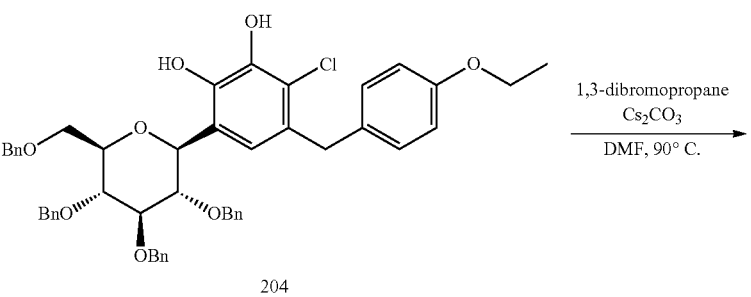
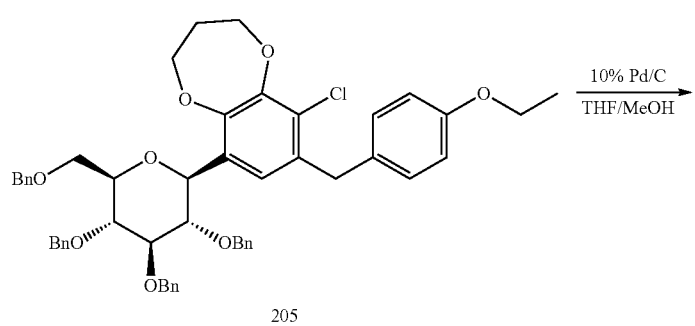

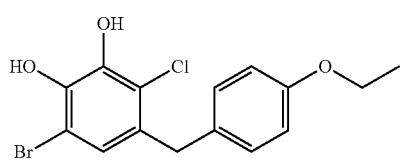 [SMILES: CCOc1ccc(Cc2cc(Br)c(O)c(O)c2Cl)cc1]

6-Bromo-3-chloro-4-(4-ethoxybenzyl)benzene-1,2-diol (201)

Similar procedure with preparation of 77 proceeded except for using compound 160 to obtain the compound 201.

$^1$H NMR (400 MHz, CDCl$_3$) δ 7.10 (d, J=8.2 Hz, 2H), 6.88 (d, J=8.2 Hz, 2H), 6.85 (s, 1H), 5.80 (br s, 1H), 5.68 (br s, 1H), 4.04 (d, J=7.0 Hz, 2H), 3.96 (s, 2H), 1.44 (t, J=7.0 Hz, 3H).

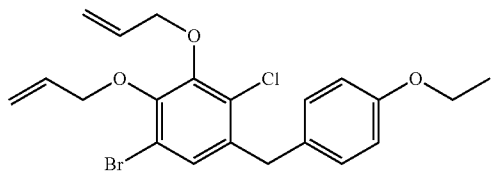 [SMILES: C=CCOc1c(Br)cc(Cc2ccc(OCC)cc2)c(Cl)c1OCC=C]

2,3-Bis(allyloxy)-1-bromo-4-chloro-5-(4-ethoxybenzyl)benzene (202)

$^1$H NMR (400 MHz, CDCl$_3$) δ 7.12 (s, 1H), 7.10 (d, J=8.2 Hz, 2H), 6.87 (d, J=8.2 Hz, 2H), 6.21-6.08 (m, 2H), 5.46-5.39 (m, 2H), 5.31-5.25 (m, 2H), 4.63-4.54 (m, 4H), 4.04 (d, J=7.0 Hz, 2H), 4.00 (s, 2H), 1.44 (t, J=7.0 Hz, 3H).

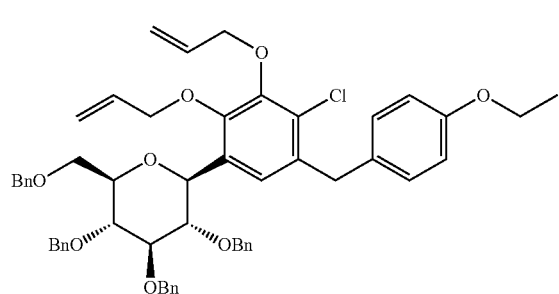 [SMILES: C=CCOc1c([C@@H]2O[C@H](COCc3ccccc3)[C@@H](OCc3ccccc3)[C@H](OCc3ccccc3)[C@H]2OCc2ccccc2)cc(Cc2ccc(OCC)cc2)c(Cl)c1OCC=C]

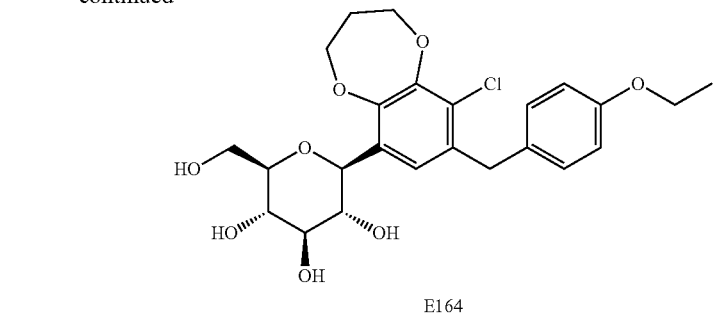

E164

(2R,3R,4R,5S,6S)-3,4,5-Tris(benzyloxy)-2-((benzyloxy)methyl)-6-(2,3-bis(allyloxy)-4-chloro-5-(4-ethoxybenzyl)phenyl)tetrahydro-2H-pyran (203)

Similar procedure with preparation of 162 proceeded except for using compound 202 to obtain the compound 203.

[M+Na]$^+$ 903.

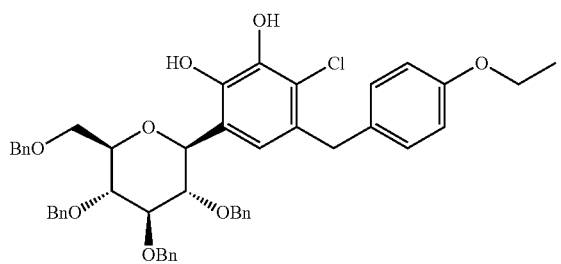

3-Chloro-4-(4-ethoxybenzyl)-6-((2S,3S,4R,5R,6R)-3,4,5-tris(benzyloxy)-6-((benzyloxy)methyl)tetrahydro-2H-pyran-2-yl)benzene-1,2-diol (204)

To a solution of compound 203 (2.82 g, 2.06 mmol) in THF (20 mL) were added NaBH$_4$ (0.23 g, 6.00 mmol) and Pd(PPh$_3$)$_4$ (0.23 g, 0.20 mmol) at 0° C. The mixture was warmed up to r.t. slowly and stirred at r.t. for 12 h. The mixture was cooled to 0° C. and aq. sat'd NH$_4$Cl solution (50 mL) was added to the mixture slowly. The mixture was extracted with EtOAc (50 mL). The organic layer was washed with brine, dried over MgSO$_4$, filtered, and concentrated in vacuo. The residue was purified by silica gel column chromatography to provide the product 204 (1.42 g, 86%).

[M+Na]$^+$ 823.

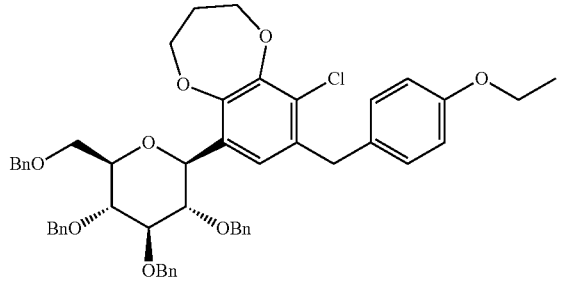 [SMILES: CCOc1ccc(Cc2cc([C@@H]3O[C@H](COCc4ccccc4)[C@@H](OCc4ccccc4)[C@H](OCc4ccccc4)[C@H]3OCc3ccccc3)c3c(c2Cl)OCCCO3)cc1]

6-Chloro-7-(4-ethoxybenzyl)-9-((2S,3S,4R,5R,6R)-3,4,5-tris(benzyloxy)-6-((benzyloxy)methyl)tetrahydro-2H-pyran-2-yl)-3,4-dihydro-2H-benzo[b][1,4]dioxepine (205)

Similar procedure with preparation of 200 proceeded except for using 1,3-dibromopropane to obtain the compound 205.
[M+Na]⁺ 863.

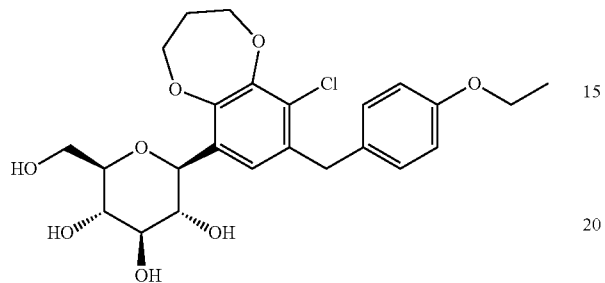

(2S,3R,4R,5S,6R)-2-(9-Chloro-8-(4-ethoxybenzyl)-3,4-dihydro-2H-benzo[b][1,4]dioxepin-6-yl)-6-(hydroxymethyl)tetrahydro-2H-pyran-3,4,5-triol (E164)

Similar procedure with preparation of E005 proceeded except for using compound 205 to obtain the compound E164.
¹H NMR (400 MHz, CD₃OD) δ 7.11 (d, J=8.8 Hz, 2H), 7.07 (s, 1H), 6.82 (d, J=8.7S Hz, 2H), 4.85 (s, 4H), 4.63-4.55 (m, 1H), 4.31-4.17 (m, 2H), 4.17-4.07 (m, 2H), 4.05-3.93 (m, 4H), 3.88 (dd, J=11.9 Hz, 1.6 Hz, 1H), 3.71-3.64 (m, 1H), 3.49-3.43 (m, 2H), 3.41-3.34 (m, 2H), 2.29-2.10 (m, 2H), 1.38 (t, J=7.0 Hz, 1H); [M+Na]⁺ 503.

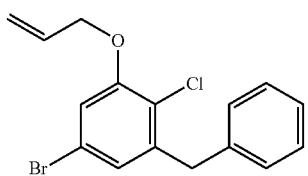 [SMILES: C=CCOc1cc(Br)cc(Cc2ccccc2)c1Cl]

1-(Allyloxy)-3-benzyl-5-bromo-2-chlorobenzene (206)

¹H NMR (400 MHz, CDCl₃) δ 7.32-7.28 (m, 2H), 7.24-7.22 (m, 1H), 7.21-7.18 (m, 2H), 6.93 (d, J=2.4 Hz, 1H), 6.91 (d, J=2.0 Hz, 1H), 6.10-6.00 (m, 1H), 5.46 (dq, J=17.2, 1.6 Hz, 1H), 5.33 (dq, J=10.8, 1.6 Hz, 1H), 4.58 (dt, J=5.2, 1.6 Hz, 2H), 4.08 (s, 2H); [M+H]⁺ 337.

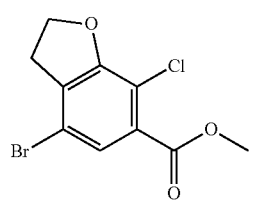

Methyl 4-bromo-7-chloro-2,3-dihydrobenzofuran-6-carboxylate (207)

¹H NMR (400 MHz, DMSO) δ 7.47 (s, 1H), 4.75 (t, J=8.8 Hz, 2H), 3.84 (s, 3H), 3.34 (s, 3H), 3.33 (t, J=9.2 Hz, 2H); [M+H]⁺ 291, 293.

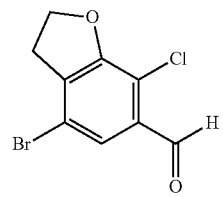 [SMILES: O=Cc1cc(Br)c2c(c1Cl)OCC2]

4-Bromo-7-chloro-2,3-dihydrobenzofuran-6-carbaldehyde (208)

¹H NMR (400 MHz, CDCl₃) δ 10.31 (s, 1H), 7.57 (s, 1H), 4.79 (t, J=9.2 Hz, 2H), 3.34 (t, J=9.2 Hz, 2H); [M+H]⁺ 261.

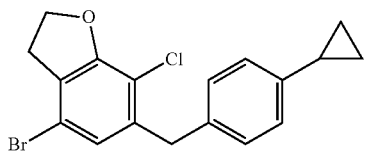 [SMILES: Clc1c(Cc2ccc(C3CC3)cc2)cc(Br)c2c1OCC2]

4-Bromo-7-chloro-6-(4-cyclopropylbenzyl)-2,3-dihydrobenzofuran (209)

¹H NMR (400 MHz, CDCl₃) δ 7.06 (d, J=8.0 Hz, 2H), 6.98 (d, J=8.4 Hz, 2H), 6.79 (s, 1H), 4.67 (t, J=8.8 Hz, 2H), 3.95 (s, 2H), 3.22 (t, J=8.8 Hz, 2H), 1.88-1.81 (m, 1H), 0.94-0.89 (m, 2H), 0.67-0.63 (m, 2H); [M+H]⁺ 363.

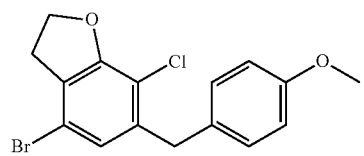 [SMILES: COc1ccc(Cc2cc(Br)c3c(c2Cl)OCC3)cc1]

4-Bromo-7-chloro-6-(4-methoxybenzyl)-2,3-dihydrobenzofuran (210)

¹H NMR (400 MHz, CDCl₃) δ 7.10 (d, J=8.4 Hz, 2H), 6.83 (d, J=8.8 Hz, 2H), 6.79 (s, 1H), 4.71 (t, J=8.8 Hz, 2H), 3.96 (s, 2H), 3.79 (s, 3H), 3.26 (t, J=8.8 Hz, 2H); [M+H]⁺ 353.

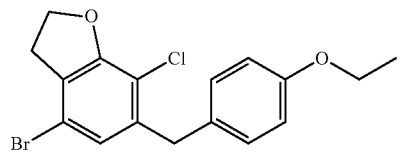 [SMILES: CCOc1ccc(Cc2cc(Br)c3c(c2Cl)OCC3)cc1]

4-Bromo-7-chloro-6-(4-ethoxybenzyl)-2,3-dihydrobenzofuran (211)

$^1$H NMR (400 MHz, CDCl$_3$) δ 7.09 (d, J=8.8 Hz, 2H), 6.81 (d, J=8.8 Hz, 2H), 6.78 (s, 1H), 4.70 (t, J=8.8 Hz, 2H), 4.00 (q, J=7.2 Hz, 2H), 3.94 (s, 2H), 3.25 (t, J=8.8 Hz, 2H), 1.40 (t, J=7.2 Hz, 3H); [M+H]$^+$ 366.

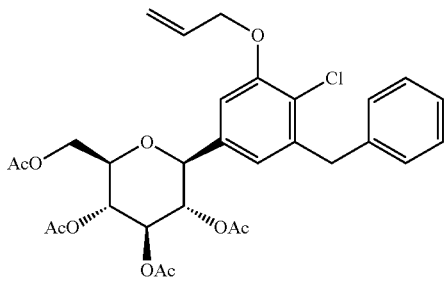 [SMILES: C=CCOc1cc([C@@H]2O[C@H](COC(C)=O)[C@@H](OC(C)=O)[C@H](OC(C)=O)[C@H]2OC(C)=O)cc(Cc2ccccc2)c1Cl]

(2R,3R,4R,5S,6S)-2-(Acetoxymethyl)-6-(3-(allyloxy)-5-benzyl-4-chlorophenyl)tetrahydro-2H-pyran-3,4,5-triyl triacetate (212)

$^1$H NMR (400 MHz, DMSO) δ 7.31-7.27 (m, 2H), 7.22-7.21 (m, 1H), 7.19-7.16 (m, 2H), 7.09 (d, J=1.6 Hz, 1H), 6.88 (d, J=1.6 Hz, 1H), 6.12-6.03 (m, 1H), 5.47 (dq, J=17.6, 2.0 Hz, 1H), 5.35 (t, J=9.6 Hz, 1H), 5.30 (dq, J=10.4, 1.6 Hz, 1H), 5.12 (t, J=9.6 Hz, 1H), 5.06 (t, J=9.6 Hz, 1H), 4.66-4.62 (m, 3H), 4.13-4.03 (m, 5H), 2.04 (s, 3H), 2.03 (s, 3H), 1.95 (s, 3H), 1.70 (s, 3H); [M+Na]$^+$ 611.

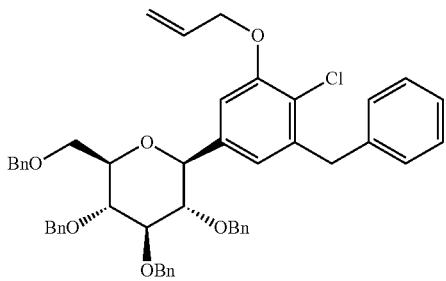 [SMILES: C=CCOc1cc([C@@H]2O[C@H](COCc3ccccc3)[C@@H](OCc3ccccc3)[C@H](OCc3ccccc3)[C@H]2OCc2ccccc2)cc(Cc2ccccc2)c1Cl]

(2S,3S,4R,5R,6R)-2-(3-(Allyloxy)-5-benzyl-4-chlorophenyl)-3,4,5-tris(benzyloxy)-6-((benzyloxy)methyl)tetrahydro-2H-pyran (213)

$^1$H NMR (400 MHz, CDCl$_3$) δ 7.36-7.31 (m, 13H), 7.26-7.19 (m, 10H), 6.94 (d, J=1.6 Hz, 2H), 6.91 (dd, J=14.8, 2.0 Hz, 2H), 6.10-6.00 (m, 1H), 5.46 (dq, J=17.2, 1.6 Hz, 1H), 5.31 (dq, J=10.8, 1.6 Hz, 1H), 4.94 (ABq, J$_{AB}$=15.2 Hz, 2H), 4.90 (d, J=10.8 Hz, 1H), 4.70-4.64 (m, 2H), 4.57 (d, J=12.4 Hz, 1H), 4.52-4.49 (m, 2H), 4.46 (d, J=10.8 Hz, 1H), 4.23-4.16 (m, 2H), 4.08 (d, J=15.2 Hz, 1H), 3.89 (d, J=10.8 Hz, 1H), 3.84-3.75 (m, 4H), 3.61-3.57 (m, 1H), 3.48-3.44 (m, 1H); [M+Na]$^+$ 803.

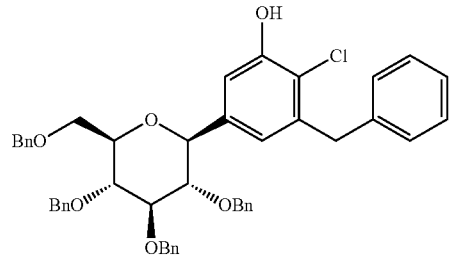 [SMILES: Oc1cc([C@@H]2O[C@H](COCc3ccccc3)[C@@H](OCc3ccccc3)[C@H](OCc3ccccc3)[C@H]2OCc2ccccc2)cc(Cc2ccccc2)c1Cl]

3-Benzyl-2-chloro-5-((2S,3S,4R,5R,6R)-3,4,5-tris(benzyloxy)-6-((benzyloxy)methyl)tetrahydro-2H-pyran-2-yl)phenol (214)

$^1$H NMR (400 MHz, CDCl$_3$) δ 7.37-7.31 (m, 13H), 7.27-7.21 (m, 8H), 7.18-7.16 (m, 2H), 7.08 (d, J=2.0 Hz, 1H), 6.98 (dd, J=7.6, 2.0 Hz, 2H), 6.89 (d, J=2.0 Hz, 1H), 4.93 (ABq, J$_{AB}$=16.0 Hz, 2H), 4.89 (d, J=10.8 Hz, 1H), 4.67 (d, J=4.8 Hz, 1H), 4.64 (d, J=6.0 Hz, 1H), 4.57 (d, J=12.4 Hz, 1H), 4.46 (d, J=10.4 Hz, 1H), 4.19-4.12 (m, 2H), 4.03 (d, J=15.2 Hz, 1H), 3.95 (d, J=10.4 Hz, 1H), 3.82-3.75 (m, 4H), 3.61-3.57 (m, 1H), 3.49-3.45 (m, 1H); [M+Na]$^+$ 763.

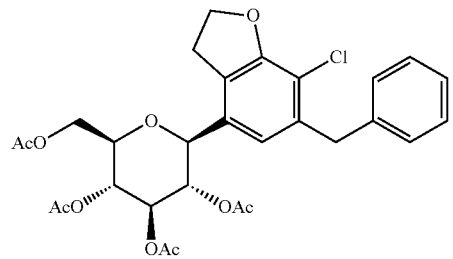 [SMILES: CC(=O)OC[C@H]1O[C@@H](c2cc(Cc3ccccc3)c(Cl)c3c2CCO3)[C@H](OC(C)=O)[C@@H](OC(C)=O)[C@@H]1OC(C)=O]

(2R,3R,4R,5S,6S)-2-(Acetoxymethyl)-6-(6-benzyl-7-chloro-2,3-dihydrobenzofuran-4-yl)tetrahydro-2H-pyran-3,4,5-triyl triacetate (215)

$^1$H NMR (400 MHz, CDCl$_3$) δ 7.32-7.28 (m, 2H), 7.25-7.18 (m, 3H), 6.59 (s, 1H), 5.30 (t, J=9.2 Hz, 2H), 5.19 (t, J=9.6 Hz, 1H), 4.77-4.68 (m, 2H), 4.35-4.32 (m, 1H), 4.31-4.26 (m, 1H), 4.21-4.14 (m, 1H), 4.11 (m, 1H), 4.02 (d, J=15.6 Hz, 1H), 3.83-3.79 (m, 1H), 3.42 (td, J=8.8, 1.6 Hz, 2H), 2.10 (s, 3H), 2.09 (s, 3H), 2.03 (s, 3H), 1.70 (s, 3H); [M+Na]$^+$ 597.

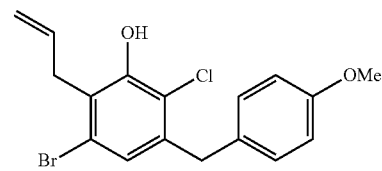 [SMILES: C=CCc1c(Br)cc(Cc2ccc(OC)cc2)c(Cl)c1O]

2-Allyl-3-bromo-6-chloro-5-(4-methoxybenzyl)phenol (216)

A solution of 1-(allyloxy)-5-bromo-2-chloro-3-(4-methoxybenzyl)benzene (1.20 g, 3.26 mmol) in diethylaniline (3 mL) was heated in a sealed tube at 200° C. for 24 h under nitrogen atmosphere. The mixture was cooled to room temperature and quenched by slow addition of 1M HCl (50~100 mL). The mixture was extracted with ethyl acetate (100~150 mL). The organic layer was dried over anhydrous MgSO$_4$, filtered and concentrated in vacuo. The residue was purified by silica gel column chromatography to provide the compound 216 (1.10 g, 2.99 mmol, 92%).

$^1$H NMR (400 MHz, CDCl$_3$) δ 7.10 (d, J=8.8 Hz, 2H), 6.95 (s, 1H), 6.84 (d, J=8.8 Hz, 2H), 5.97-5.87 (m, 1H), 5.10-5.06 (m, 1H), 5.05-5.03 (m, 1H), 3.95 (s, 2H), 3.79 (s, 3H), 3.58 (d, J=6.4 Hz, 2H); [M+H]$^+$ 369.

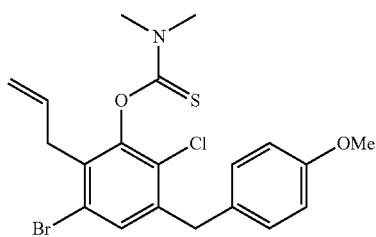 [SMILES: C=CCc1c(Br)cc(Cc2ccc(OC)cc2)c(Cl)c1OC(=S)N(C)C]

O-2-Allyl-3-bromo-6-chloro-5-(4-methoxybenzyl) phenyl dimethylcarbamothioate (217)

To a solution of compound 216 (1.62 g, 4.41 mmol) and N,N'-dimethylcarbamoyl chloride (1.09 g, 8.81 mmol) in CH$_2$Cl$_2$ (15 mL) were added DMAP (0.93 g, 7.64 mmol) and TEA (2.45 mL, 17.6 mmol) at rt. After stirring at 35° C. overnight, the reaction mixture was cooled to rt and quenched with 1M HCl (50 mL). The mixture was extracted with DCM (100 mL). The organic layer was washed with brine, dried over anhydrous MgSO$_4$, filtered and concentrated in vacuo. The residue was purified by silica gel column chromatography to provide the compound 217 (1.82 g, 4.00 mmol, 91%) as a white solid.

$^1$H NMR (400 MHz, CDCl$_3$) δ 7.23 (s, 1H), 7.10 (d, J=8.8 Hz, 2H), 6.85 (d, J=8.8 Hz, 2H), 5.92-5.82 (m, 1H), 5.07-5.05 (m, 1H), 5.04-5.00 (m, 1H), 3.98 (ABq, Δv$_{AB}$=20.8 Hz, J$_{AB}$=15.6 Hz, 2H), 3.79 (s, 3H), 3.56-3.51 (m, 1H), 3.48 (s, 3H), 3.42-3.38 (m, 1H), 3.37 (s, 3H); [M+H]$^+$ 456.

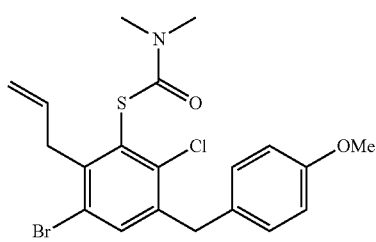 [SMILES: C=CCc1c(Br)cc(Cc2ccc(OC)cc2)c(Cl)c1SC(=O)N(C)C]

S-2-Allyl-3-bromo-6-chloro-5-(4-methoxybenzyl) phenyl dimethylcarbamothioate (218)

A solution of compound 217 (1.70 g, 3.74 mmol) in phenylether (8 mL) was stirred at 240° C. for 24 h under nitrogen atmosphere. The reaction mixture was purified by silica gel column chromatography to provide the compound 218 (1.48 g, 3.25 mmol, 87%).

$^1$H NMR (400 MHz, CDCl$_3$) δ 7.33 (s, 1H), 7.10 (d, J=8.8 Hz, 2H), 6.86 (d, J=8.8 Hz, 2H), 5.91-5.82 (m, 1H), 5.05 (dd, J=10.4, 1.6 Hz, 1H), 5.05 (dd, J=10.4, 1.6 Hz, 1H), 4.96 (dd, J=17.0, 1.8 Hz, 1H), 4.04 (s, 2H), 3.83 (d, J=6.0 Hz, 2H), 3.80 (s, 3H), 3.17 (br s, 3H), 3.03 (br s, 3H); [M+H]$^+$ 456.

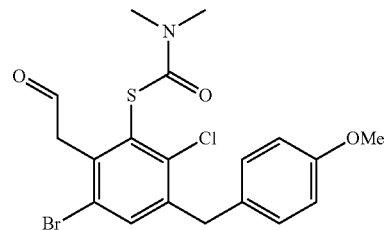 [SMILES: COc1ccc(Cc2cc(Br)c(CC=O)c(SC(=O)N(C)C)c2Cl)cc1]

S-3-Bromo-6-chloro-5-(4-methoxybenzyl)-2-(2-oxoethyl)phenyl dimethylcarbamothioate (219)

To a solution of 218 (1.48 g, 3.25 mmol) in THF/water (15 mL/15 mL) were added NaIO$_4$ (2.78 g, 13.02 mmol) and OsO$_4$ (0.4 mL, 2.5% in isopropanol). After stirring at rt overnight, the reaction was quenched with saturated Na$_2$SO$_3$ solution (20 mL), and the mixture was extracted with ethyl acetate (50 mL×2). The organic layer was washed with brine, dried over anhydrous MgSO$_4$, filtered and concentrated in vacuo. The crude product 219 was dried under high vacuum and used without further purification (1.57 g, 3.44 mmol, 106%).

$^1$H NMR (400 MHz, CDCl$_3$) δ 9.63 (s, 1H), 7.38 (s, 1H), 7.11 (d, J=8.8 Hz, 2H), 6.87 (d, J=8.8 Hz, 2H), 4.19 (d, J=1.2 Hz, 2H), 4.05 (s, 2H), 3.81 (s, 3H), 3.14 (br s, 3H), 3.01 (br s, 3H); [M+Na]$^+$ 480.

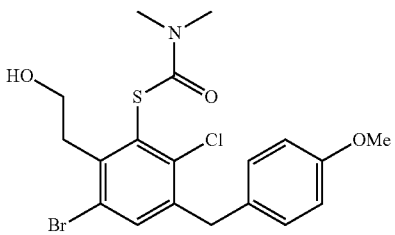 [SMILES: COc1ccc(Cc2cc(Br)c(CCO)c(SC(=O)N(C)C)c2Cl)cc1]

S-3-Bromo-6-chloro-2-(2-hydroxyethyl)-5-(4-methoxybenzyl)phenyl dimethylcarbamothioate (220)

To a solution of compound 219 (1.46 g, 3.18 mmol) in THF/MeOH (70 mL/7 mL) were added NaBH$_4$ (132 mg, 3.50 mmol) at 0° C. under nitrogen atmosphere. After stirring at 0° C. for 2 hrs, the reaction mixture was quenched with saturated NaHCO$_4$ (50 mL) and extracted with ethyl acetate (100 mL×2). The organic layer was washed with brine, dried over anhydrous MgSO$_4$, filtered and concentrated in vacuo. The residue was purified by silica gel column chromatography to provide the compound 220 (1.02 g, 2.22 mmol, 70%).

$^1$H NMR (400 MHz, CDCl$_3$) δ 7.35 (s, 1H), 7.10 (d, J=8.4 Hz, 2H), 6.86 (d, J=8.8 Hz, 2H), 4.03 (s, 2H), 3.84 (t, J=6.6 Hz, 2H), 3.80 (s, 3H), 3.40 (t, J=6.6 Hz, 2H), 3.19 (br s, 3H), 3.04 (br s, 3H); [M+H]$^+$ 460.

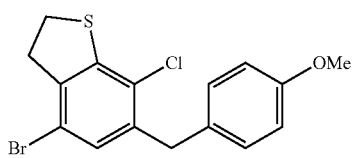 [SMILES: COc1ccc(Cc2cc(Br)c3c(c2Cl)SCC3)cc1]

4-Bromo-7-chloro-6-(4-methoxybenzyl)-2,3-dihydrobenzo[b]thiophene (221)

A mixture of compound 220 (0.96, 2.09 mmol) and KOH (0.70 g, 12.6 mmol) in THF/MeOH (9.6 mL/9.6 mL) was heated in a sealed tube at 60° C. for 4 hrs. After cooling to rt, the reaction mixture was quenched with 1M HCl (40 mL) and extracted with ethyl acetate (50 mL×2). The organic layer was washed with brine, dried over anhydrous MgSO$_4$, filtered and concentrated in vacuo. The residue was purified by silica gel column chromatography to provide the compound 221 (0.65 g, 1.76 mmol, 84%).

$^1$H NMR (400 MHz, CDCl$_3$) δ 7.09 (d, J=8.8 Hz, 2H), 6.93 (s, 1H), 6.84 (d, J=8.8 Hz, 2H), 3.93 (s, 2H), 3.79 (s, 3H), 3.46-3.36 (m, 4H); [M+H]$^+$ 371.

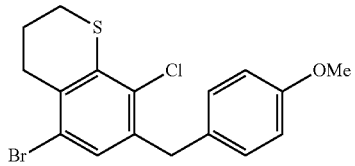 [SMILES: COc1ccc(Cc2cc(Br)c3c(c2Cl)SCCC3)cc1]

5-Bromo-8-chloro-7-(4-methoxybenzyl)thiochroman (222)

$^1$H NMR (400 MHz, CDCl$_3$) δ 7.10 (d, J=8.8 Hz, 2H), 7.08 (s, 1H), 6.84 (d, J=8.4 Hz, 2H), 3.96 (s, 2H), 3.79 (s, 3H), 3.01-2.98 (m, 2H), 2.84 (t, J=6.2 Hz, 2H), 2.15-2.09 (m, 2H); [M+H]$^+$ 385.

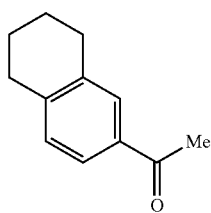 [SMILES: CC(=O)c1ccc2c(c1)CCCC2]

1-(5,6,7,8-Tetrahydronaphthalen-2-yl)ethanone (223)

$^1$H NMR (400 MHz, CDCl$_3$) δ 7.68-7.65 (m, 2H), 7.14 (d, J=8.4 Hz, 1H), 2.84-2.78 (m, 4H), 2.57 (s, 3H), 1.84-1.79 (m, 4H); [M+H]$^+$ 175.

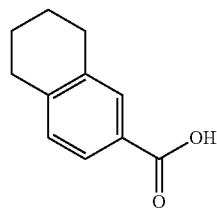 [SMILES: O=C(O)c1ccc2c(c1)CCCC2]

5,6,7,8-Tetrahydronaphthalene-2-carboxylic acid (224)

$^1$H NMR (400 MHz, CDCl$_3$) δ 7.82-7.78 (m, 2H), 7.15 (d, J=7.6 Hz, 1H), 2.86-2.78 (m, 4H), 1.84-1.79 (m, 4H); [M+H]$^+$ 177.

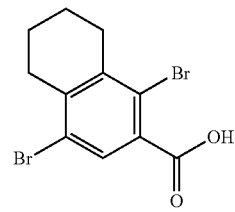 [SMILES: O=C(O)c1cc(Br)c2c(c1Br)CCCC2]

1,4-Dibromo-5,6,7,8-tetrahydronaphthalene-2-carboxylic acid (225)

$^1$H NMR (400 MHz, CDCl$_3$) δ 7.92 (s, 1H), 2.86-2.78 (m, 4H), 1.85-1.79 (m, 4H); [M+H]$^+$ 335.

PREPARATION OF FINAL DERIVATIVES

Example 001

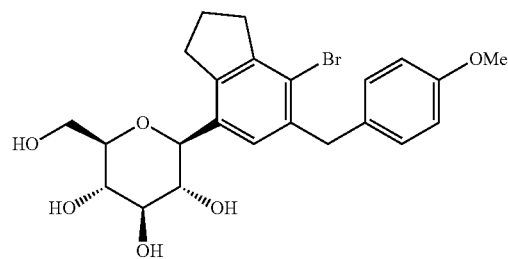

(2S,3R,4R,5S,6R)-2-(7-Bromo-6-(4-methoxybenzyl)-2,3-dihydro-1H-inden-4-yl)-6-(hydroxymethyl)tetrahydro-2H-pyran-3,4,5-triol (E001)

To a solution of compound 15 (0.94 g, 1.85 mmol) in CH$_2$Cl$_2$/CH$_3$CN (8.9 mL/8.9 mL) were added triethylsilane (0.59 mL, 3.7 mmol) and boron trifluoride diethyl etherate (0.46 mL, 3.7 mmol) at −60° C. under nitrogen atmosphere. The mixture was warmed up to −30° C. for 2 h. The reaction mixture was quenched with saturated NaHCO$_3$ solution (15 mL) and extracted with EtOAc (50 mL). The organic layer was washed with brine, dried over anhydrous MgSO$_4$, filtered and concentrated in vacuo. The residue was purified by prep HPLC (reverse phase) to provide the compound E001 (0.15 g, 0.306 mmol, 17%).

¹H NMR (400 MHz, CD₃OD) δ 7.12 (s, 1H), 7.07 (d, J=8.4 Hz, 2H), 6.77 (d, J=8.8 Hz, 2H), 4.19 (d, J=9.2 Hz, 1H), 3.98 (ABq, $\Delta v_{AB}$=15.3 Hz, $J_{AB}$=15.2 Hz, 2H), 3.84 (d, J=10.8 Hz, 1H), 3.72 (s, 3H), 3.66-3.62 (m, 1H), 3.44-3.40 (m, 2H), 3.38-3.32 (m, 2H), 3.22-3.14 (m, 1H), 3.08-3.01 (m, 1H), 2.92 (t, J=7.6 Hz, 2H), 2.06 (m, 2H); [M−OH]⁺ 461.

Example 002

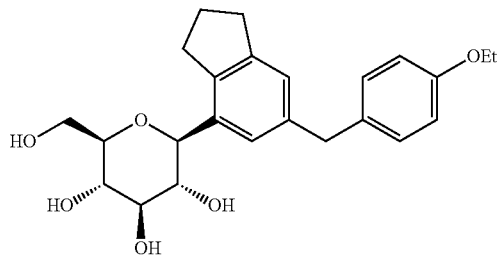 [SMILES: CCOc1ccc(Cc2cc3c(c([C@@H]4O[C@H](CO)[C@@H](O)[C@H](O)[C@H]4O)c2)CCC3)cc1]

(2S,3R,4R,5S,6R)-2-(6-(4-Ethoxybenzyl)-2,3-dihydro-1H-inden-4-yl)-6-(hydroxymethyl)tetrahydro-2H-pyran-3,4,5-triol (E002)

¹H NMR (400 MHz, CD₃OD) δ 7.08-7.03 (m, 3H), 6.93 (s, 1H), 6.76 (d, J=8.4 Hz, 2H), 4.22 (d, J=9.2 Hz, 1H), 3.96 (q, J=6.8 Hz, 2H), 3.86-3.82 (m, 3H), 3.67-3.62 (m, 1H), 3.50 (t, J=8.8 Hz, 1H), 3.46-3.42 (m, 1H), 3.37-3.35 (m, 2H), 3.06-2.97 (m, 1H), 2.94-2.85 (m, 1H), 2.81 (t, J=7.2 Hz, 2H), 2.00 (m, 2H), 1.33 (t, J=6.8 Hz, 3H); [M−OH]⁺ 397.

Example 003

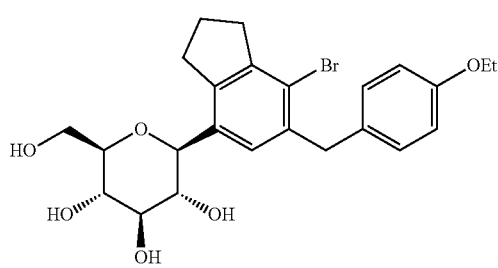

(2S,3R,4R,5S,6R)-2-(7-Bromo-6-(4-ethoxybenzyl)-2,3-dihydro-1H-inden-4-yl)-6-(hydroxymethyl)tetrahydro-2H-pyran-3,4,5-triol (E003)

¹H NMR (400 MHz, CD₃OD) δ 7.12 (s, 1H), 7.06 (d, J=8.4 Hz, 2H), 6.75 (d, J=8.8 Hz, 2H), 4.19 (d, J=9.6 Hz, 1H), 4.00 (ABq, $\Delta v_{AB}$=15.3 Hz, $J_{AB}$=15.2 Hz, 2H), 3.96 (q, J=6.8 Hz, 2H), 3.84 (d, J=11.2 Hz, 1H), 3.66-3.62 (m, 1H), 3.44-3.40 (m, 2H), 3.38-3.33 (m, 2H), 3.22-3.13 (m, 1H), 3.08-3.01 (m, 1H), 2.92 (t, J=7.6 Hz, 2H), 2.06 (m, 2H), 1.33 (t, J=6.8 Hz, 3H); [M−OH]⁺ 475.

Example 004

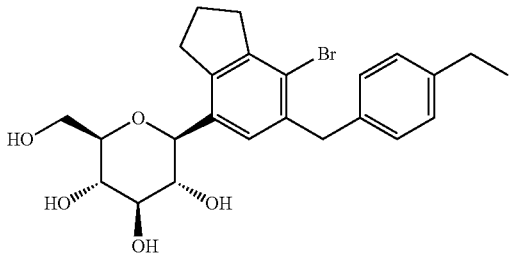

(2S,3R,4R,5S,6R)-2-(7-Bromo-6-(4-ethylbenzyl)-2,3-dihydro-1H-inden-4-yl)-6-(hydroxymethyl)tetrahydro-2H-pyran-3,4,5-triol (E004)

¹H NMR (400 MHz, CD₃OD) δ 7.20 (s, 1H), 7.12 (ABq, $\Delta v_{AB}$=7.4 Hz, $J_{AB}$=8.4 Hz, 4H), 4.26 (d, J=9.2 Hz, 1H), 4.11 (ABq, $\Delta v_{AB}$=14.8 Hz, $J_{AB}$=15.2 Hz, 2H), 3.91 (d, J=11.6 Hz, 1H), 3.73-3.68 (m, 1H), 3.52-3.47 (m, 2H), 3.44-3.40 (m, 2H), 3.29-3.21 (m, 1H), 3.16-3.07 (m, 1H), 3.00 (t, J=7.6 Hz, 2H), 2.63 (t, J=7.6 Hz, 2H), 2.13 (m, 2H), 1.24 (t, J=7.6 Hz, 3H); [M−OH]⁺ 459.

Example 005

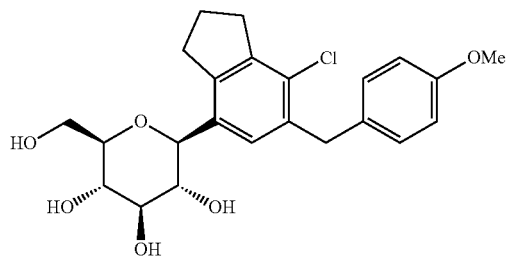

(2S,3R,4R,5S,6R)-2-(7-Chloro-6-(4-methoxybenzyl)-2,3-dihydro-1H-inden-4-yl)-6-(hydroxymethyl)tetrahydro-2H-pyran-3,4,5-triol (E005)

To a solution of compound 18 (0.87 g, 1.09 mmol) in THF/MeOH (8.9 mL/8.9 mL) were added Pd/C (10% Pd, 122 mg). The mixture was stirred at rt under hydrogen atmosphere for 15 h. The catalyst removed by filtration, and then the filtrate was concentrated in vacuo. The residue was purified by prep HPLC (reverse phase) to provide the compound E005 (0.11 g, 0.25 mmol, 23%).

¹H NMR (400 MHz, CD₃OD) δ 7.16 (s, 1H), 7.09 (d, J=8.8 Hz, 2H), 6.79 (d, J=8.8 Hz, 2H), 4.22 (d, J=6.4 Hz, 1H), 3.99 (ABq, $\Delta v_{AB}$=16.5 Hz, $J_{AB}$=15.2 Hz, 2H)), 3.86 (d, J=8.0 Hz, 1H), 3.74 (s, 3H), 3.68-3.63 (m, 1H), 3.48-3.44 (m, 2H), 3.38-3.34 (m, 2H), 3.19-3.11 (m, 1H), 3.06-2.98 (m, 1H), 2.94 (t, J=7.6 Hz, 2H), 2.081 (m, 2H); [M+Na]+ 457.

Example 006

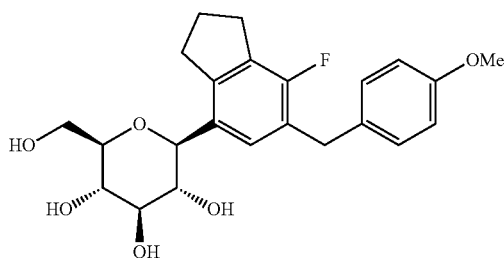 [SMILES: COc1ccc(Cc2cc([C@@H]3O[C@H](CO)[C@@H](O)[C@H](O)[C@H]3O)c3c(c2F)CCC3)cc1]

(2S,3R,4R,5S,6R)-2-(7-Fluoro-6-(4-methoxybenzyl)-2,3-dihydro-1H-inden-4-yl)-6-(hydroxymethyl)tetrahydro-2H-pyran-3,4,5-triol (E006)

$^1$H NMR (400 MHz, CD$_3$OD) δ 7.20-7.08 (m 3H), 6.79 (dt, J=8.0, 2.5 Hz, 2H), 4.20 (d, J=9.2 Hz, 1H), 3.91-3.83 (m, 3H), 3.74 (s, 3H), 3.69-3.63 (m, 1H), 3.48-3.44 (m, 2H), 3.38-3.35 (m, 2H), 3.11-3.04 (m, 1H), 2.99-2.93 (m, 1H), 2.89 (t, J=7.6 Hz, 2H), 2.09 (m, 2H); [M+Na]+ 441.

Example 007

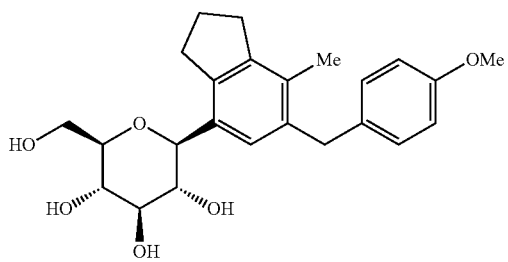

(2R,3S,4R,5R,6S)-2-(Hydroxymethyl)-6-(6-(4-methoxybenzyl)-7-methyl-2,3-dihydro-1H-inden-4-yl)tetrahydro-2H-pyran-3,4,5-triol (E007)

$^1$H NMR (400 MHz, CD$_3$OD) δ 7.05 (s, 1H), 7.00 (d, J=8.8 Hz, 2H), 6.76 (d, J=8.8 Hz, 2H), 4.23 (d, J=9.6 Hz, 1H), 3.90 (s, 2H), 3.86 (d, J=12.0 Hz, 1H), 3.72 (s, 1H), 3.68-3.64 (m, 1H), 3.54 (t, J=8.8 Hz, 1H), 3.49-3.44 (m, 1H), 3.39-3.35 (m, 2H), 3.11-3.03 (m, 1H), 3.00-2.92 (m, 1H), 2.82 (t, J=7.6 Hz, 2H), 2.08-2.00 (m, 5H); [M+Na]+ 437.

Example 008

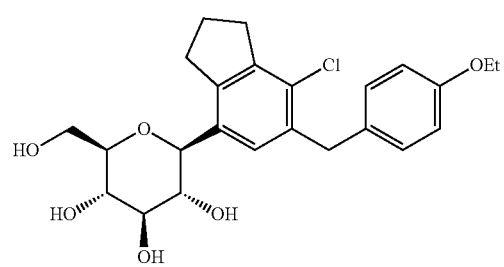 [SMILES: CCOc1ccc(Cc2cc([C@@H]3O[C@H](CO)[C@@H](O)[C@H](O)[C@H]3O)c3c(c2Cl)CCC3)cc1]

(2S,3R,4R,5S,6R)-2-(7-Chloro-6-(4-ethoxybenzyl)-2,3-dihydro-1H-inden-4-yl)-6-(hydroxymethyl)tetrahydro-2H-pyran-3,4,5-triol (E008)

$^1$H NMR (400 MHz, CD$_3$OD) δ 7.16 (s, 1H), 7.08 (d, J=8.8 Hz, 2H), 6.77 (d, J=8.8 Hz, 2H), 4.21 (d, J=9.6 Hz, 1H), 4.04-3.94 (m, 4H), 3.87 (d, J=11.2 Hz, 1H), 3.69-3.63 (m, 1H), 3.48-3.43 (m, 2H), 3.38-3.34 (m, 2H), 3.19-3.11 (m, 1H), 3.06-2.98 (m, 1H), 2.94 (t, J=7.2 Hz, 2H), 2.082 (m, 2H), 1.35 (t, J=6.8 Hz, 3H); [M+Na]+ 471.

Example 009

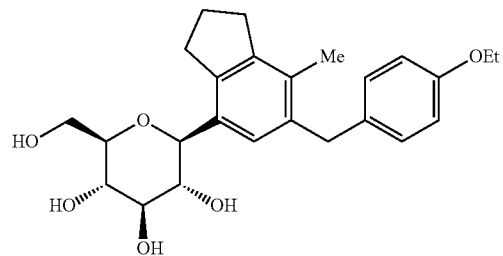 [SMILES: CCOc1ccc(Cc2cc([C@@H]3O[C@H](CO)[C@@H](O)[C@H](O)[C@H]3O)c3c(c2C)CCC3)cc1]

(2S,3R,4R,5S,6R)-2-(6-(4-Ethoxybenzyl)-7-methyl-2,3-dihydro-1H-inden-4-yl)-6-(hydroxymethyl)tetrahydro-2H-pyran-3,4,5-triol (E009)

$^1$H NMR (400 MHz, CD$_3$OD) δ 7.06 (s, 1H), 7.00 (d, J=8.8 Hz, 2H), 6.76 (d, J=8.8 Hz, 2H), 4.24 (d, J=9.2 Hz, 1H), 3.97 (q, J=6.8 Hz, 2H), 3.91 (s, 2H), 3.88 (d, J=12.4 Hz, 1H), 3.69-3.64 (m, 1H), 3.55 (t, J=8.8 Hz, 1H), 3.50-3.45 (m, 1H), 3.40-3.36 (m, 2H), 3.13-3.04 (m, 1H), 3.01-2.93 (m, 1H), 2.83 (t, J=7.2 Hz, 2H), 2.09-2.02 (m, 5H), 1.35 (t, J=7.2 Hz, 3H); [M+H]+ 451.

Example 010

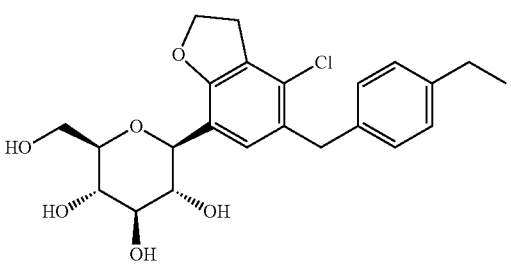 [SMILES: CCc1ccc(Cc2cc([C@@H]3O[C@H](CO)[C@@H](O)[C@H](O)[C@H]3O)c3c(c2Cl)CCO3)cc1]

(2S,3R,4R,5S,6R)-2-(4-Chloro-5-(4-ethylbenzyl)-2,3-dihydrobenzofuran-7-yl)-6-(hydroxymethyl)tetrahydro-2H-pyran-3,4,5-triol (E010)

To a solution of compound 35 (1.03 g, 1.30 mmol) in THF/MeOH (30 mL/30 mL) was added Pd/C (10% Pd, 154 mg). The mixture was stirred at rt under hydrogen atmosphere for 15 h. The catalyst removed by filtration, and then the filtrate was concentrated in vacuo. The residue was purified by prep HPLC (reverse phase) to provide the compound E010 (0.28 g, 0.64 mmol, 49%).

$^1$H NMR (400 MHz, CD$_3$OD) δ 7.12 (s, 1H), 7.07 (s, 4H), 4.61 (sext, J=8.8 Hz, 2H), 4.30 (d, J=9.6 Hz, 1H), 3.97 (ABq, Δν$_{AB}$=9.6 Hz, J$_{AB}$=15.2 Hz, 2H), 3.84 (dd, J=12.0, 1.6 Hz, 1H), 3.67-3.62 (m, 1H), 3.59 (t, J=14.8 Hz, 1H), 3.45-3.39 (m, 1H), 3.37-3.40 (m, 2H), 3.23 (t, J=8.4 Hz, 2H), 2.58 (q, J=7.6 Hz, 2H), 1.19 (t, J=7.6 Hz, 3H); [M+Na]$^+$ 457.

Example 011

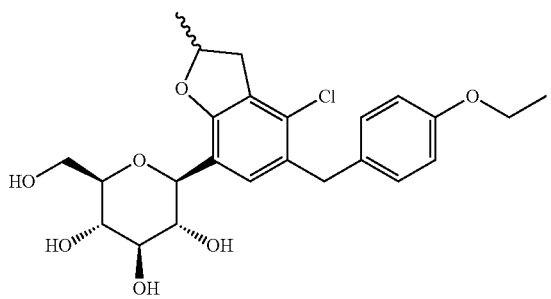 [SMILES: CCOc1ccc(Cc2cc([C@@H]3O[C@H](CO)[C@@H](O)[C@H](O)[C@H]3O)c3c(c2Cl)CC(C)O3)cc1]

(2S,3R,4R,5S,6R)-2-(4-Chloro-5-(4-ethoxybenzyl)-2-methyl-2,3-dihydrobenzofuran-7-yl)-6-(hydroxymethyl)tetrahydro-2H-pyran-3,4,5-triol (E011)

To a solution of bromide 90 (2.38 g, 6.24 mmol) in toluene/THF (30 mL/15 mL) at −78° C. under an atmosphere of nitrogen was added dropwise n-butyllithium (2.5 M in hexanes, 2.5 mL, 6.24 mmol), and the mixture was stirred for 40 min at the same temperature. Then a solution of TMS-protected gluconolactone (2.30 g, 4.80 mmol) in toluene (15 mL) was added dropwise, and the mixture was stirred for 2 hours at −78° C. The reaction mixture was quenched by addition of aqueous saturated ammonium chloride (50 mL). After complete addition, the solution was gradually raised to room temperature. The reaction mixture was stirred at r.t. for 1 hour. The organic layer was separated and the aqueous layer was extracted with EtOAc (50 mL). The combined organic layers were washed with brine, dried over anhydrous MgSO$_4$, filtered and concentrated in vacuo to yield the compound (3R,4S,5R,6R)-2-(4-chloro-5-(4-ethoxybenzyl)-2-methyl-2,3-dihydrobenzofuran-7-yl)-3,4,5-tris(trimethylsilyloxy)-6-((trimethylsilyloxy)methyl)tetrahydro-2H-pyran-2-ol, which was carried on to the next step without further purification (4.46 g).

To a solution of the crude alcohol (4.46 g, 5.79 mmol) in THF (50 mL) were added CH$_3$SO$_3$H (0.6 N in MeOH, 18 mL, 10.4 mmol) at −78° C. The mixture was allowed to slowly warm to −30° C. To a mixture was added aq. saturated NaHCO$_3$ solution (50 mL) to quench the reaction. After dilution with water, the mixture was stirred at room temperature for 30 min and extracted with EtOAc (100 mL×2). The organic layer was dried over anhydrous MgSO$_4$, filtered and concentrated in vacuo. The crude (3R,4S,5S,6R)-2-(4-chloro-5-(4-ethoxybenzyl)-2-methyl-2,3-dihydrobenzofuran-7-yl)-6-(hydroxymethyl)-2-methoxytetrahydro-2H-pyran-3,4,5-triol (2.52 g) was carried on to the next step without further purification. To a solution of the triol compound (2.52 g) in CH$_2$Cl$_2$/CH$_3$CN (25 mL/25 mL) were added triethylsilane (1.7 mL, 10.2 mmol) and boron trifluoride diethyl etherate (1.3 mL, 10.2 mmol) at −60° C. The mixture was allowed to slowly warm to −10° C. To a mixture was added aq. saturated NaHCO$_3$ solution (20 mL) to quench the reaction. The reaction mixture was stirred at r.t. and evaporated in vacuo to remove CH$_2$Cl$_2$ and CH$_3$CN. The mixture was extracted with EtOAc (100 mL×2). The combined organic layer was dried over MgSO$_4$, filtered, and concentrated in vacuo. The residue was purified using reverse phase preparative HPLC to provide the title compound E011 (81 mg, 2.8% (3-steps)).

$^1$H NMR (400 MHz, CD$_3$OD) δ 7.11 (d, J=3.5 Hz, 1H), 7.07 (d, J=8.6 Hz, 2H), 6.77 (d, J=8.6 Hz, 2H), 5.04-4.95 (m, 1H), 4.83 (s, 4H), 4.31 (t, J=8.6 Hz, 1H), 3.98 (q, J=7.0 Hz, 2H), 3.96-3.81 (m, 3H), 3.69-3.62 (m, 1H), 3.59-3.53 (m, 1H), 3.49-3.25 (m, 4H), 2.81 (dd, J=16.0 Hz, 7.4 Hz, 2H), 1.45 (t, J=6.2 Hz, 3H), 1.35 (t, J=7.0 Hz, 3H); [M+NH$_4$]$^+$ 482

Example 012

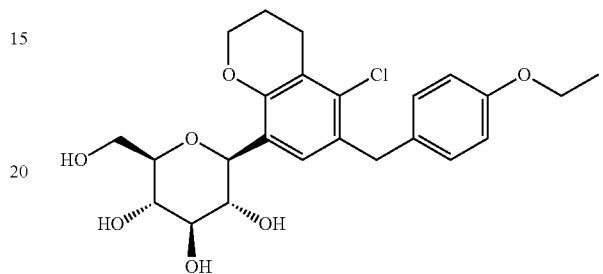

(2S,3R,4R,5S,6R)-2-(5-Chloro-6-(4-ethoxybenzyl)chroman-8-yl)-6-(hydroxymethyl)tetrahydro-2H-pyran-3,4,5-triol (E012)

To a solution of compound 30 (255 mg, 0.309 mmol) in THF/MeOH (15 mL/15 mL) was added 10% Pd/C (71 mg) at rt. The reaction mixture was stirred at r.t. for 15 hours under hydrogen and filtered off. The filtrate was concentrated in vacuo and the residue was purified using reverse phase preparative HPLC to provide the title compound E012 (51 mg, 36%).

$^1$H NMR (400 MHz, CD$_3$OD) δ 7.19 (s, 1H), 7.06 (d, J=8.8 Hz, 2H), 6.77 (d, J=8.7 Hz, 2H), 4.90 (s, 4H), 4.66-4.55 (m, 1H), 4.19-4.06 (m, 2H), 3.98 (q, J=7.0 Hz, 2H), 3.93 (ABq, Δν$_{AB}$=10.4 Hz, J$_{AB}$=15.2 Hz, 2H), 3.84 (d, J=10.6 Hz, 1H), 3.69-3.61 (m, 1H), 3.50-3.43 (m, 2H), 3.41-3.32 (m, 2H), 2.79 (t, J=6.6 Hz, 2H), 2.05-1.96 (m, 2H), 1.35 (t, J=7.0 Hz, 3H); [M+Na]$^+$ 487.

Example 013

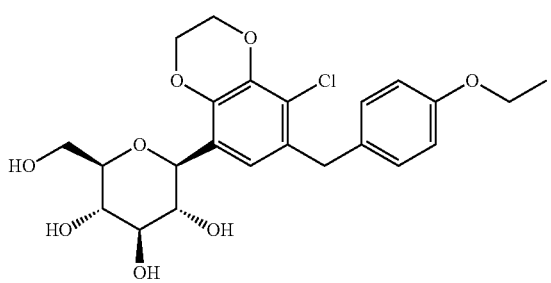

(2S,3R,4R,5S,6R)-2-(8-Chloro-7-(4-ethoxybenzyl)-2,3-dihydrobenzo[b][1,4]dioxin-5-yl)-6-(hydroxymethyl)tetrahydro-2H-pyran-3,4,5-triol (E013)

To a solution of compound 86 (509 mg, 0.615 mmol) in THF/MeOH (10 mL/10 mL) was added 10% Pd/C (77 mg) at r.t. The reaction mixture was stirred at r.t. for 15 hours under hydrogen and filtered off. The filtrate was concentrated in vacuo and the residue was purified using reverse phase preparative HPLC to provide the title compound E013 (75 mg, 10%).

$^1$H NMR (400 MHz, CD$_3$OD) δ 7.09 (d, J=8.8 Hz, 2H), 6.95 (s, 1H), 6.80 (d, J=8.7 Hz, 2H), 4.88 (s, 4H), 4.63-4.55 (m, 1H), 4.37-4.33 (m, 2H), 4.31-4.25 (m, 2H), 4.00 (q, J=7.0 Hz, 2H), 3.96 (ABq, Δv$_{AB}$=13.3 Hz, J$_{AB}$=15.2 Hz, 2H), 3.87 (d, J=11.0 Hz, 1H), 3.73-3.63 (m, 1H), 3.53-3.44 (m, 2H), 3.41-3.36 (m, 2H), 1.38 (t, J=7.0 Hz, 3H); [M+Na]$^+$ 489.

Example 014

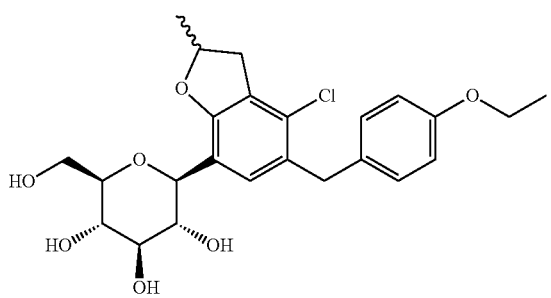 [SMILES: CCOc1ccc(Cc2cc([C@@H]3O[C@H](CO)[C@@H](O)[C@H](O)[C@H]3O)c3c(c2Cl)CC(C)O3)cc1]

(2S,3R,4R,5S,6R)-2-(4-Chloro-5-(4-ethoxybenzyl)-2-methyl-2,3-dihydrobenzofuran-7-yl)-6-(hydroxymethyl)tetrahydro-2H-pyran-3,4,5-triol (E014)

$^1$H NMR (400 MHz, CD$_3$OD) δ 7.11 (d, J=3.5 Hz, 1H), 7.07 (d, J=8.6 Hz, 2H), 6.77 (d, J=8.6 Hz, 2H), 5.04-4.95 (m, 1H), 4.83 (s, 4H), 4.31 (t, J=8.6 Hz, 1H), 3.98 (q, J=7.0 Hz, 2H), 3.96-3.81 (m, 3H), 3.69-3.62 (m, 1H), 3.59-3.53 (m, 1H), 3.49-3.25 (m, 4H), 2.81 (dd, J=16.0 Hz, 7.4 Hz, 2H), 1.45 (t, J=6.2 Hz, 3H), 1.35 (t, J=7.0 Hz, 3H); [M+NH$_4$]$^+$ 482.

Example 015

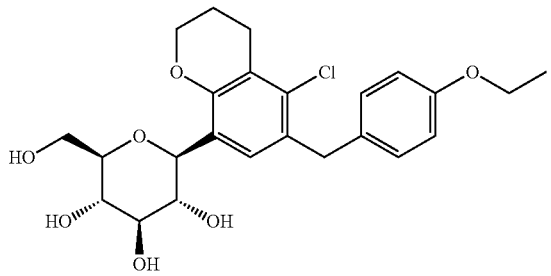

(2S,3R,4R,5S,6R)-2-(5-Chloro-6-(4-ethoxybenzyl)chroman-8-yl)-6-(hydroxymethyl)tetrahydro-2H-pyran-3,4,5-triol (E015)

$^1$H NMR (400 MHz, CD$_3$OD) δ 7.19 (s, 1H), 7.06 (d, J=8.8 Hz, 2H), 6.77 (d, J=8.7 Hz, 2H), 4.90 (s, 4H), 4.66-4.55 (m, 1H), 4.19-4.06 (m, 2H), 3.98 (q, J=7.0 Hz, 2H), 3.93 (ABq, Δv$_{AB}$=13.3 Hz, J$_{AB}$=15.2 Hz, 2H), 3.84 (d, J=10.6 Hz, 1H), 3.69-3.61 (m, 1H), 3.50-3.43 (m, 2H), 3.41-3.32 (m, 2H), 2.79 (t, J=6.6 Hz, 2H), 2.05-1.96 (m, 2H), 1.35 (t, J=7.0 Hz, 3H); [M+Na]$^+$ 487.

Example 016

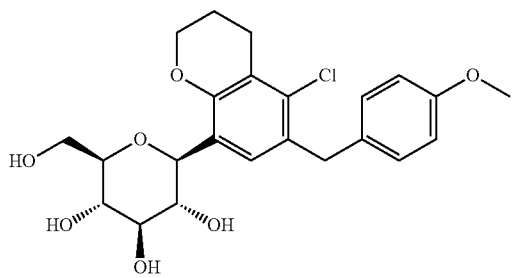

(2S,3R,4R,5S,6R)-2-(5-Chloro-6-(4-methoxybenzyl)chroman-8-yl)-6-(hydroxymethyl)tetrahydro-2H-pyran-3,4,5-triol (E016)

$^1$H NMR (400 MHz, CD$_3$OD) δ 7.19 (s, 1H), 7.08 (d, J=8.8 Hz, 2H), 6.79 (d, J=8.7 Hz, 2H), 4.87 (s, 4H), 4.64-4.57 (m, 1H), 4.21-4.07 (m, 2H), 3.96 (ABq, Δv$_{AB}$=13.3 Hz, J$_{AB}$=15.2 Hz, 2H), 3.84 (d, J=10.4 Hz, 1H), 3.75 (s, 3H), 3.71-3.60 (m, 1H), 3.49-3.42 (m, 2H), 3.38-3.33 (m, 2H), 2.79 (t, J=6.6 Hz, 2H), 2.04-1.96 (m, 2H); [M+Na]$^+$ 473.

Example 017

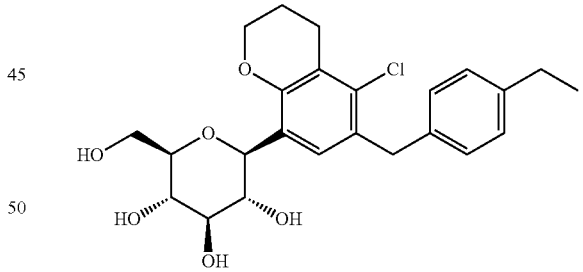

(2S,3R,4R,5S,6R)-2-(5-Chloro-6-(4-ethylbenzyl)chroman-8-yl)-6-(hydroxymethyl)tetrahydro-2H-pyran-3,4,5-triol (E017)

$^1$H NMR (400 MHz, CD$_3$OD) δ 7.23 (s, 1H), 7.09 (s, 4H), 4.92 (s, 4H), 4.68-4.61 (m, 1H), 4.24-4.11 (m, 2H), 4.02 (ABq, Δv$_{AB}$=11.8 Hz, J$_{AB}$=15.1 Hz, 2H), 3.87 (d, J=10.6 Hz, 1H), 3.73-3.62 (m, 1H), 3.53-3.47 (m, 2H), 3.43-3.31 (m, 2H), 2.82 (t, J=6.6 Hz, 2H), 2.60 (q, J=7.6 Hz, 2H), 2.07-2.01 (m, 2H), 1.22 (t, J=7.6 Hz, 3H); [M+Na]$^+$ 471.

Example 019

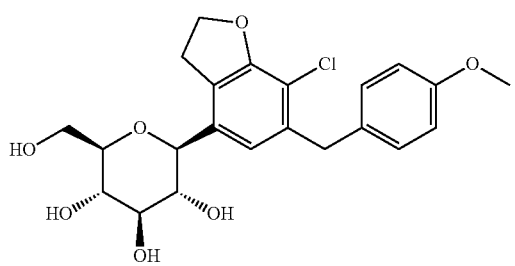 [SMILES: COc1ccc(Cc2cc([C@@H]3O[C@H](CO)[C@@H](O)[C@H](O)[C@H]3O)c3c(c2Cl)OCC3)cc1]

(2S,3R,4R,5S,6R)-2-(7-Chloro-6-(4-methoxybenzyl)-2,3-dihydrobenzofuran-4-yl)-6-(hydroxymethyl)tetrahydro-2H-pyran-3,4,5-triol (E019)

A suspension of compound 68 (340 mg, 0.48 mmol) and Pd/C (10% wt., 45 mg) in THF (4.0 mL) and MeOH (2.0 mL) was stirred at room temperature under an atmosphere of $H_2$ for 24 hours. The mixture was filtered through a Celite pad and concentrated in vacuo. The residue was purified by prep HPLC (C18) to afford the product E019 (15 mg, 7%) as a white solid.

$^1$H NMR (400 MHz, CDCl$_3$) δ 7.11-7.09 (m, 2H), 6.84 (s, 1H), 6.81-6.79 (m, 2H), 4.62 (t, J=8.6 Hz, 2H), 4.14 (d, J=9.2 Hz, 1H), 3.97 (ABq, Δv$_{AB}$=17.9 Hz, J$_{AB}$=14.8 Hz, 2H), 3.88 (dd, J=11.8, 1.4 Hz, 1H), 3.75 (s, 3H), 3.70-3.65 (m, 1H), 3.49-3.35 (m, 5H); [M+Na]$^+$ 459.

Example 020

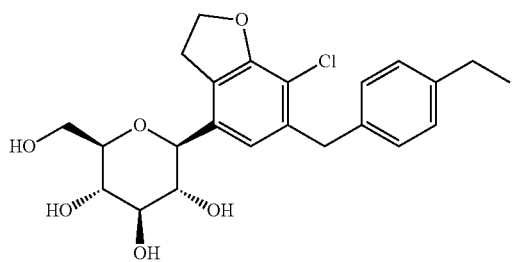

(2S,3R,4R,5S,6R)-2-(6-(4-Ethylbenzyl)-7-chloro-2,3-dihydrobenzofuran-4-yl)-6-(hydroxymethyl)-tetrahydro-2H-pyran-3,4,5-triol (E020)

A suspension of compound 72 (490 mg, 0.61 mmol) and Pd/C (10% wt., 74 mg) in THF (4 mL) and MeOH (2 mL) was stirred at room temperature under an atmosphere of $H_2$ for 14 hours. The mixture was filtered through a Celite pad and concentrated in vacuo. The residue was purified by prep HPLC (C18) to afford the product E020 (25 mg, 8%) as a brown solid.

$^1$H NMR (400 MHz, CDCl$_3$) δ 7.07 (dd, J=10.2, 8.6 Hz, 4H), 6.85 (s, 1H), 4.61 (t, J=8.8 Hz, 2H), 4.14 (d, J=9.2 Hz, 1H), 4.00 (ABq, Δv$_{AB}$=18.5 Hz, J$_{AB}$=15.0 Hz, 2H), 3.87 (dd, J=12.0, 1.2 Hz, 1H), 3.69-3.65 (m, 1H) 3.49-3.35 (m, 5H), 2.58 (q, J=7.6 Hz, 2H), 1.19 (t, J=7.6 Hz, 3H); [M+Na]$^+$ 457.

Example 021

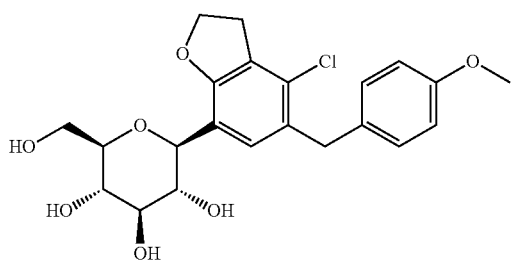

(2S,3R,4R,5S,6R)-2-(4-Chloro-5-(4-methoxybenzyl)-2,3-dihydrobenzofuran-7-yl)-6-(hydroxymethyl)tetrahydro-2H-pyran-3,4,5-triol (E021)

A suspension of compound 50 (407 mg, 0.51 mmol) and Pd/C (10% wt., 50 mg) in THF (5.0 mL) and MeOH (2.5 mL) was stirred at room temperature under an atmosphere of $H_2$ for 24 hours. The mixture was filtered through a Celite pad and concentrated in vacuo. The residue was purified by prep HPLC (C18) to afford the product E021 (65 mg, 27%) as a white solid.

$^1$H NMR (400 MHz, DMSO-d$_6$) δ 7.12 (s, 1H), 7.04 (dt, J=8.2, 2.4 Hz, 2H), 6.79 (dt, J=8.2, 2.4 Hz, 2H), 4.65-4.54 (m, 2H), 4.31 (d, J=9.6 Hz, 1H), 3.94 (ABq, Δv$_{AB}$=10.4 Hz, J$_{AB}$=15.2 Hz, 2H), 3.85 (dd, J=11.8, 1.8 Hz, 1H), 3.76 (s, 3H), 3.68-3.57 (m, 2H), 3.46-3.35 (m, 3H), 3.21 (t, J=8.6 Hz, 2H); [M+Na]$^+$ 459.

Example 022

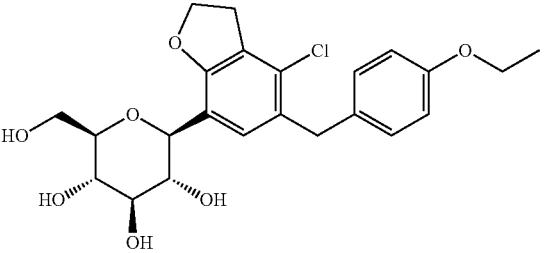 [SMILES: CCOc1ccc(Cc2cc([C@@H]3O[C@H](CO)[C@@H](O)[C@H](O)[C@H]3O)c3c(c2Cl)CCO3)cc1]

(2S,3R,4R,5S,6R)-2-(4-Chloro-5-(4-ethoxybenzyl)-2,3-dihydrobenzofuran-7-yl)-6-(hydroxymethyl)tetrahydro-2H-pyran-3,4,5-triol (E022)

$^1$H NMR (400 MHz, DMSO-d$_6$) δ 7.12 (s, 1H), 7.08 (d, J=8.8 Hz, 2H), 6.79 (d, J=8.8 Hz, 2H), 4.66-4.55 (m, 2H), 4.31 (d, J=9.6 Hz, 1H), 4.01-3.94 (m, 4H), 3.87-3.84 (m, 1H), 3.68-3.58 (m, 2H), 3.45-3.37 (m, 3H), 3.2 (t, J=8.6 Hz, 2H), 1.36 (t, J=7.0 Hz, 3H); [M+Na]$^+$ 473.

Example 023

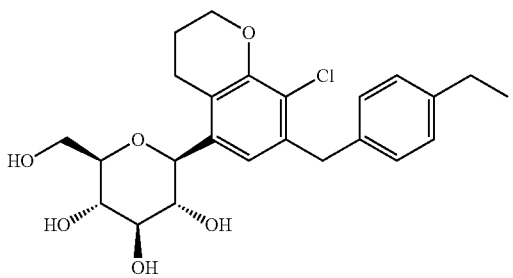

(2S,3R,4R,5S,6R)-2-(8-Chloro-7-(4-ethylbenzyl)chroman-5-yl)-6-(hydroxymethyl)tetrahydro-2H-pyran-3,4,5-triol (E023)

A suspension of 84 (170 mg, 0.21 mmol) and Pd/C (10 wt. %, 25.5 mg) in THF (2.0 mL) and MeOH (1.0 mL) was stirred at room temperature for 6 hours under atmosphere of $H_2$. The mixture was filtered through a Celite pad and concentrated in vacuo. The residue was purified by a prep HPLC to provide the product E023 (28 mg, 28%) as a white solid.

$^1$H NMR (400 MHz, CDCl$_3$) δ 7.07 (ABq, Δν$_{AB}$=7.4 Hz, J$_{AB}$=8.4 Hz, 2H), 6.98 (s, 1H), 4.38-4.36 (m, 1H), 4.22-4.18 (m, 2H), 4.02 (ABq, Δν$_{AB}$=7.2 Hz, J$_{AB}$=15.4 Hz, 2H), 3.86 (d, J=12.2 Hz, 1H), 3.65 (dd, J=12.2, 5.2 Hz, 1H), 3.52-3.45 (m, 2H), 3.41-3.34 (m, 2H), 3.03-2.82 (m, 2H), 2.58 (q, J=7.6 Hz, 2H), 2.00-1.98 (m, 2H), 1.19 (t, J=7.6 Hz, 3H); [M+Na]$^+$ 471.

Example 024

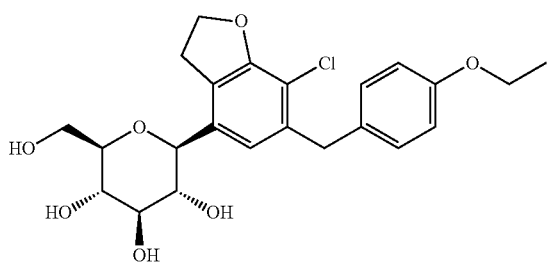

(2S,3R,4R,5S,6R)-2-(7-Chloro-6-(4-ethoxybenzyl)-2,3-dihydrobenzofuran-4-yl)-6-(hydroxymethyl)tetrahydro-2H-pyran-3,4,5-triol (E024)

A suspension of compound 81 (2.0 g, 2.46 mmol) and Pd/C (10% wt., 200 mg) in THF (12 mL) and MeOH (12 mL) was stirred at room temperature under an atmosphere of $H_2$ for 16 hours. The mixture was filtered through a Celite pad and concentrated in vacuo. The residue was purified by prep HPLC (C18) to afford the product E024 (514 mg, 46%).

$^1$H NMR (400 MHz, CD$_3$OD) δ 7.06 (dd, J=6.8, 2.0 Hz, 2H), 6.82 (s, 1H), 6.76 (dd, J=6.8, 2.0 Hz, 2H), 4.59 (t, J=8.8, Hz, 2H), 4.11 (d, J=9.2, Hz, 1H), 3.99-3.93 (m, 4H), 3.89-3.83 (m, 1H), 3.67-3.62 (m, 1H), 3.47-3.37 (m, 4H), 3.37-3.33 (m, 2H), 1.33 (t, J=7.2 Hz, 3H); [M+Na]$^+$ 473.

Example 025

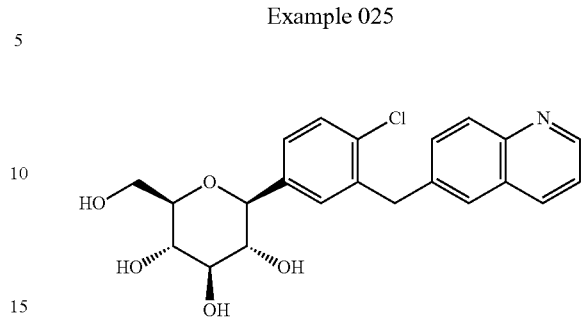

(2S,3R,4R,5S,6R)-2-(4-Chloro-3-(quinolin-6-ylmethyl)phenyl)-6-(hydroxymethyl)tetrahydro-2H-pyran-3,4,5-triol (E025)

$^1$H NMR (400 MHz, CD$_3$OD) δ 8.77 (dd, J=4.4, 1.6 Hz, 1H), 8.27 (t, J=8.4 Hz, 1H), 7.94 (t, J=8.4 Hz, 1H), 7.72-7.66 (m, 2H), 7.52-7.32 (m, 4H), 4.33 (ABq, Δν$_{AB}$=10.5 Hz, J$_{AB}$=15.6 Hz, 2H), 4.12 (d, J=9.2 Hz, 1H), 3.87 (d, J=10.4 Hz, 1H), 3.73-3.67 (m, 1H), 3.48-3.38 (m, 4H); [M+H]$^+$ 416.

Example 026

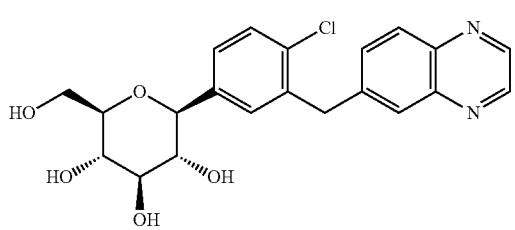

(2S,3R,4R,5S,6R)-2-(4-Chloro-3-(quinoxalin-6-ylmethyl)phenyl)-6-(hydroxymethyl)tetrahydro-2H-pyran-3,4,5-triol (E026)

$^1$H NMR (400 MHz, CD$_3$OD) δ 8.82 (s, 2H), 8.0 (dd, J=4.0, 3.2 Hz, 1H), 7.82-7.72 (m, 2H), 7.51 (dd, J=2.8, 2.0 Hz, 1H), 7.45-7.34 (m, 2H), 4.33 (ABq, Δν$_{AB}$=9.8 Hz, J$_{AB}$=15.6 Hz, 2H), 4.14 (d, J=9.6 Hz, 1H), 3.89-3.85 (m, 1H), 3.73-3.67 (m, 1H), 3.48-3.39 (m, 4H); [M+H]$^+$ 417.

Example 029

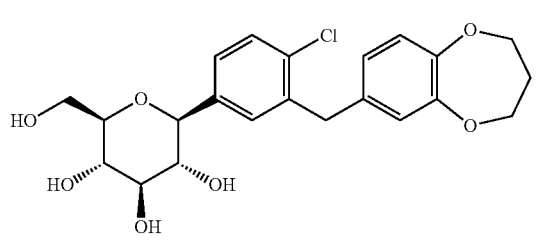

(2S,3R,4R,5S,6R)-2-(4-Chloro-3-((3,4-dihydro-2H-benzo[b][1,4]dioxepin-7-yl)methyl)phenyl)-6-(hydroxymethyl)tetrahydro-2H-pyran-3,4,5-triol (E029)

$^1$H NMR (400 MHz, CD$_3$OD) δ 7.38-7.36 (m, 2H), 7.31 (dd, J=8.0, 3.0 Hz, 1H), 6.87-6.85 (m, 1H), 6.80-6.78 (m, 2H), 4.14-4.11 (m, 5H), 4.02 (ABq, Δν$_{AB}$=18.0 Hz, J$_{AB}$=15.0 Hz, 2H), 3.92-3.88 (m, 1H), 3.74-3.67 (m, 1H), 3.50-3.41 (m, 4H), 2.14 (quint, J=5.6 Hz, 2H); [M+NH$_4$]$^+$ 454.

Example 030

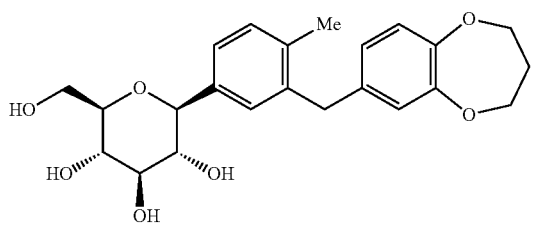

(2S,3R,4R,5S,6R)-2-(3-((3,4-Dihydro-2H-benzo[b][1,4]dioxepin-7-yl)methyl)-4-methylphenyl)-6-(hydroxymethyl)tetrahydro-2H-pyran-3,4,5-triol (E030)

$^1$H NMR (400 MHz, CD$_3$OD) δ 7.24-7.22 (m, 2H), 7.16-7.14 (m, 1H), 6.85 (d, J=8.0 Hz, 1H), 6.74-6.70 (m, 2H), 4.13-4.10 (m, 5H), 3.92-3.89 (m, 3H), 3.74-3.67 (m, 1H), 3.52-3.42 (m, 4H), 2.21 (s, 3H), 2.14 (quint, J=5.2 Hz, 2H); [M+Na]$^+$ 439.

Example 031

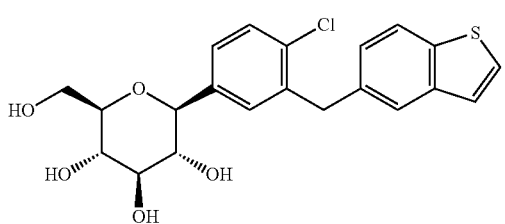 [SMILES: OC[C@H]1O[C@@H](c2ccc(Cl)c(Cc3ccc4sccc4c3)c2)[C@H](O)[C@@H](O)[C@@H]1O]

(2S,3R,4R,5S,6R)-2-(3-(Benzo[b]thiophen-5-ylmethyl)-4-chlorophenyl)-6-(hydroxymethyl)tetrahydro-2H-pyran-3,4,5-triol (E031)

$^1$H NMR (400 MHz, CD$_3$OD) δ 7.81 (d, J=8.0 Hz, 1H), 7.66 (s, 1H), 7.53 (d, J=5.6 Hz, 1H), 7.41-7.39 (m, 2H), 7.34-7.29 (m, 2H), 7.26-7.23 (m, 1H), 4.26 (ABq, Δν$_{AB}$=17.4 Hz, J$_{AB}$=15.0 Hz, 2H), 4.12 (d, J=9.2 Hz, 1H), 3.91-3.88 (m, 1H), 3.73-3.68 (m, 1H), 3.49-3.40 (m, 4H); [M+NH$_4$]$^+$ 438.

Example 032

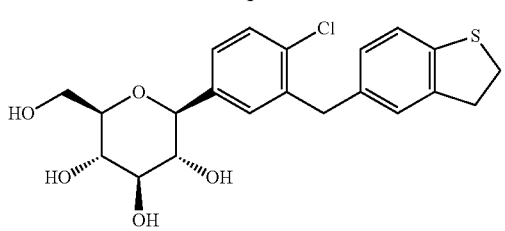

(2S,3R,4R,5S,6R)-2-(4-Chloro-3-((2,3-dihydrobenzo[b]thiophen-5-yl)methyl)phenyl)-6-(hydroxymethyl)tetrahydro-2H-pyran-3,4,5-triol (E032)

$^1$H NMR (400 MHz, CD$_3$OD) δ 7.33-7.30 (m, 2H), 7.27-7.24 (m, 1H), 7.03-7.01 (m, 2H), 6.93-6.89 (m, 2H), 4.08-4.03 (m, 2H), 4.01-3.95 (m, 3H), 3.87-3.83 (m, 1H), 3.70-3.64 (m, 1H), 3.45-3.35 (m, 4H), 3.18-3.14 (m, 2H); [M+Na]$^+$ 445.

Example 033

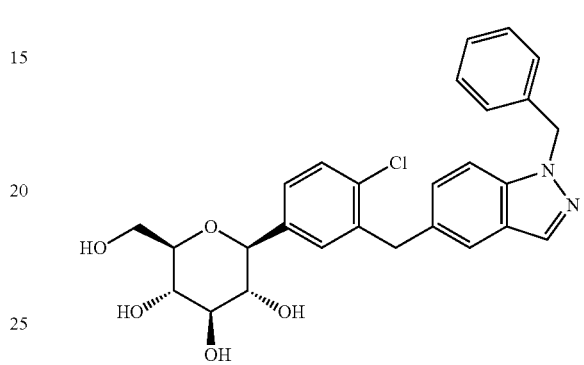

(2S,3R,4R,5S,6R)-2-(3-((1-Benzyl-1H-indazol-5-yl)methyl)-4-chlorophenyl)-6-(hydroxymethyl)tetrahydro-2H-pyran-3,4,5-triol (E033)

$^1$H NMR (400 MHz, CD$_3$OD) δ 7.98-7.97 (m, 1H), 7.56-7.55 (m, 1H), 7.46-7.36 (m, 3H), 7.32-7.27 (m, 5H), 7.19-7.14 (m, 2H), 5.61 (s, 2H), 4.26-4.16 (m, 2H), 4.10 (d, J=9.2 Hz, 1H), 3.91-3.80 (m, 1H), 3.74-3.65 (m, 1H), 3.49-3.39 (m, 4H); [M+H]$^+$ 495.

Example 034

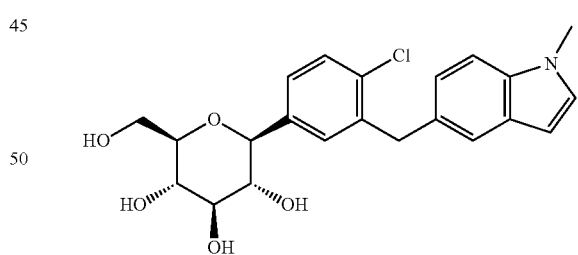

(2S,3R,4R,5S,6R)-2-(4-Chloro-3-((1-methyl-1H-indol-5-yl)methyl)phenyl)-6-(hydroxymethyl)tetrahydro-2H-pyran-3,4,5-triol (E034)

$^1$H NMR (400 MHz, CD$_3$OD) δ 7.38-7.33 (m, 3H), 7.30-7.26 (m, 2H), 7.11 (d, J=2.8 Hz, 1H), 7.06 (dd, J=8.4, 1.6 Hz, 1H), 6.35 (dd, J=3.2, 0.8 Hz, 1H), 4.20 (ABq, Δν$_{AB}$=24.0 Hz, J$_{AB}$=15.2 Hz, 2H), 4.08 (d, J=9.6 Hz, 2H), 3.89-3.86 (m, 1H), 3.78 (s, 3H), 3.71-3.67 (m, 1H), 3.48-3.37 (m, 4H); [M+Na]$^+$ 440.

Example 035

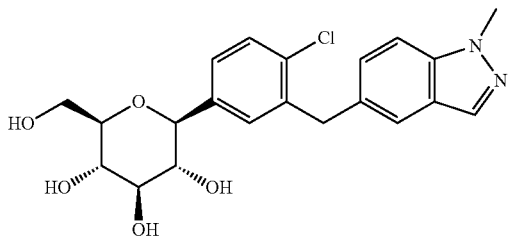 [SMILES: Cn1ncc2cc(Cc3cc([C@@H]4O[C@H](CO)[C@@H](O)[C@H](O)[C@H]4O)ccc3Cl)ccc21]

(2S,3R,4R,5S,6R)-2-(4-Chloro-3-((1-methyl-1H-indazol-5-yl)methyl)phenyl)-6-(hydroxymethyl)tetrahydro-2H-pyran-3,4,5-triol (E035)

$^1$H NMR (400 MHz, CD$_3$OD) δ 7.90-7.89 (m, 1H), 7.53-7.51 (m, 1H), 7.46-7.42 (m, 1H), 7.39-7.31 (m, 4H), 4.21 (ABq, Δv$_{AB}$=17.4 Hz, J$_{AB}$=15.0 Hz, 2H), 4.09 (d, J=9.2 Hz, 1H), 4.03 (s, 3H), 3.88-3.85 (m, 1H), 3.71-3.66 (m, 1H), 3.45-3.37 (m, 4H); [M+H]$^+$ 419.

Example 036

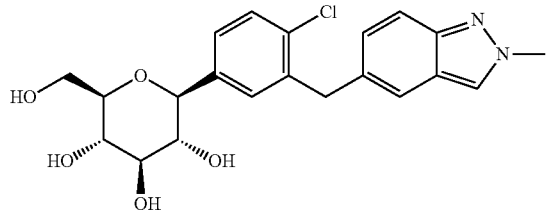 [SMILES: Cn1cc2cc(Cc3cc([C@@H]4O[C@H](CO)[C@@H](O)[C@H](O)[C@H]4O)ccc3Cl)ccc2n1]

(2S,3R,4R,5S,6R)-2-(4-Chloro-3-((2-methyl-2H-indazol-5-yl)methyl)phenyl)-6-(hydroxymethyl)tetrahydro-2H-pyran-3,4,5-triol (E036)

$^1$H NMR (400 MHz, CD$_3$OD) δ 8.04 (s, 1H), 7.48 (d, J=8.8 Hz, 1H), 7.40 (d, J=0.4 Hz, 1H), 7.37-7.35 (m, 1H), 7.30 (dd, J=8.4, 2.0 Hz, 1H), 7.20 (dd, J=8.8, 1.6 Hz, 1H), 4.21-4.15 (m, 5H), 4.09 (d, J=9.6 Hz, 1H), 3.88-3.85 (m, 1H), 3.70-3.65 (m, 1H), 3.46-3.35 (m, 4H); [M+H]$^+$ 419.

Example 037

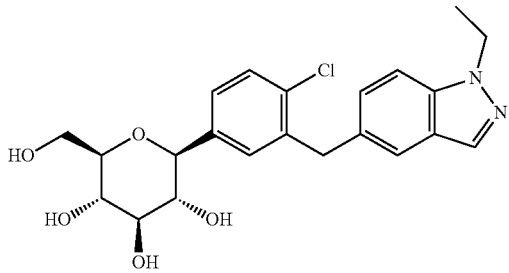 [SMILES: CCn1ncc2cc(Cc3cc([C@@H]4O[C@H](CO)[C@@H](O)[C@H](O)[C@H]4O)ccc3Cl)ccc21]

(2S,3R,4R,5S,6R)-2-(4-Chloro-3-((1-ethyl-1H-indazol-5-yl)methyl)phenyl)-6-(hydroxymethyl)tetrahydro-2H-pyran-3,4,5-triol (E037)

$^1$H NMR (400 MHz, CD$_3$OD) δ 7.87 (d, J=0.8 Hz, 1H), 7.48 (t, J=0.8 Hz, 1H), 7.44 (d, J=8.4 Hz, 1H), 7.35-7.33 (m, 2H), 7.30-7.26 (m, 2H), 4.40 (q, J=7.2 Hz, 2H), 4.18 (ABq, Δv$_{AB}$=17.4 Hz, J$_{AB}$=15.0 Hz, 2H), 4.06 (d, J=9.6 Hz, 1H), 3.85-3.82 (m, 1H), 3.67-3.63 (m, 1H), 3.43-3.32 (m, 4H), 1.41 (t, J=7.2 Hz, 3H); [M+H]$^+$ 433.

Example 038

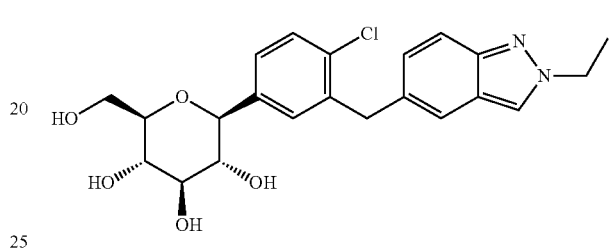

(2S,3R,4R,5S,6R)-2-(4-Chloro-3-((2-ethyl-2H-indazol-5-yl)methyl)phenyl)-6-(hydroxymethyl)tetrahydro-2H-pyran-3,4,5-triol (E038)

$^1$H NMR (400 MHz, CD$_3$OD) δ 8.08 (d, J=0.4 Hz, 1H), 7.47 (d, J=9.2 Hz, 1H), 7.39 (d, J=0.8 Hz, 1H), 7.35-7.33 (m, 2H), 7.27 (dd, J=8.2, 1.6 Hz, 1H), 7.18 (dd, J=8.8, 1.6 Hz, 1H), 4.42 (q, J=7.2 Hz, 2H), 4.14 (ABq, Δv$_{AB}$=18.6 Hz, J$_{AB}$=15.2 Hz, 2H), 4.06 (d, J=9.6 Hz, 1H), 3.85-3.82 (m, 1H), 3.67-3.63 (m, 1H), 3.43-3.32 (m, 4H), 1.54 (t, J=7.2 Hz, 3H); [M+H]$^+$ 433.

Example 039

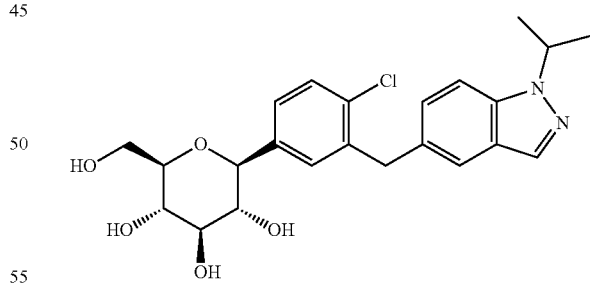

(2S,3R,4R,5S,6R)-2-(4-Chloro-3-((1-isopropyl-1H-indazol-5-yl)methyl)phenyl)-6-(hydroxymethyl)tetrahydro-2H-pyran-3,4,5-triol (E039)

$^1$H NMR (400 MHz, CD$_3$OD) δ 7.91 (s, 1H), 7.51-7.47 (m, 2H), 7.38-7.36 (m, 2H), 7.30 (dd, J=8.8, 1.6 Hz, 2H), 4.94-4.88 (m, 1H), 4.20 (ABq, Δv$_{AB}$=17.4 Hz, J$_{AB}$=15.0 Hz, 2H), 4.09 (d, J=9.6 Hz, 1H), 3.88-3.85 (m, 1H), 3.70-3.66 (m, 1H), 3.46-3.38 (m, 4H), 1.54 (s, 3H), 1.52 (s, 3H); [M+H]$^+$ 447.

Example 040

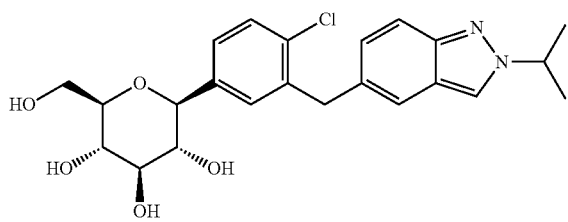 [SMILES: CC(C)n1cc2cc(Cc3cc([C@@H]4O[C@H](CO)[C@@H](O)[C@H](O)[C@H]4O)ccc3Cl)ccc2n1]

(2S,3R,4R,5S,6R)-2-(4-Chloro-3-((2-isopropyl-2H-indazol-5-yl)methyl)phenyl)-6-(hydroxymethyl)tetrahydro-2H-pyran-3,4,5-triol (E040)

$^1$H NMR (400 MHz, CD$_3$OD) δ 8.13 (d, J=0.8 Hz, 1H), 7.51 (d, J=8.8 Hz, 1H), 7.43-7.42 (m, 1H), 7.38-7.36 (m, 2H), 7.30 (dd, J=8.4, 2.0 Hz, 1H), 7.20 (dd, J=9.2, 1.6 Hz, 1H), 4.82-4.76 (m, 1H), 4.17 (ABq, Δν$_{AB}$=18.7 Hz, J$_{AB}$=15.4 Hz, 2H), 4.09 (d, J=9.6 Hz, 1H), 3.89-3.85 (m, 1H), 3.71-3.66 (m, 1H), 3.47-3.38 (m, 4H), 1.63 (s, 3H), 1.61 (s, 3H); [M+H]$^+$ 447.

Example 041

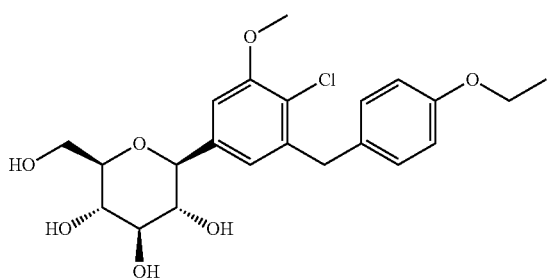 [SMILES: CCOc1ccc(Cc2cc([C@@H]3O[C@H](CO)[C@@H](O)[C@H](O)[C@H]3O)cc(OC)c2Cl)cc1]

(2S,3R,4R,5S,6R)-2-(4-Chloro-3-(4-ethoxybenzyl)-5-methoxyphenyl)-6-(hydroxymethyl)tetrahydro-2H-pyran-3,4,5-triol (E041)

$^1$H NMR (400 MHz, CD$_3$OD) δ 7.09-7.07 (m, 2H), 7.01 (d, J=1.6 Hz, 1H), 6.92 (d, J=1.6 Hz, 1H), 6.79-6.77 (m, 2H), 4.08-4.03 (m, 2H), 4.00-3.95 (m, 3H), 3.88 (s, 3H), 3.86 (d, J=2.0 Hz, 1H), 3.74-3.68 (m, 1H), 3.47-3.33 (m, 4H), 1.35 (t, J=7.2 Hz, 3H); [M+NH$_4$]$^+$ 456.

Example 042

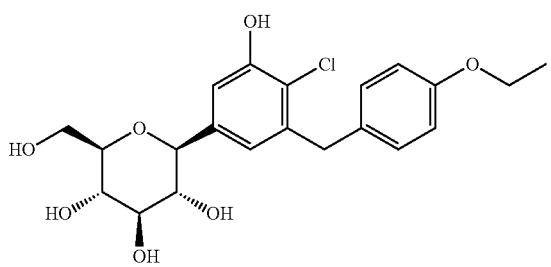 [SMILES: CCOc1ccc(Cc2cc([C@@H]3O[C@H](CO)[C@@H](O)[C@H](O)[C@H]3O)cc(O)c2Cl)cc1]

(2S,3R,4R,5S,6R)-2-(4-Chloro-3-(4-ethoxybenzyl)-5-hydroxyphenyl)-6-(hydroxymethyl)tetrahydro-2H-pyran-3,4,5-triol (E042)

$^1$H NMR (400 MHz, CD$_3$OD) δ 7.11-7.08 (m, 2H), 6.89 (d, J=2.0 Hz, 1H), 6.82 (d, J=1.6 Hz, 1H), 6.81-6.78 (m, 2H), 4.05-3.95 (m, 5H), 3.89-3.86 (m, 1H), 3.71-3.67 (m, 1H), 3.47-3.36 (m, 4H), 1.36 (t, J=7.2 Hz, 3H); [M+Na]$^+$ 447.

Example 043

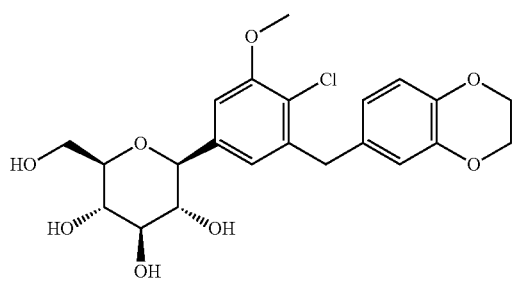 [SMILES: COc1cc([C@@H]2O[C@H](CO)[C@@H](O)[C@H](O)[C@H]2O)cc(Cc2ccc3c(c2)OCCO3)c1Cl]

(2S,3R,4R,5S,6R)-2-(4-Chloro-3-((2,3-dihydrobenzo[b][1,4]dioxin-6-yl)methyl)-5-methoxyphenyl)-6-(hydroxymethyl)tetrahydro-2H-pyran-3,4,5-triol (E043)

$^1$H NMR (400 MHz, CD$_3$OD) δ 7.02 (d, J=1.6 Hz, 1H), 6.93 (d, J=1.6 Hz, 1H), 6.70 (dd, J=8.0, 0.8 Hz, 1H), 6.65-6.62 (m, 2H), 4.18 (s, 4H), 4.09 (d, J=9.6, Hz, 1H), 3.97 (ABq, Δν$_{AB}$=22.4 Hz, J$_{AB}$=15.0 Hz, 2H), 3.92-3.86 (m, 4H), 3.71 (dd, J=12.0, 5.2 Hz, 1H), 3.48-3.35 (m, 4H); [M+Na]$^+$ 475.

Example 044

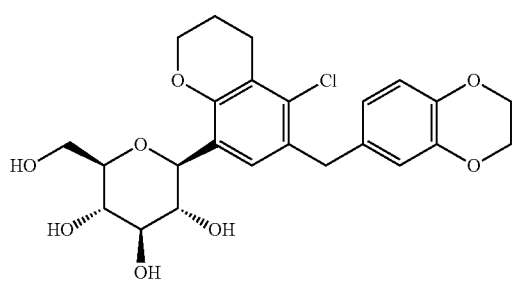 [SMILES: OC[C@H]1O[C@@H](c2cc(Cc3ccc4c(c3)OCCO4)c(Cl)c3c2OCCC3)[C@H](O)[C@@H](O)[C@@H]1O]

(2S,3R,4R,5S,6R)-2-(5-Chloro-6-((2,3-dihydrobenzo[b][1,4]dioxin-6-yl)methyl)chroman-8-yl)-6-(hydroxymethyl)tetrahydro-2H-pyran-3,4,5-triol (E044)

$^1$H NMR (400 MHz, CD$_3$OD) δ 7.18 (s, 1H), 6.68 (d, J=8.0 Hz, 1H), 6.63 (d, J=2.4 Hz, 1H), 6.61-6.59 (m, 1H), 4.62-4.60 (m, 1H), 4.18 (s, 4H), 4.15-4.11 (m, 2H), 3.91 (d, J=3.6, Hz, 2H), 3.86-3.83 (m, 1H), 3.68-3.63 (m, 1H), 3.47-3.45 (m, 2H), 3.38-3.36 (m, 2H), 2.77 (t, J=6.8 Hz, 2H), 2.04-1.98 (m, 2H); [M+NH$_4$]$^+$ 496.

Example 045

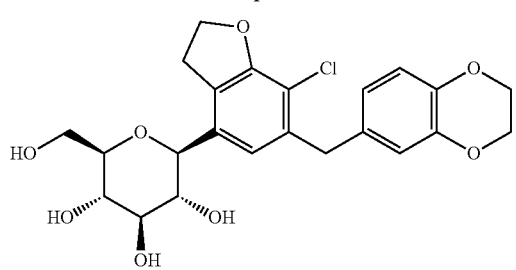

(2S,3R,4R,5S,6R)-2-(7-Chloro-6-((2,3-dihydrobenzo[b][1,4]dioxin-6-yl)methyl)-2,3-dihydrobenzofuran-4-yl)-6-(hydroxymethyl)tetrahydro-2H-pyran-3,4,5-triol (E045)

$^1$H NMR (400 MHz, CD$_3$OD) δ 6.83 (s, 1H), 6.79-6.67 (m, 1H), 6.64-6.61 (m, 2H), 4.61 (t, J=8.6, Hz, 2H), 4.17 (s, 4H), 4.14 (d, J=9.2, Hz, 1H), 3.96-3.86 (m, 3H), 3.69-3.64 (m, 1H), 3.48-3.36 (m, 6H); [M+Na]$^+$ 487.

Example 046

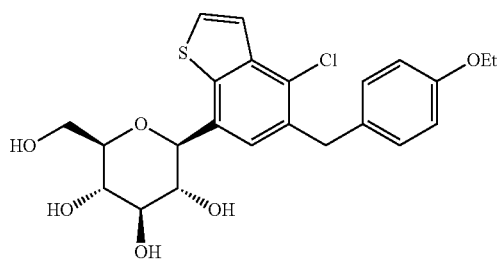 [SMILES: CCOc1ccc(Cc2cc([C@@H]3O[C@H](CO)[C@@H](O)[C@H](O)[C@H]3O)c3sccc3c2Cl)cc1]

(2S,3R,4R,5S,6R)-2-(4-Chloro-5-(4-ethoxybenzyl)benzo[b]thiophen-7-yl)-6-(hydroxymethyl)tetrahydro-2H-pyran-3,4,5-triol (E046)

To a solution of 7-bromo-4-chloro-5-(4-ethoxybenzyl)benzo[b]thiophene 99 (906 mg, 2.37 mmol) in THF (30 ml) at −78° C. was added n-BuLi (2.5M in hexane, 1.04 mmol, 2.61 mmol) not to exceed −70° C. of internal temperature. After stirring for 30 min at −78° C., per-silylated glucolactone 12 (1.11 g, 2.38 mmol) in THF (20 mL) was added to the reaction mixture dropwise. It was stirred for 10 min at −78° C., and then stirred for 4 hours with slowly warming up to room temperature. The resulting solution was quenched with aqueous sat. NH$_4$Cl solution (20 mL). Drying with MgSO$_4$ was preceded by collection of organic phase with EtOAc. After removal of volatile solvents and drying in vacuo, the crude product was used without further purification.

To a crude intermediate solution with MeOH (50 mL) was added methanesulfonic acid (3 mL), and reaction temperature was raised up to 90° C. overnight. After evaporation and drying in vacuo, the crude compound was used without further purification.

The crude intermediate was dissolved in a mixture of CH$_2$Cl$_2$ (30 mL) and CH$_3$CN (30 mL). After cooling down to −10° C., Et$_3$SiH (0.77 mL) and BF$_3$.Et$_2$O (0.39 mL) was added dropwise, maintaining internal temperature between −20~−10° C. After stirring for −10° C. for 30 min, the reaction mixture was warmed up to 0° C. and stirred for 5 hours. The resulting solution was quenched with sat NaHCO$_3$ solution, and normal work-up with EtOAc was accomplished. Prep HPLC was used for purification of the title compound (65 mg, 6% overall yield) as an off-white solid.

$^1$H NMR (CDCl$_3$) δ 8.20 (s, 1H), 7.71-7.64 (m, 2H), 7.49-7.41 (m, 2H), 7.24-7.18 (m, 2H), 4.96-4.60 (m, 2H), 4.19 (q, J=8.4 Hz, 2H), 4.12-3.88 (m, 2H), 3.77 (s, 2H), 3.82-3.60 (m, 3H), 3.57-3.49 (m, 1H), 2.65-2.63 (m, 2H), 2.41-2.35 (m, 2H), 1.35 (t, J=8.4 Hz, 3H); [M+Na]$^+$ 488.

Example 047

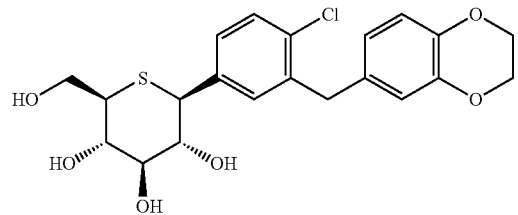

(2S,3R,4R,5S,6R)-2-(4-Chloro-3-((2,3-dihydrobenzo[b][1,4]dioxin-6-yl)methyl)phenyl)-6-(hydroxymethyl)tetrahydro-2H-thiopyran-3,4,5-triol (E047)

6-(2-chloro-5-((2S,3R,4R,5S,6R)-3,4,5-tris(benzyloxy)-6-((benzyloxy)methyl)tetrahydro-2H-thiopyran-2-yl)benzyl)-2,3-dihydrobenzo[b][1,4]dioxine (126, 204 mg, 0.26 mmol) in dichloromethane (5 mL) reacted with BCl$_3$ (1.5 mL) at 0° C. The reaction mixture was stirred at 0° C. for 0.5 h. After quenching the reaction with methanol, solvent was evaporated under a reduced pressure. Purification by reverse phase preparative HPLC (Gilson®, SunFire™ Prep, 5 to 50% acetonitrile in water gradient) provided the title compound (E047, 13 mg, 12% yield) as a white solid.

$^1$H NMR (400 MHz, CD$_3$OD) δ 7.33 (d, J=8.0 Hz, 1H), 7.22-7.19 (m, 2H), 6.73-6.70 (m, 1H), 6.65-6.63 (m, 2H), 4.19 (s, 4H), 3.95 (s, 2H), 3.93 (d, J=3.6 Hz, 1H), 3.77-3.70 (m, 3H), 3.59 (dd, J=8.8, 10.0 Hz, 1H), 3.24 (t, J=8.4 Hz, 1H), 3.02-2.97 (m, 1H); [M+Na]$^+$ 461.

Example 048

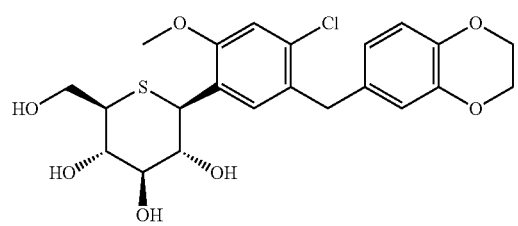 [SMILES: COc1cc(Cl)c(Cc2ccc3c(c2)OCCO3)cc1[C@@H]1S[C@H](CO)[C@@H](O)[C@H](O)[C@H]1O]

(2S,3R,4R,5S,6R)-2-(4-Chloro-5-((2,3-dihydrobenzo[b][1,4]dioxin-6-yl)methyl)-2-methoxyphenyl)-6-(hydroxymethyl)tetrahydro-2H-thiopyran-3,4,5-triol (E048)

Compound E048 (17 mg, 3.4% yield; 3 steps) was prepared according to the method described for the synthesis of E047 using compounds 123 (600 mg, 1.08 mmol) and 130 (880 mg, 2.38 mmol) as a white solid.

$^1$H NMR (400 MHz, CD$_3$OD) δ 7.22 (s, 1H), 6.98 (s, 1H), 6.70 (d, J=8.8 Hz, 1H), 6.61 (dd, J=2.0, 5.6 Hz, 2H), 4.18 (s, 4H), 3.92 (dd, J=4.0, 11.2 Hz, 1H), 4.88 (d, J=4.8 Hz, 2H), 3.82 (s, 3H), 3.73 (dd, J=6.4, 11.2 Hz, 1H), 3.59 (dd, J=9.2, 10.0 Hz, 1H), 3.24 (t, J=8.8 Hz, 1H), 3.00-2.95 (m, 1H); [M+Na]$^+$ 491.

Example 049

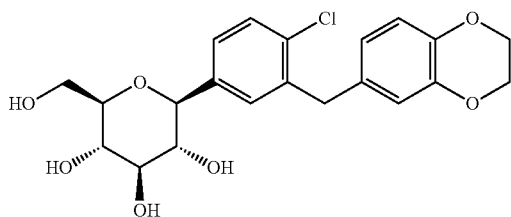

(2S,3R,4R,5S,6R)-2-(4-Chloro-3-((2,3-dihydrobenzo[b][1,4]dioxin-6-yl)methyl)phenyl)-6-(hydroxymethyl)-tetrahydro-2H-pyran-3,4,5-triol (E049)

To a solution of 6-(2-chloro-5-(2S,3S,4R,5R,6R)-3,4,5-tris(benzyloxy)-6-(benzyloxymethyl)-tetrahydro-2H-pyran-2-yl)benzyl-2,3-dihydrobenzo[b][1,4]dioxine (119) (501 mg, 0.640 mmole) was added $BCl_3$ (1M in DCM, 5.1 mL, 5.12 mmole) at 0° C. The reaction mixture was stirred at 0° C. for 30 min followed by quenching with MeOH and concentrated in vacuo. The resulting crude residue was purified by reverse phase preparative HPLC to yield the title compound (89.4 mg, 0.211 mmole, 33%) as a white solid.

$^1$H NMR (400 MHz, DMSO-$d_6$) • δ 7.37 (d, J=8.0 Hz, 1H), 7.33 (d, J=2.0 Hz, 1H), 7.23 (dd, J=8.4, 2.4 Hz, 1H), 6.76-6.74 (m, 1H), 6.65-6.63 (m, 2H), 4.94 (dd, J=4.8, 2.0 Hz, 1H), 4.82 (d, J=5.6 Hz, 1H), 4.43 (t, J=5.6 Hz, 1H), 4.18 (s, 4H), 3.99 (d, J=9.6 Hz, 1H), 3.93 (ABq, $\Delta v_{AB}$=16.4 Hz, $J_{AB}$=15.2 Hz, 2H), 3.72-3.67 (m, 1H), 3.47-3.41 (m, 1H), 3.23-3.08 (m, 5H); [M+Na]$^+$ 445.

Example 050

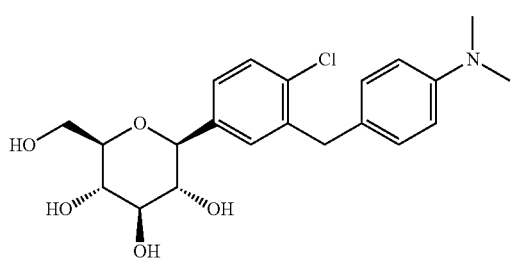 [SMILES: CN(C)c1ccc(Cc2cc([C@@H]3O[C@H](CO)[C@@H](O)[C@H](O)[C@H]3O)ccc2Cl)cc1]

(2S,3R,4R,5S,6R)-2-(4-Chloro-3-(4-dimethylamino)benzyl)phenyl)-6-(hydroxymethyl)-tetrahydro-2H-pyran-3,4,5-triol (E050)

$^1$H NMR (400 MHz, MeOD) □ δ 7.34 (d, J=8.4 Hz, 1H), 7.31 (d, J=2.0 Hz, 1H), 7.26 (dd, J=8.4, 2.0 Hz, 1H), 7.07 (d, J=8.8 Hz, 2H), 6.77 (d, J=8.4 Hz, 2H), 4.08 (d, J=9.6 Hz, 1H), 4.00 (ABq, $\Delta v_{AB}$=20.0 Hz, $J_{AB}$=15.2 Hz, 2H), 3.87 (dd, J=12.0, 1.6 Hz, 1H), 3.73-3.66 (m, 1H), 3.45-3.33 (m, 4H), 2.90 (s, 6H); [M+Na]$^+$ 430.

Example 051

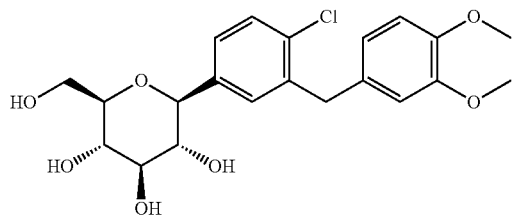 [SMILES: COc1ccc(Cc2cc([C@@H]3O[C@H](CO)[C@@H](O)[C@H](O)[C@H]3O)ccc2Cl)cc1OC]

(2S,3R,4R,5S,6R)-2-(4-Chloro-3-(3,4-dimethoxybenzyl)phenyl)-6-(hydroxymethyl)-tetrahydro-2H-pyran-3,4,5-triol (E051)

$^1$H NMR (400 MHz, MeOD) δ 7.35 (d, J=8.4 Hz, 1H), 7.33 (d, J=2.0 Hz, 1H), 7.28 (dd, J=8.0, 2.0 Hz, 1H), 6.85-6.82 (m, 2H), 6.73 (dd, J=8.0, 2.0 Hz, 1H), 4.09 (d, J=9.2 Hz, 1H), 4.04 (ABq, $\Delta v_{AB}$=11.6 Hz, $J_{AB}$=15.2 Hz, 2H), 3.87 (dd, J=12.0, 2.0 Hz, 1H), 3.79 (s, 3H), 3.77 (s, 3H), 3.71-3.67 (m, 1H), 3.45-3.26 (m, 4H); [M+Na]$^+$ 447.

Example 052

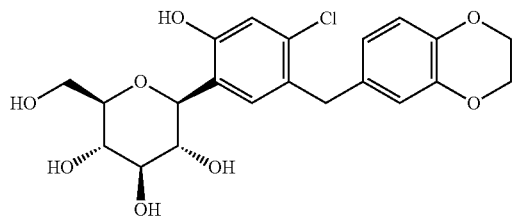

(2S,3R,4R,5S,6R)-2-(4-Chloro-5-((2,3-dihydrobenzo[b][1,4]dioxin-6-yl)methyl)-2-hydroxyphenyl)-6-(hydroxymethyl)-tetrahydro-2H-pyran-3,4,5-triol (E052)

$^1$H NMR (400 MHz, MeOD) δ 7.25 (s, 1H), 6.87 (s, 1H), 6.71 (dd, J=7.6, 0.8 Hz, 1H), 6.65-6.63 (m, 2H), 4.54 (d, J=9.2 Hz, 1H), 4.20 (s, 4H), 3.94-3.85 (m, 3H), 3.74-3.70 (m, 1H), 3.52-3.41 (m, 4H); [M+Na]$^+$ 461.

Example 053

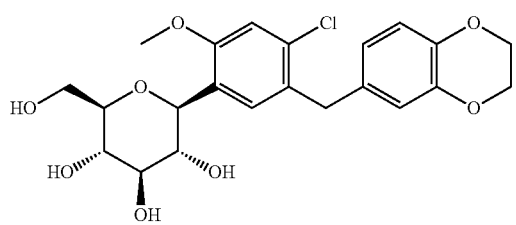

(2S,3R,4R,5S,6R)-2-(4-Chloro-5-((2,3-dihydrobenzo
[b][1,4]dioxin-6-yl)methyl)-2-methoxyphenyl)-6-
(hydroxymethyl)-tetrahydro-2H-pyran-3,4,5-triol
(E053)

$^1$H NMR (400 MHz, MeOD) δ 7.39 (d, J=26.4 Hz, 1H), 6.95 (s, 1H), 6.72-6.70 (m, 1H), 6.65-6.61 (m, 2H), 4.35-4.30 (m, 1H), 4.21-4.20 (m, 4H), 4.16 (dd, J=3.2, 1.2 Hz, 1H), 4.11-4.03 (m, 2H), 3.93-3.89 (m, 2H), 3.86 (s, 3H), 3.84-3.82 (m, 1H), 3.70-3.65 (m, 2H); [M+Na]$^+$ 475.

Example 054

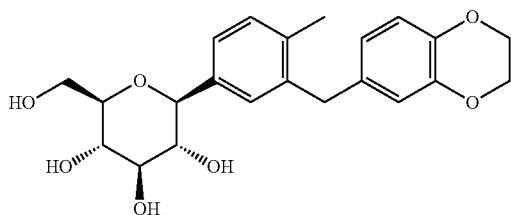 [SMILES: Cc1ccc([C@@H]2O[C@H](CO)[C@@H](O)[C@H](O)[C@H]2O)cc1Cc1ccc2c(c1)OCCO2]

(2S,3R,4R,5S,6R)-2-(3-((2,3-Dihydrobenzo[b][1,4]
dioxin-6-yl)methyl)-4-methylphenyl)-6-(hydroxym-
ethyl)-tetrahydro-2H-pyran-3,4,5-triol (E054)

$^1$H NMR (400 MHz, MeOD) δ 7.20-7.19 (m, 2H), 7.12 (d, J=8.0 Hz, 1H), 6.69 (d, J=8.4 Hz, 1H), 6.59-6.54 (m, 2H), 4.17 (s, 4H), 4.08 (d, J=9.2 Hz, 1H), 3.90-3.87 (m, 3H), 3.71-3.67 (m, 1H), 3.47-3.35 (m, 4H), 2.18 (s, 3H); [M+Na]$^+$ 425.

Example 055

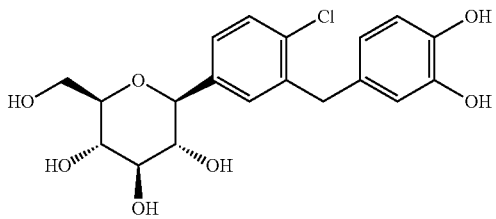 [SMILES: OC[C@H]1O[C@@H](c2ccc(Cl)c(Cc3ccc(O)c(O)c3)c2)[C@H](O)[C@@H](O)[C@@H]1O]

(2S,3R,4R,5S,6R)-2-(4-Chloro-3-(3,4-dihydroxy-
benzyl)phenyl)-6-(hydroxymethyl)-tetrahydro-2H-
pyran-3,4,5-triol (E055)

$^1$H NMR (400 MHz, DMSO-d$_6$) □ δ 8.74 (br s, 2H), 7.36 (d, J=8.4 Hz, 1H), 7.27 (d, J=2.0 Hz, 1H), 7.22 (dd, J=8.0, 2.0 Hz, 1H), 6.62 (d, J=7.6 Hz, 1H), 6.55 (d, J=2.0 Hz, 1H), 7.45 (dd, J=8.0, 2.0 Hz, 1H), 4.63 (br s, 4H), 3.98 (d, J=9.2 Hz, 1H), 3.87 (ABq, Δν$_{AB}$=20.8 Hz, J$_{AB}$=14.8 Hz, 2H), 3.69 (dd, J=12.0, 1.6 Hz, 1H), 3.44 (dd, J=11.6, 5.6 Hz, 1H), 3.28-3.09 (m, 5H); [M+Na]$^+$ 419.

Example 056

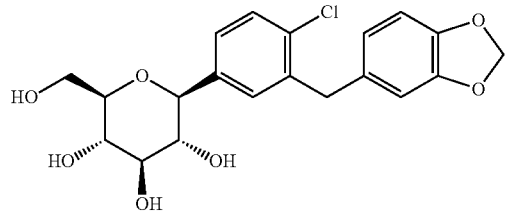 [SMILES: OC[C@H]1O[C@@H](c2ccc(Cl)c(Cc3ccc4c(c3)OCO4)c2)[C@H](O)[C@@H](O)[C@@H]1O]

(2S,3R,4R,5S,6R)-2-(3-(Benzo[d][1,3]dioxol-5-ylm-
ethyl)-4-chlorophenyl)-6-(hydroxymethyl)-tetrahy-
dro-2H-pyran-3,4,5-triol (E056)

To a solution of (2S,3R,4R,5S,6R)-2-(4-chloro-3-(3,4-di-hydroxybenzyl)phenyl)-6-(hydroxymethyl)-tetrahydro-2H-pyran-3,4,5-triol (E055) (30 mg, 0.0756 mmole) in DMF (4 mL) were added K$_2$CO$_3$ and CH$_2$I$_2$ (7.3 μL). The reaction mixture was stirred at 100° C. overnight and filtered. The resulting crude solution was purified by reverse phase preparative HPLC to yield the title compound (16 mg, 0.0401 mmole, 53%) as a brown gum.

$^1$H NMR (400 MHz, MeOD) δ 7.34 (d, J=8.4 Hz, 1H), 7.32 (d, J=2.0 Hz, 1H), 7.27 (dd, J=8.0, 2.0 Hz, 1H), 6.71-6.65 (m, 3H), 5.87 (s, 2H), 4.09 (d, J=9.6 Hz, 1H), 4.01 (ABq, Δν$_{AB}$=17.2 Hz, J$_{AB}$=15.2 Hz, 2H), 3.87 (dd, J=12.0, 2.0 Hz, 1H), 3.69 (dd, J=12.0, 5.2 Hz, 1H), 3.48-3.38 (m, 4H); [M+Na]$^+$ 431.

Example 057

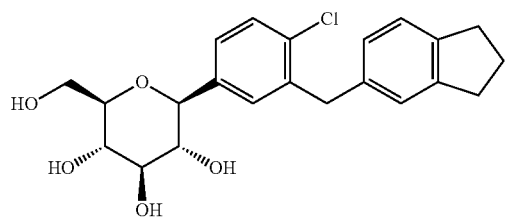 [SMILES: OC[C@H]1O[C@@H](c2ccc(Cl)c(Cc3ccc4c(c3)CCC4)c2)[C@H](O)[C@@H](O)[C@@H]1O]

(2S,3R,4R,5S,6R)-2-(4-Chloro-3-((2,3-dihydro-1H-
inden-5-yl)methyl)phenyl)-6-(hydroxymethyl)-tet-
rahydro-2H-pyran-3,4,5-triol (E057)

To a solution of (2R,3R,4R,5S,6S)-3,4,5-tris(benzyloxy)-2-(benzyloxymethyl)-6-(4-chloro-3-((2,3-dihydro-1H-inden-5-yl)methyl)phenyl)-tetrahydro-2H-pyran (122) (425 mg, 0.56 mmol) in THF:MeOH(v/v=1:1)(8 mL) at room temperature was added Pd/C. The mixture was stirred under H$_2$ for 2 h, Pd/C was removed by filtration and the solvent was removed under reduced pressure. The crude product was purified by preparative HPLC to furnish the title compound (42 mg, 0.10 mmol, 18%).

$^1$H NMR (400 MHz, CD$_3$OD) δ 7.30-7.40 (m, 3H), 6.97-7.13 (m, 3H), 4.07-4.14 (m, 3H), 3.90-3.93 (m, 1H), 3.71-

3.75 (dd, J=12.0, 5.2 Hz, 1H), 3.39-3.52 (m, 3H), 3.31-3.33 (m, 1H), 2.82-2.89 (m, 4H), 2.07 (q, J=29.6 Hz, 2H); [M+Na]⁺ 427.

Example 058

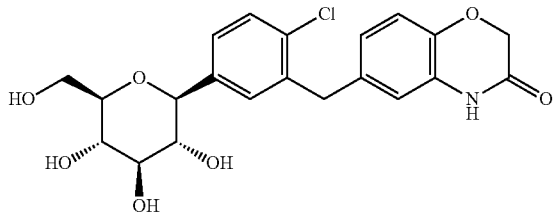 [SMILES: O=C1COc2ccc(Cc3cc([C@@H]4O[C@H](CO)[C@@H](O)[C@H](O)[C@H]4O)ccc3Cl)cc2N1]

6-(2-Chloro-5-((2S,3R,4R,5S,6R)-3,4,5-trihydroxy-6-(hydroxymethyl)-tetrahydro-2H-pyran-2-yl)benzyl)-2H-benzo[b][1,4]oxazin-3(4H)-one (E058)

$^1$H NMR (400 MHz, CD$_3$OD) □ δ 7.43 (d, J=8.4 Hz, 1H), 7.37 (dd, J=8.4, 2.0 Hz, 1H), 7.11 (d, J=2.0 Hz, 1H), 6.96-7.02 (m, 2H), 6.89-6.93 (m, 1H), 6.01-6.83 (m, 1H), 5.28 (d, J=17.2 Hz, 1H), 5.17 (d, J=16.8 Hz, 1H), 4.75-4.76 (m, 2H), 4.00-4.02 (m, 1H), 3.79-3.83 (m, 1H), 3.60-3.64 (m, 1H), 3.32-3.40 (m, 3H), 3.15 (t, J=18.0 Hz, 1H); [M+Na]⁺ 458.

Example 059

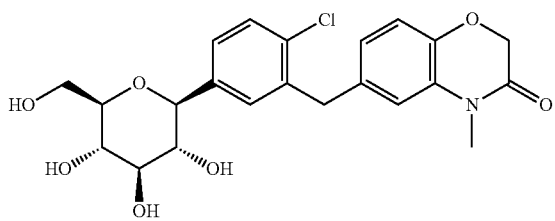

6-(2-Chloro-5-((2S,3R,4R,5S,6R)-3,4,5-trihydroxy-6-(hydroxymethyl)-tetrahydro-2H-pyran-2-yl)benzyl)-4-methyl-2H-benzo[b][1,4]oxazin-3(4H)-one (E059)

$^1$H NMR (400 MHz, CD$_3$OD) δ 7.29-7.37 (m, 3H), 7.02 (d, J=8.4 Hz, 1H), 6.91-6.93 (m, 1H), 6.80 (d, J=1.6 Hz, 1H), 4.54 (s, 2H), 4.11 (d, J=9.5 Hz, 1H), 4.05 (ABq, Δν$_{AB}$=16.0 Hz, J$_{AB}$=15.3 Hz, 2H), 3.86-3.90 (m, 1H), 3.68-3.73 (m, 1H), 3.39-3.49 (m, 3H), 3.35 (s, 1H), 3.31 (s, 3H); [M+Na]⁺ 472.

Example 060

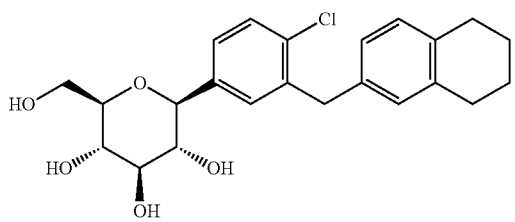

(2S,3R,4R,5S,6R)-2-(4-Chloro-3-((5,6,7,8-tetrahydronaphthalen-2-yl)methyl)phenyl)-6-(hydroxymethyl)-tetrahydro-2H-pyran-3,4,5-triol (E060)

$^1$H NMR (400 MHz, CD$_3$OD) δ 7.26-7.35 (m, 3H), 6.85-6.92 (m, 3H), 4.08 (d, J=9.6 Hz, 1H), 4.00 (ABq, Δν$_{AB}$=20.0 Hz, J$_{AB}$=15.0 Hz, 2H), 3.86-3.89 (m, 1H), 3.69 (dd, J=11.6, 5.2 Hz, 1H), 3.38-3.45 (m, 3H), 3.27-3.29 (m, 1H), 2.69 (d, J=5.2 Hz, 4H), 1.75-1.78 (m, 4H); [M+Na]⁺ 441.

Example 061

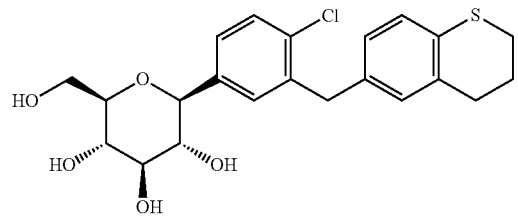 [SMILES: OC[C@H]1O[C@@H](c2ccc(Cl)c(Cc3ccc4c(c3)CCCS4)c2)[C@H](O)[C@@H](O)[C@@H]1O]

(2S,3R,4R,5S,6R)-2-(4-Chloro-3-(thiochroman-6-ylmethyl)phenyl)-6-(hydroxymethyl)-tetrahydro-2H-pyran-3,4,5-triol (E061)

$^1$H NMR (400 MHz, CD$_3$OD) δ 7.27-7.35 (m, 3H), 6.85-6.91 (m, 3H), 4.09 (d, J=9.6 Hz, 1H), 3.98 (ABq, Δν$_{AB}$=17.2 Hz, J$_{AB}$=15.2 Hz, 2H), 3.87 (dd, J=12.2, 1.6 Hz, 1H), 3.69 (dd, J=12.0, 5.2 Hz, 1H), 3.38-3.48 (m, 3H), 3.27-3.29 (m, 1H), 2.95-2.98 (m, 2H), 2.71 (t, J=6.0 Hz, 2H), 2.01-2.07 (m, 2H); [M+Na]⁺ 459.

Example 063

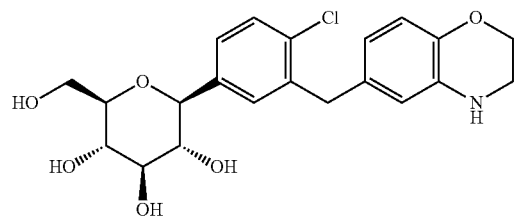 [SMILES: OC[C@H]1O[C@@H](c2ccc(Cl)c(Cc3ccc4c(c3)NCCO4)c2)[C@H](O)[C@@H](O)[C@@H]1O]

(2S,3R,4R,5S,6R)-2-(4-Chloro-3-((3,4-dihydro-2H-benzo[b][1,4]oxazin-6-yl)methyl)phenyl)-6-(hydroxymethyl)-tetrahydro-2H-pyran-3,4,5-triol (E063)

$^1$H NMR (400 MHz, MeOD) δ 7.42-7.35 (m, 3H), 6.73-6.67 (m, 2H), 6.58-6.53 (m, 2H), 4.50 (dd, J=30.0, 16.8 Hz, 2H), 4.28-4.25 (m, 2H), 4.08 (d, J=9.6 Hz, 1H), 3.85 (dd, J=12.0, 1.6 Hz, 1H), 3.68-3.64 (m, 1H), 3.43-3.35 (m, 5H), 3.24 (t, J=8.8 Hz, 1H). MNa+ 444.

Example 064

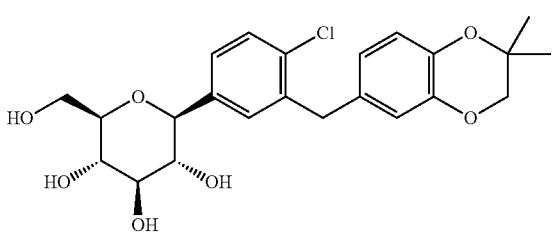 [SMILES: CC1(C)COc2cc(Cc3cc([C@@H]4O[C@H](CO)[C@@H](O)[C@H](O)[C@H]4O)ccc3Cl)ccc2O1]

(2S,3R,4R,5S,6R)-2-(4-Chloro-3-((2,2-dimethyl-2,3-dihydrobenzo[b][1,4]dioxin-6-yl)methyl)phenyl)-6-(hydroxymethyl)-tetrahydro-2H-pyran-3,4,5-triol (E064)

$^1$H NMR (400 MHz, MeOD) □ δ 7.36-7.33 (m, 2H), 7.27 (dd, J=8.0, 2.0 Hz, 1H), 6.74-6.58 (m, 3H), 4.10 (d, J=9.6 Hz, 1H), 4.03-3.93 (m, 2H), 3.89-3.84 (m, 3H), 3.71-3.67 (m, 1H), 3.48-3.27 (m, 4H), 1.29 (s, 6H); [M+Na]$^+$ 473.

Example 065

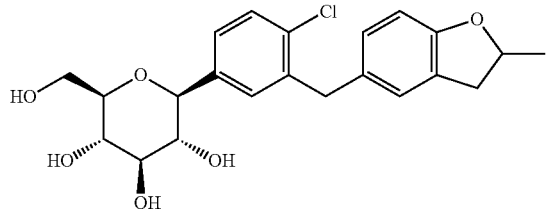 [SMILES: CC1Cc2cc(Cc3cc([C@@H]4O[C@H](CO)[C@@H](O)[C@H](O)[C@H]4O)ccc3Cl)ccc2O1]

(2S,3R,4R,5S,6R)-2-(4-Chloro-3-((2-methyl-2,3-dihydrobenzofuran-5-yl)methyl)phenyl)-6-(hydroxymethyl)-tetrahydro-2H-pyran-3,4,5-triol (E065)

$^1$H NMR (400 MHz, MeOD) □ δ 7.34 (d, J=8.4 Hz, 1H), 7.29 (d, J=1.6 Hz, 1H), 7.26 (dd, J=8.0, 2.0 Hz, 1H), 6.95 (d, J=1.6 Hz, 1H), 6.88 (dd, J=8.0, 2.0 Hz, 1H), 6.66 (d, J=8.4 Hz, 1H), 4.07 (d, J=9.2 Hz, 1H), 3.98 (ABq, Δν$_{AB}$=20.8 Hz, J$_{AB}$=16.0 Hz, 2H), 3.87 (dd, J=12.0, 1.6 Hz, 1H), 3.70-3.66 (m, 1H), 3.47-3.27 (m, 4H), 3.04-2.98 (m, 1H), 2.92-2.86 (m, 1H); [M+H]$^+$ 421.

Example 066

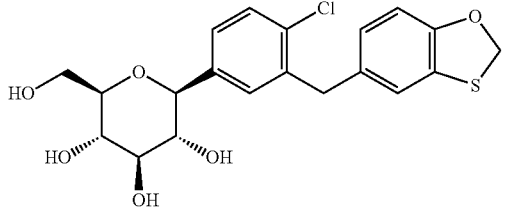

(2S,3R,4R,5S,6R)-2-(3-(Benzo[d][1,3]oxathiol-5-ylmethyl)-4-chlorophenyl)-6-(hydroxymethyl)-tetrahydro-2H-pyran-3,4,5-triol (E066)

$^1$H NMR (400 MHz, MeOD) δ 7.36-7.34 (m, 2H), 7.29 (dd, J=8.0, 2.0 Hz, 1H), 7.00 (d, J=1.6 Hz, 1H), 6.84 (dd, J=8.0, 2.0 Hz, 1H), 6.70 (d, J=8.0 Hz, 1H), 5.64 (s, 2H), 4.10 (d, J=9.6 Hz, 1H), 4.00 (ABq, Δν$_{AB}$=16.8 Hz, J$_{AB}$=15.2 Hz, 2H), 3.88 (dd, J=12.4, 2.0 Hz, 1H), 3.72-3.68 (m, 1H), 3.48-3.28 (m, 4H); [M+Na]$^+$ 447.

Example 067

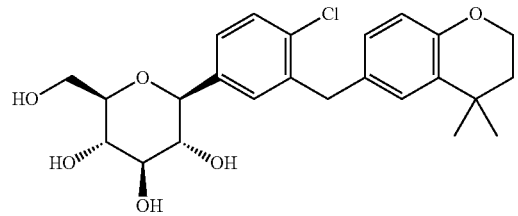 [SMILES: CC1(C)CCOc2ccc(Cc3cc([C@@H]4O[C@H](CO)[C@@H](O)[C@H](O)[C@H]4O)ccc3Cl)cc21]

(2S,3R,4R,5S,6R)-2-(4-Chloro-3-((4,4-dimethyl-chroman-6-yl)methyl)phenyl)-6-(hydroxymethyl)-tetrahydro-2H-pyran-3,4,5-triol (E067)

$^1$H NMR (400 MHz, MeOD) δ 7.34 (d, J=8.0 Hz, 1H), 7.31 (d, J=2.0 Hz, 1H), 7.26 (dd, J=8.4, 2.0 Hz, 1H), 7.18 (d, J=2.0 Hz, 1H), 6.84-6.47 (m, 2H), 4.12-4.06 (m, 3H), 4.00 (ABq, Δν$_{AB}$=15.2 Hz, J$_{AB}$=15.2 Hz, 2H), 3.87 (dd, J=12.0, 1.6 Hz, 1H), 3.70-3.66 (m, 1H), 3.47-3.25 (m, 4H), 1.81-1.77 (m, 2H), 1.29 (s, 6H); [M+Na]$^+$ 471.

Example 068

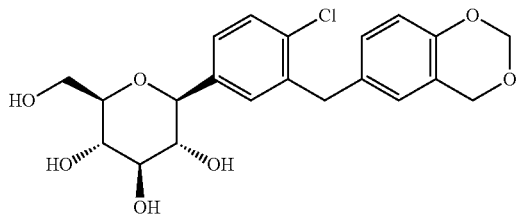 [SMILES: OC[C@H]1O[C@@H](c2ccc(Cl)c(Cc3ccc4c(c3)COCO4)c2)[C@H](O)[C@@H](O)[C@@H]1O]

(2S,3R,4R,5S,6R)-2-(3-((4H-Benzo[d][1,3]dioxin-6-yl)methyl)-4-chlorophenyl)-6-(hydroxymethyl)-tetrahydro-2H-pyran-3,4,5-triol (E068)

$^1$H NMR (400 MHz, MeOD) □ δ 7.34 (d, J=8.0 Hz, 1H), 7.32 (d, J=1.6 Hz, 1H), 7.28 (dd, J=8.0, 2.0 Hz, 1H), 6.99 (dd, J=8.4, 2.0 Hz, 1H), 6.83 (s, 1H), 6.72 (d, J=8.4 Hz, 1H), 5.19 (s, 2H), 4.82 (s, 2H), 4.08 (d, J=9.6 Hz, 1H), 4.02 (ABq, Δν$_{AB}$=14.0 Hz, J$_{AB}$=15.2 Hz, 2H), 3.87 (dd, J=12.4, 2.0 Hz, 1H), 3.71-3.67 (m, 1H), 3.48-3.26 (m, 4H); [M+Na]$^+$ 445.

Example 069

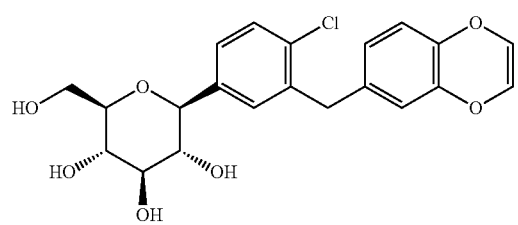

(2S,3R,4R,5S,6R)-2-(3-(Benzo[b][1,4]dioxin-6-yl)methyl)-4-chlorophenyl)-6-(hydroxymethyl)-tetrahydro-2H-pyran-3,4,5-triol (E069)

¹H NMR (400 MHz, MeOD) δ 7.35 (d, J=8.4 Hz, 1H), 7.33 (d, J=2.0 Hz, 1H), 7.29 (dd, J=8.4, 2.0 Hz, 1H), 6.66 (dd, J=8.4, 2.0 Hz, 1H), 6.51 (d, J=8.0 Hz, 1H), 6.44 (d, J=2.0 Hz, 1H), 5.93 (ABq, Δv_{AB}=4.4 Hz, J_{AB}=3.6 Hz, 2H), 4.11 (d, J=9.6 Hz, 1H), 3.93 (ABq, Δv_{AB}=16.8 Hz, J_{AB}=15.2 Hz, 2H), 3.88 (dd, J=12.4, 2.0 Hz, 1H), 3.72-3.68 (m, 1H), 3.49-3.27 (m, 4H); [M+Na]⁺ 443.

Example 072

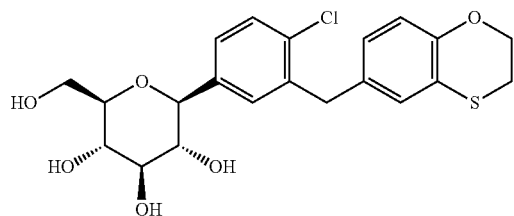

(2S,3R,4R,5S,6R)-2-(4-Chloro-3-((2,3-dihydrobenzo[b][1,4]oxathiin-6-yl)methyl)phenyl)-6-(hydroxymethyl)-tetrahydro-2H-pyran-3,4,5-triol (E072)

¹H NMR (400 MHz, MeOD) δ 7.35 (d, J=8.4 Hz, 1H), 7.32 (d, J=2.4 Hz, 1H), 7.28 (dd, J=8.0, 2.0 Hz, 1H), 6.81-6.78 (m, 2H), 6.67 (dd, J=7.2, 1.6 Hz, 1H), 4.34-4.32 (m, 2H), 4.10 (d, J=9.6 Hz, 1H), 3.96 (ABq, Δv_{AB}=19.2 Hz, J_{AB}=15.2 Hz, 2H), 3.88 (dd, J=12.0, 1.6 Hz, 1H), 3.72-3.67 (m, 1H), 3.48-3.27 (m, 4H), 3.12-3.09 (m, 2H); [M+Na]⁺ 461.

Example 073

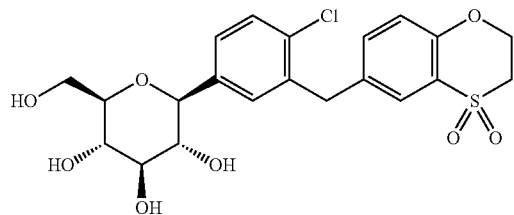 [SMILES: O=S1(=O)CCOc2ccc(Cc3cc([C@@H]4O[C@H](CO)[C@@H](O)[C@H](O)[C@H]4O)ccc3Cl)cc21]

(2S,3R,4R,5S,6R)-2-(4-Chloro-3-((1,1-dioxo-2,3-dihydrobenzo[b][1,4]oxathiin-6-yl)methyl)phenyl)-6-(hydroxymethyl)-tetrahydro-2H-pyran-3,4,5-triol (E073)

To a solution of (2S,3R,4R,5S,6R)-2-(4-chloro-3-((2,3-dihydrobenzo[b][1,4]oxathiin-6-yl)methyl)phenyl)-6-(hydroxymethyl)-tetrahydro-2H-pyran-3,4,5-triol (E072) (50 mg, 0.114 mmole) in CH₂Cl₂ was added mCPBA (76.6 mg, 0.342 mmole). The reaction mixture was stirred at ambient temperature overnight and concentrated in vacuo. The resulting crude residue was purified by reverse phase preparative HPLC to yield the title compound (18.4 mg, 0.0391 mmole, 34%) as an off-white solid.

¹H NMR (400 MHz, MeOD) δ 7.64-7.56 (m, 1H), 7.40-7.31 (m, 4H), 7.03-6.82 (m, 1H), 4.78-4.75 (m, 2H), 4.14-4.10 (m, 3H), 3.88 (dd, J=12.4, 2.4 Hz, 1H), 3.70 (dd, J=16.8, 5.2 Hz, 1H), 3.62-3.59 (m, 2H), 3.47-3.27 (m, 4H); [M+Na]⁺ 493.

Example 074

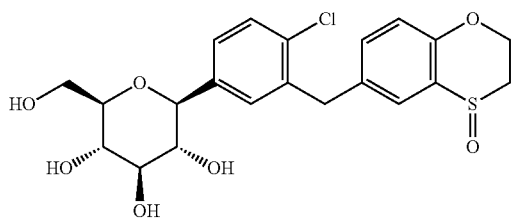 [SMILES: O=S1CCOc2ccc(Cc3cc([C@@H]4O[C@H](CO)[C@@H](O)[C@H](O)[C@H]4O)ccc3Cl)cc21]

(2S,3R,4R,5S,6R)-2-(4-Chloro-3-((1-oxo-2,3-dihydrobenzo[b][1,4]oxathiin-6-yl)methyl)phenyl)-6-(hydroxymethyl)-tetrahydro-2H-pyran-3,4,5-triol (E074)

To a solution of (2S,3R,4R,5S,6R)-2-(4-chloro-3-((2,3-dihydrobenzo[b][1,4]oxathiin-6-yl)methyl)phenyl)-6-(hydroxymethyl)-tetrahydro-2H-pyran-3,4,5-triol (E072) (50 mg, 0.114 mmole) in DCM was added mCPBA (25.5 mg, 0.114 mmole) at 0° C. The reaction mixture was stirred at ambient temperature overnight and concentrated in vacuo. The resulting crude residue was purified by reverse phase preparative HPLC to yield the title compound (21.4 mg, 0.0470 mmole, 31%) as a white solid.

¹H NMR (400 MHz, MeOD) δ 7.43-7.31 (m, 5H), 6.98 (d, J=8.4 Hz, 1H), 4.60-4.57 (m, 2H), 4.13-4.11 (m, 3H), 3.88 (dd, J=12.0, 2.0 Hz, 1H), 3.70 (dd, J=22.4, 5.2 Hz, 1H), 3.49-3.24 (m, 4H), 3.21-3.16 (m, 2H); [M+Na]⁺ 477.

Example 075

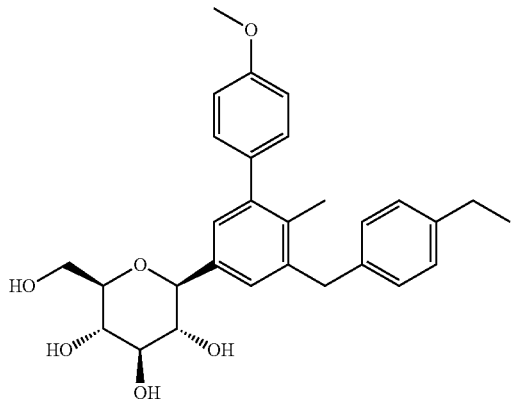 [SMILES: CCc1ccc(Cc2cc([C@@H]3O[C@H](CO)[C@@H](O)[C@H](O)[C@H]3O)cc(-c3ccc(OC)cc3)c2C)cc1]

(2S,3R,4R,5S,6R)-2-(5-(4-(Ethylbenzyl)-4'-methoxy-6-methylbiphenyl-3-yl)-6-(hydroxymethyl)-tetrahydro-2H-pyran-3,4,5-triol (E075)

To a solution of (2R,3R,4R,5S,6S)-2-(acetoxymethyl)-6-(5-(4-ethylbenzyl)-4'-methoxy-6-methylbiphenyl-3-yl)-tetrahydro-2H-pyran-3,4,5-triyl triacetate (450 mg, 0.696 mmole) in MeOH (10 mL) was added NaOMe (25 wt % in MeOH, 2.1 mL, 9.05 mmole). The reaction mixture was stirred at ambient temperature for 2 h before AcOH (3 mL) was added. Purification by reverse phase preparative HPLC provided the title compound (207 mg, 0.433 mmole, 62%) as a white solid. $^1$H NMR (400 MHz, MeOD) δ 7.26 (d, J=1.6 Hz, 1H), 7.21-7.18 (m, 3H), 7.10 (d, J=3.2 Hz, 4H), 6.97 (d, J=8.8 Hz, 2H), 4.14 (d, J=9.2 Hz, 1H), 4.05 (s, 1H), 3.91 (dd, J=11.6, 1.2 Hz, 1H), 3.85 (s, 3H), 3.74-3.70 (m, 1H), 3.50-3.42 (m, 4H), 3.62 (q, J=7.6 Hz, 2H), 2.09 (s, 3H), 1.23 (t, J=7.6 Hz, 3H); [M+Na]$^+$ 501.

Example 076

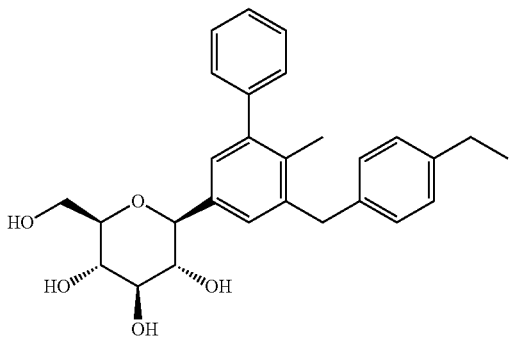 [SMILES: CCc1ccc(Cc2cc([C@@H]3O[C@H](CO)[C@@H](O)[C@H](O)[C@H]3O)cc(-c3ccccc3)c2C)cc1]

(2S,3R,4R,5S,6R)-2-(5-(4-(Ethylbenzyl)-6-methylbiphenyl-3-yl)-6-(hydroxymethyl)-tetrahydro-2H-pyran-3,4,5-triol (E076)

$^1$H NMR (400 MHz, DMSO-d$_6$) δ 7.42 (t, J=7.2 Hz, 2H), 7.36-7.32 (m, 1H), 7.26 (d, J=6.8 Hz, 2H), 7.18 (s, 1H), 7.10 (q, J=7.6 Hz, 4H), 7.05 (d, J=1.2 Hz, 1H), 4.91 (d, J=5.2 Hz, 2H), 4.77 (d, J=5.6 Hz, 1H), 4.42 (t, J=5.6 Hz, 1H), 4.08 (q, J=5.2 Hz, 1H), 4.03-3.94 (m, 3H), 3.68 (dd, J=10.4, 5.6 Hz, 1H), 3.29-3.12 (m, 4H), 2.56 (q, J=7.6 Hz, 2H), 2.05 (s, 3H), 1.15 (t, J=7.6 Hz, 3H); [M+Na]$^+$ 471.

Example 077

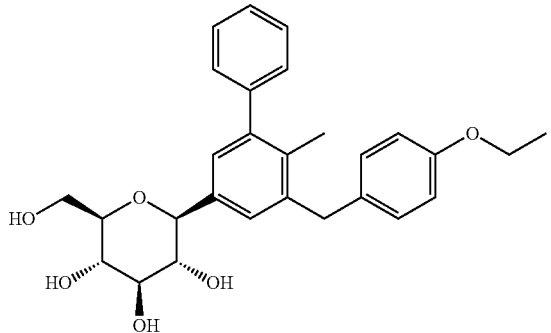 [SMILES: CCOc1ccc(Cc2cc([C@@H]3O[C@H](CO)[C@@H](O)[C@H](O)[C@H]3O)cc(-c3ccccc3)c2C)cc1]

(2S,3R,4R,5S,6R)-2-(5-(4-(Ethoxybenzyl)-6-methylbiphenyl-3-yl)-6-(hydroxymethyl)-tetrahydro-2H-pyran-3,4,5-triol (E077)

$^1$H NMR (400 MHz, DMSO-d$_6$MeOD) δ 7.42 (t, J=7.2 Hz, 2H), 7.36-7.32 (m, 1H), 7.26 (d, J=7.2 Hz, 2H), 7.16 (s, 1H), 7.09-7.04 (m, 3H), 6.84 (d, J=8.8 Hz, 2H), 4.91-4.89 (m, 2H), 4.76 (d, J=5.6 Hz, 1H), 4.42 (t, J=5.6 Hz, 1H), 4.00-3.95 (m, 5H), 3.71-3.67 (m, 1H), 3.46-3.40 (m, 1H), 3.29-3.12 (m, 4H), 2.05 (s, 3H), 1.30 (t, J=7.2 Hz, 3H); [M+Na]$^+$ 487.

Example 078

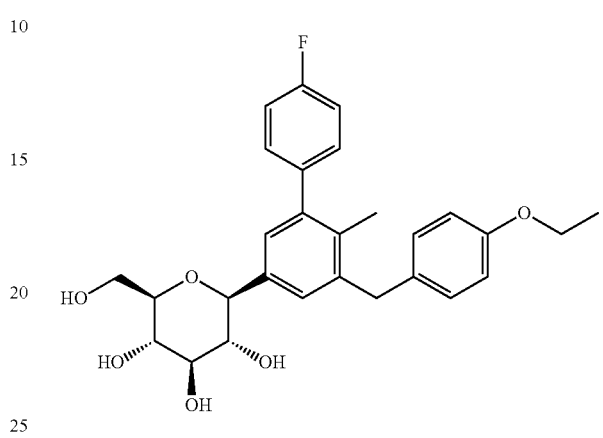

(2S,3R,4R,5S,6R)-2-(5-(4-(Ethoxybenzyl)-4'-fluoro-6-methylbiphenyl-3-yl)-6-(hydroxymethyl)-tetrahydro-2H-pyran-3,4,5-triol (E078)

$^1$H NMR (400 MHz, MeOD) δ 7.30-7.26 (m, 3H), 7.17-7.06 (m, 5H), 7.82 (dt, J=8.8, 2.0 Hz, 2H), 4.14 (d, J=9.2 Hz, 1H), 4.04-3.98 (m, 5H), 3.90 (d, J=12.0 Hz, 1H), 3.73-3.69 (m, 1H), 3.49-3.37 (m, 3H), 2.07 (s, 3H), 1.37 (t, J=7.2 Hz, 3H); [M+Na]$^+$ 505.

Example 079

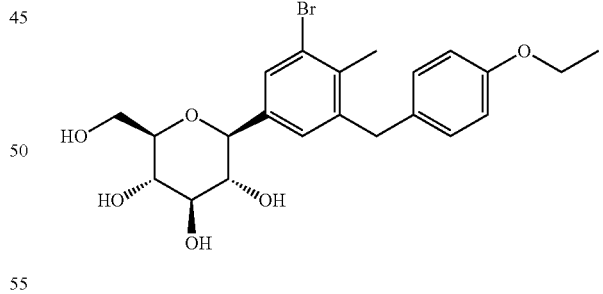

(2S,3R,4R,5S,6R)-2-(3-Bromo-5-(4-ethoxybenzyl)-4-methylphenyl)-6-(hydroxymethyl)-tetrahydro-2H-pyran-3,4,5-triol (E079)

$^1$H NMR (400 MHz, MeOD) δ 7.56 (s, 1H), 7.23 (s, 1H), 7.02 (d, J=8.4 Hz, 2H), 6.81 (d, J=8.8 Hz, 2H), 4.09 (d, J=9.6 Hz, 1H), 4.05-3.97 (m, 4H), 3.90 (d, J=12.0 Hz, 1H), 3.73 (dd, J=12.0, 5.6 Hz, 1H), 3.48-3.37 (m, 4H), 2.28 (s, 3H), 1.37 (t, J=7.2 Hz, 3H); [M+Na]$^+$ 489.

Example 081

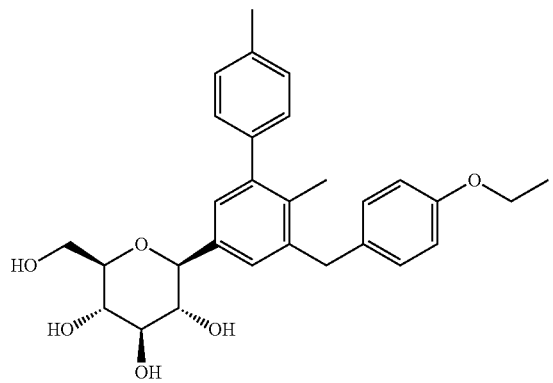

(2S,3R,4R,5S,6R)-2-(5-(4-Ethoxybenzyl)-4',6-dimethylbiphenyl-3-yl)-6-(hydroxymethyl)-tetrahydro-2H-pyran-3,4,5-triol (E081)

$^1$H NMR (400 MHz, MeOD) δ 7.25-7.21 (m, 3H), 7.17-7.14 (m, 3H), 7.08 (d, J=8.8 Hz, 2H), 6.83 (d, J=8.8 Hz, 2H), 4.14 (d, J=9.2 Hz, 1H), 4.05-3.99 (m, 4H), 3.91 (dd, J=12.0, 1.6 Hz, 1H), 3.74-3.69 (m, 1H), 3.50-3.42 (m, 4H), 2.40 (s, 3H), 2.08 (s, 3H), 1.39 (t, J=7.2 Hz, 3H); [M+Na]$^+$ 501.

Example 083

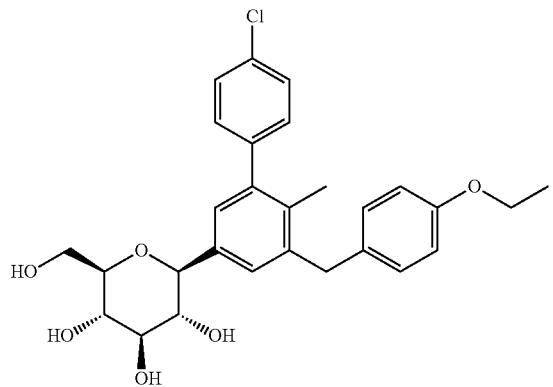 [SMILES: CCOc1ccc(Cc2cc([C@@H]3O[C@H](CO)[C@@H](O)[C@H](O)[C@H]3O)cc(-c3ccc(F)cc3)c2C)cc1]

(2S,3R,4R,5S,6R)-2-(4'-Chloro-5-(4-ethoxybenzyl)-6-methylbiphenyl-3-yl)-6-(hydroxymethyl)-tetrahydro-2H-pyran-3,4,5-triol (E083)

$^1$H NMR (400 MHz, MeOD) δ 7.39 (d, J=8.4 Hz, 2H), 7.26-7.23 (m, 3H), 7.15 (d, J=1.6 Hz, 1H), 7.05 (d, J=8.8 Hz, 2H), 6.80 (d, J=8.8 Hz, 2H), 4.12 (d, J=9.2 Hz, 1H), 4.01-3.96 (m, 4H), 3.88 (dd, J=12.0, 1.6 Hz, 1H), 3.71-3.67 (m, 1H), 3.47-3.35 (m, 4H), 2.05 (s, 3H), 1.36 (t, J=7.2 Hz, 3H); [M+Na]$^+$ 521.

Example 084

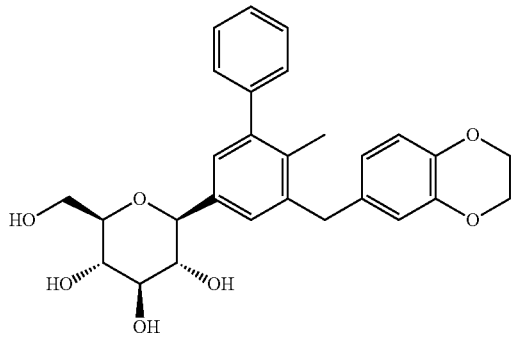 [SMILES: Cc1c(Cc2ccc3c(c2)OCCO3)cc([C@@H]2O[C@H](CO)[C@@H](O)[C@H](O)[C@H]2O)cc1-c1ccccc1]

(2S,3R,4R,5S,6R)-2-(5-((2,3-Dihydrobenzo[b][1,4]dioxin-6-yl)methyl)-6-methylbiphenyl-3-yl)-6-(hydroxymethyl)-tetrahydro-2H-pyran-3,4,5-triol (E084)

$^1$H NMR (400 MHz, MeOD) δ 7.19-7.15 (m, 2H), 7.12-7.08 (m, 1H), 7.05-7.02 (m, 3H), 6.95 (d, J=1.6 Hz, 1H), 6.50 (d, J=8.4 Hz, 1H), 6.42-6.38 (m, 2H), 3.97 (s, 4H), 3.92 (d, J=9.2 Hz, 1H), 3.74 (s, 2H), 3.67 (d, J=12.0 Hz, 1H), 3.50-3.46 (m, 1H), 3.29-3.19 (m, 4H), 1.84 (s, 3H); [M+Na]$^+$ 501.

Example 085

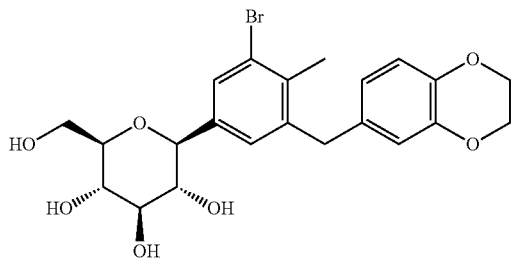 [SMILES: Cc1c(Br)cc([C@@H]2O[C@H](CO)[C@@H](O)[C@H](O)[C@H]2O)cc1Cc1ccc2c(c1)OCCO2]

(2S,3R,4R,5S,6R)-2-(3-Bromo-5-((2,3-dihydrobenzo[b][1,4]dioxin-6-yl)methyl)-4-methylphenyl)-6-(hydroxymethyl)-tetrahydro-2H-pyran-3,4,5-triol (E085)

$^1$H NMR (400 MHz, MeOD) δ 7.34 (d, J=1.6 Hz, 1H), 7.00 (d, J=1.6 Hz, 1H), 6.49 (d, J=8.0 Hz, 1H), 6.36-6.32 (m, 2H), 3.97 (s, 4H), 3.86 (d, J=9.6 Hz, 1H), 3.73 (s, 2H), 3.68 (dd, J=12.0, 2.0 Hz, 1H), 3.50 (dd, J=12.0, 5.6 Hz, 1H), 3.25-3.18 (m, 4H), 2.05 (s, 3H); [M+Na]$^+$ 503.

Example 086

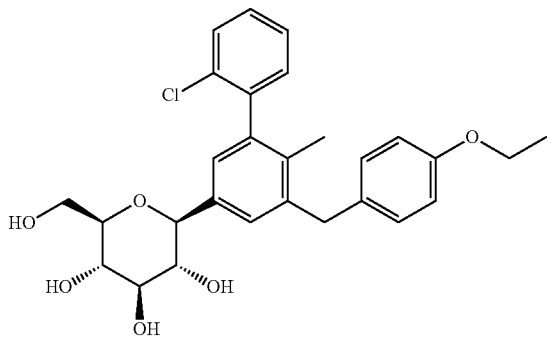 [SMILES: CCOc1ccc(Cc2cc([C@@H]3O[C@H](CO)[C@@H](O)[C@H](O)[C@H]3O)cc(-c3ccccc3Cl)c2C)cc1]

207

(2S,3R,4R,5S,6R)-2-(6'-Chloro-5-(4-ethoxybenzyl)-6-methylbiphenyl-3-yl)-6-(hydroxymethyl)-tetrahydro-2H-pyran-3,4,5-triol (E086)

$^1$H NMR (400 MHz, MeOD) δ 7.47-7.44 (m, 1H), 7.34-7.32 (m, 2H), 7.28 (dd, J=14.4, 2.0 Hz, 1H), 7.23-7.22 (m, 1H), 7.10-7.04 (m, 3H), 6.80 (d, J=8.8 Hz, 2H), 4.13 (d, J=9.6 Hz, 1H), 4.01-3.96 (m, 4H), 3.90-3.86 (m, 1H), 3.71-3.66 (m, 1H), 3.47-3.38 (m, 4H), 1.93 (d, J=2.8 Hz, 3H), 1.36 (t, J=7.2 Hz, 3H); [M+Na]$^+$ 521.

Example 087

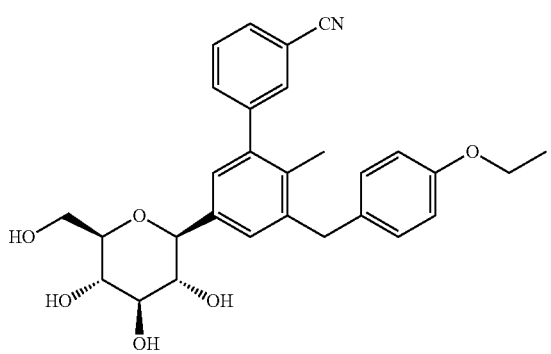 [SMILES: CCOc1ccc(Cc2cc([C@@H]3O[C@H](CO)[C@@H](O)[C@H](O)[C@H]3O)cc(-c3cccc(C#N)c3)c2C)cc1]

3'-(4-Ethoxybenzyl)-2'-methyl-5'-((2S,3R,4R,5S,6R)-3,4,5-trihydroxy-6-(hydroxymethyl)-tetrahydro-2H-pyran-2-yl)biphenyl-3-carbonitrile (E087)

$^1$H NMR (400 MHz, MeOD) δ 7.70-7.68 (m, 1H), 7.64 (d, J=1.2 Hz, 1H), 7.59-7.57 (m, 2H), 7.30 (d, J=1.6 Hz, 1H), 7.17 (d, J=1.6 Hz, 1H), 7.06 (d, J=8.8 Hz, 2H), 6.80 (d, J=8.8 Hz, 2H), 4.13 (d, J=9.6 Hz, 1H), 4.01-3.96 (m, 4H), 3.90-3.86 (m, 1H), 3.72-3.68 (m, 1H), 3.50-3.35 (m, 4H), 2.06 (s, 3H), 1.35 (t, J=7.2 Hz, 3H); [M+Na]$^+$ 512.

Example 088

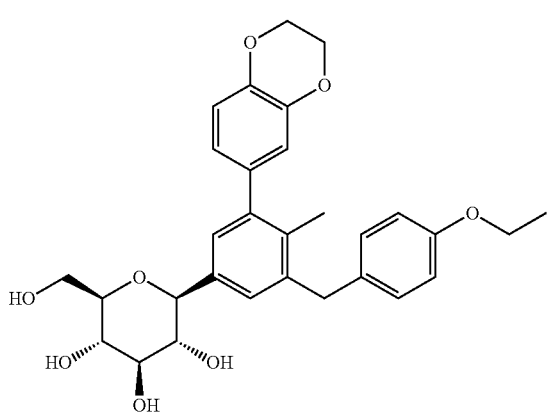 [SMILES: CCOc1ccc(Cc2cc([C@@H]3O[C@H](CO)[C@@H](O)[C@H](O)[C@H]3O)cc(-c3ccc4c(c3)OCCO4)c2C)cc1]

(2S,3R,4R,5S,6R)-2-(3-(2,3-Dihydrobenzo[b][1,4]dioxin-6-yl)-5-(4-ethylbenzyl)-4-methylphenyl)-6-(hydroxymethyl)-tetrahydro-2H-pyran-3,4,5-triol (E088)

$^1$H NMR (400 MHz, MeOD) δ 7.22 (d, J=1.6 Hz, 1H), 7.13 (d, J=1.6 Hz, 1H), 7.07 (dd, J=13.2, 8.4 Hz, 4H), 6.83 (d, J=8.0 Hz, 1H), 6.72 (d, J=1.6 Hz, 1H), 6.69 (dd, J=8.4, 2.0 Hz, 1H), 4.25 (s, 4H), 4.10 (d, J=9.2 Hz, 1H), 4.02 (s, 2H), 3.88 (dd, J=12.0, 1.6 Hz, 1H), 3.71-3.67 (m, 1H), 3.49-3.38 (m, 4H), 2.59 (q, J=7.6 Hz, 2H), 2.06 (s, 3H), 1.20 (t, J=7.6 Hz, 3H); [M+Na]$^+$ 529.

Example 089

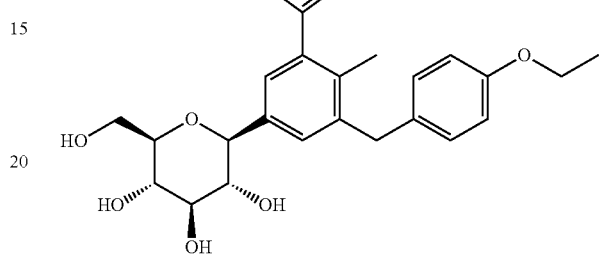

(2S,3R,4R,5S,6R)-2-(3-(4-Ethoxybenzyl)-4-methyl-5-(thiophen-3-yl)phenyl)-6-(hydroxymethyl)-tetrahydro-2H-pyran-3,4,5-triol (E089)

$^1$H NMR (400 MHz, MeOD) δ 7.42 (dd, J=4.8, 3.2 Hz, 1H), 7.23-7.22 (m, 3H), 7.08-7.04 (m, 3H), 6.79 (d, J=8.8 Hz, 2H), 4.11 (d, J=9.2 Hz, 1H), 4.01-3.96 (m, 4H), 3.88 (dd, J=12.0, 1.6 Hz, 1H), 3.72-3.67 (m, 1H), 3.48-3.39 (m, 4H), 2.12 (s, 3H), 1.35 (t, J=7.2 Hz, 3H); [M+Na]$^+$ 493.

Example 090

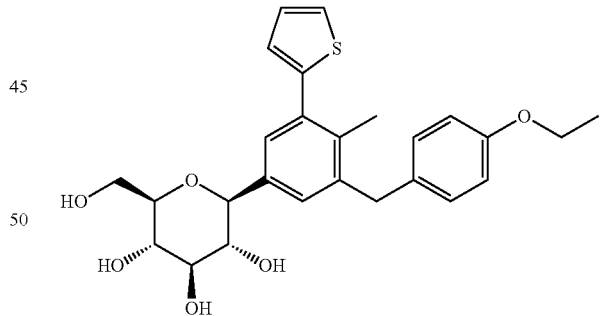

(2S,3R,4R,5S,6R)-2-(3-(4-Ethoxybenzyl)-4-methyl-5-(thiophen-2-yl)phenyl)-6-(hydroxymethyl)-tetrahydro-2H-pyran-3,4,5-triol (E090)

$^1$H NMR (400 MHz, MeOD) δ 7.39 (dd, J=5.2, 1.2 Hz, 1H), 7.31 (d, J=1.6 Hz, 1H), 7.26 (d, J=1.6 Hz, 1H), 7.08-7.04 (m, 3H), 6.96 (dd, J=3.6, 1.2 Hz, 1H), 6.80 (d, J=8.4 Hz, 2H), 4.11 (d, J=9.2 Hz, 1H), 4.01-3.96 (m, 4H), 3.88 (dd, J=11.2 Hz, 1H), 3.72-3.67 (m, 1H), 3.47-3.35 (m, 4H), 2.18 (s, 3H), 1.36 (t, J=7.2 Hz, 3H); [M+Na]$^+$ 493.

Example 091

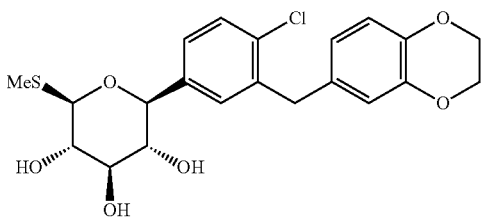 [SMILES: CS[C@H]1O[C@@H](c2ccc(Cl)c(Cc3ccc4c(c3)OCCO4)c2)[C@H](O)[C@@H](O)[C@@H]1O]

(2S,3R,4R,5S,6R)-2-(4-Chloro-3-((2,3-dihydrobenzo[b][1,4]dioxin-6-yl)methyl)phenyl)-6-(methylthio)tetrahydro-2H-pyran-3,4,5-triol (E091)

To a suspension of compound 138 (50 mg, 0.09 mmol) in CH$_3$OH (5.0 mL) was added NaOMe (100 μL, 25% solution in CH$_3$OH) at room temperature. After 1 h, the resulting mixture was concentrated in vacuo. The crude was purified by preparative HPLC (reverse phase) to provide the title compound (29 mg, 74%) as a white solid.

$^1$H NMR (400 MHz, CDCl$_3$) δ 7.31 (d, J=8.0 Hz, 1H), 7.19-7.14 (m, 2H), 6.75 (d, J=8.8 Hz, 1H), 6.65-6.63 (m, 2H), 4.32 (d, J=9.2 Hz, 1H), 4.16 (s, 4H), 4.09 (d, J=8.8 Hz, 1H), 3.94 (ABq, Δv$_{AB}$=23.1 Hz, J$_{AB}$=15.4 Hz, 2H), 3.61-3.58 (m, 1H), 3.52-3.43 (m, 2H), 2.11 (s, 3H); [M+Na]$^+$ 461.

Example 092

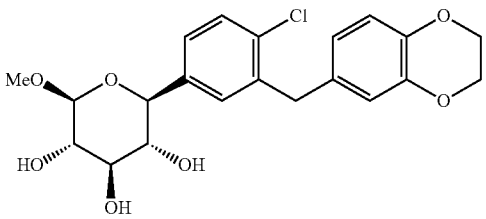

(2S,3R,4R,5S,6S)-2-(4-Chloro-3-((2,3-dihydrobenzo[b][1,4]dioxin-6-yl)methyl)phenyl)-6-methoxy-tetrahydro-2H-pyran-3,4,5-triol (E092)

To a suspension of compound 140 (40 mg, 0.07 mmol) in CH$_3$OH (5.0 mL) was added NaOMe (100 μL, 25% solution in CH$_3$OH) at room temperature. After 1 h, the resulting mixture was concentrated in vacuo. The crude was purified by preparative HPLC (reverse phase) to provide the title compound (18 mg, 62%) as a white solid.

$^1$H NMR (400 MHz, CDCl$_3$) δ 7.28-7.22 (m, 2H), 7.18 (d, J=8.0 Hz, 1H), 6.73-6.70 (m, 1H), 6.63-6.61 (m, 2H), 4.19 (d, J=7.2 Hz, 1H), 4.10 (s, 4H), 4.02 (d, J=9.2 Hz, 1H), 3.91 (ABq, Δv$_{AB}$=27.6 Hz, J$_{AB}$=15.0 Hz, 2H), 3.54-3.51 (m, 1H), 3.46-3.37 (m, 2H), 3.35 (s, 3H); [M+Na]$^+$ 445.

Example 093

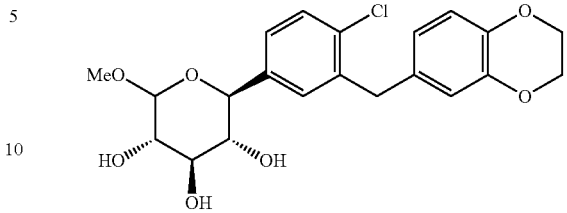

(2S,3R,4R,5S)-2-(4-Chloro-3-((2,3-dihydrobenzo[b][1,4]dioxin-6-yl)methyl)phenyl)-6-methoxytetrahydro-2H-pyran-3,4,5-triol (E093)

A solution of 0.35M HCl in CH$_3$OH was prepared by adding AcCl (25 μL, 0.35 mmol) to CH$_3$OH (1.0 mL) at 0° C., and stirring for 15 min. Compound 136 (50 mg, 0.11 mmol) was treated with this solution for 2 h at 80° C. in a sealed vial. The reaction mixture cooled to room temperature, and quenched with K$_2$CO$_3$ until basic. The mixture was diluted with CH$_2$Cl$_2$, filtered, and concentrated in vacuo. The crude was purified by preparative HPLC (reverse phase) to provide the title compound (22 mg, 48%) as a white solid.

$^1$H NMR (400 MHz, CDCl$_3$) δ 7.34 (d, J=8.4 Hz, 1H), 7.25-7.17 (m, 2H), 6.77-6.74 (m, 1H), 6.67-6.65 (m, 2H), 4.79 (d, J=4.0 Hz, 1H α), 4.38 (d, J=9.6 Hz, 1H α), 4.27 (d, J=7.6 Hz, 1H β), 4.17 (s, 4H), 4.10 (d, J=9.2 Hz, 1H β), 4.03-3.91 (m, 2H), 3.81 (t, J=9.2 Hz, 1H α), 3.64-3.58 (m, 1H), 3.50-3.40 (m, 1H), 3.46 (s, 3H β), 3.37 (s, 3H α); [M+Na]$^+$ 445.

Example 094

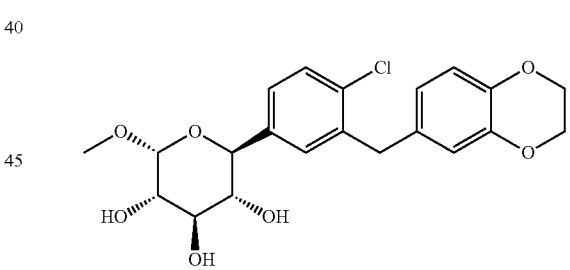

(2S,3R,4R,5S,6R)-2-(4-Chloro-3-((2,3-dihydrobenzo[b][1,4]dioxin-6-yl)methyl)phenyl)-6-methoxy-tetrahydro-2H-pyran-3,4,5-triol (E094)

To a suspension of compound 143 (40 mg, 0.07 mmol) in CH$_3$OH (5.0 mL) was added NaOMe (100 μL, 25% solution in CH$_3$OH) at room temperature. After 1 h, the resulting mixture was concentrated in vacuo. The crude was purified by preparative HPLC (reverse phase) to provide the title compound (12 mg, 42%) as a white solid.

$^1$H NMR (400 MHz, CDCl$_3$) δ 7.29-7.24 (m, 2H), 7.14-7.12 (m, 1H), 6.73-6.71 (m, 1H), 6.63-6.61 (m, 2H), 4.71 (d, J=2.8 Hz, 1H), 4.34 (d, J=9.6 Hz, 1H), 4.11 (s, 4H), 3.94-3.90 (m, 2H), 3.83-3.79 (m, 1H), 3.54 (d, J=8.0 Hz, 1H), 3.39-3.34 (m, 1H), 3.28 (s, 3H); [M+Na]$^+$ 445.

Example 095

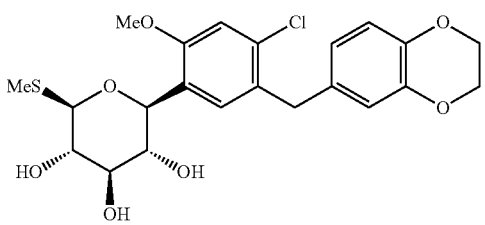 [SMILES: COc1cc(Cl)c(Cc2ccc3c(c2)OCCO3)cc1[C@@H]1O[C@H](SC)[C@@H](O)[C@H](O)[C@H]1O]

(2S,3R,4R,5S,6R)-2-(4-Chloro-5-((2,3-dihydrobenzo[b][1,4]dioxin-6-yl)methyl)-2-methoxyphenyl)-6-(methylthio)-tetrahydro-2H-pyran-3,4,5-triol (E095)

$^1$H NMR (400 MHz, CD$_3$OD) δ 7.23 (s, 1H), 7.01 (s, 1H), 6.70 (d, J=8.8 Hz, 1H), 6.64-6.63 (m, 2H), 4.63 (d, J=9.6 Hz, 1H), 4.35 (d, J=9.6 Hz, 1H), 4.18 (s, 4H), 3.92-3.91 (m, 2H), 3.82 (s, 3H), 3.53 (t, J=8.8 Hz, 1H), 3.47 (t, J=8.8 Hz, 1H), 3.37-3.32 (m, 1H), 2.11 (s, 3H); [M+Na]$^+$ 491.

Example 096

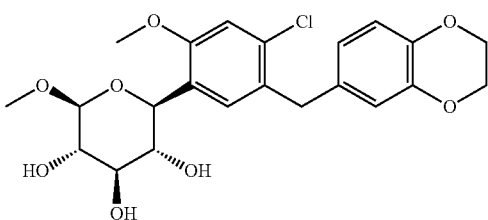 [SMILES: COc1cc(Cl)c(Cc2ccc3c(c2)OCCO3)cc1[C@@H]1O[C@H](OC)[C@@H](O)[C@H](O)[C@H]1O]

(2S,3R,4R,5S,6S)-2-(4-Chloro-5-((2,3-dihydrobenzo[b][1,4]dioxin-6-yl)methyl)-2-methoxyphenyl)-6-methoxy-tetrahydro-2H-pyran-3,4,5-triol (E096)

$^1$H NMR (400 MHz, CD$_3$OD) δ 7.27 (s, 1H), 7.01 (s, 1H), 6.70 (dd, J=6.8, 2.4 Hz, 1H), 6.65-6.63 (m, 2H), 4.64 (d, J=9.2 Hz, 1H), 4.28 (d, J=7.6 Hz, 1H), 4.18 (s, 4H), 3.92 (ABq, Δv$_{AB}$=8.1 Hz, J$_{AB}$=15.2 Hz, 2H), 3.82 (s, 3H), 3.52-3.42 (m, 2H), 3.46 (s, 3H), 3.28-3.25 (m, 1H); [M+Na]$^+$ 475.

Example 097

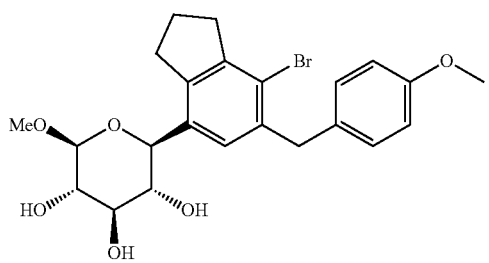

(2S,3R,4R,5S,6S)-2-(7-Bromo-6-(4-methoxybenzyl)-2,3-dihydro-1H-inden-4-yl)-6-methoxy-tetrahydro-2H-pyran-3,4,5-triol (E097)

$^1$H NMR (400 MHz, CDCl$_3$) δ 7.11-7.09 (m, 3H), 6.79 (d, J=8.4 Hz, 2H), 4.29 (d, J=7.6 Hz, 1H), 4.23 (d, J=8.8 Hz, 1H), 4.03 (ABq, Δv$_{AB}$=21.2 Hz, J$_{AB}$=15.4 Hz, 2H), 3.75 (s, 3H), 3.65-3.61 (m, 2H), 3.52-3.47 (m, 1H), 3.51 (s, 3H), 3.18-3.09 (m, 1H), 3.05-2.99 (m, 1H), 2.96 (t, J=7.6 Hz, 2H), 2.07 (m, 2H); [M+Na]$^+$ 501.

Example 098

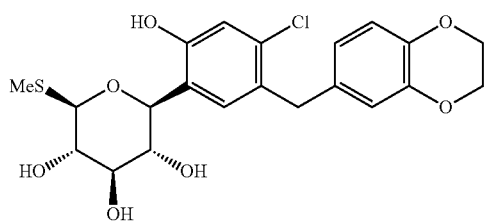 [SMILES: CS[C@H]1O[C@@H](c2cc(Cc3ccc4c(c3)OCCO4)c(Cl)cc2O)[C@H](O)[C@@H](O)[C@@H]1O]

(2S,3R,4R,5S,6R)-2-(4-Chloro-5-((2,3-dihydrobenzo[b][1,4]dioxin-6-yl)methyl)-2-hydroxyphenyl)-6-(methylthio)-tetrahydro-2H-pyran-3,4,5-triol (E098)

$^1$H NMR (400 MHz, CD$_3$OD) δ 7.14 (s, 1H), 6.79 (s, 1H), 6.70-6.68 (m, 1H), 6.64-6.61 (m, 2H), 4.63 (d, J=9.2 Hz, 1H), 4.39 (d, J=9.6 Hz, 1H), 4.18 (s, 4H), 3.86-3.85 (m, 2H), 3.49-3.46 (m, 2H), 3.36-3.33 (m, 1H), 2.13 (s, 3H); [M+Na]$^+$ 477.

Example 099

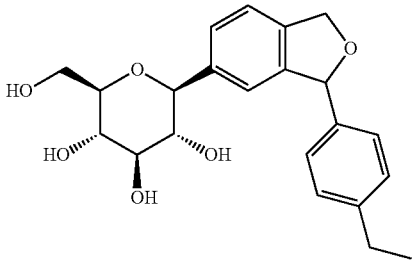 [SMILES: CCc1ccc(C2OCc3ccc([C@@H]4O[C@H](CO)[C@@H](O)[C@H](O)[C@H]4O)cc32)cc1]

(2S,3R,4R,5S,6R)-2-(3-(4-Ethylphenyl)-1,3-dihydroisobenzofuran-5-yl)-6-(hydroxymethyl)-tetrahydro-2H-pyran-3,4,5-triol (E099)

To a suspension of 151 (380 mg, 0.68 mmol) in CH$_3$OH (5.0 mL) was added K$_2$CO$_3$ (65 mg, 0.47 mmol) at room temperature. After 1.5 h, the resulting mixture was filtered, and then purified by preparative HPLC (reverse phase) to provide the title compound (145 mg, 55%) as an off-white solid.

$^1$H NMR (400 MHz, DMSO-d$_6$) δ 7.31-7.22 (m, 4H), 7.20-7.18 (m, 2H), 6.98 (d, J=19.6 Hz, 1H), 6.09 (br s, 1H), 5.26 (dt, J=12.4, 3.6 Hz, 1H), 5.08 (d, J=11.6 Hz, 1H), 4.81 (br s, 4H), 3.98 (dd, J=9.2, 7.2 Hz, 1H), 3.67-3.63 (m, 1H), 3.44-3.35 (m, 1H), 3.25-3.01 (m, 4H), 2.59 (q, J=7.6 Hz, 2H), 1.17 (t, J=7.6 Hz, 3H); [M+H]$^+$ 387.

Example 100

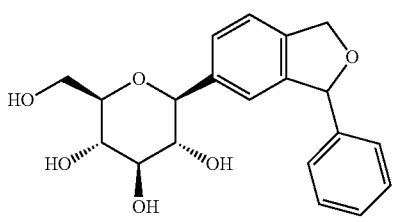 [SMILES: OC[C@H]1O[C@@H](c2ccc3c(c2)C(c2ccccc2)OC3)[C@H](O)[C@@H](O)[C@@H]1O]

(2R,3S,4R,5R,6S)-2-(Hydroxymethyl)-6-(3-phenyl-1,3-dihydroisobenzofuran-5-yl)-tetrahydro-2H-pyran-3,4,5-triol (E100)

$^1$H NMR (400 MHz, DMSO-d$_6$) δ 7.37-7.32 (m, 4H), 7.31-7.26 (m, 3H), 6.99 (d, J=20.0 Hz, 1H), 6.13 (br s, 1H), 5.29 (dt, J=12.4, 2.8 Hz, 1H), 5.10 (d, J=11.6 Hz, 1H), 4.75 (br s, 4H), 3.98 (dd, J=9.2, 7.6 Hz, 1H), 3.65 (ddd, J=11.6, 4.8, 1.6 Hz, 1H), 3.44-3.35 (m, 1H), 3.25-3.01 (m, 4H); [M+H]$^+$ 359.

Example 101

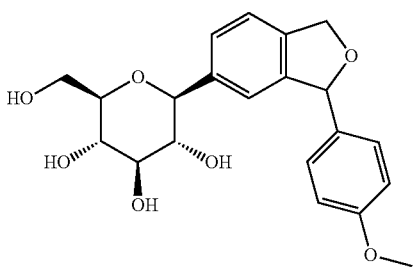 [SMILES: COc1ccc(C2OCc3ccc([C@@H]4O[C@H](CO)[C@@H](O)[C@H](O)[C@H]4O)cc32)cc1]

(2R,3S,4R,5R,6S)-2-(Hydroxymethyl)-6-(3-(4-methoxyphenyl)-1,3-dihydroisobenzofuran-5-yl)-tetrahydro-2H-pyran-3,4,5-triol (E101)

$^1$H NMR (400 MHz, DMSO-d$_6$) δ 7.31-7.22 (m, 4H), 6.97-6.89 (m, 3H), 6.07 (br s, 1H), 5.23 (dq, J=12.6, 2.4 Hz, 1H), 5.06 (d, J=11.6 Hz, 1H), 4.92-4.89 (m, 2H), 4.74-4.70 (m, 1H), 4.41 (br s, 1H), 3.98 (dd, J=9.2, 7.6 Hz, 1H), 3.74 (s, 3H), 3.67-3.64 (m, 1H), 3.44-3.36 (m, 1H), 3.25-3.02 (m, 4H); [M+H]$^+$ 389.

Example 102

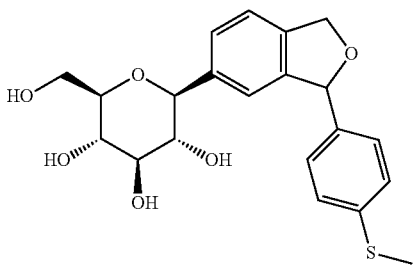 [SMILES: CSc1ccc(C2OCc3ccc([C@@H]4O[C@H](CO)[C@@H](O)[C@H](O)[C@H]4O)cc32)cc1]

(2R,3S,4R,5R,6S)-2-(Hydroxymethyl)-6-(3-(4-(methylthio)phenyl)-1,3-dihydroisobenzofuran-5-yl)-tetrahydro-2H-pyran-3,4,5-triol (E102)

$^1$H NMR (400 MHz, DMSO-d$_6$) δ 7.30-7.22 (m, 6H), 6.98 (d, J=18.4 Hz, 1H), 6.09 (br s, 1H), 5.26 (dt, J=11.6, 2.8 Hz, 1H), 5.08 (d, J=11.6 Hz, 1H), 4.91 (br s, 2H), 4.74 (br s, 1H), 4.42 (br s, 1H), 3.98 (dd, J=9.2, 7.2 Hz, 1H), 3.66 (dd, J=11.2, 3.6 Hz, 1H), 3.45-3.36 (m, 1H), 3.25-3.02 (m, 4H), 2.46 (s, 3H); [M+H]$^+$ 405.

Example 103

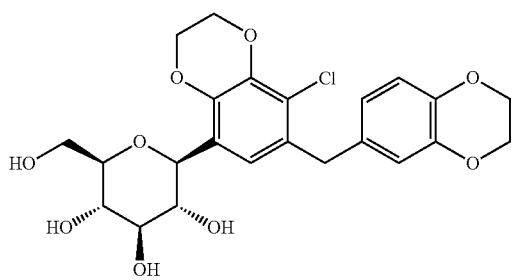 [SMILES: OC[C@H]1O[C@@H](c2cc(Cc3ccc4c(c3)OCCO4)c(Cl)c3c2OCCO3)[C@H](O)[C@@H](O)[C@@H]1O]

(2S,3R,4R,5S,6R)-2-(8-Chloro-7-((2,3-dihydrobenzo[b][1,4]dioxin-6-yl)methyl)-2,3-dihydrobenzo[b][1,4]dioxin-5-yl)-6-(hydroxymethyl)tetrahydro-2H-pyran-3,4,5-triol (E103)

$^1$H NMR (400 MHz, CD$_3$OD) δ 6.95 (s, 1H), 6.74-6.61 (m, 3H), 4.88 (s, 4H), 4.61-4.56 (m, 1H), 4.37-4.32 (m, 2H), 4.31-4.24 (m, 2H), 4.20 (s, 3H), 3.92 (ABq, Δν$_{AB}$=11.5 Hz, J$_{AB}$=15.1 Hz, 2H), 3.88 (d, J=11.2 Hz, 1H), 3.73-3.64 (m, 1H), 3.53-3.43 (m, 2H), 3.41-3.31 (m, 3H); [M+Na]$^+$ 503.

Example 104

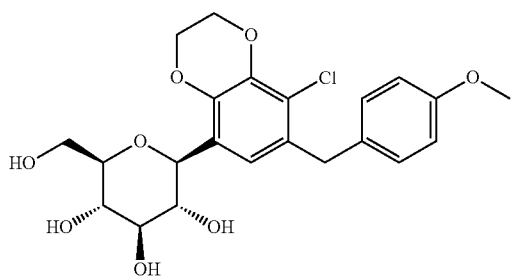

(2S,3R,4R,5S,6R)-2-(8-Chloro-7-(4-methoxybenzyl)-2,3-dihydrobenzo[b][1,4]dioxin-5-yl)-6-(hydroxymethyl)tetrahydro-2H-pyran-3,4,5-triol (E104)

$^1$H NMR (400 MHz, CD$_3$OD) δ 7.09 (d, J=8.8 Hz, 2H), 6.95 (s, 1H), 6.80 (d, J=8.7 Hz, 2H), 4.88 (s, 4H), 4.63-4.55 (m, 1H), 4.37-4.33 (m, 2H), 4.31-4.25 (m, 2H), 3.96 (ABq, Δν$_{AB}$=13.3 Hz, J$_{AB}$=15.2 Hz, 2H), 3.87 (d, J=11.0 Hz, 1H), 3.77 (s, 3H), 3.73-3.64 (m, 1H), 3.52-3.45 (m, 2H), 3.41-3.35 (m, 2H); [M+Na]$^+$ 475.

Example 105

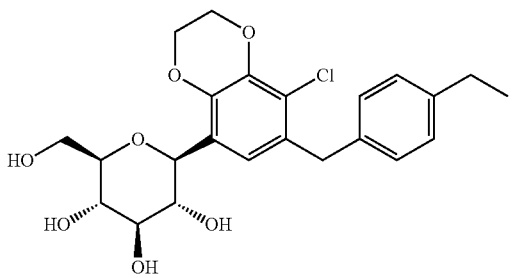

(2S,3R,4R,5S,6R)-2-(8-Chloro-7-(4-ethylbenzyl)-2,3-dihydrobenzo[b][1,4]dioxin-5-yl)-6-(hydroxymethyl)tetrahydro-2H-pyran-3,4,5-triol (E105)

$^1$H NMR (400 MHz, CD$_3$OD) δ 7.10 (s, 4H), 4.86 (s, 5H), 4.62-4.54 (m, 1H), 4.37-4.32 (m, 2H), 4.31-4.25 (m, 2H), 4.01 (ABq, Δv$_{AB}$=11.8 Hz, J$_{AB}$=15.1 Hz, 2H), 3.88 (d, J=10.5 Hz, 1H), 3.73-3.63 (m, 1H), 3.54-3.44 (m, 2H), 3.41-3.36 (m, 2H), 2.61 (q, J=7.6 Hz, 2H), 1.22 (t, J=7.6 Hz, 3H); [M+Na]$^+$ 473.

Example 106

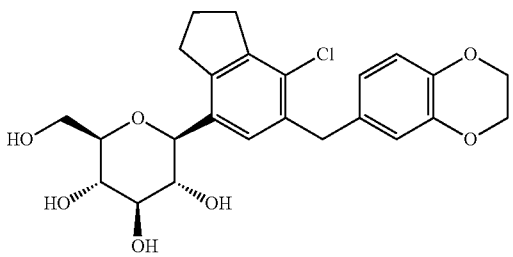

(2S,3R,4R,5S,6R)-2-(7-Chloro-6-((2,3-dihydrobenzo[b][1,4]dioxin-6-yl)methyl)-2,3-dihydro-1H-inden-4-yl)-6-(hydroxymethyl)tetrahydro-2H-pyran-3,4,5-triol (E106)

$^1$H NMR (400 MHz, CD$_3$OD) δ 7.19 (s, 1H), 6.72 (d, J=8.0 Hz, 2H), 6.68-6.64 (m, 2H), 4.21 (d, J=9.2 Hz, 1H), 4.21 (s, 4H), 3.98 (ABq, Δv$_{AB}$=16.4 Hz, J$_{AB}$=15.0 Hz, 2H), 3.90 (d, J=11.2 Hz, 1H), 3.72-3.65 (m, 1H), 3.52-3.46 (m, 2H), 3.43-3.38 (m, 2H), 3.23-3.14 (m, 1H), 3.09-3.02 (m, 1H), 2.98 (t, J=7.4 Hz, 2H), 2.12 (m, 2H), 1.35 (t, J=6.8 Hz, 3H); [M+Na]$^+$ 485.

Example 107

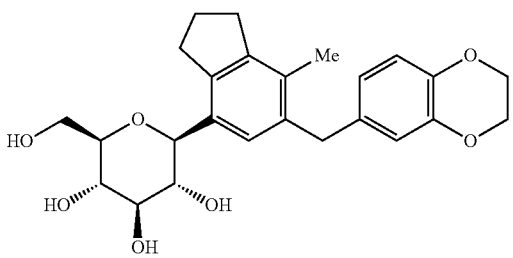 [SMILES: Cc1c(Cc2ccc3c(c2)OCCO3)cc([C@@H]2O[C@H](CO)[C@@H](O)[C@H](O)[C@H]2O)c2c1CCC2]

(2S,3R,4R,5S,6R)-2-(6-((2,3-Dihydrobenzo[b][1,4]dioxin-6-yl)methyl)-7-methyl-2,3-dihydro-1H-inden-4-yl)-6-(hydroxymethyl)tetrahydro-2H-pyran-3,4,5-triol (E107)

$^1$H NMR (400 MHz, CD$_3$OD) δ 7.08 (s, 1H), 6.70 (d, J=8.0 Hz, 2H), 6.60 (dd, J=8.4, 2.0 Hz, 1H), 6.55 (d, J=2.0 Hz, 1H), 4.27 (d, J=9.2 Hz, 1H), 4.20 (s, 4H), 3.93-3.89 (m, 3H), 3.73-3.67 (m, 1H), 3.59 (t, J=7.0 Hz, 1H), 3.53-3.48 (m, 1H), 3.44-3.40 (m, 2H), 3.16-3.08 (m, 1H), 3.04-2.96 (m, 1H), 2.86 (t, J=7.4 Hz, 2H), 2.12-2.05 (m, 5H); [M+Na]$^+$ 465.

Example 108

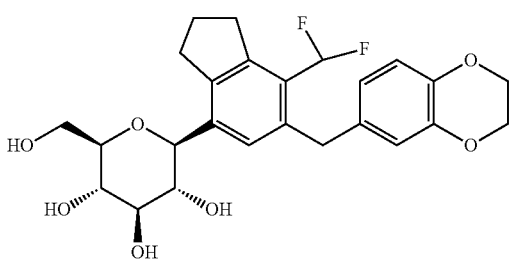 [SMILES: OC[C@H]1O[C@@H](c2cc(Cc3ccc4c(c3)OCCO4)c(C(F)F)c3c2CCC3)[C@H](O)[C@@H](O)[C@@H]1O]

(2S,3R,4R,5S,6R)-2-(7-(Difluoromethyl)-6-((2,3-dihydrobenzo[b][1,4]dioxin-6-yl)methyl)-2,3-dihydro-1H-inden-4-yl)-6-(hydroxymethyl)tetrahydro-2H-pyran-3,4,5-triol (E108)

$^1$H NMR (400 MHz, CD$_3$OD) δ 7.20 (s, 1H), 6.93 (t, J=54.4 Hz, 1H), 6.74 (d, J=8.4 Hz, 1H), 6.64-6.56 (m, 2H), 4.33 (d, J=9.2 Hz, 1H), 4.22 (s, 4H), 4.06 (ABq, Δv$_{AB}$=12.0 Hz, J$_{AB}$=16.0 Hz, 2H), 3.92 (d, J=12.4 Hz, 1H), 3.74-3.70 (m, 1H), 3.56-3.50 (m, 2H), 3.47-3.42 (m, 2H), 3.19-3.08 (m, 3H), 3.03-2.95 (m, 1H), 2.17-2.08 (m, 2H); [M+Na]$^+$ 501.

Example 109

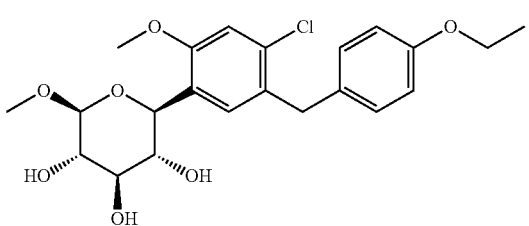

(2S,3R,4R,5S,6S)-2-(4-Chloro-5-(4-ethoxybenzyl)-2-methoxyphenyl)-6-methoxytetrahydro-2H-pyran-3,4,5-triol (E109)

$^1$H NMR (400 MHz, CD$_3$OD) δ 7.26 (s, 1H), 7.08 (d, J=6.8 Hz, 2H), 7.01 (s, 1H), 6.79 (d, J=6.8 Hz, 2H), 4.63 (d, J=9.6 Hz, 1H), 4.27 (d, J=7.6 Hz, 1H), 4.01-3.95 (m, 4H), 3.82 (s, 3H), 3.51-3.42 (m, 5H), 3.28-3.24 (m, 1H), 1.36 (t, J=6.8 Hz, 3H); [M+Na]$^+$ 461.

Example 110

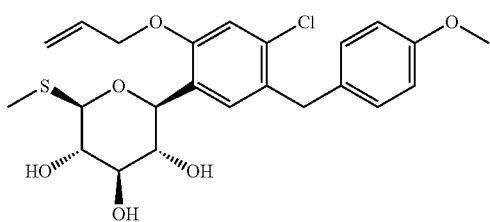

(2S,3R,4R,5S,6R)-2-(2-(Allyloxy)-4-chloro-5-(4-methoxybenzyl)phenyl)-6-(methylthio)tetrahydro-2H-pyran-3,4,5-triol (E110)

$^1$H NMR (400 MHz, CD$_3$OD) δ 7.23 (s, 1H), 7.10 (d, J=8.8 Hz, 2H), 7.01 (s, 1H), 6.81 (d, J=8.8 Hz, 2H), 6.12-6.02 (m, 1H), 5.43 (dq, J=17.2, 1.6 Hz, 1H), 5.26 (dq, J=10.8, 1.6 Hz, 1H), 4.63 (d, J=10.0 Hz, 1H), 4.58-4.57 (m, 2H), 4.35 (d, J=9.6 Hz, 1H), 3.97 (br s, 2H), 3.75 (s, 3H), 3.59-3.56 (m, 1H), 3.46 (t, J=8.8 Hz, 1H), 3.36-3.33 (m, 2H), 2.10 (s, 3H); [M+Na]$^+$ 489.

Example 111

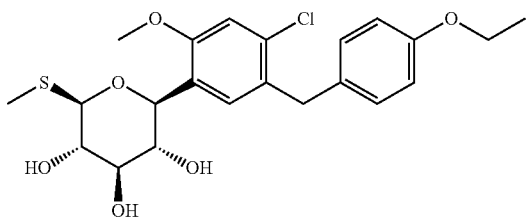

(2S,3R,4R,5S,6R)-2-(4-Chloro-5-(4-ethoxybenzyl)-2-methoxyphenyl)-6-(methylthio)tetrahydro-2H-pyran-3,4,5-triol (E111)

$^1$H NMR (400 MHz, DMSO-d$_6$) δ 7.25 (s, 1H), 7.08 (d, J=8.4 Hz, 2H), 7.04 (s, 1H), 6.82 (d, J=8.8 Hz, 2H), 4.46 (d, J=9.6 Hz, 1H), 4.26 (d, J=9.6 Hz, 1H), 3.99-3.91 (m, 4H), 3.77 (s, 3H), 3.40-3.24 (m, 2H), 3.17-3.12 (m, 1H), 2.00 (s, 3H), 1.29 (t, J=6.8 Hz, 3H); [M+Na]$^+$ 477.

Example 112

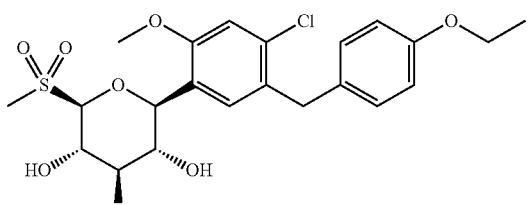

(2S,3R,4R,5S,6R)-2-(4-Chloro-5-(4-ethoxybenzyl)-2-methoxyphenyl)-6-(methylsulfonyl)tetrahydro-2H-pyran-3,4,5-triol (E112)

$^1$H NMR (400 MHz, DMSO-d$_6$) δ 7.29 (s, 1H), 7.09-7.06 (m, 3H), 6.81 (d, J=6.8 Hz, 2H), 4.60 (d, J=9.2 Hz, 1H), 4.46 (d, J=9.6 Hz, 1H), 3.99-3.92 (m, 4H), 3.78 (s, 3H), 3.64-3.59 (m, 1H), 3.43-3.38 (m, 2H), 2.90 (s, 3H), 1.30 (t, J=6.8 Hz, 3H); [M+Na]$^+$ 509.

Example 113

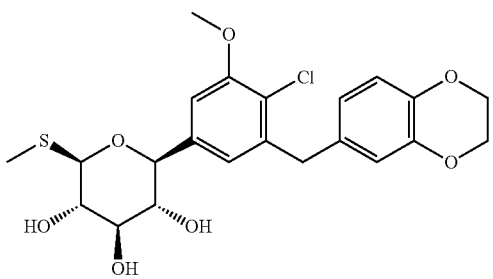 [SMILES: COc1cc([C@@H]2O[C@H](SC)[C@@H](O)[C@H](O)[C@H]2O)cc(Cc2ccc3c(c2)OCCO3)c1Cl]

(2S,3R,4R,5S,6R)-2-(4-Chloro-3-((2,3-dihydrobenzo[b][1,4]dioxin-6-yl)methyl)-5-methoxyphenyl)-6-(methylthio)tetrahydro-2H-pyran-3,4,5-triol (E113)

$^1$H NMR (400 MHz, CD$_3$OD) δ 6.98 (d, J=2.0 Hz, 1H), 6.88 (d, J=1.6 Hz, 1H), 6.71-6.69 (m, 1H), 6.66-6.63 (m, 2H), 4.40 (d, J=9.6 Hz, 1H), 4.18 (br s, 4H), 4.14 (d, J=9.6 Hz, 1H), 3.97 (ABq, Δv$_{AB}$=13.0 Hz, J$_{AB}$=15.2 Hz, 2H), 3.89 (s, 3H), 3.46 (t, J=8.8 Hz, 1H), 3.37 (t, J=9.6 Hz, 1H), 2.15 (s, 3H); [M+Na]$^+$ 491.

Example 114

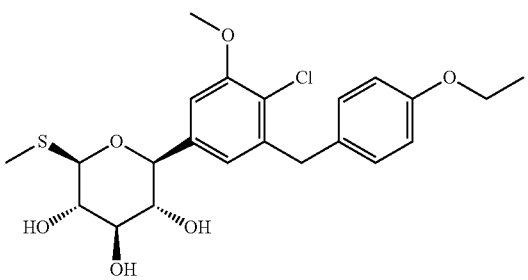 [SMILES: CCOc1ccc(Cc2cc([C@@H]3O[C@H](SC)[C@@H](O)[C@H](O)[C@H]3O)cc(OC)c2Cl)cc1]

(2S,3R,4R,5S,6R)-2-(4-Chloro-3-(4-ethoxybenzyl)-5-methoxyphenyl)-6-(methylthio)tetrahydro-2H-pyran-3,4,5-triol (E114)

$^1$H NMR (400 MHz, CD$_3$OD) δ 7.09 (d, J=8.8 Hz, 2H), 6.97 (d, J=1.6 Hz, 1H), 6.87 (d, J=1.6 Hz, 1H), 6.79 (d, J=8.8 Hz, 2H), 4.39 (d, J=9.6 Hz, 1H), 4.13 (d, J=9.2 Hz, 1H), 4.06-3.96 (m, 4H), 3.88 (s, 3H), 3.47-3.42 (m, 1H), 3.38-3.34 (m, 2H), 2.14 (s, 3H), 1.35 (t, J=6.8 Hz, 3H); [M+Na]$^+$ 477.

Example 115

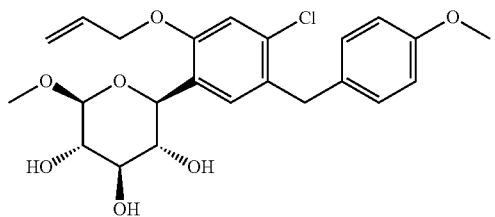

(2S,3R,4R,5S,6S)-2-(2-(Allyloxy)-4-chloro-5-(4-methoxybenzyl)phenyl)-6-methoxytetrahydro-2H-pyran-3,4,5-triol (E115)

$^1$H NMR (400 MHz, CD$_3$OD) δ 7.27 (s, 1H), 7.10 (d, J=8.8 Hz, 2H), 7.01 (s, 1H), 6.81 (d, J=8.4 Hz, 2H), 6.12-6.03 (m, 1H), 5.44 (dq, J=17.2, 1.6 Hz, 1H), 5.27 (dq, J=10.8, 1.6 Hz, 1H), 4.65 (d, J=9.6 Hz, 1H), 4.60-4.57 (m, 2H), 4.27 (d, J=7.6 Hz, 1H), 3.97 (br s, 2H), 3.75 (s, 3H), 3.56 (t, J=9.2 Hz, 1H), 3.48-3.41 (m, 4H), 3.29-3.25 (m, 2H); [M+Na]$^+$ 473.

Example 116

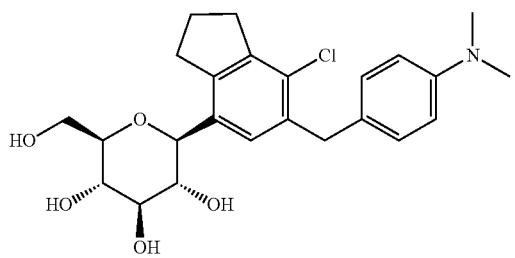 [SMILES: CN(C)c1ccc(Cc2cc([C@@H]3O[C@H](CO)[C@@H](O)[C@H](O)[C@H]3O)c3c(c2Cl)CCC3)cc1]

(2S,3R,4R,5S,6R)-2-(7-Chloro-6-(4-(dimethylamino)benzyl)-2,3-dihydro-1H-inden-4-yl)-6-(hydroxymethyl)tetrahydro-2H-pyran-3,4,5-triol (E116)

$^1$H NMR (400 MHz, CD$_3$OD) δ 7.15 (s, 1H), 7.04 (d, J=8.8 Hz, 2H), 6.71 (d, J=8.8 Hz, 2H), 4.22-4.19 (m, 1H), 3.96 (ABq, Δν$_{AB}$=18.0 Hz, J$_{AB}$=15.0 Hz, 2H), 3.88-3.85 (m, 1H), 3.68-3.63 (m, 1H), 3.47-3.44 (m, 2H), 3.38-3.36 (m, 2H), 3.19-3.10 (m, 1H), 3.06-2.99 (m, 1H), 2.94 (t, J=7.2 Hz, 2H), 2.86 (s, 6H), 2.12-2.04 (m, 2H); [M+H]$^+$ 448.

Example 117

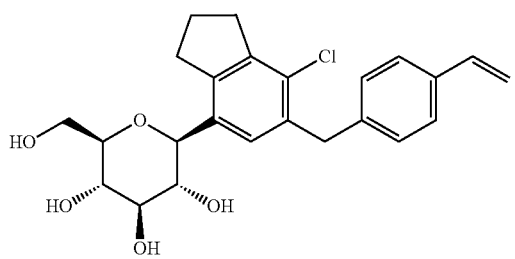

(2S,3R,4R,5S,6R)-2-(7-Chloro-6-(4-vinylbenzyl)-2,3-dihydro-1H-inden-4-yl)-6-(hydroxymethyl)tetrahydro-2H-pyran-3,4,5-triol (E117)

$^1$H NMR (400 MHz, CD$_3$OD) δ 7.30 (d, J=8.4 Hz, 2H), 7.20 (s, 1H), 7.14 (d, J=8.0 Hz, 2H), 6.68 (dd, J=17.6, 11.2 Hz, 1H), 5.70 (dd, J=17.6, 0.8 Hz, 1H), 5.15 (d, J=11.2 Hz, 1H), 4.24-4.21 (m, 1H), 4.06 (ABq, Δν$_{AB}$=16.5 Hz, J$_{AB}$=15.2 Hz, 2H), 3.88-3.85 (m, 1H), 3.69-3.64 (m, 1H), 3.49-3.43 (m, 2H), 3.40-3.35 (m, 2H), 3.20-3.11 (m, 1H), 3.07-2.99 (m, 1H), 2.95 (t, J=7.2 Hz, 2H), 2.12-2.05 (m, 2H); [M+Na]$^+$ 453.

Example 118

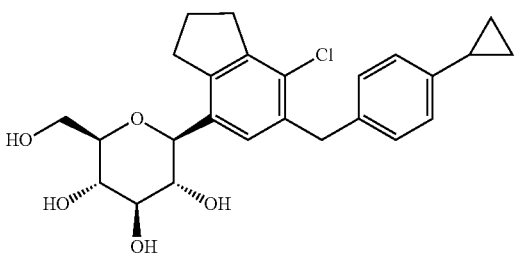

(2S,3R,4R,5S,6R)-2-(7-Chloro-6-(4-cyclopropylbenzyl)-2,3-dihydro-1H-inden-4-yl)-6-(hydroxymethyl)tetrahydro-2H-pyran-3,4,5-triol (E118)

$^1$H NMR (400 MHz, CD$_3$OD) δ 7.17 (s, 1H), 7.05 (d, J=8.0 Hz, 2H), 6.94 (d, J=8.0 Hz, 2H), 4.23-4.20 (m, 1H), 4.01 (ABq, Δν$_{AB}$=17.0 Hz, J$_{AB}$=15.2 Hz, 2H), 3.88-3.85 (m, 1H), 3.68-3.63 (m, 1H), 3.48-3.42 (m, 2H), 3.39-3.36 (m, 2H), 3.19-3.11 (m, 1H), 3.06-2.98 (m, 1H), 2.94 (t, J=7.6 Hz, 2H), 2.12-2.05 (m, 2H), 1.87-1.80 (m, 1H), 0.92-0.87 (m, 2H), 0.63-0.59 (m, 2H); [M+Na]$^+$ 467.

Example 119

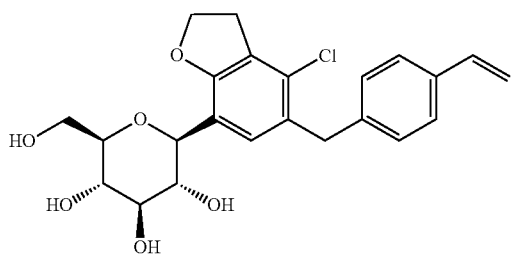 [SMILES: C=Cc1ccc(Cc2cc([C@@H]3O[C@H](CO)[C@@H](O)[C@H](O)[C@H]3O)c3c(c2Cl)CCO3)cc1]

(2S,3R,4R,5S,6R)-2-(4-Chloro-5-(4-vinylbenzyl)-2,3-dihydrobenzofuran-7-yl)-6-(hydroxymethyl)tetrahydro-2H-pyran-3,4,5-triol (E119)

$^1$H NMR (400 MHz, CD$_3$OD) δ 7.31 (d, J=8.4 Hz, 2H), 7.14-7.12 (m, 3H), 6.68 (dd, J=17.6, 11.2 Hz, 1H), 5.70 (dd, J=17.6, 0.8 Hz, 1H), 5.15 (dd, J=11.2, 0.8 Hz, 1H), 4.67-4.56 (m, 2H), 4.31 (d, J=9.6 Hz, 1H), 4.01 (ABq, Δν$_{AB}$=10.4 Hz, J$_{AB}$=15.4 Hz, 2H), 3.87-3.83 (m, 1H), 3.67-3.63 (m, 1H), 3.61-3.56 (m, 1H), 3.45-3.41 (m, 1H), 3.39-3.35 (m, 2H), 3.23 (t, J=8.8 Hz, 2H); [M+Na]⁺ 455.

Example 120

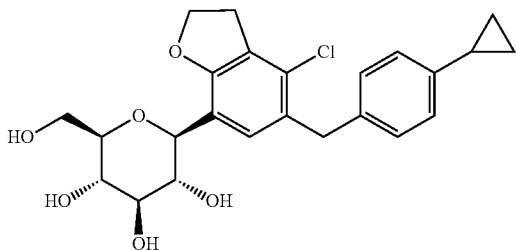 [SMILES: OC[C@H]1O[C@@H](c2cc(Cc3ccc(C4CC4)cc3)c(Cl)c3c2OCC3)[C@H](O)[C@@H](O)[C@@H]1O]

(2S,3R,4R,5S,6R)-2-(4-Chloro-5-(4-cyclopropylbenzyl)-2,3-dihydrobenzofuran-7-yl)-6-(hydroxymethyl)tetrahydro-2H-pyran-3,4,5-triol (E120)

¹H NMR (400 MHz, CD₃OD) δ 7.11 (s, 1H), 7.04 (d, J=8.0 Hz, 2H), 6.94 (d, J=8.0 Hz, 2H), 4.64-4.57 (m, 2H), 4.29 (d, J=9.6 Hz, 1H), 3.96 (ABq, Δν$_{AB}$=10.4 Hz, J$_{AB}$=15.4 Hz, 2H), 3.86-3.83 (m, 1H), 3.67-3.63 (m, 1H), 3.60 (t, J=8.8 Hz, 1H), 3.45-3.41 (m, 1H), 3.39-3.35 (m, 2H), 3.22 (t, J=8.8 Hz, 2H), 1.87-1.81 (m, 1H), 0.92-0.87 (m, 2H), 0.63-0.59 (m, 2H); [M+Na]⁺ 469.

Example 121

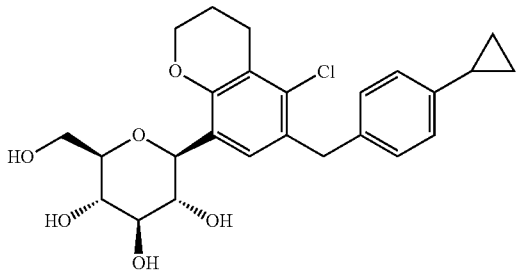

(2S,3R,4R,5S,6R)-2-(5-Chloro-6-(4-cyclopropylbenzyl)chroman-8-yl)-6-(hydroxymethyl)tetrahydro-2H-pyran-3,4,5-triol (E121)

¹H NMR (400 MHz, CD₃OD) δ 7.19 (s, 1H), 7.04 (d, J=8.0 Hz, 2H), 6.94 (d, J=8.0 Hz, 2H), 4.63-4.60 (m, 1H), 4.18-4.08 (m, 2H), 3.96 (ABq, Δν$_{AB}$=13.6 Hz, J$_{AB}$=15.2 Hz, 2H), 3.86-3.83 (m, 1H), 3.67-3.63 (m, 1H), 3.48-3.43 (m, 2H), 3.39-3.35 (m, 2H), 2.78 (t, J=6.8 Hz, 2H), 2.04-1.98 (m, 2H), 1.87-1.80 (m, 1H), 0.92-0.87 (m, 2H), 0.63-0.58 (m, 2H); [M+Na]⁺ 483.

Example 122

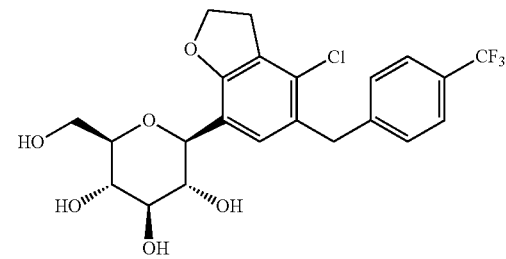

(2S,3R,4R,5S,6R)-2-(4-Chloro-5-(4-(trifluoromethyl)benzyl)-2,3-dihydrobenzofuran-7-yl)-6-(hydroxymethyl)tetrahydro-2H-pyran-3,4,5-triol (E122)

¹H NMR (400 MHz, CD₃OD) δ 7.53 (d, J=8.0 Hz, 2H), 7.36 (d, J=8.0 Hz, 2H), 7.20 (s, 1H), 4.67-4.56 (m, 2H), 4.33 (d, J=9.6 Hz, 1H), 4.15-4.07 (m, 2H), 3.87-3.83 (m, 1H), 3.68-3.56 (m, 2H), 3.47-3.36 (m, 3H), 3.23 (t, J=8.6 Hz, 2H); [M+Na]⁺ 497.

Example 123

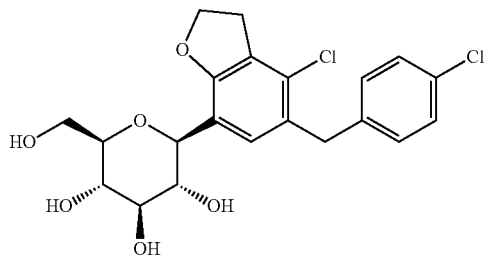 [SMILES: OC[C@H]1O[C@@H](c2cc(Cc3ccc(Cl)cc3)c(Cl)c3c2OCC3)[C@H](O)[C@@H](O)[C@@H]1O]

(2S,3R,4R,5S,6R)-2-(4-Chloro-5-(4-chlorobenzyl)-2,3-dihydrobenzofuran-7-yl)-6-(hydroxymethyl)tetrahydro-2H-pyran-3,4,5-triol (E123)

¹H NMR (400 MHz, CD₃OD) δ 7.24-7.21 (m, 2H), 7.17-7.14 (m, 3H), 4.67-4.56 (m, 2H), 4.31 (d, J=9.6 Hz, 1H), 4.00 (ABq, Δν$_{AB}$=8.9 Hz, J$_{AB}$=15.4 Hz, 2H), 3.86-3.83 (m, 1H), 3.68-3.56 (m, 2H), 3.46-3.36 (m, 3H), 3.23 (t, J=8.8 Hz, 2H); [M+Na]⁺ 463.

Example 124

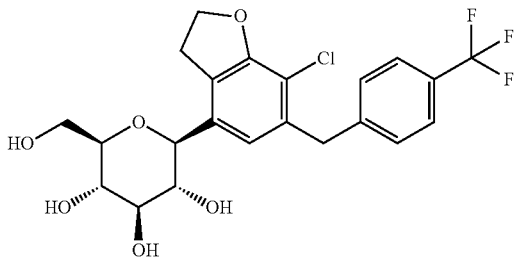

(2S,3R,4R,5S,6R)-2-(7-Chloro-6-(4-(trifluoromethyl)benzyl)-2,3-dihydrobenzofuran-4-yl)-6-(hydroxymethyl)tetrahydro-2H-pyran-3,4,5-triol (E124)

¹H NMR (400 MHz, CD₃OD) δ 7.53 (d, J=8.0 Hz, 2H), 7.37 (d, J=8.0 Hz, 2H), 6.91 (s, 1H), 4.63 (t, J=8.8 Hz, 2H), 4.17-4.13 (m, 3H), 3.89-3.86 (m, 1H), 3.70-3.65 (m, 1H), 3.48-3.41 (m, 3H), 3.38-3.34 (m, 3); [M+Na]⁺ 497.

Example 125

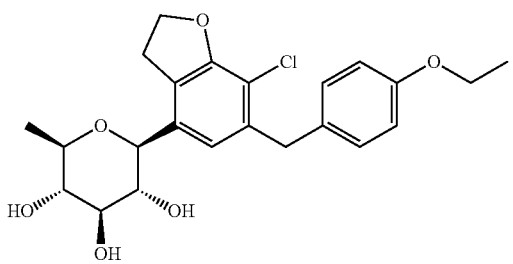 [SMILES: CCOc1ccc(Cc2cc([C@@H]3O[C@H](C)[C@@H](O)[C@H](O)[C@H]3O)c3c(c2Cl)OCC3)cc1]

(2S,3R,4S,5S,6R)-2-(7-Chloro-6-(4-ethoxybenzyl)-
2,3-dihydrobenzofuran-4-yl)-6-methyltetrahydro-
2H-pyran-3,4,5-triol (E125)

¹H NMR (400 MHz, CD₃OD) δ 7.09-7.06 (m, 2H), 6.79-6.76 (m, 3H), 4.61 (t, J=8.6 Hz, 2H), 4.11-4.09 (m, 1H), 4.01-3.95 (m, 4H), 3.44-3.36 (m, 4H), 3.11-3.07 (m, 1H), 1.35 (t, J=7.0 Hz, 3H), 1.28 (d, J=6.0 Hz, 3H); [M+Na]⁺ 457.

Example 126

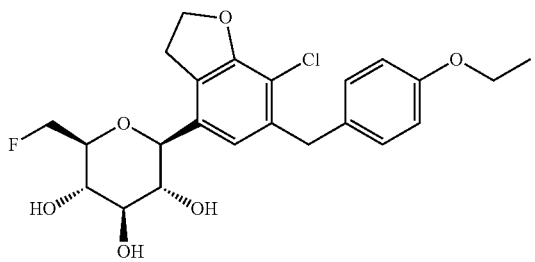 [SMILES: CCOc1ccc(Cc2cc([C@@H]3O[C@H](CF)[C@@H](O)[C@H](O)[C@H]3O)c3c(c2Cl)OCC3)cc1]

(2S,3R,4R,5S,6S)-2-(7-Chloro-6-(4-ethoxybenzyl)-
2,3-dihydrobenzofuran-4-yl)-6-(fluoromethyl)tet-
rahydro-2H-pyran-3,4,5-triol (E126)

¹H NMR (400 MHz, CD₃OD) δ 7.09-7.07 (m, 2H), 6.80-6.77 (m, 3H), 4.68-4.55 (m, 3H), 4.15 (d, J=9.2 Hz, 1H), 4.00-3.95 (m, 3H), 3.53-3.39 (m, 4H), 3.26-3.24 (m, 1H), 1.35 (t, J=7.0 Hz, 3H); [M+Na]⁺ 475.

Example 127

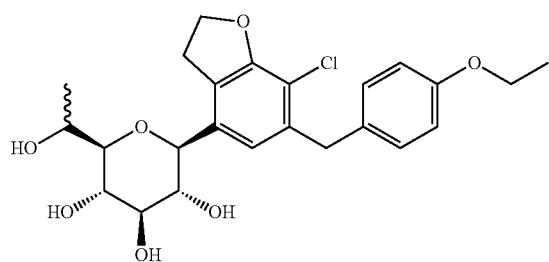 [SMILES: CCOc1ccc(Cc2cc([C@@H]3O[C@H](C(C)O)[C@@H](O)[C@H](O)[C@H]3O)c3c(c2Cl)OCC3)cc1]

(2S,3R,4R,5S,6R)-2-(7-Chloro-6-(4-ethoxybenzyl)-
2,3-dihydrobenzofuran-4-yl)-6-(1-hydroxyethyl)
tetrahydro-2H-pyran-3,4,5-triol (E127)

¹H NMR (400 MHz, CD₃OD) δ 7.10-7.06 (m, 2H), 6.88 (s, 1H), 6.79-6.76 (m, 2H), 4.60 (t, J=8.8 Hz, 2H), 4.12-4.07 (m, 2H), 4.01-3.95 (m, 4H), 3.62 (t, J=9.4 Hz, 1H), 3.47-3.40 (m, 3H), 3.47-3.34 (m, 1H), 3.15 (dd, J=9.6, 2.0 Hz, 1H), 1.35 (t, J=7.0 Hz, 3H), 1.24 (d, J=6.4 Hz, 3H), 2:1 mixture; [M+Na]⁺ 487.

Example 128

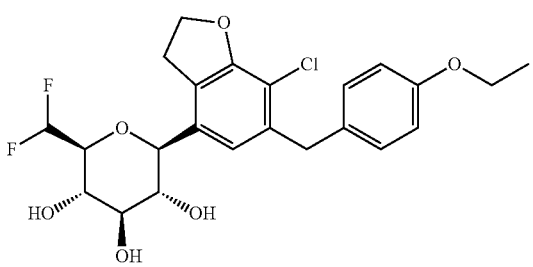 [SMILES: CCOc1ccc(Cc2cc([C@@H]3O[C@H](C(F)F)[C@@H](O)[C@H](O)[C@H]3O)c3c(c2Cl)OCC3)cc1]

(2S,3R,4R,5S,6S)-2-(7-Chloro-6-(4-ethoxybenzyl)-
2,3-dihydrobenzofuran-4-yl)-6-(difluoromethyl)tet-
rahydro-2H-pyran-3,4,5-triol (E128)

¹H NMR (400 MHz, CD₃OD) δ 7.09-7.07 (m, 2H), 6.80-6.76 (m, 3H), 6.04 (td, J=54.0, 0.8 Hz, 1H), 4.61 (t, J=8.8 Hz, 2H), 4.16 (d, J=2.0 Hz, 1H), 4.01-3.95 (m, 4H), 3.66-3.34 (m, 6H), 3.29-3.27 (m, 1H), 1.35 (t, J=7.0 Hz, 3H); [M+Na]⁺ 493.

Example 129

(2S,3R,4R,5S,6R)-2-(6-(4-Ethoxybenzyl)-7-methyl-
2,3-dihydrobenzofuran-4-yl)-6-(hydroxymethyl)
tetrahydro-2H-pyran-3,4,5-triol (E129)

¹H NMR (400 MHz, CD₃OD) δ 7.01-6.99 (m, 2H), 6.77-6.75 (m, 3H), 4.51 (t, J=8.8 Hz, 2H), 4.14 (d, J=9.2 Hz, 1H), 3.98 (q, J=7.0 Hz, 2H), 3.89-3.87 (m, 3H), 3.69-3.65 (m, 1H), 3.52-3.45 (m, 2H), 3.38-3.34 (m, 2H), 3.27-3.18 (m, 1H), 1.99 (s, 3H), 1.35 (t, J=7.0 Hz, 3H); [M+Na]⁺ 453.

Example 130

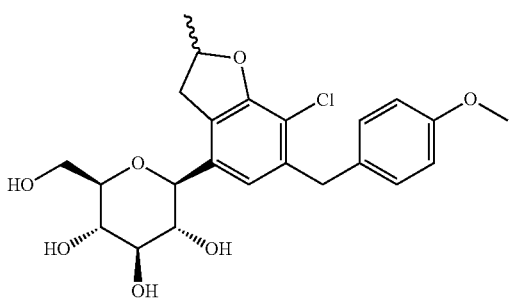

(2S,3R,4R,5S,6R)-2-(7-Chloro-6-(4-methoxybenzyl)-2-methyl-2,3-dihydrobenzofuran-4-yl)-6-(hydroxymethyl)tetrahydro-2H-pyran-3,4,5-triol (E130)

$^1$H NMR (400 MHz, CD$_3$OD) δ 7.09 (d, J=8.4 Hz, 2H), 6.82-6.78 (m, 3H), 5.00-4.94 (m, 1H), 4.11 (dd, J=9.2, 3.6 Hz, 1H), 3.96 (ABq, Δν$_{AB}$=18.5 Hz, J$_{AB}$=15.0 Hz, 2H), 3.88-3.85 (m, 1H), 3.75 (s, 3H), 3.68-3.64 (m, 1H), 3.60-3.54 (m, 1H), 3.45-3.36 (m, 5H), 3.06-3.00 (m, 1H), 1.46 (d, J=6.4 Hz, 3H) 1:1 mixture; [M+Na]$^+$ 473.

Example 131

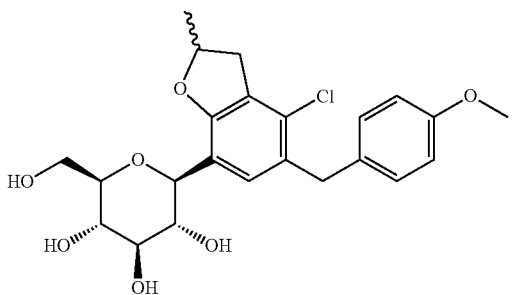

(2S,3R,4R,5S,6R)-2-(4-Chloro-5-(4-methoxybenzyl)-2-methyl-2,3-dihydrobenzofuran-7-yl)-6-(hydroxymethyl)tetrahydro-2H-pyran-3,4,5-triol (E131)

$^1$H NMR (400 MHz, CD$_3$OD) 7.12-7.07 (m, 3H), 6.80-6.78 (m, 2H), 5.02-4.95 (m, 1H), 4.61 (t, J=9.0 Hz, 1H), 3.93 (ABq, Δν$_{AB}$=13.7 Hz, J$_{AB}$=15.4 Hz, 2H), 3.86-3.83 (m, 1H), 3.74 (s, 3H), 3.67-3.63 (m, 1H), 3.59-3.54 (m, 1H), 3.45-3.49 (m, 4H), 2.84-2.78 (m, 1H), 1.45 (d, J=6.2 Hz, 3H) 1:1 mixture; [M+Na]$^+$ 473.

Example 132

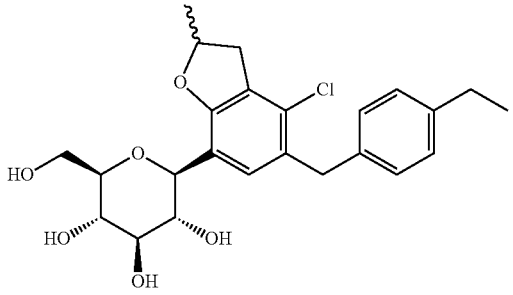

(2S,3R,4R,5S,6R)-2-(4-Chloro-5-(4-ethylbenzyl)-2-methyl-2,3-dihydrobenzofuran-7-yl)-6-(hydroxymethyl)tetrahydro-2H-pyran-3,4,5-triol (E132)

$^1$H NMR (400 MHz, CD$_3$OD) 7.13 (s, 1H), 7.10-7.04 (m, 4H), 5.02-4.94 (m, 1H), 4.31 (dd, J=9.6, 8.4 Hz, 1H), 3.97 (ABq, Δν$_{AB}$=8.4 Hz, J$_{AB}$=16.8 Hz, 2H), 3.86-3.83 (m, 1H), 3.67-3.62 (m, 1H), 3.59-3.54 (m, 1H), 3.46-3.37 (m, 3H), 2.85-2.79 (m, 1H), 2.58 (q, J=7.6 Hz, 2H), 1.45 (d, J=6.2 Hz, 3H), 1.19 (t, J=7.6 Hz, 3H) 1:1 mixture; [M+Na]$^+$ 471.

Example 133

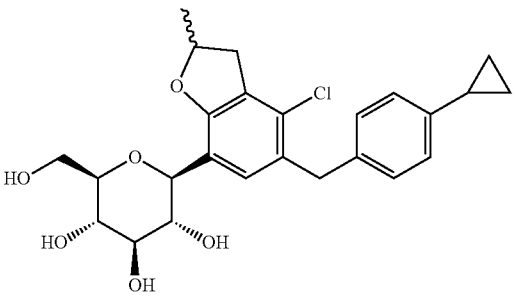

(2S,3R,4R,5S,6R)-2-(4-Chloro-5-(4-cyclopropylbenzyl)-2-methyl-2,3-dihydrobenzofuran-7-yl)-6-(hydroxymethyl)tetrahydro-2H-pyran-3,4,5-triol (E133)

$^1$H NMR (400 MHz, CD$_3$OD) 7.11 (s, 1H), 7.05-7.03 (m, 2H), 6.95-6.93 (m, 2H), 5.02-4.94 (m, 1H), 4.31 (dd, J=9.6, 8.4 Hz, 1H), 3.95 (ABq, Δν$_{AB}$=12.0 Hz, J$_{AB}$=16.4 Hz, 2H), 3.86-3.83 (m, 1H), 3.67-3.63 (m, 1H), 3.59-3.54 (m, 1H), 3.45-3.42 (m, 1H), 3.39-3.35 (m, 4H), 2.85-2.79 (m, 1H), 1.87-1.80 (m, 1H), 1.45 (d, J=6.2 Hz, 3H), 0.92-0.87 (m, 2H), 0.63-0.59 (m, 2H) 1:1 mixture; [M+Na]$^+$ 483.

Example 134

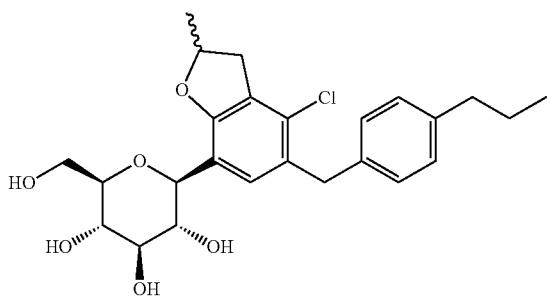

(2S,3R,4R,5S,6R)-2-(4-Chloro-2-methyl-5-(4-propylbenzyl)-2,3-dihydrobenzofuran-7-yl)-6-(hydroxymethyl)tetrahydro-2H-pyran-3,4,5-triol (E134)

$^1$H NMR (400 MHz, CD$_3$OD) 7.13 (s, 1H), 7.09-7.03 (m, 4H), 5.00-4.94 (m, 1H), 4.31 (dd, J=9.6, 8.4 Hz, 1H), 3.97 (ABq, Δν$_{AB}$=19.0 Hz, J$_{AB}$=13.0 Hz, 2H), 3.86-3.83 (m, 1H), 3.67-3.63 (m, 1H), 3.59-3.54 (m, 1H), 3.45-3.42 (m, 1H), 3.39-3.35 (m, 3H), 2.85-2.79 (m, 1H), 2.53 (t, J=7.6 Hz, 2H), 1.65-1.56 (m, 2H), 1.45 (d, J=6.0 Hz, 3H), 0.91 (t, J=7.4 Hz, 3H) 1:1 mixture; [M+Na]⁺ 485.

Example 135

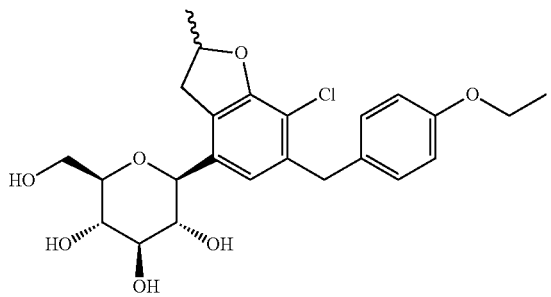

(2S,3R,4R,5S,6R)-2-(7-Chloro-6-(4-ethoxybenzyl)-2-methyl-2,3-dihydrobenzofuran-4-yl)-6-(hydroxymethyl)tetrahydro-2H-pyran-3,4,5-triol (E135)

¹H NMR (400 MHz, CD₃OD) 7.09-7.07 (m, 2H), 6.82-6.77 (m, 3H), 5.00-4.94 (m, 1H), 4.11 (dd, J=8.8, 3.6 Hz, 1H), 4.00-3.95 (m, 4H), 3.90-3.86 (m, 1H), 3.69-3.64 (m, 1H), 3.60-3.54 (m, 1H), 3.45-3.40 (m, 2H), 3.39-3.34 (m, 2H), 2.93-2.87 (m, 1H), 1.46 (d, J=6.0 Hz, 3H), 1.35 (t, J=7.0 Hz, 3H) 1:1 mixture; [M+Na]⁺ 487.

Example 136

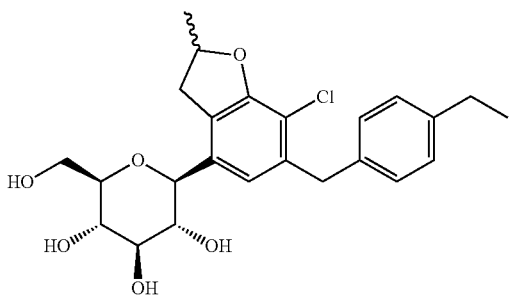

(2S,3R,4R,5S,6R)-2-(7-Chloro-6-(4-ethylbenzyl)-2-methyl-2,3-dihydrobenzofuran-4-yl)-6-(hydroxymethyl)tetrahydro-2H-pyran-3,4,5-triol (E136)

¹H NMR (400 MHz, CD₃OD) 7.10-7.05 (m, 4H), 6.84 (s, 1H), 5.01-4.95 (m, 1H), 4.11 (dd, J=8.8, 3.6 Hz, 1H), 3.99 (ABq, Δv$_{AB}$=19.5 Hz, J$_{AB}$=15.0 Hz, 2H), 3.89-3.86 (m, 1H), 3.68-3.64 (m, 1H), 3.60-3.54 (m, 1H), 3.46-3.35 (m, 4H), 2.93-2.87 (m, 1H), 2.58 (q, J=7.6 Hz, 2H), 1.46 (d, J=6.4 Hz, 3H), 1.19 (t, J=7.4 Hz, 3H) 1:1 mixture; [M+Na]⁺ 471.

Example 137

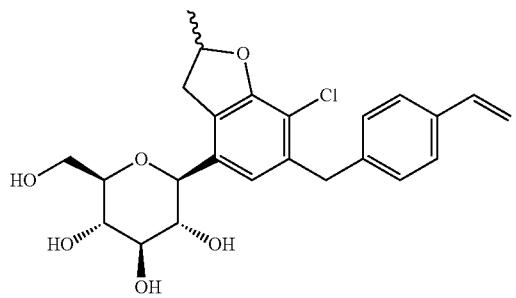 [SMILES: C=Cc1ccc(Cc2cc([C@@H]3O[C@H](CO)[C@@H](O)[C@H](O)[C@H]3O)c3c(c2Cl)OC(C)C3)cc1]

(2S,3R,4R,5S,6R)-2-(7-Chloro-2-methyl-6-(4-vinylbenzyl)-2,3-dihydrobenzofuran-4-yl)-6-(hydroxymethyl)tetrahydro-2H-pyran-3,4,5-triol (E137)

¹H NMR (400 MHz, CD₃OD) 7.31 (d, J=8.4 Hz, 2H), 7.14 (d, J=8.0 Hz, 2H), 6.86 (s, 1H), 5.71 (dd, J=17.6, 0.8 Hz, 1H), 5.16 (dd, J=10.8, 0.8 Hz, 1H), 5.02-4.95 (m, 1H), 4.12 (dd, J=8.8, 3.6 Hz, 1H), 4.02 (ABq, Δv$_{AB}$=18.0 Hz, J$_{AB}$=15.2 Hz, 2H), 3.89-3.86 (m, 1H), 3.68-3.64 (m, 1H), 3.61-3.55 (m, 1H), 3.46-3.35 (m, 4H), 2.94-2.88 (m, 1H), 1.46 (d, J=6.0 Hz, 3H) 1:1 mixture; [M+Na]⁺ 469.

Example 138

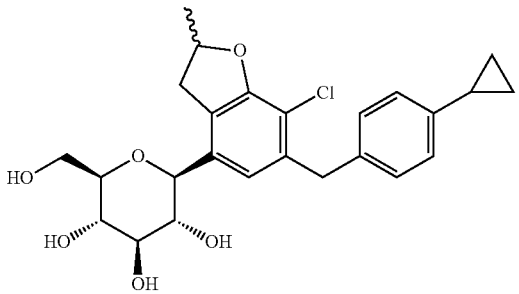 [SMILES: CC1Cc2c([C@@H]3O[C@H](CO)[C@@H](O)[C@H](O)[C@H]3O)cc(Cc3ccc(C4CC4)cc3)c(Cl)c2O1]

(2S,3R,4R,5S,6R)-2-(7-Chloro-6-(4-cyclopropylbenzyl)-2-methyl-2,3-dihydrobenzofuran-4-yl)-6-(hydroxymethyl)tetrahydro-2H-pyran-3,4,5-triol (E138

¹H NMR (400 MHz, CD₃OD) 7.05 (d, J=8.0 Hz, 2H), 6.94 (d, J=8.0 Hz, 2H), 6.83 (s, 1H), 5.02-4.94 (m, 1H), 4.10 (dd, J=8.8, 3.6 Hz, 1H), 3.97 (ABq, Δv$_{AB}$=19.6 Hz, J$_{AB}$=15.2 Hz, 2H), 3.89-3.86 (m, 1H), 3.68-3.64 (m, 1H), 3.60-3.55 (m, 1H), 3.45-3.42 (m, 5H), 2.93-2.87 (m, 1H), 1.87-1.80 (m, 1H), 1.46 (d, J=6.4 Hz, 3H), 0.93-0.88 (m, 2H), 0.63-0.59 (m, 2H) 1:1 mixture; [M+Na]⁺ 483.

Example 139

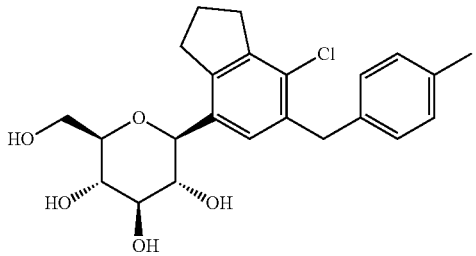 [SMILES: Cc1ccc(Cc2cc([C@@H]3O[C@H](CO)[C@@H](O)[C@H](O)[C@H]3O)c3c(c2Cl)CCC3)cc1]

(2S,3R,4R,5S,6R)-2-(7-Chloro-6-(4-methylbenzyl)-2,3-dihydro-1H-inden-4-yl)-6-(hydroxymethyl)tetrahydro-2H-pyran-3,4,5-triol (E139)

¹H NMR (400 MHz, CD₃OD) 7.17 (s, 1H), 7.07-7.02 (m, 4H), 4.23-4.20 (m, 1H), 4.02 (ABq, Δν$_{AB}$=16.8 Hz, J$_{AB}$=14.8 Hz, 2H), 3.88-3.85 (m, 1H), 3.68-3.63 (m, 1H), 3.48-3.43 (m, 2H), 3.40-3.35 (m, 2H), 3.19-3.11 (m, 1H), 3.06-2.98 (m, 1H), 2.95 (t, J=12.2 Hz, 2H), 2.27 (s, 3H), 2.12-2.04 (m, 2H); [M+Na]⁺ 441.

Example 140

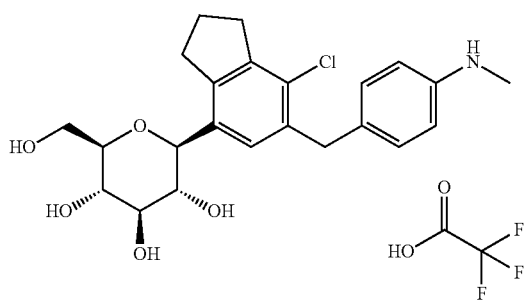 [SMILES: CNc1ccc(Cc2cc([C@@H]3O[C@H](CO)[C@@H](O)[C@H](O)[C@H]3O)c3c(c2Cl)CCC3)cc1 ; O=C(O)C(F)(F)F]

(2S,3R,4R,5S,6R)-2-(7-Chloro-6-(4-(methylamino)benzyl)-2,3-dihydro-1H-inden-4-yl)-6-(hydroxymethyl)tetrahydro-2H-pyran-3,4,5-triol 2,2,2-trifluoroacetate (E140)

¹H NMR (400 MHz, CD₃OD) 7.40-7.32 (m, 4H), 7.25 (s, 1H), 4.29-4.23 (m, 1H), 4.14 (s, 2H), 3.98-3.86 (m, 1H), 3.69-3.65 (m, 1H), 3.50-3.45 (m, 2H), 3.43-3.37 (m, 2H), 3.20-3.13 (m, 1H), 3.07-3.02 (m, 1H), 3.05 (s, 3H), 2.93 (t, J=7.4 Hz, 2H), 2.13-2.06 (m, 2H); [M+Na]⁺ 456.

Example 141

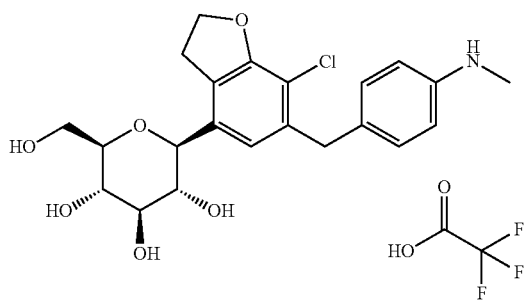 [SMILES: CNc1ccc(Cc2cc([C@@H]3O[C@H](CO)[C@@H](O)[C@H](O)[C@H]3O)c3c(c2Cl)OCC3)cc1 ; O=C(O)C(F)(F)F]

(2S,3R,4R,5S,6R)-2-(7-Chloro-6-(4-(methylamino)benzyl)-2,3-dihydrobenzofuran-4-yl)-6-(hydroxymethyl)tetrahydro-2H-pyran-3,4,5-triol 2,2,2-trifluoroacetate (E141)

¹H NMR (400 MHz, CD₃OD) 7.41-7.34 (m, 4H), 6.91 (s, 1H), 4.62 (t, J=8.8 Hz, 2H), 4.18-4.10 (m, 3H), 3.98-3.87 (m, 1H), 3.70-3.66 (m, 1H), 3.48-3.42 (m, 3H), 3.39-3.36 (m, 3H), 3.04 (s, 3H); [M+Na]⁺ 458.

Example 142

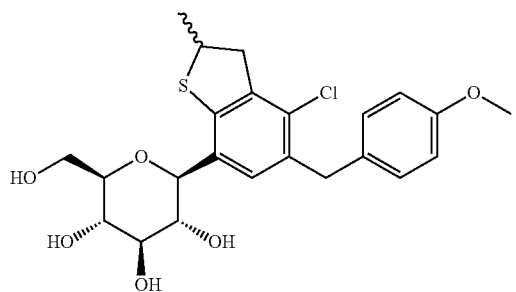 [SMILES: COc1ccc(Cc2cc([C@@H]3O[C@H](CO)[C@@H](O)[C@H](O)[C@H]3O)c3c(c2Cl)CC(C)S3)cc1]

(2S,3R,4R,5S,6R)-2-(4-Chloro-5-(4-methoxybenzyl)-2-methyl-2,3-dihydrobenzo[b]thiophen-7-yl)-6-(hydroxymethyl)tetrahydro-2H-pyran-3,4,5-triol (E142)

¹H NMR (400 MHz, CD₃OD) 7.13-7.08 (m, 3H), 6.80 (d, J=8.4 Hz, 2H), 4.10 (dd, J=9.4, 4.2 Hz, 1H), 4.02-3.96 (m, 2H), 3.92-3.86 (m, 2H), 3.75 (s, 3H), 3.69-3.61 (m, 2H), 3.51-3.40 (m, 2H), 3.38-3.35 (m, 2H), 3.31-3.06 (m, 1H), 2.99-2.92 (m, 1H), 1.36 (d, J=6.4 Hz, 3H) 1.5:1 mixture; [M+Na]⁺ 489.

Example 143

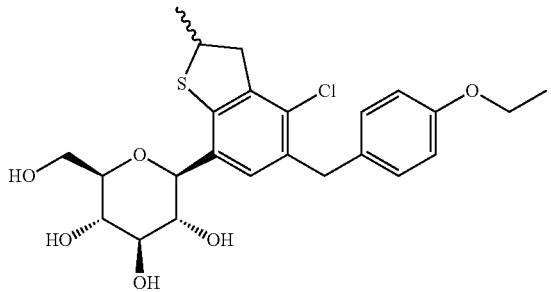 [SMILES: CCOc1ccc(Cc2cc([C@@H]3O[C@H](CO)[C@@H](O)[C@H](O)[C@H]3O)c3c(c2Cl)CC(C)S3)cc1]

(2S,3R,4R,5S,6R)-2-(4-Chloro-5-(4-ethoxybenzyl)-2-methyl-2,3-dihydrobenzo[b]thiophen-7-yl)-6-(hydroxymethyl)tetrahydro-2H-pyran-3,4,5-triol (E143)

¹H NMR (400 MHz, CD₃OD) 7.13-7.06 (m, 3H), 6.79 (d, J=8.4 Hz, 2H), 4.10 (dd, J=9.4, 4.4 Hz, 1H), 4.02-3.96 (m, 4H), 3.88-3.85 (m, 2H), 3.70-3.61 (m, 2H), 3.48-3.40 (m, 2H), 3.38-3.36 (m, 2H), 3.11-3.06 (m, 1H), 2.99-2.92 (m, 1H), 1.35 (d, J=6.8 Hz, 3H), 1.35 (t, J=7.0 Hz, 3H) 1.5:1 mixture; [M+Na]⁺ 503.

Example 144

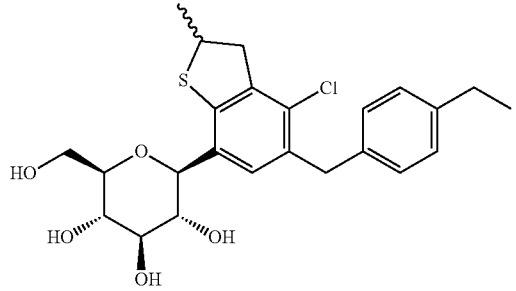 [SMILES: CCc1ccc(Cc2cc([C@@H]3O[C@H](CO)[C@@H](O)[C@H](O)[C@H]3O)c3c(c2Cl)CC(C)S3)cc1]

(2S,3R,4R,5S,6R)-2-(4-Chloro-5-(4-ethylbenzyl)-2-methyl-2,3-dihydrobenzo[b]thiophen-7-yl)-6-(hydroxymethyl)tetrahydro-2H-pyran-3,4,5-triol (E144)

$^1$H NMR (400 MHz, CD$_3$OD) 7.13 (s, 1H), 7.08-7.04 (m, 4H), 4.09 (dd, J=7.4, 2.2 Hz, 1H), 4.03-3.94 (m, 2H), 3.87-3.84 (m, 2H), 3.68-3.60 (m, 2H), 3.47-3.40 (m, 2H), 3.39-3.35 (m, 2H), 3.10-3.05 (m, 1H), 2.97-2.91 (m, 1H), 2.57 (q, J=7.6 Hz, 2H), 1.35 (d, J=6.8 Hz, 3H), 1.18 (t, J=7.6 Hz, 3H) 2:1 mixture; [M+Na]$^+$ 487.

Example 145

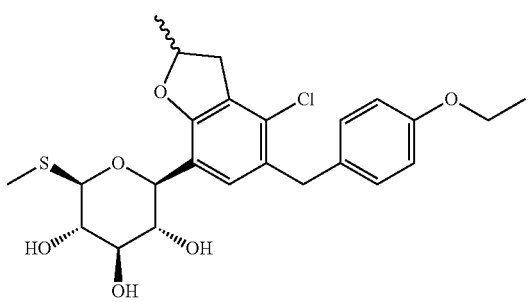 [SMILES: CCOc1ccc(Cc2cc([C@@H]3O[C@H](SC)[C@@H](O)[C@H](O)[C@H]3O)c3c(c2Cl)CC(C)O3)cc1]

(2S,3R,4R,5S,6R)-2-(4-Chloro-5-(4-ethoxybenzyl)-2-methyl-2,3-dihydrobenzofuran-7-yl)-6-(methylthio)tetrahydro-2H-pyran-3,4,5-triol (E145)

$^1$H NMR (400 MHz, CDCl$_3$) 7.08 (d, J=8.4 Hz, 2H), 6.99 (s, 1H), 6.80 (d, J=8.4 Hz, 2H), 5.05-4.94 (m, 1H), 4.44-4.35 (m, 2H), 3.99 (q, J=7.0 Hz, 2H), 3.94-3.89 (m, 2H), 3.78-3.66 (m, 2H), 3.57-3.49 (m, 1H), 3.39-3.30 (m, 1H), 2.87-2.79 (m, 1H), 2.15 (d, J=3.2 Hz, 3H), 1.45 (d, J=7.4 Hz, 3H), 1.39 (t, J=7.0 Hz, 3H) 2:1 mixture; [M+Na]$^+$ 503.

Example 146

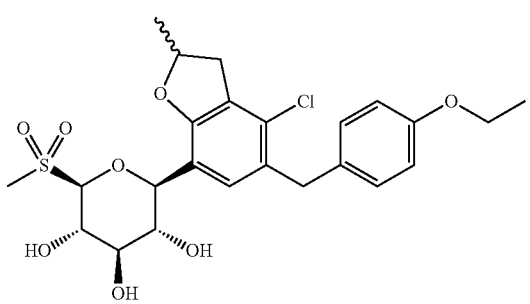 [SMILES: CCOc1ccc(Cc2cc([C@@H]3O[C@H](S(C)(=O)=O)[C@@H](O)[C@H](O)[C@H]3O)c3c(c2Cl)CC(C)O3)cc1]

(2S,3R,4R,5S,6R)-2-(4-Chloro-5-(4-ethoxybenzyl)-2-methyl-2,3-dihydrobenzofuran-7-yl)-6-(methylsulfonyl)tetrahydro-2H-pyran-3,4,5-triol (E146)

$^1$H NMR (400 MHz, CDCl$_3$) 7.04-7.02 (m, 3H), 6.73 (d, J=7.2 Hz, 2H), 4.88-4.82 (m, 1H), 4.55-4.49 (m, 2H), 4.04-4.02 (m, 1H), 3.92-3.85 (m, 6H), 3.24-3.22 (m, 3H), 2.80 (s, 3H), 2.74-2.71 (m, 1H), 1.35-1.32 (m, 6H) 2:1 mixture; [M+Na]$^+$ 535.

Example 147

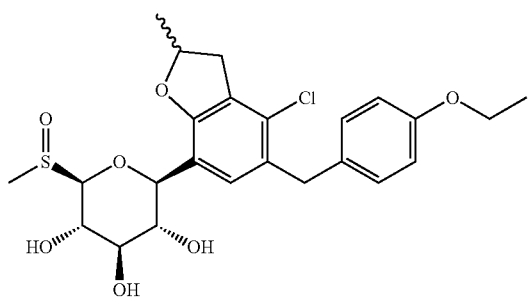 [SMILES: CCOc1ccc(Cc2cc([C@@H]3O[C@H](S(C)=O)[C@@H](O)[C@H](O)[C@H]3O)c3c(c2Cl)CC(C)O3)cc1]

(2S,3R,4R,5S,6R)-2-(4-Chloro-5-(4-ethoxybenzyl)-2-methyl-2,3-dihydrobenzofuran-7-yl)-6-((S)-methylsulfinyl)tetrahydro-2H-pyran-3,4,5-triol (E147)

$^1$H NMR (400 MHz, CDCl$_3$) 7.03-7.01 (m, 3H), 6.74 (d, J=6.8 Hz, 2H), 4.92-4.88 (m, 1H), 4.51-4.45 (m, 1H), 4.23-4.08 (m, 1H), 3.95-3.80 (m, 6H), 3.34-3.22 (m, 1H), 2.78-2.74 (m, 1H), 2.64 (s, 3H), 2.48-2.44 (m, 1H), 1.37-1.33 (m, 6H) 2:1 mixture; [M+Na]$^+$ 519.

Example 148

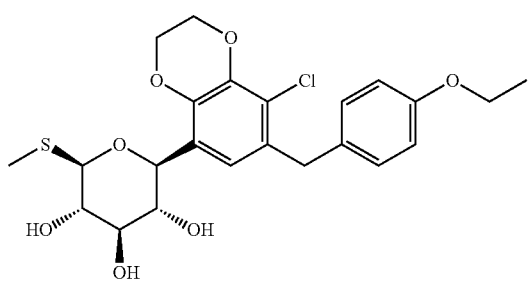 [SMILES: CCOc1ccc(Cc2cc([C@@H]3O[C@H](SC)[C@@H](O)[C@H](O)[C@H]3O)c3c(c2Cl)OCCO3)cc1]

(2S,3R,4R,5S,6R)-2-(8-Chloro-7-(4-ethoxybenzyl)-2,3-dihydrobenzo[b][1,4]dioxin-5-yl)-6-(methylthio)tetrahydro-2H-pyran-3,4,5-triol (E148)

$^1$H NMR (400 MHz, CDCl$_3$) 7.08 (d, J=8.4 Hz, 2H), 6.81 (s, 1H), 6.79 (d, J=2.4 Hz, 2H), 4.67 (d, J=9.6 Hz, 1H), 4.38-4.34 (m, 3H), 4.31-4.25 (m, 2H), 4.02-3.97 (m, 4H), 3.70-3.62 (m, 2H), 3.55-3.51 (m, 1H), 2.78 (br. s, 1H), 2.49 (br. s, 1H), 2.14 (s, 3H), 2.10 (br. s, 1H), 1.39 (t, J=7.0 Hz, 3H); [M+Na]$^+$ 505.

Example 149

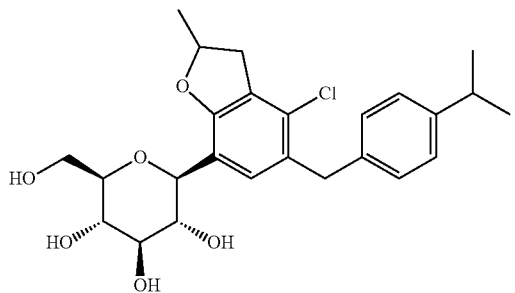 [SMILES: CC1Cc2c(Cl)c(Cc3ccc(C(C)C)cc3)cc([C@@H]3O[C@H](CO)[C@@H](O)[C@H](O)[C@H]3O)c2O1]

233

(2S,3R,4R,5S,6R)-2-(4-Chloro-5-(4-isopropylbenzyl)-2-methyl-2,3-dihydrobenzofuran-7-yl)-6-(hydroxymethyl)tetrahydro-2H-pyran-3,4,5-triol (E149)

$^1$H NMR (400 MHz, CD$_3$OD) δ 7.11 (d, J=4.2 Hz, 1H), 7.07 (s, 4H), 4.99-4.91 (m, 1H), 4.29 (t, J=9.2 Hz, 1H), 3.94 (s, 2H), 3.83 (d, J=11.9 Hz, 1H), 3.65-3.60 (m, 1H), 3.55 (t, J=9.2 Hz, 1H), 3.45-3.39 (m, 1H), 3.37-3.30 (m, 3H), 3.28 (quint, J=1.6 Hz, 4H), 2.84-2.76 (m, 2H), 1.42 (t, J=6.28 Hz, 3H), 1.19 (d, J=6.9 Hz, 6H); M+Na$^+$ 485.

Example 150

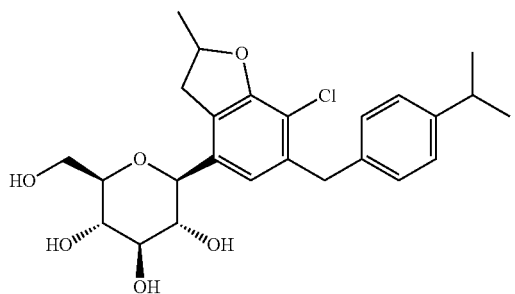 [SMILES: CC1Cc2c([C@@H]3O[C@H](CO)[C@@H](O)[C@H](O)[C@H]3O)cc(Cc3ccc(C(C)C)cc3)c(Cl)c2O1]

(2S,3R,4R,5S,6R)-2-(7-Chloro-6-(4-isopropylbenzyl)-2-methyl-2,3-dihydrobenzofuran-4-yl)-6-(hydroxymethyl)tetrahydro-2H-pyran-3,4,5-triol (E150)

$^1$H NMR (400 MHz, CD$_3$OD) δ 7.07 (s, 4H), 6.82 (d, J=7.0 Hz, 1H), 4.09 (dd, J=8.8, 3.7 Hz, 1H), 3.97 (ABq, J=15.26 Hz, 2H), 3.85 (d, J=12.0 Hz, 1H), 3.65-3.62 (m, 1H), 3.55 (q, J=8.1 Hz, 1H), 3.40-3.37 (m, 2H), 3.33-3.98 (m, 2H), 3.05-2.99 (m, 1H), 2.91-2.78 (m, 2H), 1.44 (d, J=6.24 Hz, 3H), 1.19 (d, J=6.9 Hz, 6H); M+Na$^+$ 485.

Example 151

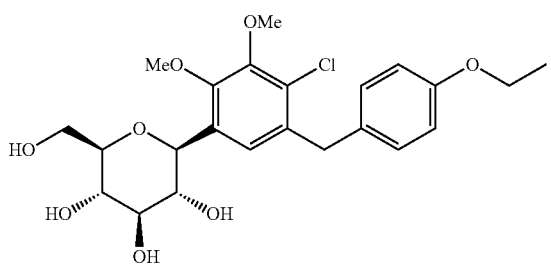 [SMILES: CCOc1ccc(Cc2cc([C@@H]3O[C@H](CO)[C@@H](O)[C@H](O)[C@H]3O)c(OC)c(OC)c2Cl)cc1]

(2S,3R,4R,5S,6R)-2-(4-Chloro-5-(4-ethoxybenzyl)-2,3-dimethoxyphenyl)-6-(hydroxymethyl)tetrahydro-2H-pyran-3,4,5-triol (E151)

$^1$H NMR (400 MHz, CD$_3$OD) δ 7.14 (s, 1H), 7.12 (d, J=8.8 Hz, 2H), 7.82 (d, J=8.7 Hz, 2H), 4.87 (s, 4H), 4.56 (d, J=9.2 Hz, 1H), 4.13-3.94 (m, 4H), 3.93-3.84 (m, 7H), 3.67 (dd, J=11.9 Hz, 5.7 Hz, 1H), 3.59-3.45 (m, 2H), 3.42-3.34 (m, 2H), 1.38 (t, J=7.0 Hz, 3H); [M+Na]$^+$ 491.

234

Example 152

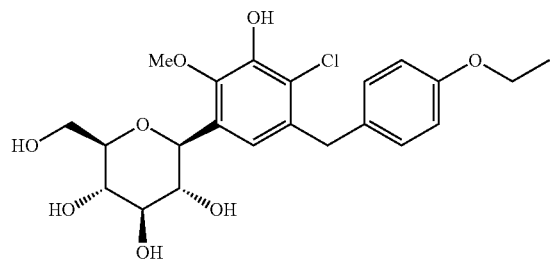 [SMILES: CCOc1ccc(Cc2cc([C@@H]3O[C@H](CO)[C@@H](O)[C@H](O)[C@H]3O)c(OC)c(O)c2Cl)cc1]

(2S,3R,4R,5S,6R)-2-(4-Chloro-5-(4-ethoxybenzyl)-3-hydroxy-2-methoxyphenyl)-6-(hydroxymethyl)tetrahydro-2H-pyran-3,4,5-triol (E152)

$^1$H NMR (400 MHz, CD$_3$OD) δ 7.11 (d, J=8.6 Hz, 2H), 6.86 (s, 1H), 6.82 (d, J=8.7 Hz, 2H), 4.87 (s, 4H), 4.52 (d, J=9.6 Hz, 1H), 4.06-3.97 (m, 4H), 3.91-3.83 (m, 4H), 3.66 (dd, J=12.0 Hz, 5.6 Hz, 1H), 3.59 (t, J=9.2 Hz, 1H), 3.50 (t, J=8.4 Hz, 1H), 3.46-3.34 (m, 2H), 1.38 (t, J=7.0 Hz, 3H); [M+Na]$^+$ 477.

Example 153

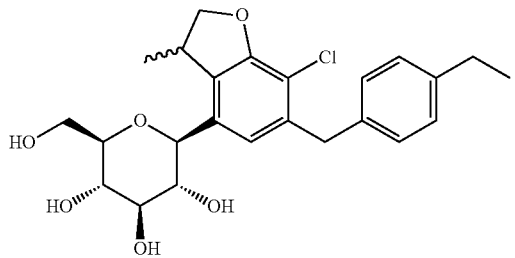 [SMILES: CCc1ccc(Cc2cc([C@@H]3O[C@H](CO)[C@@H](O)[C@H](O)[C@H]3O)c3c(c2Cl)OCC3C)cc1]

(2S,3R,4R,5S,6R)-2-(7-Chloro-6-(4-ethylbenzyl)-3-methyl-2,3-dihydrobenzofuran-4-yl)-6-(hydroxymethyl)tetrahydro-2H-pyran-3,4,5-triol (E153)

$^1$H NMR (400 MHz, CD$_3$OD) δ 7.13-7.07 (m, 4H), 6.98 (s, 0.7H), 6.92 (s, 0.3H), 4.87 (s, 4H), 4.68-4.55 (m, 1H), 4.33-4.24 (m, 2H), 4.08-3.98 (m, 2H), 3.90 (dd, J=12.7 Hz, 0.9 Hz, 1H), 3.81-3.60 (m, 2H), 3.51-3.33 (m, 4H), 2.61 (q, J=7.6 Hz, 2H), 1.39 (d, J=6.9 Hz, 0.9H), 1.33 (d, J=7.0 Hz, 2.1H), 1.22 (t, J=7.6 Hz, 3H); [M+Na]$^+$ 471.

Example 154

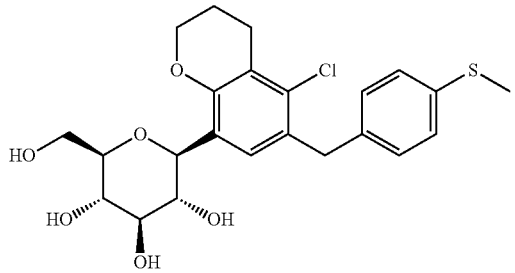 [SMILES: CSc1ccc(Cc2cc([C@@H]3O[C@H](CO)[C@@H](O)[C@H](O)[C@H]3O)c3c(c2Cl)CCCO3)cc1]

(2S,3R,4R,5S,6R)-2-(5-Chloro-6-(4-(methylthio)benzyl)chroman-8-yl)-6-(hydroxymethyl)tetrahydro-2H-pyran-3,4,5-triol (E154)

Similar procedure with preparation of E015 was used.
$^1$H NMR (400 MHz, CD$_3$OD) δ 7.24 (s, 1H), 7.18 (d, J=8.5 Hz, 2H), 7.13 (d, J=8.6 Hz, 2H), 4.85 (s, 4H), 4.68-4.60 (m, 1H), 4.21-4.11 (m, 2H), 4.01 (ABq, Δν$_{AB}$=11.8 Hz, J$_{AB}$=15.1 Hz, 2H), 3.91-3.84 (m, 1H), 3.71-3.64 (m, 1H), 3.52-3.46 (m, 2H), 3.41-3.35 (m, 2H), 2.82 (t, J=6.6 Hz, 2H), 2.46 (s, 3H), 2.09-2.00 (m, 2H); [M+Na]$^+$ 489.

Example 155

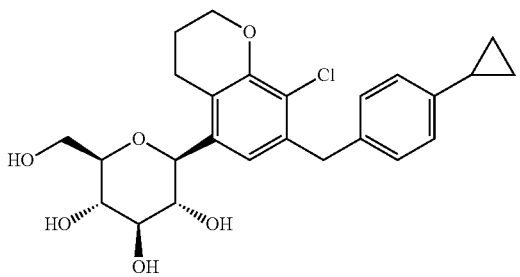 [SMILES: OC[C@H]1O[C@@H](c2cc(Cc3ccc(C4CC4)cc3)c(Cl)c3c2CCCO3)[C@H](O)[C@@H](O)[C@@H]1O]

(2S,3R,4R,5S,6R)-2-(8-Chloro-7-(4-cyclopropylbenzyl)chroman-5-yl)-6-(hydroxymethyl)tetrahydro-2H-pyran-3,4,5-triol (E155)

$^1$H NMR (400 MHz, CD$_3$OD) δ 7.08 (d, J=8.2 Hz, 2H), 7.00 (s, 1H), 6.97 (d, J=8.2 Hz, 2H), 4.90 (s, 4H), 4.43-4.37 (m, 1H), 4.38-4.16 (m, 2H), 4.03 (ABq, Δν$_{AB}$=10.0 Hz, J$_{AB}$=15.0 Hz, 2H), 3.92-3.85 (m, 1H), 3.71-3.64 (m, 1H), 3.55-3.44 (m, 2H), 3.37-3.32 (m, 2H), 3.05-2.92 (m, 1H), 2.91-2.83 (m, 1H), 2.07-1.99 (m, 2H), 1.91-1.82 (m, 1H), 0.97-0.90 (m, 2H), 0.66-0.61 (m, 2H); [M+Na]$^+$ 483.

Example 156

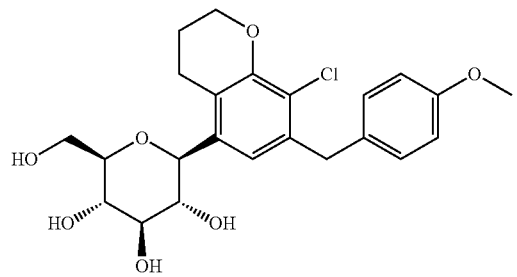 [SMILES: COc1ccc(Cc2cc([C@@H]3O[C@H](CO)[C@@H](O)[C@H](O)[C@H]3O)c3c(c2Cl)OCCC3)cc1]

(2S,3R,4R,5S,6R)-2-(8-Chloro-7-(4-methoxybenzyl)chroman-5-yl)-6-(hydroxymethyl)tetrahydro-2H-pyran-3,4,5-triol (E156)

$^1$H NMR (400 MHz, CD$_3$OD) δ 7.12 (d, J=8.7 Hz, 2H), 7.00 (s, 1H), 6.81 (d, J=8.7 Hz, 2H), 4.91 (s, 4H), 4.42-4.36 (m, 1H), 4.25-4.19 (m, 2H), 4.01 (ABq, Δν$_{AB}$=10.0 Hz, J$_{AB}$=15.1 Hz, 2H), 3.91-3.85 (m, 1H), 3.77 (s, 3H), 3.71-3.63 (m, 1H), 3.55-3.33 (m, 4H), 3.05-2.97 (m, 1H), 2.93-2.84 (m, 1H), 2.05-1.99 (m, 2H); [M+Na]$^+$ 473.

Example 157

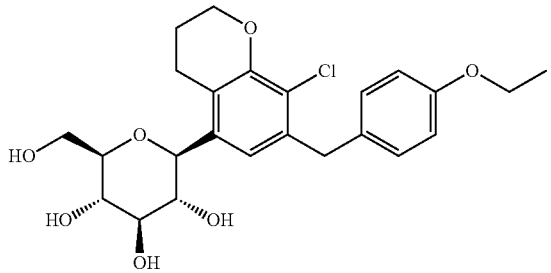 [SMILES: CCOc1ccc(Cc2cc([C@@H]3O[C@H](CO)[C@@H](O)[C@H](O)[C@H]3O)c3c(c2Cl)OCCC3)cc1]

(2S,3R,4R,5S,6R)-2-(8-Chloro-7-(4-ethoxybenzyl)chroman-5-yl)-6-(hydroxymethyl)tetrahydro-2H-pyran-3,4,5-triol (E157)

Similar procedure with preparation of E156 was used.
$^1$H NMR (400 MHz, CD$_3$OD) δ 7.11 (d, J=8.7 Hz, 2H), 7.00 (s, 1H), 6.80 (d, J=8.7 Hz, 2H), 4.95 (s, 4H), 4.42-4.37 (m, 1H), 4.26-4.19 (m, 2H), 4.06-3.95 (m, 4H), 3.92-3.85 (m, 1H), 3.71-3.63 (m, 1H), 3.55-3.45 (m, 2H), 3.43-3.37 (m, 2H), 3.07-2.97 (m, 1H), 2.94-2.83 (m, 1H), 2.07-1.99 (m, 2H), 1.38 (t, J=7.0 Hz, 3H); [M+Na]$^+$ 487.

Example 158

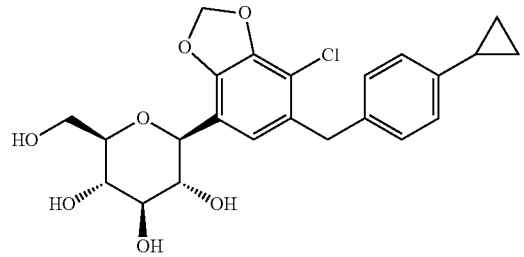 [SMILES: OC[C@H]1O[C@@H](c2cc(Cc3ccc(C4CC4)cc3)c(Cl)c3c2OCO3)[C@H](O)[C@@H](O)[C@@H]1O]

(2S,3R,4R,5S,6R)-2-(7-Chloro-6-(4-cyclopropylbenzyl)benzo[d][1,3]dioxol-4-yl)-6-(hydroxymethyl)tetrahydro-2H-pyran-3,4,5-triol (E158)

$^1$H NMR (400 MHz, CD$_3$OD) δ 7.07 (d, J=8.2 Hz, 2H), 6.98 (d, J=8.2 Hz, 2H), 6.88 (s, 1H), 6.06 (dd, J=7.0 Hz, 1.0 Hz, 2H), 4.85 (s, 4H), 4.28 (d, J=9.6 Hz, 1H), 3.98 (ABq, Δν$_{AB}$=10.9 Hz, J$_{AB}$=15.2 Hz, 2H), 3.88 (d, J=10.5 Hz, 1H), 3.72-3.63 (m, 1H), 3.60 (t, J=9.2 Hz, 1H), 3.49-3.33 (m, 3H), 1.93-1.81 (m, 1H), 0.97-0.89 (m, 2H), 0.68-0.60 (m, 2H); [M+Na]$^+$ 471.

Example 159

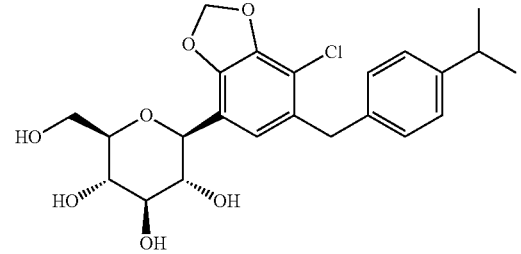 [SMILES: CC(C)c1ccc(Cc2cc([C@@H]3O[C@H](CO)[C@@H](O)[C@H](O)[C@H]3O)c3c(c2Cl)OCO3)cc1]

237

(2S,3R,4R,5S,6R)-2-(7-Chloro-6-(4-isopropylbenzyl)benzo[d][1,3]dioxol-4-yl)-6-(hydroxymethyl)tetrahydro-2H-pyran-3,4,5-triol (E159)

Similar procedure with preparation of E158 proceeded except for using compound 197 to obtain the compound E159.

$^1$H NMR (400 MHz, CD$_3$OD) δ 7.17-7.09 (m, 4H), 6.89 (s, 1H), 6.06 (dd, J=7.4 Hz, 1.1 Hz, 2H), 4.87 (s, 4H), 4.28 (d, J=9.6 Hz, 1H), 4.00 (ABq, Δv$_{AB}$=9.6 Hz, J$_{AB}$=15.2 Hz, 2H), 3.88 (dd, J=12.0 Hz, 1.6 Hz, 1H), 3.71-3.63 (m, 1H), 3.64-3.55 (m, 1H), 3.52-3.23 (m, 3H), 2.94-2.79 (m, 1H), 1.24 (d, J=6.9 Hz, 6H); [M+Na]$^+$ 473.

Example 160

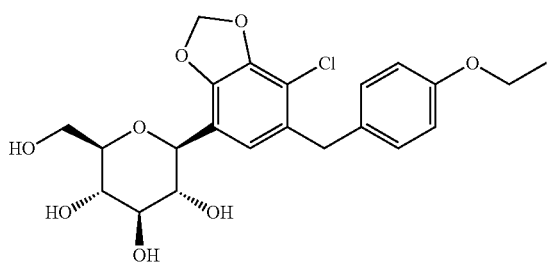 [SMILES: CCOc1ccc(Cc2cc([C@@H]3O[C@H](CO)[C@@H](O)[C@H](O)[C@H]3O)c3c(c2Cl)OCO3)cc1]

(2S,3R,4R,5S,6R)-2-(7-Chloro-6-(4-ethoxybenzyl)benzo[d][1,3]dioxol-4-yl)-6-(hydroxymethyl)tetrahydro-2H-pyran-3,4,5-triol (E160)

$^1$H NMR (400 MHz, CD$_3$OD) δ 7.10 (d, J=8.8 Hz, 2H), 6.87 (s, 1H), 6.82 (d, J=8.7 Hz, 2H), 6.06 (dd, J=6.9 Hz, 1.1 Hz, 2H), 4.86 (s, 4H), 4.28 (d, J=9.6 Hz, 1H), 4.02 (ABq, Δv$_{AB}$=12.1 Hz, J$_{AB}$=7.0 Hz, 2H), 3.96 (d, J=3.6 Hz, 2H), 3.89 (dd, J=11.9 Hz, 1.6 Hz, 1H), 3.71-3.64 (m, 1H), 3.66-3.57 (m, 1H), 3.49-3.43 (m, 1H), 3.41-3.35 (m, 2H), 1.38 (t, J=7.0 Hz, 3H); [M+Na]$^+$ 473.

Example 161

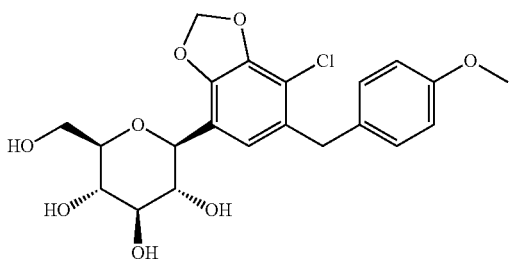 [SMILES: COc1ccc(Cc2cc([C@@H]3O[C@H](CO)[C@@H](O)[C@H](O)[C@H]3O)c3c(c2Cl)OCO3)cc1]

(2S,3R,4R,5S,6R)-2-(7-Chloro-6-(4-methoxybenzyl)benzo[d][1,3]dioxol-4-yl)-6-(hydroxymethyl)tetrahydro-2H-pyran-3,4,5-triol (E161)

$^1$H NMR (400 MHz, CD$_3$OD) δ 7.12 (d, J=8.8 Hz, 2H), 6.88 (s, 1H), 6.83 (d, J=8.8 Hz, 2H), 6.06 (dd, J=7.1 Hz, 1.1 Hz, 2H), 4.89 (s, 4H), 4.28 (d, J=9.6 Hz, 1H), 3.97 (ABq, Δv$_{AB}$=11.1 Hz, J$_{AB}$=15.2 Hz, 2H), 3.92-3.85 (m, 1H), 3.77 (s, 3H), 3.73-3.63 (m, 1H), 3.62-3.55 (m, 1H), 3.49-3.32 (m, 3H); [M+Na]$^+$ 461.

238

Example 162

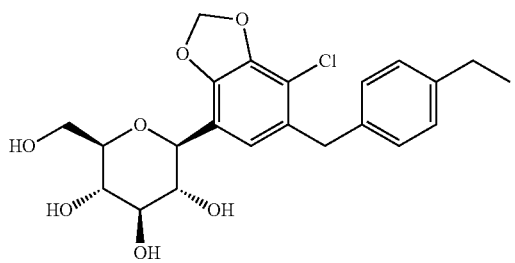 [SMILES: CCc1ccc(Cc2cc([C@@H]3O[C@H](CO)[C@@H](O)[C@H](O)[C@H]3O)c3c(c2Cl)OCO3)cc1]

(2S,3R,4R,5S,6R)-2-(7-Chloro-6-(4-ethylbenzyl)benzo[d][1,3]dioxol-4-yl)-6-(hydroxymethyl)tetrahydro-2H-pyran-3,4,5-triol (E162)

$^1$H NMR (400 MHz, CD$_3$OD) δ 7.10 (s, 4H), 6.89 (s, 1H), 6.06 (dd, J=7.0 Hz, 1.1 Hz, 2H), 4.86 (s, 4H), 4.28 (d, J=9.6 Hz, 1H), 4.00 (ABq, Δv$_{AB}$=10.4 Hz, J$_{AB}$=15.2 Hz, 2H), 3.89 (dd, J=12.0 Hz, 1.6 Hz, 1H), 3.71-3.63 (m, 1H), 3.64-3.55 (m, 1H), 3.51-3.43 (m, 1H), 3.41-3.35 (m, 2H), 2.62 (q, J=7.6 Hz, 2H), 1.22 (t, J=7.6 Hz, 3H); [M+Na]$^+$ 459.

Example 163

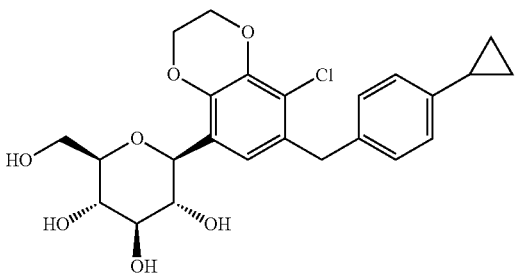 [SMILES: OC[C@H]1O[C@@H](c2cc(Cc3ccc(C4CC4)cc3)c(Cl)c3c2OCCO3)[C@H](O)[C@@H](O)[C@@H]1O]

(2S,3R,4R,5S,6R)-2-(8-Chloro-7-(4-cyclopropylbenzyl)-2,3-dihydrobenzo[b][1,4]dioxin-5-yl)-6-(hydroxymethyl)tetrahydro-2H-pyran-3,4,5-triol (E163)

$^1$H NMR (400 MHz, CD$_3$OD) δ 7.07 (d, J=8.2 Hz, 2H), 6.97 (d, J=8.2 Hz, 2H), 6.95 (s, 1H), 4.86 (s, 4H), 4.63-4.54 (m, 1H), 4.36-4.31 (m, 2H), 4.30-4.22 (m, 2H), 3.99 (ABq, Δv$_{AB}$=13.4 Hz, J$_{AB}$=15.2 Hz, 2H), 3.88 (d, J=11.5 Hz, 1H), 3.72-3.63 (m, 1H), 3.53-3.43 (m, 2H), 3.40-3.35 (m, 2H), 1.90-1.82 (m, 1H), 0.96-0.89 (m, 2H), 0.66-0.59 (m, 2H); [M+Na]$^+$ 485.

Example 164

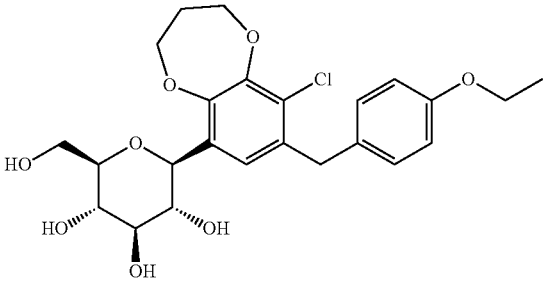 [SMILES: CCOc1ccc(Cc2cc([C@@H]3O[C@H](CO)[C@@H](O)[C@H](O)[C@H]3O)c3c(c2Cl)OCCCO3)cc1]

(2S,3R,4R,5S,6R)-2-(9-Chloro-8-(4-ethoxybenzyl)-3,4-dihydro-2H-benzo[b][1,4]dioxepin-6-yl)-6-(hydroxymethyl)tetrahydro-2H-pyran-3,4,5-triol (E164)

$^1$H NMR (400 MHz, CD$_3$OD) δ 7.11 (d, J=8.8 Hz, 2H), 7.07 (s, 1H), 6.82 (d, J=8.7S Hz, 2H), 4.85 (s, 4H), 4.63-4.55 (m, 1H), 4.31-4.17 (m, 2H), 4.17-4.07 (m, 2H), 4.05-3.93 (m, 4H), 3.88 (dd, J=11.9 Hz, 1.6 Hz, 1H), 3.71-3.64 (m, 1H), 3.49-3.43 (m, 2H), 3.41-3.34 (m, 2H), 2.29-2.10 (m, 2H), 1.38 (t, J=7.0 Hz, 1H); [M+Na]$^+$ 503.

Example 165

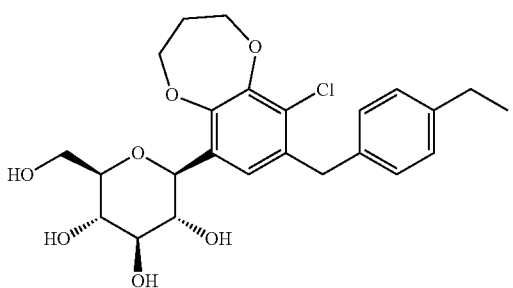 [SMILES: CCc1ccc(Cc2cc([C@@H]3O[C@H](CO)[C@@H](O)[C@H](O)[C@H]3O)c3c(c2Cl)OCCCO3)cc1]

(2S,3R,4R,5S,6R)-2-(9-Chloro-8-(4-ethylbenzyl)-3,4-dihydro-2H-benzo[b][1,4]dioxepin-6-yl)-6-(hydroxymethyl)tetrahydro-2H-pyran-3,4,5-triol (E165)

$^1$H NMR (400 MHz, CD$_3$OD) δ 7.10 (s, 4H), 4.86 (s, 4H), 4.63-4.56 (m, 1H), 4.31-4.19 (m, 2H), 4.17-4.07 (m, 2H), 4.01 (ABq, Δv$_{AB}$=11.8 Hz, J$_{AB}$=15.1 Hz, 2H), 3.88 (dd, J=11.9 Hz, 1.4 Hz, 1H), 3.73-3.63 (m, 1H), 3.52-3.44 (m, 2H), 3.41-3.33 (m, 2H), 2.61 (q, J=7.6 Hz, 2H), 2.31-2.11 (m, 2H), 1.22 (t, J=7.6 Hz, 3H); [M+Na]$^+$ 487.

Example 166

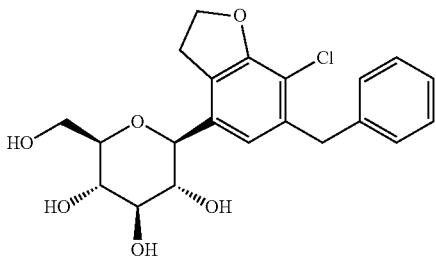 [SMILES: OC[C@H]1O[C@@H](c2cc(Cc3ccccc3)c(Cl)c3c2CCO3)[C@H](O)[C@@H](O)[C@@H]1O]

(2S,3R,4R,5S,6R)-2-(6-Benzyl-7-chloro-2,3-dihydrobenzofuran-4-yl)-6-(hydroxymethyl)tetrahydro-2H-pyran-3,4,5-triol (E166)

$^1$H NMR (400 MHz, CD$_3$OD) δ 7.28-7.24 (m, 2H), 7.22-7.15 (m, 3H), 6.89 (s, 1H), 4.65 (t, J=8.8 Hz, 2H), 4.17 (d, J=8.8 Hz, 1H), 4.07 (ABq, Δv$_{AB}$=18.0 Hz, J$_{AB}$=14.8 Hz, 2H), 3.92-3.89 (m, 1H), 3.72-3.68 (m, 1H), 3.52-3.42 (m, 3H), 3.40-3.38 (m, 2H), 3.36-3.30 (m, 2H); [M+Na]$^+$ 429.

Example 168

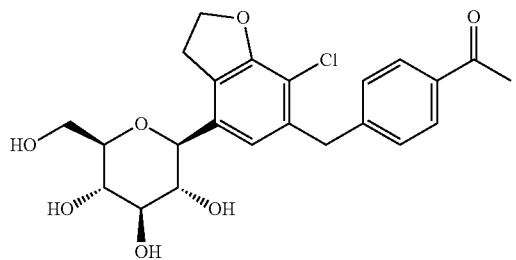 [SMILES: CC(=O)c1ccc(Cc2cc([C@@H]3O[C@H](CO)[C@@H](O)[C@H](O)[C@H]3O)c3c(c2Cl)OCC3)cc1]

1-(4-((7-Chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)phenyl)ethanone (E168)

$^1$H NMR (400 MHz, CD$_3$OD) δ 7.93 (dt, J=8.4, 1.6 Hz, 2H), 7.36 (d, J=8.4 Hz, 2H), 6.95 (s, 1H), 4.67 (t, J=8.8 Hz, 2H), 4.21 (d, J=9.2 Hz, 1H), 4.17 (d, J=5.2 Hz, 2H), 3.94-3.91 (m, 1H), 3.75-3.70 (m, 1H), 3.55-3.47 (m, 3H), 3.45-3.38 (m, 3H), 2.61 (s, 3H); [M+H]$^+$ 449, [M+Na]$^+$ 471.

Example 169

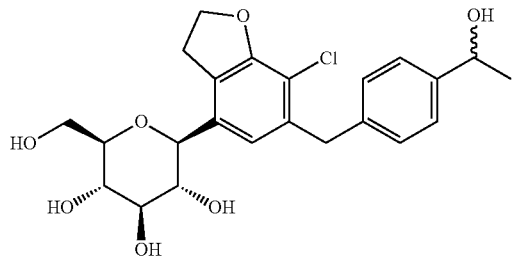

(2S,3R,4R,5S,6R)-2-(7-Chloro-6-(4-(1-hydroxyethyl)benzyl)-2,3-dihydrobenzofuran-4-yl)-6-(hydroxymethyl)tetrahydro-2H-pyran-3,4,5-triol (E169)

$^1$H NMR (400 MHz, CD$_3$OD) δ 7.29 (d, J=8.0 Hz, 2H), 7.20 (d, J=8.0 Hz, 2H), 6.91 (s, 1H), 4.82 (q, J=6.4 Hz, 1H), 4.66 (t, J=8.8 Hz, 2H), 4.18 (d, J=9.2 Hz, 1H), 4.07 (ABq, Δv$_{AB}$=17.5 Hz, J$_{AB}$=15.2 Hz, 2H), 3.92 (dd, J=12.0, 1.6 Hz, 1H), 3.74-3.69 (m, 1H), 3.54-3.44 (m, 3H), 3.42-3.31 (m, 3H), 1.45 (d, J=6.4 Hz, 3H); [M+Na]$^+$ 473.

Example 170

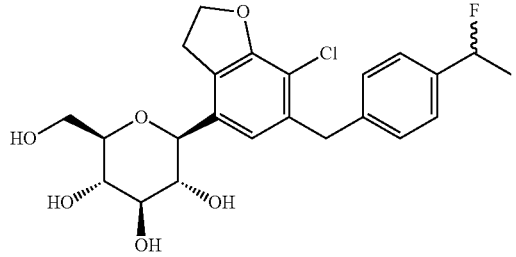

(2S,3R,4R,5S,6R)-2-(7-Chloro-6-(4-(1-fluoroethyl)
benzyl)-2,3-dihydrobenzofuran-4-yl)-6-(hydroxym-
ethyl)tetrahydro-2H-pyran-3,4,5-triol (E170)

$^1$H NMR (400 MHz, CD$_3$OD) δ 7.28 (d, J=8.0 Hz, 2H), 7.19 (d, J=8.4 Hz, 2H), 6.91 (s, 1H), 4.81 (q, J=6.4 Hz, 1H), 4.66 (t, J=8.8 Hz, 2H), 4.18 (d, J=9.2 Hz, 1H), 4.07 (ABq, Δv$_{AB}$=17.4 Hz, J$_{AB}$=15.2 Hz, 2H), 3.92 (d, J=11.2 Hz, 1H), 3.74-3.69 (m, 1H), 3.54-3.44 (m, 3H), 3.42-3.39 (m, 3H), 1.45 (d, J=6.4 Hz, 1H); [M+Na]$^+$ 475.

Example 171

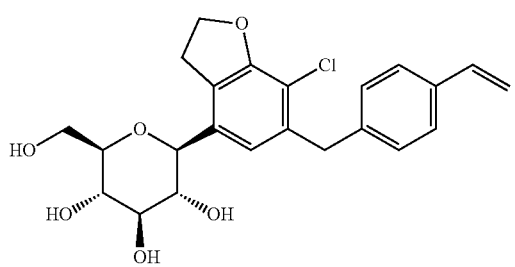 [SMILES: C=Cc1ccc(Cc2cc([C@@H]3O[C@H](CO)[C@@H](O)[C@H](O)[C@H]3O)c3c(c2Cl)OCC3)cc1]

(2S,3R,4R,5S,6R)-2-(7-Chloro-6-(4-vinylbenzyl)-2,
3-dihydrobenzofuran-4-yl)-6-(hydroxymethyl)tet-
rahydro-2H-pyran-3,4,5-triol (E171)

$^1$H NMR (400 MHz, CD$_3$OD) δ 7.34 (d, J=8.0 Hz, 2H), 7.18 (d, J=8.0 Hz, 2H), 6.90 (s, 1H), 6.72 (dd, J=17.6, 11.2 Hz, 1H), 5.74 (dd, J=17.6, 1.2 Hz, 1H), 5.19 (dd, J=10.8, 1.2 Hz, 1H), 4.66 (t, J=8.8 Hz, 2H), 4.18 (d, J=8.8 Hz, 1H), 4.07 (ABq, Δv$_{AB}$=17.4 Hz, J$_{AB}$=15.2 Hz, 2H), 3.91 (dd, J=11.6, 1.2 Hz, 1H), 3.73-3.69 (m, 1H), 3.53-3.44 (m, 3H), 3.41-3.31 (m, 3H), 1.45 (d, J=6.4 Hz, 1H); [M+Na]$^+$ 455.

Example 172

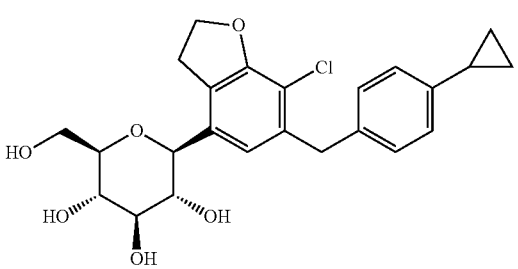 [SMILES: OC[C@H]1O[C@@H](c2cc(Cc3ccc(C4CC4)cc3)c(Cl)c3c2CCO3)[C@H](O)[C@@H](O)[C@@H]1O]

(2S,3R,4R,5S,6R)-2-(7-Chloro-6-(4-cyclopropylben-
zyl)-2,3-dihydrobenzofuran-4-yl)-6-(hydroxymethyl)
tetrahydro-2H-pyran-3,4,5-triol (E172)

$^1$H NMR (400 MHz, CD$_3$OD) δ 7.02 (d, J=8.0 Hz, 2H), 6.92 (d, J=8.0 Hz, 2H), 6.81 (s, 1H), 4.59 (t, J=8.8 Hz, 2H), 4.11 (d, J=9.2 Hz, 1H), 3.96 (ABq, Δv$_{AB}$=19.0 Hz, J$_{AB}$=15.2 Hz, 2H), 3.87-3.84 (m, 1H), 3.67-3.63 (m, 1H), 3.47-3.37 (m, 3H), 3.35-3.33 (m, 3H), 1.85-1.79 (m, 1H), 0.91-0.86 (m, 2H), 0.61-0.57 (m, 2H); [M+Na]$^+$ 469.

Example 173

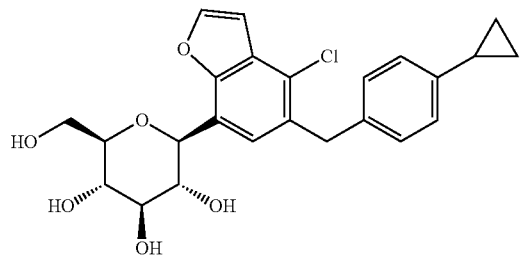 [SMILES: OC[C@H]1O[C@@H](c2cc(Cc3ccc(C4CC4)cc3)c(Cl)c3ccoc23)[C@H](O)[C@@H](O)[C@@H]1O]

(2S,3R,4R,5S,6R)-2-(4-Chloro-5-(4-cyclopropylben-
zyl)benzofuran-7-yl)-6-(hydroxymethyl)tetrahydro-
2H-pyran-3,4,5-triol (E173)

$^1$H NMR (400 MHz, CD$_3$OD) δ 7.37 (dd, J=8.4, 0.8 Hz, 1H), 7.16 (d, J=8.4 Hz, 1H), 7.08 (d, J=8.0 Hz, 1H), 7.00 (d, J=8.0 Hz, 1H), 6.87 (s, 1H), 4.42-4.41 (m, 1H), 4.01-4.36 (m, 1H), 4.31-4.29 (m, 1H), 4.15 (s, 2H), 4.12-4.10 (m, 1H), 3.92-3.88 (m, 1H), 3.77-3.73 (m, 1H), 1.92-1.85 (m, 1H), 0.97-0.92 (m, 2H), 0.68-0.64 (m, 2H); [M+Na]$^+$ 467.

Example 174

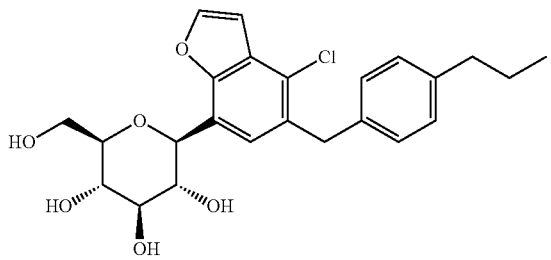 [SMILES: CCCc1ccc(Cc2cc([C@@H]3O[C@H](CO)[C@@H](O)[C@H](O)[C@H]3O)c3occc3c2Cl)cc1]

(2S,3R,4R,5S,6R)-2-(4-Chloro-5-(4-propylbenzyl)
benzofuran-7-yl)-6-(hydroxymethyl)tetrahydro-2H-
pyran-3,4,5-triol (E174)

$^1$H NMR (400 MHz, CD$_3$OD) δ 7.38 (dd, J=8.4, 0.8 Hz, 1H), 7.19 (d, J=8.4 Hz, 1H), 7.10 (s, 4H), 6.96 (d, J=0.8 Hz, 1H), 4.43 (d, J=10.0 Hz, 1H), 4.17 (s, 2H), 3.92 (dd, J=12.0, 2.0 Hz, 1H), 3.78 (dd, J=9.6, 8.8 Hz, 1H), 3.71 (dd, J=12.0, 5.2 Hz, 1H), 3.54-3.44 (m, 2H), 2.56 (t, J=7.6 Hz, 2H), 1.63 (sect, J=7.2 Hz, 2H), 0.94 (t, J=7.6 Hz, 2H); [M+Na]$^+$ 469.

Example 175

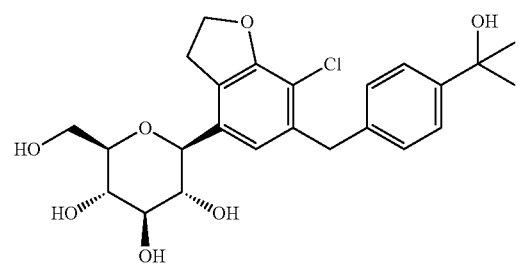 [SMILES: CC(C)(O)c1ccc(Cc2cc([C@@H]3O[C@H](CO)[C@@H](O)[C@H](O)[C@H]3O)c3c(c2Cl)OCC3)cc1]

(2S,3R,4R,5S,6R)-2-(7-Chloro-6-(4-(2-hydroxypropan-2-yl)benzyl)-2,3-dihydrobenzofuran-4-yl)-6-(hydroxymethyl)tetrahydro-2H-pyran-3,4,5-triol (E175)

$^1$H NMR (400 MHz, CD$_3$OD) δ 7.39 (d, J=8.4 Hz, 2H), 7.16 (d, J=8.4 Hz, 2H), 6.90 (s, 1H), 6.64 (t, J=8.8 Hz, 2H), 4.17 (d, J=9.2 Hz, 1H), 4.05 (ABq, Δv$_{AB}$=17.0 Hz, J$_{AB}$=15.2 Hz, 2H), 3.91 (d, J=11.6 Hz, 1H), 3.72-3.68 (m, 1H), 3.48-3.45 (m, 3H), 3.40-3.38 (m, 3H), 1.53 (s, 6H); [M+Na]$^+$ 487.

Example 176

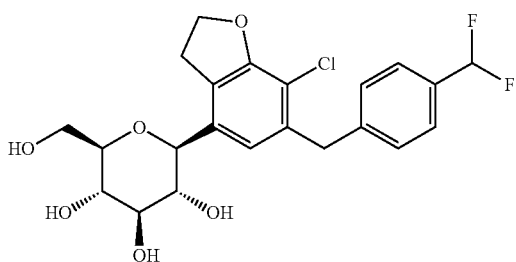 [SMILES: OC[C@H]1O[C@@H](c2cc(Cc3ccc(C(F)F)cc3)c(Cl)c3c2CCO3)[C@H](O)[C@@H](O)[C@@H]1O]

(2S,3R,4R,5S,6R)-2-(7-Chloro-6-(4-(difluoromethyl)benzyl)-2,3-dihydrobenzofuran-4-yl)-6-(hydroxymethyl)tetrahydro-2H-pyran-3,4,5-triol (E176)

$^1$H NMR (400 MHz, CD$_3$OD) δ 7.44 (d, J=8.0 Hz, 2H), 7.32 (d, J=8.0 Hz, 2H), 6.92 (s, 1H), 6.72 (t, J=56.4 Hz, 1H), 4.65 (t, J=8.8 Hz, 2H), 4.18 (d, J=9.2 Hz, 2H), 4.13 (d, J=6.0 Hz, 2H), 3.93-3.89 (m, 1H), 373-3.68 (m, 1H), 3.51-3.45 (m, 3H), 3.43-3.37 (m, 3H); [M+Na]$^+$ 479.

Example 177

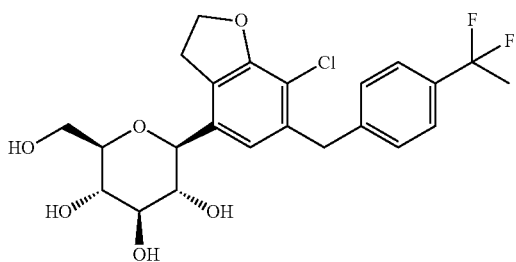 [SMILES: CC(F)(F)c1ccc(Cc2cc([C@@H]3O[C@H](CO)[C@@H](O)[C@H](O)[C@H]3O)c3c(c2Cl)OCC3)cc1]

(2S,3R,4R,5S,6R)-2-(7-Chloro-6-(4-(1,1-difluoroethyl)benzyl)-2,3-dihydrobenzofuran-4-yl)-6-(hydroxymethyl)tetrahydro-2H-pyran-3,4,5-triol (E177)

$^1$H NMR (400 MHz, CD$_3$OD) δ 7.43 (d, J=8.4 Hz, 2H), 7.29 (d, J=8.8 Hz, 2H), 6.92 (s, 1H), 4.65 (t, J=8.8 Hz, 2H), 4.18 (d, J=8.8 Hz, 1H), 4.11 (d, J=6.0 Hz, 2H), 3.92-3.89 (m, 1H), 3.73-3.68 (m, 1H), 3.53-3.45 (m, 3H), 1.90 (t, J=18.4 Hz, 3H); [M+Na]$^+$ 493.

Example 178

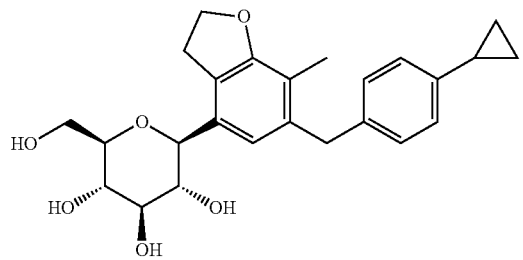

(2S,3R,4R,5S,6R)-2-(6-(4-Cyclopropylbenzyl)-7-methyl-2,3-dihydrobenzofuran-4-yl)-6-(hydroxymethyl)tetrahydro-2H-pyran-3,4,5-triol (E178)

$^1$H NMR (400 MHz, CD$_3$OD) δ 7.01 (d, J=8.4 Hz, 2H), 6.96 (d, J=8.0 Hz, 2H), 6.78 (s, 1H), 4.54 (t, J=8.8 Hz, 2H), 4.17 (d, J=8.8 Hz, 1H), 3.92 (m, 2H), 3.93-3.89 (m, 1H), 3.72-3.68 (m, 1H), 3.55-3.47 (m, 2H), 3.43-3.37 (m, 4H), 2.01 (s, 3H), 1.90-1.83 (m, 1H), 0.95-0.90 (m, 2H), 0.65-0.61 (m, 2H); [M+Na]$^+$ 449, [M+K]$^+$ 465.

Example 179

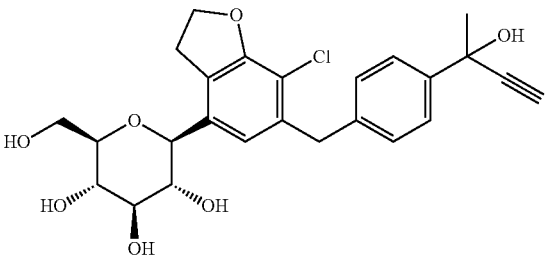 [SMILES: C#CC(C)(O)c1ccc(Cc2cc([C@@H]3O[C@H](CO)[C@@H](O)[C@H](O)[C@H]3O)c3c(c2Cl)OCC3)cc1]

(2S,3R,4R,5S,6R)-2-(7-Chloro-6-(4-(2-hydroxybut-3-yn-2-yl)benzyl)-2,3-dihydrobenzofuran-4-yl)-6-(hydroxymethyl)tetrahydro-2H-pyran-3,4,5-triol (E179)

$^1$H NMR (400 MHz, CD$_3$OD) δ 7.51 (d, J=8.4 Hz, 2H), 7.17 (d, J=8.0 Hz, 2H), 6.87 (s, 1H), 4.62 (t, J=8.8 Hz, 2H), 4.15 (d, J=8.8 Hz, 1H), 4.04 (ABq, Δv$_{AB}$=17.4 Hz, J$_{AB}$=15.2 Hz, 2H), 3.89-3.86 (m, 1H), 3.70-3.65 (m, 1H), 3.49-3.42 (m, 3H), 3.41-3.35 (m, 3H), 2.98 (s, 1H), 1.68 (s, 3H); [M+Na]$^+$ 449, [M+K]$^+$ 497.

Example 180

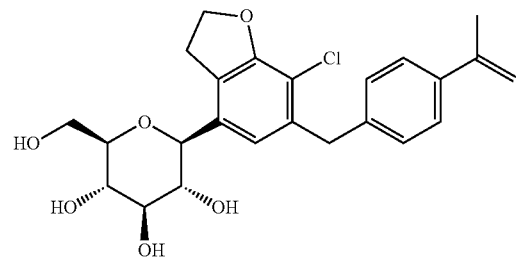 [SMILES: C=C(C)c1ccc(Cc2cc([C@@H]3O[C@H](CO)[C@@H](O)[C@H](O)[C@H]3O)c3c(c2Cl)OCC3)cc1]

(2S,3R,4R,5S,6R)-2-(7-Chloro-6-(4-(prop-1-en-2-yl)benzyl)-2,3-dihydrobenzofuran-4-yl)-6-(hydroxymethyl)tetrahydro-2H-pyran-3,4,5-triol (E180)

$^1$H NMR (400 MHz, CD$_3$OD) δ 7.35 (d, J=8.8 Hz, 2H), 7.13 (d, J=8.8 Hz, 2H), 6.85 (s, 1H), 5.31-5.30 (m, 1H), 5.01-5.00 (m, 1H), 4.60 (t, J=8.8 Hz, 2H), 4.13 (d, J=9.2 Hz, 1H), 4.02 (ABq, Δν$_{AB}$=17.4 Hz, J$_{AB}$=15.2 Hz, 2H), 3.88-3.85 (m, 1H), 3.69-3.64 (m, 1H), 3.48-3.39 (m, 3H), 3.37-3.26 (m, 3H), 2.10-2.09 (m, 3H); [M+Na]$^+$ 469.

Example 181

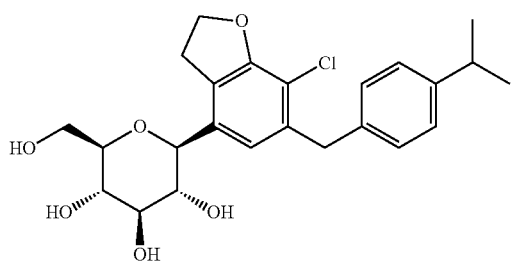

(2S,3R,4R,5S,6R)-2-(7-Chloro-6-(4-isopropylbenzyl)-2,3-dihydrobenzofuran-4-yl)-6-(hydroxymethyl)tetrahydro-2H-pyran-3,4,5-triol (E181)

$^1$H NMR (400 MHz, CD$_3$OD) δ 7.13 (s, 4H), 6.88 (s, 1H), 4.64 (t, J=8.8 Hz, 2H), 4.17 (d, J=9.2 Hz, 1H), 4.03 (ABq, Δν$_{AB}$=18.1 Hz, J$_{AB}$=15.2 Hz, 2H), 3.90 (dd, J=12.0, 1.2 Hz, 1H), 3.72-3.68 (m, 1H), 3.52-3.42 (m, 3H), 3.40-3.33 (m, 3H), 2.87 (sept, 1H), 1.24 (d, J=7.2 Hz, 6H); [M+Na]$^+$ 471.

Example 182

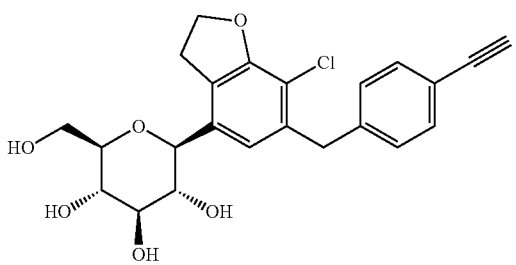

(2S,3R,4R,5S,6R)-2-(7-Chloro-6-(4-ethynylbenzyl)-2,3-dihydrobenzofuran-4-yl)-6-(hydroxymethyl)tetrahydro-2H-pyran-3,4,5-triol (E182)

$^1$H NMR (400 MHz, CD$_3$OD) δ 7.36 (d, J=8.4 Hz, 2H), 7.19 (d, J=8.4 Hz, 2H), 6.90 (s, 1H), 4.64 (t, J=8.8 Hz, 2H), 4.18 (d, J=9.2 Hz, 2H), 4.07 (ABq, Δν$_{AB}$=15.3 Hz, J$_{AB}$=15.2 Hz, 2H), 3.92-3.90 (m, 1H), 3.73-3.69 (m, 1H), 3.52-3.45 (m, 3H), 3.44-3.38 (m, 3H); [M+Na]$^+$ 453.

Example 183

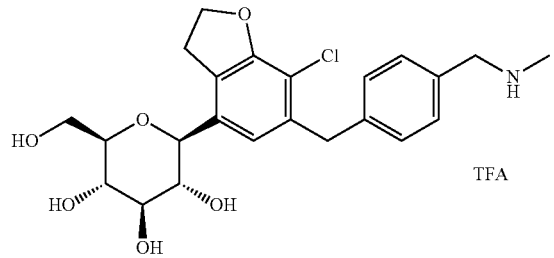 [SMILES: CNCc1ccc(Cc2cc([C@@H]3O[C@H](CO)[C@@H](O)[C@H](O)[C@H]3O)c3c(c2Cl)OCC3)cc1]

(2S,3R,4R,5S,6R)-2-(7-Chloro-6-(4-((methylamino)methyl)benzyl)-2,3-dihydrobenzofuran-4-yl)-6-(hydroxymethyl)tetrahydro-2H-pyran-3,4,5-triol trifluoro acetic acid salt (E183)

[M+H]$^+$ 450, [M+Na]$^+$ 472.

Example 184

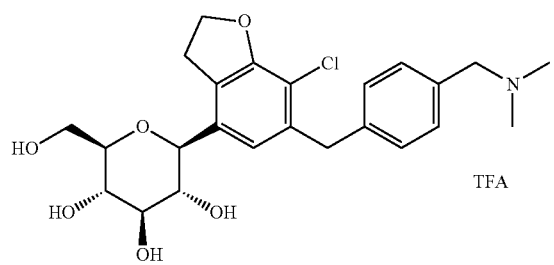 [SMILES: CN(C)Cc1ccc(Cc2cc([C@@H]3O[C@H](CO)[C@@H](O)[C@H](O)[C@H]3O)c3c(c2Cl)OCC3)cc1]

(2S,3R,4R,5S,6R)-2-(7-Chloro-6-(4-((dimethylamino)methyl)benzyl)-2,3-dihydrobenzofuran-4-yl)-6-(hydroxymethyl)tetrahydro-2H-pyran-3,4,5-triol trifluoro acetic acid salt (E184)

[M+H]$^+$ 464, [M+Na]$^+$ 486.

Example 185

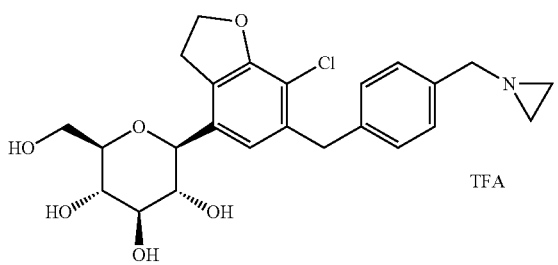 [SMILES: OC[C@H]1O[C@@H](c2cc(Cc3ccc(CN4CC4)cc3)c(Cl)c3c2CCO3)[C@H](O)[C@@H](O)[C@@H]1O]

(2S,3R,4R,5S,6R)-2-(6-(4-(Aziridin-1-ylmethyl)
benzyl)-7-chloro-2,3-dihydrobenzofuran-4-yl)-6-
(hydroxymethyl)tetrahydro-2H-pyran-3,4,5-triol
trifluoro acetic acid salt (E185)

$^1$H NMR (400 MHz, CD$_3$OD) δ 7.38 (d, J=8.4 Hz, 2H), 7.29 (d, J=8.0 Hz, 2H), 6.89 (s, 1H), 4.62 (t, J=8.8 Hz, 2H), 4.18 (s, 2H), 4.15 (d, J=9.2 Hz, 2H), 4.09 (d, J=4.4 Hz, 2H), 3.90-3.87 (m, 1H), 3.80-3.77 (m, 2H), 3.70-3.66 (m, 1H), 3.50-3.41 (m, 3H), 3.39-3.34 (m, 3H), 3.11-3.08 (m, 2H); [M+H]$^+$ 462, [M+Na]$^+$ 484.

Example 186

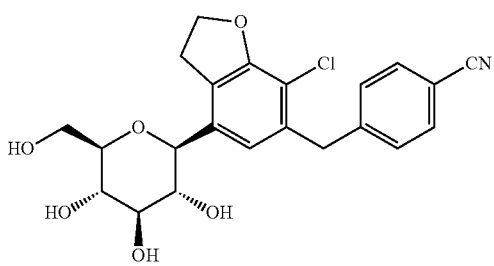 [SMILES: N#Cc1ccc(Cc2cc([C@@H]3O[C@H](CO)[C@@H](O)[C@H](O)[C@H]3O)c3c(c2Cl)OCC3)cc1]

4-((7-Chloro-4-((2S,3R,4R,5S,6R)-3,4,5-trihydroxy-
6-(hydroxymethyl)tetrahydro-2H-pyran-2-yl)-2,3-
dihydrobenzofuran-6-yl)methyl)benzonitrile (E186)

$^1$H NMR (400 MHz, CD$_3$OD) δ 7.60 (d, J=8.4 Hz, 2H), 7.36 (d, J=8.4 Hz, 2H), 6.92 (s, 1H), 4.63 (t, J=8.8 Hz, 2H), 4.17 (ABq, Δν$_{AB}$=24.7 Hz, J$_{AB}$=36.0 Hz, 2H), 4.14 (d, J=3.2 Hz, 2H), 3.90-3.87 (m, 1H), 3.70-3.66 (m, 1H), 3.51-3.41 (m, 3H), 3.39-3.33 (m, 3H); [M+Na]$^+$ 454.

Example 187

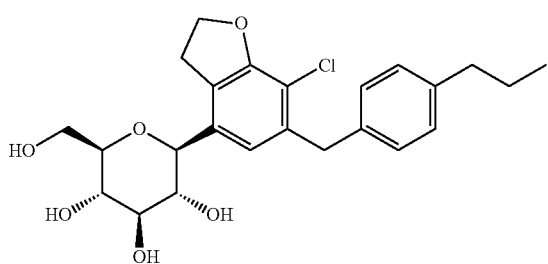

(2S,3R,4R,5S,6R)-2-(7-Chloro-6-(4-propylbenzyl)-
2,3-dihydrobenzofuran-4-yl)-6-(hydroxymethyl)
tetrahydro-2H-pyran-3,4,5-triol (E187)

$^1$H NMR (400 MHz, CD$_3$OD) δ 7.07 (d, J=8.0 Hz, 2H), 7.03 (d, J=8.4 Hz, 2H), 6.84 (s, 1H), 4.60 (t, J=8.8 Hz, 2H), 4.13 (d, J=9.2 Hz, 2H), 3.99 (ABq, Δν$_{AB}$=18.4 Hz, J$_{AB}$=14.8 Hz, 2H), 3.86 (dd, J=11.6, 0.8 Hz, 1H), 3.68-3.64 (m, 1H), 3.48-3.38 (m, 3H), 3.36-3.25 (m, 3H), 2.52 (t, J=7.2 Hz, 2H), 1.59 (sept, J=7.2 Hz, 2H), 0.90 (t, J=7.2 Hz, 3H); [M+Na]$^+$ 471.

Example 188

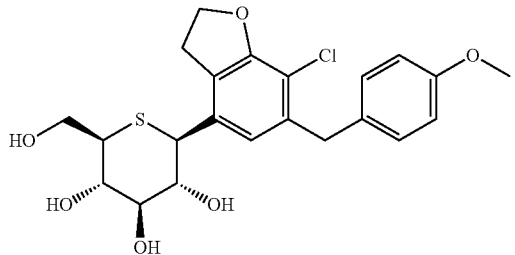

(2S,3R,4R,5S,6R)-2-(7-Chloro-6-(4-methoxyben-
zyl)-2,3-dihydrobenzofuran-4-yl)-6-(hydroxymethyl)
tetrahydro-2H-thiopyran-3,4,5-triol (E188)

$^1$H NMR (400 MHz, CD$_3$OD) δ 7.07 (d, J=8.4 Hz, 2H), 6.79 (d, J=8.8 Hz, 2H), 6.76 (s, 1H), 4.63 (td, J=8.0, 1.6 Hz, 2H), 3.95 (s, 2H), 3.92 (d, J=3.6 Hz, 1H), 3.79-3.75 (m, 3H), 3.74 (s, 3H), 3.71 (d, J=6.4 Hz, 1H), 3.56 (dd, J=10.0, 8.8 Hz, 1H), 3.42-3.35 (m, 2H), 3.24-3.20 (m, 1H), 3.01-2.96 (m, 1H), 0.90 (t, J=7.2 Hz, 3H); [M+Na]$^+$ 475.

Example 189

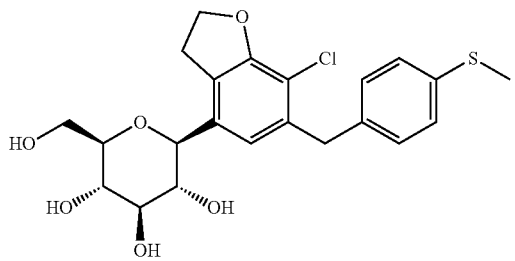

(2S,3R,4R,5S,6R)-2-(7-Chloro-6-(4-(methylthio)
benzyl)-2,3-dihydrobenzofuran-4-yl)-6-(hydroxym-
ethyl)tetrahydro-2H-pyran-3,4,5-triol (E189)

$^1$H NMR (400 MHz, MeOD) δ 7.17 (d, J=8.4 Hz, 2H), 7.12 (d, J=8.4 Hz, 2H), 6.87 (s, 1H), 6.65-6.60 (m, 2H), 4.16 (d, J=9.2 Hz, 1H), 4.01 (ABq, Δν$_{AB}$=16.9 Hz, J$_{AB}$=15.0 Hz, 2H), 3.89 (d, J=11.6 Hz, 1H), 3.71-3.66 (m, 1H), 3.48-3.36 (m, 6H), 2.44 (s, 3H); [M+Na]$^+$ 475.

Example 190

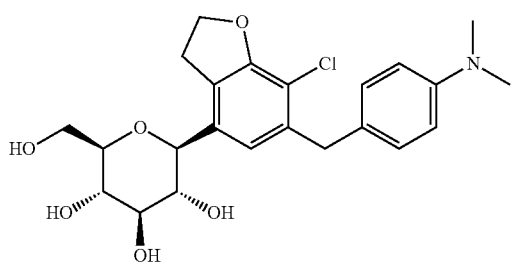 [SMILES: CN(C)c1ccc(Cc2cc([C@@H]3O[C@H](CO)[C@@H](O)[C@H](O)[C@H]3O)c3c(c2Cl)OCC3)cc1]

(2S,3R,4R,5S,6R)-2-(7-Chloro-6-(4-(dimethylamino)benzyl)-2,3-dihydrobenzofuran-4-yl)-6-(hydroxymethyl)tetrahydro-2H-pyran-3,4,5-triol (E190)

$^1$H NMR (400 MHz, MeOD) δ 7.06 (d, J=8.8 Hz, 2H), 6.85 (s, 1H), 6.73 (d, J=8.8 Hz, 2H), 4.63 (t, J=8.8 Hz, 2H), 4.16 (d, J=8.8 Hz, 1H), 3.96 (ABq, Δv$_{AB}$=20.0 Hz, J$_{AB}$=15.0 Hz, 2H), 3.90 (dd, J=12.4 Hz, 1.2 Hz, 1H), 3.72-3.67 (m, 1H), 3.51-3.3.83 (m, 6H), 2.88 (s, 6H); [M+H]$^+$ 450.

Example 191

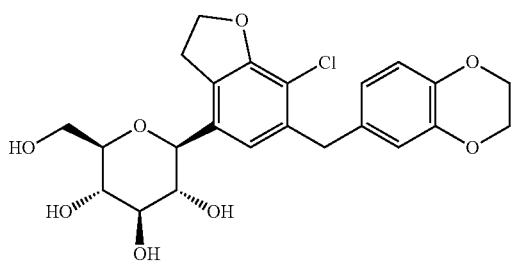 [SMILES: OC[C@H]1O[C@@H](c2cc(Cc3ccc4c(c3)OCCO4)c(Cl)c3c2CCO3)[C@H](O)[C@@H](O)[C@@H]1O]

(2S,3R,4R,5S,6R)-2-(4-Chloro-5-((2,3-dihydrobenzo[b][1,4]dioxin-6-yl)methyl)-2,3-dihydrobenzofuran-7-yl)-6-(hydroxymethyl)tetrahydro-2H-pyran-3,4,5-triol (E191)

$^1$H NMR (400 MHz, MeOD) δ 7.14 (s, 1H), 6.73-6.71 (m, 1H), 6.67-6.64 (m, 2H), 4.70-4.59 (m, 2H), 4.33 (d, J=9.6 Hz, 1H), 4.21 (s, 4H), 3.92 (ABq, Δv$_{AB}$=8.6 Hz, J$_{AB}$=11.8 Hz, 2H), 3.88 (dd, J=12.0, 2.0 Hz, 1H), 3.71-3.66 (m, 1H), 3.63 (t, J=9.2 Hz, 1H), 3.49-3.38 (m, 3H), 3.26 (t, J=8.8 Hz, 2H); [M+Na]+ 487.

Example 192

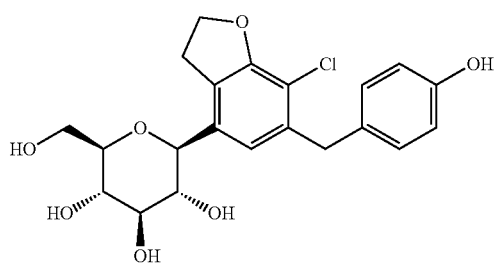 [SMILES: OC[C@H]1O[C@@H](c2cc(Cc3ccc(O)cc3)c(Cl)c3c2CCO3)[C@H](O)[C@@H](O)[C@@H]1O]

(2S,3R,4R,5S,6R)-2-(7-Chloro-6-(4-hydroxybenzyl)-2,3-dihydrobenzofuran-4-yl)-6-(hydroxymethyl)tetrahydro-2H-pyran-3,4,5-triol (E192)

$^1$H NMR (400 MHz, MeOD) δ 7.01 (d, J=8.6 Hz, 2H), 6.84 (s, 1H), 6.68 (d, J=8.6 Hz, 2H), 4.63 (t, J=8.6 Hz, 2H), 4.15 (d, J=9.2 Hz, 1H), 3.95 (ABq, Δv$_{AB}$=19.4 Hz, J$_{AB}$=14.8 Hz, 2H), 3.89 (dd, J=12.2, 1.4 Hz, 1H), 3.71-3.67 (m, 1H), 3.50-3.38 (m, 6H); [M+Na]+ 445.

Example 193

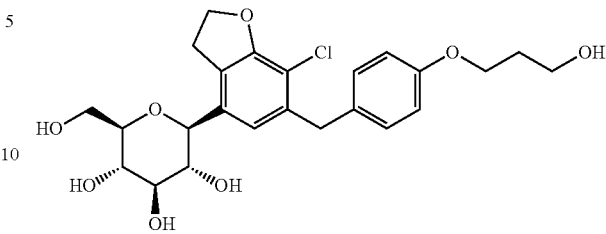

(2S,3R,4R,5S,6R)-2-(7-Chloro-6-(4-(3-hydroxypropoxy)benzyl)-2,3-dihydrobenzofuran-4-yl)-6-(hydroxymethyl)tetrahydro-2H-pyran-3,4,5-triol (E193)

$^1$H NMR (400 MHz, MeOD) δ 7.11 (d, J=8.8 Hz, 2H), 6.86 (s, 1H), 6.83 (d, J=8.8 Hz, 2H), 4.64 (t, J=8.8 Hz, 2H), 4.16 (d, J=9.2 Hz, 1H), 4.05 (t, J=6.2 Hz, 2H), 4.00-3.94 (m, 2H), 3.90 (dd, J=11.8, 1.4 Hz, 1H), 3.85-3.83 (m, 1H), 3.75 (t, J=6.2 Hz, 2H), 3.71-3.67 (m, 1H), 3.51-3.38 (m, 5H), 2.01-1.95 (m, 2H); [M+Na]+ 503.

Example 194

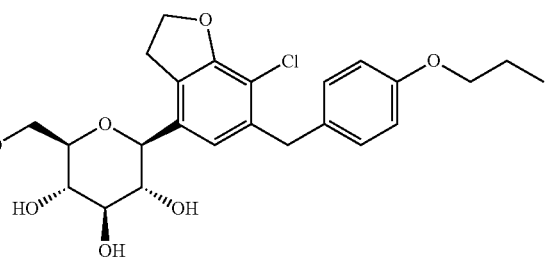

(2S,3R,4R,5S,6R)-2-(7-Chloro-6-(4-propoxybenzyl)-2,3-dihydrobenzofuran-4-yl)-6-(hydroxymethyl)tetrahydro-2H-pyran-3,4,5-triol (E194)

$^1$H NMR (400 MHz, MeOD) δ 7.11 (d, J=8.6 Hz, 2H), 6.87 (s, 1H), 6.82 (d, J=8.6 Hz, 2H), 4.65 (t, J=8.8 Hz, 2H), 4.17 (d, J=9.2 Hz, 1H), 4.00 (ABq, Δv$_{AB}$=18.1 Hz, J$_{AB}$=15.1 Hz, 2H), 3.93-3.89 (m, 3H), 3.72-3.68 (m, 1H), 3.52-3.40 (m, 6H), 1.84-1.75 (m, 2H), 1.06 (t, J=7.4 Hz, 3H); [M+Na]+ 487.

Example 195

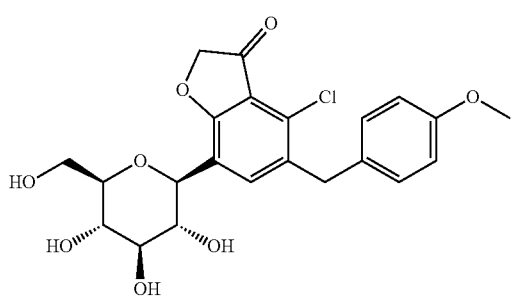 [SMILES: COc1ccc(Cc2cc([C@@H]3O[C@H](CO)[C@@H](O)[C@H](O)[C@H]3O)c3c(c2Cl)C(=O)CO3)cc1]

4-Chloro-5-(4-methoxybenzyl)-7-((2S,3R,4R,5S, 6R)-3,4,5-trihydroxy-6-(hydroxymethyl)tetrahydro-2H-pyran-2-yl)benzofuran-3(2H)-one (E195)

$^1$H NMR (400 MHz, MeOD) δ 7.72 (s, 1H), 7.15 (d, J=8.8 Hz, 2H), 6.85 (d, J=8.8 Hz, 2H), 4.76 (s, 2H), 4.52 (d, J=9.6 Hz, 1H), 4.09 (ABq, $\Delta v_{AB}$=20.1 Hz, $J_{AB}$=15.2 Hz, 2H), 3.89 (d, J=11.6 Hz, 1H), 3.78 (s, 3H), 3.72-3.69 (m, 1H), 3.61-3.57 (m, 1H), 3.53-3.43 (m, 3H); [M+H]+ 451.

Example 196

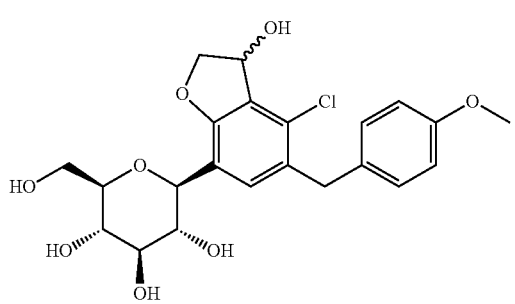 [SMILES: COc1ccc(Cc2cc([C@@H]3O[C@H](CO)[C@@H](O)[C@H](O)[C@H]3O)c3c(c2Cl)C(O)CO3)cc1]

(2S,3R,4R,5S,6R)-2-(4-Chloro-3-hydroxy-5-(4-methoxybenzyl)-2,3-dihydrobenzofuran-7-yl)-6-(hydroxymethyl)tetrahydro-2H-pyran-3,4,5-triol (E196)

$^1$H NMR (400 MHz, MeOD) δ 7.30 (s, 1H), 7.13 (d, J=8.4 Hz, 2H), 6.82 (d, J=8.8 Hz, 2H), 5.41-5.37 (m, 1H), 4.59-4.52 (m, 1H), 4.49-4.43 (m, 1H), 4.39-4.36 (m, 1H), 4.06-4.01 (m, 2H), 3.87 (d, J=10.8 Hz, 1H), 3.77 (s, 3H), 3.70-3.66 (m, 1H), 3.61 (td, J=9.1, 2.7 Hz, 1H), 3.49-3.39 (m, 3H); [M-H$_2$O]+ 434.

Example 197

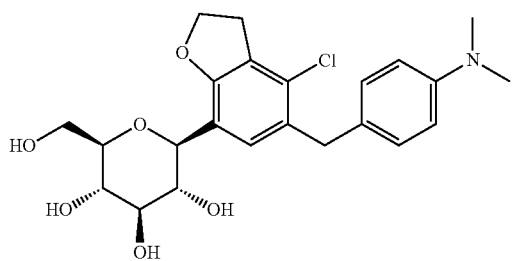

(2S,3R,4R,5S,6R)-2-(4-Chloro-5-(4-(dimethylamino)benzyl)-2,3-dihydrobenzofuran-7-yl)-6-(hydroxymethyl)tetrahydro-2H-pyran-3,4,5-triol (E197)

$^1$H NMR (400 MHz, MeOD) δ 7.12 (s, 1H), 7.05 (d, J=8.8 Hz, 2H), 6.73 (d, J=8.8 Hz, 2H), 4.66-4.57 (m, 2H), 4.31 (d, J=9.6 Hz, 1H), 3.93-3.86 (m, 3H), 3.69-3.64 (m, 1H), 3.61 (d, J=9.6 Hz, 1H), 3.48-3.37 (m, 3H), 3.25 (t, J=8.8 Hz, 2H), 2.88 (s, 6H); [M+H]$^+$ 450.

Example 198

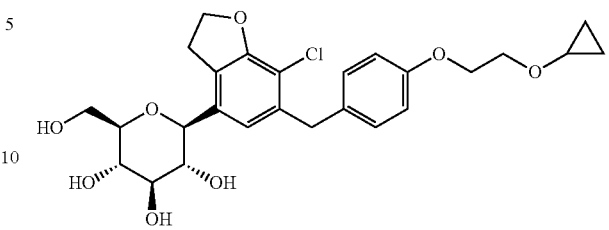

(2S,3R,4R,5S,6R)-2-(7-Chloro-6-(4-(2-cyclopropoxyethoxy)benzyl)-2,3-dihydrobenzofuran-4-yl)-6-(hydroxymethyl)tetrahydro-2H-pyran-3,4,5-triol (E198)

$^1$H NMR (400 MHz, MeOD) δ 7.10 (d, J=8.6 Hz, 2H), 6.85 (s, 1H), 6.82 (d, J=8.6 Hz, 2H), 4.62 (t, J=8.6 Hz, 2H), 4.14 (d, J=8.8 Hz, 1H), 4.073-4.05 (m, 2H), 3.98 (ABq, $\Delta v_{AB}$=18.0 Hz, $J_{AB}$=15.0 Hz, 2H), 3.91 (d, J=13.6 Hz, 1H), 3.84-3.82 (m, 2H), 3.70-3.65 (m, 1H), 3.50-3.36 (m, 7H), 0.59-0.54 (m, 2H), 0.53-0.47 (m, 2H); [M+Na]$^+$ 529.

Example 199

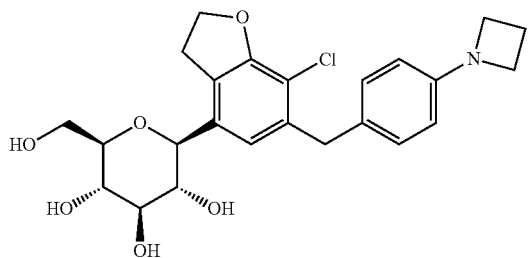

(2S,3R,4R,5S,6R)-2-(6-(4-(Azetidin-1-yl)benzyl)-7-chloro-2,3-dihydrobenzofuran-4-yl)-6-(hydroxymethyl)tetrahydro-2H-pyran-3,4,5-triol (E199)

$^1$H NMR (400 MHz, MeOD) δ 6.97 (d, J=8.6 Hz, 2H), 6.82 (s, 1H), 6.58 (d, J=8.6 Hz, 2H), 4.62 (t, J=8.8 Hz, 2H), 4.13 (d, J=9.2 Hz, 1H), 3.96-3.86 (m, 3H), 3.69-3.66 (m, 3H), 3.49-3.39 (m, 6H), 3.16 (t, J=7.0 Hz, 2H) 1.85-1.78 (m, 2H); [M+Na]$^+$ 480.

Example 200

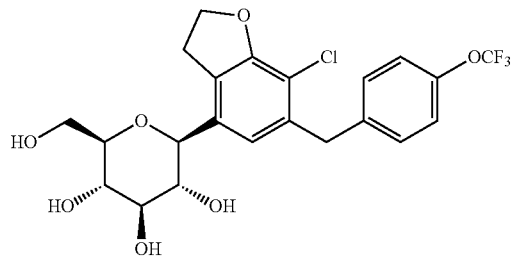

(2S,3R,4R,5S,6R)-2-(7-Chloro-6-(4-(trifluoromethoxy)benzyl)-2,3-dihydrobenzofuran-4-yl)-6-(hydroxymethyl)tetrahydro-2H-pyran-3,4,5-triol (E200)

¹H NMR (400 MHz, MeOD) δ 7.27 (d, J=8.2 Hz, 2H), 7.14 (d, J=8.2 Hz, 2H), 6.90 (s, 1H), 4.62 (t, J=8.8 Hz, 2H), 4.16 (d, J=8.8 Hz, 1H), 4.07 (ABq, Δν$_{AB}$=13.6 Hz, J$_{AB}$=15.2 Hz, 2H), 3.88 (dd, J=11.8, 1.4 Hz, 1H), 3.70-3.65 (m, 1H), 3.50-3.33 (m, 6H); [M+Na]+ 513.

Example 201

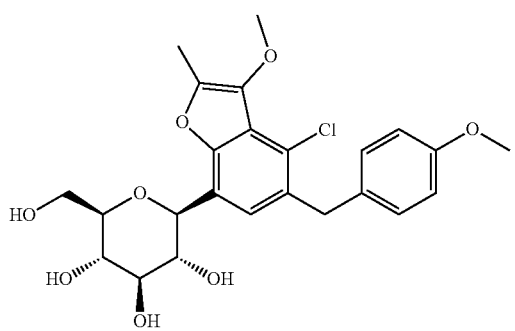 [SMILES: COc1ccc(Cc2cc([C@@H]3O[C@H](CO)[C@@H](O)[C@H](O)[C@H]3O)c3oc(C)c(OC)c3c2Cl)cc1]

(2S,3R,4R,5S,6R)-2-(4-Chloro-3-methoxy-5-(4-methoxybenzyl)-2-methylbenzofuran-7-yl)-6-(hydroxymethyl)tetrahydro-2H-pyran-3,4,5-triol (E201)

¹H NMR (400 MHz, MeOD) δ 7.24 (s, 1H), 7.12 (d, J=8.6 Hz, 2H), 6.80 (d, J=8.6 Hz, 2H), 4.60 (d, J=9.6 Hz, 1H), 4.10 (ABq, Δν$_{AB}$=15.6 Hz, J$_{AB}$=15.2 Hz, 2H), 3.87 (dd, J=11.8, 1.4 Hz, 1H), 3.84 (s, 3H), 3.74 (s, 3H), 3.71-3.65 (m, 2H), 3.50 (t, J=8.8 Hz, 1H), 3.44-3.42 (m, 2H), 2.40 (s, 3H); [M+H]+ 479.

Example 202

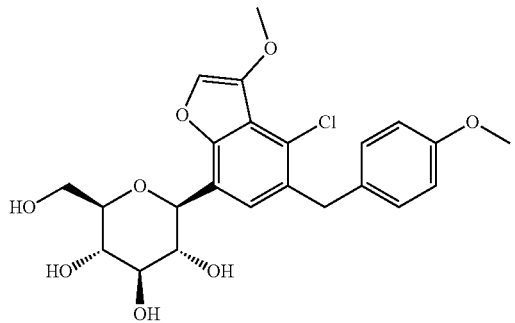 [SMILES: COc1ccc(Cc2cc([C@@H]3O[C@H](CO)[C@@H](O)[C@H](O)[C@H]3O)c3occ(OC)c3c2Cl)cc1]

(2S,3R,4R,5S,6R)-2-(4-Chloro-3-methoxy-5-(4-methoxybenzyl)benzofuran-7-yl)-6-(hydroxymethyl)tetrahydro-2H-pyran-3,4,5-triol (E202)

¹H NMR (400 MHz, MeOD) δ 7.51 (s, 1H), 7.29 (s, 1H), 7.10 (d, J=8.8 Hz, 2H), 6.80 (d, J=8.8 Hz, 2H), 4.59 (d, J=9.6 Hz, 1H), 4.10 (ABq, Δν$_{AB}$=17.5 Hz, J$_{AB}$=15.2 Hz, 2H), 3.88-3.85 (m, 5H), 3.74 (s, 3H), 3.69-3.64 (m, 2H), 3.52-3.45 (m, 2H), 3.43-3.39 (m, 2H); [M+Na]+ 487.

Example 203

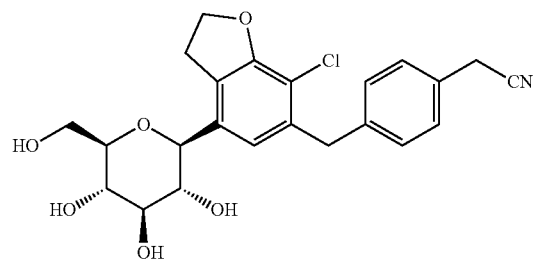 [SMILES: N#CCc1ccc(Cc2cc([C@@H]3O[C@H](CO)[C@@H](O)[C@H](O)[C@H]3O)c3c(c2Cl)OCC3)cc1]

2-(4-((7-Chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)phenyl)acetonitrile (E203)

¹H NMR (400 MHz, MeOD) δ 7.19 (q, J=7.6 Hz, 4H), 6.84 (s, 1H), 4.58 (t, J=8.8 Hz, 2H), 4.11 (d, J=8.8 Hz, 1H), 4.01 (ABq, Δν$_{AB}$=15.8 Hz, J$_{AB}$=15.0 Hz, 2H), 3.86-3.83 (m, 1H), 3.80 (s, 2H), 3.66-3.61 (m, 1H), 3.46-3.11 (m, 6H); [M+H]+ 446.

Example 204

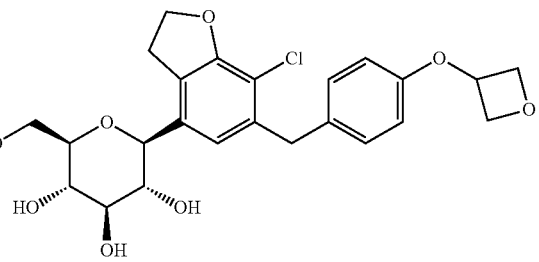

(2S,3R,4R,5S,6R)-2-(7-Chloro-6-(4-(oxetan-3-yloxy)benzyl)-2,3-dihydrobenzofuran-4-yl)-6-(hydroxymethyl)tetrahydro-2H-pyran-3,4,5-triol (E204)

¹H NMR (400 MHz, MeOD) δ 7.07 (d, J=8.6 Hz, 2H), 6.81 (s, 1H), 6.60 (d, J=8.6 Hz, 2H), 5.21-5.16 (m, 1H), 4.95 (t, J=6.8 Hz, 2H), 4.64-4.56 (m, 4H), 4.10 (d, J=8.8 Hz, 1H), 3.94 (ABq, Δν$_{AB}$=16.4 Hz, J$_{AB}$=15.0 Hz, 2H), 3.84 (d, J=11.6 Hz, 1H), 3.65-3.61 (m, 1H), 3.45-3.35 (m, 4H), 3.34-3.30 (m, 2H); [M+Na]+ 501.

Example 205

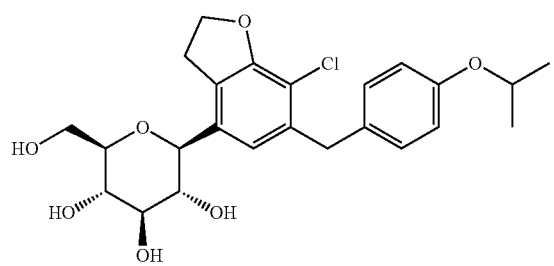 [SMILES: CC(C)Oc1ccc(Cc2cc([C@@H]3O[C@H](CO)[C@@H](O)[C@H](O)[C@H]3O)c3c(c2Cl)OCC3)cc1]

(2S,3R,4R,5S,6R)-2-(7-Chloro-6-(4-isopropoxyben-zyl)-2,3-dihydrobenzofuran-4-yl)-6-(hydroxymethyl)tetrahydro-2H-pyran-3,4,5-triol (E205)

$^1$H NMR (400 MHz, MeOD) δ 7.04 (d, J=8.8 Hz, 2H), 6.80 (s, 1H), 6.73 (d, J=8.8 Hz, 2H), 4.57 (t, J=8.8 Hz, 2H), 4.51-4.45 (m, 1H), 4.10 (d, J=8.8 Hz, 1H), 3.92 (ABq, $\Delta v_{AB}$=18.0 Hz, $J_{AB}$=15.0 Hz, 2H), 3.84 (d, J=11.2 Hz, 1H), 3.65-3.60 (m, 1H), 3.43-3.35 (m, 4H), 3.33-3.31 (m, 2H), 1.23 (d, J=6.0 Hz, 6H); [M+Na]+ 487.

Example 206

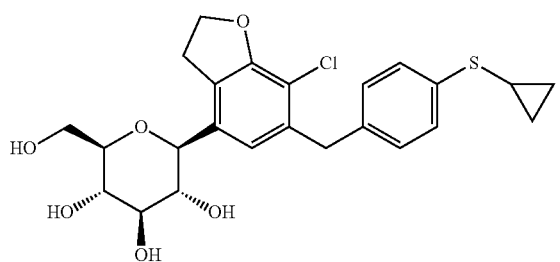 [SMILES: OC[C@H]1O[C@@H](c2cc(Cc3ccc(SC4CC4)cc3)c(Cl)c3c2CCO3)[C@H](O)[C@@H](O)[C@@H]1O]

(2S,3R,4R,5S,6R)-2-(7-Chloro-6-(4-(cyclopropylthio)benzyl)-2,3-dihydrobenzofuran-4-yl)-6-(hydroxymethyl)tetrahydro-2H-pyran-3,4,5-triol (E206)

$^1$H NMR (400 MHz, MeOD) δ 7.20 (d, J=8.2 Hz, 2H), 7.03 (d, J=8.2 Hz, 2H), 6.83 (s, 1H), 4.58 (t, J=8.6 Hz, 2H), 4.11 (d, J=9.2 Hz, 1H), 3.96 (ABq, $\Delta v_{AB}$=17.0 Hz, $J_{AB}$=15.2 Hz, 2H), 3.84 (d, J=11.6 Hz, 1H), 3.66-3.61 (m, 2H), 3.45-3.31 (m, 5H), 2.18-2.12 (m, 1H), 1.02-0.98 (m, 2H), 0.56-0.52 (m, 2H); [M+Na]$^+$ 501.

Example 207

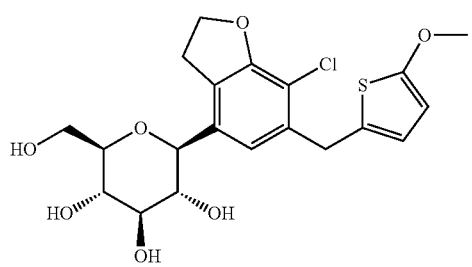 [SMILES: COc1ccc(Cc2cc([C@@H]3O[C@H](CO)[C@@H](O)[C@H](O)[C@H]3O)c3c(c2Cl)OCC3)s1]

(2S,3R,4R,5S,6R)-2-(7-Chloro-6-((5-methoxythiophen-2-yl)methyl)-2,3-dihydrobenzofuran-4-yl)-6-(hydroxymethyl)tetrahydro-2H-pyran-3,4,5-triol (E207)

$^1$H NMR (400 MHz, MeOD) δ 6.88 (s, 1H), 6.37 (d, J=4.0 Hz, 1H), 5.96 (d, J=4.0 Hz, 1H), 4.61 (t, J=8.6 Hz, 2H), 4.96 (d, J=8.8 Hz, 1H), 4.01 (ABq, $\Delta v_{AB}$=18.6 Hz, $J_{AB}$=15.2 Hz, 2H), 3.88-3.85 (m, 1H), 3.78 (s, 3H), 3.68-3.64 (m, 1H), 3.48-3.35 (m, 6H); [M+H]$^+$ 443.

Example 208

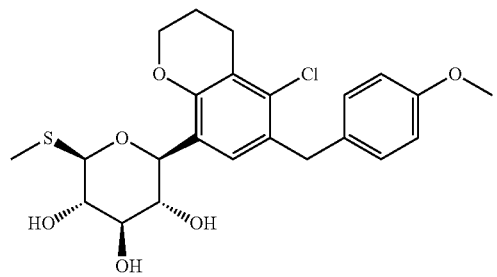

(2S,3R,4R,5S,6R)-2-(5-Chloro-6-(4-methoxybenzyl)chroman-8-yl)-6-(methylthio)tetrahydro-2H-pyran-3,4,5-triol (E208)

$^1$H NMR (400 MHz, CDCL$_3$) δ 7.09 (d, J=8.6 Hz, 2H), 7.07 (s, 1H), 6.81 (d, J=8.6 Hz, 2H), 4.72 (d, J=9.6 Hz, 1H), 4.23-4.18 (m, 1H), 4.13-4.08 (m, 1H), 3.99 (ABq, $\Delta v_{AB}$=10.5 Hz, $J_{AB}$=15.6 Hz, 2H), 3.78 (s, 3H), 3.71 (t, J=9.0 Hz, 1H), 3.592-3.513 (m, 2H), 3.49 (brs, 1H), 2.82-2.78 (m, 2H), 2.52 (brs, 1H), 2.31 (brs, 1H), 2.14 (s, 3H), 2.06-2.02 (m, 2H); [M+Na]$^+$ 489.

Example 209

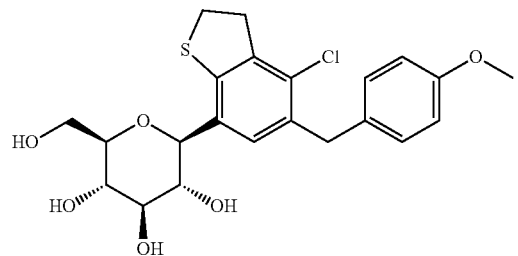

(2S,3R,4R,5S,6R)-2-(4-Chloro-5-(4-methoxybenzyl)-2,3-dihydrobenzo[b]thiophen-7-yl)-6-(hydroxymethyl)tetrahydro-2H-pyran-3,4,5-triol (E209)

$^1$H NMR (400 MHz, MeOD) δ 7.15 (s, 1H), 7.12 (d, J=8.4 Hz, 2H), 6.84 (d, J=8.4 Hz, 2H), 4.16 (d, J=9.2 Hz, 1H), 4.01 (ABq, $\Delta v_{AB}$=13.7 Hz, $J_{AB}$=17.2 Hz, 2H), 3.92-3.89 (m, 1H), 3.78 (s, 3H), 3.74-3.67 (m, 2H), 3.50-3.39 (m, 5H), 3.37-3.36 (m, 2H); [M+Na]$^+$ 475.

Example 210

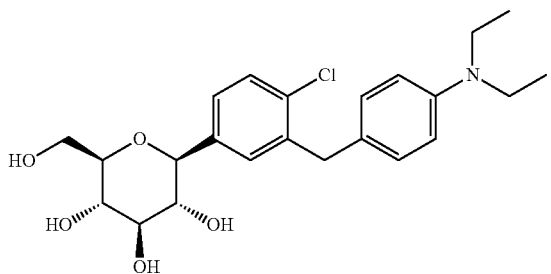 [SMILES: CCN(CC)c1ccc(Cc2cc([C@@H]3O[C@H](CO)[C@@H](O)[C@H](O)[C@H]3O)ccc2Cl)cc1]

(2S,3R,4R,5S,6R)-2-(4-Chloro-3-(4-(diethylamino)benzyl)phenyl)-6-(hydroxymethyl)tetrahydro-2H-pyran-3,4,5-triol (E210)

$^1$H NMR (400 MHz, CD$_3$OD$_3$) δ 7.49 (q, J=18.6, 8.6 Hz, 4H), 7.38 (d, J=8.0 Hz, 1H), 7.39-7.33 (m, 2H), 4.21 (s, 2H), 4.14 (d, J=9.6 Hz, 1H), 3.90-3.87 (m, 1H), 3.72-3.68 (m, 2H), 3.48-3.44 (m, 1H), 3.41-3.39 (m, 2H), 1.29 (s, 4H), 1.13 (t, J=7.8 Hz, 6H); [M+H$^+$] 436.

Example 211

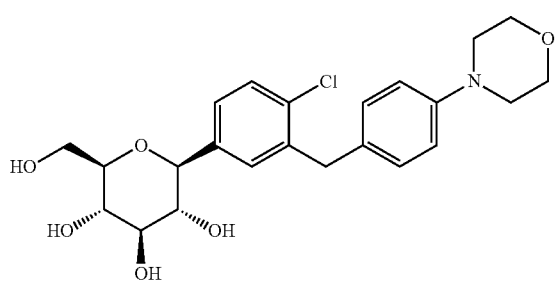 [SMILES: OC[C@H]1O[C@@H](c2ccc(Cl)c(Cc3ccc(N4CCOCC4)cc3)c2)[C@H](O)[C@@H](O)[C@@H]1O]

(2S,3R,4R,5S,6R)-2-(4-Chloro-3-(4-morpholinobenzyl)phenyl)-6-(hydroxymethyl)tetrahydro-2H-pyran-3,4,5-triol (E211)

$^1$H NMR (400 MHz, CD$_3$OD$_3$) δ 7.35-7.26 (m, 3H), 7.09 (d, J=8.4 Hz, 2H), 6.87 (d, J=8.8 Hz, 2H), 4.08 (d, J=9.6 Hz, 1H), 4.01 (ABq, J=19.1 Hz, 2H), (dd, J=11.8, 1.8 Hz, 1H), 3.80 (t, J=4.8 Hz, 4H), 3.69 (dd, J=11.8, 5.4 Hz, 1H), 3.48-3.35 (m, 3H), 3.29-3.27 (m, 1H), 3.07 (t, J=4.8 Hz, 4H); [M+Na$^+$] 472.

Example 212

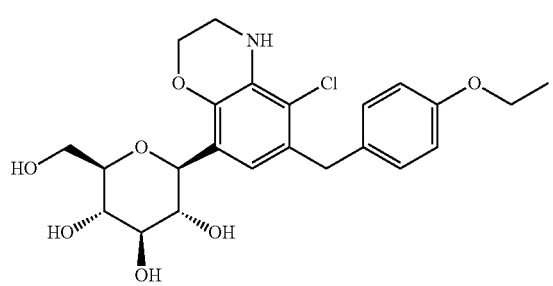 [SMILES: CCOc1ccc(Cc2cc([C@@H]3O[C@H](CO)[C@@H](O)[C@H](O)[C@H]3O)c3c(c2Cl)NCCO3)cc1]

(2S,3R,4R,5S,6R)-2-(5-Chloro-6-(4-ethoxybenzyl)-3,4-dihydro-2H-benzo[b][1,4]oxazin-8-yl)-6-(hydroxymethyl)tetrahydro-2H-pyran-3,4,5-triol (E212)

$^1$H NMR (400 MHz, CD$_3$OD$_3$) δ 7.08 (d, J=8.8 Hz, 2H), 6.78 (d, J=8.8 Hz, 2H), 6.68 (s, 1H), 4.60 (d, J=9.2 Hz, 1H), 4.22-4.15 (m, 2H), 3.98 (ABq, J=12.0 Hz, 2H), 3.92 (d, J=3.2 Hz, 2H), 3.86 (d, J=12.0 Hz, 1H), 3.68-3.64 (m, 1H), 3.52-3.48 (m, 2H), 3.44 (t, J=4.4 Hz, 2H), 3.38-3.37 (m, 2H), 1.36 (t, J=7.0 Hz, 3H), 1.30 (s, 1H); [M−H$^+$] 465.

Example 213

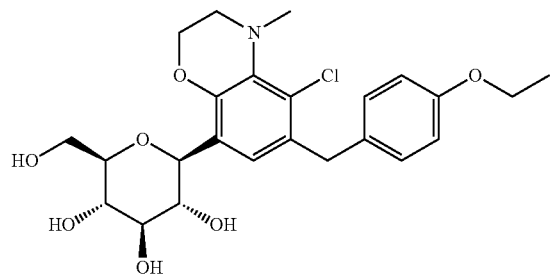 [SMILES: CCOc1ccc(Cc2cc([C@@H]3O[C@H](CO)[C@@H](O)[C@H](O)[C@H]3O)c3c(c2Cl)N(C)CCO3)cc1]

(2S,3R,4R,5S,6R)-2-(5-Chloro-6-(4-ethoxybenzyl)-4-methyl-3,4-dihydro-2H-benzo[b][1,4]oxazin-8-yl)-6-(hydroxymethyl)tetrahydro-2H-pyran-3,4,5-triol (E213)

$^1$H NMR (400 MHz, CD$_3$OD$_3$) δ 7.08-7.06 (m, 3H), 6.77 (d, J=8.4 Hz, 2H), 4.64-4.62 (m, 1H), 4.21-4.18 (m, 2H), 4.00-3.95 (m, 4H), 3.85 (d, J=12.0 Hz, 1H), 3.67-3.63 (m, 1H), 3.49-3.47 (m, 2H), 3.38-3.35 (m, 2H), 3.09 (q, J=2.8 Hz, 2H), 2.80 (s, 3H), 1.35 (t, J=7.0 Hz, 3H); [M+H$^+$] 480.

Example 214

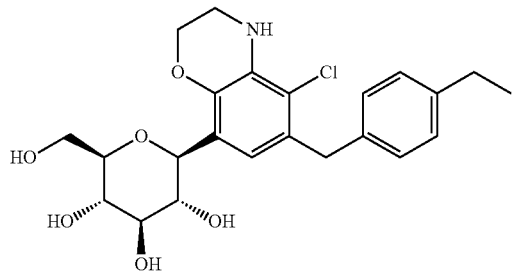 [SMILES: CCc1ccc(Cc2cc([C@@H]3O[C@H](CO)[C@@H](O)[C@H](O)[C@H]3O)c3c(c2Cl)NCCO3)cc1]

(2S,3R,4R,5S,6R)-2-(5-Chloro-6-(4-ethylbenzyl)-3,4-dihydro-2H-benzo[b][1,4]oxazin-8-yl)-6-(hydroxymethyl)tetrahydro-2H-pyran-3,4,5-triol (E214)

$^1$H NMR (400 MHz, CD$_3$OD$_3$) δ 7.06 (d, J=2.4 Hz, 4H), 6.68 (s, 1H), 4.58 (d, J=9.2 Hz, 1H), 4.19-4.17 (m, 2H), 3.94 (d, J=2.0 Hz, 2H), 3.86-3.83 (m, 1H), 3.68-3.63 (m, 1H), 3.49-3.43 (m, 5H), 3.37-3.35 (m, 2H), 2.58 (d, J=7.6 Hz, 2H), 1.19 (t, J=7.6 Hz, 3H); [M+H$^+$] 450.

Example 215

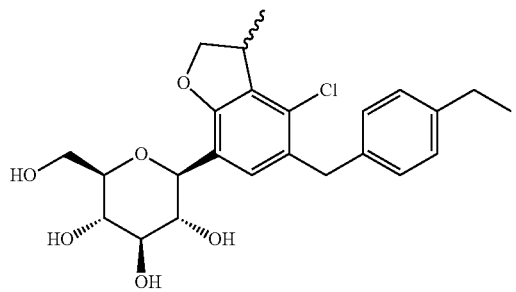 [SMILES: CCc1ccc(Cc2cc([C@@H]3O[C@H](CO)[C@@H](O)[C@H](O)[C@H]3O)c3c(c2Cl)C(C)CO3)cc1]

(2S,3R,4R,5S,6R)-2-(4-Chloro-5-(4-ethylbenzyl)-3-methyl-2,3-dihydrobenzofuran-7-yl)-6-(hydroxymethyl)tetrahydro-2H-pyran-3,4,5-triol (E215)

$^1$H NMR (400 MHz, CD$_3$OD$_3$) δ 7.18 (d, J=4.0 Hz, 1H), 7.09 (s, 4H), 4.65-4.57 (m, 1H), 4.36 (t, J=10.8 Hz, 1H), 4.28-4.22 (m, 1H), 4.00 (ABq, J=10.4 Hz, 2H), 3.89-3.86 (m, 1H), 3.71-3.62 (m, 2H), 3.60-3.40 (m, 4H), 2.60 (q, J=7.6 Hz, 2H), 1.35 (d, J=6.8 Hz, 3H), 1.21 (t, J=7.6 Hz, 3H); [M+Na$^+$] 471.

Example 216

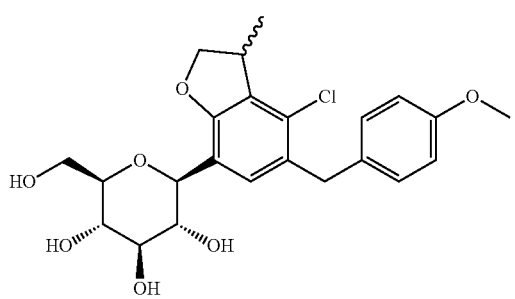 [SMILES: COc1ccc(Cc2cc([C@@H]3O[C@H](CO)[C@@H](O)[C@H](O)[C@H]3O)c3c(c2Cl)C(C)CO3)cc1]

(2S,3R,4R,5S,6R)-2-(4-Chloro-5-(4-methoxybenzyl)-3-methyl-2,3-dihydrobenzofuran-7-yl)-6-(hydroxymethyl)tetrahydro-2H-pyran-3,4,5-triol (E216)

$^1$H NMR (400 MHz, CD$_3$OD$_3$) δ 7.14 (d, J=4.0 Hz, 1H), 7.08 (d, J=8.4 Hz, 2H), 6.79 (d, J=8.8 Hz, 2H), 4.63-4.55 (m, 1H), 4.36-4.30 (m, 1H), 4.25-4.19 (m, 1H), 3.94 (ABq, J=10.5 Hz, 2H), 3.85 (d, J=12.4 Hz, 1H), 3.72 (s, 3H), 3.69-3.60 (m, 2H), 3.56-3.35 (m, 4H), 1.32 (d, J=6.8 Hz, 3H); [M+Na$^+$] 473.

Example 217

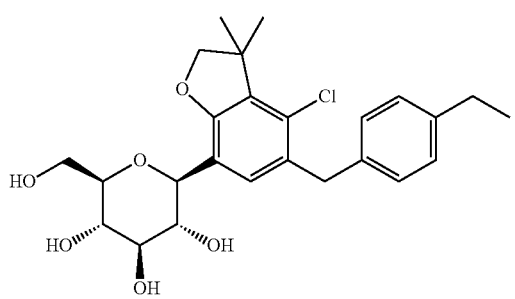

(2S,3R,4R,5S,6R)-2-(4-Chloro-5-(4-ethylbenzyl)-3,3-dimethyl-2,3-dihydrobenzofuran-7-yl)-6-(hydroxymethyl)tetrahydro-2H-pyran-3,4,5-triol (E217)

$^1$H NMR (400 MHz, CD$_3$OD$_3$) δ 7.18 (s, 1H), 7.10 (s, 4H), 4.37□d, J=9.6 Hz, 1H), 4.26□ABq, J=10.2 Hz, 2H), 4.01□ABq, J=11.1 Hz, 2H), 3.88□d, J=11.6 Hz, 1H), 3.71-3.60 (m, 2H), 3.40-3.50 (m, 3H), 2.61 (dd, J=15.2, 7.6 Hz, 2H), 1.48 (s, 6H), 1.22 (t, J=7.6 Hz, 3H); [M+Na$^+$] 485.

Example 218

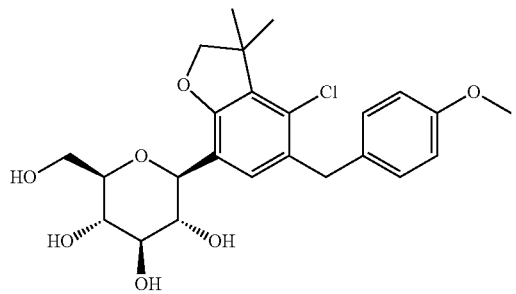 [SMILES: COc1ccc(Cc2cc([C@@H]3O[C@H](CO)[C@@H](O)[C@H](O)[C@H]3O)c3c(c2Cl)C(C)(C)CO3)cc1]

(2S,3R,4R,5S,6R)-2-(4-Chloro-5-(4-methoxybenzyl)-3,3-dimethyl-2,3-dihydrobenzofuran-7-yl)-6-(hydroxymethyl)tetrahydro-2H-pyran-3,4,5-triol (E218)

$^1$H NMR (400 MHz, CD$_3$OD$_3$) δ 7.14 (s, 1H), 7.09 (d, J=8.8 Hz, 2H), 6.80 (d, J=8.4 Hz, 2H), 4.38 (d, J=9.6 Hz, 1H), 4.24 (ABq, J=8.9 Hz, 2H), 3.87-3.84 (m, 1H), 3.74 (s, 3H), 3.68-3.63 (m, 1H), 3.59 (t, J=9.4 Hz, 1H), 3.44-3.36 (m, 3H), 1.46 (s, 6H); [M+Na$^+$] 487.

Example 219

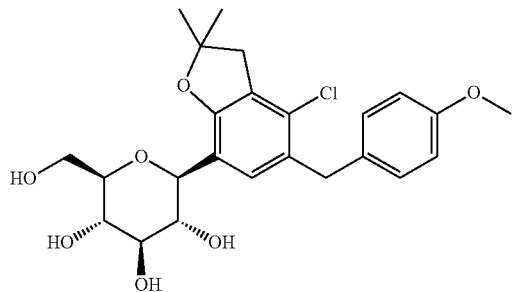 [SMILES: COc1ccc(Cc2cc([C@@H]3O[C@H](CO)[C@@H](O)[C@H](O)[C@H]3O)c3c(c2Cl)CC(C)(C)O3)cc1]

(2S,3R,4R,5S,6R)-2-(4-Chloro-5-(4-methoxybenzyl)-2,2-dimethyl-2,3-dihydrobenzofuran-7-yl)-6-(hydroxymethyl)tetrahydro-2H-pyran-3,4,5-triol (E219)

$^1$H NMR (400 MHz, CD$_3$OD$_3$) δ 7.15 (s, 1H), 7.08 (d, J=7.2 Hz, 2H), 6.78 (d, J=7.2 Hz, 2H), 4.34 (d, J=9.2 Hz, 1H), 3.93-3.84 (m, 3H), 3.71-3.66 (m, 4H), 3.57-3.46 (m, 2H), 3.42-3.35 (m, 2H), 3.02 (s, 2H), 1.46 (d, J=4.0 Hz, 6H); [M+Na$^+$] 487.

Example 220

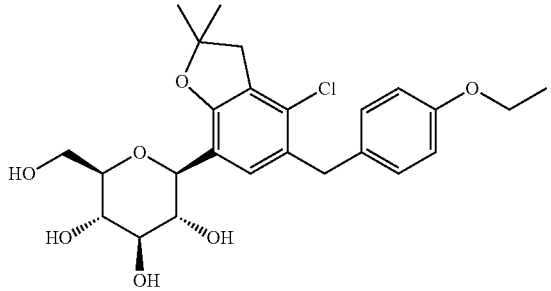 [SMILES: CCOc1ccc(Cc2cc([C@@H]3O[C@H](CO)[C@@H](O)[C@H](O)[C@H]3O)c3c(c2Cl)CC(C)(C)O3)cc1]

(2S,3R,4R,5S,6R)-2-(4-Chloro-5-(4-ethoxybenzyl)-2,2-dimethyl-2,3-dihydrobenzofuran-7-yl)-6-(hydroxymethyl)tetrahydro-2H-pyran-3,4,5-triol (E220)

$^1$H NMR (400 MHz, CD$_3$OD$_3$) δ 7.15 (s, 1H), 7.07 (d, J=8.4 Hz, 2H), 6.77 (d, J=8.4 Hz, 2H), 4.34 (d, J=9.2 Hz, 1H), 3.97-3.92 (m, 4H), 3.85 (d, J=11.6 Hz, 1H), 3.69-3.65 (m, 1H), 3.57-3.46 (m, 2H), 3.42-3.35 (m, 2H), 3.02 (s, 2H), 1.46 (d, J=5.2 Hz, 6H), 1.34 (t, J=6.8 Hz, 3H); [M+Na$^+$] 501.

Example 221

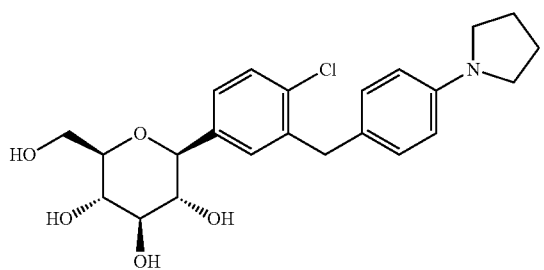 [SMILES: OC[C@H]1O[C@@H](c2ccc(Cl)c(Cc3ccc(N4CCCC4)cc3)c2)[C@H](O)[C@@H](O)[C@@H]1O]

(2S,3R,4R,5S,6R)-2-(4-Chloro-3-(4-(pyrrolidin-1-yl)benzyl)-6-(hydroxymethyl)-tetrahydro-2H-pyran-3,4,5-triol (E221)

$^1$H NMR (400 MHz, MeOD) δ 7.35-7.31 (m, 2H), 7.26 (dd, J=8.4, 2.0 Hz, 1H), 7.09 (d, J=8.4 Hz, 2H), 6.70 (br s, 2H), 4.08 (d, J=9.6 Hz, 1H), 4.01 (d, J=10.0 Hz, 1H), 3.87 (dd, J=12.0, 1.6 Hz, 1H), 3.71-3.66 (m, 1H), 3.49-3.27 (m, 9H), 2.07-2.04 (m, 4H); [M+Na]$^+$ 456.

Example 222

Step 1

(3S,4R,5R,6R)-2-(2-(Allyloxy)-3-bromo-4-chloro-5-(4-ethoxybenzyl)phenyl)-3,4,5-tris(benzyloxy)-6-(benzyloxymethyl)-tetrahydro-2H-pyran

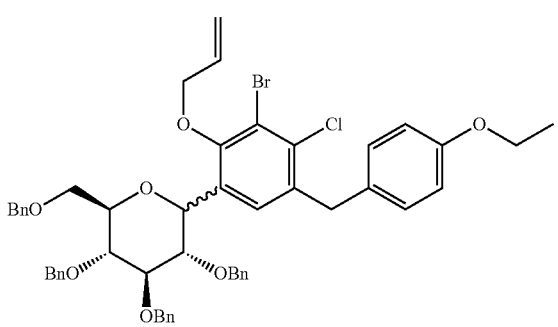 [SMILES: C=CCOc1c(C2O[C@H](COCc3ccccc3)[C@@H](OCc3ccccc3)[C@H](OCc3ccccc3)[C@H]2OCc2ccccc2)cc(Cc2ccc(OCC)cc2)c(Cl)c1Br]

To a solution of 2-bromo-3-chloro-4-(4-ethoxybenzyl)-6-((3S,4R,5R,6R)-3,4,5-tris(benzyloxy)-6-(benzyloxymethyl)-tetrahydro-2H-pyran-2-yl)phenol (500 mg, 0.579 mmole) in acetone (15 mL) were added K$_2$CO$_3$ (120 mg, 0.869 mmole) and allyl bromide (75 µL, 0.869 mmole) continuously. The resulting solution was stirred at 60° C. overnight, diluted with a saturated NaHCO$_3$ and extracted with ethyl acetate. The organic layer was washed with water then brine, dried over MgSO$_4$, filtered, and concentrated in vacuo. The crude residue was purified on Biotage® purification apparatus to yield the title compound (325 mg, 62%) as a colorless gum.
[M+Na]$^+$ 925.

Step 2

4-Chloro-5-(4-ethoxybenzyl)-3-methyl-7-((3S,4R,5R,6R)-3,4,5-tris(benzyloxy)-6-(benzyloxymethyl)-tetrahydro-2H-pyran-2-yl)-2,3-dihydrobenzofuran

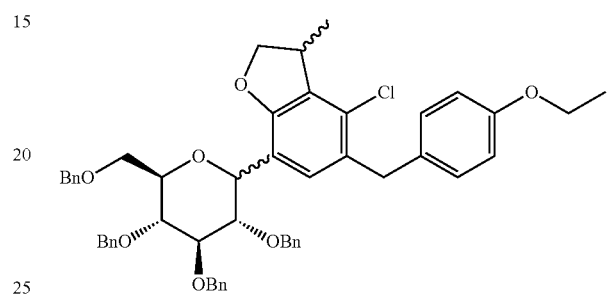

To a solution of (3S,4R,5R,6R)-2-(2-(allyloxy)-3-bromo-4-chloro-5-(4-ethoxybenzyl)phenyl)-3,4,5-tris(benzyloxy)-6-(benzyloxymethyl)-tetrahydro-2H-pyran (325 mg, 0.359 mmole) in toluene (15 mL) were added tributyltin hydride (0.29 mL, 1.08 mmole) and AIBN (5.9 mg, 0.0359 mmole) in one portion. The resulting solution was refluxed overnight. The reaction mixture was filtered on the KF pad followed by concentrated in vacuo. The crude residue was purified on Biotage® purification apparatus to yield the title compound (102 mg, 34%) as a colorless gum.
[M+Na]$^+$ 847.

Step 3

2S,3R,4R,5S,6R)-2-(4-Chloro-5-(4-ethoxybenzyl)-3-methyl-2,3-dihydrobenzofuran-7-yl)-6-(hydroxymethyl)-tetrahydro-2H-pyran-3,4,5-triol

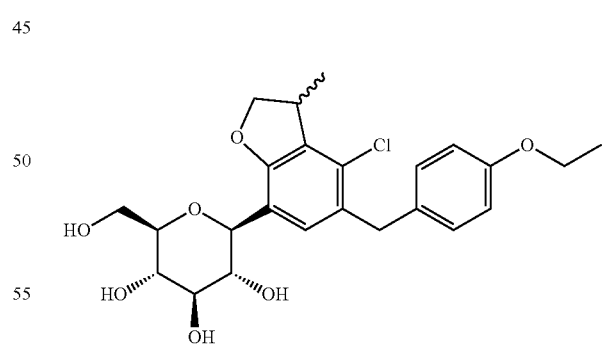

To a solution of 4-chloro-5-(4-ethoxybenzyl)-3-methyl-7-((3S,4R,5R,6R)-3,4,5-tris(benzyloxy)-6-(benzyloxymethyl)-tetrahydro-2H-pyran-2-yl)-2,3-dihydrobenzofuran (102 mg, 0.124 mmol) in THF/MeOH (4 mL/2 mL) was added 10% Pd/C (50 mg) at rt. The reaction mixture was stirred at r.t. for 15 hours under hydrogen and filtered off. The filtrate was concentrated in vacuo and the residue was purified using reverse phase preparative HPLC to provide the title compound (24 mg, 42%) as a white solid.

(2S,3R,4R,5S,6R)-2-(4-Chloro-5-(4-ethoxybenzyl)-3-methyl-2,3-dihydrobenzofuran-7-yl)-6-(hydroxymethyl)-tetrahydro-2H-pyran-3,4,5-triol (E222)

$^1$H NMR (400 MHz, MeOD) δ 7.12 (d, J=4.0 Hz, 1H), 7.07 (d, J=8.4 Hz, 2H), 6.78 (dd, J=6.8, 2.0 Hz, 2H), 4.62 (dd, J=18.4, 8.8 Hz, 1H), 4.31 (ABq, Δν$_{AB}$=6.4 Hz, J$_{AB}$=9.6 Hz, 1H), 4.28-4.22 (m, 1H), 3.98 (q, J=7.2 Hz, 2H), 3.95 (d, J=4.0 Hz, 1H), 3.85 (dd, J=12.0, 1.6 Hz, 1H), 3.67-3.55 (m, 3H), 3.46-3.35 (m, 3H), 1.37-1.29 (m, 6H); [M+Na]$^+$ 487.

Example 223 was synthesized as the same method of preparation of Example 222 using 3-bromo-2-methylpropene instead of allyl bromide.

Example 223

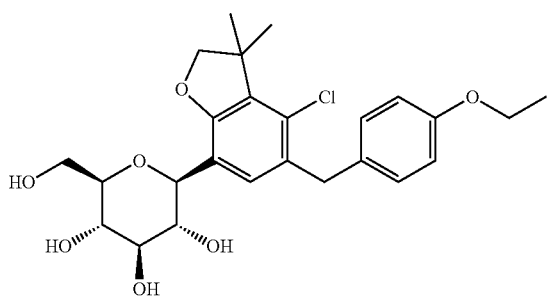

(2S,3R,4R,5S,6R)-2-(4-Chloro-5-(4-ethoxybenzyl)-3,3-dimethyl-2,3-dihydrobenzofuran-7-yl)-6-(hydroxymethyl)-tetrahydro-2H-pyran-3,4,5-triol (E223)

$^1$H NMR (400 MHz, MeOD) δ 7.13 (s, 1H), 7.07 (dd, J=6.8, 2.0 Hz, 2H), 6.79 (dd, J=6.8, 2.0 Hz, 2H), 4.33 (d, J=9.6 Hz, 1H), 4.24 (ABq, Δν$_{AB}$=8.8 Hz, J$_{AB}$=8.4 Hz, 2H), 4.01-3.95 (m, 4H), 3.85 (dd, J=12.0, 1.6 Hz, 1H), 3.67-3.56 (m, 2H), 3.49-3.36 (m, 3H), 1.46 (d, J=0.8 Hz, 6H), 1.36 (t, J=7.6 Hz, 3H); [M+Na]$^+$ 501.

Example 224 and 225 were synthesized as the same method of preparation of Example 222 and 223 using 2-bromo-6-chloro-5-(4-ethoxybenzyl)-3-((3S,4R,5R,6R)-3,4,5-tris(benzyloxy)-6-(benzyloxymethyl)-tetrahydro-2H-pyran-2-yl)phenol instead of 2-bromo-3-chloro-4-(4-ethoxybenzyl)-6-((3S,4R,5R,6R)-3,4,5-tris(benzyloxy)-6-(benzyloxymethyl)-tetrahydro-2H-pyran-2-yl)phenol.

Example 224

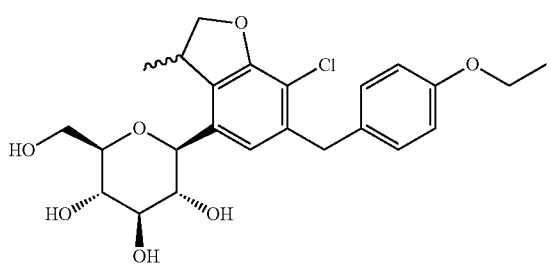 [SMILES: CCOc1ccc(Cc2cc([C@@H]3O[C@H](CO)[C@@H](O)[C@H](O)[C@H]3O)c3c(c2Cl)OCC3C)cc1]

(2S,3R,4R,5S,6R)-2-(7-Chloro-6-(4-ethoxybenzyl)-3-methyl-2,3-dihydrobenzofuran-4-yl)-6-(hydroxymethyl)-tetrahydro-2H-pyran-3,4,5-triol (E224)

$^1$H NMR (400 MHz, MeOD) δ 7.10-7.08 (m, 2H), 6.93-6.87 (m, 1H), 6.79-6.77 (m, 2H), 4.63-4.55 (m, 1H), 4.30-4.22 (m, 2H), 4.01-3.96 (m, 4H), 3.87 (dd, J=12.0, 1.6 Hz, 1H), 3.77-3.57 (m, 2H), 3.49-3.39 (m, 4H), 1.37-1.29 (m, 6H); [M+Na]$^+$ 487.

Example 225

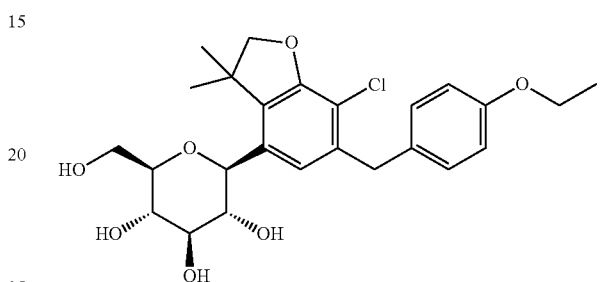

(2S,3R,4R,5S,6R)-2-(7-Chloro-6-(4-ethoxybenzyl)-3,3-dimethyl-2,3-dihydrobenzofuran-4-yl)-6-(hydroxymethyl)-tetrahydro-2H-pyran-3,4,5-triol (E225)

$^1$H NMR (400 MHz, MeOD) δ 7.10 (d, J=8.8 Hz, 2H), 6.93 (s, 1H), 6.79 (d, J=8.8 Hz, 2H), 4.45 (d, J=9.6 Hz, 1H), 4.23 (ABq, Δν$_{AB}$=9.6 Hz, J$_{AB}$=8.8 Hz, 2H), 4.01-3.96 (m, 4H), 3.84 (dd, J=12.0, 1.6 Hz, 1H), 3.66-3.61 (m, 2H), 3.49-3.45 (m, 1H), 3.39-3.37 (m, 2H), 1.46 (d, J=10.0 Hz, 6H), 1.35 (t, J=7.6 Hz, 3H); [M+Na]$^+$ 501.

Example 226

Step 1

Ethyl 2-(2-bromo-6-chloro-5-(4-ethoxybenzyl)-3-((3S,4R,5R,6R)-3,4,5-tris(benzyloxy)-6-(benzyloxymethyl)-tetrahydro-2H-pyran-2-yl)phenoxy)acetate

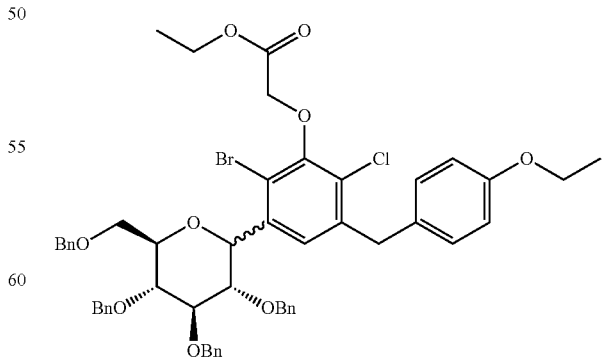

To a solution of 2-bromo-3-chloro-4-(4-ethoxybenzyl)-6-((3S,4R,5R,6R)-3,4,5-tris(benzyloxy)-6-(benzyloxymethyl)-tetrahydro-2H-pyran-2-yl)phenol (1.00 g, 1.16 mmole) in acetone (15 mL) were added K$_2$CO$_3$ (240 mg, 1.74 mmole) and allyl bromide (0.19 mL, 1.74 mmole) continuously. The resulting solution was stirred at 60° C. overnight, diluted with a saturated NaHCO$_3$ and extracted with ethyl acetate. The organic layer was washed with water then brine, dried over MgSO$_4$, filtered, and concentrated in vacuo. The crude residue was purified on Biotage® purification apparatus to yield the title compound (1.09 g, 99%) as a colorless gum.

[M+Na]$^+$ 971.

Step 2: 2-(2-Bromo-6-chloro-5-(4-ethoxybenzyl)-3-((3S,4R,5R,6R)-3,4,5-tris(benzyloxy)-6-(benzyloxymethyl)-tetrahydro-2H-pyran-2-yl)phenoxy) acetic acid

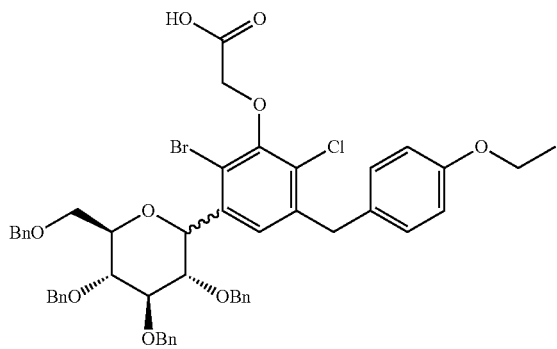 [SMILES: CCOc1ccc(Cc2cc(C3O[C@H](COCc4ccccc4)[C@@H](OCc4ccccc4)[C@H](OCc4ccccc4)[C@H]3OCc3ccccc3)c(Br)c(OCC(=O)O)c2Cl)cc1]

To a solution of ethyl 2-(2-bromo-6-chloro-5-(4-ethoxybenzyl)-3-((3S,4R,5R,6R)-3,4,5-tris(benzyloxy)-6-(benzyloxymethyl)-tetrahydro-2H-pyran-2-yl)phenoxy)acetate (1.09 g, 1.14 mmole) in a mixture of THF/MeOH/H$_2$O (12 mL/4 mL/4 mL) was added LiOH.H$_2$O (144 mg, 3.42 mmole). The resulting solution was stirred at rt overnight. The reaction mixture was concentrated in vacuo and diluted with water. The resulting solution was acidified with 1N—HCl solution followed by extraction with ethyl acetate. The organic layer was dried over MgSO$_4$, filtered, and concentrated in vacuo to yield the title compound (1.03 g, 98%) as a brown gum.

[M+Na]$^+$ 943.

Step 3: 2-(2-Bromo-6-chloro-5-(4-ethoxybenzyl)-3-((3S,4R,5R,6R)-3,4,5-tris(benzyloxy)-6-(benzyloxymethyl)-tetrahydro-2H-pyran-2-yl)phenoxy)-N-methoxy-N-methylacetamide

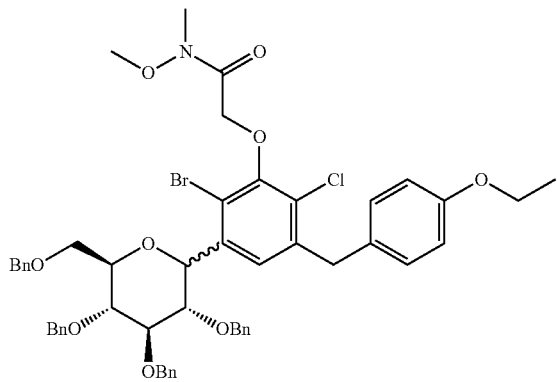 [SMILES: CCOc1ccc(Cc2cc(C3O[C@H](COCc4ccccc4)[C@@H](OCc4ccccc4)[C@H](OCc4ccccc4)[C@H]3OCc3ccccc3)c(Br)c(OCC(=O)N(C)OC)c2Cl)cc1]

To a solution of 2-(2-bromo-6-chloro-5-(4-ethoxybenzyl)-3-((3S,4R,5R,6R)-3,4,5-tris(benzyloxy)-6-(benzyloxymethyl)-tetrahydro-2H-pyran-2-yl)phenoxy)acetic acid (1.03 g, 1.12 mmole) in DMF (20 mL) were added dimethylhydroxylamine, HCl (131 mg, 1.34 mmole), EDC (257 mg, 1.34 mmole), HOBt (181 mg, 1.34 mmole) and NMM (0.44 mL, 4.03 mmole) continuously. The resulting solution was stirred at rt overnight, diluted with a saturated NaHCO$_3$ and extracted with ethyl acetate. The organic layer was washed with water then brine, dried over MgSO$_4$, filtered, and concentrated in vacuo. The crude residue was purified on Biotage® purification apparatus to yield the title compound (1.02 g, 94%) as a colorless gum.

[M+Na]$^+$ 986.

Step 4: 7-Chloro-6-(4-ethoxybenzyl)-4-((3S,4R,5R,6R)-3,4,5-tris(benzyloxy)-6-(benzyloxymethyl)-tetrahydro-2H-pyran-2-yl)benzofuran-3(2H)-one

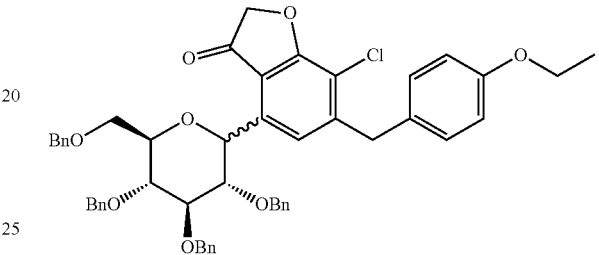

To a solution of 2-(2-bromo-6-chloro-5-(4-ethoxybenzyl)-3-((3S,4R,5R,6R)-3,4,5-tris(benzyloxy)-6-(benzyloxymethyl)-tetrahydro-2H-pyran-2-yl)phenoxy)-N-methoxy-N-methylacetamide (1.02 g, 1.06 mmole) in THF (15 mL) was added nBuLi (1.3 mL, 3.18 mmole, 2.5M in hexane) at −78° C. The resulting solution was warmed up to rt and stirred overnight, diluted with a saturated NH$_4$Cl and extracted with ethyl acetate. The organic layer was washed with water then brine, dried over MgSO$_4$, filtered, and concentrated in vacuo. The crude residue was purified on Biotage® purification apparatus to yield the title compound (429 mg, 49%) as a yellow gum.

[M+Na]$^+$ 847.

Step 5: 7-Chloro-6-(4-ethoxybenzyl)-4-(2S,3R,4R,5S,6R)-3,4,5-trihydroxy-6-(hydroxymethyl)-tetrahydro-2H-pyran-2-yl)benzofuran-3(2H)-one

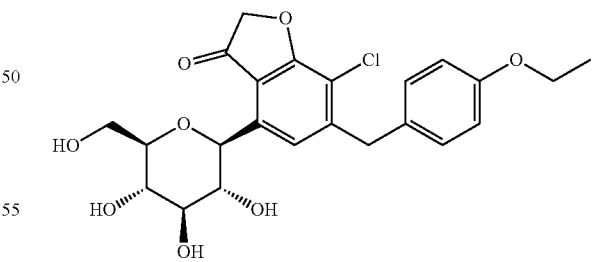

To a solution of 7-chloro-6-(4-ethoxybenzyl)-4-((3S,4R,5R,6R)-3,4,5-tris(benzyloxy)-6-(benzyloxymethyl)-tetrahydro-2H-pyran-2-yl)benzofuran-3 (2H)-one (144 mg, 0.174 mmol) in THF/MeOH (4 mL/2 mL) was added 10% Pd/C (14 mg) at rt. The reaction mixture was stirred at r.t. for 15 hours under hydrogen and filtered off. The filtrate was concentrated in vacuo and the residue was purified using reverse phase preparative HPLC to provide the title compound (32 mg, 39%) as a yellow solid.

7-Chloro-6-(4-ethoxybenzyl)-4-(2S,3R,4R,5S,6R)-3,4,5-trihydroxy-6-(hydroxymethyl)-tetrahydro-2H-pyran-2-yl)benzofuran-3(2H)-one (E226)

¹H NMR (400 MHz, MeOD) δ 7.25 (s, 1H) 7.13 (d, J=8.8 Hz, 2H), 6.81 (d, J=8.8 Hz, 2H), 5.06 (d, J=9.2 Hz, 1H), 4.85-4.74 (m, 2H), 4.12 (ABq, $\Delta v_{AB}$=16.8 Hz, $J_{AB}$=14.8 Hz, 2H), 3.99 (q, J=7.2 Hz, 2H), 3.84 (dd, J=12.0, 2.0 Hz, 1H), 3.68 (dd, J=12.0, 2.8 Hz, 1H), 3.53-3.43 (m, 4H), 1.35 (t, J=7.6 Hz, 3H); [M+Na]⁺ 487.

Example 227

Step 1: 7-Chloro-6-(4-ethoxybenzyl)-4-((3S,4R,5R,6R)-3,4,5-tris(benzyloxy)-6-(benzyloxymethyl)-tetrahydro-2H-pyran-2-yl)-2,3-dihydrobenzofuran-3-ol

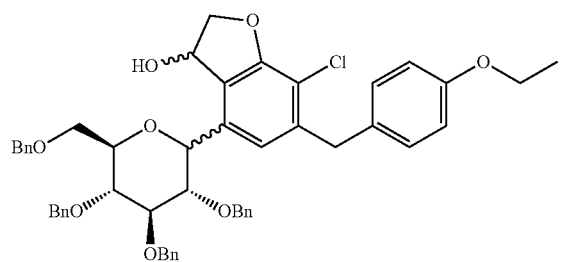 [SMILES: CCOc1ccc(Cc2cc(C3O[C@H](COCc4ccccc4)[C@@H](OCc4ccccc4)[C@H](OCc4ccccc4)[C@H]3OCc3ccccc3)c3c(c2Cl)OCC3=O)cc1]

To a solution of 7-chloro-6-(4-ethoxybenzyl)-4-((3S,4R,5R,6R)-3,4,5-tris(benzyloxy)-6-(benzyloxymethyl)-tetrahydro-2H-pyran-2-yl)benzofuran-3(2H)-one (285 mg, 0.345 mmole) in THF/MeOH (9 mL/3 mL) was added NaBH₄ (39.2 mg, 1.04 mmole) at 0° C. The resulting solution was stirred at 0° C. for 1 hr, diluted with 1N—HCl and extracted with ethyl acetate. The organic layer was washed with water then brine, dried over MgSO₄, filtered, and concentrated in vacuo. The crude residue was purified on Biotage® purification apparatus to yield the title compound (260 mg, 91%) as a yellow gum.
[M+Na]⁺ 849.

Step 2: 7-Chloro-6-(4-ethoxybenzyl)-3-methoxy-4-((3S,4R,5R,6R)-3,4,5-tris(benzyloxy)-6-(benzyloxymethyl)-tetrahydro-2H-pyran-2-yl)-2,3-dihydrobenzofuran

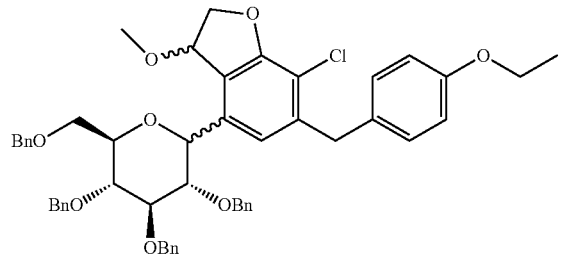 [SMILES: CCOc1ccc(Cc2cc(C3O[C@H](COCc4ccccc4)[C@@H](OCc4ccccc4)[C@H](OCc4ccccc4)[C@H]3OCc3ccccc3)c3c(c2Cl)OCC3OC)cc1]

To a mixture solution of 7-chloro-6-(4-ethoxybenzyl)-4-((3S,4R,5R,6R)-3,4,5-tris(benzyloxy)-6-(benzyloxymethyl)-tetrahydro-2H-pyran-2-yl)-2,3-dihydrobenzofuran-3-ol (260 mg, 0.314 mmole) and iodomethane (40 μL, 0.628 mmole) in DMF (10 mL) was added NaH (25.1 mg, 0.628 mmole) at 0° C. The resulting solution was stirred at rt overnight, diluted with sat. NaHCO₃ and extracted with ethyl acetate. The organic layer was washed with water then brine, dried over MgSO₄, filtered, and concentrated in vacuo. The crude residue was purified on Biotage® purification apparatus to yield the title compound (238 mg, 90%) as a yellow gum.
[M+Na]⁺ 863.

Step 3

(2S,3R,4R,5S,6R)-2-(7-Chloro-6-(4-ethoxybenzyl)-3-methoxy-2,3-dihydrobenzofuran-4-yl)-6-(hydroxymethyl)-tetrahydro-2H-pyran-3,4,5-triol

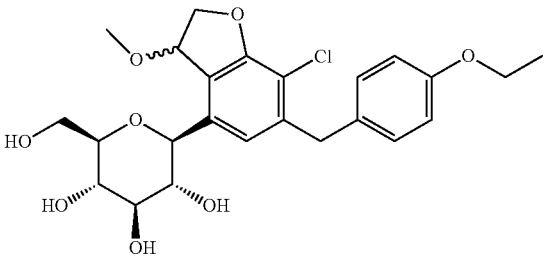

To a solution of 7-chloro-6-(4-ethoxybenzyl)-3-methoxy-4-((3S,4R,5R,6R)-3,4,5-tris(benzyloxy)-6-(benzyloxymethyl)-tetrahydro-2H-pyran-2-yl)-2,3-dihydrobenzofuran (124 mg, 0.147 mmol) in THF/MeOH (4 mL/2 mL) was added 10% Pd/C (12 mg) at rt. The reaction mixture was stirred at r.t. for 15 hours under hydrogen and filtered off. The filtrate was concentrated in vacuo and the residue was purified using reverse phase preparative HPLC to provide the title compound (38 mg, 54%) as a white solid.

(2S,3R,4R,5S,6R)-2-(7-Chloro-6-(4-ethoxybenzyl)-3-methoxy-2,3-dihydrobenzofuran-4-yl)-6-(hydroxymethyl)-tetrahydro-2H-pyran-3,4,5-triol (E227)

¹H NMR (400 MHz, MeOD) δ 7.09 (d, J=8.8 Hz, 2H), 6.93 (s, 1H), 6.76 (d, J=8.4 Hz, 2H), 5.46 (dd, J=6.0, 1.6 Hz, 1H), 4.66 (dd, J=11.2, 1.6 Hz, 1H), 4.45 (dd, J=10.8, 6.0 Hz, 1H), 4.26 (d, J=9.6 Hz, 1H), 4.06-3.87 (m, 5H), 3.72 (dd, J=12.0, 5.6 Hz, 1H), 3.55-3.50 (m, 1H), 3.46-3.37 (m, 3H), 3.36 (s, 3H), 1.35 (t, J=7.6 Hz, 3H); [M+Na]⁺ 503.

Example 228

Step 1

7-Cyclopropyl-6-(4-ethoxybenzyl)-4-((3S,4R,5R,6R)-3,4,5-tris(benzyloxy)-6-(benzyloxymethyl)-tetrahydro-2H-pyran-2-yl)-2,3-dihydrobenzofuran

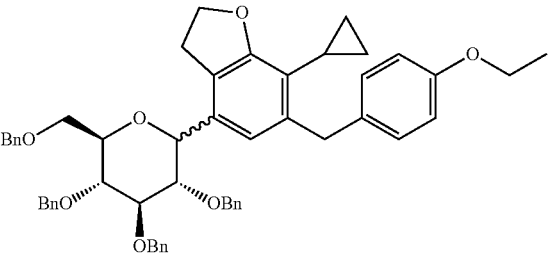 [SMILES: CCOc1ccc(Cc2cc(C3O[C@H](COCc4ccccc4)[C@@H](OCc4ccccc4)[C@H](OCc4ccccc4)[C@H]3OCc3ccccc3)c3c(c2C2CC2)OCC3)cc1]

To a solution of 7-chloro-6-(4-ethoxybenzyl)-4-((3S,4R,5R,6R)-3,4,5-tris(benzyloxy)-6-(benzyloxymethyl)-tetrahydro-2H-pyran-2-yl)-2,3-dihydrobenzofuran (235 mg, 0.290 mmole) in toluene (10 mL) were added cyclopropylboronic acid (49.8 mg, 0.580 mmole), Pd(OAc)₂ (19.5 mg, 0.0290 mmole), 2-dicyclohexylphosphino-2',6'-dimethoxybiphenyl (23.8 mg, 0.0580 mmole), and $K_3PO_4$ (246 mg, 1.16 mmole). The resulting solution was stirred at 110° C. overnight, diluted with water and extracted with ethyl acetate. The organic layer was washed with water then brine, dried over $MgSO_4$, filtered, and concentrated in vacuo. The crude residue was purified on Biotage® purification apparatus to yield the title compound (102 mg, 43%) as a yellow gum.

$[M+Na]^+$ 839.

Step 2

(2S,3R,4R,5S,6R)-2-(7-Cyclopropyl-6-(4-ethoxybenzyl)-2,3-dihydrobenzofuran-4-yl)-6-(hydroxymethyl)-tetrahydro-2H-pyran-3,4,5-triol

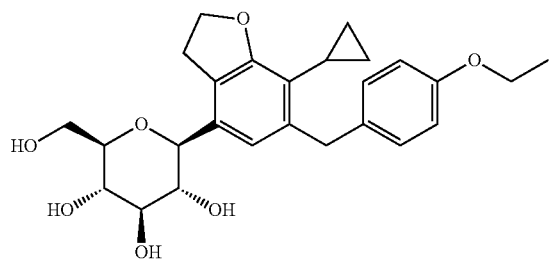 [SMILES: CCOc1ccc(Cc2cc([C@@H]3O[C@H](CO)[C@@H](O)[C@H](O)[C@H]3O)c3c(c2C2CC2)OCC3)cc1]

To a solution of 7-chloro-6-(4-ethoxybenzyl)-3-methoxy-4-((3S,4R,5R,6R)-3,4,5-tris(benzyloxy)-6-(benzyloxymethyl)-tetrahydro-2H-pyran-2-yl)-2,3-dihydrobenzofuran (102 mg, 0.125 mmol) in THF/MeOH (4 mL/2 mL) was added 10% Pd/C (10 mg) at rt. The reaction mixture was stirred at r.t. for 15 hours under hydrogen and filtered off. The filtrate was concentrated in vacuo and the residue was purified using reverse phase preparative HPLC to provide the title compound (17 mg, 29%) as a white solid.

(2S,3R,4R,5S,6R)-2-(7-Cyclopropyl-6-(4-ethoxybenzyl)-2,3-dihydrobenzofuran-4-yl)-6-(hydroxymethyl)-tetrahydro-2H-pyran-3,4,5-triol (E228)

$^1$H NMR (400 MHz, MeOD) δ 7.03 (d, J=8.8 Hz, 2H), 6.77 (s, 1H), 6.75 (d, J=9.2 Hz, 2H), 4.46 (t, J=8.8 Hz, 2H), 4.13 (d, J=9.2 Hz, 1H), 4.04 (d, J=6.8 Hz, 2H), 3.97 (q, J=6.8 Hz, 2H), 3.88 (dd, J=12.0, 1.6 Hz, 1H), 3.69-3.64 (m, 1H), 3.50-3.43 (m, 2H), 3.37-3.35 (m, 2H), 3.20-3.12 (m, 2H), 1.49-1.42 (m, 1H), 1.35 (t, J=7.2 Hz, 3H), 0.76-0.74 (m, 4H); $[M+Na]^+$ 456.

Example 229 was isolated as byproduct in the course of preparation of Example 228.

Example 229

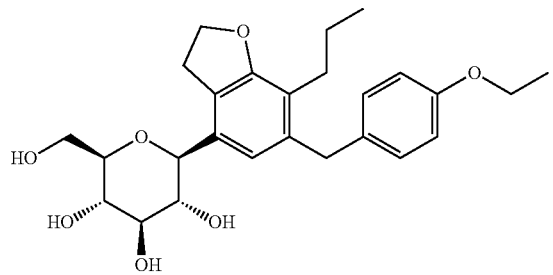 [SMILES: CCCc1c(Cc2ccc(OCC)cc2)cc([C@@H]2O[C@H](CO)[C@@H](O)[C@H](O)[C@H]2O)c2c1OCC2]

(2S,3R,4R,5S,6R)-2-(6-(4-Ethoxybenzyl)-7-propyl-2,3-dihydrobenzofuran-4-yl)-6-(hydroxymethyl)-tetrahydro-2H-pyran-3,4,5-triol (E229)

$^1$H NMR (400 MHz, MeOD) δ 7.10-6.96 (m, 2H), 6.80-6.74 (m, 3H), 4.50 (t, J=8.8 Hz, 2H), 4.14 (d, J=9.2 Hz, 1H), 4.08-4.04 (m, 1H), 4.02-3.95 (m, 2H), 3.90-3.85 (m, 3H), 3.73-3.65 (m, 1H), 3.53-3.42 (m, 2H), 3.38-3.33 (m, 3H), 3.26-3.18 (m, 1H), 2.48-2.44 (m, 1H), 1.37-1.33 (m, 5H), 0.84 (t, J=7.2 Hz, 3H); $[M+Na]^+$ 481.

Example 230

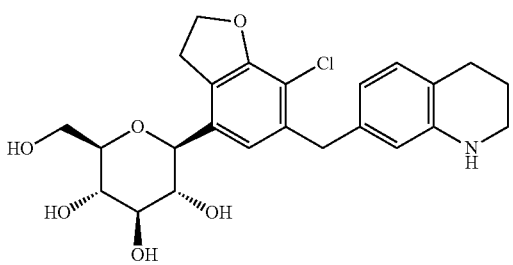

(2S,3R,4R,5S,6R)-2-(7-Chloro-6-((1,2,3,4-tetrahydroquinolin-7-yl)methyl)-2,3-dihydrobenzofuran-4-yl)-6-(hydroxymethyl)-tetrahydro-2H-pyran-3,4,5-triol (E230)

$^1$H NMR (400 MHz, MeOD) δ 6.82 (s, 1H), 6.76 (d, J=7.6 Hz, 2H), 6.41 (dd, J=7.6, 1.2 Hz, 1H), 6.34 (d, J=1.2 Hz, 1H), 4.61 (t, J=8.8 Hz, 2H), 4.13 (d, J=8.8 Hz, 1H), 3.87 (dd, J=26.0, 14.8 Hz, 3H), 3.69-3.65 (m, 1H), 3.48-3.40 (m, 3H), 3.37-3.35 (m, 4H), 3.18 (t, J=7.2 Hz, 2H), 2.68 (t, J=6.4 Hz, 2H), 1.90-1.84 (m, 2H); $[M+Na]^+$ 484.

Example 231

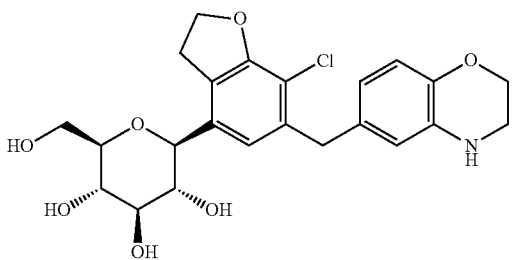 [SMILES: OC[C@H]1O[C@@H](c2cc(Cc3ccc4c(c3)NCCO4)c(Cl)c3c2CCO3)[C@H](O)[C@@H](O)[C@@H]1O]

(2S,3R,4R,5S,6R)-2-(7-Chloro-6-((3,4-dihydro-2H-benzo[b][1,4]oxazin-6-yl)methyl)-2,3-dihydrobenzofuran-4-yl)-6-(hydroxymethyl)-tetrahydro-2H-pyran-3,4,5-triol (E231)

$^1$H NMR (400 MHz, MeOD) δ 6.82 (s, 1H), 6.55 (d, J=8.0 Hz, 1H), 6.45-6.41 (m, 2H), 4.61 (t, J=8.8 Hz, 2H), 4.15-4.12 (m, 3H), 3.91-3.85 (m, 4H), 3.69-3.65 (m, 2H), 3.49-3.35 (m, 7H); $[M+Na]^+$ 486.

Example 232

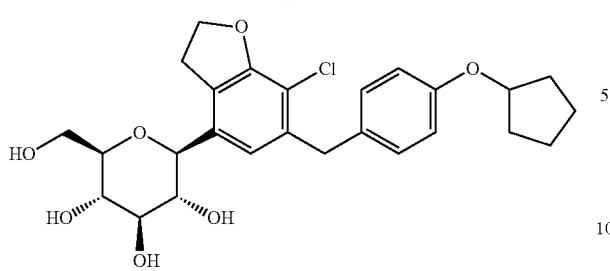

(2S,3R,4R,5S,6R)-2-(7-Chloro-6-(4-(cyclopentyloxy)benzyl)-2,3-dihydrobenzofuran-4-yl)-6-(hydroxymethyl)-tetrahydro-2H-pyran-3,4,5-triol (E232)

$^1$H NMR (400 MHz, MeOD) δ 7.07 (d, J=8.8 Hz, 2H), 6.84 (s, 1H), 6.75 (d, J=8.4 Hz, 2H), 4.75-4.73 (m, 1H), 4.61 (t, J=8.8 Hz, 2H), 4.14 (d, J=9.2 Hz, 1H), 3.96 (ABq, Δν$_{AB}$=18.4 Hz, J$_{AB}$=15.2 Hz, 2H), 3.88 (d, J=10.8 Hz, 1H), 3.69-3.65 (m, 1H), 3.49-3.33 (m, 6H), 1.94-1.85 (m, 2H), 1.80-1.72 (m, 4H), 1.66-1.59 (m, 2H); [M+Na]$^+$ 513.

Example 233

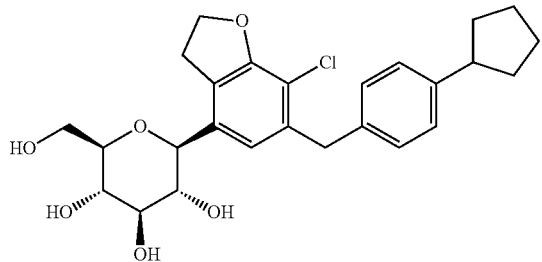 [SMILES: OC[C@H]1O[C@@H](c2cc(Cc3ccc(C4CCCC4)cc3)c(Cl)c3c2CCO3)[C@H](O)[C@@H](O)[C@@H]1O]

(2S,3R,4R,5S,6R)-2-(7-Chloro-6-(4-cyclopentylbenzyl)-2,3-dihydrobenzofuran-4-yl)-6-(hydroxymethyl)-tetrahydro-2H-pyran-3,4,5-triol (E233)

$^1$H NMR (400 MHz, MeOD) δ 7.09 (dd, J=13.6, 8.4 Hz, 4H), 6.85 (s, 1H), 4.62 (t, J=8.8 Hz, 2H), 4.14 (d, J=9.2 Hz, 1H), 4.00 (ABq, Δν$_{AB}$=18.4 Hz, J$_{AB}$=15.2 Hz, 2H), 3.87 (d, J=10.8 Hz, 1H), 3.69-3.64 (m, 1H), 3.49-3.33 (m, 6H), 3.01-2.86 (m, 1H), 2.05-1.99 (m, 2H), 1.85-1.76 (m, 2H), 1.75-1.63 (m, 2H), 1.60-1.51 (m, 2H); [M+Na]$^+$ 497.

Example 234

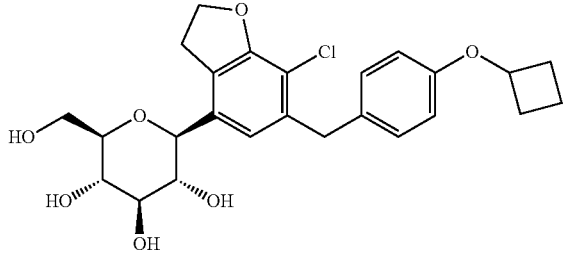 [SMILES: OC[C@H]1O[C@@H](c2cc(Cc3ccc(OC4CCC4)cc3)c(Cl)c3c2CCO3)[C@H](O)[C@@H](O)[C@@H]1O]

(2S,3R,4R,5S,6R)-2-(7-Chloro-6-(4-cyclobutoxybenzyl)-2,3-dihydrobenzofuran-4-yl)-6-(hydroxymethyl)-tetrahydro-2H-pyran-3,4,5-triol (E234)

$^1$H NMR (400 MHz, MeOD) δ 7.06 (d, J=8.4 Hz, 2H), 6.83 (s, 1H), 6.70 (d, J=8.8 Hz, 2H), 4.63-4.59 (m, 3H), 4.13 (d, J=8.8 Hz, 1H), 3.95 (ABq, Δν$_{AB}$=18.4 Hz, J$_{AB}$=14.8 Hz, 2H), 3.88 (d, J=11.2 Hz, 1H), 3.69-3.65 (m, 1H), 3.47-3.35 (m, 6H), 2.49-2.39 (m, 2H), 2.13-2.04 (m, 2H), 1.89-1.64 (m, 2H); [M+Na]$^+$ 499.

Example 235

(2S,3R,4R,5S,6R)-2-(6-(4-tert-Butylbenzyl)-7-chloro-2,3-dihydrobenzofuran-4-yl)-6-(hydroxymethyl)-tetrahydro-2H-pyran-3,4,5-triol (E235)

$^1$H NMR (400 MHz, MeOD) δ 7.27 (d, J=8.4 Hz, 2H), 7.10 (d, J=8.4 Hz, 2H), 6.86 (s, 1H), 4.62 (t, J=8.8 Hz, 2H), 4.14 (d, J=9.2 Hz, 1H), 4.00 (ABq, Δν$_{AB}$=18.4 Hz, J$_{AB}$=14.8 Hz, 2H), 3.87 (d, J=10.8 Hz, 1H), 3.69-3.65 (m, 1H), 3.49-3.35 (m, 6H), 1.28 (s, 9H); [M+Na]$^+$ 485.

Example 236

(2S,3R,4R,5S,6R)-2-(7-Chloro-6-(4-cyclobutylbenzyl)-2,3-dihydrobenzofuran-4-yl)-6-(hydroxymethyl)-tetrahydro-2H-pyran-3,4,5-triol (E236)

$^1$H NMR (400 MHz, MeOD) δ 7.09 (s, 4H), 6.84 (s, 1H), 4.61 (t, J=8.8 Hz, 2H), 4.14 (d, J=8.8 Hz, 1H), 4.00 (ABq, Δν$_{AB}$=18.2 Hz, J$_{AB}$=15.2 Hz, 2H), 3.87 (dd, J=12.0, 1.2 Hz, 1H), 3.69-3.65 (m, 1H), 3.54-3.33 (m, 6H), 2.34-2.27 (m, 2H), 2.16-1.95 (m, 3H), 1.89-1.80 (m, 1H); [M+Na]$^+$ 483.

Example 237

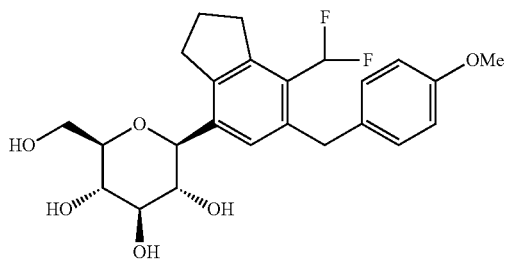 [SMILES: COc1ccc(Cc2cc([C@@H]3O[C@H](CO)[C@@H](O)[C@H](O)[C@H]3O)c3c(c2C(F)F)CCC3)cc1]

(2S,3R,4R,5S,6R)-2-(7-(Difluoromethyl)-6-(4-methoxybenzyl)-2,3-dihydro-1H-inden-4-yl)-6-(hydroxymethyl)tetrahydro-2H-pyran-3,4,5-triol (E237)

$^1$H NMR (400 MHz, CD$_3$OD) δ 7.21 (s, 1H), 7.07 (d, J=8.8 Hz, 2H), 6.88 (d, J=54.4 Hz, 1H), 6.84 (d, J=8.8 Hz, 2H), 4.33 (d, J=9.2 Hz, 1H), 4.11 (ABq, Δv$_{AB}$=12.7 Hz, J$_{AB}$=16.0 Hz, 2H), 3.92 (d, J=11.2 Hz, 1H), 3.79 (s, 3H), 3.74-3.69 (m, 1H), 3.56-3.49 (m, 2H), 3.46-3.41 (m, 2H), 3.16-3.08 (m, 3H), 3.03-2.95 (m, 1H), 2.17-2.07 (m, 2H); [M+Na]$^+$ 473.

Example 238

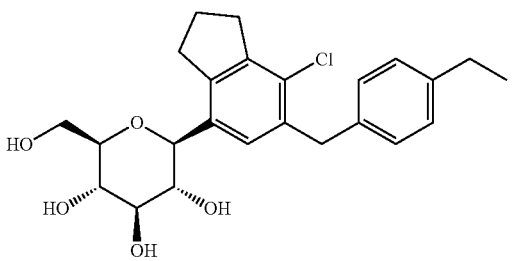 [SMILES: CCc1ccc(Cc2cc([C@@H]3O[C@H](CO)[C@@H](O)[C@H](O)[C@H]3O)c3c(c2Cl)CCC3)cc1]

(2S,3R,4R,5S,6R)-2-(7-Chloro-6-(4-ethylbenzyl)-2,3-dihydro-1H-inden-4-yl)-6-(hydroxymethyl)tetrahydro-2H-pyran-3,4,5-triol (E238)

$^1$H NMR (400 MHz, CD$_3$OD) δ 7.21 (s, 1H), 7.11 (d, J=3.2 Hz, 4H), 4.26 (d, J=9.2 Hz, 1H), 4.06 (ABq, Δv$_{AB}$=15.9 Hz, J$_{AB}$=15.2 Hz, 2H), 3.90 (d, J=12.8 Hz, 1H), 3.73-3.67 (m, 1H), 3.53-3.46 (m, 2H), 3.43-3.39 (m, 2H), 3.21-3.15 (m, 1H), 3.11-3.02 (m, 1H), 2.98 (t, J=3.2 Hz, 2H), 2.62 (q, J=3.2 Hz, 2H), 2.16-2.07 (m, 2H), 1.23 (t, J=7.6 Hz, 3H).

Example 239

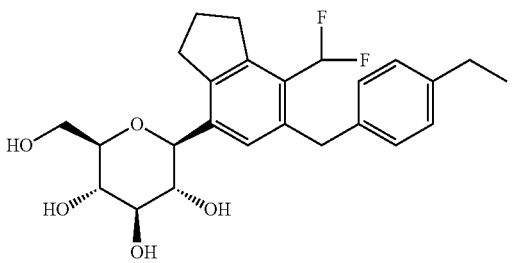 [SMILES: CCc1ccc(Cc2cc([C@@H]3O[C@H](CO)[C@@H](O)[C@H](O)[C@H]3O)c3c(c2C(F)F)CCC3)cc1]

(2S,3R,4R,5S,6R)-2-(7-(Difluoromethyl)-6-(4-ethylbenzyl)-2,3-dihydro-1H-inden-4-yl)-6-(hydroxymethyl)tetrahydro-2H-pyran-3,4,5-triol (E239)

$^1$H NMR (400 MHz, CD$_3$OD) δ 7.21 (s, 1H), 7.13-7.10 (m, 2H), 7.08-7.04 (m, 2H), 6.87 (d, J=54.4 Hz, 1H), 4.33 (d, J=12.0 Hz, 1H), 4.14 (ABq, Δv$_{AB}$=12.3 Hz, J$_{AB}$=16.8 Hz, 2H), 3.91 (d, J=12.4 Hz, 1H), 3.74-3.68 (m, 1H), 3.54-3.48 (m, 2H), 3.44-3.41 (m, 2H), 3.17-3.09 (m, 3H), 3.03-2.94 (m, 1H), 2.62 (q, J=7.5 Hz, 2H), 2.16-2.07 (m, 2H), 1.23 (t, J=9.0 Hz, 3H); [M+Na]$^+$ 471.

Example 240

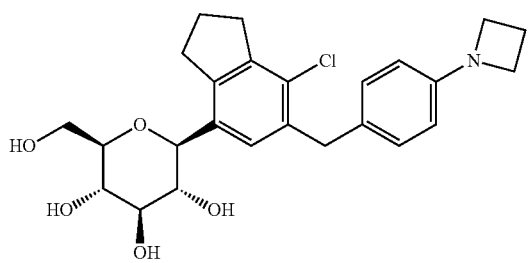 [SMILES: OC[C@H]1O[C@@H](c2cc(Cc3ccc(N4CCC4)cc3)c(Cl)c3c2CCC3)[C@H](O)[C@@H](O)[C@@H]1O]

(2S,3R,4R,5S,6R)-2-(6-(4-(Azetidin-1-yl)benzyl)-7-chloro-2,3-dihydro-1H-inden-4-yl)-6-(hydroxymethyl)tetrahydro-2H-pyran-3,4,5-triol (E240)

$^1$H NMR (400 MHz, CD$_3$OD) δ 7.14 (s, 1H), 6.95 (d, J=8.4 Hz, 2H), 6.56 (d, J=8.4 Hz, 2H), 4.20 (d, J=9.0 Hz, 1H), 3.92 (ABq, Δv$_{AB}$=18.9 Hz, J$_{AB}$=14.8 Hz, 2H), 3.86 (d, J=11.2 Hz, 1H), 3.66 (t, J=6.2 Hz, 1H), 3.65-3.63 (m, 1H), 3.48-3.42 (m, 2H), 3.38-3.35 (m, 2H), 3.18-3.10 (m, 3H), 3.05-2.97 (m, 1H), 2.93 (t, J=7.6 Hz, 2H), 2.11-2.04 (m, 2H), 1.83-1.77 (m, 2H); [M+NH$_4$]$^+$ 478.

Example 241

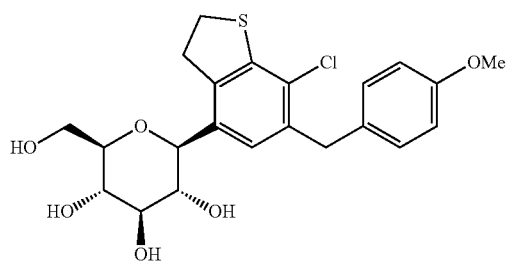 [SMILES: COc1ccc(Cc2cc([C@@H]3O[C@H](CO)[C@@H](O)[C@H](O)[C@H]3O)c3c(c2Cl)SCC3)cc1]

(2S,3R,4R,5S,6R)-2-(7-Chloro-6-(4-methoxybenzyl)-2,3-dihydrobenzo[b]thiophen-4-yl)-6-(hydroxymethyl)tetrahydro-2H-pyran-3,4,5-triol (E241)

$^1$H NMR (400 MHz, CD$_3$OD) δ 7.07 (d, J=8.8 Hz, 2H), 7.04 (s, 1H), 6.78 (d, J=8.4 Hz, 2H), 4.20 (d, J=8.8 Hz, 1H), 3.91 (ABq, Δv$_{AB}$=15.8 Hz, J$_{AB}$=15.0 Hz, 2H), 3.86 (d, J=11.2 Hz, 1H), 3.73 (s, 3H), 3.68-3.63 (m, 1H), 3.60-3.52 (m, 1H), 3.47-3.39 (m, 3H), 3.38-3.32 (m, 4H); [M+Na]$^+$=475.

Example 242

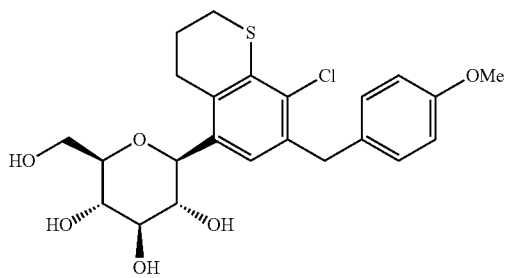

(2S,3R,4R,5S,6R)-2-(8-Chloro-7-(4-methoxybenzyl)
thiochroman-5-yl)-6-(hydroxymethyl)tetrahydro-2H-
pyran-3,4,5-triol (E242)

$^1$H NMR (400 MHz, CD$_3$OD) δ 7.15 (s, 1H), 7.07 (d, J=8.8 Hz, 2H), 6.79 (d, J=8.8 Hz, 2H), 4.48 (d, J=8.8 Hz, 1H), 3.98 (ABq, Δv$_{AB}$=9.6 Hz, J$_{AB}$=15.0 Hz, 2H), 3.86 (d, J=12.0 Hz, 1H), 3.74 (s, 3H), 3.67-3.62 (m, 1H), 3.51-3.44 (m, 2H), 3.41-3.36 (m, 2H), 3.07-2.96 (m, 3H), 2.94-2.86 (m, 1H), 2.12-2.06 (m, 2H); [M+Na]$^+$=489.

Example 243

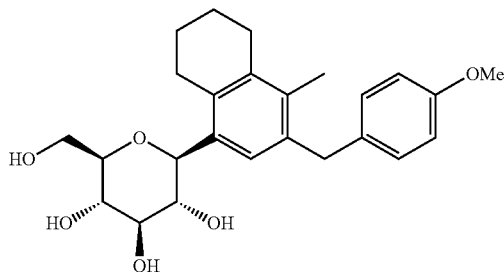

(2R,3S,4R,5R,6S)-2-(Hydroxymethyl)-6-(3-(4-meth-
oxybenzyl)-4-methyl-5,6,7,8-tetrahydronaphthalen-
1-yl)tetrahydro-2H-pyran-3,4,5-triol (E243)

$^1$H NMR (400 MHz, CD$_3$OD) δ 7.20 (s, 1H), 7.05 (d, J=8.8 Hz, 2H), 6.82 (d, J=8.8 Hz, 2H), 4.53 (d, J=9.6 Hz, 1H), 3.98 (s, 2H), 3.91 (d, J=11.6 Hz, 1H), 3.78 (s, 3H), 3.72-3.67 (m, 1H), 3.66 (t, J=9.2 Hz, 1H), 3.57-3.52 (m, 1H), 3.46-3.42 (m, 2H), 3.03-2.85 (m, 2H), 2.69 (t, J=5.8 Hz, 2H), 2.07 (s, 3H), 1.88-1.77 (m, 4H); [M+Na]$^+$=451.

In Vitro Assay

Test 1: Cloning and Cell Line Construction for Human SGLT2

Human SGLT2 (hSGLT2) gene was amplified by PCR from cDNA-Human Adult Normal Tissue Kidney (Invitrogen). The hSGLT2 sequence was cloned into pcDNA3.1(+) for mammalian expression and stably transfected into chinese hamster ovary (CHO) cells. SGLT2-expressing clones were selected based on resistance to G418 antibiotic (Geneticin) and activity in the $^{14}$C-α-methyl-D-glucopyranoside ($^{14}$C-AMG) uptake assay.

Test 2: Inhibitory Effects on Human SGLT2 Activities

For sodium-dependent glucose transport assay, cells expressing hSGLT2 were seeded into a 96-well culture plate at a density of 5×10$^4$ cells/well in RPMI medium 1640 containing 10% fetal bovine serum. The cells were used 1 day after plating. They were incubated in pretreatment buffer (10 mM HEPES, 5 mM Tris, 140 mM choline chloride, 2 mM KCl, 1 mM CaCl$_2$, and 1 mM MgCl$_2$, pH 7.4) at 37° C. for 10 min. They were then incubated in uptake buffer (10 mM HEPES, 5 mM Tris, 140 mM NaCl, 2 mM KCl, 1 mM CaCl$_2$, 1 mM MgCl$_2$, and 1 mM $^{14}$C-nonlabeled AMG pH 7.4) containing $^{14}$C-labeled AMG (8 μM) and the inventive compound or dimethyl sulfoxide (DMSO) vehicle at 37° C. for 2 h. Cells were washed twice with washing buffer (pretreatment buffer containing 10 mM AMG at room temperature) and then the radioactivity was measured using a liquid scintillation counter. IC$_{50}$ was determined by nonlinear regression analysis using GraphPad PRISM [Katsuno, K. et al. *J. Pharmacol. Exp. Ther.* 2007, 320, 323-330; Han, S. et al. *Diabetes*, 2008, 57, 1723-1729]. The inventive compounds and their IC$_{50}$ are shown in following Table 1.

TABLE 1 hSGLT2 Inhibitory Activity

| Compound | Structure | Name | IC$_{50}$ (nM) |
|---|---|---|---|
| E001 | (structure shown) | (2S,3R,4R,5S,6R)-2-(7-bromo-6-(4-methoxybenzyl)-2,3-dihydro-1H-inden-4-yl)-6-(hydroxymethyl)tetrahydro-2H-pyran-3,4,5-triol | 1.15 |

TABLE 1-continued hSGLT2 Inhibitory Activity

| Compound | Structure | Name | IC$_{50}$ (nM) |
|---|---|---|---|
| E002 | 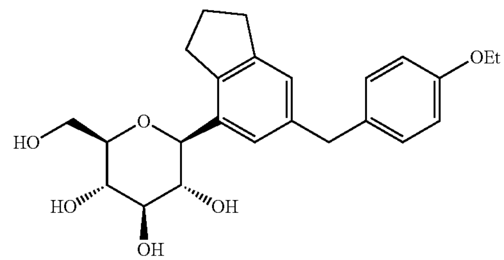 [SMILES: CCOc1ccc(Cc2cc3c(c([C@@H]4O[C@H](CO)[C@@H](O)[C@H](O)[C@H]4O)c2)CCC3)cc1] | (2S,3R,4R,5S,6R)-2-(6-(4-ethoxybenzyl)-2,3-dihydro-1H-inden-4-yl)-6-(hydroxymethyl)tetrahydro-2H-pyran-3,4,5-triol | 9.00 |
| E003 | 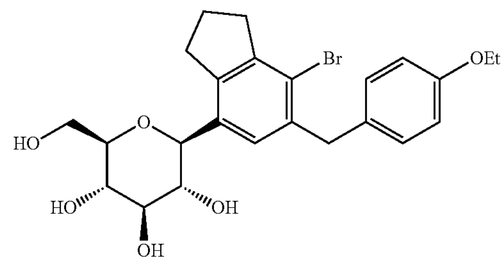 | (2S,3R,4R,5S,6R)-2-(7-bromo-6-(4-ethoxybenzyl)-2,3-dihydro-1H-inden-4-yl)-6-(hydroxymethyl)tetrahydro-2H-pyran-3,4,5-triol | 0.738 |
| E004 | 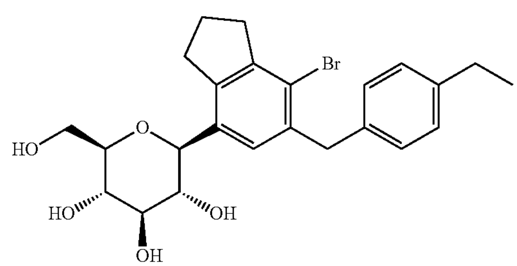 | (2S,3R,4R,5S,6R)-2-(7-bromo-6-(4-ethoxybenzyl)-2,3-dihydro-1H-inden-4-yl)-6-(hydroxymethyl)tetrahydro-2H-pyran-3,4,5-triol | 0.661 |
| E005 | 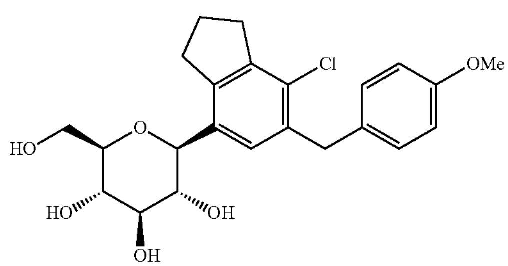 | (2S,3R,4R,5S,6R)-2-(7-chloro-6-(4-methoxybenzyl)-2,3-dihydro-1H-inden-4-yl)-6-(hydroxymethyl)tetrahydro-2H-pyran-3,4,5-triol | 0.681 |
| E006 | 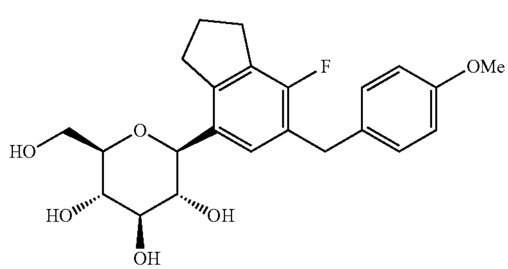 [SMILES: COc1ccc(Cc2cc([C@@H]3O[C@H](CO)[C@@H](O)[C@H](O)[C@H]3O)c3c(c2F)CCC3)cc1] | (2S,3R,4R,5S,6R)-2-(7-fluoro-6-(4-methoxybenzyl)-2,3-dihydro-1H-inden-4-yl)-6-(hydroxymethyl)tetrahydro-2H-pyran-3,4,5-triol | 2.03 |

TABLE 1-continued hSGLT2 Inhibitory Activity

| Compound | Structure | Name | IC$_{50}$ (nM) |
|---|---|---|---|
| E007 | 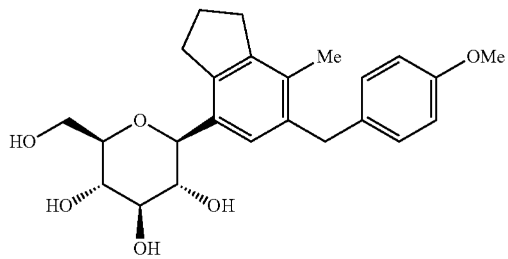 [SMILES: COc1ccc(Cc2cc([C@@H]3O[C@H](CO)[C@@H](O)[C@H](O)[C@H]3O)c3c(c2C)CCC3)cc1] | (2R,3S,4R,5R,6S)-2-(hydroxymethyl)-6-(6-(4-methoxybenzyl)-7-methyl-2,3-dihydro-1H-inden-4-yl)tetrahydro-2H-pyran-3,4,5-triol | 0.793 |
| E008 | 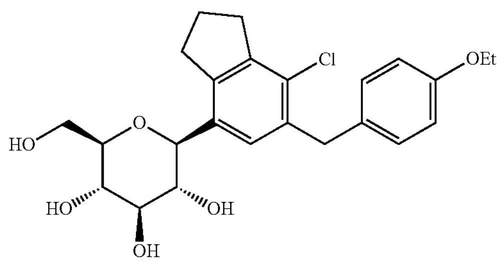 [SMILES: CCOc1ccc(Cc2cc([C@@H]3O[C@H](CO)[C@@H](O)[C@H](O)[C@H]3O)c3c(c2Cl)CCC3)cc1] | (2S,3R,4R,5S,6R)-2-(7-chloro-6-(4-ethoxybenzyl)-2,3-dihydro-1H-inden-4-yl)-6-(hydroxymethyl)tetrahydro-2H-pyran-3,4,5-triol | 0.551 |
| E009 | 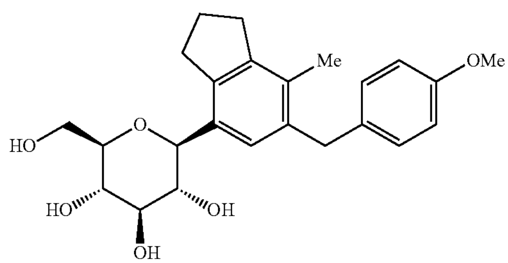 [SMILES: COc1ccc(Cc2cc([C@@H]3O[C@H](CO)[C@@H](O)[C@H](O)[C@H]3O)c3c(c2C)CCC3)cc1] | (2S,3R,4R,5S,6R)-2-(6-(4-ethoxybenzyl)-7-methyl-2,3-dihydro-1H-inden-4-yl)-6-(hydroxymethyl)tetrahydro-2H-pyran-3,4,5-triol | 1.18 |
| E010 | 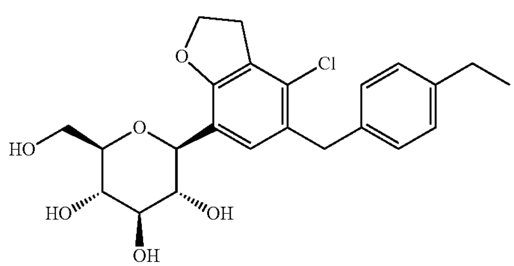 | (2S,3R,4R,5S,6R)-2-(4-chloro-5-(4-ethylbenzyl)-2,3-dihydrobenzofuran-7-yl)-6-(hydroxymethyl)tetrahydro-2H-pyran-3,4,5-triol | 0.884 |
| E011 | 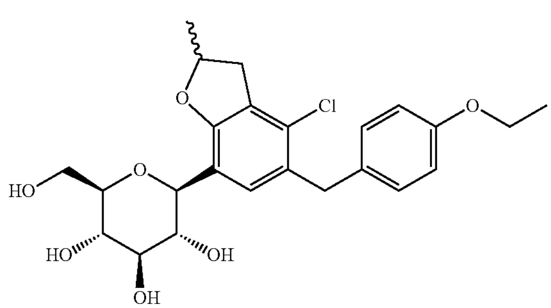 [SMILES: CCOc1ccc(Cc2cc([C@@H]3O[C@H](CO)[C@@H](O)[C@H](O)[C@H]3O)c3c(c2Cl)CC(C)O3)cc1] | (2S,3R,4R,5S,6R)-2-(4-chloro-5-(4-ethoxybenzyl)-2-methyl-2,3-dihydrobenzofuran-7-yl)-6-(hydroxymethyl)tetrahydro-2H-pyran-3,4,5-triol | 1.28 |

TABLE 1-continued hSGLT2 Inhibitory Activity

| Compound | Structure | Name | IC$_{50}$ (nM) |
|---|---|---|---|
| E012 | 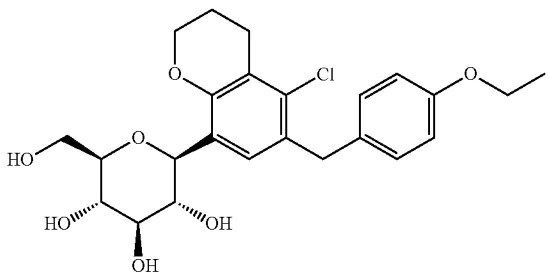 | (2S,3R,4R,5S,6R)-2-(5-chloro-6-(4-ethoxybenzyl)chroman-8-yl)-6-(hydroxymethyl)tetrahydro-2H-pyran-3,4,5-triol | 1.55 |
| E013 | 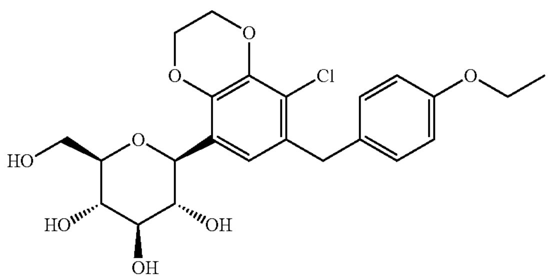 [SMILES: CCOc1ccc(Cc2cc([C@@H]3O[C@H](CO)[C@@H](O)[C@H](O)[C@H]3O)c3c(c2Cl)CCCO3)cc1] | (2S,3R,4R,5S,6R)-2-(8-chloro-7-(4-ethoxybenzyl)-2,3-dihydrobenzo[b][1,4]dioxin-5-yl)-6-(hydroxymethyl)tetrahydro-2H-pyran-3,4,5-triol | 1.27 |
| E016 | 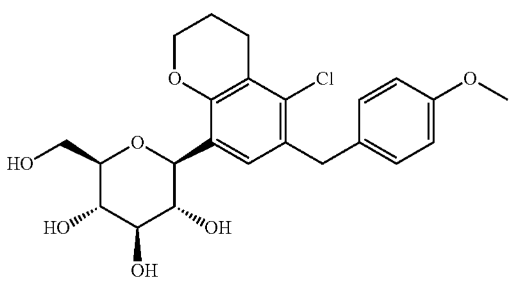 | (2S,3R,4R,5S,6R)-2-(5-chloro-6-(4-methoxybenzyl)chroman-8-yl)-6-(hydroxymethyl)tetrahydro-2H-pyran-3,4,5-triol | 0.978 |
| E017 | 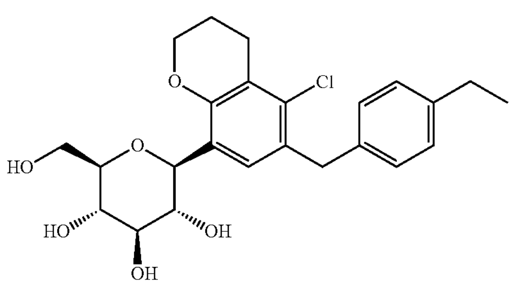 [SMILES: CCc1ccc(Cc2cc([C@@H]3O[C@H](CO)[C@@H](O)[C@H](O)[C@H]3O)c3c(c2Cl)CCCO3)cc1] | (2S,3R,4R,5S,6R)-2-(5-chloro-6-(4-ethylbenzyl)chroman-8-yl)-6-(hydroxymethyl)tetrahydro-2H-pyran-3,4,5-triol | 0.845 |
| E019 | 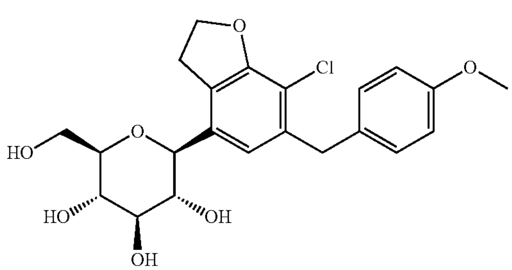 [SMILES: COc1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-chloro-6-(4-methoxybenzyl)-2,3-dihydrobenzofuran-4-yl)-6-(hydroxymethyl)tetrahydro-2H-pyran-3,4,5-triol | 1.53 |

TABLE 1-continued hSGLT2 Inhibitory Activity

| Compound | Structure | Name | IC$_{50}$ (nM) |
|---|---|---|---|
| E020 | 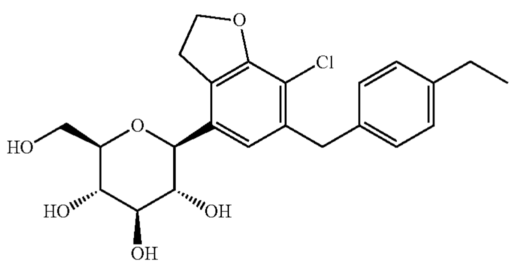 | (2S,3R,4R,5S,6R)-2-(6-(4-ethylbenzyl)-7-chloro-2,3-dihydrobenzofuran-4-yl)-6-(hydroxymethyl)-tetrahydro-2H-pyran-3,4,5-triol | 0.715 |
| E021 | 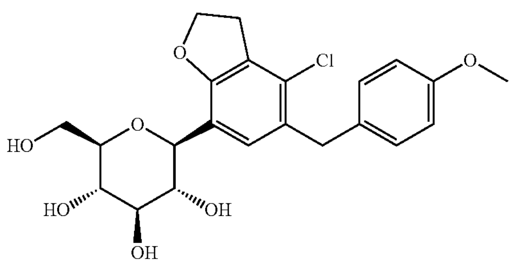 | (2S,3R,4R,5S,6R)-2-(4-chloro-5-(4-methoxybenzyl)-2,3-dihydrobenzofuran-7-yl)-6-(hydroxymethyl)tetrahydro-2H-pyran-3,4,5-triol | 1.72 |
| E022 | 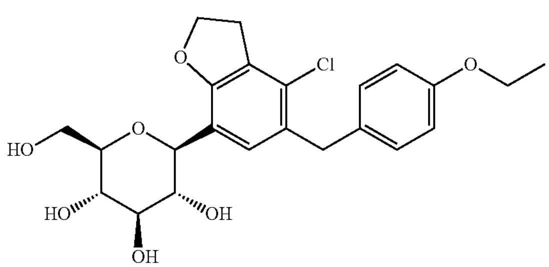 | (2S,3R,4R,5S,6R)-2-(4-chloro-5-(4-ethoxybenzyl)-2,3-dihydrobenzofuran-7-yl)-6-(hydroxymethyl)tetrahydro-2H-pyran-3,4,5-triol | 0.833 |
| E023 | 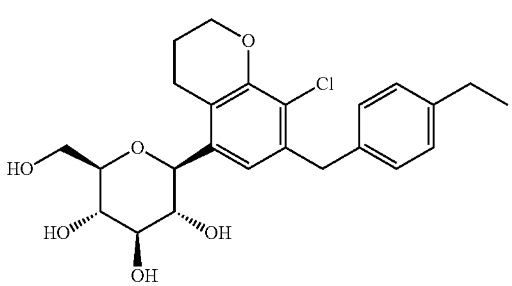 | (2S,3R,4R,5S,6R)-2-(8-chloro-7-(4-ethylbenzyl)chroman-5-yl)-6-(hydroxymethyl)tetrahydro-2H-pyran-3,4,5 triol | 0.753 |
| E024 | 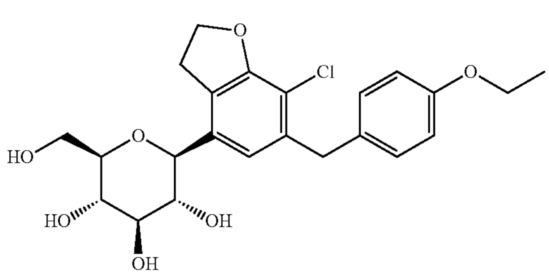 | (2S,3R,4R,5S,6R)-2-(7-chloro-6-(4-ethoxybenzyl)-2,3-dihydrobenzofuran-4-yl)-6-(hydroxymethyl)tetrahydro-2H-pyran-3,4,5-triol | 1.52 |

TABLE 1-continued hSGLT2 Inhibitory Activity

| Compound | Structure | Name | IC$_{50}$ (nM) |
|---|---|---|---|
| E025 | 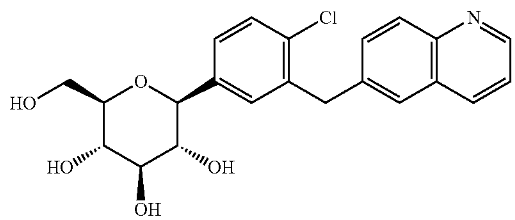 [SMILES: OC[C@H]1O[C@@H](c2ccc(Cl)c(Cc3ccc4ncccc4c3)c2)[C@H](O)[C@@H](O)[C@@H]1O] | (2S,3R,4R,5S,6R)-2-(4-chloro-3-(quinolin-6-ylmethyl)phenyl)-6-(hydroxymethyl)tetrahydro-2H-pyran-3,4,5-triol | 1.85 |
| E026 | 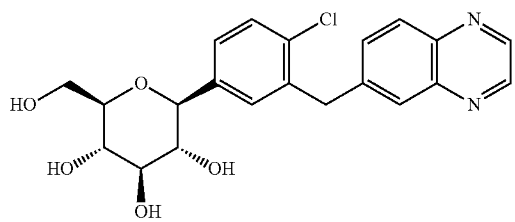 | (2S,3R,4R,5S,6R)-2-(4-chloro-3-(quinoxalin-6-ylmethyl)phenyl)-6-(hydroxymethyl)tetrahydro-2H-pyran-3,4,5-triol | 8.63 |
| E029 | 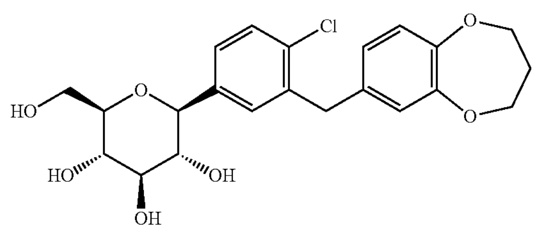 | (2S,3R,4R,5S,6R)-2-(4-chloro-3-((3,4-dihydro-2H-benzo[b][1,4]dioxepin-7-yl)methyl)phenyl)-6-(hydroxymethyl)tetrahydro-2H-pyran-3,4,5-triol | 4.38 |
| E030 | 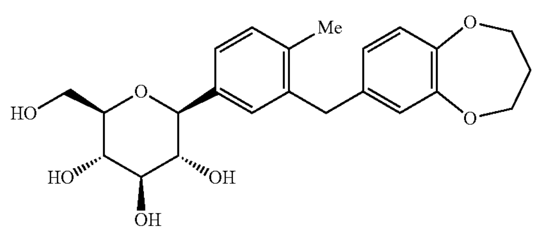 [SMILES: OC[C@H]1O[C@@H](c2ccc(Cl)c(Cc3ccc4c(c3)OCCCO4)c2)[C@H](O)[C@@H](O)[C@@H]1O] | (2S,3R,4R,5S,6R)-2-(3-((3,4-dihydro-2H-benzo[b][1,4]dioxepin-7-yl)methyl)-4-methylphenyl)-6-(hydroxymethyl)tetrahydro-2H-pyran-3,4,5-triol | 9.62 |
| E031 | 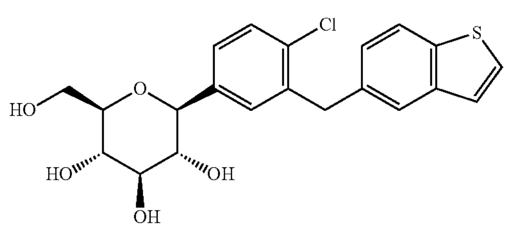 [SMILES: OC[C@H]1O[C@@H](c2ccc(Cl)c(Cc3ccc4sccc4c3)c2)[C@H](O)[C@@H](O)[C@@H]1O] | (2S,3R,4R,5S,6R)-2-(3-(benzo[b]thiophen-5-ylmethyl)-4-chlorophenyl)-6-(hydroxymethyl)tetrahydro-2H-pyran-3,4,5-triol | 0.865 |
| E032 | 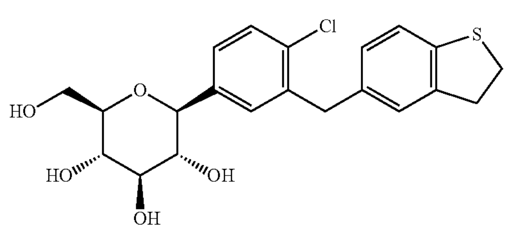 | (2S,3R,4R,5S,6R)-2-(4-chloro-3-((2,3-dihydrobenzo[b]thiophen-5-yl)methyl)phenyl)-6-(hydroxymethyl)tetrahydro-2H-pyran-3,4,5-triol | 2.16 |

TABLE 1-continued hSGLT2 Inhibitory Activity

| Compound | Structure | Name | IC$_{50}$ (nM) |
|---|---|---|---|
| E033 | 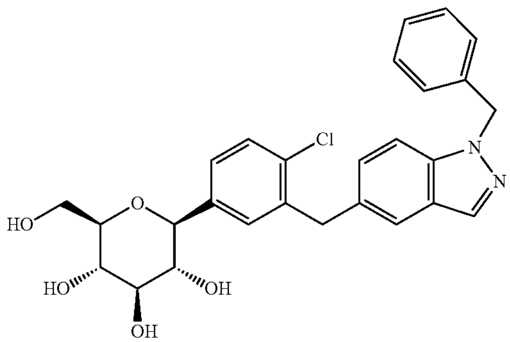 [SMILES: OC[C@H]1O[C@@H](c2ccc(Cl)c(Cc3ccc4c(cnn4Cc4ccccc4)c3)c2)[C@H](O)[C@@H](O)[C@@H]1O] | (2S,3R,4R,5S,6R)-2-(3-((1-benzyl-1H-indazol-5-yl)methyl)-4-chlorophenyl)-6-(hydroxymethyl)tetrahydro-2H-pyran-3,4,5-triol | 2.39 |
| E034 | 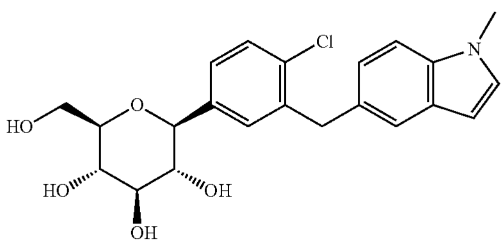 [SMILES: Cn1ccc2cc(Cc3cc([C@@H]4O[C@H](CO)[C@@H](O)[C@H](O)[C@H]4O)ccc3Cl)ccc21] | (2S,3R,4R,5S,6R)-2-(4-chloro-3-((1-methyl-1H-indol-5-yl)methyl)phenyl)-6-(hydroxymethyl)tetrahydro-2H-pyran-3,4,5-triol | 2.98 |
| E035 | 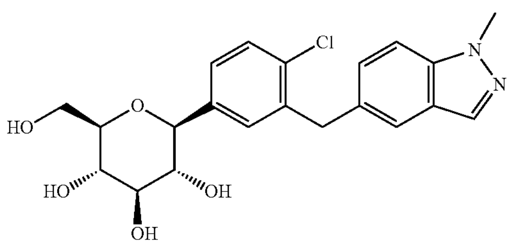 [SMILES: Cn1ncc2cc(Cc3cc([C@@H]4O[C@H](CO)[C@@H](O)[C@H](O)[C@H]4O)ccc3Cl)ccc21] | (2S,3R,4R,5S,6R)-2-(4-chloro-3-((1-methyl-1H-indazol-5-yl)methyl)phenyl)-6-(hydroxymethyl)tetrahydro-2H-pyran-3,4,5-triol | 1.72 |
| E036 | 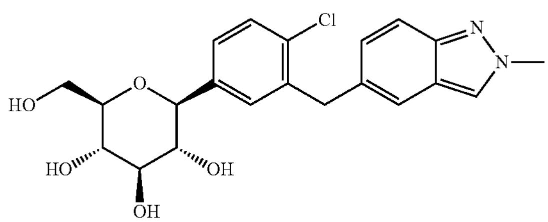 [SMILES: Cn1cc2cc(Cc3cc([C@@H]4O[C@H](CO)[C@@H](O)[C@H](O)[C@H]4O)ccc3Cl)ccc2n1] | (2S,3R,4R,5S,6R)-2-(4-chloro-3-((2-methyl-2H-indazol-5-yl)methyl)phenyl)-6-(hydroxymethyl)tetrahydro-2H-pyran-3,4,5-triol | 2.31 |
| E037 | 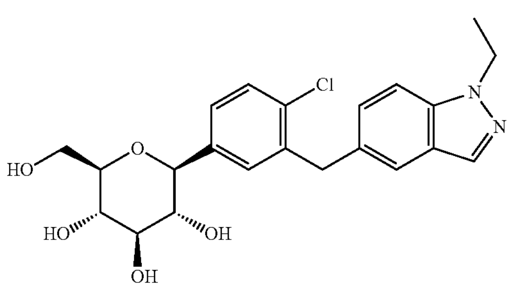 [SMILES: CCn1ncc2cc(Cc3cc([C@@H]4O[C@H](CO)[C@@H](O)[C@H](O)[C@H]4O)ccc3Cl)ccc21] | (2S,3R,4R,5S,6R)-2-(4-chloro-3-((1-ethyl-1H-indazol-5-yl)methyl)phenyl)-6-(hydroxymethyl)tetrahydro-2H-pyran-3,4,5-triol | 1.58 |

TABLE 1-continued hSGLT2 Inhibitory Activity

| Compound | Structure | Name | IC$_{50}$ (nM) |
|---|---|---|---|
| E038 | 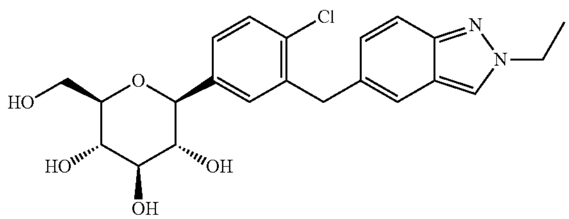 [SMILES: CCn1cc2cc(Cc3cc([C@@H]4O[C@H](CO)[C@@H](O)[C@H](O)[C@H]4O)ccc3Cl)ccc2n1] | (2S,3R,4R,5S,6R)-2-(4-chloro-3-((2-ethyl-2H-indazol-5-yl)methyl)phenyl)-6-(hydroxymethyl)tetrahydro-2H-pyran-3,4,5-triol | 1.76 |
| E039 | 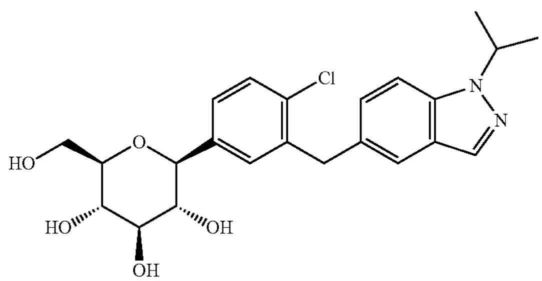 [SMILES: CC(C)n1ncc2cc(Cc3cc([C@@H]4O[C@H](CO)[C@@H](O)[C@H](O)[C@H]4O)ccc3Cl)ccc21] | (2S,3R,4R,5S,6R)-2-(4-chloro-3-((1-isopropyl-1H-indazol-5-yl)methyl)phenyl)-6-(hydroxymethyl)tetrahydro-2H-pyran-3,4,5-triol | 1.76 |
| E040 | 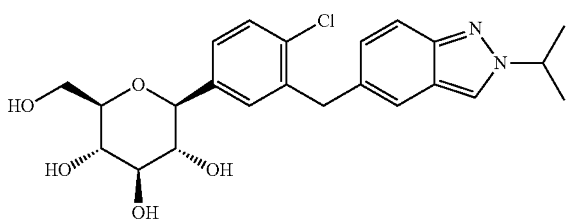 [SMILES: CC(C)n1cc2cc(Cc3cc([C@@H]4O[C@H](CO)[C@@H](O)[C@H](O)[C@H]4O)ccc3Cl)ccc2n1] | (2S,3R,4R,5S,6R)-2-(4-chloro-3-((2-isopropyl-2H-indazol-5-yl)methyl)phenyl)-6-(hydroxymethyl)tetrahydro-2H-pyran-3,4,5-triol | 4.44 |
| E043 | 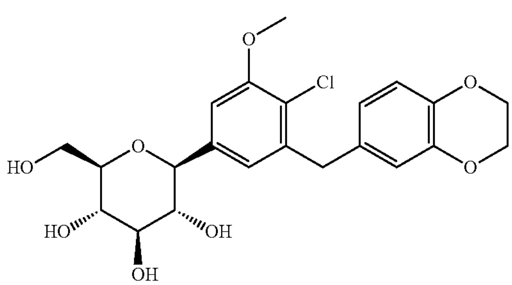 [SMILES: COc1cc([C@@H]2O[C@H](CO)[C@@H](O)[C@H](O)[C@H]2O)cc(Cc2ccc3c(c2)OCCO3)c1Cl] | (2S,3R,4R,5S,6R)-2-(4-chloro-3-((2,3-dihydrobenzo[b][1,4]dioxin-6-yl)methyl)-5-methoxyphenyl)-6-(hydroxymethyl)tetrahydro-2H-pyran-3,4,5-triol | 2.68 |
| E044 | 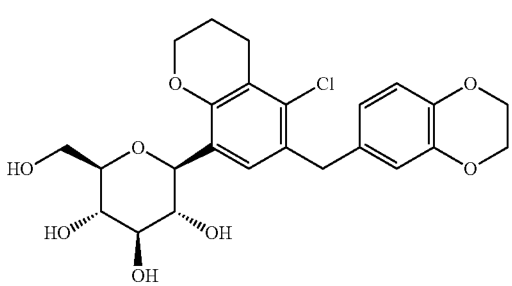 [SMILES: OC[C@H]1O[C@@H](c2cc(Cc3ccc4c(c3)OCCO4)c(Cl)c3c2OCCC3)[C@H](O)[C@@H](O)[C@@H]1O] | (2S,3R,4R,5S,6R)-2-(5-chloro-6-((2,3-dihydrobenzo[b][1,4]dioxin-6-yl)methyl)chroman-8-yl)-6-(hydroxymethyl)tetrahydro-2H-pyran-3,4,5-triol | 1.65 |

TABLE 1-continued hSGLT2 Inhibitory Activity

| Compound | Structure | Name | IC$_{50}$ (nM) |
|---|---|---|---|
| E045 | 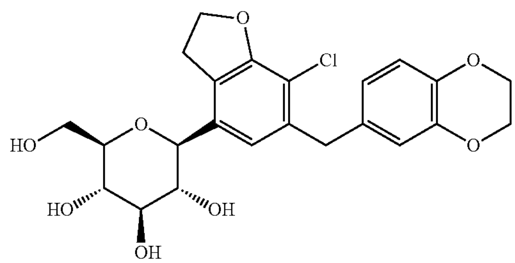 | (2S,3R,4R,5S,6R)-2-(7-chloro-6-((2,3-dihydrobenzo[b][1,4]dioxin-6-yl)methyl)chroman-4-yl)-6-(hydroxymethyl)tetrahydro-2H-pyran-3,4,5-triol | 1.37 |
| E046 | 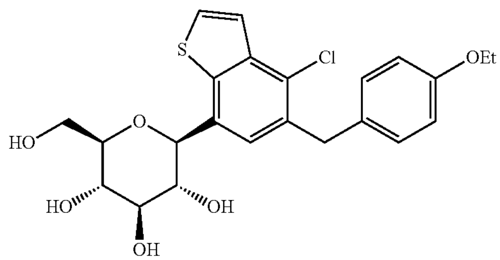 [SMILES: CCOc1ccc(Cc2cc([C@@H]3O[C@H](CO)[C@@H](O)[C@H](O)[C@H]3O)c3sccc3c2Cl)cc1] | (2S,3R,4R,5S,6R)-2-(4-chloro-5-(4-ethoxybenzyl)benzo[b]thiophen-7-yl)-6-(hydroxymethyl)tetrahydro-2H-pyran-3,4,5-triol | 275 |
| E047 | 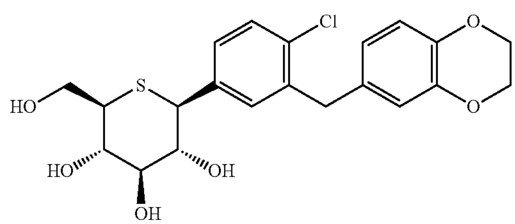 | (2S,3R,4R,5S,6R)-2-(4-chloro-3-((2,3-dihydrobenzo[b][1,4]dioxin-6-yl)methyl)phenyl)-6-(hydroxymethyl)tetrahydro-2H-thiopyran-3,4,5-triol | 4.17 |
| E048 | 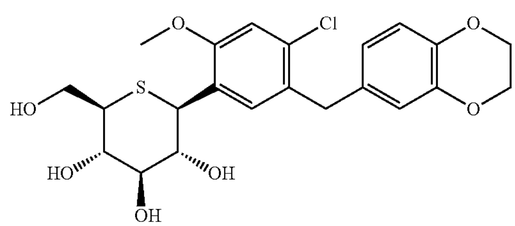 | (2S,3R,4R,5S,6R)-2-(4-Chloro-5-((2,3-dihydrobenzo[b][1,4]dioxin-6-yl)methyl)-2-methoxyphenyl)-6-(hydroxymethyl)tetrahydro-2H-thiopyran-3,4,5-triol | 2.62 |
| E049 | 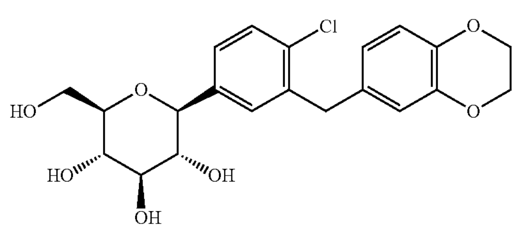 [SMILES: OC[C@H]1S[C@@H](c2ccc(Cl)c(Cc3ccc4c(c3)OCCO4)c2)[C@H](O)[C@@H](O)[C@@H]1O] | (2S,3R,4R,5S,6R)-2-(4-Chloro-3-((2,3-dihydrobenzo[b][1,4]dioxin-6-yl)methyl)phenyl)-6-(hydroxymethyl)-tetrahydro-2H-pyran-3,4,5-triol | 1.23 |
| E052 | 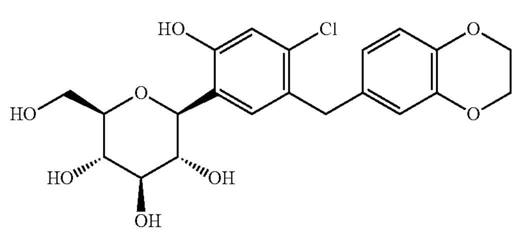 [SMILES: OC[C@H]1O[C@@H](c2cc(Cc3ccc4c(c3)OCCO4)c(Cl)cc2O)[C@H](O)[C@@H](O)[C@@H]1O] | (2S,3R,4R,5S,6R)-2-(4-Chloro-5-((2,3-dihydrobenzo[b][1,4]dioxin-6-yl)methyl)-2-hydroxyphenyl)-6-(hydroxymethyl)-tetrahydro-2H-pyran-3,4,5-triol | 1.64 |

TABLE 1-continued hSGLT2 Inhibitory Activity

| Compound | Structure | Name | IC$_{50}$ (nM) |
|---|---|---|---|
| E054 | 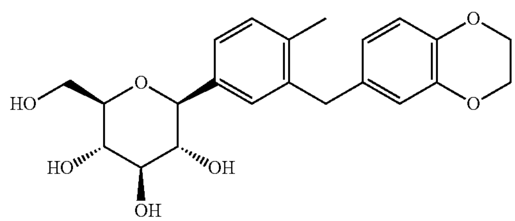 [SMILES: Cc1ccc([C@@H]2O[C@H](CO)[C@@H](O)[C@H](O)[C@H]2O)cc1Cc1ccc2c(c1)OCCO2] | (2S,3R,4R,5S,6R)-2-(3-((2,3-Dihydrobenzo[b][1,4]dioxin-6-yl)methyl)-4-methylphenyl)-6-(hydroxymethyl)-tetrahydro-2H-pyran-3,4,5-triol | 2.02 |
| E056 | 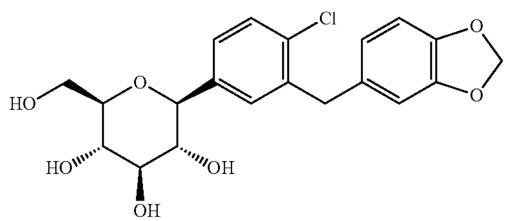 [SMILES: OC[C@H]1O[C@@H](c2ccc(Cl)c(Cc3ccc4c(c3)OCO4)c2)[C@H](O)[C@@H](O)[C@@H]1O] | (2S,3R,4R,5S,6R)-2-(3-(Benzo[d][1,3]dioxol-5-ylmethyl)-4-chlorophenyl)-6-(hydroxymethyl)-tetrahydro-2H-pyran-3,4,5-triol | 2.58 |
| E057 | 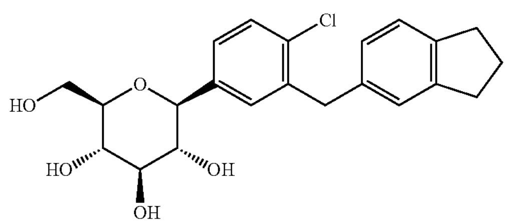 | (2S,3R,4R,5S,6R)-2-(4-Chloro-3-((2,3-dihydro-1H-inden-5-yl)methyl)phenyl)-6-(hydroxymethyl)-tetrahydro-2H-pyran-3,4,5-triol | 2.15 |
| E060 | 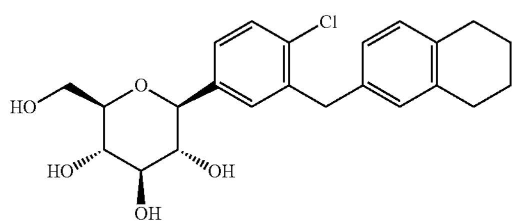 [SMILES: OC[C@H]1O[C@@H](c2ccc(Cl)c(Cc3ccc4c(c3)CCCC4)c2)[C@H](O)[C@@H](O)[C@@H]1O] | (2S,3R,4R,5S,6R)-2-(4-Chloro-3-((5,6,7,8-tetrahydronaphthalen-2-yl)methyl)phenyl)-6-(hydroxymethyl)-tetrahydro-2H-pyran-3,4,5-triol | 2.99 |
| E061 | 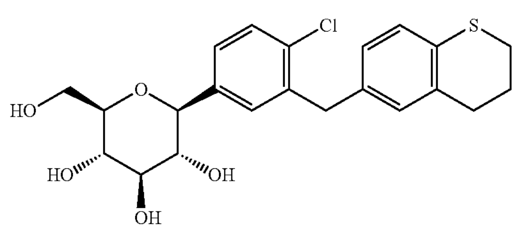 | (2S,3R,4R,5S,6R)-2-(4-Chloro-3-(thiochroman-6-ylmethyl)phenyl)-6-(hydroxymethyl)-tetrahydro-2H-pyran-3,4,5-triol | 3.35 |
| E064 | 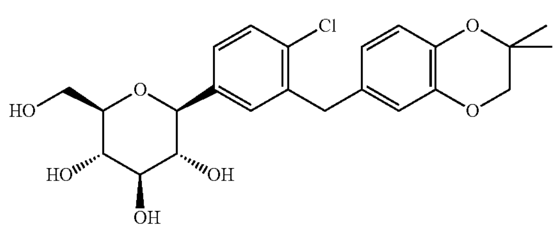 [SMILES: CC1(C)COc2cc(Cc3cc([C@@H]4O[C@H](CO)[C@@H](O)[C@H](O)[C@H]4O)ccc3Cl)ccc2O1] | (2S,3R,4R,5S,6R)-2-(4-Chloro-3-((2,2-dimethyl-2,3-dihydrobenzo[b][1,4]dioxin-6-yl)methyl)phenyl)-6-(hydroxymethyl)-tetrahydro-2H-pyran-3,4,5-triol | 5.78 |

TABLE 1-continued hSGLT2 Inhibitory Activity

| Compound | Structure | Name | IC$_{50}$ (nM) |
|---|---|---|---|
| E065 | 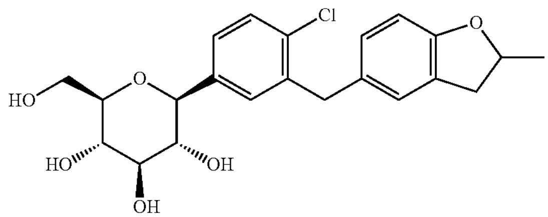 [SMILES: CC1Cc2cc(Cc3cc([C@@H]4O[C@H](CO)[C@@H](O)[C@H](O)[C@H]4O)ccc3Cl)ccc2O1] | (2S,3R,4R,5S,6R)-2-(4-Chloro-3-((2-methyl-2,3-dihydrobenzofuran-5-yl)methyl)phenyl)-6-(hydroxymethyl)-tetrahydro-2H-pyran-3,4,5-triol | 7.62 |
| E066 | 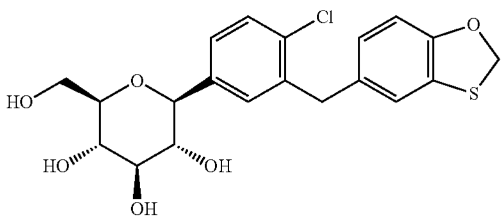 | (2S,3R,4R,5S,6R)-2-(3-(Benzo[d][1,3]oxathiol-5-ylmethyl)-4-chlorophenyl)-6-(hydroxymethyl)-tetrahydro-2H-pyran-3,4,5-triol | 3.67 |
| E068 | 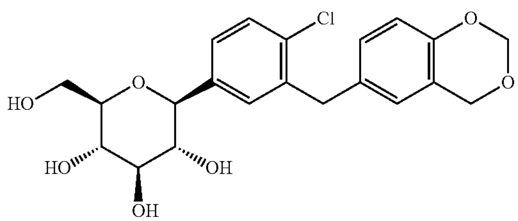 [SMILES: OC[C@H]1O[C@@H](c2ccc(Cl)c(Cc3ccc4c(c3)COCO4)c2)[C@H](O)[C@@H](O)[C@@H]1O] | (2S,3R,4R,5S,6R)-2-(3-((4H-Benzo[d][1,3]dioxin-6-yl)methyl)-4-chlorophenyl)-6-(hydroxymethyl)-tetrahydro-2H-pyran-3,4,5-triol | 9.47 |
| E069 | 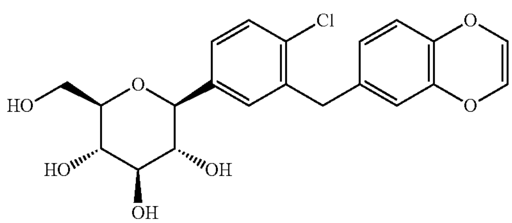 [SMILES: OC[C@H]1O[C@@H](c2ccc(Cl)c(Cc3ccc4c(c3)OC=CO4)c2)[C@H](O)[C@@H](O)[C@@H]1O] | (2S,3R,4R,5S,6R)-2-(3-(Benzo[b][1,4]dioxin-6-ylmethyl)-4-chlorophenyl)-6-(hydroxymethyl)-tetrahydro-2H-pyran-3,4,5-triol | 0.788 |
| E072 | 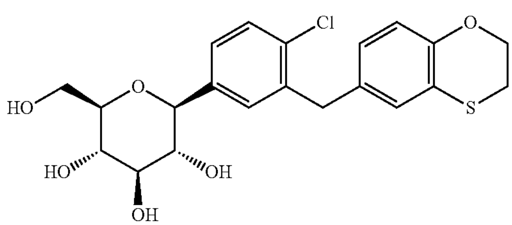 | (2S,3R,4R,5S,6R)-2-(4-Chloro-3-((2,3-dihydrobenzo[b][1,4]oxathiin-6-yl)methyl)phenyl)-6-(hydroxymethyl)-tetrahydro-2H-pyran-3,4,5-triol | 1.75 |
| E073 | 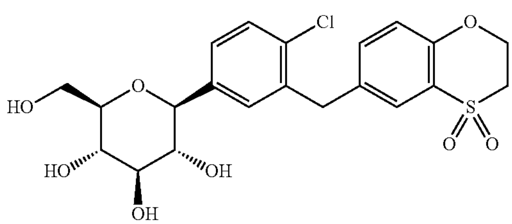 [SMILES: O=S1(=O)CCOc2ccc(Cc3cc([C@@H]4O[C@H](CO)[C@@H](O)[C@H](O)[C@H]4O)ccc3Cl)cc21] | (2S,3R,4R,5S,6R)-2-(4-Chloro-3-((1,1-dioxo-2,3-dihydrobenzo[b][1,4]oxathiin-6-yl)methyl)phenyl)-6-(hydroxymethyl)-tetrahydro-2H-pyran-3,4,5-triol | 78.5 |

TABLE 1-continued hSGLT2 Inhibitory Activity

| Compound | Structure | Name | IC$_{50}$ (nM) |
|---|---|---|---|
| E076 | 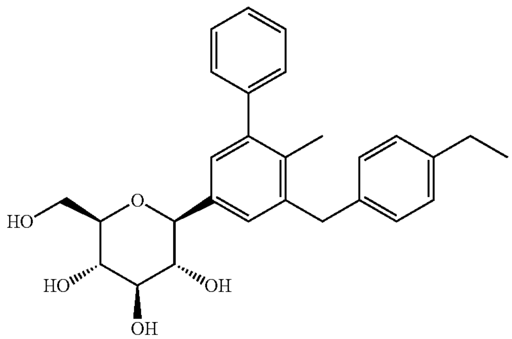 [SMILES: CCc1ccc(Cc2cc([C@@H]3O[C@H](CO)[C@@H](O)[C@H](O)[C@H]3O)cc(-c3ccccc3)c2C)cc1] | (2S,3R,4R,5S,6R)-2-(5-(4-(Ethylbenzyl)-6-methylbiphenyl-3-yl)-6-(hydroxymethyl)-tetrahydro-2H-pyran-3,4,5-triol | 9.63 |
| E077 | 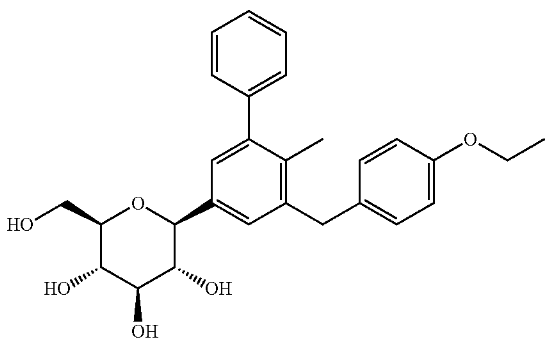 [SMILES: CCOc1ccc(Cc2cc([C@@H]3O[C@H](CO)[C@@H](O)[C@H](O)[C@H]3O)cc(-c3ccccc3)c2C)cc1] | (2S,3R,4R,5S,6R)-2-(5-(4-(Ethoxybenzyl)-6-methylbiphenyl-3-yl)-6-(hydroxymethyl)-tetrahydro-2H-pyran-3,4,5-triol | 3.84 |
| E078 | 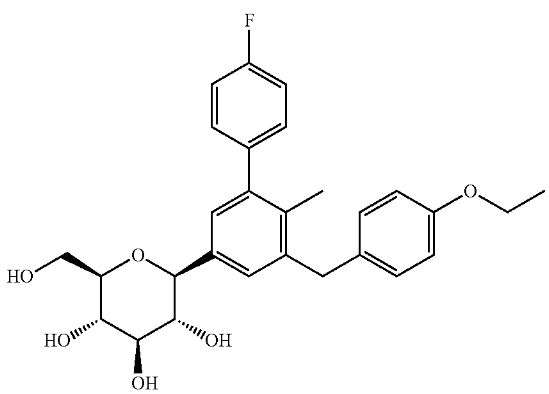 [SMILES: CCOc1ccc(Cc2cc([C@@H]3O[C@H](CO)[C@@H](O)[C@H](O)[C@H]3O)cc(-c3ccc(F)cc3)c2C)cc1] | (2S,3R,4R,5S,6R)-2-(5-(4-(Ethoxybenzyl)-4'-fluoro-6-methylbiphenyl-3-yl)-6-(hydroxymethyl)-tetrahydro-2H-pyran-3,4,5-triol | 93.3 |
| E084 | 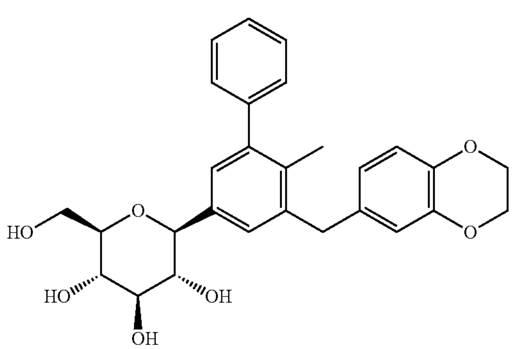 [SMILES: Cc1c(Cc2ccc3c(c2)OCCO3)cc([C@@H]2O[C@H](CO)[C@@H](O)[C@H](O)[C@H]2O)cc1-c1ccccc1] | (2S,3R,4R,5S,6R)-2-(5-((2,3-Dihydrobenzo[b][1,4]dioxin-6-yl)methyl)-6-methylbiphenyl-3-yl)-6-(hydroxymethyl)-tetrahydro-2H-pyran-3,4,5-triol | 5.30 |

TABLE 1-continued hSGLT2 Inhibitory Activity

| Compound | Structure | Name | IC$_{50}$ (nM) |
|---|---|---|---|
| E085 | 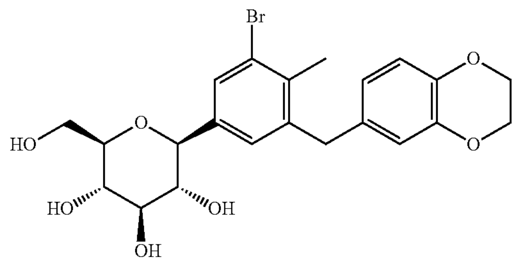 [SMILES: Cc1c(Br)cc([C@@H]2O[C@H](CO)[C@@H](O)[C@H](O)[C@H]2O)cc1Cc1ccc2c(c1)OCCO2] | (2S,3R,4R,5S,6R)-2-(3-Bromo-5-((2,3-dihydrobenzo[b][1,4]dioxin-6-yl)methyl)-4-methylphenyl)-6-(hydroxymethyl)-tetrahydro-2H-pyran-3,4,5-triol | 1.82 |
| E086 | 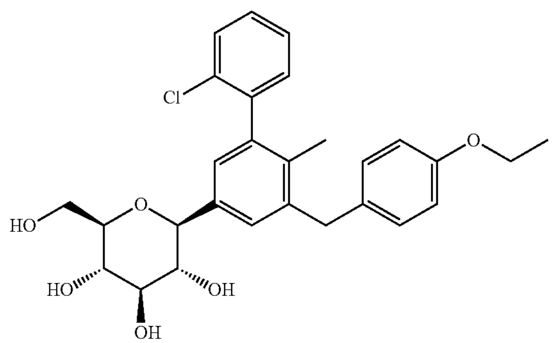 [SMILES: CCOc1ccc(Cc2cc([C@@H]3O[C@H](CO)[C@@H](O)[C@H](O)[C@H]3O)cc(-c3ccccc3Cl)c2C)cc1] | (2S,3R,4R,5S,6R)-2-(6'-Chloro-5-(4-ethoxybenzyl)-6-methylbiphenyl-3-yl)-6-(hydroxymethyl)-tetrahydro-2H-pyran-3,4,5-triol | 15.4 |
| E087 | 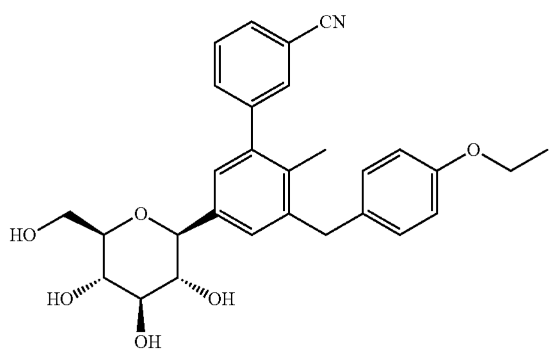 [SMILES: CCOc1ccc(Cc2cc([C@@H]3O[C@H](CO)[C@@H](O)[C@H](O)[C@H]3O)cc(-c3cccc(C#N)c3)c2C)cc1] | 3'-(4-Ethoxybenzyl)-2'-methyl-5'-((2S,3R,4R,5S,6R)-3,4,5-trihydroxy-6-(hydroxymethyl)-tetrahydro-2H-pyran-2-yl)biphenyl-3-carbonitrile | 38.9 |
| E089 | 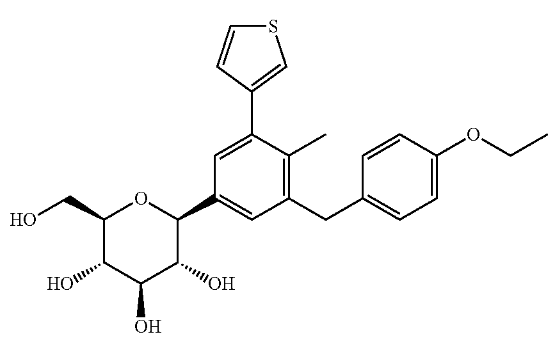 [SMILES: CCOc1ccc(Cc2cc([C@@H]3O[C@H](CO)[C@@H](O)[C@H](O)[C@H]3O)cc(-c3ccsc3)c2C)cc1] | (2S,3R,4R,5S,6R)-2-(3-(4-Ethoxybenzyl)-4-methyl-5-(thiophen-3-yl)phenyl)-6-(hydroxymethyl)-tetrahydro-2H-pyran-3,4,5-triol | 2.55 |

TABLE 1-continued hSGLT2 Inhibitory Activity

| Compound | Structure | Name | IC$_{50}$ (nM) |
|---|---|---|---|
| E090 | 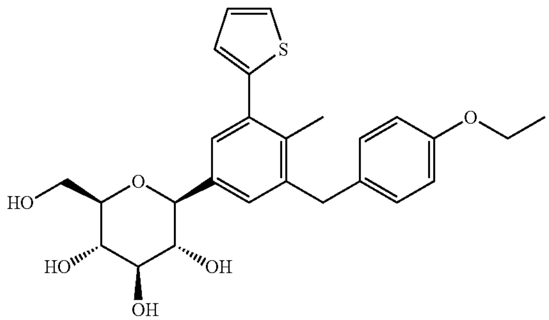 [SMILES: CCOc1ccc(Cc2cc([C@@H]3O[C@H](CO)[C@@H](O)[C@H](O)[C@H]3O)cc(-c3cccs3)c2C)cc1] | (2S,3R,4R,5S,6R)-2-(3-(4-Ethoxybenzyl)-4-methyl-5-(thiophen-2-yl)phenyl)-6-(hydroxymethyl)-tetrahydro-2H-pyran-3,4,5-triol | 3.73 |
| E091 | 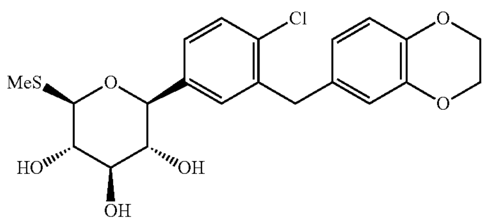 [SMILES: CS[C@H]1O[C@@H](c2ccc(Cl)c(Cc3ccc4c(c3)OCCO4)c2)[C@H](O)[C@@H](O)[C@@H]1O] | (2S,3R,4R,5S,6R)-2-(4-Chloro-3-((2,3-dihydrobenzo[b][1,4]dioxin-6-yl)methyl)phenyl)-6-(methylthio)tetrahydro-2H-pyran-3,4,5-triol | 0.629 |
| E092 | 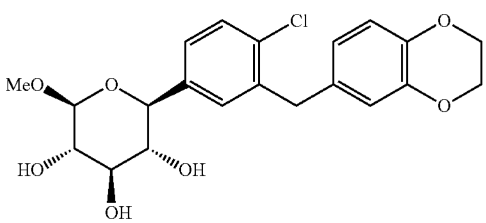 | (2S,3R,4R,5S,6S)-2-(4-Chloro-3-((2,3-dihydrobenzo[b][1,4]dioxin-6-yl)methyl)phenyl)-6-methoxy-tetrahydro-2H-pyran-3,4,5-triol | 8.65 |
| E093 | 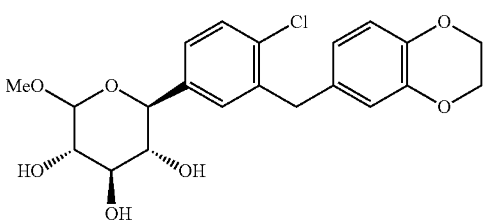 [SMILES: COC1O[C@@H](c2ccc(Cl)c(Cc3ccc4c(c3)OCCO4)c2)[C@H](O)[C@@H](O)[C@@H]1O] | (2S,3R,4R,5S)-2-(4-Chloro-3-((2,3-dihydrobenzo[b][1,4]dioxin-6-yl)methyl)phenyl)-6-methoxytetrahydro-2H-pyran-3,4,5-triol | 16.8 |
| E094 | 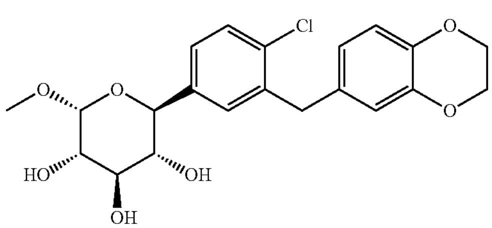 [SMILES: CO[C@@H]1O[C@@H](c2ccc(Cl)c(Cc3ccc4c(c3)OCCO4)c2)[C@H](O)[C@@H](O)[C@@H]1O] | (2S,3R,4R,5S,6R)-2-(4-Chloro-3-((2,3-dihydrobenzo[b][1,4]dioxin-6-yl)methyl)phenyl)-6-methoxy-tetrahydro-2H-pyran-3,4,5-triol | 53.9 |
| E095 | 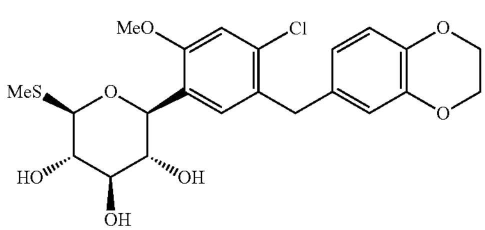 [SMILES: COc1cc(Cl)c(Cc2ccc3c(c2)OCCO3)cc1[C@@H]1O[C@H](SC)[C@@H](O)[C@H](O)[C@H]1O] | (2S,3R,4R,5S,6R)-2-(4-Chloro-5-((2,3-dihydrobenzo[b][1,4]dioxin-6-yl)methyl)-2-methoxyphenyl)-6-(methylthio)-tetrahydro-2H-pyran-3,4,5-triol | 0.628 |

TABLE 1-continued hSGLT2 Inhibitory Activity

| Compound | Structure | Name | IC$_{50}$ (nM) |
|---|---|---|---|
| E096 | 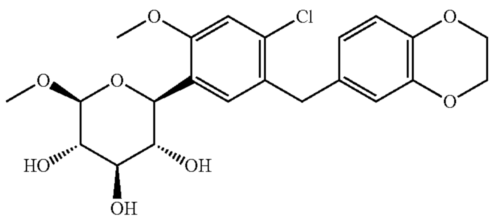 [SMILES: COc1cc(Cl)c(Cc2ccc3c(c2)OCCO3)cc1[C@@H]1O[C@H](OC)[C@@H](O)[C@H](O)[C@H]1O] | (2S,3R4R,5S,6S)-2-(4-Chloro-5-((2,3-dihydrobenzo[b][1,4]dioxin-6-yl)methyl)-2-methoxyphenyl)-6-methoxy-tetrahydro-2H-pyran-3,4,5-triol | 18.5 |
| E097 | 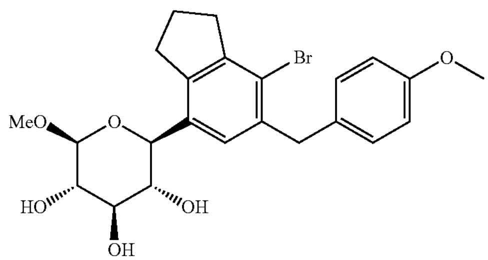 [SMILES: COc1ccc(Cc2cc([C@@H]3O[C@H](OC)[C@@H](O)[C@H](O)[C@H]3O)c3c(c2Br)CCC3)cc1] | (2S,3R,4R,5S,6S)-2-(7-Bromo-6-(4-methoxybenzyl)-2,3-dihydro-1H-inden-4-yl)-6-methoxy-tetrahydro-2H-pyran-3,4,5-triol | 3.83 |
| E098 | 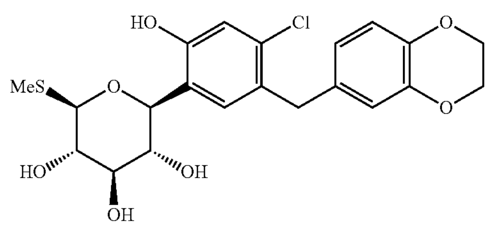 [SMILES: CS[C@H]1O[C@@H](c2cc(Cc3ccc4c(c3)OCCO4)c(Cl)cc2O)[C@H](O)[C@@H](O)[C@@H]1O] | (2S,3R,4R,5S,6R)-2-(4-Chloro-5-((2,3-dihydrobenzo[b][1,4]dioxin-6-yl)methyl)-2-hydroxyphenyl)-6-(methylthio)-tetrahydro-2H-pyran-3,4,5-triol | 0.454 |
| E099 | 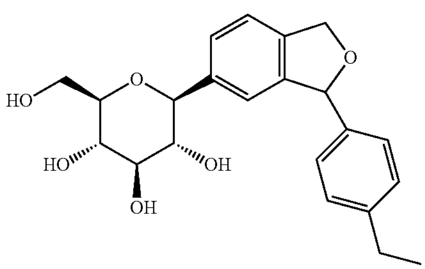 | (2S,3R,4R,5S,6R)-2-(3-(4-Ethylphenyl)-1,3-dihydroisobenzofuran-5-yl)-6-(hydroxymethyl)-tetrahydro-2H-pyran-3,4,5-triol | 56.2 |
| E102 | 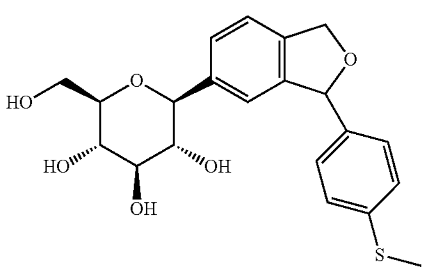 [SMILES: CSc1ccc(C2OCc3ccc([C@@H]4O[C@H](CO)[C@@H](O)[C@H](O)[C@H]4O)cc32)cc1] | (2R,3S,4R,5R,6S)-2-(Hydroxymethyl)-6-(3-(4-(methylthio)phenyl)-1,3-dihydroisobenzofuran-5-yl)4etrahydro-2H-pyran-3,4,5-triol | 75.7 |
| E103 | 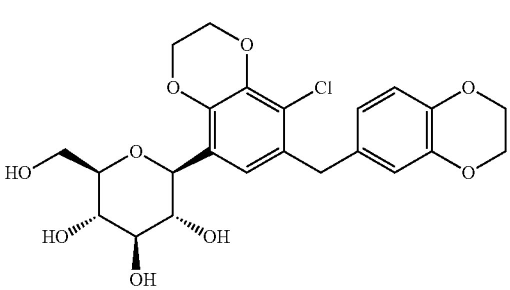 [SMILES: OC[C@H]1O[C@@H](c2cc(Cc3ccc4c(c3)OCCO4)c(Cl)c3c2OCCO3)[C@H](O)[C@@H](O)[C@@H]1O] | (2S,3R,4R,5S,6R)-2-(8-chloro-7-((2,3-dihydrobenzo[b][1,4]dioxin-6-yl)methyl)-2,3-dihydrobenzo[b][1,4]dioxin-5-yl)-6-(hydroxymethyl)tetrahydro-2H-pyran-3,4,5-triol | 1.82 |

TABLE 1-continued hSGLT2 Inhibitory Activity

| Compound | Structure | Name | IC$_{50}$ (nM) |
|---|---|---|---|
| E104 | 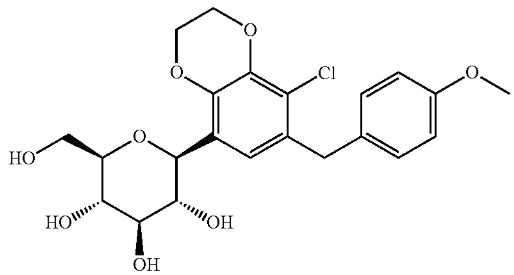 | (2S,3R,4R,5S,6R)-2-(8-chloro-7-(4-methoxybenzyl)-2,3-dihydrobenzo[b][1,4]dioxin-5-yl)-6-(hydroxymethyl)tetrahydro-2H-pyran-3,4,5-triol | 2.00 |
| E105 | 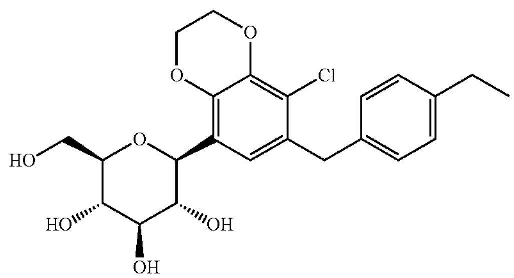 | (2S,3R,4R,5S,6R)-2-(8-chloro-7-(4-ethylbenzyl)-2,3-dihydrobenzo[b][1,4]dioxin-5-yl)-6-(hydroxymethyl)tetrahydro-2H-pyran-3,4,5-triol | 0.923 |
| E106 | 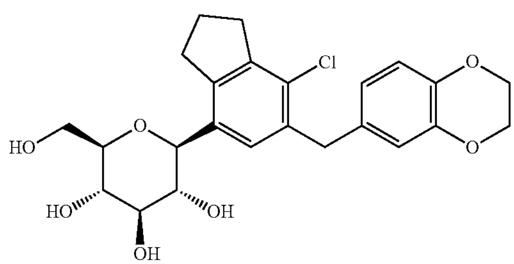 [SMILES: OC[C@H]1O[C@@H](c2cc(Cc3ccc4c(c3)OCCO4)c(Cl)c3c2CCC3)[C@H](O)[C@@H](O)[C@@H]1O] | (2S,3R,4R,5S,6R)-2-(7-chloro-6-((2,3-dihydrobenzo[b][1,4]dioxin-6-yl)methyl)-2,3-dihydro-1H-inden-4-yl)-6-(hydroxymethyl)tetrahydro-2H-pyran-3,4,5-triol | 0.616 |
| E107 | 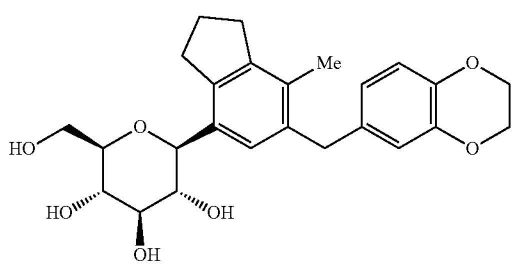 [SMILES: Cc1c(Cc2ccc3c(c2)OCCO3)cc([C@@H]2O[C@H](CO)[C@@H](O)[C@H](O)[C@H]2O)c2c1CCC2] | (2S,3R,4R,5S,6R)-2-(6-((2,3-dihydrobenzo[b][1,4]dioxin-6-yl)methyl)-7-methyl-2,3-dihydro-1H-inden-4-yl)-6-(hydroxymethyl)tetrahydro-2H-pyran-3,4,5 triol | 0.860 |
| E108 | 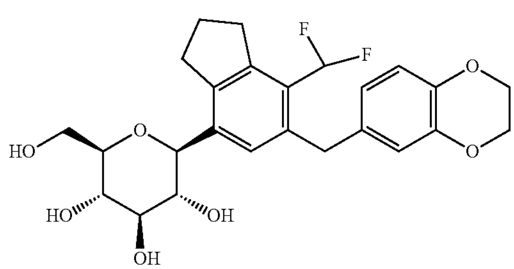 [SMILES: OC[C@H]1O[C@@H](c2cc(Cc3ccc4c(c3)OCCO4)c(C(F)F)c3c2CCC3)[C@H](O)[C@@H](O)[C@@H]1O] | (2S,3R,4R,5S,6R)-2-(7-(difluoromethyl)-6-((2,3-dihydrobenzo[b][1,4]dioxin-6-yl)methyl)-2,3-dihydro-1H-inden-4-yl)-6-(hydroxymethyl)tetrahydro-2H-pyran-3,4,5-triol | 1.26 |

TABLE 1-continued hSGLT2 Inhibitory Activity

| Compound | Structure | Name | IC$_{50}$ (nM) |
|---|---|---|---|
| E109 | 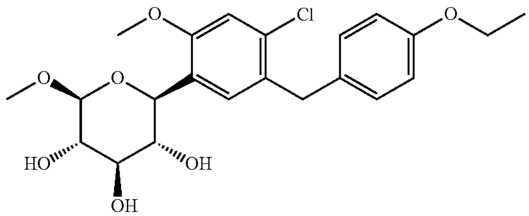 | (2S,3R,4R,5S,6S)-2-(4-Chloro-5-(4-ethoxybenzyl)-2-methoxyphenyl)-6-methoxytetrahydro-2H-pyran-3,4,5-triol | 29.1 |
| E110 | 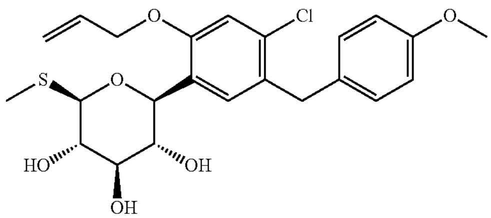 | (2S,3R,4R,5S,6R)-2-(2-(Allyloxy)-4-chloro-5-(4-methoxybenzyl)phenyl)-6-(methylthio)tetrahydro-2H-pyran-3,4,5-triol | 0.504 |
| E111 | 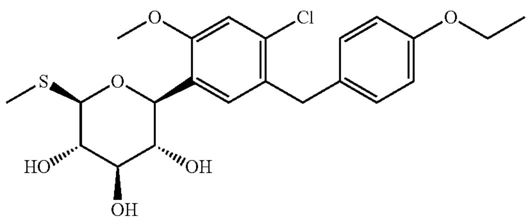 [SMILES: CCOc1ccc(Cc2cc([C@@H]3O[C@H](SC)[C@@H](O)[C@H](O)[C@H]3O)c(OC)cc2Cl)cc1] | (2S,3R,4R,5S,6R)-2-(4-Chloro-5-(4-ethoxybenzyl)-2-methoxyphenyl)-6-(methylthio)tetrahydro-2H-pyran-3,4,5-triol | 0.783 |
| E112 | 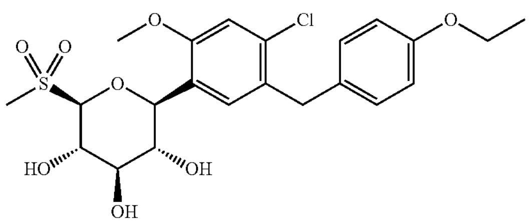 [SMILES: CCOc1ccc(Cc2cc([C@@H]3O[C@H](S(C)(=O)=O)[C@@H](O)[C@H](O)[C@H]3O)c(OC)cc2Cl)cc1] | (2S,3R,4R,5S,6R)-2-(4-Chloro-5-(4-ethoxybenzyl)-2-methoxyphenyl)-6-(methylsulfonyl)tetrahydro-2H-pyran-3,4,5-triol | 7.44 |
| E113 | 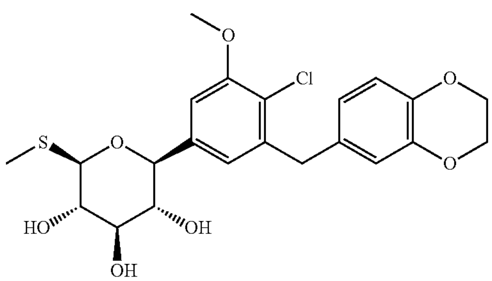 [SMILES: COc1cc([C@@H]2O[C@H](SC)[C@@H](O)[C@H](O)[C@H]2O)cc(Cc2ccc3c(c2)OCCO3)c1Cl] | (2S,3R,4R,5S,6R)-2-(4-Chloro-3-((2,3-dihydrobenzo[b][1,4]dioxin-6-yl)methyl)-5-methoxyphenyl)-6-(methylthio)tetrahydro-2H-pyran-3,4,5-triol | 0.551 |
| E114 | 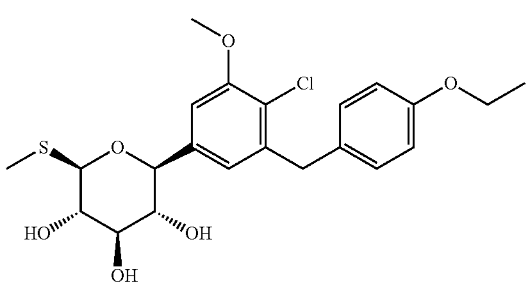 [SMILES: CCOc1ccc(Cc2cc([C@@H]3O[C@H](SC)[C@@H](O)[C@H](O)[C@H]3O)cc(OC)c2Cl)cc1] | (2S,3R,4R,5S,6R)-2-(4-Chloro-3-(4-ethoxybenzyl)-5-methoxyphenyl)-6-(methylthio)tetrahydro-2H-pyran-3,4,5-triol | 0.308 |

TABLE 1-continued hSGLT2 Inhibitory Activity

| Compound | Structure | Name | IC$_{50}$ (nM) |
|---|---|---|---|
| E115 | 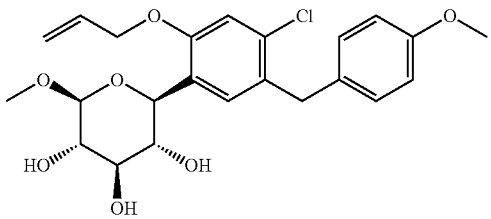 | (2S,3R,4R,5S,6S)-2-(2-(Allyloxy)-4-chloro-5-(4-methoxybenzyl)phenyl)-6-methoxytetrahydro-2H-pyran-3,4,5-triol | 7.06 |
| E116 | 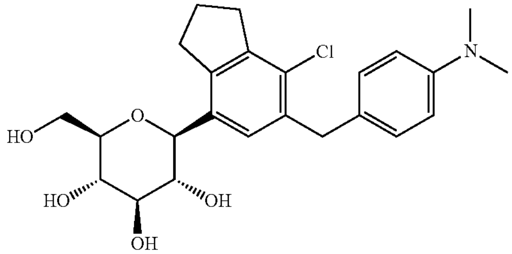 [SMILES: CN(C)c1ccc(Cc2cc([C@@H]3O[C@H](CO)[C@@H](O)[C@H](O)[C@H]3O)c3c(c2Cl)CCC3)cc1] | (2S,3R,4R,5S,6R)-2-(7-Chloro-6-(4-(dimethylamino)benzyl)-2,3-dihydro-1H-inden-4-yl)-6-(hydroxymethyl)tetrahydro-2H-pyran-3,4,5-triol | 0.475 |
| E117 | 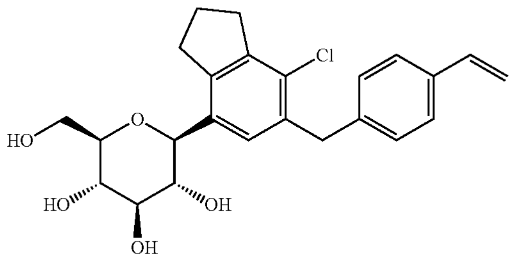 | (2S,3R,4R,5S,6R)-2-(7-Chloro-6-(4-vinylbenzyl)-2,3-dihydro-1H-inden-4-yl)-6-(hydroxymethyl)tetrahydro-2H-pyran-3,4,5-triol | 0.742 |
| E118 | 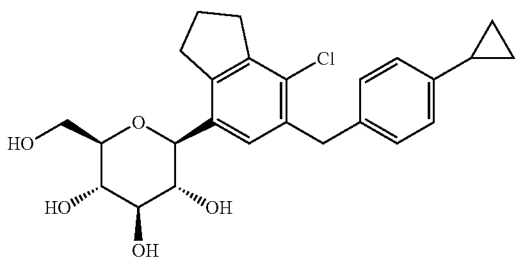 | (2S,3R,4R,5S,6R)-2-(7-Chloro-6-(4-cyclopropylbenzyl)-2,3-dihydro-1H-inden-4-yl)-6-(hydroxymethyl)tetrahydro-2H-pyran-3,4,5-triol | 0.678 |
| E119 | 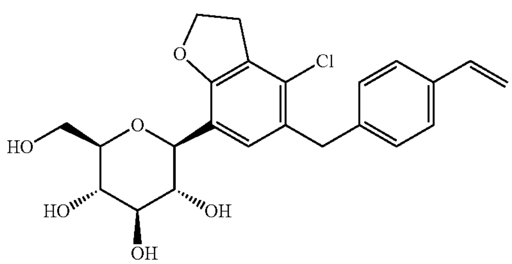 [SMILES: C=Cc1ccc(Cc2cc([C@@H]3O[C@H](CO)[C@@H](O)[C@H](O)[C@H]3O)c3c(c2Cl)CCO3)cc1] | (2S,3R,4R,5S,6R)-2-(4-Chloro-5-(4-vinylbenzyl)-2,3-dihydrobenzofuran-7-yl)-6-(hydroxymethyl)tetrahydro-2H-pyran-3,4,5-triol | 1.38 |
| E120 | 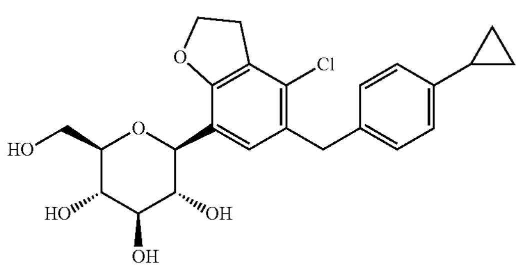 [SMILES: OC[C@H]1O[C@@H](c2cc(Cc3ccc(C4CC4)cc3)c(Cl)c3c2OCC3)[C@H](O)[C@@H](O)[C@@H]1O] | (2S,3R,4R,5S,6R)-2-(4-Chloro-5-(4-cyclopropylbenzyl)-2,3-dihydrobenzofuran-7-yl)-6-(hydroxymethyl)tetrahydro-2H-pyran-3,4,5-triol | 1.09 |

TABLE 1-continued hSGLT2 Inhibitory Activity

| Compound | Structure | Name | IC$_{50}$ (nM) |
|---|---|---|---|
| E121 | 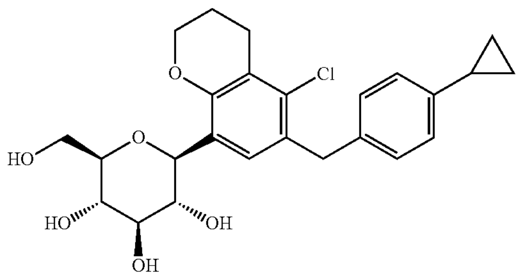 [SMILES: OC[C@H]1O[C@@H](c2cc(Cc3ccc(C4CC4)cc3)c(Cl)c3c2OCCC3)[C@H](O)[C@@H](O)[C@@H]1O] | ((2S,3R,4R,5S,6R)-2-(5-Chloro-6-(4-cyclopropylbenzyl)chroman-8-yl)-6-(hydroxymethyl)tetrahydro-2H-pyran-3,4,5-triol | 0.851 |
| E122 | 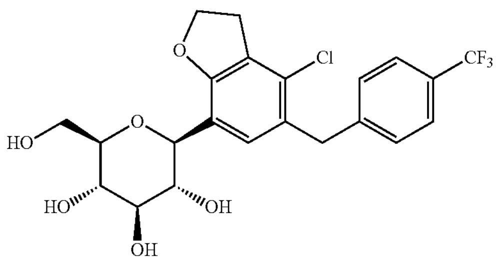 [SMILES: OC[C@H]1O[C@@H](c2cc(Cc3ccc(C(F)(F)F)cc3)c(Cl)c3c2OCC3)[C@H](O)[C@@H](O)[C@@H]1O] | (2S,3R,4R,5S,6R)-2-(4-chloro-5-(4-(trifluoromethyl)benzyl)-2,3-dihydrobenzofuran-7-yl)-6-(hydroxymethyl)tetrahydro-2H-pyran-3,4,5-triol | 1.97 |
| E123 | 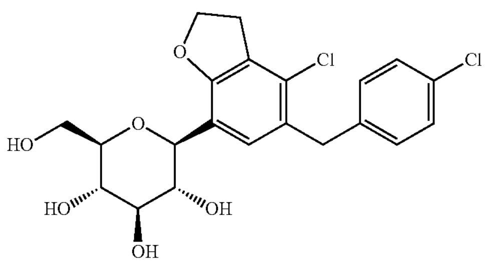 [SMILES: OC[C@H]1O[C@@H](c2cc(Cc3ccc(Cl)cc3)c(Cl)c3c2OCC3)[C@H](O)[C@@H](O)[C@@H]1O] | (2S,3R,4R,5S,6R)-2-(4-chloro-5-(4-chlorobenzyl)-2,3-dihydrobenzofuran-7-6-(hydroxymethyl)tetrahydro-2H-pyran-3,4,5-triol | 1.82 |
| E124 | 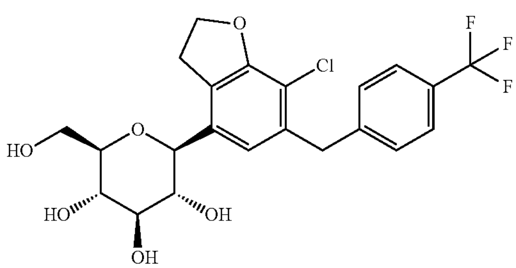 [SMILES: OC[C@H]1O[C@@H](c2cc(Cc3ccc(C(F)(F)F)cc3)c(Cl)c3c2CCO3)[C@H](O)[C@@H](O)[C@@H]1O] | (2S,3R,4R,5S,6R)-2-(7-chloro-6-(4-(trifluoromethyl)benzyl)-2,3-dihydrobenzofuran-4-yl)-6-(hydroxymethyl)tetrahydro-2H-pyran-3,4,5-triol | 1.25 |
| E125 | 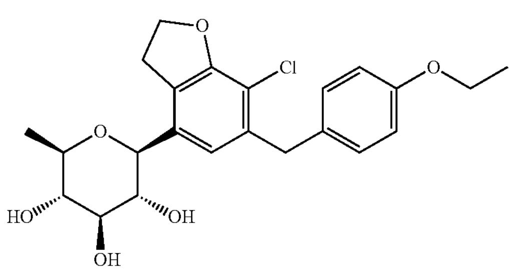 [SMILES: CCOc1ccc(Cc2cc([C@@H]3O[C@H](C)[C@@H](O)[C@H](O)[C@H]3O)c3c(c2Cl)OCC3)cc1] | (2S,3R,4S,5S,6R)-2-(7-chloro-6-(4-ethoxybenzyl)-2,3-dihydrobenzofuran-4-yl)-6-methyltetrahydro-2H-pyran-3,4,5-triol | 0.728 |

татBLE 1-continued hSGLT2 Inhibitory Activity

| Compound | Structure | Name | IC$_{50}$ (nM) |
|---|---|---|---|
| E126 | 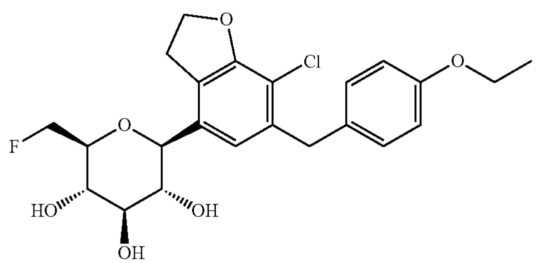 [SMILES: CCOc1ccc(Cc2cc([C@@H]3O[C@H](CF)[C@@H](O)[C@H](O)[C@H]3O)c3c(c2Cl)OCC3)cc1] | (2S,3R,4R,5S,6S)-2-(7-chloro-6-(4-ethoxybenzyl)-2,3-dihydrobenzofuran-4-yl)-6-(fluoromethyl)tetrahydro-2H-pyran-3,4,5-triol | 3.21 |
| E127 | 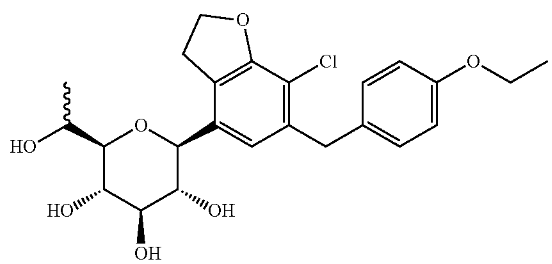 [SMILES: CCOc1ccc(Cc2cc([C@@H]3O[C@H](C(C)O)[C@@H](O)[C@H](O)[C@H]3O)c3c(c2Cl)OCC3)cc1] | (2S,3R,4R,5S,6R)-2-(7-chloro-6-(4-ethoxybenzyl)-2,3-dihydrobenzofuran-4-yl)-6-(1-hydroxyethyl)tetrahydro-2H-pyran-3,4,5-triol | 1.35 |
| E128 | 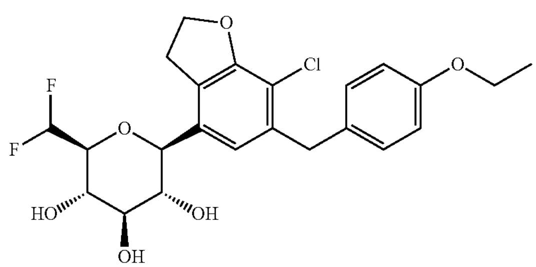 [SMILES: CCOc1ccc(Cc2cc([C@@H]3O[C@H](C(F)F)[C@@H](O)[C@H](O)[C@H]3O)c3c(c2Cl)OCC3)cc1] | (2S,3R,4R,5S,6S)-2-(7-chloro-6-(4-ethoxybenzyl)-2,3-dihydrobenzofuran-4-yl)-6-(difluoromethyl)tetrahydro-2H-pyran-3,4,5-triol | — |
| E129 | 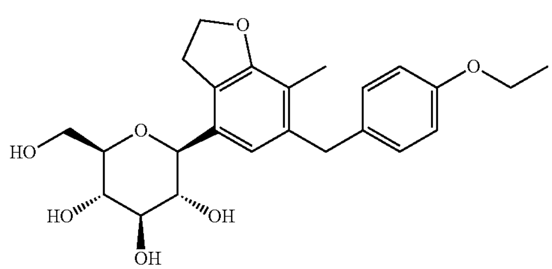 [SMILES: CCOc1ccc(Cc2cc([C@@H]3O[C@H](CO)[C@@H](O)[C@H](O)[C@H]3O)c3c(c2C)OCC3)cc1] | (2S,3R,4R,5S,6R)-2-(6-(4-ethoxybenzyl)-7-methyl-2,3-dihydrobenzofuran-4-yl)-6-(hydroxymethyl)tetrahydro-2H-pyran-3,4,5-triol | 1.28 |
| E130 | 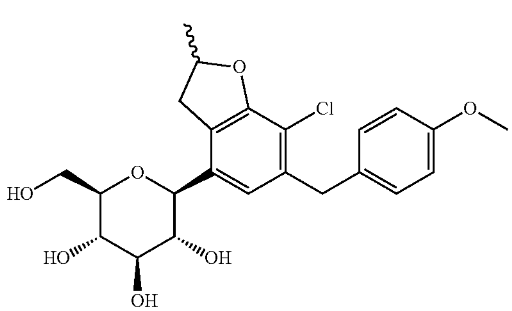 | (2S,3R,4R,5S,6R)-2-(7-chloro-6-(4-methoxybenzyl)-2-methyl-2,3-dihydrobenzofuran-4-yl)-6-(hydroxymethyl)tetrahydro-2H-pyran-3,4,5-triol | 1.78 |

TABLE 1-continued hSGLT2 Inhibitory Activity

| Compound | Structure | Name | IC$_{50}$ (nM) |
|---|---|---|---|
| E131 | 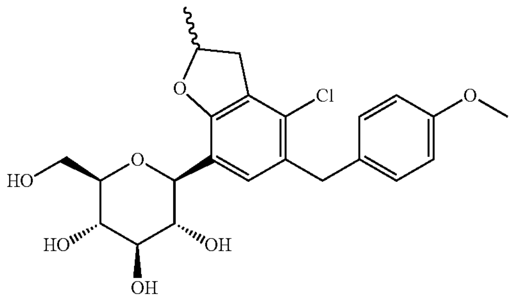 [SMILES: COc1ccc(Cc2cc([C@@H]3O[C@H](CO)[C@@H](O)[C@H](O)[C@H]3O)c3c(c2Cl)CC(C)O3)cc1] | (2S,3R,4R,5S,6R)-2-(4-chloro-5-(4-methoxybenzyl)-2-methyl-2,3-dihydrobenzofuran-7-yl)-6-(hydroxymethyl)tetrahydro-2H-pyran-3,4,5-triol | 1.02 |
| E132 | 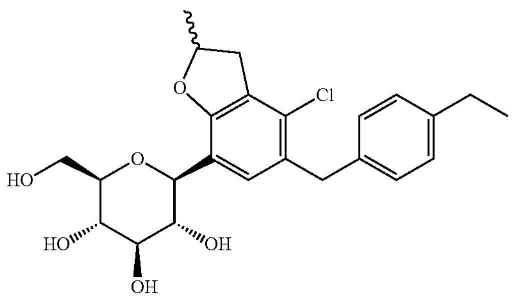 | (2S,3R,4R,5S,6R)-2-(4-chloro-5-(4-ethylbenzyl)-2-methyl-2,3-dihydrobenzofuran-7-yl)-6-(hydroxymethyl)tetrahydro-2H-pyran-3,4,5-triol | 0.706 |
| E133 | 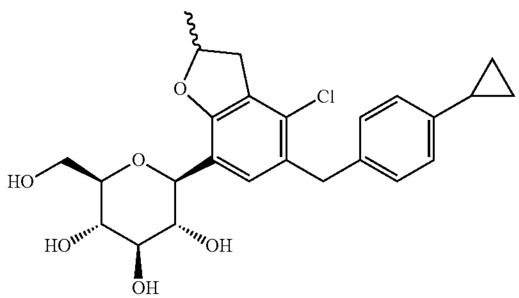 [SMILES: CC1Cc2c(Cl)c(Cc3ccc(C4CC4)cc3)cc([C@@H]3O[C@H](CO)[C@@H](O)[C@H](O)[C@H]3O)c2O1] | (2S,3R,4R,5S,6R)-2-(4-chloro-5-(4-cyclopropylbenzyl)-2-methyl-2,3-dihydrobenzofuran-7-yl)-6-(hydroxymethyl)tetrahydro-2H-pyran-3,4,5-triol | 1.11 |
| E134 | 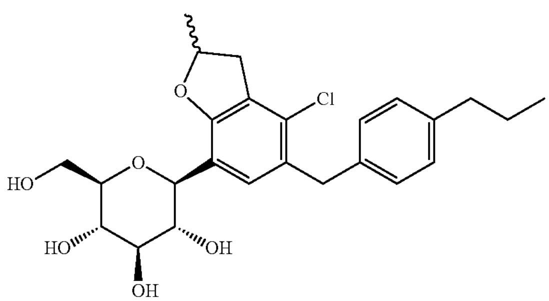 [SMILES: CCCc1ccc(Cc2cc([C@@H]3O[C@H](CO)[C@@H](O)[C@H](O)[C@H]3O)c3c(c2Cl)CC(C)O3)cc1] | (2S,3R,4R,5S,6R)-2-(4-chloro-2-methyl-5-(4-propylbenzyl)-2,3-dihydrobenzofuran-7-yl)-6-(hydroxymethyl)tetrahydro-2H-pyran-3,4,5-triol | 0.885 |
| E135 | 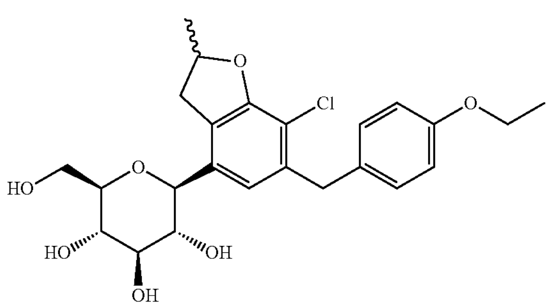 | (2S,3R,4R,5S,6R)-2-(7-chloro-6-(4-ethoxybenzyl)-2-methyl-2,3-dihydrobenzofuran-4-yl)-6-(hydroxymethyl)tetrahydro-2H-pyran-3,4,5-triol | 1.65 |

TABLE 1-continued hSGLT2 Inhibitory Activity

| Compound | Structure | Name | IC$_{50}$ (nM) |
|---|---|---|---|
| E136 | 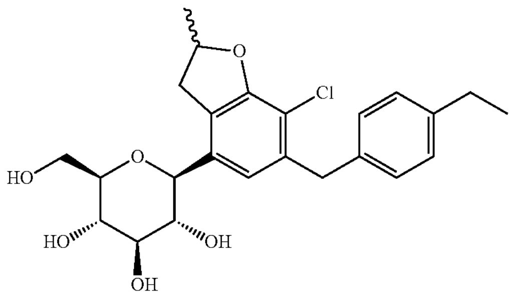 [SMILES: CCc1ccc(Cc2cc([C@@H]3O[C@H](CO)[C@@H](O)[C@H](O)[C@H]3O)c3c(c2Cl)OC(C)C3)cc1] | (2S,3R,4R,5S,6R)-2-(7-chloro-6-(4-ethylbenzyl)-2-methyl-2,3-dihydrobenzofuran-4-yl)-6-(hydroxymethyl)tetrahydro-2H-pyran-3,4,5-triol | 0.835 |
| E137 | 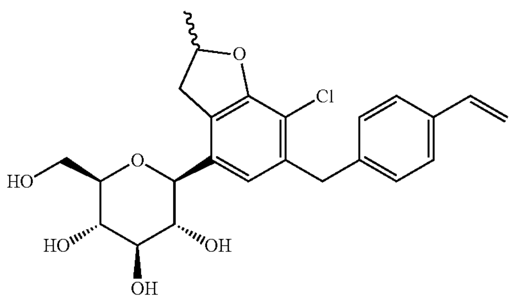 [SMILES: C=Cc1ccc(Cc2cc([C@@H]3O[C@H](CO)[C@@H](O)[C@H](O)[C@H]3O)c3c(c2Cl)OC(C)C3)cc1] | (2S,3R,4R,5S,6R)-2-(7-chloro-2-methyl-6-(4-vinylbenzyl)-2,3-dihydrobenzofuran-4-yl)-6-(hydroxymethyl)tetrahydro-2H-pyran-3,4,5-triol | 1.00 |
| E138 | 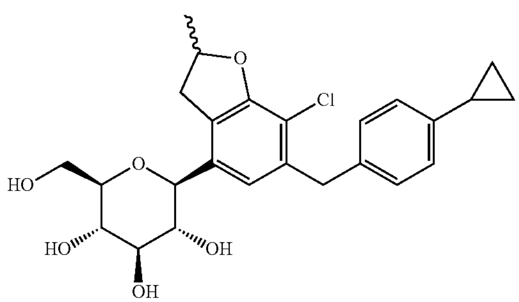 [SMILES: CC1Cc2c([C@@H]3O[C@H](CO)[C@@H](O)[C@H](O)[C@H]3O)cc(Cc3ccc(C4CC4)cc3)c(Cl)c2O1] | ((2S,3R,4R,5S,6R)-2-(7-chloro-6-(4-cyclopropylbenzyl)-2-methyl-2,3-dihydrobenzofuran-4-yl)-6-(hydroxymethyl)tetrahydro-2H-pyran-3,4,5-triol | 1.13 |
| E139 | 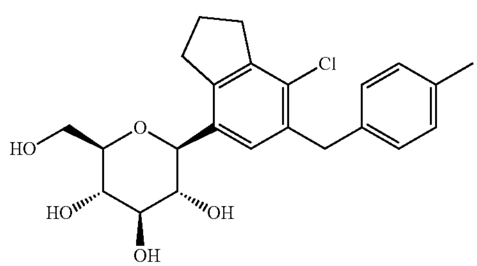 [SMILES: Cc1ccc(Cc2cc([C@@H]3O[C@H](CO)[C@@H](O)[C@H](O)[C@H]3O)c3c(c2Cl)CCC3)cc1] | (2S,3R,4R,5S,6R)-2-(7-chloro-6-(4-methylbenzyl)-2,3-dihydro-1H-inden-4-yl)-6-(hydroxymethyl)tetrahydro-2H-pyran-3,4,5-triol | 0.808 |
| E140 | 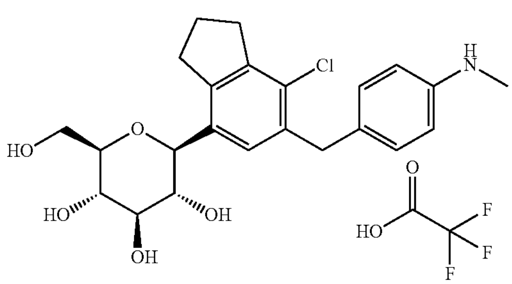 | (2S,3R,4R,5S,6R)-2-(7-chloro-6-(4-(methylamino)benzyl)-2,3-dihydro-1H-inden-4-yl)-6-(hydroxymethyl)tetrahydro-2H-pyran-3,4,5-triol 2,2,2-trifluoroacetate | 1.34 |

TABLE 1-continued hSGLT2 Inhibitory Activity

| Compound | Structure | Name | IC$_{50}$ (nM) |
|---|---|---|---|
| E141 | 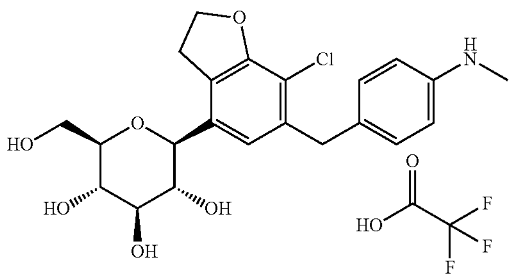 | (2S,3R,4R,5S,6R)-2-(7-chloro-6-(4-(methylamino)benzyl)-2,3-dihydrobenzofuran-4-yl)-6-(hydroxymethyl)tetrahydro-2H-pyran-3,4,5-triol 2,2,2-trifluoroacetate | 2.82 |
| E142 | 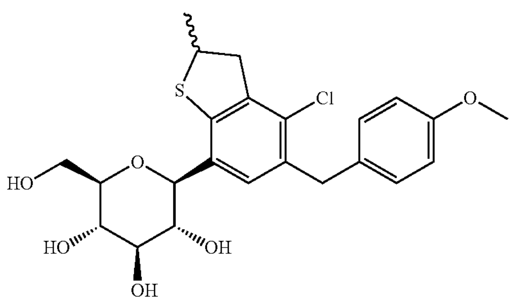 [SMILES: COc1ccc(Cc2cc([C@@H]3O[C@H](CO)[C@@H](O)[C@H](O)[C@H]3O)c3c(c2Cl)CC(C)S3)cc1] | (2S,3R,4R,5S,6R)-2-(4-chloro-5-(4-methoxybenzyl)-2-methyl-2,3-dihydrobenzo[b]thiophen-7-yl)-6-(hydroxymethyl)tetrahydro-2H-pyran-3,4,5-triol | 1.09 |
| E143 | 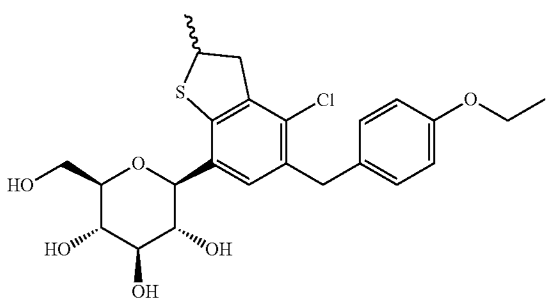 | (2S,3R,4R,5S,6R)-2-(4-chloro-5-(4-ethoxybenzyl)-2-methyl-2,3-dihydrobenzo[b]thiophen-7-yl)-6-(hydroxymethyl)tetrahydro-2H-pyran-3,4,5-triol | 1.03 |
| E144 | 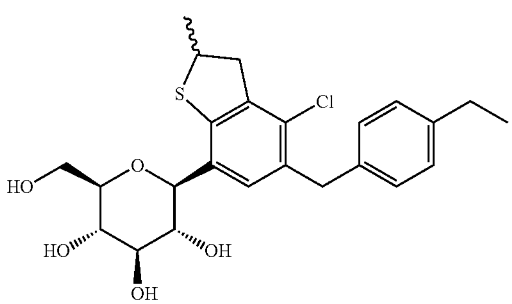 | (2S,3R,4R,5S,6R)-2-(4-chloro-5-(4-ethylbenzyl)-2-methyl-2,3-dihydrobenzo[b]thiophen-7-yl)-6-(hydroxymethyl)tetrahydro-2H-pyran-3,4,5-triol | 0.976 |
| E145 | 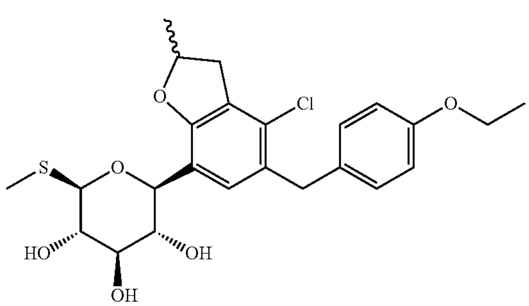 [SMILES: CCOc1ccc(Cc2cc([C@@H]3O[C@H](SC)[C@@H](O)[C@H](O)[C@H]3O)c3c(c2Cl)CC(C)O3)cc1] | (2S,3R,4R,5S,6R)-2-(4-chloro-5-(4-ethoxybenzyl)-2-methyl-2,3-dihydrobenzofuran-7-yl)-6-(methylthio)tetrahydro-2H-pyran-3,4,5-triol | 0.685 |

TABLE 1-continued hSGLT2 Inhibitory Activity

| Compound | Structure | Name | IC$_{50}$ (nM) |
|---|---|---|---|
| E146 | 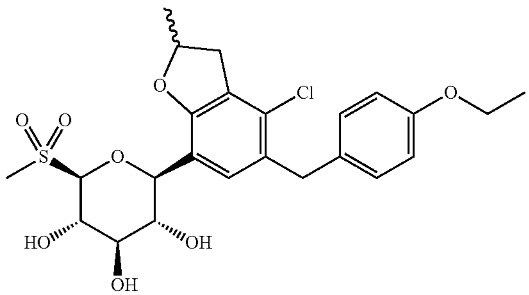 [SMILES: CCOc1ccc(Cc2cc([C@@H]3O[C@H](S(C)(=O)=O)[C@@H](O)[C@H](O)[C@H]3O)c3c(c2Cl)CC(C)O3)cc1] | (2S,3R,4R,5S,6R)-2-(4-chloro-5-(4-ethoxybenzyl)-2-methyl-2,3-dihydrobenzofuran-7-yl)-6-(methylsulfonyl)tetrahydro-2H-pyran-3,4,5-triol | 3.45 |
| E147 | 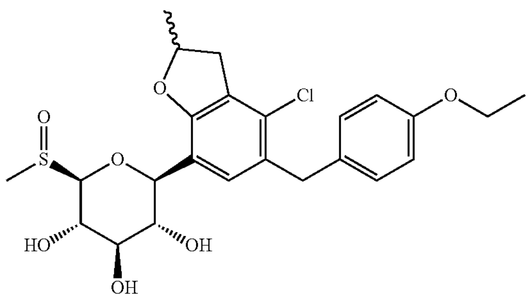 [SMILES: CCOc1ccc(Cc2cc([C@@H]3O[C@H](S(C)=O)[C@@H](O)[C@H](O)[C@H]3O)c3c(c2Cl)CC(C)O3)cc1] | (2S,3R,4R,5S,6R)-2-(4-chloro-5-(4-ethoxybenzyl)-2-methyl-2,3-dihydrobenzofuran-7-yl)-6-((S)-methylsulfinyl)tetrahydro-2H-pyran-3,4,5-triol | 5.40 |
| E148 | 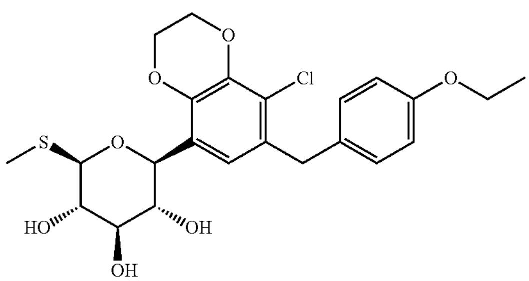 [SMILES: CCOc1ccc(Cc2cc([C@@H]3O[C@H](SC)[C@@H](O)[C@H](O)[C@H]3O)c3c(c2Cl)OCCO3)cc1] | (2S,3R,4R,5S,6R)-2-(8-chloro-7-(4-ethoxybenzyl)-2,3-dihydrobenzo[b][1,4]dioxin-5-yl)-6-methylthio)tetrahydro-2H-pyran-3,4,5-triol | — |
| E149 | 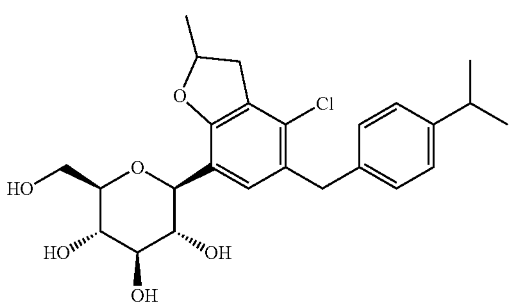 [SMILES: CC1Cc2c(Cl)c(Cc3ccc(C(C)C)cc3)cc([C@@H]3O[C@H](CO)[C@@H](O)[C@H](O)[C@H]3O)c2O1] | (2S,3R,4R,5S,6R)-2-(4-chloro-5-(4-isopropylbenzyl)-2-methyl-2,3-dihydrobenzofuran-7-yl)-6-(hydroxymethyl)tetrahydro-2H-pyran-3,4,5-triol | 1.80 |
| E150 | 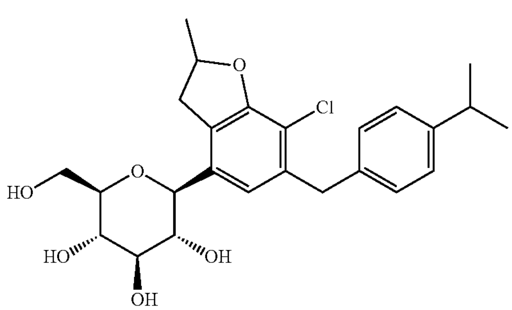 [SMILES: CC1Cc2c([C@@H]3O[C@H](CO)[C@@H](O)[C@H](O)[C@H]3O)cc(Cc3ccc(C(C)C)cc3)c(Cl)c2O1] | (2S,3R,4R,5S,6R)-2-(7-Chloro-6-(4-isopropylbenzyl)-2-methyl-2,3-dihydrobenzofuran-4-yl)-6-(hydroxymethyl)tetrahydro-2H-pyran-3,4,5-triol | 1.44 |

TABLE 1-continued hSGLT2 Inhibitory Activity

| Compound | Structure | Name | IC$_{50}$ (nM) |
|---|---|---|---|
| E151 | 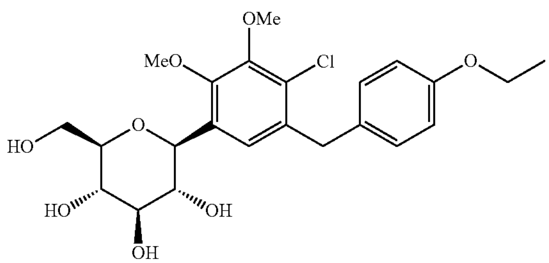 [SMILES: CCOc1ccc(Cc2cc([C@@H]3O[C@H](CO)[C@@H](O)[C@H](O)[C@H]3O)c(OC)c(OC)c2Cl)cc1] | (2S,3R,4R,5S,6R)-2-(4-chloro-5-(4-ethoxybenzyl)-2,3-dimethoxyphenyl)-6-(hydroxymethyl)tetrahydro-2H-pyran-3,4,5-triol | — |
| E152 | 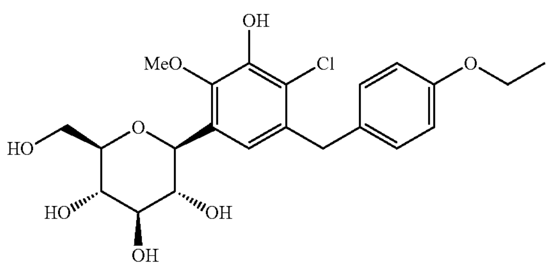 | (2S,3R,4R,5S,6R)-2-(4-chloro-5-(4-ethoxybenzyl)-3-hydroxy-2-methoxyphenyl)-6-(hydroxymethyl)tetrahydro-2H-pyran-3,4,5-triol | — |
| E153 | 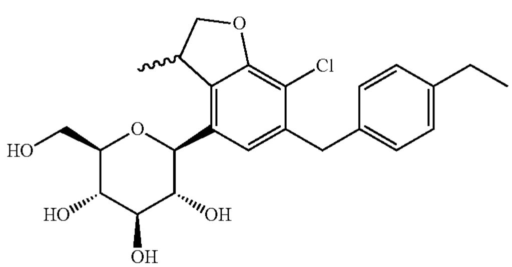 [SMILES: CCc1ccc(Cc2cc([C@@H]3O[C@H](CO)[C@@H](O)[C@H](O)[C@H]3O)c3c(c2Cl)OCC3C)cc1] | (2S,3R,4R,5S,6R)-2-(7-chloro-6-(4-ethylbenzyl)-3-methyl-2,3-dihydrobenzofuran-4-yl)-6-(hydroxymethyl)tetrahydro-2H-pyran-3,4,5-triol | 0.721 |
| E154 | 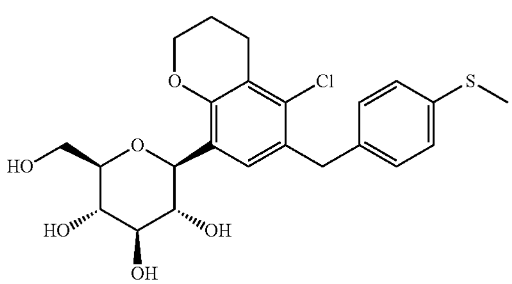 | (2S,3R,4R,5S,6R)-2-(5-chloro-6-(4-(methylthio)benzyl)chroman-8-yl)-6-(hydroxymethyl)tetrahydro-2H-pyran-3,4,5-triol | 1.01 |
| E155 | 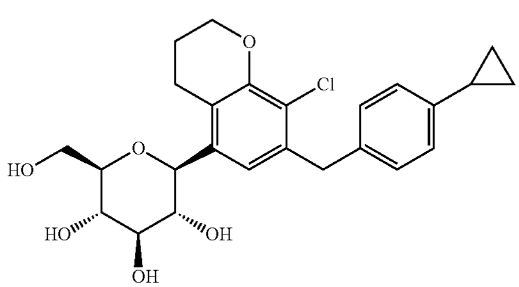 | (2S,3R,4R,5S,6R)-2-(8-chloro-7-(4-cyclopropylbenzyl)chroman-5-yl)-6-(hydroxymethyl)tetrahydro-2H-pyran-3,4,5-triol | 0.881 |

TABLE 1-continued hSGLT2 Inhibitory Activity

| Compound | Structure | Name | IC$_{50}$ (nM) |
|---|---|---|---|
| E156 | 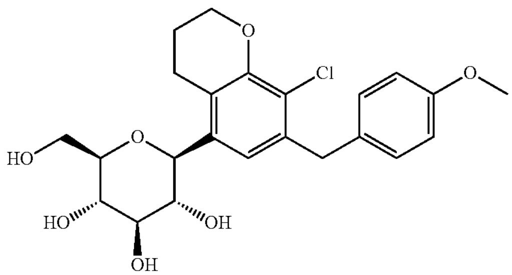 | (2S,3R,4R,5S,6R)-2-(8-chloro-7-(4-methoxybenzyl)chroman-5-yl)-6-(hydroxymethyl)tetrahydro-2H-pyran-3,4,5-triol | 2.09 |
| E157 | 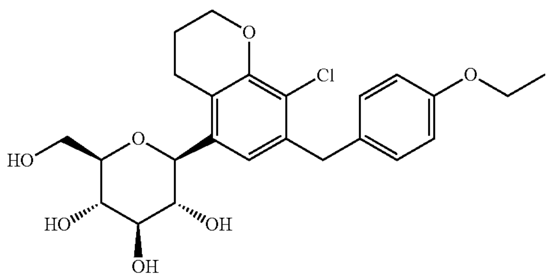 [SMILES: CCOc1ccc(Cc2cc([C@@H]3O[C@H](CO)[C@@H](O)[C@H](O)[C@H]3O)c3c(c2Cl)OCCC3)cc1] | (2S,3R,4R,5S,6R)-2-(8-chloro-7-(4-ethoxybenzyl)chroman-5-yl)-6-(hydroxymethyl)tetrahydro-2H-pyran-3,4,5-triol | 1.28 |
| E158 | 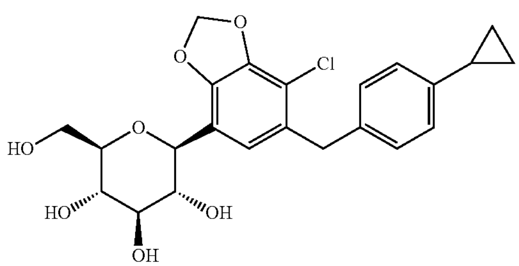 [SMILES: OC[C@H]1O[C@@H](c2cc(Cc3ccc(C4CC4)cc3)c(Cl)c3c2OCO3)[C@H](O)[C@@H](O)[C@@H]1O] | (2S,3R,4R,5S,6R)-2-(7-chloro-6-(4-cyclopropylbenzyl)benzo[d][1,3]dioxol-4-yl)-6-(hydroxymethyl)tetrahydro-2H-pyran-3,4,5-triol | 0.366 |
| E159 | 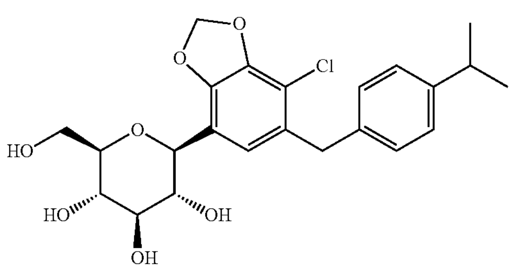 | (2S,3R,4R,5S,6R)-2-(7-chloro-6-(4-isopropylbenzyl)benzo[d][1,3]dioxol-4-yl)-6-(hydroxymethyl)tetrahydro-2H-pyran-3,4,5-triol | 0.872 |
| E160 | 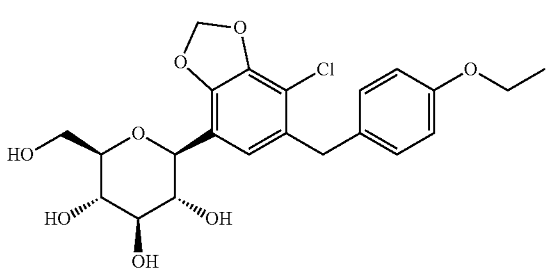 [SMILES: CCOc1ccc(Cc2cc([C@@H]3O[C@H](CO)[C@@H](O)[C@H](O)[C@H]3O)c3c(c2Cl)OCO3)cc1] | (2S,3R,4R,5S,6R)-2-(7-chloro-6-(4-ethoxybenzyl)benzo[d][1,3]dioxol-4-yl)-6-(hydroxymethyl)tetrahydro-2H-pyran-3,4,5-triol | 1.08 |

TABLE 1-continued hSGLT2 Inhibitory Activity

| Compound | Structure | Name | IC$_{50}$ (nM) |
|---|---|---|---|
| E161 | 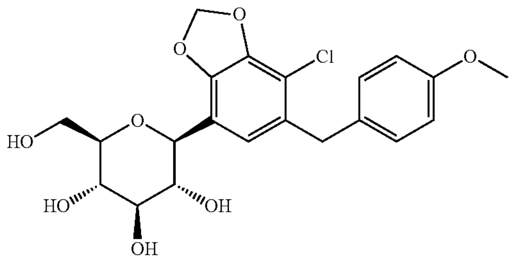 | (2S,3R,4R,5S,6R)-2-(7-chloro-6-(4-methoxybenzyl)benzo[d][1,3]dioxol-4-yl)-6-(hydroxymethyl)tetrahydro-2H-pyran-3,4,5-triol | 1.15 |
| E162 | 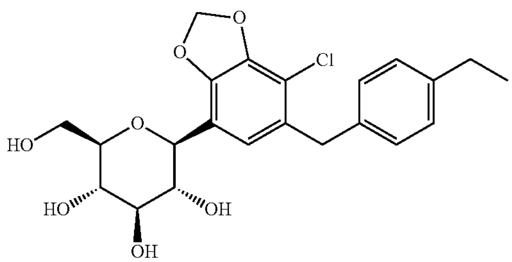 | (2S,3R,4R,5S,6R)-2-(7-chloro-6-(4-ethylbenzyl)benzo[d][1,3]dioxol-4-yl)-6-(hydroxymethyl)tetrahydro-2H-pyran-3,4,5-triol | 0.404 |
| E163 | 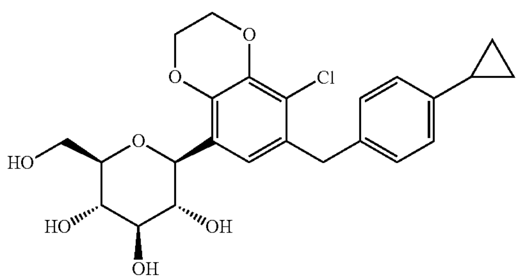 [SMILES: OC[C@H]1O[C@@H](c2cc(Cc3ccc(C4CC4)cc3)c(Cl)c3c2OCCO3)[C@H](O)[C@@H](O)[C@@H]1O] | (2S,3R,4R,5S,6R)-2-(8-chloro-7-(4-cyclopropylbenzyl)-2,3-dihydrobenzo[b][1,4]dioxin-5-yl)-6-(hydroxymethyl)tetrahydro-2H-pyran-3,4,5-triol | 0.651 |
| E164 | 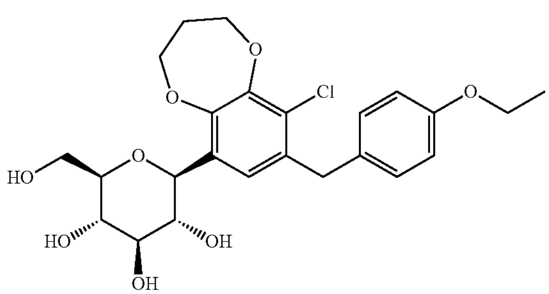 [SMILES: CCOc1ccc(Cc2cc([C@@H]3O[C@H](CO)[C@@H](O)[C@H](O)[C@H]3O)c3c(c2Cl)OCCCO3)cc1] | (2S,3R,4R,5S,6R)-2-(9-chloro-8-(4-ethoxybenzyl)-3,4-dihydro-2H-benzo[b][1,4]dioxepin-6-yl)-6-(hydroxymethyl)tetrahydro-2H-pyran-3,4,5-triol | 1.28 |
| E165 | 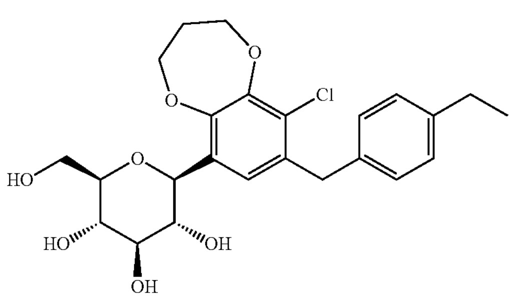 [SMILES: CCc1ccc(Cc2cc([C@@H]3O[C@H](CO)[C@@H](O)[C@H](O)[C@H]3O)c3c(c2Cl)OCCCO3)cc1] | (2S,3R,4R,5S,6R)-2-(9-chloro-8-(4-ethylbenzyl)-3,4-dihydro-2H-benzo[b][1,4]dioxepin-6-yl)-6-(hydroxymethyl)tetrahydro-2H-pyran-3,4,5-triol | 1.08 |

TABLE 1-continued hSGLT2 Inhibitory Activity

| Compound | Structure | Name | IC$_{50}$ (nM) |
|---|---|---|---|
| E166 | 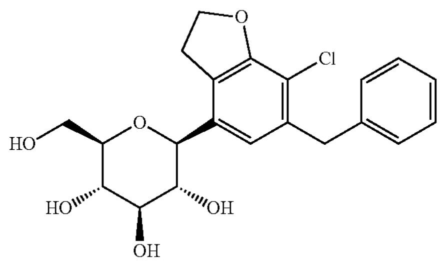 [SMILES: OC[C@H]1O[C@@H](c2cc(Cc3ccccc3)c(Cl)c3c2CCO3)[C@H](O)[C@@H](O)[C@@H]1O] | (2S,3R,4R,5S,6R)-2-(6-Benzyl-7-chloro-2,3-dihydrobenzofuran-4-yl)-6-(hydroxymethyl)tetrahydro-2H-pyran-3,4,5-triol | 4.22 |
| E168 | 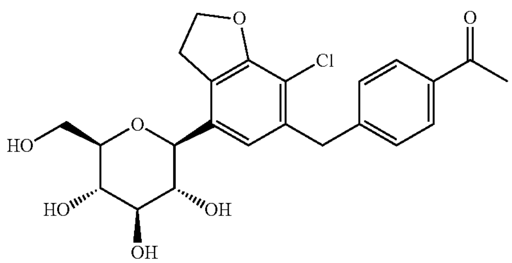 [SMILES: CC(=O)c1ccc(Cc2cc([C@@H]3O[C@H](CO)[C@@H](O)[C@H](O)[C@H]3O)c3c(c2Cl)OCC3)cc1] | 1-(4-((7-Chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)phenyl)ethanone | 0.960 |
| E169 | 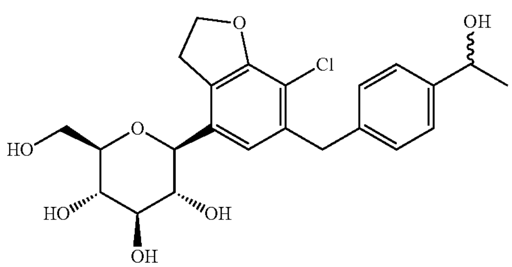 | (2S,3R,4R,5S,6R)-2-(7-Chloro-6-(4-(1-hydroxyethyl)benzyl)-2,3-dihydrobenzofuran-4-yl)-6-(hydroxymethyl)tetrahydro-2H-pyran-3,4,5-triol | 2.12 |
| E170 | 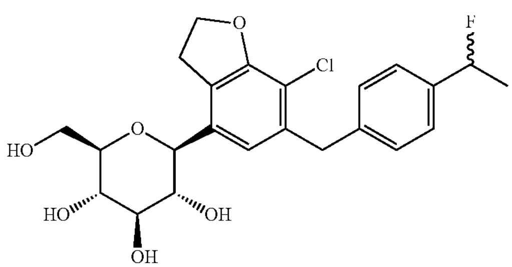 | (2S,3R,4R,5S,6R)-2-(7-Chloro-6-(4-(1-fluoroethyl)benzyl)-2,3-dihydrobenzofuran-4-yl)-6-(hydroxymethyl)tetrahydro-2H-pyran-3,4,5-triol | 1.46 |
| E171 | 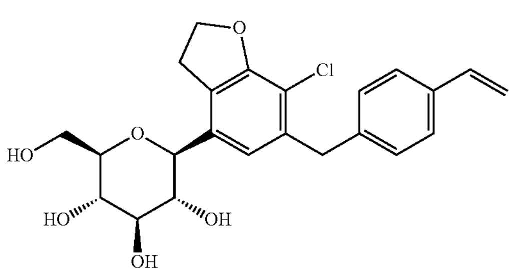 [SMILES: C=Cc1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-Chloro-6-(4-vinylbenzyl)-2,3-dihydrobenzofuran-4-yl)-6-(hydroxymethyl)tetrahydro-2H-pyran-3,4,5-triol | 0.366 |

TABLE 1-continued hSGLT2 Inhibitory Activity

| Compound | Structure | Name | IC$_{50}$ (nM) |
|---|---|---|---|
| E172 | 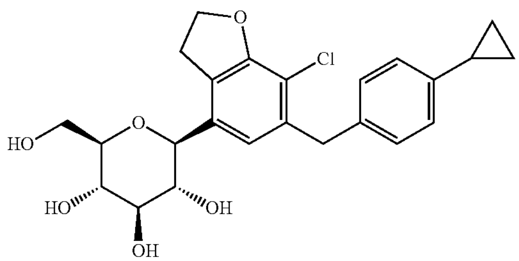 | (2S,3R,4R,5S,6R)-2-(7-Chloro-6-(4-cyclopropylbenzyl)-2,3-dihydrobenzofuran-4-yl)-6-(hydroxymethyl)tetrahydro-2H-pyran-3,4,5-triol | 0.463 |
| E173 | 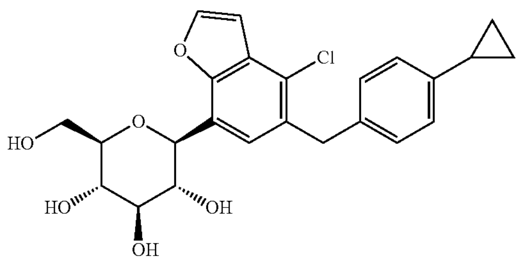 [SMILES: OC[C@H]1O[C@@H](c2cc(Cc3ccc(C4CC4)cc3)c(Cl)c3ccoc23)[C@H](O)[C@@H](O)[C@@H]1O] | (2S,3R,4R,5S,6R)-2-(4-Chloro-5-(4-cyclopropylbenzyl)benzofuran-7-yl)-6-(hydroxymethyl)tetrahydro-2H-pyran-3,4,5-triol | 18.1 |
| E174 | 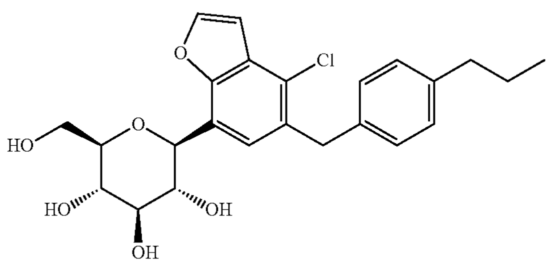 [SMILES: CCCc1ccc(Cc2cc([C@@H]3O[C@H](CO)[C@@H](O)[C@H](O)[C@H]3O)c3occc3c2Cl)cc1] | (2S,3R,4R,5S,6R)-2-(4-Chloro-5-(4-propylbenzyl)benzofuran-7-yl)-6-(hydroxymethyl)tetrahydro-2H-pyran-3,4,5-triol | 574 |
| E175 | 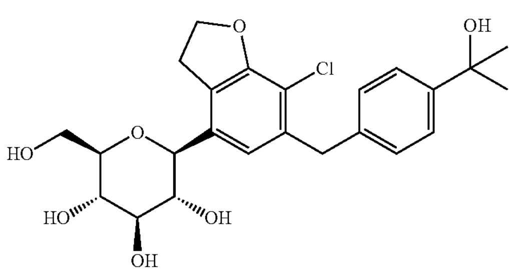 [SMILES: CC(C)(O)c1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-Chloro-6-(4-(2-hydroxypropan-2-yl)benzyl)-2,3-dihydrobenzofuran-4-yl)-6-(hydroxymethyl)tetrahydro-2H-pyran-3,4,5 triol | 2.03 |
| E176 | 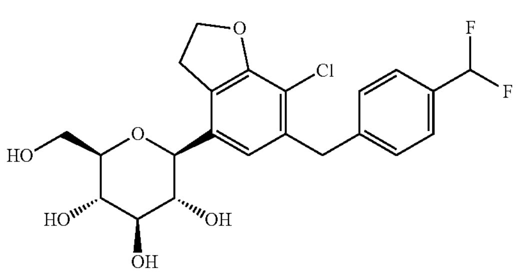 [SMILES: OC[C@H]1O[C@@H](c2cc(Cc3ccc(C(F)F)cc3)c(Cl)c3c2CCO3)[C@H](O)[C@@H](O)[C@@H]1O] | (2S,3R,4R,5S,6R)-2-(7-chloro-6-(4-(difluoromethyl)benzyl)-2,3-dihydrobenzofuran-4-yl)-6-(hydroxymethyl)tetrahydro-2H-pyran-3,4,5-triol | 1.14 |

TABLE 1-continued hSGLT2 Inhibitory Activity

| Compound | Structure | Name | IC$_{50}$ (nM) |
|---|---|---|---|
| E177 | 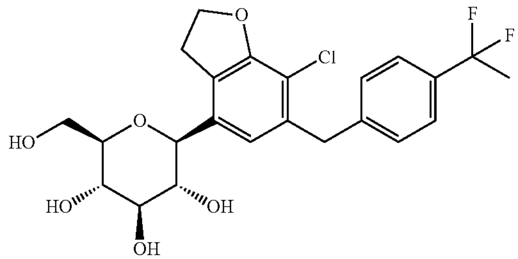 [SMILES: CC(F)(F)c1ccc(Cc2cc([C@@H]3O[C@H](CO)[C@@H](O)[C@H](O)[C@H]3O)c3c(c2Cl)OCC3)cc1] | (2S3R,4R,5S,6R)-2-(7-Chloro-6-(4-(1,1-difluoroethyl)benzyl)-2,3-dihydrobenzofuran-4-yl)-6-(hydroxymethyl)tetrahydro-2H-pyran-3,4,5-triol | 0.910 |
| E178 | 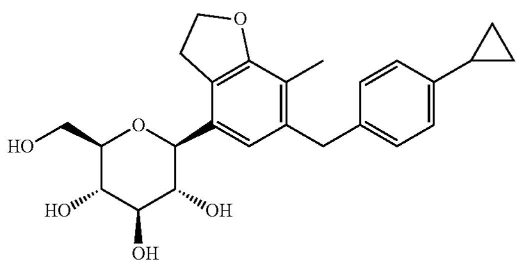 | (2S,3R,4R,5S,6R)-2-(6-(4-Cyclopropylbenzyl)-7-methyl-2,3-dihydrobenzofuran-4-yl)-6-(hydroxymethyl)tetrahydro-2H-pyran-3,4,5 triol | 1.16 |
| E179 | 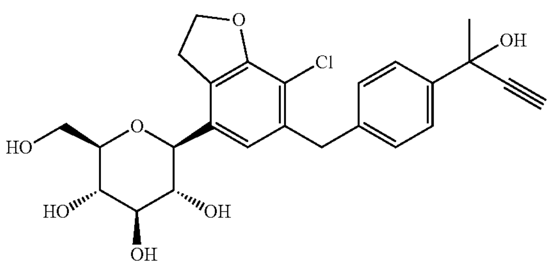 [SMILES: C#CC(C)(O)c1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-Chloro-6-(4-(2-hydroxybut-3-yn-2-yl)benzyl)-2,3-dihydrobenzofuran-4-yl)-6-(hydroxymethyl)tetrahydro-2H-pyran-3,4,5-triol | 5.20 |
| E180 | 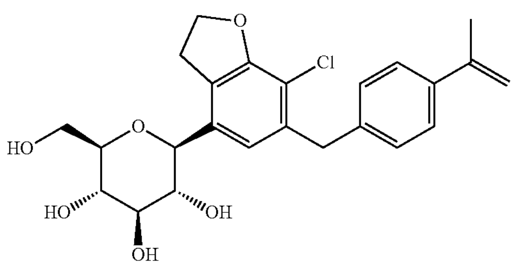 [SMILES: C=C(C)c1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-Chloro-6-(4-(prop-1-en-2-yl)benzyl)-2,3-dihydrobenzofuran-4-yl)-6-(hydroxymethyl)tetrahydro-2H-pyran-3,4,5-triol | 0.574 |
| E181 | 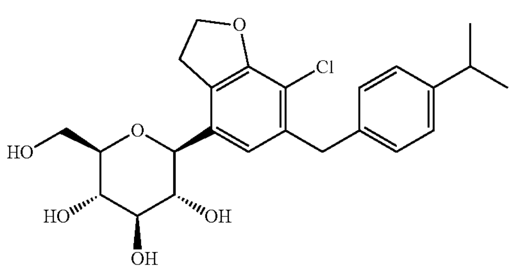 | (2S,3R,4R,5S,6R)-2-(7-Chloro-6-(4-isopropylbenzyl)-2,3-dihydrobenzofuran-4-yl)-6-(hydroxymethyl)tetrahydro-2H-pyran-3,4,5-triol | 0.794 |

TABLE 1-continued hSGLT2 Inhibitory Activity

| Compound | Structure | Name | IC$_{50}$ (nM) |
|---|---|---|---|
| E182 | 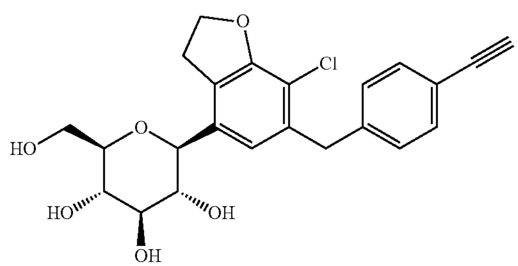 [SMILES: C#Cc1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-Chloro-6-(4-ethynylbenzyl)-2,3-dihydrobenzofuran-4-yl)-6-(hydroxymethyl)tetrahydro-2H-pyran-3,4,5-triol | 1.03 |
| E183 | 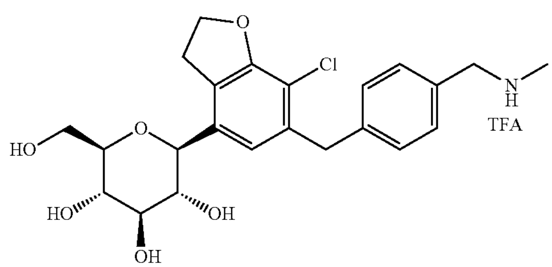 [SMILES: CNCc1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-Chloro-6-(4-((methylamino)methyl)benzyl)-2,3-dihydrobenzofuran-4-yl)-6-(hydroxymethyl)tetrahydro-2H-pyran-3,4,5-triol trifluoro acetic acid salt | 122 |
| E184 | 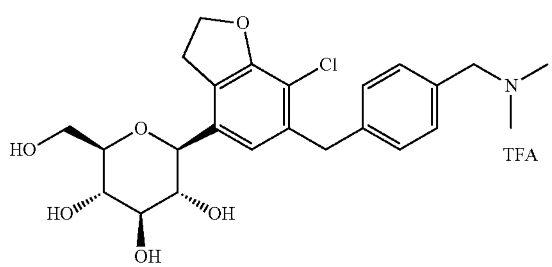 [SMILES: CN(C)Cc1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-Chloro-6-(4-((dimethylamino)methyl)benzyl)-2,3-dihydrobenzofuran-4-yl)-6-(hydroxymethyl)tetrahydro-2H-pyran-3,4,5-triol trifluoro acetic acid salt | 162 |
| E185 | 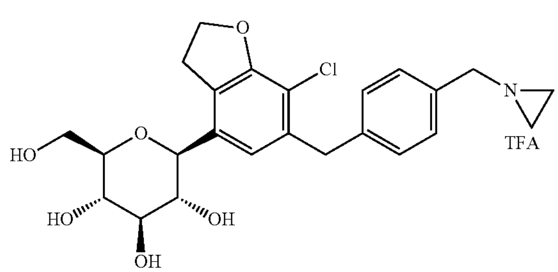 [SMILES: OC[C@H]1O[C@@H](c2cc(Cc3ccc(CN4CC4)cc3)c(Cl)c3c2CCO3)[C@H](O)[C@@H](O)[C@@H]1O] | (2S,3R,4R,5S,6R)-2-(6-(4-(Aziridin-1-ylmethyl)benzyl)-7-chloro-2,3-dihydrobenzofuran-4-yl)-6-(hydroxymethyl)tetrahydro-2H-pyran-3,4,5-triol trifluoro acetic acid salt | 164 |
| E186 | 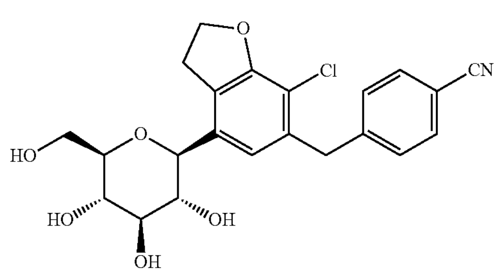 [SMILES: N#Cc1ccc(Cc2cc([C@@H]3O[C@H](CO)[C@@H](O)[C@H](O)[C@H]3O)c3c(c2Cl)OCC3)cc1] | 4-((7-Chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)benzonitrile | 6.06 |

TABLE 1-continued hSGLT2 Inhibitory Activity

| Compound | Structure | Name | IC$_{50}$ (nM) |
|---|---|---|---|
| E187 | 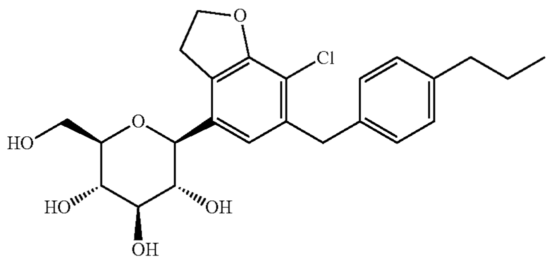 | (2S,3R,4R,5S,6R)-2-(7-chloro-6-(4-propylbenzyl)-2,3-dihydrobenzofuran-4-yl)-6-(hydroxymethyl)tetrahydro-2H-pyran-3,4,5-triol | 1.17 |
| E188 | 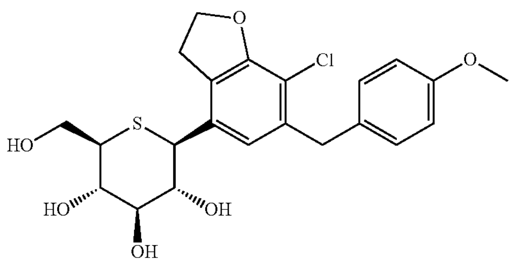 | (2S,3R,4R,5S,6R)-2-(7-chloro-6-(4-methoxybenzyl)-2,3-dihydrobenzofuran-4-yl)-6-(hydroxymethyl)tetrahydro-2H-thiopyran-3,4,5-triol | — |
| E189 | 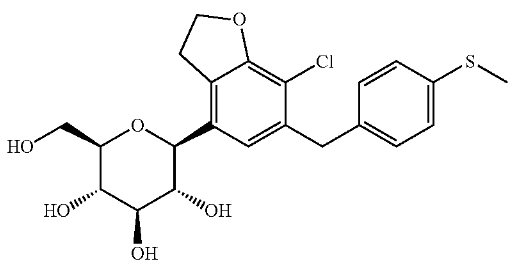 | (2S,3R,4R,5S,6R)-2-(7-chloro-6-(4-(methylthio)benzyl)-2,3-dihydrobenzofuran-4-yl)-6-(hydroxymethyl)tetrahydro-2H-pyran-3,4,5-triol | — |
| E190 | 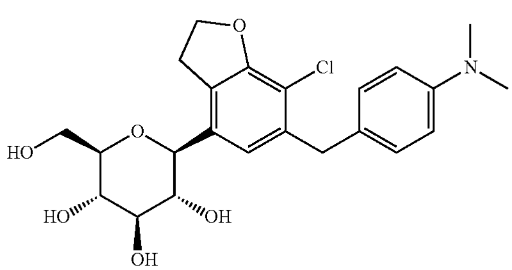 [SMILES: CN(C)c1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-chloro-6-(4-(dimethylamino)benzyl)-2,3-dihydrobenzofuran-4-yl)-6-(hydroxymethyl)tetrahydro-2H-pyran-3,4,5-triol | 1.11 |
| E191 | 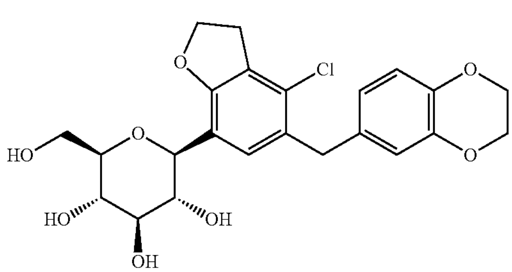 [SMILES: OC[C@H]1O[C@@H](c2cc(Cc3ccc4c(c3)OCCO4)c(Cl)c3c2OCC3)[C@H](O)[C@@H](O)[C@@H]1O] | (2S,3R,4R,5S,6R)-2-(4-chloro-5-((2,3-dihydrobenzo[b][1,4]dioxin-6-yl)methyl)-2,3-dihydrobenzofuran-7-yl)-6-(hydroxymethyl)tetrahydro-2H-pyran-3,4,5-triol | 1.57 |

TABLE 1-continued hSGLT2 Inhibitory Activity

| Compound | Structure | Name | IC$_{50}$ (nM) |
|---|---|---|---|
| E192 | 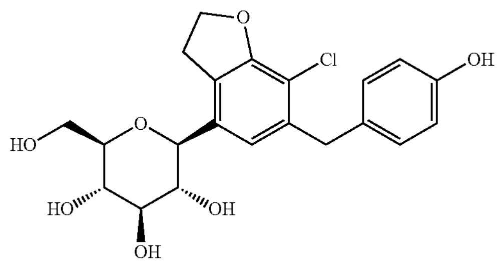 [SMILES: OC[C@H]1O[C@@H](c2cc(Cc3ccc(O)cc3)c(Cl)c3c2CCO3)[C@H](O)[C@@H](O)[C@@H]1O] | (2S,3R,4R,5S,6R)-2-(7-chloro-6-(4-hydroxybenzyl)-2,3-dihydrobenzofuran-4-yl)-6-(hydroxymethyl)tetrahydro-2H-pyran-3,4,5-triol | 1.63 |
| E193 | 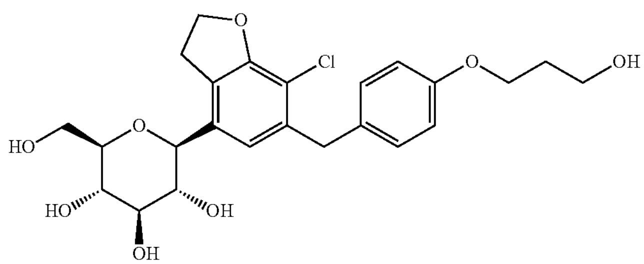 [SMILES: OCCCOc1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-chloro-6-(4-(3-hydroxypropoxy)benzyl)-2,3-dihydrobenzofuran-4-yl)-6-(hydroxymethyl)tetrahydro-2H-pyran-3,4,5-triol | 1.87 |
| E194 | 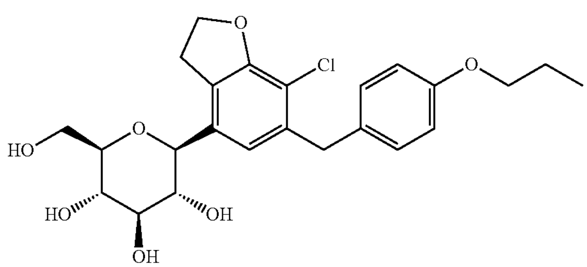 [SMILES: CCCOc1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-chloro-6-(4-propoxybenzyl)-2,3-dihydrobenzofuran-4-yl)-6-(hydroxymethyl)tetrahydro-2H-pyran-3,4,5-triol | 1.22 |
| E195 | 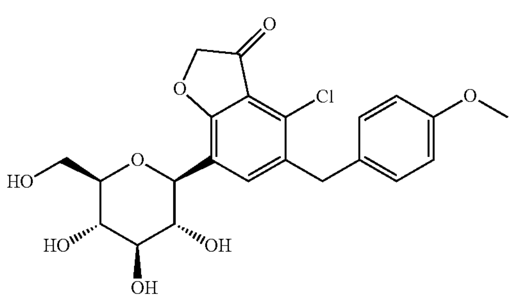 [SMILES: COc1ccc(Cc2cc([C@@H]3O[C@H](CO)[C@@H](O)[C@H](O)[C@H]3O)c3c(c2Cl)C(=O)CO3)cc1] | 4-chloro-5-(4-methoxybenzyl)-7-((2S,3R,4R,5S,6R)-3,4,5-trihydroxy-6-(hydroxymethyl)tetrahydro-2H-pyran-2-yl)benzofuran-3(2H)-one | 35.1 |
| E196 | 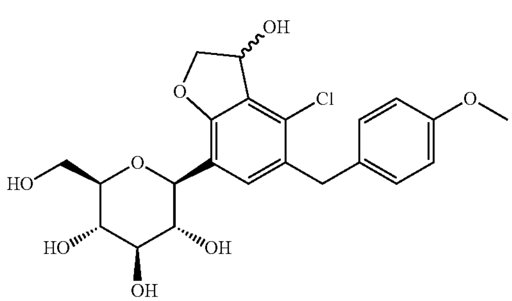 [SMILES: COc1ccc(Cc2cc([C@@H]3O[C@H](CO)[C@@H](O)[C@H](O)[C@H]3O)c3c(c2Cl)C(O)CO3)cc1] | (2S,3R,4R,5S,6R)-2-(4-chloro-3-hydroxy-5-(4-methoxybenzyl)-2,3-dihydrobenzofuran-7-yl)-6-(hydroxymethyl)tetrahydro-2H-pyran-3,4,5-triol | 3.56 |

TABLE 1-continued hSGLT2 Inhibitory Activity

| Compound | Structure | Name | IC$_{50}$ (nM) |
|---|---|---|---|
| E197 | 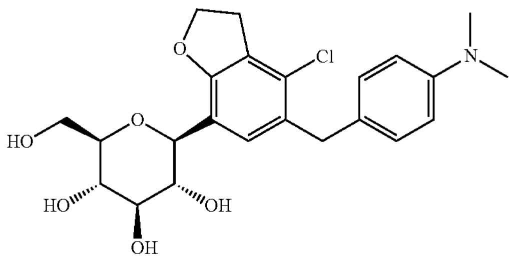 | (2S,3R,4R,5S,6R)-2-(4-chloro-5-(4-(dimethylamino)benzyl)-2,3-dihydrobenzofuran-7-yl)-6-(hydroxymethyl)tetrahydro-2H-pyran-3,4,5-triol | 3.22 |
| E198 | 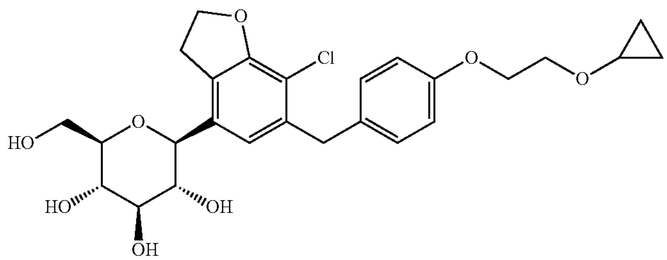 [SMILES: OC[C@H]1O[C@@H](c2cc(Cc3ccc(OCCOC4CC4)cc3)c(Cl)c3c2CCO3)[C@H](O)[C@@H](O)[C@@H]1O] | (2S,3R,4R,5S,6R)-2-(7-chloro-6-(4-(2-cyclopropoxyethoxy)benzyl)-2,3-dihydrobenzofuran-4-yl)-6-(hydroxymethyl)tetrahydro-2H-pyran-3,4,5-triol | 2.02 |
| E199 | 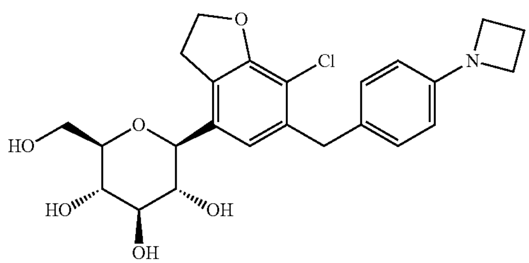 [SMILES: OC[C@H]1O[C@@H](c2cc(Cc3ccc(N4CCC4)cc3)c(Cl)c3c2CCO3)[C@H](O)[C@@H](O)[C@@H]1O] | (2S,3R,4R,5S,6R)-2-(6-(4-(azetidin-1-yl)benzyl)-7-chloro-2,3-dihydrobenzofuran-4-yl)-6-(hydroxymethyl)tetrahydro-2H-pyran-3,4,5-triol | 3.49 |
| E200 | 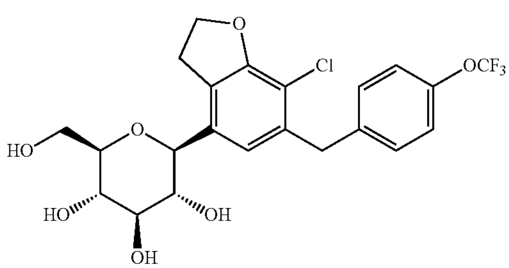 [SMILES: OC[C@H]1O[C@@H](c2cc(Cc3ccc(OC(F)(F)F)cc3)c(Cl)c3c2CCO3)[C@H](O)[C@@H](O)[C@@H]1O] | (2S,3R,4R,5S,6R)-2-(7-chloro-6-(4-(trifluoromethoxy)benzyl)-2,3-dihydrobenzofuran-4-yl)-6-(hydroxymethyl)tetrahydro-2H-pyran-3,4,5-triol | 1.08 |
| E201 | 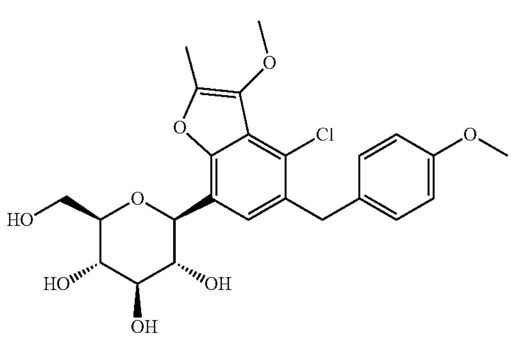 [SMILES: COc1ccc(Cc2cc([C@@H]3O[C@H](CO)[C@@H](O)[C@H](O)[C@H]3O)c3oc(C)c(OC)c3c2Cl)cc1] | (2S,3R,4R,5S,6R)-2-(4-chloro-3-methoxy-5-(4-methoxybenzyl)-2-methylbenzofuran-7-yl)-6-(hydroxymethyl)tetrahydro-2H-pyran-3,4,5-triol | 49.4 |

TABLE 1-continued hSGLT2 Inhibitory Activity

| Compound | Structure | Name | IC$_{50}$ (nM) |
|---|---|---|---|
| E202 | 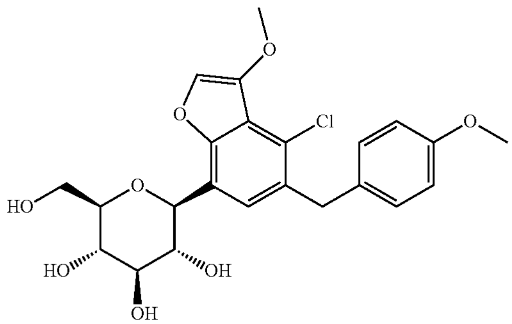 | (2S,3R,4R,5S,6R)-2-(4-chloro-3-methoxy-5-(4-methoxybenzyl)benzofuran-7-yl)-6-(hydroxymethyl)tetrahydro-2H-pyran-3,4,5-triol | 42.3 |
| E203 | 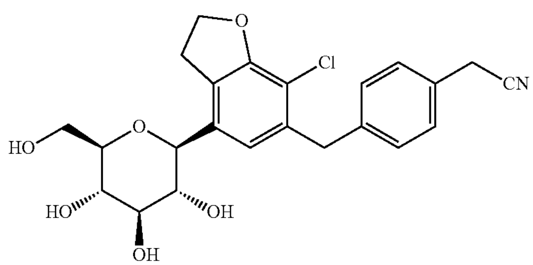 [SMILES: N#CCc1ccc(Cc2cc([C@@H]3O[C@H](CO)[C@@H](O)[C@H](O)[C@H]3O)c3c(c2Cl)OCC3)cc1] | 2-(4-((7-chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)phenyl)acetonitrile | 1.81 |
| E204 | 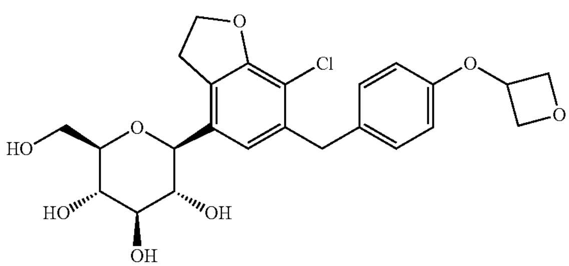 [SMILES: OC[C@H]1O[C@@H](c2cc(Cc3ccc(OC4COC4)cc3)c(Cl)c3c2CCO3)[C@H](O)[C@@H](O)[C@@H]1O] | (2S,3R,4R,5S,6R)-2-(7-chloro-6-(4-(oxetan-3-yloxy)benzyl)-2,3-dihydrobenzofuran-4-yl)-6-(hydroxymethyl)tetrahydro-2H-pyran-3,4,5-triol | 5.05 |
| E205 | 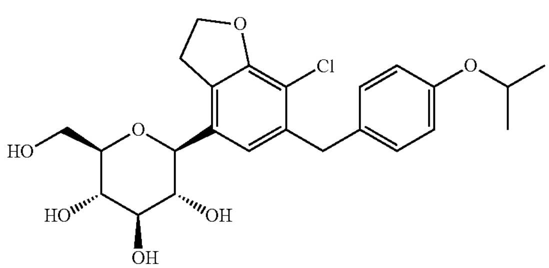 [SMILES: CC(C)Oc1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(7-chloro-6-(4-isopropoxybenzyl)-2,3-dihydrobenzofuran-4-yl)-6-(hydroxymethyl)tetrahydro-2H-pyran-3,4,5-triol | 1.96 |
| E206 | 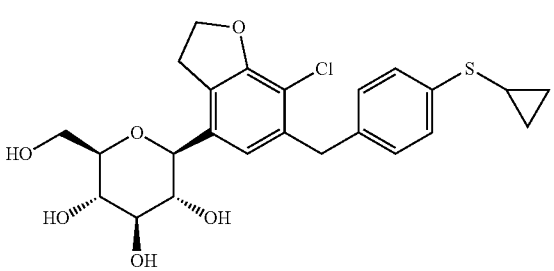 [SMILES: OC[C@H]1O[C@@H](c2cc(Cc3ccc(SC4CC4)cc3)c(Cl)c3c2CCO3)[C@H](O)[C@@H](O)[C@@H]1O] | (2S,3R,4R,5S,6R)-2-(7-chloro-6-(4-(cyclopropylthio)benzyl)-2,3-dihydrobenzofuran-4-yl)-6-(hydroxymethyl)tetrahydro-2H-pyran-3,4,5-triol | 1.88 |

TABLE 1-continued hSGLT2 Inhibitory Activity

| Compound | Structure | Name | IC$_{50}$ (nM) |
|---|---|---|---|
| E207 | 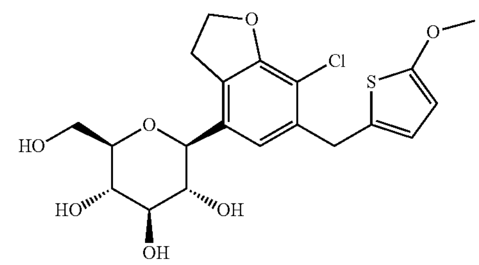 [SMILES: COc1ccc(Cc2cc([C@@H]3O[C@H](CO)[C@@H](O)[C@H](O)[C@H]3O)c3c(c2Cl)OCC3)s1] | (2S,3R,4R,5S,6R)-2-(7-chloro-6-((5-methoxythiophen-2-yl)methyl)-2,3-dihydrobenzofuran-4-yl)-6-(hydroxymethyl)tetrahydro-2H-pyran-3,4,5-triol | 3.75 |
| E208 | 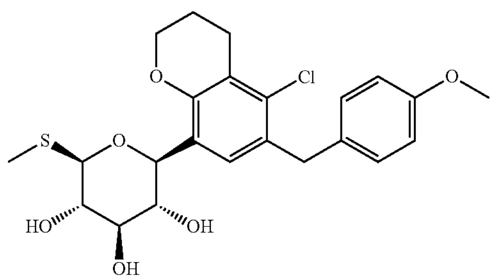 | (2S,3R,4R,5S,6R)-2-(5-chloro-6-(4-methoxybenzyl)chroman-8-yl)-6-(methylthio)tetrahydro-2H-pyran-3,4,5-triol | — |
| E209 | 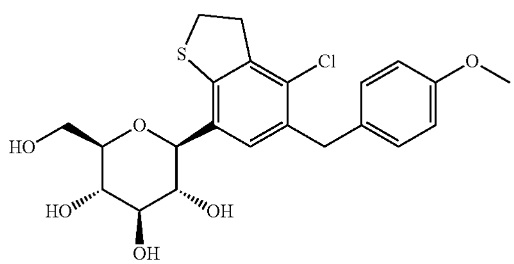 [SMILES: COc1ccc(Cc2cc([C@@H]3O[C@H](CO)[C@@H](O)[C@H](O)[C@H]3O)c3c(c2Cl)CCS3)cc1] | (2S,3R,4R,5S,6R)-2-(4-chloro-5-(4-methoxybenzyl)-2,3-dihydrobenzo[b]thiophen-7-yl)-6-(hydroxymethyl)tetrahydro-2H-pyran-3,4,5-triol | — |
| E210 | 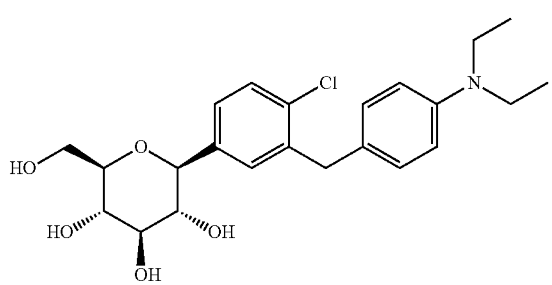 [SMILES: CCN(CC)c1ccc(Cc2cc([C@@H]3O[C@H](CO)[C@@H](O)[C@H](O)[C@H]3O)ccc2Cl)cc1] | (2S,3R,4R,5S,6R)-2-(4-chloro-3-(4-(diethylamino)benzyl)phenyl)-6-(hydroxymethyl)tetrahydro-2H-pyran-3,4,5-triol | 89.3 |
| E211 | 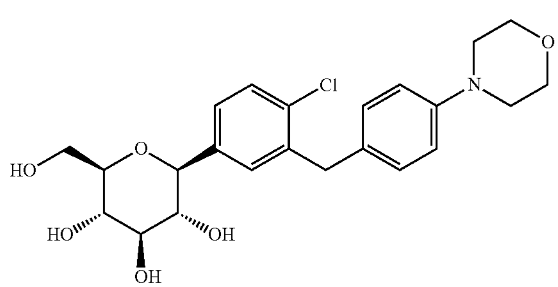 [SMILES: OC[C@H]1O[C@@H](c2ccc(Cl)c(Cc3ccc(N4CCOCC4)cc3)c2)[C@H](O)[C@@H](O)[C@@H]1O] | (2S,3R,4R,5S,6R)-2-(4-chloro-3-(4-morpholinobenzyl)phenyl)-6-(hydroxymethyl)tetrahydro-2H-pyran-3,4,5-triol | 9.08 |

TABLE 1-continued hSGLT2 Inhibitory Activity

| Compound | Structure | Name | IC$_{50}$ (nM) |
|---|---|---|---|
| E212 | 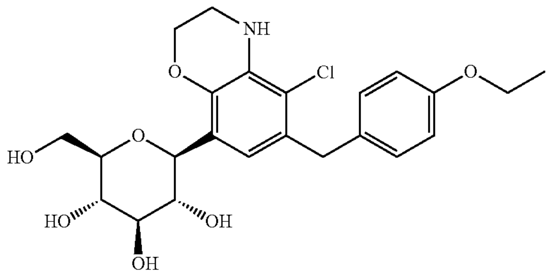 | (2S,3R,4R,5S,6R)-2-(5-chloro-6-(4-ethoxybenzyl)-3,4-dihydro-2H-benzo[b][1,4]oxazin-8-yl)-6-(hydroxymethyl)tetrahydro-2H-pyran-3,4,5-triol | 2.42 |
| E213 | 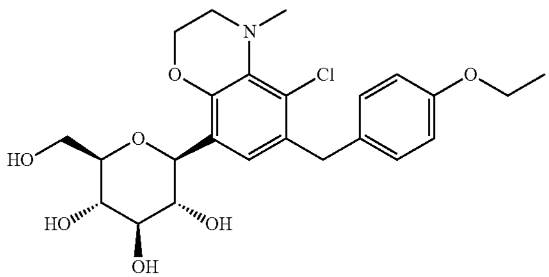 [SMILES: CCOc1ccc(Cc2cc([C@@H]3O[C@H](CO)[C@@H](O)[C@H](O)[C@H]3O)c3c(c2Cl)N(C)CCO3)cc1] | (2S,3R,4R,5S,6R)-2-(5-chloro-6-(4-ethoxybenzyl)-4-methyl-3,4-dihydro-2H-benzo[b][1,4]oxazin-8-yl)-6-(hydroxymethyl)tetrahydro-2H-pyran-3,4,5-triol | 6.12 |
| E214 | 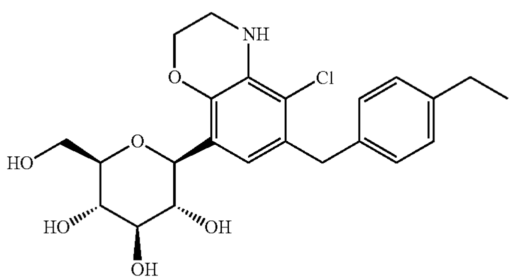 [SMILES: CCc1ccc(Cc2cc([C@@H]3O[C@H](CO)[C@@H](O)[C@H](O)[C@H]3O)c3c(c2Cl)NCCO3)cc1] | (2S,3R,4R,5S,6R)-2-(5-chloro-6-(4-ethylbenzyl)-3,4-dihydro-2H-benzo[b][1,4]oxazin-8-yl)-6-(hydroxymethyl)tetrahydro-2H-pyran-3,4,5-triol | 3.17 |
| E215 | 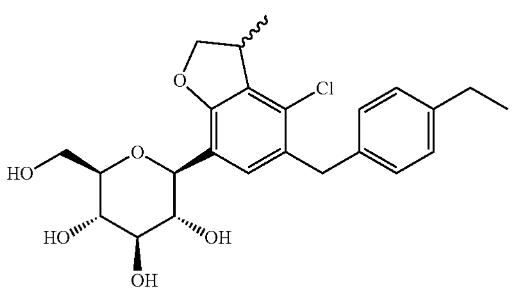 [SMILES: CCc1ccc(Cc2cc([C@@H]3O[C@H](CO)[C@@H](O)[C@H](O)[C@H]3O)c3c(c2Cl)C(C)CO3)cc1] | (2S,3R,4R,5S,6R)-2-(4-chloro-5-(4-ethylbenzyl)-3-methyl-2,3-dihydrobenzofuran-7-yl)-6-(hydroxymethyl)tetrahydro-2H-pyran-3,4,5-triol | 0.891 |
| E216 | 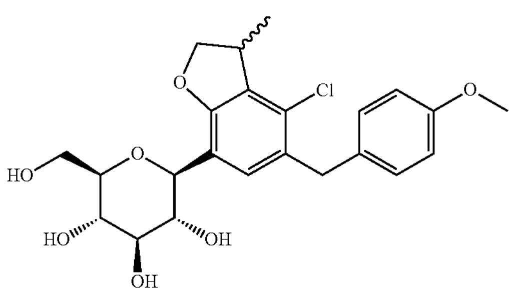 [SMILES: COc1ccc(Cc2cc([C@@H]3O[C@H](CO)[C@@H](O)[C@H](O)[C@H]3O)c3c(c2Cl)C(C)CO3)cc1] | (2S,3R,4R,5S,6R)-2-(4-chloro-5-(4-methoxybenzyl)-3-methyl-2,3-dihydrobenzofuran-7-yl)-6-(hydroxymethyl)tetrahydro-2H-pyran-3,4,5-triol | 1.22 |

TABLE 1-continued hSGLT2 Inhibitory Activity

| Compound | Structure | Name | IC$_{50}$ (nM) |
|---|---|---|---|
| E217 | 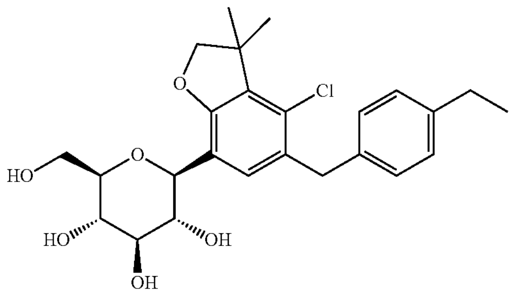 | (2S,3R,4R,5S,6R)-2-(4-chloro-5-(4-ethylbenzyl)-3,3-dimethyl-2,3-dihydrobenzofuran-7-yl)-6-(hydroxymethyl)tetrahydro-2H-pyran-3,4,5-triol | 1.76 |
| E218 | 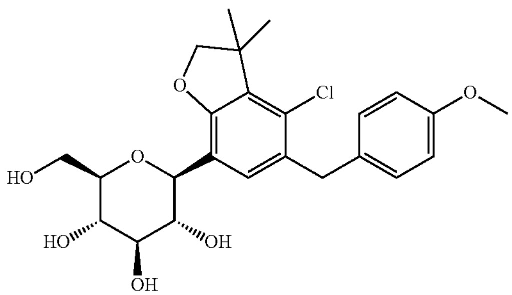 | (2S,3R,4R,5S,6R)-2-(4-chloro-5-(4-methoxybenzyl)-3,3-dimethyl-2,3-dihydrobenzofuran-7-yl)-6-(hydroxymethyl)tetrahydro-2H-pyran-3,4,5-triol | 4.66 |
| E219 | 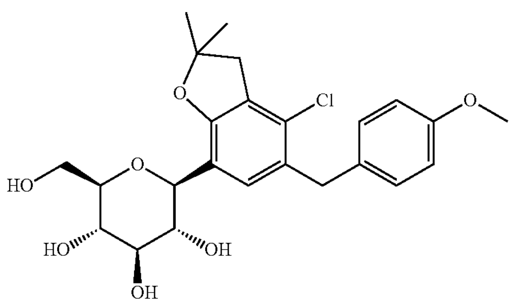 [SMILES: COc1ccc(Cc2cc([C@@H]3O[C@H](CO)[C@@H](O)[C@H](O)[C@H]3O)c3c(c2Cl)CC(C)(C)O3)cc1] | (2S,3R,4R,5S,6R)-2-(4-chloro-5-(4-methoxybenzyl)-2,2-dimethyl-2,3-dihydrobenzofuran-7-yl)-6-(hydroxymethyl)tetrahydro-2H-pyran-3,4,5-triol | 1.61 |
| E220 | 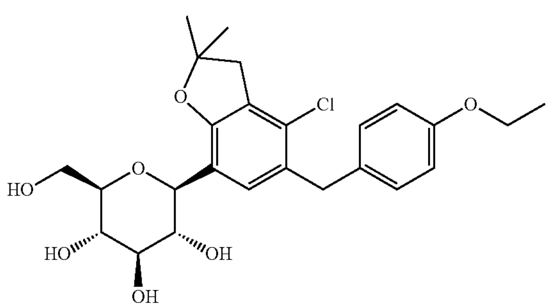 [SMILES: CCOc1ccc(Cc2cc([C@@H]3O[C@H](CO)[C@@H](O)[C@H](O)[C@H]3O)c3c(c2Cl)CC(C)(C)O3)cc1] | (2S,3R,4R,5S,6R)-2-(4-chloro-5-(4-ethoxybenzyl)-2,2-dimethyl-2,3-dihydrobenzofuran-7-yl)-6-(hydroxymethyl)tetrahydro-2H-pyran-3,4,5-triol | 1.27 |
| E221 | 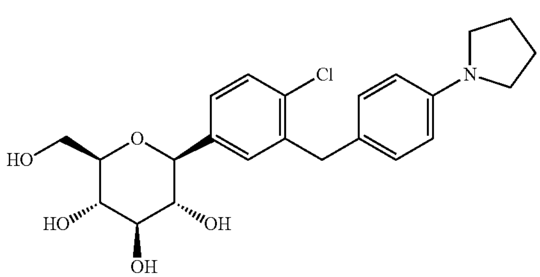 [SMILES: OC[C@H]1O[C@@H](c2ccc(Cl)c(Cc3ccc(N4CCCC4)cc3)c2)[C@H](O)[C@@H](O)[C@@H]1O] | (2S,3R,4R,5S,6R)-2-(4-Chloro-3-(4-(pyrrolidin-1-yl)benzyl)-6-(hydroxymethyl)-tetrahydro-2H-pyran-3,4,5-triol | 2.17 |

TABLE 1-continued hSGLT2 Inhibitory Activity

| Compound | Structure | Name | IC$_{50}$ (nM) |
|---|---|---|---|
| E222 | 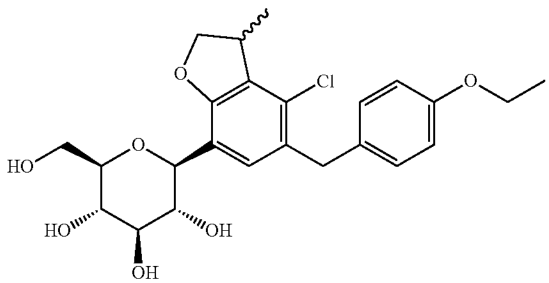 [SMILES: CCOc1ccc(Cc2cc([C@@H]3O[C@H](CO)[C@@H](O)[C@H](O)[C@H]3O)c3c(c2Cl)C(C)CO3)cc1] | (2S,3R,4R,5S,6R)-2-(4-Chloro-5-(4-ethoxybenzyl)-3-methyl-2,3-dihydrobenzofuran-7-yl)-6-(hydroxymethyl)-tetrahydro-2H-pyran-3,4,5-triol | 1.99 |
| E223 | 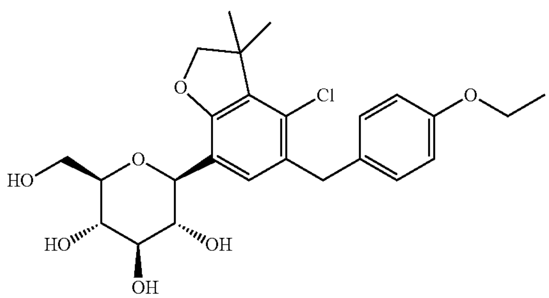 [SMILES: CCOc1ccc(Cc2cc([C@@H]3O[C@H](CO)[C@@H](O)[C@H](O)[C@H]3O)c3c(c2Cl)C(C)(C)CO3)cc1] | (2S,3R,4R,5S,6R)-2-(4-Chloro-5-(4-ethoxybenzyl)-3,3-dimethyl-2,3-dihydrobenzofuran-7-yl)-6-(hydroxymethyl)-tetrahydro-2H-pyran-3,4,5-triol | 4.16 |
| E224 | 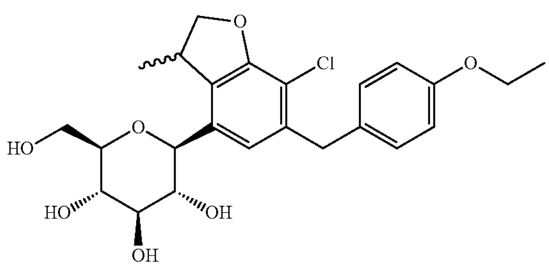 [SMILES: CCOc1ccc(Cc2cc([C@@H]3O[C@H](CO)[C@@H](O)[C@H](O)[C@H]3O)c3c(c2Cl)OCC3C)cc1] | (2S,3R,4R,5S,6R)-2-(7-Chloro-6-(4-ethoxybenzyl)-3-methyl-2,3-dihydrobenzofuran-4-yl)-6-(hydroxymethyl)-tetrahydro-2H-pyran-3,4,5-triol | 0.867 |
| E225 | 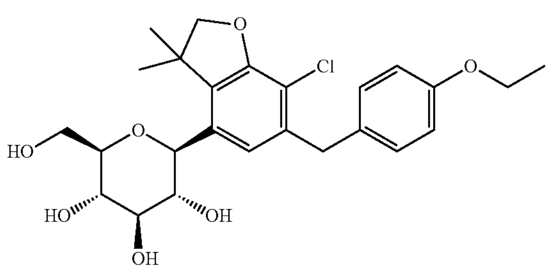 [SMILES: CCOc1ccc(Cc2cc([C@@H]3O[C@H](CO)[C@@H](O)[C@H](O)[C@H]3O)c3c(c2Cl)OCC3(C)C)cc1] | (2S,3R,4R,5S,6R)-2-(7-Chloro-6-(4-ethoxybenzyl)-3,3-dimethyl-2,3-dihydrobenzofuran-4-yl)-6-(hydroxymethyl)-tetrahydro-2H-pyran-3,4,5-triol | 1.82 |
| E226 | 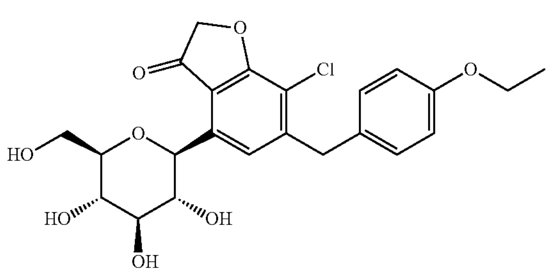 [SMILES: CCOc1ccc(Cc2cc([C@@H]3O[C@H](CO)[C@@H](O)[C@H](O)[C@H]3O)c3c(c2Cl)OCC3=O)cc1] | 7-Chloro-6-(4-ethoxybenzyl)-4-(2S3R,4R,5S,6R)-3,4,5-trihydroxy-6-(hydroxymethyl)-tetrahydro-2H-pyran-2-yl)benzofuran-3(2H)-one | 10.5 |

TABLE 1-continued hSGLT2 Inhibitory Activity

| Compound | Structure | Name | IC$_{50}$ (nM) |
|---|---|---|---|
| E227 | 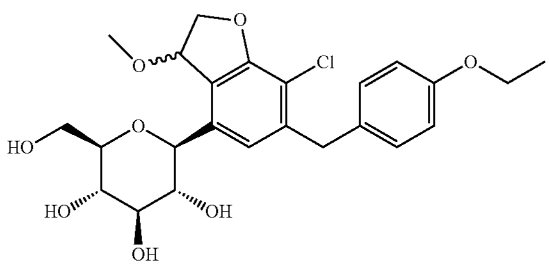 [SMILES: CCOc1ccc(Cc2cc([C@@H]3O[C@H](CO)[C@@H](O)[C@H](O)[C@H]3O)c3c(c2Cl)OCC3OC)cc1] | (2S,3R,4R,5S,6R)-2-(7-Chloro-6-(4-ethoxybenzyl)-3-methoxy-2,3-dihydrobenzofuran-4-yl)-6-(hydroxymethyl)-tetrahydro-2H-pyran-3,4,5-triol | 8.99 |
| E228 | 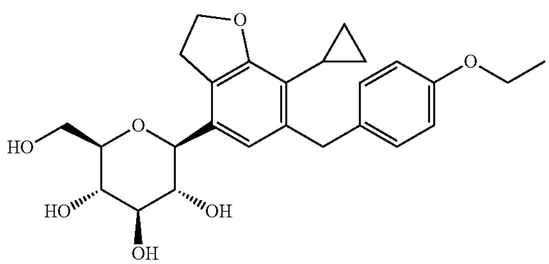 [SMILES: CCOc1ccc(Cc2cc([C@@H]3O[C@H](CO)[C@@H](O)[C@H](O)[C@H]3O)c3c(c2C2CC2)OCC3)cc1] | (2S,3R,4R,5S,6R)-2-(7-Cyclopropyl-6-(4-ethoxybenzyl)-2,3-dihydrobenzofuran-4-yl)-6-(hydroxymethyl)-tetrahydro-2H-pyran-3,4,5-triol | 13.8 |
| E229 | 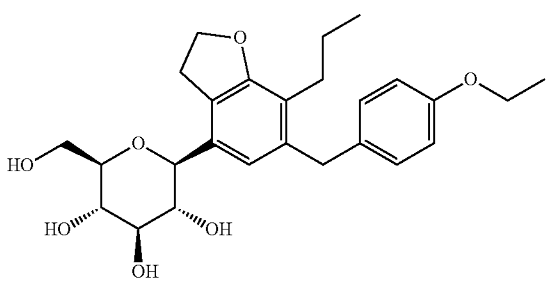 [SMILES: CCCc1c(Cc2ccc(OCC)cc2)cc([C@@H]2O[C@H](CO)[C@@H](O)[C@H](O)[C@H]2O)c2c1OCC2] | (2S,3R,4R,5S,6R)-2-(6-(4-Ethoxybenzyl)-7-propyl-2,3-dihydrobenzofuran-4-yl)-6-(hydroxymethyl)-tetrahydro-2H-pyran-3,4,5-triol | 5.60 |
| E230 | 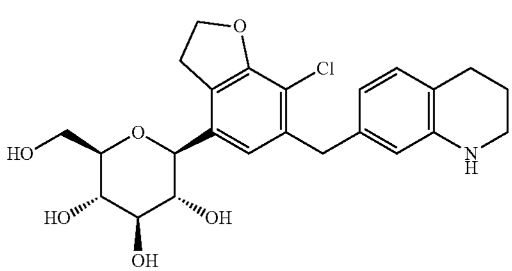 | (2S,3R,4R,5S,6R)-2-(7-Chloro-6-((1,2,3,4-tetrahydroquinolin-7-yl)methyl)-2,3-dihydrobenzofuran-4-yl)-6-(hydroxymethyl)-tetrahydro-2H-pyran-3,4,5-triol | 2.49 |
| E231 | 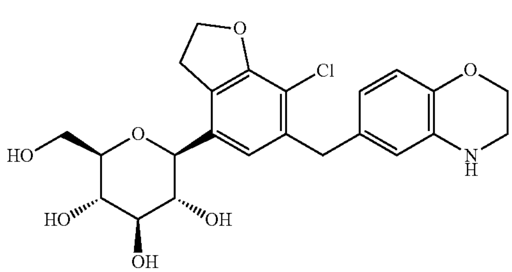 [SMILES: OC[C@H]1O[C@@H](c2cc(Cc3ccc4c(c3)NCCO4)c(Cl)c3c2CCO3)[C@H](O)[C@@H](O)[C@@H]1O] | (2S,3R,4R,5S,6R)-2-(7-Chloro-6-((3,4-dihydro-2H-benzo[b][1,4]oxazin-6-yl)methyl)-2,3-dihydrobenzofuran-4-yl)-6-(hydroxymethyl)-tetrahydro-2H-pyran-3,4,5-triol | 5.56 |

TABLE 1-continued hSGLT2 Inhibitory Activity

| Compound | Structure | Name | IC$_{50}$ (nM) |
|---|---|---|---|
| E232 | 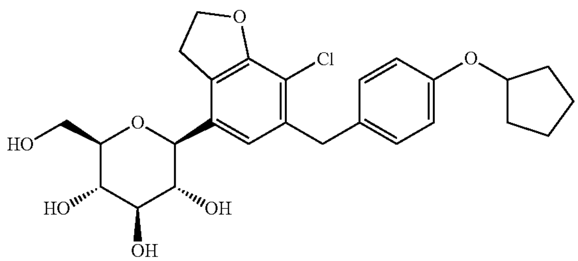 [SMILES: OC[C@H]1O[C@@H](c2cc(Cc3ccc(OC4CCCC4)cc3)c(Cl)c3c2CCO3)[C@H](O)[C@@H](O)[C@@H]1O] | (2S,3R,4R,5S,6R)-2-(7-Chloro-6-(4-(cyclopentyloxy)benzyl)-2,3-dihydrobenzofuran-4-yl)-6-(hydroxymethyl)-tetrahydro-2H-pyran-3,4,5-triol | 1.60 |
| E233 | 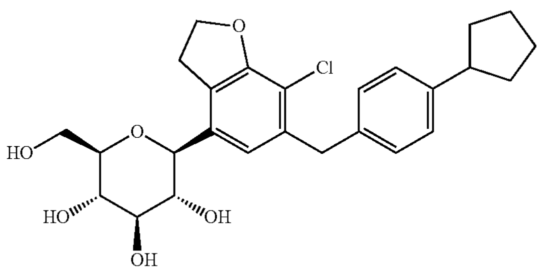 [SMILES: OC[C@H]1O[C@@H](c2cc(Cc3ccc(C4CCCC4)cc3)c(Cl)c3c2CCO3)[C@H](O)[C@@H](O)[C@@H]1O] | (2S,3R,4R,5S,6R)-2-(7-Chloro-6-(4-cyclopentylbenzyl)-2,3-dihydrobenzofuran-4-yl)-6-(hydroxymethyl)-tetrahydro-2H-pyran-3,4,5-triol | 1.16 |
| E234 | 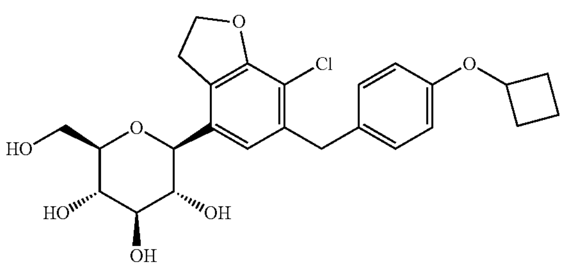 [SMILES: OC[C@H]1O[C@@H](c2cc(Cc3ccc(OC4CCC4)cc3)c(Cl)c3c2CCO3)[C@H](O)[C@@H](O)[C@@H]1O] | (2S,3R,4R,5S,6R)-2-(7-Chloro-6-(4-cyclobutoxybenzyl)-2,3-dihydrobenzofuran-4-yl)-6-(hydroxymethyl)-tetrahydro-2H-pyran-3,4,5-triol | 2.82 |
| E235 | 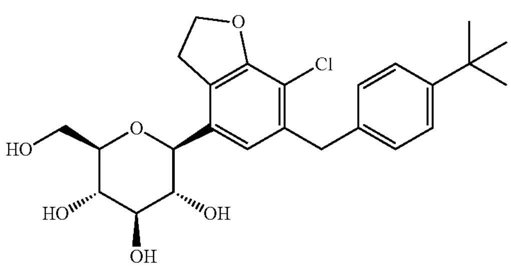 [SMILES: CC(C)(C)c1ccc(Cc2cc([C@@H]3O[C@H](CO)[C@@H](O)[C@H](O)[C@H]3O)c3c(c2Cl)OCC3)cc1] | (2S,3R,4R,5S,6R)-2-(6-(4-tert-Butylbenzyl)-7-chloro-2,3-dihydrobenzofuran-4-yl)-6-(hydroxymethyl)-tetrahydro-2H-pyran-3,4,5-triol | — |
| E236 | 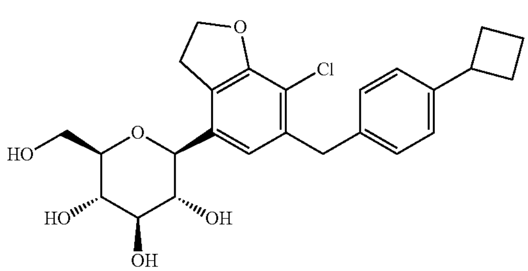 [SMILES: OC[C@H]1O[C@@H](c2cc(Cc3ccc(C4CCC4)cc3)c(Cl)c3c2CCO3)[C@H](O)[C@@H](O)[C@@H]1O] | (2S,3R,4R,5S,6R)-2-(7-Chloro-6-(4-cyclobutylbenzyl)-2,3-dihydrobenzofuran-4-yl)-6-(hydroxymethyl)-tetrahydro-2H-pyran-3,4,5-triol | — |

TABLE 1-continued hSGLT2 Inhibitory Activity

| Compound | Structure | Name | IC$_{50}$ (nM) |
|---|---|---|---|
| E237 | 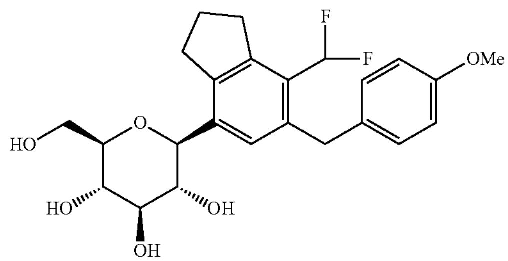 [SMILES: COc1ccc(Cc2cc([C@@H]3O[C@H](CO)[C@@H](O)[C@H](O)[C@H]3O)c3c(c2C(F)F)CCC3)cc1] | (2S,3R,4R,5S,6R)-2-(7-(difluoromethyl)-6-(4-methoxybenzyl)-2,3-dihydro-1H-inden-4-yl)-6-(hydroxymethyl)tetrahydro-2H-pyran-3,4,5-triol | 0.734 |
| E238 | 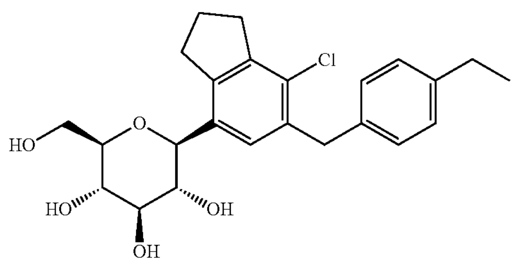 [SMILES: CCc1ccc(Cc2cc([C@@H]3O[C@H](CO)[C@@H](O)[C@H](O)[C@H]3O)c3c(c2Cl)CCC3)cc1] | (2S,3R,4R,5S,6R)-2-(7-chloro-6-(4-ethylbenzyl)-2,3-dihydro-1H-inden-4-yl)-6-(hydroxymethyl)tetrahydro-2H-pyran-3,4,5-triol | 0.627 |
| E239 | 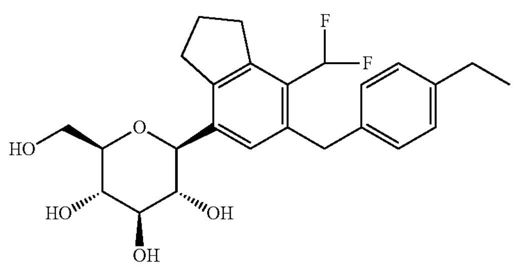 [SMILES: CCc1ccc(Cc2cc([C@@H]3O[C@H](CO)[C@@H](O)[C@H](O)[C@H]3O)c3c(c2C(F)F)CCC3)cc1] | (2S,3R,4R,5S,6R)-2-(7-(difluoromethyl)-6-(4-ethylbenzyl)-2,3-dihydro-1H-inden-4-yl)-6-(hydroxymethyl)tetrahydro-2H-pyran-3,4,5-triol | 0.718 |
| E240 | 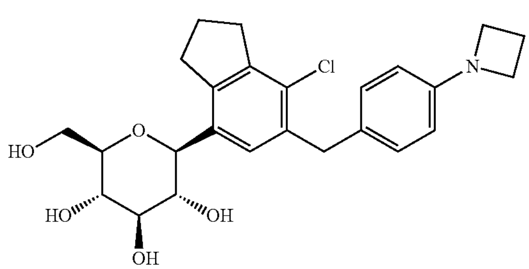 [SMILES: OC[C@H]1O[C@@H](c2cc(Cc3ccc(N4CCC4)cc3)c(Cl)c3c2CCC3)[C@H](O)[C@@H](O)[C@@H]1O] | (2S,3R,4R,5S,6R)-2-(6-(4-(azetidin-1-yl)benzyl)-7-chloro-2,3-dihydro-1H-inden-4-yl)-6-(hydroxymethyl)tetrahydro-2H-pyran-3,4,5-triol | 1.75 |
| E241 | 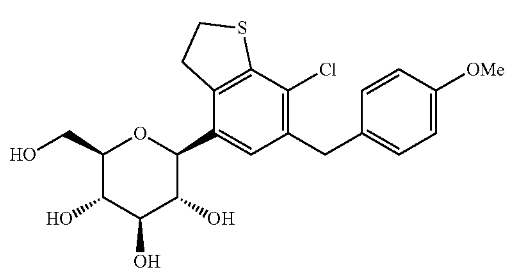 [SMILES: COc1ccc(Cc2cc([C@@H]3O[C@H](CO)[C@@H](O)[C@H](O)[C@H]3O)c3c(c2Cl)SCC3)cc1] | (2S,3R,4R,5S,6R)-2-(7-chloro-6-(4-methoxybenzyl)-2,3-dihydrobenzo[b]thiophen-4-yl)-6-(hydroxymethyl)tetrahydro-2H-pyran-3,4,5-triol | 0.902 |

TABLE 1-continued hSGLT2 Inhibitory Activity

| Compound | Structure | Name | IC$_{50}$ (nM) |
|---|---|---|---|
| E242 | 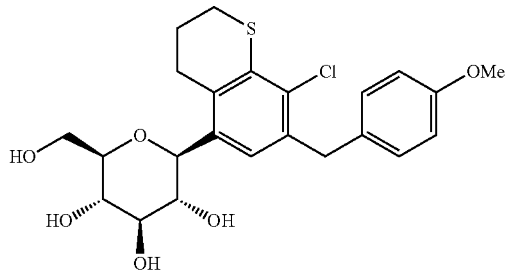 [SMILES: COc1ccc(Cc2cc([C@@H]3O[C@H](CO)[C@@H](O)[C@H](O)[C@H]3O)c3c(c2Cl)SCCC3)cc1] | (2S,3R,4R,5S,6R)-2-(8-chloro-7-(4-methoxybenzyl)thiochroman-5-yl)-6-(hydroxymethyl)tetrahydro-2H-pyran-3,4,5-triol | 0.552 |
| E243 | 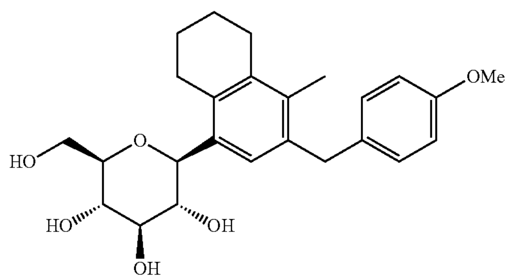 [SMILES: COc1ccc(Cc2cc([C@@H]3O[C@H](CO)[C@@H](O)[C@H](O)[C@H]3O)c3c(c2C)CCCC3)cc1] | (2R,3S,4R,5R,6S)-2-(hydroxymethyl)-6-(3-(4-methoxybenzyl)-4-methyl-5,6,7,8-tetrahydronaphthalen-1-yl)tetrahydro-2H-pyran-3,4,5-triol | — |

*Reference compound dapagliflozin IC$_{50}$ = 1.35 ± 0.15 nM (in-house assay).
**These data were obtained by single determinations.

Figure 2:
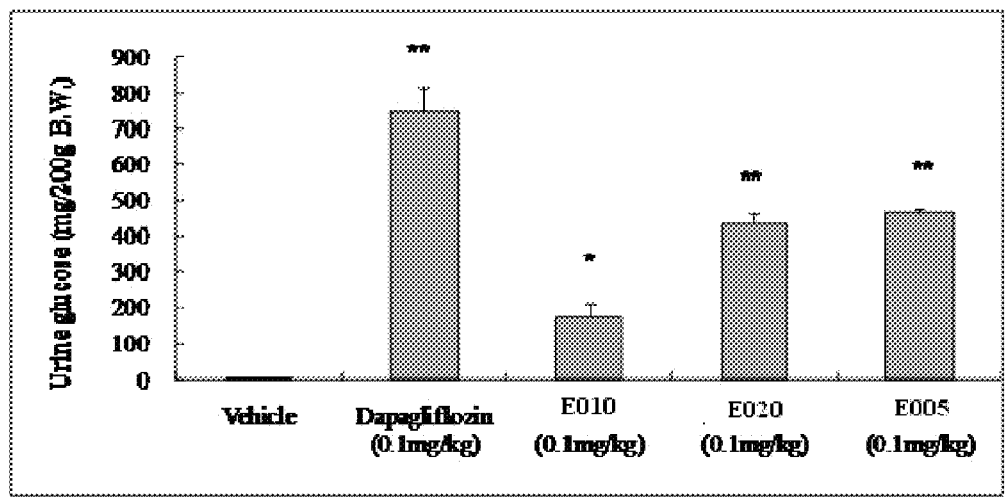
FIGS. 2A and 2B are graphs depicting the effects of single oral administration of dapagliflozin, and the inventive compounds (E005, E010, and E020) on urinary glucose excretion (A) and urine volume (B) in normal SD rats.
Figure 2:
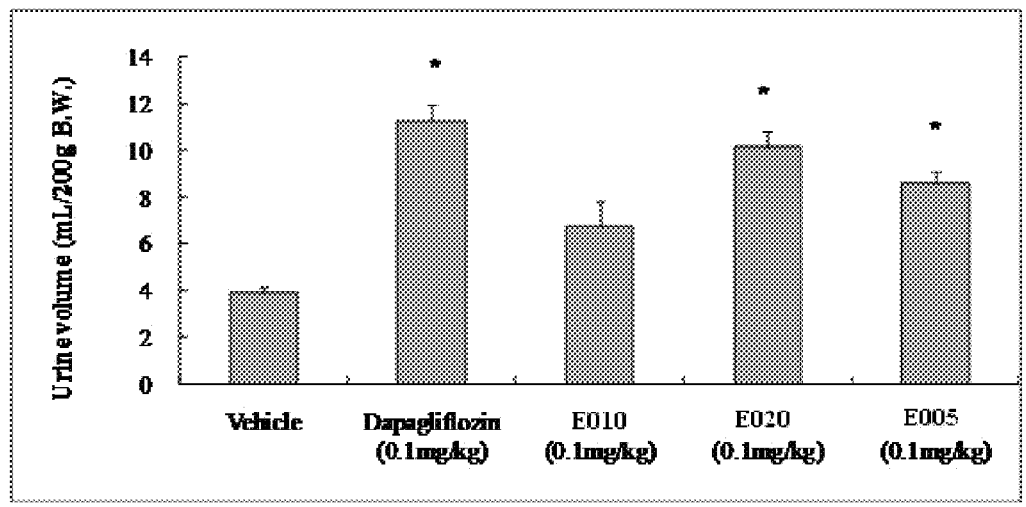

In Vivo Assay
Test 3: Urinary Glucose Excretion in Normal Animals
  Animals
  Male Sprague-Dawley (SD) rats were purchased by Charles River Laboratory. All animals were housed at 23±2° C. under a 12-h light/dark cycle (light on 7:00) and were fed a standard chow and water ad libitum.
  Urinary Glucose Excretion in Normal Animal
  For glucosuria assessment, overnight-fasted SD rats (5 weeks of ages) were placed into metabolism cages for baseline urine collection over 24 h. Rats were weighed, randomized into experimental groups (n=4) and orally administered with 50% aqueous glucose solution (2 g/kg) and the inventive compound (E005, E010, and E020). Rats were returned to metabolism cages for 24 h urine collection. After the urine volume had been measured, the glucose concentration in the urine was determined using a LabAssay™ (Wako Pure Chemicals). These data were normalized per 200 g body weight [Katsuno, K. et al. *J. Pharmacol. Exp. Ther.* 2007, 320, 323-330; Han, S. et al. *Diabetes,* 2008, 57, 1723-1729].
  The results were shown in FIG. 2. FIG. 2 represents effects of single oral administration of dapagliflozin, and the inventive compounds (E005, E010, and E020) on urinary glucose excretion (A) and urine volume (B) in normal SD rats. All results are expressed as means±S.E.M. The statistical analysis was performed using a one-way ANOVA followed by Dunnett's post hoc test. *P<0.05, **P<0.01 versus vehicle.
  As shown above, the inventive compounds exhibited inhibitory activities against sodium-dependent glucose cotransporter 2 (SGLT2) and are thus effective as SGLT2 inhibitors.

What is claimed is:
1. A compound of formula I, or a pharmaceutically acceptable salt or a prodrug thereof:

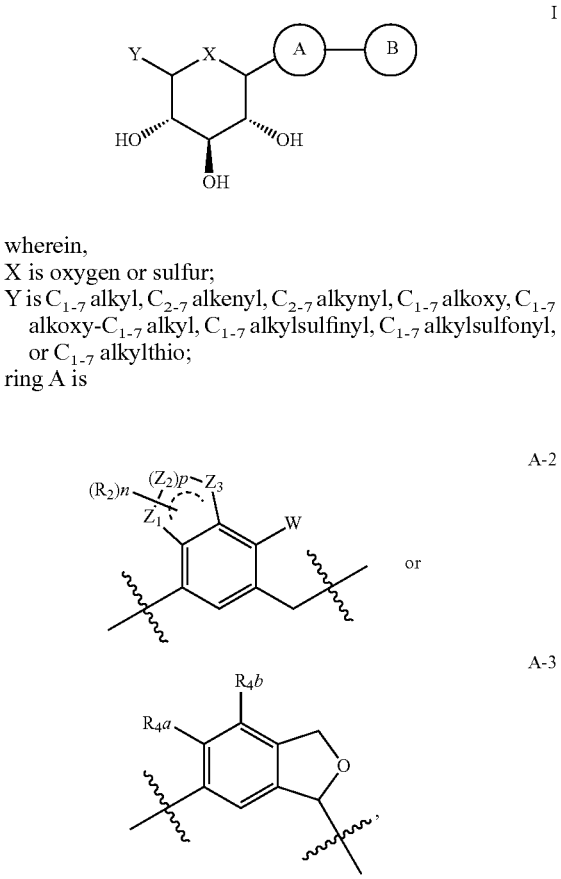

wherein,
X is oxygen or sulfur;
Y is C$_{1-7}$ alkyl, C$_{2-7}$ alkenyl, C$_{2-7}$ alkynyl, C$_{1-7}$ alkoxy, C$_{1-7}$ alkoxy-C$_{1-7}$ alkyl, C$_{1-7}$ alkylsulfinyl, C$_{1-7}$ alkylsulfonyl, or C$_{1-7}$ alkylthio;
ring A is said $R_{4a}$, $R_{4b}$, and W being each independently selected from the group consisting of hydrogen, halogen, hydroxy, mercapto, cyano, nitro, amino, carboxy, $C_{1-7}$ alkyl, $C_{2-7}$ alkenyl, $C_{2-7}$ alkynyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, $C_{1-7}$ alkanoyl, $C_{1-7}$ alkanoylamino, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, 5 to 13-membered heteroaryl, or 5 to 10-membered heterocycloalkyl, said $R_2$ being each independently hydroxy, $C_{1-7}$ alkyl, or $C_{1-7}$ alkoxy, said n being an integer of 0 to 3, said $Z_1$, $Z_2$, and $Z_3$ being each independently —$CH_2$—, —CH═, —O—, —S—, —NH—, or —N═, wherein at least one of $Z_1$, $Z_2$, and $Z_3$ is —O—, —S—, —NH—, or —N═, and said p being an integer of 1 to 3;

ring B is

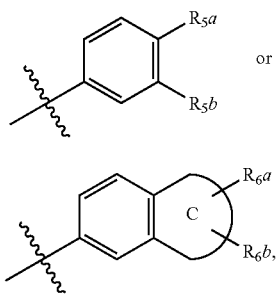

wherein, said $R_{5a}$, $R_{5b}$, $R_{6a}$, and $R_{6b}$ being each independently selected from the group consisting of hydrogen, halogen, hydroxy, mercapto, cyano, nitro, amino, carboxy, oxo, $C_{1-7}$ alkyl, $C_{1-7}$ alkylthio, $C_{2-7}$ alkenyl, $C_{2-7}$ alkynyl, $C_{1-7}$alkoxy, $C_{1-7}$ alkoxy-$C_{1-7}$ alkyl, $C_{2-7}$ alkenyl-$C_{1-7}$alkyloxy, $C_{2-7}$ alkynyl-$C_{1-7}$alkyloxy, $C_{3-10}$ cycloalkyl, $C_{3-7}$ cycloalkylthio, $C_{5-10}$ cycloalkenyl, $C_{3-10}$ cycloalkyloxy, $C_{3-10}$ cycloalkyloxy-$C_{1-7}$ alkoxy, phenyl-$C_{1-7}$ alkyl, $C_{1-7}$ alkylthio-phenyl, phenyl-$C_{1-7}$ alkoxy, mono- or di-$C_{1-7}$ alkylamino, mono- or di-$C_{1-7}$ alkylamino-$C_{1-7}$ alkyl, $C_{1-7}$ alkanoyl, $C_{1-7}$ alkanoylamino, $C_{1-7}$alkylcarbonyl, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfinyl, $C_{6-14}$ arylsulfanyl, $C_{6-14}$ arylsulfonyl, $C_{6-14}$ aryl, 5 to 13-membered heteroaryl, 5 to 10-membered heterocycloalkyl, 5 to 10-membered heterocycloalkyl-$C_{1-7}$ alkyl, or 5 to 10-membered heterocycloalkyl-$C_{1-7}$ alkoxy, and said ring C being $C_{3-10}$ cycloalkyl, $C_{5-10}$ cycloalkenyl, $C_{6-14}$ aryl, 5 to 13-membered heteroaryl, or 5 to 10-membered heterocycloalkyl;

said alkyl, alkenyl, alkynyl, or alkoxy is optionally substituted with at least one substituent selected from the group consisting of halogen, hydroxy, cyano, nitro, amino, mercapto, $C_{1-7}$ alkyl, and $C_{2-7}$ alkynyl; and said cycloalkyl, cycloalkenyl, aryl, heteroaryl, or heterocycloalkyl is optionally substituted with at least one substituent selected from the group consisting of halogen, hydroxy, cyano, nitro, amino, mercapto, $C_{1-4}$ alkyl, and $C_{1-4}$ alkoxy.

2. The compound of claim 1, wherein said ring A-2 is selected from the group consisting of:

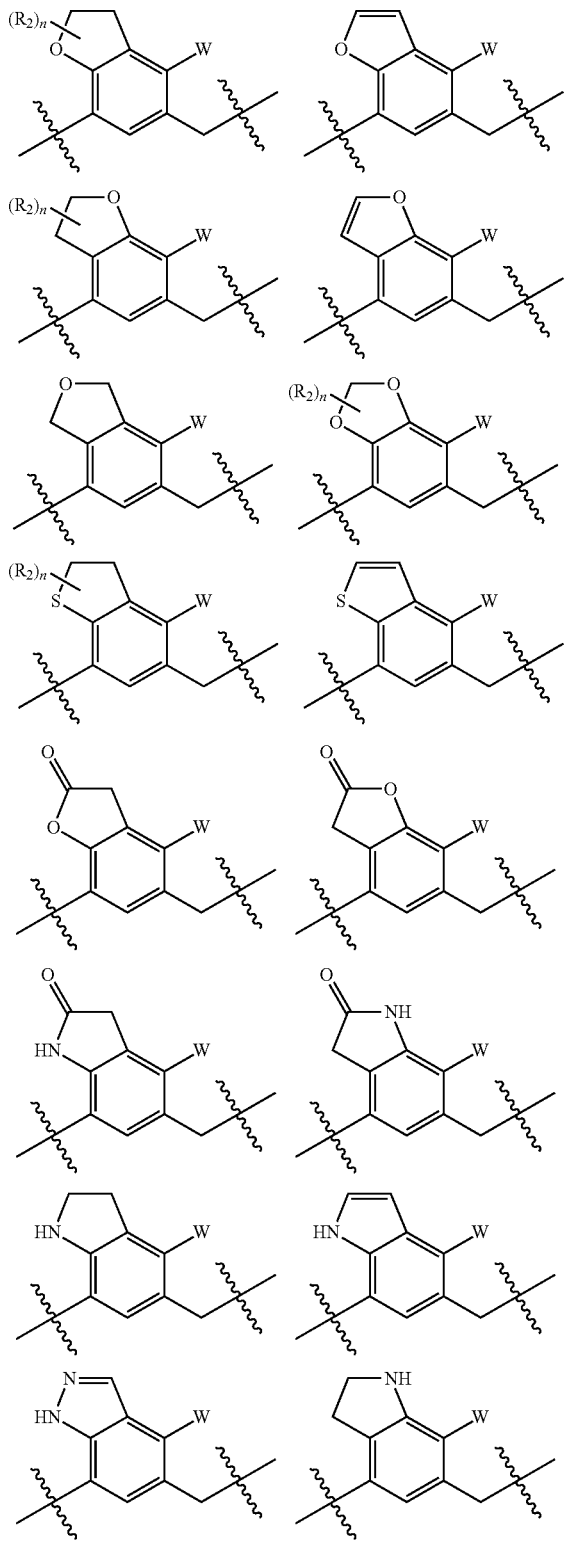

363
-continued
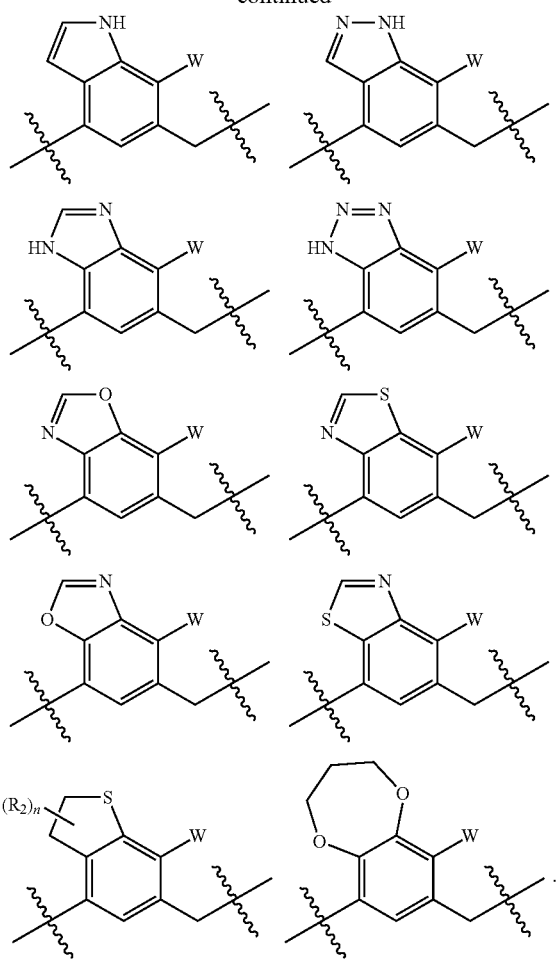
3. The compound of claim 1, wherein said ring B-1 is selected from the group consisting of:
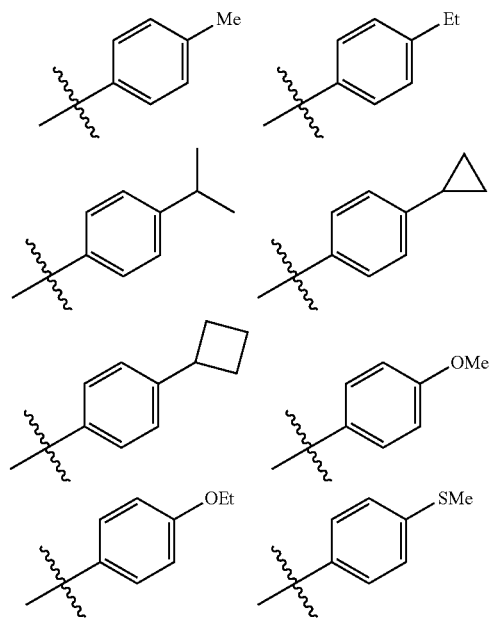
364
-continued
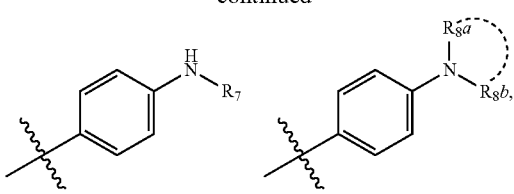
in which $R_7$ is hydrogen, or $C_{1-7}$ alkyl, and
$R_{8a}$ and $R_{8b}$ are each independently $C_{1-7}$ alkyl, or $R_{8a}$ and $R_{8b}$ are connected to form a 5 to 10-membered heterocycloalkyl.
4. The compound of claim 1, wherein said ring B-2 is selected from the group consisting of:
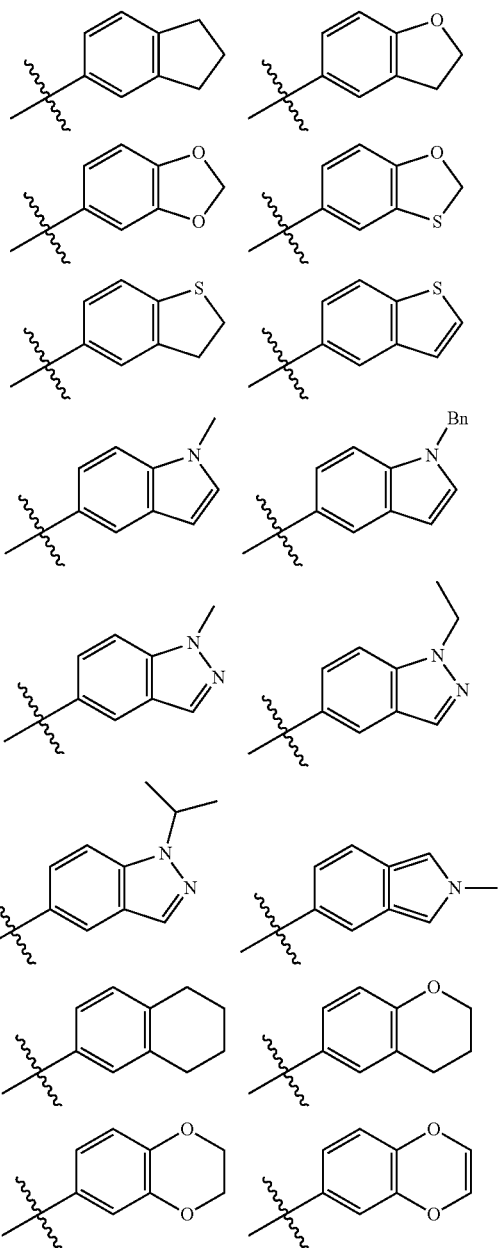

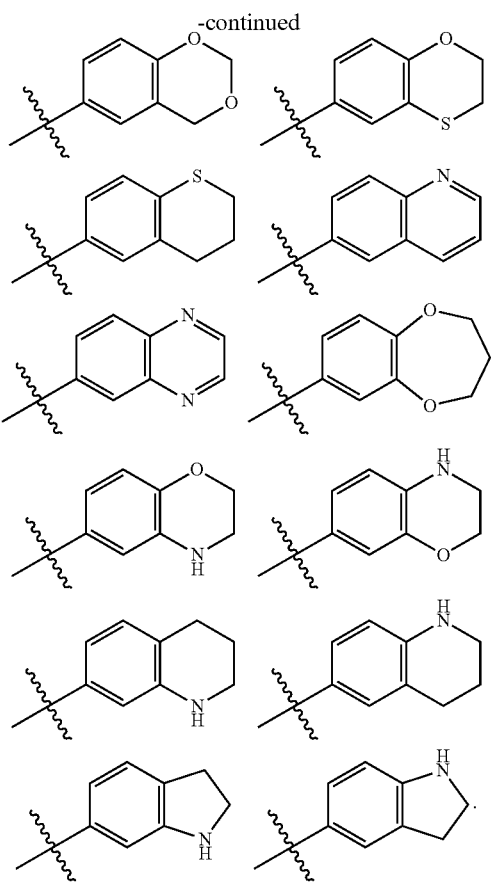

5. The compound of claim 1, wherein said ring A is a dihydrobenzofuran, dihydroisobenzofuran, benzofuran, dihydrobenzothiophene, benzothiophene, chroman, chromene, isochroman, isochromene, benzodioxole, benzodioxane, benzooxazine, tetrahydroquinoline, tetrahydroquinoxaline, tetrahydroisoquinoline, indazole, indole, indoline, benzoimidazole, benzooxazole, benzothiazole, benzotriazole, quinazoline, quinoxaline, cinnoline, phthalazine, or benzotriazine ring, which is optionally substituted with a substituent as defined in claim 1.

6. The compound of claim 1, wherein said ring B is a quinoline, quinoxaline, 3,4-dihydro-2H-benzo[b][1,4]dioxepine, 2,3-dihydrobenzo[b]thiophene, indazole, indole, 2,3-dihydrobenzo[b][1,4]dioxine, benzodioxole, indane, tetrahydronaphthalene, 3,4-dihydro-2H-thiochromene, dihydrobenzofuran, benzo[d][1,3]oxathiole, tetrahydroquinoline, or 3,4-dihydro-2H-benzo[b][1,4]oxazine ring, which is optionally substituted with a substituent as defined in claim 1.

7. The compound of claim 1, which is selected from the group consisting of:
(1) (2S,3R,4R,5S,6R)-2-(4-chloro-5-(4-ethylbenzyl)-2,3-dihydrobenzofuran-7-yl)-6-(hydroxymethyl)tetrahydro-2H-pyran-3,4,5-triol;
(2) (2S,3R,4R,5S,6R)-2-(4-chloro-5-(4-ethoxybenzyl)-2-methyl-2,3-dihydrobenzofuran-7-yl)-6-(hydroxymethyl)tetrahydro-2H-pyran-3,4,5-triol;
(3) (2S,3R,4R,5S,6R)-2-(5-chloro-6-(4-ethoxybenzyl)chroman-8-yl)-6-(hydroxymethyl)tetrahydro-2H-pyran-3,4,5-triol;
(4) (2S,3R,4R,5S,6R)-2-(8-chloro-7-(4-ethoxybenzyl)-2,3-dihydrobenzo[b][1,4]dioxin-5-yl)-6-(hydroxymethyl)tetrahydro-2H-pyran-3,4,5-triol;
(5) (2S,3R,4R,5S,6R)-2-(5-chloro-6-(4-methoxybenzyl)chroman-8-yl)-6-(hydroxymethyl)tetrahydro-2H-pyran-3,4,5-triol;
(6) (2S,3R,4R,5S,6R)-2-(5-chloro-6-(4-ethylbenzyl)chroman-8-yl)-6-(hydroxymethyl)tetrahydro-2H-pyran-3,4,5-triol;
(7) (2S,3R,4R,5S,6R)-2-(7-chloro-6-(4-methoxybenzyl)-2,3-dihydrobenzofuran-4-yl)-6-(hydroxymethyl)tetrahydro-2H-pyran-3,4,5-triol;
(8) (2S,3R,4R,5S,6R)-2-(6-(4-ethylbenzyl)-7-chloro-2,3-dihydrobenzofuran-4-yl)-6-(hydroxymethyl)-tetrahydro-2H-pyran-3,4,5-triol;
(9) (2S,3R,4R,5S,6R)-2-(4-chloro-5-(4-methoxybenzyl)-2,3-dihydrobenzofuran-7-yl)-6-(hydroxymethyl)tetrahydro-2H-pyran-3,4,5-triol;
(10) (2S,3R,4R,5S,6R)-2-(4-chloro-5-(4-ethoxybenzyl)-2,3-dihydrobenzofuran-7-yl)-6-(hydroxymethyl)tetrahydro-2H-pyran-3,4,5-triol;
(11) (2S,3R,4R,5S,6R)-2-(8-chloro-7-(4-ethylbenzyl)chroman-5-yl)-6-(hydroxymethyl)tetrahydro-2H-pyran-3,4,5-triol;
(12) (2S,3R,4R,5S,6R)-2-(7-chloro-6-(4-ethoxybenzyl)-2,3-dihydrobenzofuran-4-yl)-6-(hydroxymethyl)tetrahydro-2H-pyran-3,4,5-triol;
(13) (2S,3R,4R,5S,6R)-2-(5-chloro-6-((2,3-dihydrobenzo[b][1,4]dioxin-6-yl)methyl)chroman-8-yl)-6-(hydroxymethyl)tetrahydro-2H-pyran-3,4,5-triol;
(14) (2S,3R,4R,5S,6R)-2-(7-chloro-6-((2,3-dihydrobenzo[b][1,4]dioxin-6-yl)methyl)-2,3-dihydrobenzofuran-4-yl)-6-(hydroxymethyl)tetrahydro-2H-pyran-3,4,5-triol;
(15) (2S,3R,4R,5S,6R)-2-(8-chloro-7-((2,3-dihydrobenzo[b][1,4]dioxin-6-yl)methyl)-2,3-dihydrobenzo[b][1,4]dioxin-5-yl)-6-(hydroxymethyl)tetrahydro-2H-pyran-3,4,5-triol;
(16) (2S,3R,4R,5S,6R)-2-(8-chloro-7-(4-methoxybenzyl)-2,3-dihydrobenzo[b][1,4]dioxin-5-yl)-6-(hydroxymethyl)tetrahydro-2H-pyran-3,4,5-triol;
(17) (2S,3R,4R,5S,6R)-2-(8-chloro-7-(4-ethylbenzyl)-2,3-dihydrobenzo[b][1,4]dioxin-5-yl)-6-(hydroxymethyl)tetrahydro-2H-pyran-3,4,5-triol;
(18) (2S,3R,4R,5S,6R)-2-(4-chloro-5-(4-vinylbenzyl)-2,3-dihydrobenzofuran-7-yl)-6-(hydroxymethyl)tetrahydro-2H-pyran-3,4,5-triol;
(19) (2S,3R,4R,5S,6R)-2-(4-chloro-5-(4-cyclopropylbenzyl)-2,3-dihydrobenzofuran-7-yl)-6-(hydroxymethyl)tetrahydro-2H-pyran-3,4,5-triol;
(20) ((2S,3R,4R,5S,6R)-2-(5-chloro-6-(4-cyclopropylbenzyl)chroman-8-yl)-6-(hydroxymethyl)tetrahydro-2H-pyran-3,4,5-triol;
(21) (2S,3R,4R,5S,6R)-2-(4-chloro-5-(4-(trifluoromethyl)benzyl)-2,3-dihydrobenzofuran-7-yl)-6-(hydroxymethyl)tetrahydro-2H-pyran-3,4,5-triol;
(22) (2S,3R,4R,5S,6R)-2-(4-chloro-5-(4-chlorobenzyl)-2,3-dihydrobenzofuran-7-yl)-6-(hydroxymethyl)tetrahydro-2H-pyran-3,4,5-triol;
(23) (2S,3R,4R,5S,6R)-2-(7-chloro-6-(4-(trifluoromethyl)benzyl)-2,3-dihydrobenzofuran-4-yl)-6-(hydroxymethyl)tetrahydro-2H-pyran-3,4,5-triol;
(24) (2S,3R,4S,5S,6R)-2-(7-chloro-6-(4-ethoxybenzyl)-2,3-dihydrobenzofuran-4-yl)-6-methyltetrahydro-2H-pyran-3,4,5-triol;
(25) (2S,3R,4R,5S,6S)-2-(7-chloro-6-(4-ethoxybenzyl)-2,3-dihydrobenzofuran-4-yl)-6-(fluoromethyl)tetrahydro-2H-pyran-3,4,5-triol;
(26) (2S,3R,4R,5S,6R)-2-(7-chloro-6-(4-ethoxybenzyl)-2,3-dihydrobenzofuran-4-yl)-6-(1-hydroxyethyl)tetrahydro-2H-pyran-3,4,5-triol;

(27) (2S,3R,4R,5S,6S)-2-(7-chloro-6-(4-ethoxybenzyl)-2,3-dihydrobenzofuran-4-yl)-6-(difluoromethyl)tetrahydro-2H-pyran-3,4,5-triol;

(28) (2S,3R,4R,5S,6R)-2-(6-(4-ethoxybenzyl)-7-methyl-2,3-dihydrobenzofuran-4-yl)-6-(hydroxymethyl)tetrahydro-2H-pyran-3,4,5-triol;

(29) (2S,3R,4R,5S,6R)-2-(7-chloro-6-(4-methoxybenzyl)-2-methyl-2,3-dihydrobenzofuran-4-yl)-6-(hydroxymethyl)tetrahydro-2H-pyran-3,4,5-triol;

(30) (2S,3R,4R,5S,6R)-2-(4-chloro-5-(4-methoxybenzyl)-2-methyl-2,3-dihydrobenzofuran-7-yl)-6-(hydroxymethyl)tetrahydro-2H-pyran-3,4,5-triol;

(31) (2S,3R,4R,5S,6R)-2-(4-chloro-5-(4-ethylbenzyl)-2-methyl-2,3-dihydrobenzofuran-7-yl)-6-(hydroxymethyl)tetrahydro-2H-pyran-3,4,5-triol;

(32) (2S,3R,4R,5S,6R)-2-(4-chloro-5-(4-cyclopropylbenzyl)-2-methyl-2,3-dihydrobenzofuran-7-yl)-6-(hydroxymethyl)tetrahydro-2H-pyran-3,4,5-triol;

(33) (2S,3R,4R,5S,6R)-2-(4-chloro-2-methyl-5-(4-propylbenzyl)-2,3-dihydrobenzofuran-7-yl)-6-(hydroxymethyl)tetrahydro-2H-pyran-3,4,5-triol;

(34) (2S,3R,4R,5S,6R)-2-(7-chloro-6-(4-ethoxybenzyl)-2-methyl-2,3-dihydrobenzofuran-4-yl)-6-(hydroxymethyl)tetrahydro-2H-pyran-3,4,5-triol;

(35) (2S,3R,4R,5S,6R)-2-(7-chloro-6-(4-ethylbenzyl)-2-methyl-2,3-dihydrobenzofuran-4-yl)-6-(hydroxymethyl)tetrahydro-2H-pyran-3,4,5-triol;

(36) (2S,3R,4R,5S,6R)-2-(7-chloro-2-methyl-6-(4-vinylbenzyl)-2,3-dihydrobenzofuran-4-yl)-6-(hydroxymethyl)tetrahydro-2H-pyran-3,4,5-triol;

(37) ((2S,3R,4R,5S,6R)-2-(7-chloro-6-(4-cyclopropylbenzyl)-2-methyl-2,3-dihydrobenzofuran-4-yl)-6-(hydroxymethyl)tetrahydro-2H-pyran-3,4,5-triol;

(38) (2S,3R,4R,5S,6R)-2-(7-chloro-6-(4-(methylamino)benzyl)-2,3-dihydrobenzofuran-4-yl)-6-(hydroxymethyl)tetrahydro-2H-pyran-3,4,5-triol 2,2,2-trifluoroacetate

(39) (2S,3R,4R,5S,6R)-2-(4-chloro-5-(4-methoxybenzyl)-2-methyl-2,3-dihydrobenzo[b]thiophen-7-yl)-6-(hydroxymethyl)tetrahydro-2H-pyran-3,4,5-triol;

(40) (2S,3R,4R,5S,6R)-2-(4-chloro-5-(4-ethoxybenzyl)-2-methyl-2,3-dihydrobenzo[b]thiophen-7-yl)-6-(hydroxymethyl)tetrahydro-2H-pyran-3,4,5-triol;

(41) (2S,3R,4R,5S,6R)-2-(4-chloro-5-(4-ethylbenzyl)-2-methyl-2,3-dihydrobenzo[b]thiophen-7-yl)-6-(hydroxymethyl)tetrahydro-2H-pyran-3,4,5-triol;

(42) (2S,3R,4R,5S,6R)-2-(4-chloro-5-(4-ethoxybenzyl)-2-methyl-2,3-dihydrobenzofuran-7-yl)-6-(methylthio)tetrahydro-2H-pyran-3,4,5-triol;

(43) (2S,3R,4R,5S,6R)-2-(4-chloro-5-(4-ethoxybenzyl)-2-methyl-2,3-dihydrobenzofuran-7-yl)-6-(methylsulfonyl)tetrahydro-2H-pyran-3,4,5-triol;

(44) (2S,3R,4R,5S,6R)-2-(4-chloro-5-(4-ethoxybenzyl)-2-methyl-2,3-dihydrobenzofuran-7-yl)-6-((S)-methylsulfinyl)tetrahydro-2H-pyran-3,4,5-triol;

(45) (2S,3R,4R,5S,6R)-2-(8-chloro-7-(4-ethoxybenzyl)-2,3-dihydrobenzo[b][1,4]dioxin-5-yl)-6-(methylthio)tetrahydro-2H-pyran-3,4,5-triol;

(46) (2S,3R,4R,5S,6R)-2-(4-chloro-5-(4-isopropylbenzyl)-2-methyl-2,3-dihydrobenzofuran-7-yl)-6-(hydroxymethyl)tetrahydro-2H-pyran-3,4,5-triol;

(47) (2S,3R,4R,5S,6R)-2-(4-chloro-5-(4-isopropylbenzyl)-2-methyl-2,3-dihydrobenzofuran-7-yl)-6-(hydroxymethyl)tetrahydro-2H-pyran-3,4,5-triol;

(48) (2S,3R,4R,5S,6R)-2-(5-chloro-6-(4-(methylthio)benzyl)chroman-8-yl)-6-(hydroxymethyl)tetrahydro-2H-pyran-3,4,5-triol;

(49) (2S,3R,4R,5S,6R)-2-(8-chloro-7-(4-cyclopropylbenzyl)chroman-5-yl)-6-(hydroxymethyl)tetrahydro-2H-pyran-3,4,5-triol;

(50) (2S,3R,4R,5S,6R)-2-(8-chloro-7-(4-methoxybenzyl)chroman-5-yl)-6-(hydroxymethyl)tetrahydro-2H-pyran-3,4,5-triol;

(51) (2S,3R,4R,5S,6R)-2-(8-chloro-7-(4-ethoxybenzyl)chroman-5-yl)-6-(hydroxymethyl)tetrahydro-2H-pyran-3,4,5-triol;

(52) (2S,3R,4R,5S,6R)-2-(7-chloro-6-(4-cyclopropylbenzyl)benzo[d][1,3]dioxol-4-yl)-6-(hydroxymethyl)tetrahydro-2H-pyran-3,4,5-triol;

(53) (2S,3R,4R,5S,6R)-2-(7-chloro-6-(4-isopropylbenzyl)benzo[d][1,3]dioxol-4-yl)-6-(hydroxymethyl)tetrahydro-2H-pyran-3,4,5-triol;

(54) (2S,3R,4R,5S,6R)-2-(7-chloro-6-(4-ethoxybenzyl)benzo[d][1,3]dioxol-4-yl)-6-(hydroxymethyl)tetrahydro-2H-pyran-3,4,5-triol;

(55) (2S,3R,4R,5S,6R)-2-(7-chloro-6-(4-methoxybenzyl)benzo[d][1,3]dioxol-4-yl)-6-(hydroxymethyl)tetrahydro-2H-pyran-3,4,5-triol;

(56) (2S,3R,4R,5S,6R)-2-(7-chloro-6-(4-ethylbenzyl)benzo[d][1,3]dioxol-4-yl)-6-(hydroxymethyl)tetrahydro-2H-pyran-3,4,5-triol;

(57) (2S,3R,4R,5S,6R)-2-(8-chloro-7-(4-cyclopropylbenzyl)-2,3-dihydrobenzo[b][1,4]dioxin-5-yl)-6-(hydroxymethyl)tetrahydro-2H-pyran-3,4,5-triol;

(58) (2S,3R,4R,5S,6R)-2-(9-chloro-8-(4-ethoxybenzyl)-3,4-dihydro-2H-benzo[b][1,4]dioxepin-6-yl)-6-(hydroxymethyl)tetrahydro-2H-pyran-3,4,5-triol;

(59) (2S,3R,4R,5S,6R)-2-(9-chloro-8-(4-ethylbenzyl)-3,4-dihydro-2H-benzo[b][1,4]dioxepin-6-yl)-6-(hydroxymethyl)tetrahydro-2H-pyran-3,4,5-triol;

(60) (2S,3R,4R,5S,6R)-2-(6-benzyl-7-chloro-2,3-dihydrobenzofuran-4-yl)-6-(hydroxymethyl)tetrahydro-2H-pyran-3,4,5-triol;

(61) 1-(4-((7-chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)phenyl)ethanone;

(62) (2S,3R,4R,5S,6R)-2-(7-chloro-6-(4-(1-hydroxyethyl)benzyl)-2,3-dihydrobenzofuran-4-yl)-6-(hydroxymethyl)tetrahydro-2H-pyran-3,4,5-triol;

(63) (2S,3R,4R,5S,6R)-2-(7-chloro-6-(4-(1-fluoroethyl)benzyl)-2,3-dihydrobenzofuran-4-yl)-6-(hydroxymethyl)tetrahydro-2H-pyran-3,4,5-triol;

(64) (2S,3R,4R,5S,6R)-2-(7-chloro-6-(4-vinylbenzyl)-2,3-dihydrobenzofuran-4-yl)-6-(hydroxymethyl)tetrahydro-2H-pyran-3,4,5-triol;

(65) (2S,3R,4R,5S,6R)-2-(7-chloro-6-(4-cyclopropylbenzyl)-2,3-dihydrobenzofuran-4-yl)-6-(hydroxymethyl)tetrahydro-2H-pyran-3,4,5-triol;

(66) (2S,3R,4R,5S,6R)-2-(4-chloro-5-(4-cyclopropylbenzyl)benzofuran-7-yl)-6-(hydroxymethyl)tetrahydro-2H-pyran-3,4,5-triol;

(67) (2S,3R,4R,5S,6R)-2-(7-chloro-6-(4-(2-hydroxypropan-2-yl)benzyl)-2,3-dihydrobenzofuran-4-yl)-6-(hydroxymethyl)tetrahydro-2H-pyran-3,4,5-triol;

(68) (2S,3R,4R,5S,6R)-2-(7-chloro-6-(4-(difluoromethyl)benzyl)-2,3-dihydrobenzofuran-4-yl)-6-(hydroxymethyl)tetrahydro-2H-pyran-3,4,5-triol;

(69) (2S,3R,4R,5S,6R)-2-(7-chloro-6-(4-(1,1-difluoroethyl)benzyl)-2,3-dihydrobenzofuran-4-yl)-6-(hydroxymethyl)tetrahydro-2H-pyran-3,4,5-triol;

(70) (2S,3R,4R,5S,6R)-2-(6-(4-cyclopropylbenzyl)-7-methyl-2,3-dihydrobenzofuran-4-yl)-6-(hydroxymethyl)tetrahydro-2H-pyran-3,4,5-triol;

(71) (2S,3R,4R,5S,6R)-2-(7-chloro-6-(4-(2-hydroxybut-3-yn-2-yl)benzyl)-2,3-dihydrobenzofuran-4-yl)-6-(hydroxymethyl)tetrahydro-2H-pyran-3,4,5-triol;
(72) (2S,3R,4R,5S,6R)-2-(7-chloro-6-(4-(prop-1-en-2-yl)benzyl)-2,3-dihydrobenzofuran-4-yl)-6-(hydroxymethyl)tetrahydro-2H-pyran-3,4,5-triol;
(73) (2S,3R,4R,5S,6R)-2-(7-chloro-6-(4-isopropylbenzyl)-2,3-dihydrobenzofuran-4-yl)-6-(hydroxymethyl)tetrahydro-2H-pyran-3,4,5-triol;
(74) (2S,3R,4R,5S,6R)-2-(7-chloro-6-(4-ethynylbenzyl)-2,3-dihydrobenzofuran-4-yl)-6-(hydroxymethyl)tetrahydro-2H-pyran-3,4,5-triol;
(75) 4-((7-chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)benzonitrile;
(76) (2S,3R,4R,5S,6R)-2-(7-chloro-6-(4-propylbenzyl)-2,3-dihydrobenzofuran-4-yl)-6-(hydroxymethyl)tetrahydro-2H-pyran-3,4,5-triol;
(77) (2S,3R,4R,5S,6R)-2-(7-chloro-6-(4-methoxybenzyl)-2,3-dihydrobenzofuran-4-yl)-6-(hydroxymethyl)tetrahydro-2H-thiopyran-3,4,5-triol;
(78) (2S,3R,4R,5S,6R)-2-(7-chloro-6-(4-(methylthio)benzyl)-2,3-dihydrobenzofuran-4-yl)-6-(hydroxymethyl)tetrahydro-2H-pyran-3,4,5-triol;
(79) (2S,3R,4R,5S,6R)-2-(7-chloro-6-(4-(dimethylamino)benzyl)-2,3-dihydrobenzofuran-4-yl)-6-(hydroxymethyl)tetrahydro-2H-pyran-3,4,5-triol;
(80) (2S,3R,4R,5S,6R)-2-(4-chloro-5-((2,3-dihydrobenzo[b][1,4]dioxin-6-yl)methyl)-2,3-dihydrobenzofuran-7-yl)-6-(hydroxymethyl)tetrahydro-2H-pyran-3,4,5-triol;
(81) (2S,3R,4R,5S,6R)-2-(7-chloro-6-(4-hydroxybenzyl)-2,3-dihydrobenzofuran-4-yl)-6-(hydroxymethyl)tetrahydro-2H-pyran-3,4,5-triol;
(82) (2S,3R,4R,5S,6R)-2-(7-chloro-6-(4-(3-hydroxypropoxyl)benzyl)-2,3-dihydrobenzofuran-4-yl)-6-(hydroxymethyl)tetrahydro-2H-pyran-3,4,5-triol;
(83) (2S,3R,4R,5S,6R)-2-(7-chloro-6-(4-propoxybenzyl)-2,3-dihydrobenzofuran-4-yl)-6-(hydroxymethyl)tetrahydro-2H-pyran-3,4,5-triol;
(84) 4-chloro-5-(4-methoxybenzyl)-7-((2S,3R,4R,5S,6R)-3,4,5-trihydroxy-6-(hydroxymethyl)tetrahydro-2H-pyran-2-yl)benzofuran-3(2H)-one;
(85) (2S,3R,4R,5S,6R)-2-(4-chloro-3-hydroxy-5-(4-methoxybenzyl)-2,3-dihydrobenzofuran-7-yl)-6-(hydroxymethyl)tetrahydro-2H-pyran-3,4,5-triol;
(86) (2S,3R,4R,5S,6R)-2-(4-chloro-5-(4-(dimethylamino)benzyl)-2,3-dihydrobenzofuran-7-yl)-6-(hydroxymethyl)tetrahydro-2H-pyran-3,4,5-triol;
(87) (2S,3R,4R,5S,6R)-2-(7-chloro-6-(4-(2-cyclopropoxyethoxyl)benzyl)-2,3-dihydrobenzofuran-4-yl)-6-(hydroxymethyl)tetrahydro-2H-pyran-3,4,5-triol;
(88) (2S,3R,4R,5S,6R)-2-(6-(4-(azetidin-1-yl)benzyl)-7-chloro-2,3-dihydrobenzofuran-4-yl)-6-(hydroxymethyl)tetrahydro-2H-pyran-3,4,5-triol;
(89) (2S,3R,4R,5S,6R)-2-(7-chloro-6-(4-(trifluoromethoxy)benzyl)-2,3-dihydrobenzofuran-4-yl)-6-(hydroxymethyl)tetrahydro-2H-pyran-3,4,5-triol;
(90) 2-(4-((7-chloro-4-((2S,3R,4R,5S,6R)-3,4,5-trihydroxy-6-(hydroxymethyl)tetrahydro-2H-pyran-2-yl)-2,3-dihydrobenzofuran-6-yl)methyl)phenyl)acetonitrile;
(91) (2S,3R,4R,5S,6R)-2-(7-chloro-6-(4-(oxetan-3-yloxy)benzyl)-2,3-dihydrobenzofuran-4-yl)-6-(hydroxymethyl)tetrahydro-2H-pyran-3,4,5-triol;
(92) (2S,3R,4R,5S,6R)-2-(7-chloro-6-(4-isopropoxybenzyl)-2,3-dihydrobenzofuran-4-yl)-6-(hydroxymethyl)tetrahydro-2H-pyran-3,4,5-triol;
(93) (2S,3R,4R,5S,6R)-2-(7-chloro-6-(4-(cyclopropylthio)benzyl)-2,3-dihydrobenzofuran-4-yl)-6-(hydroxymethyl)tetrahydro-2H-pyran-3,4,5-triol;
(94) (2S,3R,4R,5S,6R)-2-(7-chloro-6-((5-methoxythiophen-2-yl)methyl)-2,3-dihydrobenzofuran-4-yl)-6-(hydroxymethyl)tetrahydro-2H-pyran-3,4,5-triol;
(95) (2S,3R,4R,5S,6R)-2-(5-chloro-6-(4-methoxybenzyl)chroman-8-yl)-6-(methylthio)tetrahydro-2H-pyran-3,4,5-triol;
(96) (2S,3R,4R,5S,6R)-2-(4-chloro-5-(4-methoxybenzyl)-2,3-dihydrobenzo[b]thiophen-7-yl)-6-(hydroxymethyl)tetrahydro-2H-pyran-3,4,5-triol;
(97) (2S,3R,4R,5S,6R)-2-(5-chloro-6-(4-ethoxybenzyl)-3,4-dihydro-2H-benzo[b][1,4]oxazin-8-yl)-6-(hydroxymethyl)tetrahydro-2H-pyran-3,4,5-triol;
(98) (2S,3R,4R,5S,6R)-2-(5-chloro-6-(4-ethoxybenzyl)-4-methyl-3,4-dihydro-2H-benzo[b][1,4]oxazin-8-yl)-6-(hydroxymethyl)tetrahydro-2H-pyran-3,4,5-triol;
(99) (2S,3R,4R,5S,6R)-2-(5-chloro-6-(4-ethylbenzyl)-3,4-dihydro-2H-benzo[b][1,4]oxazin-8-yl)-6-(hydroxymethyl)tetrahydro-2H-pyran-3,4,5-triol;
(100) (2S,3R,4R,5S,6R)-2-(4-chloro-5-(4-ethylbenzyl)-3-methyl-2,3-dihydrobenzofuran-7-yl)-6-(hydroxymethyl)tetrahydro-2H-pyran-3,4,5-triol;
(101) (2S,3R,4R,5S,6R)-2-(4-chloro-5-(4-methoxybenzyl)-3-methyl-2,3-dihydrobenzofuran-7-yl)-6-(hydroxymethyl)tetrahydro-2H-pyran-3,4,5-triol;
(102) (2S,3R,4R,5S,6R)-2-(4-chloro-5-(4-ethylbenzyl)-3,3-dimethyl-2,3-dihydrobenzofuran-7-yl)-6-(hydroxymethyl)tetrahydro-2H-pyran-3,4,5-triol;
(103) (2S,3R,4R,5S,6R)-2-(4-chloro-5-(4-methoxybenzyl)-3,3-dimethyl-2,3-dihydrobenzofuran-7-yl)-6-(hydroxymethyl)tetrahydro-2H-pyran-3,4,5-triol;
(104) (2S,3R,4R,5S,6R)-2-(4-chloro-5-(4-methoxybenzyl)-2,2-dimethyl-2,3-dihydrobenzofuran-7-yl)-6-(hydroxymethyl)tetrahydro-2H-pyran-3,4,5-triol;
(105) (2S,3R,4R,5S,6R)-2-(4-chloro-5-(4-ethoxybenzyl)-2,2-dimethyl-2,3-dihydrobenzofuran-7-yl)-6-(hydroxymethyl)tetrahydro-2H-pyran-3,4,5-triol;
(106) (2S,3R,4R,5S,6R)-2-(4-chloro-5-(4-ethoxybenzyl)-3-methyl-2,3-dihydrobenzofuran-7-yl)-6-(hydroxymethyl)-tetrahydro-2H-pyran-3,4,5-triol;
(107) (2S,3R,4R,5S,6R)-2-(4-chloro-5-(4-ethoxybenzyl)-3,3-dimethyl-2,3-dihydrobenzofuran-7-yl)-6-(hydroxymethyl)-tetrahydro-2H-pyran-3,4,5-triol;
(108) (2S,3R,4R,5S,6R)-2-(7-chloro-6-(4-ethoxybenzyl)-3-methyl-2,3-dihydrobenzofuran-4-yl)-6-(hydroxymethyl)-tetrahydro-2H-pyran-3,4,5-triol;
(109) (2S,3R,4R,5S,6R)-2-(7-chloro-6-(4-ethoxybenzyl)-3,3-dimethyl-2,3-dihydrobenzofuran-4-yl)-6-(hydroxymethyl)-tetrahydro-2H-pyran-3,4,5-triol;
(110) 7-chloro-6-(4-ethoxybenzyl)-4-(2S,3R,4R,5S,6R)-3,4,5-trihydroxy-6-(hydroxymethyl)-tetrahydro-2H-pyran-2-yl)benzofuran-3(2H)-one
(111) (2S,3R,4R,5S,6R)-2-(7-chloro-6-(4-ethoxybenzyl)-3-methoxy-2,3-dihydrobenzofuran-4-yl)-6-(hydroxymethyl)-tetrahydro-2H-pyran-3,4,5-triol;
(112) (2S,3R,4R,5S,6R)-2-(7-cyclopropyl-6-(4-ethoxybenzyl)-2,3-dihydrobenzofuran-4-yl)-6-(hydroxymethyl)-tetrahydro-2H-pyran-3,4,5-triol;
(113) (2S,3R,4R,5S,6R)-2-(6-(4-ethoxybenzyl)-7-propyl-2,3-dihydrobenzofuran-4-yl)-6-(hydroxymethyl)-tetrahydro-2H-pyran-3,4,5-triol;
(114) (2S,3R,4R,5S,6R)-2-(7-chloro-6-((1,2,3,4-tetrahydroquinolin-7-yl)methyl)-2,3-dihydrobenzofuran-4-yl)-6-(hydroxymethyl)-tetrahydro-2H-pyran-3,4,5-triol;

(115) (2S,3R,4R,5S,6R)-2-(7-chloro-6-((3,4-dihydro-2H-benzo[b][1,4]oxazin-6-yl)methyl)-2,3-dihydrobenzofuran-4-yl)-6-(hydroxymethyl)-tetrahydro-2H-pyran-3,4,5-triol;

(116) (2S,3R,4R,5S,6R)-2-(7-chloro-6-(4-(cyclopentyloxy)benzyl)-2,3-dihydrobenzofuran-4-yl)-6-(hydroxymethyl)-tetrahydro-2H-pyran-3,4,5-triol;

(117) (2S,3R,4R,5S,6R)-2-(7-chloro-6-(4-cyclopentylbenzyl)-2,3-dihydrobenzofuran-4-yl)-6-(hydroxymethyl)-tetrahydro-2H-pyran-3,4,5-triol;

(118) (2S,3R,4R,5S,6R)-2-(7-chloro-6-(4-cyclobutoxybenzyl)-2,3-dihydrobenzofuran-4-yl)-6-(hydroxymethyl)-tetrahydro-2H-pyran-3,4,5-triol;

(119) (2S,3R,4R,5S,6R)-2-(6-(4-tert-butylbenzyl)-7-chloro-2,3-dihydrobenzofuran-4-yl)-6-(hydroxymethyl)-tetrahydro-2H-pyran-3,4,5-triol;

(120) (2S,3R,4R,5S,6R)-2-(7-chloro-6-(4-cyclobutylbenzyl)-2,3-dihydrobenzofuran-4-yl)-6-(hydroxymethyl)-tetrahydro-2H-pyran-3,4,5-triol;

(121) (2S,3R,4R,5S,6R)-2-(7-(difluoromethyl)-6-(4-methoxybenzyl)-2,3-dihydro-1H-inden-4-yl)-6-(hydroxymethyl)tetrahydro-2H-pyran-3,4,5-triol;

(122) (2S,3R,4R,5S,6R)-2-(7-chloro-6-(4-methoxybenzyl)-2,3-dihydrobenzo[b]thiophen-4-yl)-6-(hydroxymethyl)tetrahydro-2H-pyran-3,4,5-triol;

(123) (2S,3R,4R,5S,6R)-2-(8-chloro-7-(4-methoxybenzyl)thiochroman-5-yl)-6-(hydroxymethyl)tetrahydro-2H-pyran-3,4,5-triol;

(124) (2S,3R,4R,5S,6R)-2-(4-chloro-5-((2,3-dihydrobenzo[b][1,4]dioxin-6-yl)methyl)-2-methoxyphenyl)-6-(hydroxymethyl)tetrahydro-2H-thiopyran-3,4,5-triol; and (125) (2S,3R,4R,5S,6R)-2-(7-chloro-6-(4-isopropylbenzyl)-2-methyl-2,3-dihydrobenzofuran-4-yl)-6-(hydroxymethyl)tetrahydro-2H-pyran-3,4,5-triol.

8. A method for preparing a compound of formula I-a, comprising:

a) reacting a compound of formula II with a compound of formula III to obtain a compound of formula IV; and (b) deprotecting and reducing the compound of formula IV to obtain a compound of formula I-a,

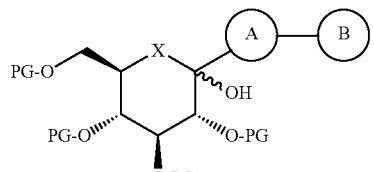

II

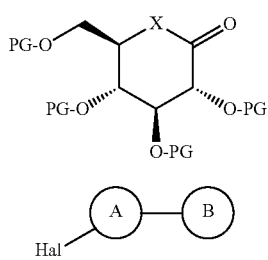

III

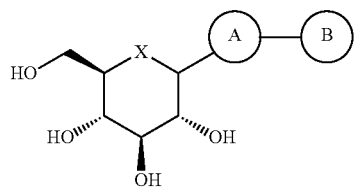

IV

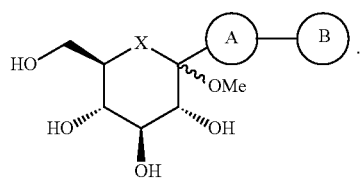

I-a wherein, X, ring A and ring B are same as defined in claim 1, Hal is halogen, and PG is trimethylsilyl or benzyl.

9. The method of claim 8, wherein step (b) is carried out by deprotecting the compound of formula IV to obtain a compound of formula V, and reducing the compound of formula V to obtain the compound of formula I-a, when PG is trimethylsilyl:

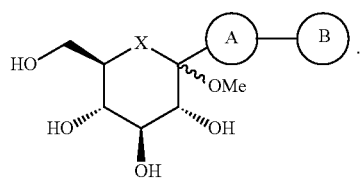

V

10. The method of claim 8, wherein step (b) is carried out by reducing the compound of formula IV to obtain a compound of formula VI, and deprotecting the compound of formula VI to obtain the compound of formula I-a, when PG is benzyl:

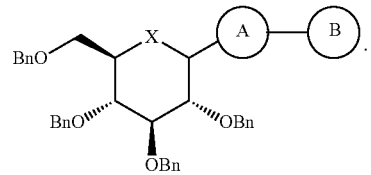

VI

11. A pharmaceutical composition, comprising as an active ingredient the compound of formula I of claim 1 or a pharmaceutically acceptable salt or a prodrug thereof, and a pharmaceutically acceptable carrier.

12. A method for treating a diabetes in a mammal, which comprises administering the compound of formula I of claim 1 or a pharmaceutically acceptable salt or a prodrug thereof to the mammal.

* * * * *